US008859591B2

(12) United States Patent
Aspnes et al.

(10) Patent No.: US 8,859,591 B2
(45) Date of Patent: Oct. 14, 2014

(54) GLUCAGON RECEPTOR MODULATORS

(71) Applicant: Pfizer Inc., New York, NY (US)

(72) Inventors: Gary Erik Aspnes, Rockville, RI (US); Mary Theresa Didiuk, Madison, CT (US); Kevin James Filipski, Reading, MA (US); Angel Guzman-Perez, Belmont, MA (US); Esther Cheng Yin Lee, Shirley, MA (US); Jeffrey Allen Pfefferkorn, Acton, MA (US); Benjamin Dawson Stevens, Cambridge, MA (US); Meihua Mike Tu, Acton, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 13/934,322

(22) Filed: Jul. 3, 2013

(65) Prior Publication Data

US 2013/0296355 A1  Nov. 7, 2013

Related U.S. Application Data

(63) Continuation of application No. 13/367,459, filed on Feb. 7, 2012, now Pat. No. 8,507,533.

(60) Provisional application No. 61/440,578, filed on Feb. 8, 2011, provisional application No. 61/441,044, filed on Feb. 9, 2011, provisional application No. 61/585,834, filed on Jan. 12, 2012.

(51) Int. Cl.
| | |
|---|---|
| *A61K 31/415* | (2006.01) |
| *A61K 31/4427* | (2006.01) |
| *A61K 31/497* | (2006.01) |
| *A61K 31/501* | (2006.01) |
| *A61K 31/506* | (2006.01) |
| *C07D 231/00* | (2006.01) |
| *C07D 233/00* | (2006.01) |
| *C07D 237/06* | (2006.01) |
| *C07D 239/24* | (2006.01) |
| *C07D 241/10* | (2006.01) |
| *C07D 233/61* | (2006.01) |
| *C07D 231/54* | (2006.01) |
| *C07D 207/34* | (2006.01) |
| *C07D 487/04* | (2006.01) |
| *C07D 403/12* | (2006.01) |
| *C07D 249/08* | (2006.01) |
| *C07D 231/16* | (2006.01) |
| *C07D 231/14* | (2006.01) |
| *C07D 233/68* | (2006.01) |
| *C07D 231/12* | (2006.01) |

(Continued)

(52) U.S. Cl.
CPC ............ *C07D 403/12* (2013.01); *C07D 233/61* (2013.01); *C07D 231/54* (2013.01); *C07D 207/34* (2013.01); *C07D 487/04* (2013.01); *C07D 249/08* (2013.01); *C07D 231/16* (2013.01); *C07D 231/14* (2013.01); *C07D 233/68* (2013.01); *C07D 231/12* (2013.01); *C07D 249/06* (2013.01); *C07D 233/84* (2013.01); *C07D 405/14* (2013.01); *C07D 401/12* (2013.01); *C07D 403/04* (2013.01); *C07D 233/64* (2013.01); *C07D 231/18* (2013.01); *C07D 401/14* (2013.01); *C07D 261/08* (2013.01); *C07D 401/04* (2013.01); *C07D 231/56* (2013.01); *C07D 233/70* (2013.01)

USPC ........... 514/336; 544/238; 544/242; 544/336; 546/268.1; 548/250; 514/252.1; 514/256; 514/272; 514/354; 514/359

(58) Field of Classification Search
USPC ............... 548/250; 514/336, 354, 359, 252.1, 514/256; 546/268.1; 544/238, 242, 336
See application file for complete search history.

(56) References Cited

U.S. PATENT DOCUMENTS

| | | | |
|---|---|---|---|
| 5,776,954 | A | 7/1998 | de Laszlo et al. |
| 5,837,719 | A | 11/1998 | de Laszlo et al. |

(Continued)

FOREIGN PATENT DOCUMENTS

| | | |
|---|---|---|
| CN | 102206172 | 10/2011 |
| DE | 10300398 | 1/2003 |

(Continued)

OTHER PUBLICATIONS

Shen, et al., "A survey of small molecule glucagon receptor antagonists from recent patents (2006-2010)", Expert Opinion on Therapeutic Patents, vol. 21 (8), pp. 1211-1240 (2011 ).*

(Continued)

*Primary Examiner* — Kamal Saeed
*Assistant Examiner* — Janet L Coppins
(74) *Attorney, Agent, or Firm* — James T. Wasicak

(57) ABSTRACT

The present invention provides a compound of Formula (I)

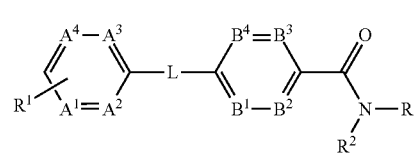

or a pharmaceutically acceptable salt thereof wherein $R^1$, $R^2$, $R^3$, $A^1$, $A^2$, $A^3$, $A^4$, L, $B^1$, $B^2$, $B^3$ and $B^4$ are as defined herein. The compounds of Formula I have been found to act as glucagon antagonists or inverse agonists. Consequently, the compounds of Formula I and the pharmaceutical compositions thereof are useful for the treatment of diseases, disorders, or conditions mediated by glucagon.

18 Claims, 1 Drawing Sheet

(51) Int. Cl.
| | | |
|---|---|---|
| C07D 249/06 | (2006.01) | |
| C07D 233/84 | (2006.01) | |
| C07D 405/14 | (2006.01) | |
| C07D 401/12 | (2006.01) | |
| C07D 403/04 | (2006.01) | |
| C07D 233/64 | (2006.01) | |
| C07D 231/18 | (2006.01) | |
| C07D 401/14 | (2006.01) | |
| C07D 261/08 | (2006.01) | |
| C07D 401/04 | (2006.01) | |
| C07D 231/56 | (2006.01) | |
| C07D 233/70 | (2006.01) | |

(56) References Cited

U.S. PATENT DOCUMENTS

| | | | |
|---|---|---|---|
| 5,880,139 | A | 3/1999 | Chang |
| 5,939,359 | A | 8/1999 | Engel et al. |
| 6,103,720 | A | 8/2000 | Lubisch et al. |
| 6,211,242 | B1 | 4/2001 | Setoi et al. |
| 6,218,431 | B1 | 4/2001 | Schoen et al. |
| 7,151,114 | B2 | 12/2006 | Streicher et al. |
| 7,687,534 | B2 | 3/2010 | Stelmach et al. |
| 2003/0203946 | A1 | 10/2003 | Behrens et al. |
| 2004/0097552 | A1 | 5/2004 | Duffy et al. |
| 2004/0097557 | A1 | 5/2004 | Duffy et al. |
| 2004/0209928 | A1 | 10/2004 | Kurukulasuriya et al. |
| 2004/0209943 | A1 | 10/2004 | Erickson et al. |
| 2004/0266856 | A1 | 12/2004 | Chu et al. |
| 2005/0272794 | A1 | 12/2005 | Parmee et al. |
| 2006/0094764 | A1 | 5/2006 | Anderskewitz et al. |
| 2006/0122256 | A1 | 6/2006 | Gillespie et al. |
| 2007/0088070 | A1 | 4/2007 | Parmee et al. |
| 2007/0088071 | A1 | 4/2007 | Kim et al. |
| 2012/0053173 | A1 | 3/2012 | Banno et al. |
| 2012/0059012 | A1 | 3/2012 | Fujii et al. |

FOREIGN PATENT DOCUMENTS

| | | |
|---|---|---|
| GB | 2292149 | 2/1996 |
| JP | 10259176 | 9/1998 |
| JP | 2005 60835 | 3/2005 |
| JP | 2009040702 | 2/2009 |
| WO | 92 19210 | 11/1992 |
| WO | 94 14427 | 7/1994 |
| WO | 9421590 | 9/1994 |
| WO | 9609818 | 4/1996 |
| WO | 97 16442 | 5/1997 |
| WO | 98 04528 | 2/1998 |
| WO | 98 22109 | 5/1998 |
| WO | 98 24780 | 6/1998 |
| WO | 98 24782 | 6/1998 |
| WO | 99 01423 | 1/1999 |
| WO | 99 24404 | 5/1999 |
| WO | 99 32448 | 7/1999 |
| WO | 00 64876 | 11/2000 |
| WO | 00 69810 | 11/2000 |
| WO | 0064888 | 11/2000 |
| WO | 02 00612 | 1/2002 |
| WO | 02 40446 | 5/2002 |
| WO | 02704624 | 9/2002 |
| WO | 03 048109 | 6/2003 |
| WO | 03 051357 | 6/2003 |
| WO | 03047626 | 6/2003 |
| WO | 03 053938 | 7/2003 |
| WO | 03055482 | 7/2003 |
| WO | 03 064404 | 8/2003 |
| WO | 03 080545 | 10/2003 |
| WO | 03 087044 | 10/2003 |
| WO | 03097619 | 11/2003 |
| WO | 2004 002480 | 1/2004 |
| WO | 2004002481 | 1/2004 |
| WO | 2004 024066 | 3/2004 |
| WO | 2004 050039 | 6/2004 |
| WO | 2004 056763 | 7/2004 |
| WO | 2004063147 | 7/2004 |
| WO | 2004 069158 | 8/2004 |
| WO | 2004092146 | 10/2004 |
| WO | 2004 100875 | 11/2004 |
| WO | 2004099170 | 11/2004 |
| WO | 2005014534 | 2/2005 |
| WO | 2005 058845 | 6/2005 |
| WO | 2005 065680 | 7/2005 |
| WO | 2005 118542 | 12/2005 |
| WO | 2005 123668 | 12/2005 |
| WO | 2006 014618 | 2/2006 |
| WO | 2006 017055 | 2/2006 |
| WO | 2006 042850 | 4/2006 |
| WO | 2006 086488 | 8/2006 |
| WO | 2006 102067 | 9/2006 |
| WO | 2006 104826 | 10/2006 |
| WO | 2007 015999 | 2/2007 |
| WO | 2007022380 | 2/2007 |
| WO | 2007040445 | 4/2007 |
| WO | 2007059195 | 5/2007 |
| WO | 2007072179 | 6/2007 |
| WO | 2007091396 | 8/2007 |
| WO | 2007 106181 | 9/2007 |
| WO | 2007 111864 | 10/2007 |
| WO | 2007 114855 | 10/2007 |
| WO | 2007 120270 | 10/2007 |
| WO | 2007 120284 | 10/2007 |
| WO | 2007 123581 | 11/2007 |
| WO | 2007 136577 | 11/2007 |
| WO | 2008 042223 | 4/2008 |
| WO | 2008 098244 | 8/2008 |
| WO | 2009 035558 | 3/2009 |
| WO | 2009 057784 | 5/2009 |
| WO | 2009 110520 | 9/2009 |
| WO | 2009 111700 | 9/2009 |
| WO | 2009 125424 | 10/2009 |
| WO | 2009 140342 | 11/2009 |
| WO | 2010 019828 | 2/2010 |
| WO | 2010 019830 | 2/2010 |
| WO | 2010 030722 | 3/2010 |
| WO | 2010 039789 | 4/2010 |
| WO | 2010 071750 | 6/2010 |
| WO | 2010 080971 | 7/2010 |
| WO | 2010 088061 | 8/2010 |
| WO | 2010 098948 | 9/2010 |
| WO | 2010 098994 | 9/2010 |
| WO | 2010 131669 | 11/2010 |
| WO | 2010 144664 | 12/2010 |
| WO | 2011 007722 | 1/2011 |
| WO | 2011 037815 | 3/2011 |
| WO | 2011 119541 | 9/2011 |
| WO | 2011 119559 | 9/2011 |
| WO | 2011 027849 | 10/2011 |

OTHER PUBLICATIONS

Djuric, et al., "Glucagon receptor antagonists for the treatment of type II diabetes: current prospects", Current Opinion in Investigational Drugs vol. 3(11), pp. 1617-1623 (2002).

Kurukulasuriya, et al., "Towards a potent small molecule Glucagon receptor antagonist", Abstracts of Papers, 228th ACS National Meeting, Philadelphia, PA, United States, Aug. 22-26, 2004, MEDI-035.

Sinz, et al., "Discovery of 2-acylindoles as potent, orally active human glucagon receptor antagonists." Abstracts of Papers, 235th ACS National Meeting, New Orleans, LA, United States, Apr. 6-10, 2008, MEDI-016.

Collins, et al., CP-99,711: A nonpeptide glucagon receptor antagonist. Bioorganic & Medicinal Chemistry Letters, vol. 2(9), pp. 915-918 (1992).

Kumar, et al., "Quantitative Structure-Activity Relationships of Selective Antagonists of Glucagon Receptor Using QuaSAR Descriptors", Chem. Pharm. Bull., vol. 54(11), pp. 1586-1591 (2006).

Madsen, et al., "Advances in Non-Peptide Glucagon Receptor Antagonists", Current Pharm. Design, vol. 5(9), pp. 683-691 (1999).

Parker, et al., "Effects of skyrin, a receptor-selective glucagon antagonist, in rat and human hepatocytes", Diabetes vol. 49(12), pp. 2079-2086 (2000).

(56) References Cited

OTHER PUBLICATIONS

Qureshi, et al., "A novel glucagon receptor antagonist inhibits glucagon-mediated biological effects", Diabetes, vol. 53(12), pp. 3267-3273 (2004).
Petersen, et al., "Effects of a novel glucagon receptor antagonist (Bay 27/9955) on glucagon-stimulated glucose production in humans", Diabetologia, vol. 44(11), pp. 2018-2024 (2001).
Winzell, et al., "Glucagon receptor antagonism improves islet function in mice with insulin resistance induced by a high-fat diet", Diabetologia, vol. 50(7), pp. 1453-1462 (2007).
Mu, et al., "Chronic treatment with a glucagon receptor antagonist lowers glucose and moderately raises circulating glucagon and glucagon-like peptide 1 without severe alpha cell hypertrophy in diet-induced obese mice", Diabetologia, vol. 54(9), pp. 2381-2391 (2011).
Ling, et al., "Small-molecule glucagon receptor antagonists", Drugs of the Future, vol. 27(10), pp. 987-993 (2002).
Guillon, et al., "Synthesis of new pyrrolo[1,2-a]quinoxalines: potential non-peptide glucagon receptor antagonists", European Journal of Medicinal Chemistry, vol. 33(4), pp. 293-308 (1998).
Dallas-Yang, et al., Hepatic glucagon receptor binding and glucose-lowering in vivo by peptidyl and non-peptidyl glucagon receptor antagonists. European Journal of Pharmacology, vol. 501(1-3), pp. 225-234 (2004).
Yang, et al., "Cloning and expression of canine glucagon receptor and its use to evaluate glucagon receptor antagonists in vitro and in vivo", European Journal of Pharmacology, vol. 555(1), pp. 8-16 (2007).
Sloop, et al., "Glucagon as a target for the treatment of Type 2 diabetes", Expert Opinion on Therapeutic Targets, vol. 9(3), pp. 593-600 (2005).
Ling, et al., "Approaches to glucagon receptor antagonists", Expert Opinion on Therapeutic Patents, vol. 13(1), pp. 15-22 (2003).
Kurukulasuriya, et al., "Progress towards glucagon receptor antagonist therapy for Type 2 diabetes", Expert Opinion on Therapeutic Patents, vol. 15(12), pp. 1739-1749 (2005).
Shen, et al., "A survey of small molecule glucagon receptor antagonists from recent patents (2006-2010)", Expert Opinion on Therapeutic Patents, vol. 21(8), pp. 1211-1240 (2011).
Cascieri, et al., "Characterization of a novel, non-peptidyl antagonist of the human glucagon receptor", Journal of Biological Chemistry, vol. 274(13), pp. 8694-8697 (1999).
Johansen, et al., "Labelling of a potent glucagon receptor antagonist with tritium, carbon-14 and stable isotopes", Journal of Labelled Compounds and Radiopharmaceuticals, vol. 50(5-6), pp. 466-467 (2007).
Madsen, et al., "Discovery and Structure-Activity Relationship of the First Non-Peptide Competitive Human Glucagon Receptor Antagonists", Journal of Medicinal Chemistry, vol. 41(26), pp. 5150-5157 (1998).
Ling, et al., Identification of Alkylidene Hydrazides as Glucagon Receptor Antagonists, Journal of Medicinal Chemistry, vol. 44(19), pp. 3141-3149 (2001).
Madsen, et al., "Optimization of Alkylidene Hydrazide Based Human Glucagon Receptor Antagonists. Discovery of the Highly Potent and Orally Available 3-Cyano-4-hydroxybenzoic Acid [1-(2,3,5,6-Tetramethylbenzyl)-1H-indol-4-ylmethylene]hydrazide. Journal of Medicinal Chemistry", vol. 45(26), pp. 5755-5775 (2002).
Lau, et al., "New b-alanine derivatives are orally available glucagon receptor antagonists", Journal of Medicinal Chemistry, vol. 50(1), pp. 113-128 (2007).
Kodra, et al., "Novel Glucagon Receptor Antagonists with Improved Selectivity over the Glucose-Dependent Insulinotropic Polypeptide Receptor", Journal of Medicinal Chemistry, vol. 51(17), pp. 5387-5396 (2008).
Madsen, et al., "Human Glucagon Receptor Antagonists with Thiazole Cores. A Novel Series with Superior Pharmacokinetic Properties", Journal of Medicinal Chemistry, vol. 52(9), pp. 2989-3000 (2009).
Rivera, et al., "A novel glucagon receptor antagonist, NNC 25-0926, blunts hepatic glucose production in the conscious dog", Journal of Pharmacology and Experimental Therapeutics, vol. 321(2), pp. 743-752 (2007).
Chen, et al., "Insight into the bioactivity and metabolism of human glucagon receptor antagonists from 3D-QSAR analyses", QSAR & Combinatorial Science, vol. 23(8), pp. 603-620 (2004).
Ladouceur, et al., "4-Phenylpyridine glucagon receptor antagonists: synthetic approaches to the sterically hindered chiral hydroxy group", Tetrahedron Letters, vol. 43(25), pp. 4455-4458 (2002).
Filipski, et al., "A novel series of glucagon receptor antagonists with reduced molecular weight and lipophilicity", Bioorganic & Medicinal Chemistry Letters, vol. 22(1), pp. 415-420 (2012).
Sinz, et al., "Discovery of cyclic guanidines as potent, orally active, human glucagon receptor antagonists", Bioorganic & Medicinal Chemistry Letters, vol. 21(23), pp. 7131-7136 (2011).
Sinz, et al., "Discovery of N-Aryl-2-acylindole human glucagon receptor antagonists", Bioorganic & Medicinal Chemistry Letters, vol. 21(23), pp. 7124-7130 (2011).
Shen, et al., "Discovery of novel, potent, selective, and orally active human glucagon receptor antagonists containing a pyrazole core", Bioorganic & Medicinal Chemistry Letters, vol. 21(1), pp. 76-81 (2011).
Kim, et al., "Discovery of potent, orally active benzimidazole glucagon receptor antagonists", Bioorganic & Medicinal Chemistry Letters, vol. 18(13), pp. 3701-3705 (2008).
DeMong, et al., "Glucagon receptor antagonists for type II diabetes", Annual Reports in Medicinal Chemistry, vol. 43, pp. 119-137 (2008).
Liang, et al., "Design and synthesis of conformationally constrained tri-substituted ureas as potent antagonists of the human glucagon receptor", Bioorganic & Medicinal Chemistry Letters, vol. 17(3), pp. 587-592 (2007).
Karthikeyan, et al., "Quantitative structure activity relationships of some selective inhibitors of glucagon receptor: a Hansch approach", Asian Journal of Biochemistry, vol. 1(4), pp. 307-315 (2006).
Cohen, et al., "Direct observation (NMR) of the efficacy of glucagon receptor antagonists in murine liver expressing the human glucagon receptor", Bioorganic & Medicinal Chemistry, vol. 14(5), pp. 1506-1517 (2006).
Shen, et al., "Discovery of novel, potent, and orally active spiro-urea human glucagon receptor antagonists", Bioorganic & Medicinal Chemistry Letters, vol. 15(20), pp. 4564-4569 (2005).
Duffy, et al., "Discovery and investigation of a novel class of thiophene-derived antagonists of the human glucagon receptor", Bioorganic & Medicinal Chemistry Letters, vol. 15(5), pp. 1401-1405 (2005).
Kurukulasuriya, et al., "Biaryl amide glucagon receptor antagonists", Bioorganic & Medicinal Chemistry Letters, vol. 14(9), pp. 2047-2050 (2004).
Smith, et al., "Optimization of the 4-aryl group of 4-aryl-pyridine glucagon antagonists: development of an efficient, alternative synthesis", Bioorganic & Medicinal Chemistry Letters, vol. 12(9), pp. 1303-1306 (2002).
Ling, et al., "Human glucagon receptor antagonists based on alkylidene hydrazides", Bioorganic & Medicinal Chemistry Letters, vol. 12(4), pp. 663-666 (2002).
Ladouceur, et al., "Integration of optimized substituent patterns to produce highly potent 4-aryl-pyridine glucagon receptor antagonists", Bioorganic & Medicinal Chemistry Letters, vol. 12(23), pp. 3421-3424 (2002).
Ladouceur, et al., "Discovery of 5-Hydroxyalkyl-4-phenylpyridines as a New Class of Glucagon Receptor Antagonists", Bioorganic & Medicinal Chemistry Letters, vol. 12(3), pp. 461-464 (2002).
Chang, et al., "Substituted Imidazoles as Glucagon Receptor Antagonists", Bioorganic & Medicinal Chemistry Letters, vol. 11(18), pp. 2549-2553 (2001).
deLaszlo, et al., "Potent, orally absorbed glucagon receptor antagonists", Bioorganic & Medicinal Chemistry Letters, vol. 9(5), pp. 641-646 (1999).
Kodra, et al., "Nonpeptide orally bioavailable glucagon receptor antagonists", Abstracts of Papers, 237th ACS National Meeting, Salt Lake City, UT, United States, Mar. 22-26, 2009, MEDI-166.

(56) References Cited

OTHER PUBLICATIONS

Dai, et al., "Discovery of a highly potent and selective imidazolone-based glucagon receptor antagonist", Abstracts of Papers, 241st ACS National Meeting & Exposition, Anaheim, CA, United States, Mar. 27-31, 2011, MEDI-22.

Parmee, "Discovery of MK-0893: A glucagon receptor antagonist for the treatment of type II diabetes", Abstracts of Papers, 241st ACS National Meeting & Exposition, Anaheim, CA, United States, Mar. 27-31, 2011, MEDI-31.

Handlon, et al., Glucagon receptor antagonists for the treatment of type 2 diabetes. Abstracts of Papers, 226th ACS National Meeting, New York, NY, United States, Sep. 7-11, 2003, MEDI-164.

Marsham, et al., "Qunazoline antifolate thymidylate synthase inhibitors: bridge modifications and conformationally restricted analogs in the C2-methyl series", Journal of Medicinal Chemistry, vol. 34(7), pp. 2209-2218 (1991).

JPET Fast Forward, Published on Feb. 16, 2007 as DOI:10.1124/JPET.106.115717, "A novel glucagon receptor antagonist, NNC25,0926, blunts hepatic glucose production in the conscious dog".

Business Wire, Sep. 17, 2007, "Metabasis Therapeutics Presents Promising Preclinical Results with Its Novel Glucagon Antagonist for the Treatment of Type 2 Diabetes", http://findarticles.com/p/articles/mi_m0EIN/is_2007_Sept_17/ai_n19522058/, downloaded Oct. 19, 2010.

\* cited by examiner

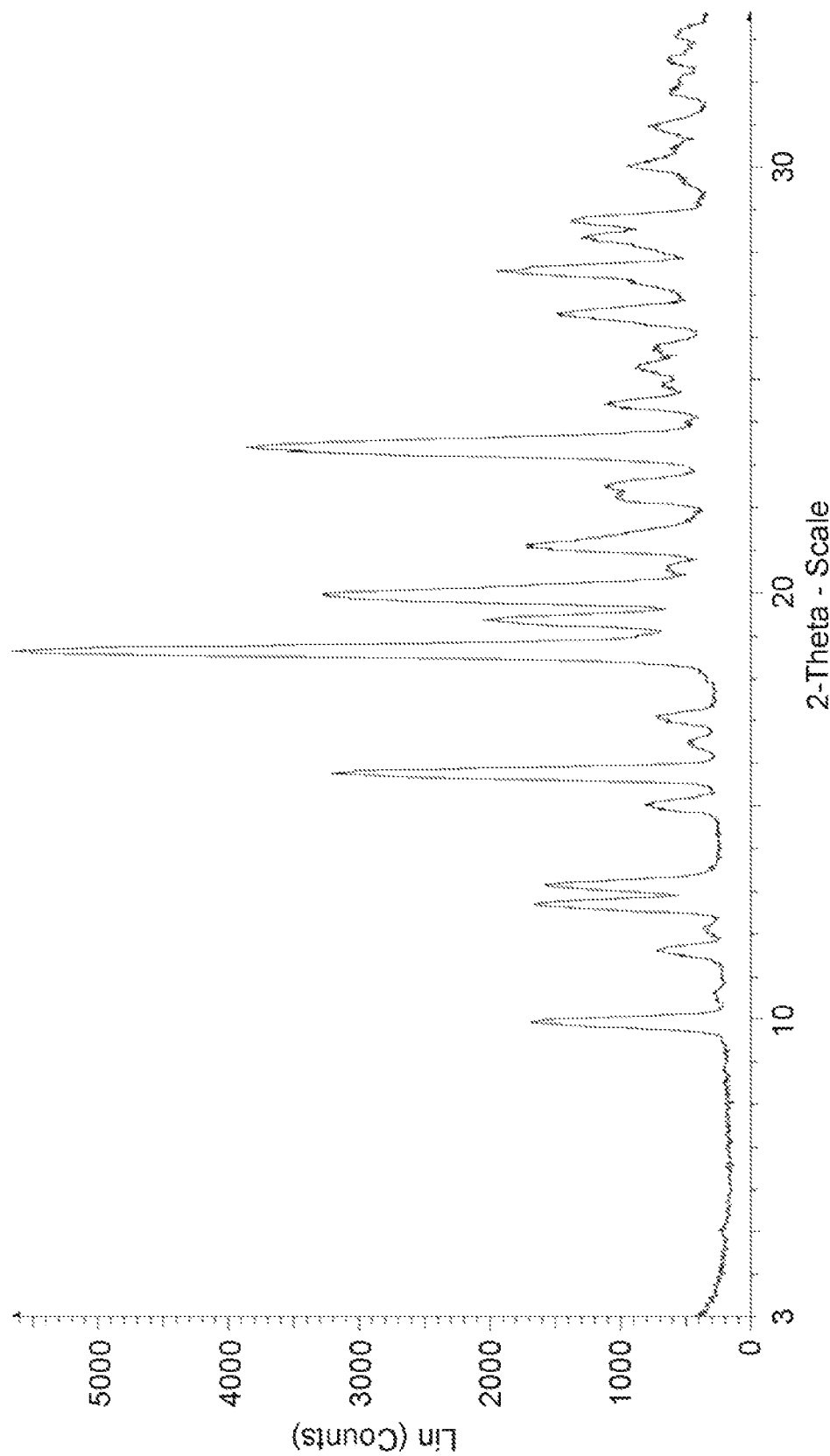

GLUCAGON RECEPTOR MODULATORS

This application is a continuation of U.S. application Ser. No. 13/367,459 filed Feb. 7, 2012, which claims the benefit of priority from U.S. Provisional Application No. 61/440,578, filed Feb. 8, 2011, U.S. Provisional Application No. 61/441,044, filed Feb. 9, 2011, and U.S. Provisional Application No. 61/585,834, filed Jan. 12, 2012, each application is hereby incorporated by reference.

FIELD OF THE INVENTION

The present invention relates to compounds that are antagonists, mixed agonists/antagonists, partial agonists, negative allosteric modulators or inverse agonists of the glucagon receptor, pharmaceutical compositions comprising the compounds, and the uses of the compounds or compositions.

BACKGROUND

Diabetes is a major public health concern because of its increasing prevalence and associated health risks. The disease is characterized by metabolic defects in the production and utilization of carbohydrates which result in the failure to maintain appropriate blood glucose levels. Two major forms of diabetes are recognized. Type I diabetes, or insulin-dependent diabetes mellitus (IDDMT1DM), is the result of an absolute deficiency of insulin. Type II diabetes, or non-insulin dependent diabetes mellitus (NIDDMT2DM), often occurs with normal, or even elevated levels of insulin and appears to be the result of the inability of tissues and cells to respond appropriately to insulin. Aggressive control of NIDDM T2DM with medication is essential; otherwise it can progress into β-cell failure and insulin dependence.

Glucagon is a twenty nine amino acid peptide which is secreted from the α cells of the pancreas into the hepatic portal vein thereby exposing the liver to higher levels of this hormone than non-hepatic tissues. Plasma glucagon levels decrease in response to hyperglycemia, hyperinsulinemia, elevated plasma non-esterified fatty acid levels and somatostatin whereas glucagon secretion is increased in response to hypoglycemia and elevated plasma amino acid levels. Glucagon, through activation of its receptor, is a potent activator of hepatic glucose production by activating glycogenolysis and gluconeogenesis.

The glucagon receptor is a 62 kDa protein that is activated by glucagon and is a member of the class B G-protein coupled family of receptors. Other closely related G-protein coupled receptors include glucagon-like peptide-1 receptor (GLP-1), glucagon-like peptide-2 receptor (GLP-2) and gastric inhibitory polypeptide receptor. The glucagon receptor is encoded by the GCGR gene in humans and these receptors are mainly expressed in the liver with lesser amounts found in the kidney, heart, adipose tissue, spleen, thymus, adrenal glands, pancreas, cerebral cortex and gastrointestinal tract. Stimulation of the glucagon receptor results in activation of adenylate cycase and increased levels of intracellular cAMP.

Reports have indicated that an uncommon missense mutation in the GCGR gene is correlated with diabetes mellitus type 2 and one reported inactivating mutation of the glucagon receptor in humans causes resistance to glucagon and is associated with pancreatic α-cell hyperplasia, nesidioblastosis, hyperglucagonemia and pancreatic neuroendocrine tumors. In rodent studies with GCGR knockout mice and mice treated with GCGR antisense oligonucleotides the mice exhibited improved fasting glucose, glucose tolerance and pancreatic β-cell function. In both healthy control animals and animal models of type 1 and type 2 diabetes, removal of circulating glucagon with selective and specific antibodies has resulted in a reduction of the glycemic level. More specifically, treatment of both mice and cynomolgus monkeys with GCGR-antagonizing antibodies (mAb B and mAb Ac) has been shown to improve glycemic control without causing hypoglycemia. Recent mice studies have further shown that antagonism of the glucagon receptor results in improved glucose homeostasis through a mechanism which requires a functional GLP-1 receptor. Antagonism of the glucagon receptor resulted in compensatory overproduction of GLP-1, likely from the pancreatic α-cells, and this may play an important role in intraislet regulation and maintenance of β-cell function.

A promising area of diabetes research involves the use of small molecule antagonists, mixed agonists/antagonists, partial agonists, negative allosteric modulators or inverse agonists of the glucagon receptor to lower the level of circulating glucagon and thereby lower the glycemic level. Therapeutically, it is anticipated that inactivation of the glucagon receptor would be an effective strategy for lowering blood glucose by reducing hepatic glucose output and normalizing glucose stimulated insulin secretion. Consequently, a glucagon antagonist, mixed agonist/antagonist, partial agonist, negative allosteric modulator or inverse agonist may provide therapeutic treatment for NIDDM T2DM and associated complications, inter alia, hyperglycemia, dyslipidemia, insulin resistance syndrome, hyperinsulinemia, hypertension, and obesity.

Several drugs in five major categories, each acting by different mechanisms, are available for treating hyperglycemia and subsequently, NIDDM T2DM (Moller, D. E., "New drug targets for Type 2 diabetes and the metabolic syndrome" Nature 414; 821-827, (2001)): (A) Insulin secretogogues, including sulphonyl-ureas (e.g., glipizide, glimepiride, glyburide) and meglitinides (e.g., nateglidine and repaglinide) enhance secretion of insulin by acting on the pancreatic beta-cells. While this therapy can decrease blood glucose level, it has limited efficacy and tolerability, causes weight gain and often induces hypoglycemia. (B) Biguanides (e.g., metformin) are thought to act primarily by decreasing hepatic glucose production. Biguanides often cause gastrointestinal disturbances and lactic acidosis, further limiting their use. (C) Inhibitors of alpha-glucosidase (e.g., acarbose) decrease intestinal glucose absorption. These agents often cause gastrointestinal disturbances. (D) Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia. (E) Insulin is used in more severe cases, either alone or in combination with the above agents.

Ideally, an effective new treatment for NIDDM T2DM would meet the following criteria: (a) it would not have significant side effects including induction of hypoglycemia; (b) it would not cause weight gain; (c) it would at least partially replace insulin by acting via mechanism(s) that are independent from the actions of insulin; (d) it would desirably be metabolically stable to allow less frequent usage; and (e) it would be usable in combination with tolerable amounts of any of the categories of drugs listed herein.

A number of publications have appeared which disclose non-peptide compounds which act at the glucagon receptor. For example, WO 03/048109, WO 2004/002480, WO 2005/123668, WO 2005/118542, WO 2006/086488, WO 2006/102067, WO 2007/106181, WO 2007/114855, WO 2007/

120270, WO 2007/123581 and Kurukulasuriya et al. *Bioorganic & Medicinal Chemistry Letters*, 2004, 14(9), 2047-2050 each disclose non-peptide compounds that act as glucagon receptor antagonists. Although investigations are on-going, there still exists a need for a more effective and safe therapeutic treatment for diabetes, particularly NIDDM.

BRIEF DESCRIPTION OF THE DRAWINGS

FIG. 1 provides the powder X-ray diffraction for the exemplified compound as noted.

SUMMARY OF THE INVENTION

The present invention provides compounds of Formula I that act as glucagon receptor modulators, in particular, glucagon antagonists; therefore, may be used in the treatment of diseases mediated by such antagonism (e.g., diseases related to Type 2 diabetes, and diabetes-related and obesity-related co-morbidities). A first embodiment of the present invention are compounds of Formula I

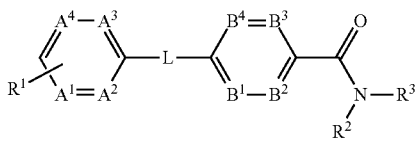

I or a pharmaceutically acceptable salt thereof, wherein $R^1$ is a 5 membered heteroaryl group attached through either a carbon or nitrogen atom and which is optionally fused to a $(C_4-C_7)$cycloalkyl, phenyl or 6 membered heteroaryl; wherein the optionally fused 5 membered heteroaryl is optionally substituted with one to four substituents each independently selected from halo, —S(O)$_2$(C$_1$-C$_3$)alkyl, —S—(C$_1$-C$_3$)alkyl, hydroxy, —C(O)NR$^a$R$^b$, (C$_3$-C$_5$)cycloalkyl, cyano, phenyl which is optionally substituted with one to three halo, cyano, (C$_1$-C$_3$)alkyl or (C$_1$-C$_3$)alkoxy, 6 membered heteroaryl which is optionally substituted with one to three halo, cyano, (C$_1$-C$_3$)alkyl or (C$_1$-C$_3$)alkoxy, (C$_1$-C$_6$)alkyl optionally substituted with one to three fluoro, or (C$_1$-C$_6$)alkoxy optionally substituted with one to three fluoro; R$^a$ and R$^b$ are each independently H or (C$_1$-C$_3$)alkyl; $R^2$ is H or methyl; $R^3$ is tetrazolyl, —CH$_2$—tetrazolyl, —(CH$_2$)$_2$SO$_3$H or —(CH$_2$)$_2$CO$_2$H, —CH$_2$CHFCO$_2$H or —CH$_2$CHOHCO$_2$H; $A^1$, $A^2$, $A^3$ and $A^4$ are each independently CR$^4$ or N, with the proviso that no more than two of $A^1$, $A^2$, $A^3$ and $A^4$ are N; $R^4$ at each occurrence is independently H, halo, cyano, (C$_1$-C$_3$)alkyl optionally substituted with one to three fluoro, or (C$_1$-C$_3$)alkoxy optionally substituted with one to three fluoro; L is —X—CH(R$^5$)— or —CH(R$^5$)—X—; X is CH$_2$, O or NH; $R^5$ is (C$_1$-C$_6$)alkyl which is optionally substituted with one to three fluoro, hydroxy or methoxy, (C$_3$-C$_7$)cycloakyl which is optionally substituted with one to two (C$_1$-C$_3$)alkyl which are optionally substituted with one to three fluoro and wherein one to two carbons of the (C$_3$-C$_7$)cycloalkyl can be replaced with a NH, N(C$_1$-C$_3$)alkyl, O or S; or (C$_3$-C$_7$)cycloalkyl-(C$_1$-C$_6$)alkyl wherein the (C$_3$-C$_7$)cycloalkyl group of said (C$_3$-C$_7$)cycloakyl-(C$_1$-C$_6$)alkyl is optionally substituted with one to two (C$_1$-C$_3$)alkyl which are optionally substituted with one to three fluoro; $B^1$, $B^2$, $B^3$ and $B^4$ are each independently CR$^6$ or N, with the proviso that no more than two of $B^1$, $B^2$, $B^3$ and $B^4$ are N; and $R^6$ at each occurrence is independently H, halo, (C$_1$-C$_3$)alkyl optionally substituted with one to three fluoro, or (C$_1$-C$_3$)alkoxy optionally substituted with one to three fluoro.

A second embodiment of the present invention is the compound of the first embodiment or a pharmaceutically acceptable salt thereof, wherein $R^1$ is a 5 membered heteroaryl attached through a nitrogen atom to the carbon between $A^1$ and $A^4$ of the ring containing $A^1$, $A^2$, $A^3$ and $A^4$; $R^2$ is hydrogen; and $R^3$ is —(CH$_2$)$_2$CO$_2$H.

A third embodiment of the present invention is the compound of the first or second embodiments or a pharmaceutically acceptable salt thereof, wherein X is O. A fourth embodiment of the present invention is the compound of the first or second embodiments or a pharmaceutically acceptable salt thereof, wherein X is NH. A fifth embodiment of the present invention is the compound of the first or second embodiments or a pharmaceutically acceptable salt thereof, wherein X is CH$_2$.

A sixth embodiment of the present invention is the compound of the third or fourth embodiments or a pharmaceutically acceptable salt thereof wherein $R^2$ is hydrogen; $R^3$ is —(CH$_2$)$_2$CO$_2$H; L is —X—CH(R$^5$)—; $A^1$, $A^2$, $A^3$ and $A^4$ are each independently CR$^4$; or $A^4$ is N and $A^1$, $A^2$ and $A^3$ are each CR$^4$; or $A^1$ and $A^4$ are each N and $A^2$ and $A^3$ are each CR$^4$; or $A^2$ and $A^4$ are each N and $A^1$ and $A^3$ are each CR$^4$; $R^4$ at each occurrence is independently H or methyl; $B^1$, $B^2$, $B^3$ and $B^4$ are each CR$^6$; or $B^1$ is N and $B^2$, $B^3$ and $B^4$ are each CR$^6$; or $B^2$ and $B^3$ are each N and $B^1$ and $B^4$ are each CR$^6$; or $B^1$ and $B^4$ are each N and $B^2$ and $B^3$ are each CR$^6$; and $R^6$ at each occurrence is H.

A seventh embodiment of the present invention is the compound of the third embodiment or a pharmaceutically acceptable salt thereof wherein $R^2$ is hydrogen; $R^3$ is —(CH$_2$)$_2$CO$_2$H; L is —X—CH(R$^5$)—; $A^1$, $A^2$, $A^3$ and $A^4$ are each CR$^4$; or $A^4$ is N and $A^1$, $A^2$ and $A^3$ are each CR$^4$; or $A^1$ and $A^4$ are each N and $A^2$ and $A^3$ are each CR$^4$; or $A^2$ and $A^4$ are each N and $A^1$ and $A^3$ are each CR$^4$; $R^4$ at each occurrence is independently H or methyl; $B^1$, $B^2$, $B^3$ and $B^4$ are each CR$^6$; and $R^6$ at each occurrence is independently H or methyl.

An eighth embodiment of the present invention is the compound of the fourth embodiment or a pharmaceutically acceptable salt thereof wherein $R^2$ is hydrogen; $R^3$ is —(CH$_2$)CO$_2$H; L is —CH(R$^5$)—X—; $A^4$ is N and $A^1$, $A^2$ and $A^3$ are each CR$^4$; or $A^1$ and $A^4$ are each N and $A^2$ and $A^3$ are each CR$^4$; or $A^2$ and $A^4$ are each N and $A^1$ and $A^3$ are each CR$^4$; $R^4$ at each occurrence is independently H or methyl; $B^1$, $B^2$, $B^3$ and $B^4$ are each CR$^6$; and $R^6$ at each occurrence is independently H or methyl.

A ninth embodiment of the present invention is the compound of the fourth embodiment or a pharmaceutically acceptable salt thereof wherein $R^2$ is hydrogen; $R^3$ is —(CH$_2$)$_2$CO$_2$H; L is —CH(R$^5$)—X—; $A^1$, $A^2$, $A^3$ and $A^4$ are each independently CR$^4$; $R^4$ at each occurrence is independently H or methyl; one of $B^1$, $B^2$, $B^3$ and $B^4$ is N and the others are each CR$^6$; and $R^6$ at each occurrence is independently H or methyl.

A tenth embodiment of the present invention is the compound of the sixth through ninth embodiments or a pharmaceutically acceptable salt thereof wherein $R^5$ is ethyl, propyl, isopropyl, isobutyl, neopentyl, cyclopropyl, cyclobutyl, dimethylcyclobutyl, cyclopentyl or cyclopropylmethyl.

An eleventh embodiment of the present invention is the compound of the tenth embodiment or a pharmaceutically acceptable salt thereof wherein $R^1$ is imidazolyl, pyrazolyl, triazolyl or indazolyl optionally substituted with one to two substituents each independently selected from methyl, trifluoromethyl, ethyl, propyl, isopropyl, butyl, t-butyl, methoxy, ethoxy, cyano, chloro or fluoro.

A twelfth embodiment of the present invention is the compound of the first embodiment or a pharmaceutically acceptable salt thereof wherein $R^1$ is imidazolyl, pyrazolyl, triazolyl or indazolyl optionally substituted with one to two substituents each independently selected from methyl, trifluoromethyl, ethyl, propyl, isopropyl, butyl, t-butyl, methoxy, ethoxy, cyano, chloro or fluoro; L is —X—CHR$^5$—; X is O; and $R^5$ is ethyl, propyl, isopropyl, isobutyl, neopentyl, cyclopropyl, cyclobutyl, dimethylcyclobutyl, cyclopentyl or cyclopropylmethyl.

A thirteenth embodiment of the present invention is the compound of the first embodiment or a pharmaceutically acceptable salt thereof wherein $R^1$ is imidazolyl, pyrazolyl, triazolyl or indazolyl optionally substituted with one to two substituents each independently selected from methyl, trifluoromethyl, ethyl, propyl, isopropyl, butyl, t-butyl, methoxy, ethoxy, cyano, chloro or fluoro; L is —CHR$^5$—X—; X is NH; and $R^5$ is ethyl, propyl, isopropyl, isobutyl, neopentyl, cyclopropyl, cyclobutyl, dimethylcyclobutyl, cyclopentyl or cyclopropylmethyl.

A fourteenth embodiment of the present invention is the compound of the twelfth or thirteenth embodiments or a pharmaceutically acceptable salt thereof wherein $R^1$ is 4-trifluoromethylpyrazol-1-yl or 4-trifluoromethylimidazol-1-yl.

A fifteenth embodiment of the present invention is a compound selected from the group consisting of:
(+/−)-3-(4-(1-(3-methyl-4-(4-(trifluoromethyl)-1H-imidazol-1-yl)phenylamino)butyl)benzamido)propanoic acid; (+/−)-3-(4-(3-methyl-1-(4-(4-(trifluoromethyl)-1H-imidazol-1-yl)phenyl)butoxy)benzamido)propanoic acid; (+/−)-3-(6-(1-(4-(4-(trifluoromethyl)-1H-pyrazol-1-yl)phenoxy)butyl)nicotinamido)propanoic acid; (+/−)-3-(4-(4-methyl-1-(4-(4-(trifluoromethyl)-1H-pyrazol-1-yl)phenyl)pentan-2-yl)benzamido)propanoic acid; (+/−)-3-(4-(1-(6-(4-(trifluoromethyl)-1H-pyrazol-1-yl)pyridine-3-ylamino)butyl)benzamido)propanoic acid; (R)-3-(4-(1-(6-(4-(trifluoromethyl)-1H-pyrazol-1-yl)pyridine-3-ylamino)butyl)benzamido)propenoic acid; (S)-3-(4-(1-(6-(4-(trifluoromethyl)-1H-pyrazol-1-yl)pyridine-3-ylamino)butyl)benzamido)propanoic acid; (+/−)-3-(4-(cyclopentyl(6-(4-(trifluoromethyl)-1H-imidazol-1-yl)pyridine-3-ylamino)methyl)benzamido)propanoic acid; (+/−)-3-(4-(1-(6-(4-(trifluoromethyl)-1 imidazol-1-yl)yridine-3-ylamino)butyl)benzamido)propanoic acid; (R)-3-(4-(1-(6-(4-(trifluoromethyl)-1H-imidazol-1-yl)pyridine-3-ylamino)butyl)benzamido)propanoic acid; (S)-3-(4-(1-(6-(4-(trifluoromethyl)-1H-imidazol-1-yl)yridine-3-ylamino)butyl)benzamido)propanoic acid; (+/−)-3-(4-(1-(4-(4-(trifluoromethyl)-1H-pyrazol-1-yl)phenylamino)butyl)benzamido)propanoic acid; (+/−)-3-(4-(1-(3,5-dimethyl-4-(4-(trifluoromethyl)-1H-pyrazol-1-yl)phenylamino)butyl)benzamido)propanoic acid; (R)-3-(4-(1-(3,5-dimethyl-4-(4-(trifluoromethyl)-1H-pyrazol-1-yl)phenylamino)butyl)benzamido)propenoic acid; (S)-3-(4-(1-(3,5-dimethyl-4-(4-(trifluoromethyl)-1H-pyrazol-1-yl)phenylamino)butyl)benzamido)propanoic acid; (+/−)-3-(4-(1-(4-(4-(trifluoromethyl)-1H-imidazol-1-yl)phenylamino)butyl)benzamido)propanoic acid; (R)-3-(4-(1-(4-(4-(trifluoromethyl)-1H-imidazol-1-yl)phenylamino)butyl)benzamido)propanoic acid; (S)-3-(4-(1-(4-(4-(trifluoromethyl)-1H-imidazol-1-yl)phenylamino)butyl)benzamido)propanoic acid; (+/−)-3-(4-(1-(4-(4-(trifluoromethyl)-1H-imidazol-1-yl)phenoxy)butyl)benzamido)propanoic acid; (+/−)-3-(4-(1-(4-(4-(methylthio)-1H-pyrazol-1-yl)phenoxy)butyl)benzamido)propanoic acid; (+/−)-3-(4-(1-(4-(3-tert-butyl-1H-pyrazol-1-yl)phenoxy)butyl)benzamido)propanoic acid; (+/−)-3-(4-(1-(4-(4-chloro-3-methyl-1H-pyrazol-1-yl)phenoxy)butyl)benzamido)propanoic acid; (+/−)-3-(4-(1-(4-(4-chloro-1H-pyrazol-1-yl)phenoxy)butyl)benzamido)propanoic acid; (+/−)-3-(4-(1-(4-(4-ethyl-3-methyl-1H-pyrazol-1-yl)phenoxy)butyl)benzamido)propanoic acid; (+/−)-3-(4-(1-(4-(3,5-diethyl-1H-pyrazol-1-yl)phenoxy)butyl)benzamido)propanoic acid; (+/−)-3-(4-(1-(4-(4-methyl-1H-pyrazol-1-yl)phenoxy)butyl)benzamido)propanoic acid; (+/−)-3-(4-(1-(4-(3-isopropyl-1H-pyrazol-1-yl)phenoxy)butyl)benzamido) propanoic acid; (+/−)-3-(4-(1-(4-(4-fluoro-1H-pyrazol-1-yl)phenoxy)butyl)benzamido)propanoic acid; (+/−)-3-(4-(1-(4-(3-methyl-1H-pyrazol-1-yl)phenoxy)butyl)benzamido) propanoic acid; (+/−)-3-(4-(1-(4-(2H-1,2,3-triazol-2-yl)phenoxy)butyl)benzamido)propanoic acid; (+/−)-3-(4-(1-(4-(3-butyl-1H-pyrazol-1-yl)phenoxy)butyl)benzamido) propanoic acid; (+/−)-3-(4-(1-(4-(5-ethoxy-3-methyl-1H-pyrazol-1-yl)phenoxy)butyl)benzamido)propanoic acid; (+/−)-3-(4-(1-(4-(5-methoxy-3-methyl-1H-pyrazol-1-yl)phenoxy)butyl)benzamido)propanoic acid; (+/−)-3-(4-(1-(4-(4-butyl-1H-imidazol-1-yl)phenoxy)butyl)benzamido)propanoic acid; (+/−)-3-(4-(1-(4-(2-cyano-3,4,5-trimethyl-1H-pyrrol-1-yl)phenoxy)butyl)benzamido)propanoic acid; (+/−)-3-(4-(1-(4-(3-cyano-2,4-dimethyl-1H-pyrrol-1-yl)phenoxy)butyl)benzamido)propanoic acid; (+/−)-3-(4-(1-(4-(2-cyano-3-methyl-1H-pyrrol-1-yl)phenoxy)butyl)benzamido) propanoic acid; (+/−)-3-(6-(1-(4-(3-propyl-1H-pyrazol-1-yl)phenoxy)butyl) nicotinamido)propanoic acid; (+/−)-3-(4-(1-(4-(3,4-dimethyl-1H-pyrazol-1-yl)phenoxy)butyl)benzamido)propanoic acid; (+/−)-3-(4-(1-(4-(1H-pyrazol-1-yl)phenoxy)butyl)benzamido)propanoic acid; (+/−)-3-(4-(1-(4-(1H-imidazo[1,2-b]pyrazol-1-yl)phenoxy)butyl)benzamido)propanoic acid; (+/−)-3-(4-(1-(4-(3-ethyl-1H-pyrazol-1-yl)phenoxy)butyl)benzamido)propanoic acid; (+/−)-3-(4-(1-(4-(4-chloro-5-methyl-1H-imidazol-1-yl)phenoxy)butyl)benzamido)propanoic acid; (+/−)-3-(4-(1-(4-(4,5-diethyl-1H-imidazol-1-yl)phenoxy)butyl)benzamido)propanoic acid; (+/−)-3-(4-(1-(4-(3,5-dimethyl-1H-pyrazol-1-yl)phenoxy)butyl)benzamido) propanoic acid; (+/−)-3-(4-(1-(4-(3-methyl-1H-1,2,4-triazol-1-yl)phenoxy)butyl) benzamido)propanoic acid; (+/−)-3-(4-(1-(4-(1H-1,2,4-triazol-1-yl)phenoxy)butyl)benzamido)propanoic acid; (+/−)-3-(4-(1-(4-(2-butyl-1H-imidazol-1-yl)phenoxy)butyl)benzamido)propanoic acid; (+/−)-3-(4-(1-(4-(4,5-dimethyl-1H-imidazol-1-yl)phenoxy)butyl)benzamido)propanoic acid; (+/−)-3-(4-(1-(4-(1-propyl-1H-pyrazol-4-yl)phenoxy)butyl)benzamido)propanoic acid; (+/−)-3-(4-(1-(4-(1H-pyrazol-3-yl)phenoxy)butyl)benzamido)propanoic acid; (+/−)-3-(4-(1-(4-(3,5-dimethylisoxazol-4-yl)phenoxy)butyl)benzamido)propanoic acid; (+/−)-3-(4-(1-(4-(1-ethyl-3-(trifluoromethyl)-1H-pyrazol-5-yl)phenoxy)butyl)benzamido) propanoic acid; (+/−)-3-(4-(1-(4-(1-methyl-1H-pyrazol-4-yl)phenoxy)butyl)benzamido)propanoic acid; (+/−)-3-(4-(1-(4-(1,5-dimethyl-1H-pyrazol-4-yl)phenoxy)butyl) benzamido)propanoic acid; (+/−)-3-(4-(1-(4-(1H-pyrazol-4-yl)phenoxy)butyl)benzamido)propanoic acid; (+/−)-3-(4-(1-(4-(1-methyl-1H-pyrazol-5-yl)phenoxy)butyl)benzamido) propanoic acid; (+/−)-3-(4-(1-(4-(1,3,5-methyl-1H-pyrazol-4-yl)phenoxy)butyl)benzamido)propanoic acid; (+/−)-3-(4-(1-(4-(4-(trifluoromethyl)-1H-pyrazol-1-yl)phenoxy)butyl) benzamido)propanoic acid; (R)-3-(4-(1-(4-(4-(trifluoromethyl)-1H-pyrazol-1-yl)phenoxy)butyl) benzamido)propanoic acid; (S)-3-(4-(1-(4-(4-(trifluoromethyl)-1H-pyrazol-1-yl)phenoxy)butyl) benzamido)propanoic acid; (+/−)-3-(4-(1-(6-(4-phenyl-1H-pyrazol-1-yl)pyridine-3-ylamino)butyl)benzamido) propanoic acid; (+/−)-3-(4-(1-(4-(4-fluoro-1H-pyrazol-1-yl)phenylamino)butyl)benzamido)propanoic acid; (+/−)-3-(6-

(3-methyl-1-(4-(4-(trifluoromethyl)-1H-pyrazol-1-yl)phenyl)butylamino)nicotinamido)propanoic acid; (+/−)-3-(4-(2-cyclopropyl-1-(4-(4-(trifluoromethyl)-1H-pyrazol-1-yl)phenoxy)ethyl)benzamido)propanoic acid; (+/−)-3-(4-(cyclopentyl(4-(4-(trifluoromethyl)-1H-pyrazol-1-yl)phenoxy)methyl)benzamido)propanoic acid; (R)-3-(4-(cyclopentyl(4-(4-(trifluoromethyl)-1H-pyrazol-1-yl)phenoxy)methyl)benzamido) propanoic acid; (S)-3-(4-(cyclopentyl(4-(4-(trifluromethyl)-1H-pyrazol-1-yl)phenoxy)methyl)benzamido)propanoic acid; (+/−)-3-(4-(cyclobutyl(4-(4-(trifluoromethyl)-1H-pyrazol-1-yl)phenoxy)methyl)benzamido)propanoic acid; (+/−)-3-(4-(1-(4-(3-(trifluoromethyl)-1H-pyrazol-1-yl)phenoxy)butyl)benzamido)propanoic acid; (+/−)-3-(4-(3,3-dimethyl-1-(4-(4-(trifluoromethyl)-1H-pyrazol-1-yl)phenoxy)butyl)benzamido)propanoic acid; (+/−)-3-(4-(1-(4-(4-methyl-3-(trifluoromethyl)-1H-pyrazol-1-yl)phenoxy)butyl)benzamido)propanoic acid; (+/−)-3-(4-(1-(4-(3-(trifluoromethyl)-1H-1,2,4-triazol-1-yl)phenoxy)butyl)benzamido)propanoic acid; (+/−)-3-(4-(1-(4-(3-methyl-(trifluoromethyl)-1H-pyrazol-1-yl)phenoxy)butyl)benzamido)propanoic acid; (+/−)-3-(4-(1-(4-(2-methyl-4-(trifluoromethyl)-imidazol-1-yl)phenoxy)butyl)benzamido)propanoic acid; (+/−)-3-(4-(cyclopropyl(4-(4-(trifluoromethyl)-1H-pyrazol-1-yl)phenoxy)methyl)benzamido)propenoic acid; (+/−)-3-(4-(2-methyl-1-(4-(4-(trifluoromethyl)-1H-pyrazol-1-yl)phenoxy)propyl)benzamido)propanoic acid; (+/−)-3-(4-(1-(4-(4-(trifluoromethyl)-1H-pyrazol-1-yl)phenoxy)propyl)benzamido)propanoic acid; (+/−)-3-(4-(3-methyl-1-(4-(4-(trifluoromethyl)-1H-imidazol-1-yl)phenyl)butoxy)benzamido)propanoic acid; (+/−)-3-(4-(3-methyl-1-(4-(4-(trifluoromethyl)-1H-pyrazol-1-yl)phenoxy)butyl)benzamido)propanoic acid; (+/−)-3-(4-(1-(3,5-dimethyl-4-(4-(trifluoromethyl)-1H-pyrazol-1-yl)phenoxy)butyl)benzamido)propanoic acid; (S)-3-(4-(1-(3,5-dimethyl-4-(4-(trifluoromethyl)-1H-pyrazol-1-yl)phenoxy)butyl)benzamido)propanoic acid; (R)-3-(4-(1-(3,5-dimethyl-4-(4-(trifluoromethyl)-1H-pyrazol-1-yl)phenoxy)butyl)benzamido)propanoic acid; (+/−)-3-(4-(1-(5-(4-(trifluoromethyl)-1H-pyrazol-1-yl)pyridine-2-yloxy)butyl)benzamido)propanoic acid; (+/−)-3-(4-(1-(6-(4-(trifluoromethyl)-1H-pyrazol-1-yl)pyridine-3-yloxy)butyl)benzamido)propanoic acid; (+/−)-3-(4-(1-(6-(4-(trifluoromethyl)-1H-imidazol-1-yl)pyridine-3-yloxy)butyl)benzamido)propanoic acid; (+/−)-3-(4-(1-(4-(4-cyano-1H-pyrazol-1-yl)phenoxy)butyl)benzamido)propanoic acid; (+/−)-3-(4-(1-(4-(4,5,6,7-tetrahydro-2H-indazol-2-yl)phenoxy)butyl)benzamido)propanoic acid; (+/−)-3-(4-(1-(4-(5,6-dihydrocyclopenta[c]pyrazol-2(4H)-yl)phenoxy)butyl)benzamido)propanoic acid; (+/−)-3-(4-(1-(4-(2H-indazol-2-yl)phenoxy)butyl)benzamido)propanoic acid; (+/−)-3-(4-(1-(4-(4-methyl-1H-1,2,3-triazol-1-yl)phenylamino)butyl)benzamido)propanoic acid; (+/−)-3-(2-(3-methyl-1-(4-(4-(trifluoromethyl)-1H-pyrazol-1-yl)phenyl)butylamino)pyrimidine-5-carboxamido)propanoic acid; (+/−)-3-(4-(cyclopentyl(6-(4-(trifluoromethyl)-1H-pyrazol-1-yl)pyridine-3-ylamino)methyl)benzamido)propanoic acid; (R)-3-(4-(cyclopentyl(6-(4-(trifluoromethyl)-1H-pyrazol-1-yl)pyridine-3-ylamino)methyl)benzamido)propanoic acid; (S)-3-(4-(cyclopentyl(6-(4-(trifluoromethyl)-1H-pyrazol-1-yl)pyridine-3-ylamino)methyl)benzamido)propanoic acid; (R)-3-(4-(cyclopentyl(6-(4-(trifluoromethyl)-1H-imidazol-1-yl)pyridin-3-ylamino)methyl)benzamido)propanoic acid; (S)-3-(4-(cyclopentyl(6-(4-(trifluoromethyl)-1H-imidazol-1-yl)pyridin-3-ylamino)methyl)benzamido)propanoic acid; (+/−)-3-(2-(cyclohexyl(6-(4-(trifluoromethyl)-1H-imidazol-1-yl)pyridine-3-yl)methylamino)nicotinamido)propanoic acid; (+/−)-3-(4-(3,3-dimethyl-1-(6-(4-(trifluoromethyl)-1H-imidazol-1-yl)pyridine-3-ylamino)butyl)benzamido) propanoic acid; (+/−)-3-(4-(cyclohexyl(6-(4-(trifluoromethyl)-1H-pyrazol-1-yl)pyridine-3-ylamino)methyl) benzamido)propenoic acid; (+/−)-3-(6-(3-methyl-1-(5-methyl-6-(4-(trifluoromethyl)-1H-pyrazol-1-yl)pyridin-3-ylamino)butyl)nicotinamido)propanoic acid; (R)-3-(4-(1-(4-(4-(trifluoromethyl)-1H-pyrazol-1-yl)phenylamino)butyl)benzamido)propanoic acid; and (S)-3-(4-(1-(4-(4-(trifluoromethyl)-1H-pyrazol-1-yl)phenylamino)butyl)benzamido)propanoic acid; or a pharmaceutically acceptable salt thereof.

A sixteenth embodiment of the present invention is a compound selected from the group consisting of: (+/−)-3-(4-(1-(3,5-dimethyl-4-(4-(trifluoromethyl)-1H-pyrazol-1-yl)phenoxy)butyl)benzamido)propanoic acid; (S)-3-(4-(1-(3,5-dimethyl-4-(4-(trifluoromethyl)-1H-pyrazol-1-yl)phenoxy)butyl)benzamido)propanoic acid; (R)-3-(4-(1-(3,5-dimethyl-4-(4-(trifluoromethyl)-1H-pyrazol-1-yl)phenoxy)butyl)benzamido)propanoic acid; (+/−)-3-(4-(cyclopentyl(6-(4-(trifluoromethyl)-1H-imidazol-1-yl)pyridin-3-ylamino)methyl)benzamido)propanoic acid; (R)-3-(4-(cyclopentyl(6-(4-(trifluoromethyl)-1H-imidazol-1-yl)pyridin-3-ylamino)methyl)benzamido)propanoic acid; and (S)-3-(4-(cyclopentyl(6-(4-(trifluoromethyl)-1H-imidazol-1-yl)pyridin-3-ylamino)methyl)benzamido)propanoic acid; or a pharmaceutically acceptable salt thereof.

A seventeenth embodiment of the present invention is the compound (−)-3-(4-(1-(3,5-dimethyl-4-(4-(trifluoromethyl)-1H-pyrazol-1-yl)phenoxy)butyl)benzamido) propanoic acid or a pharmaceutically acceptable salt thereof. An eighteenth embodiment of the present invention is the crystalline form of the compound of the seventeenth embodiment with the powder X-ray diffraction spectrum substantially as shown in FIG. 1.

Preferred $R^1$ groups include optionally substituted pyrazolyl, imidazolyl and indazolyl. Preferred embodiments of the ring containing $A^1$, $A^2$, $A^3$ and $A^4$ include phenyl, methyl substituted phenyl, dimethyl-substituted phenyl, pyridinyl, pyrimidinyl and pyrazinyl. Preferred embodiments of the ring containing $B^1$, $B^2$, $B^3$ and $B^4$ include phenyl, pyridinyl, pyrimidinyl and pyrazinyl. A preferred embodiment of $R^3$ is —$(CH_2)_2CO_2H$.

Another embodiment of the present invention is the compound of formula I according to the first embodiment or a pharmaceutically acceptable salt thereof with the exception that $R^5$ is $(C_3-C_7)$cycloalkyl which can be further substituted with one to three fluoro. Yet another embodiment of the present invention is the compound of formula I according to the first embodiment or a pharmaceutically acceptable salt thereof with the exception that $R^1$ is a 5 membered heteroaryl which can be fused to another 5 membered heteroaryl. Yet another embodiment of the present invention are the compounds as set forth in Examples 105-193.

Another aspect of the present invention is a pharmaceutical composition that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include anti-obesity agents and/or anti-diabetic agents (described herein below).

In yet another aspect of the present invention is a method for treating a disease, condition, or disorder mediated by glucagon, in particular, deactivation of the glucagon receptor, in a mammal that includes the step of administering to a mammal, preferably a human, in need of such treatment a therapeutically effective amount of a compound of the present invention, or a pharmaceutical composition thereof.

Diseases, disorders, or conditions mediated by glucagon include Type II diabetes, hyperglycemia, metabolic syndrome, impaired glucose tolerance, glucosuria, cataracts, diabetic neuropathy, diabetic nephropathy, diabetic retinopathy, obesity, dyslididemia, hypertension, hyperinsulinemia, and insulin resistance syndrome. Preferred diseases, disorders, or conditions include Type II diabetes, hyperglycemia, impaired glucose tolerance, obesity, and insulin resistance syndrome. More preferred are Type II diabetes, hyperglycemia, and obesity. Most preferred is Type II diabetes.

In yet another aspect of the present invention is a method of reducing the level of blood glucose in a mammal, preferably a human, which includes the step of administering to a mammal in need of such treatment a therapeutically effective amount of a compound of the present invention, or a pharmaceutical composition thereof.

Compounds of the present invention may be administered in combination with other pharmaceutical agents (in particular, anti-obesity and anti-diabetic agents described herein below). The combination therapy may be administered as (a) a single pharmaceutical composition which comprises a compound of the present invention, at least one additional pharmaceutical agent described herein and a pharmaceutically acceptable excipient, diluent, or carrier, or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

DEFINITIONS

As used herein, the term "alkyl" refers to a hydrocarbon radical of the general formula $C_nH_{2n+1}$. The alkane radical may be straight or branched. For example, the term "($C_1$-$C_6$) alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, alkylsulfonyl, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls).

The term "cycloalkyl" refers to nonaromatic rings that are fully hydrogenated and may exist as a single ring, bicyclic ring or a spiral ring. Unless specified otherwise, the carbocyclic ring is generally a 3- to 8-membered ring. For example, ($C_3$-$C_7$)cycloalkyl include groups such as cyclopropyl, cyclobutyl, cyclopentyl, cyclohexyl, cyclohexenyl, cycloheptyl, norbornyl (bicyclo[2.2.1]heptyl) and the like. In certain embodiments one or more of the carbon atoms in a cycloalkyl may be replaced with a heteroatom as specified, such as with an O, S, NH or N-alkyl.

The phrase "5 membered heteroaryl" or "6 membered heteroaryl" means a radical of a 5 or 6 membered heteroaromatic ring, respectively. The heteroaromatic ring can contain 1 to 4 heteroatoms selected from N, O and S. 5 to 6 membered heteroaryl groups include pyrrolyl, furanyl, thienyl, imidazolyl, thiazolyl, oxazolyl, triazolyl, tetrazolyl, pyridinyl, pyrimidinyl, pyrazinyl, triazinyl and the like. Preferred 5 to 6 membered heteroaryl groups include pyrazolyl, imidazolyl, pyridinyl, pyrimidinyl or pyrazinyl. The heteroaryl group may be fused to another ring when specified. For example, a 5 membered heteroaryl such as a pyrazole may be fused with a phenyl to provide an indazole.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated" or "modulating", or "modulate(s)", as used herein, unless otherwise indicated, refers to the changes in activity of the glucagon receptor as a result of action of the compounds of the present invention.

The terms "mediated" or "mediating" or "mediate(s)", as used herein, unless otherwise indicated, refers to the treatment or prevention the particular disease, condition, or disorder, (ii) attenuation, amelioration, or elimination of one or more symptoms of the particular disease, condition, or disorder, or (iii) prevention or delay of the onset of one or more symptoms of the particular disease, condition, or disorder described herein, by modulation of glucagon.

The term "compounds of the present invention" (unless specifically identified otherwise) refer to compounds of Formula I and any pharmaceutically acceptable salts of the compounds, as well as, all stereoisomers (including diastereoisomers and enantiomers), tautomers, conformational isomers, and isotopically labeled compounds. Hydrates and solvates of the compounds of the present invention are considered compositions of the present invention, wherein the compound is in association with water or solvent, respectively.

DETAILED DESCRIPTION

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). Similarly, a "hydroxy-protecting group" refers to a substituent of a hydroxy group that blocks or protects the hydroxy functionality. Suitable hydroxyl-protecting groups (O-Pg) include for example, allyl, acetyl, silyl, benzyl, para-methoxybenzyl, trityl, and the like. The need for such protection is readily determined by one skilled in the art. For a general description of protecting groups and their use, see T. W. Greene, *Protective Groups in Organic Synthesis*, John Wiley & Sons, New York, 1991.

Reaction Scheme I outlines the general procedures that can be used to provide compounds of the present invention of Formula I.

Reaction Scheme I

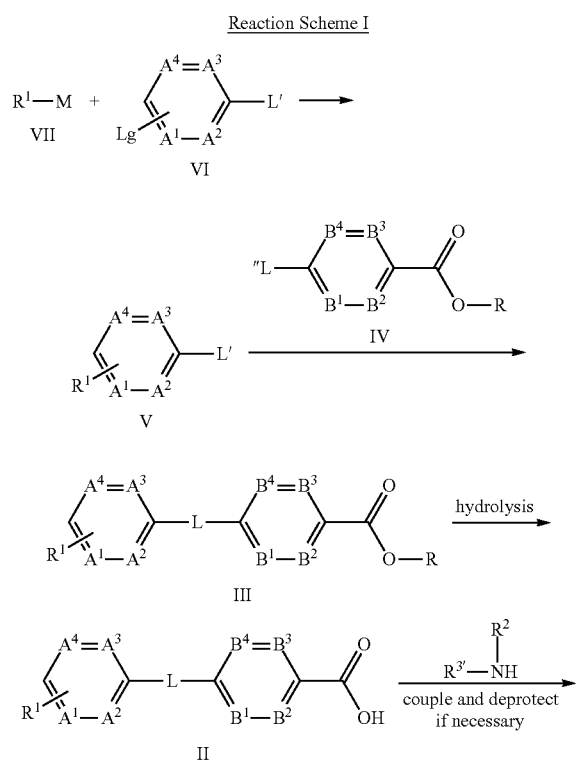

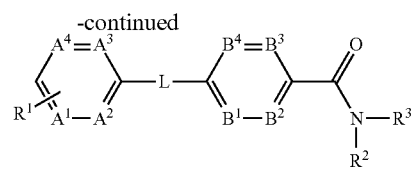

I

Reaction Scheme I provides a general route which can be employed to prepare compounds of Formula I. More specific details of the transformations depicted are provided in Reaction Schemes II-VII below. It is to be understood that the reaction schemes are illustrative and are not to be construed as a limitation in any manner. In step one of Reaction Scheme I the compound $R^1$-M of Formula VII and the compound of Formula VI are coupled. In the compound of Formula VII, $R^1$ is a 5 membered optionally fused and optionally substituted heteroaryl group. The group M can represent either hydrogen when attached to nitrogen in the heteroaryl group $R^1$ or an appropriate metal species when attached to a carbon in the heteroaryl group $R^1$. When M is a metal attached to a carbon in the group $R^1$ the coupling reaction can be carried out using a palladium catalyzed coupling reaction. When M represents hydrogen attached to nitrogen in the heteroaryl $R^1$ group the nucleophilic displacement reaction to form the compound of Formula V can be carried out in an appropriate solvent in the presence of a base. In the compound of Formula VI Lg is an appropriate leaving group, such as a halide or triflate. The compound of Formula V can then be reacted with the compound of Formula IV to provide the compound of Formula III. In the compound of Formula V L' represents a precursor group which is, along with R" in the compound of Formula IV is converted into the linker L in the compound of Formula III. The compound of Formula III can then be hydrolyzed to provide the free acid of Formula II which can then be subjected to an amide coupling reaction with the amine $R^{3'}R^2NH$, followed by deprotection if necessary to provide the compound of Formula I. The group R in the amine $R^{3'}R^2NH$ can represent either $R^3$ itself or a protected version of $R^3$ which can be subsequently deprotected to provide $R^3$.

Reaction Scheme II outlines another general procedure that can be used to provide compounds of the present invention having Formula I.

Reaction Scheme II

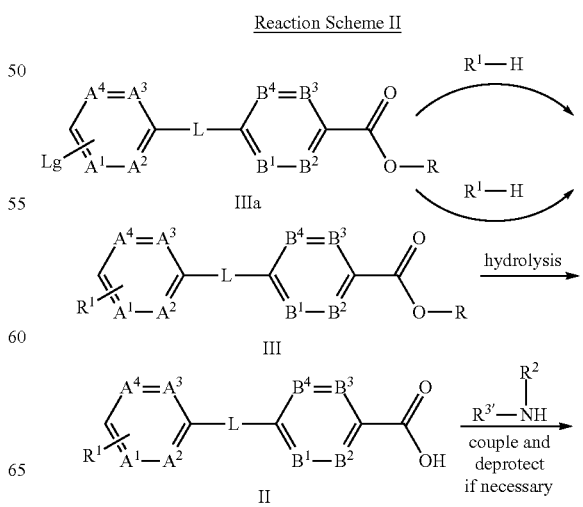

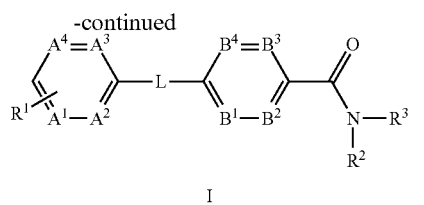

I

The ester compound of Formula III may be formed by reaction of an appropriate heteroaryl compound $R^1$—H or a metallated heteroaryl compound $R^1$-M with the compound of Formula IIIa. The reaction with $R^1$—H can be employed when the hydrogen depicted in $R^1$—H is attached to nitrogen in the $R^1$ heteroaryl group. The reaction can be carried out in an appropriate solvent such as dimethyl sulfoxide and a base such as potassium carbonate in the presence of copper(I) iodide. The reaction between the compound of Formula IIIa and $R^1$-M can be carried out by a palladium catalysed coupling reaction. Preferably, the reaction is carried out between the boronate ester $R^1$-M (where M is $B(OR')_2$ and R' is H or lower alkyl or both R's together form an appropriate cyclic group) and the compound of Formula IIa (wherein Lg is $OSO_2CF_3$, Cl, Br or I) using a suitable palladium catalyst, a suitable phosphine ligand and a suitable base in the presence of a suitable solvent at a temperature of typically from room temperature up to around reflux (or at temperatures above the boiling point of the solvent e.g. 120° C. using microwave conditions).

A suitable palladium catalyst is tris(dibenzylideneacetone)dipalladium, bis (dibenzylideneacetone) palladium, palladium acetate or (1,1'-bis(diphenylphosphino)ferrocene)dichloropalladium. A suitable phosphine ligand is tricyclohexylphosphine, triphenylphosphine or 2-dicyclohexylphosphino-2',6'-dimethoxylbiphenyl. A suitable base is sodium carbonate, potassium carbonate, potassium phosphate or sodium hydrogen carbonate and solvents are DME, 1,4-dioxane or THF/water.

Alternatively, the cross coupling may be carried out between the trimethyl stannane of general Formula $R^1$-M (wherein M is $SnMe_3$) and the compound of Formula IIIa using a suitable catalyst, such as tetrakis(triphenylphosphine)palladium, an optional copper (I) source, such as copper (I) chloride, a suitable base, such as cesium fluoride, and a suitable solvent, such as N,N-dimethylformamide, at a temperature of typically around 80° C. to 120° C. Further alternative methods using metallated compounds $R^1$-M (where M is MgX' or ZnX' and X' is a halide) with the derivative IIIa using a suitable palladium catalyst, a suitable phosphine base, an optional copper (I) source, and a suitable base in the presence of a suitable solvent at a temperature of typically around reflux, can also be employed.

Suitable palladium catalysts are tris(dibenzylideneacetone)dipalladium, bis(dibenzylidene acetone)palladium, palladium acetate or (1,1'-bis(diphenylphosphino)ferrocene)dichloropalladium. Suitable phosphine bases are tricyclohexylphosphphine or 2-dicyclohexylphosphino-2',6'-dimethoxybiphenyl. A suitable copper (I) source is copper (I) chloride. Suitable bases are potassium carbonate or sodium hydrogen carbonate. Suitable solvents are DME, 1,4-dioxane or THF/water.

The compound of Formula III then undergo hydrolysis to provide the compound of Formula II. Depending on which R group is present in the ester of Formula III, appropriate acid or base catalyzed hydrolysis can be carried out to provide the corresponding free acid in the compound of Formula II. For example, when R represents methyl, hydrolysis is typically carried out with aqueous sodium hydroxide or lithium hydroxide in a mixture of methanol and tetrahydrofuran at a temperature from room temperature up to 80° C. for 15 minutes to 24 hours.

Conversion of the compound of Formula II to provide the compound of Formula I can be carried out using standard amide coupling conditions. Amide coupling is carried out using standard literature conditions. The acid of Formula II can be converted to the corresponding acid chloride using a suitable chlorinating agent, such as oxalyl chloride or thionyl chloride, in a suitable solvent, such as dichloromethane or toluene, optionally in the presence of catalytic DMF, at a suitable temperature, typically of between 0° C. and room temperature. The acid chloride can then be reacted with the amine of generic formula $R^{3'}$—$NH_2$ in the presence of a base, such as triethylamine or diisopropylethylamine, in a suitable solvent, such as dichloromethane or toluene, at a temperature of between 0° C. and room temperature. $R^{3'}$ can represent either $R^3$ itself or a protected version of $R^3$ which can be subsequently deprotected to provide R. Alternatively, the acid of Formula II can be converted to a suitable activated species with a coupling agent, such as EDCl.HCl, HBTU, HATU, PyBop, DCC, or CDI, in a suitable solvent, such as dichloromethane, acetonitrile or DMF. In the presence of EDCl.HCl, HOBT is typically added. EDCl is 1-ethyl-3-(3-dimethylaminopropyl)carbodiimide; HBTU is O-Benzotriazole-N,N,N',N'-tetramethyuronium hexafluorophosphate; HATU is O-(7-Azabenzotriazol-1-yl)-N,N,N',N'-tetramethyluronium hexafluorophosphate; PyBop is Benzotriazol-1-yloxytripyrrolidinophosphonium hexafluorophosphate; DCC is dicyclohexylcarbodiimide; CDI is N,N'-carbonyldiimidazole and HOBT is 1-hydroxy benzotriazole. A suitable base, such as triethylamine or diisopropylethylamine, is also used and the reaction is typically carried out at room temperature. In the instance where $R^{3'}$ represents a protected version of $R^3$, subsequent deprotection can then be carried out by methods known in the art to provide $R^3$. For example, when $R^3$ is an ester, appropriate acid or base catalyzed hydrolysis can be carried out to provide the corresponding free acid in the compound of Formula I.

Reaction Scheme III outlines the general procedures one could use to provide compounds of the present invention having Formula Ia. The compounds of Formula Ia are of Formula wherein L is —$C(R^5)$—X—, X is NH and $R^2$ is H.

Reaction Scheme III

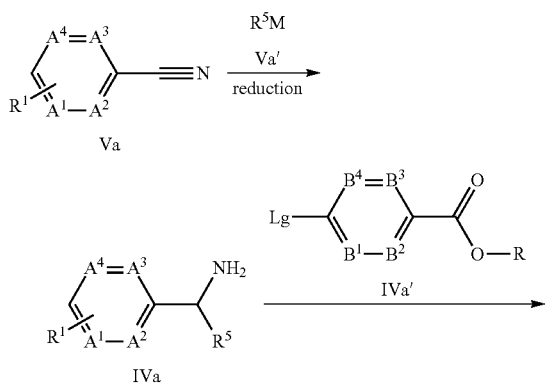

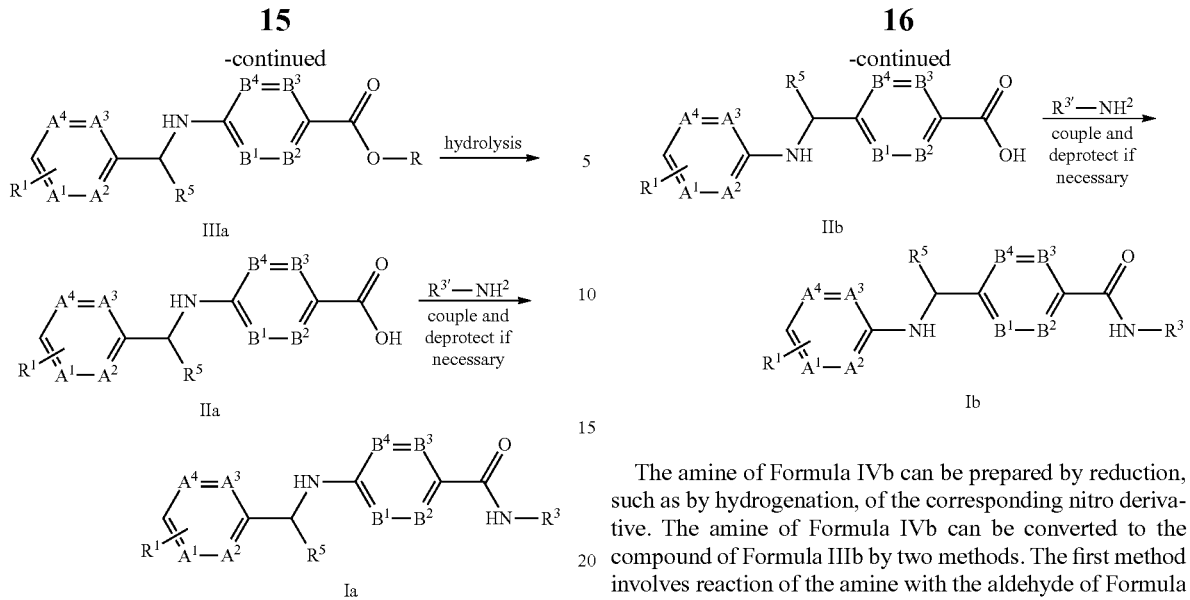

The nitrile of Formula Va is reacted with an appropriate Grignard reagent $R^5$-M wherein M represents a magnesium halide such as magnesium chloride or magnesium bromide. The reaction is carried out in an appropriate solvent such as tetrahydrofuran or a mixture of tetrahydrofuran and diethyl ether. The reaction is typically carried out at 0° C. to 100° C. and microwave irradiation of the reaction mixture is preferred. Upon completion of the Grignard reaction the reaction mixture is then subjected to reduction using an appropriate reducing agent such as sodium borohydride in an appropriate solvent such as methanol to provide the amine compound of Formula IVa. The compound of Formula IVa is then converted to the compound of Formula Ia as previously described for Reaction Scheme II.

Reaction Scheme IV provides the preparation of compounds where L is —XCHR$^5$— and X is NH as depicted.

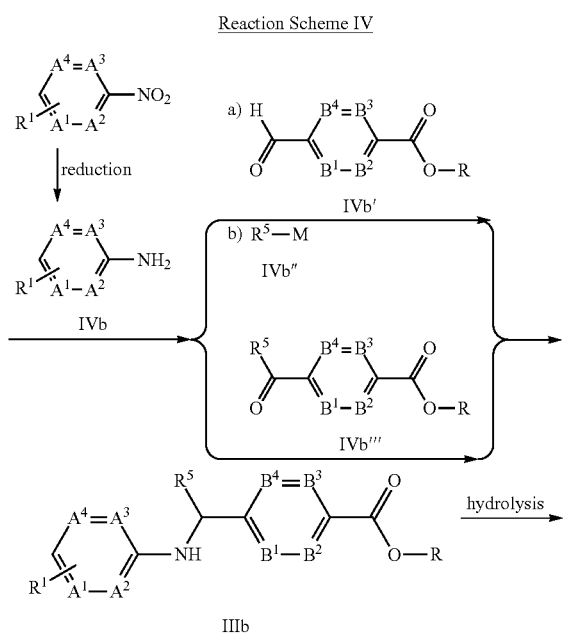

Reaction Scheme IV

The amine of Formula IVb can be prepared by reduction, such as by hydrogenation, of the corresponding nitro derivative. The amine of Formula IVb can be converted to the compound of Formula IIIb by two methods. The first method involves reaction of the amine with the aldehyde of Formula IVb' followed by alkylation of the resulting aldimine with an appropriate alkylating reagent $R^5$-M of Formula IVb". The reaction of the amine of Formula IVb with the aldehyde of Formula IVb' to provide the corresponding aldimine is carried out in an appropriate solvent, such as toluene, typically in the presence of molecular sieves, at a temperature from room temperature up to 100° C. for a period of 1 to 24 hours. The reaction mixture containing the aldimine can be filtered and concentrated. The resulting residue can then be redissolved in a solvent appropriate for the alkylation reaction, such as tetrahydrofuran. Typically, an appropriate metallated alkylating agent, such as a Grignard reagent $R^5$-M of Formula IVb" where M represents a metal such as a magnesium halide is employed. The alkylation reaction can be carried out at a temperature of 0° C. to 60° C. for a period of 1 to 24 hours to provide the compound of Formula IIIb. When $R^5$-M represents a Grignard reagent addition of zinc chloride to the reaction mixture may be desirable to increase the yield of the compound of Formula IIIb (see Ishihara, K. et al.; JACS, 2006, 128, 9998.

Alternatively, the compound of Formula IIIb can be prepared by reaction of an amine of Formula IVb and a ketone of Formula IVb''' followed by reduction of the resulting imine. The reaction can be carried out under typical reductive amination conditions to provide the compound of Formula IIIb. For example, the amine of Formula IVb and ketone IVb''' in an appropriate solvent such as dimethoxyethane and in the presence of molecular sieves and para-toluene sulfonic acid can be reacted at room temperature up to 120° C. (sealed tube) for 1 to 24 hours. The reaction mixture can then be allowed to cool to room temperature and be treated with an appropriate reducing agent, such as sodium cyanoborohydride in methanol, and in the presence of acetic acid for 1 to 24 hours to provide the compound of Formula IIIb.

The compound of Formula IIIb can be hydrolyzed to provide the free acid compound of Formula IIb by methods as previously described for the preparation of the compound of Formula IIa in Reaction Scheme II. The free acid compound of Formula IIb can then undergo amide coupling conditions followed by deprotection if necessary to provide the compound of Formula Ib as previously described for the conversion of the compound of Formula IIa to Formula Ia in Reaction Scheme II.

Reaction Scheme V outlines the general procedures that can be used to provide compounds of the present invention having Formula Ic. The compounds of Formula Ic are of Formula I wherein L is —X—C(R⁵)—, X is O and R² is H.

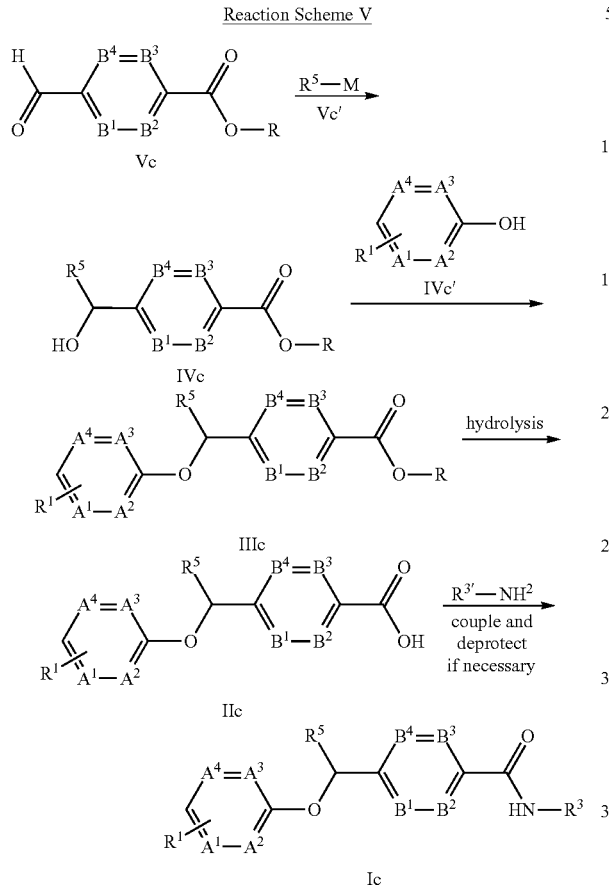

The compound of Formula IVc is prepared by reaction of an aldehyde of Formula Vc with an appropriate metallated alkylating compound R⁵-M (Vc'). Typically, R⁵-M is a Grignard reagent in which M represents a magnesium halide, such as magnesium chloride or magnesium bromide. The reaction is carried out in an appropriate solvent, such as tetrahydrofuran, at a temperature from about −78° C. to room temperature for a period of 15 minutes to 24 hours to provide the alcohol of Formula IVc. The alcohol IVc is then coupled with the phenol of Formula IVc' using phenolic ether Mitsunobu reaction conditions (see e.g Mitsunobu, O.; Synthesis, 1981, 1; Lepore, S. D. et al. J. Org. Chem., 2003, 68(21), 8261-8263) to provide the compound of Formula IIIc. This reaction is typically carried out in an appropriate solvent such as tetrahydrofuran in the presence of an appropriate coupling reagent such as diethylazodicarboxylate (DEAD) or diisopropylazodicarboxylate (DIAD) and a phosphine ligand such as triphenylphosphine. The reaction is typically run at a temperature from about 0° C. to room temperature for 1 to 24 hours. The compound IIc can then be hydrolyzed to the compound of Formula IIc followed by amide formation and deprotection, as necessary, to provide the compound of Formula Ic as previously described for the corresponding steps in Reaction Scheme II.

Reaction Scheme VI outlines the general procedures that can be used to provide compounds of the present invention having Formula Id. The compounds of Formula Id are of Formula I wherein L is —C(R⁵)—X—, X is O and R² is H.

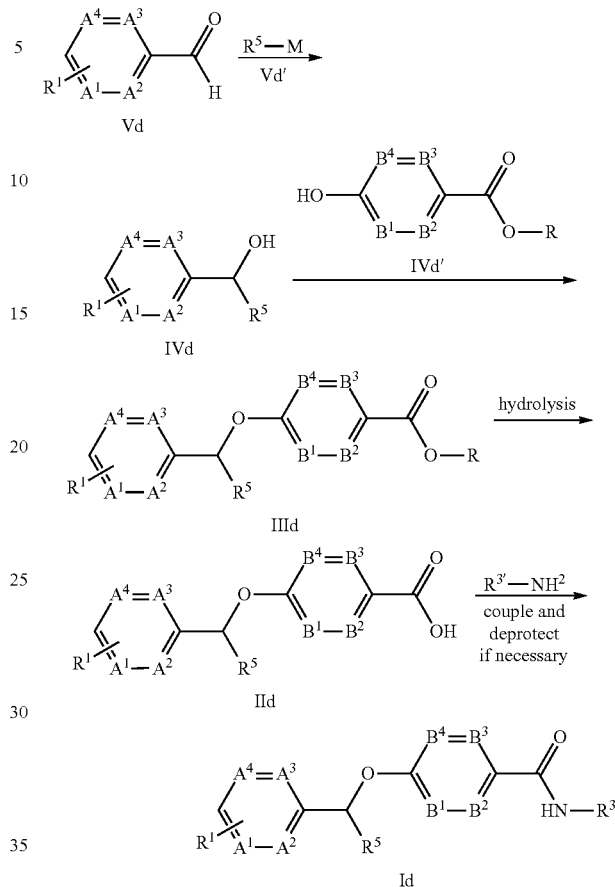

The compound of Formula Id is prepared in an analogous manner to the preparation of the compound of Formula Ic in Reaction Scheme V by substituting the compounds of Formula Vd, Vd', IVd, IVd', IId and IId for the compounds Vc, Vc', IVc, IVc', IIIc and IIIc as previously described.

Reaction Scheme VII outlines the general procedures one could use to provide compounds of the present invention having Formula Ia. The compounds of Formula Ia are of Formula I wherein R¹ is in the para position, L is —X—C(R⁵)—, X is CH₂ and R² is H.

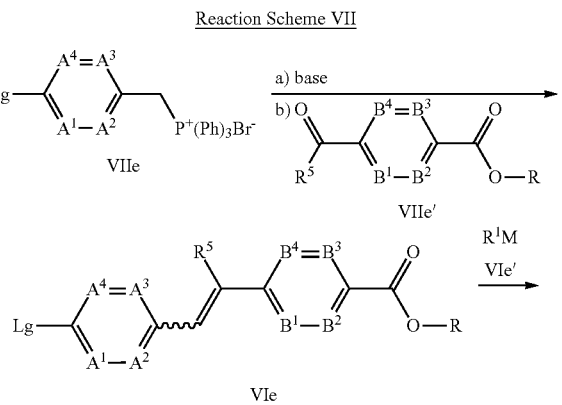

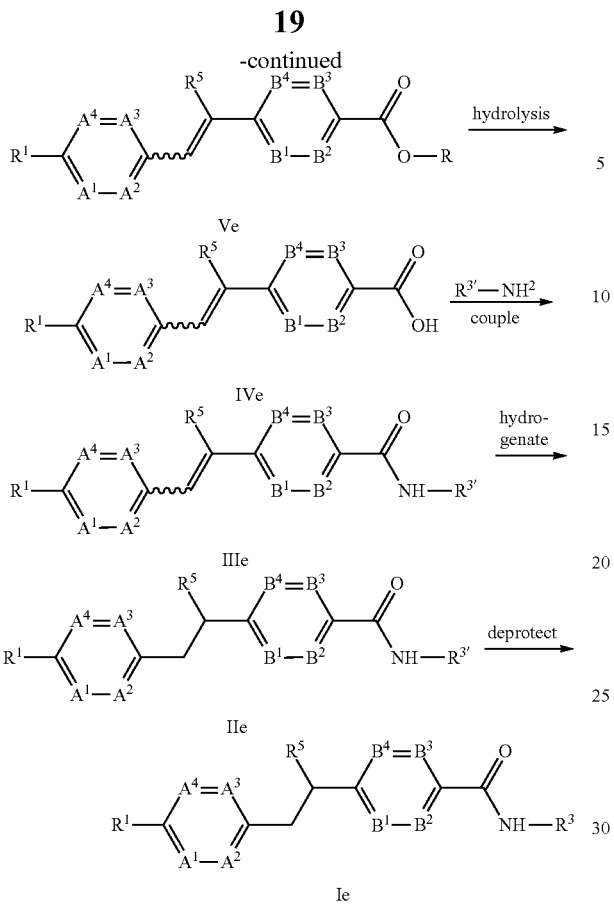

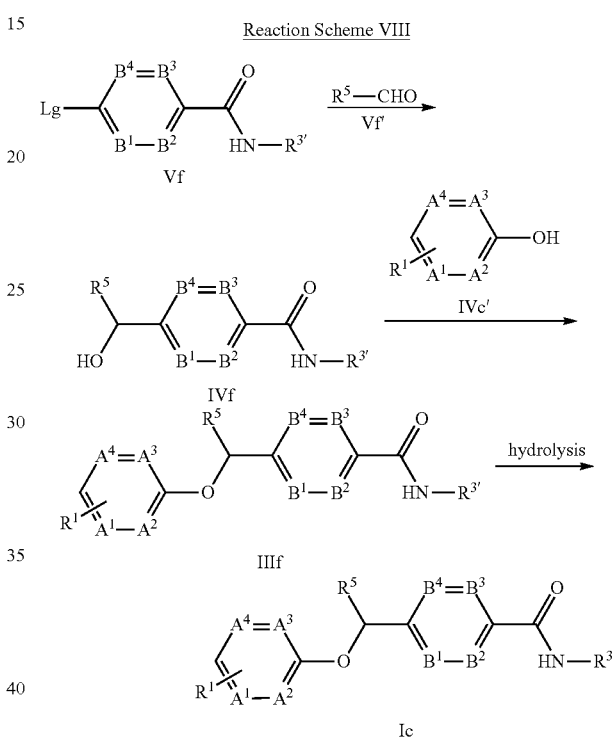

dium on carbon (Pd/C), in an appropriate solvent such as methanol at a temperature from room temperature up to 50° C. Hydrogenation apparatus such as the ThalesNano H-Cube® hydrogenator (ThalesNano, Budapest, Hungary) with a 10% Pd/C cartridge can be employed for this step. The compound of Formula IIe can then be deprotected as necessary and as previously described for Reaction Scheme II to provide the compound of Formula Ie.

Reaction Scheme VIII outlines another general procedure that can be used to provide compounds of the present invention having Formula Ic. The compounds of Formula Ic are of Formula I wherein L is —X—C($R^5$)—, X is O and $R^2$ is H.

Reaction Scheme VIII

The phosphomium bromide compound of Formula VIIe may be treated with an appropriate base and then reacted with the ketone derivative of Formula VIIe' to provide the olefinic compound of Formula VIe. The compound of Formula VIIe is typically treated with a base such as lithium bis(trimethylsilyl)amide (LHMDS) in an appropriate solvent such as toluene at −78° C. up to room temperature. Other bases that can be employed include lithium amides such as lithium diisopropylamide (LDA), lithium 2,2,6,6-tetramethyl piperidide (LTMP) or lithium diethyl amide as well as alkyl lithiums such as methyl lithium or n-butyl lithium.

The compound of Formula VIe can then be reacted with the heteroaryl compound $R^1$-M (VIe' wherein M is hydrogen when attached to nitrogen or an appropriate metal when attached to carbon). When M is a metal attached to a carbon in the heteroaryl represented by $R^1$ the reaction is typically a palladium catalyzed coupling reaction, as was described previously for the first step in Reaction Scheme II to provide the compound of Formula Ve. When M is hydrogen attached to nitrogen in the heteroaryl $R^1$, the nucleophilic substitution reaction is typically carried out in an appropriate solvent in the presence of a base. The compound of Formula Ve is then subjected to hydrolysis, typically in methanol and tetrahydrofuran using sodium hydroxide as base at 0° C. to room temperature for a period of 1 to 24 hours to provide the free acid of formula IVe. The free acid of Formula IVe can then be reacted with the amine $R^{3'}$—$NH_2$ using the amide coupling conditions previously described for Reaction Scheme II to provide the compound of Formula IIIe. The compound of Formula IIIe is then subjected to hydrogenation to reduce the olefinic moiety and provide the compound of Formula IIe. The hydrogenation is typically carried out in the presence of an appropriate hydrogenation catalyst, such as 10% palla- The compound of Formula Vf in which Lg is an appropriate halide, preferably iodide, and $R^{3'}$ represents a protected $R^3$ group (such as an ester of an appropriate $R^3$ carboxylic acid group) can be treated with magnesium in an appropriate solvent to provide the corresponding Grignard reagent. The Grignard reagent can then be reacted with the aldehyde $R^5$—CHO to provide the compound of Formula IVf. The compound of Formula IVf can undergo Mitsunobu coupling with the compound of Formula IVc' as previously described for Reaction Scheme V to provide the compound of Formula IIIf. Deprotection of the compound of Formula IIIf, for example by hydrolysis of an ester as previously described, then provides the compound of Formula Ic.

The compounds of the present invention may be isolated and used per se, or when possible, in the form of its pharmaceutically acceptable salt. The term "salts" refers to inorganic and organic salts of a compound of the present invention. These salts can be prepared in situ during the final isolation and purification of a compound, or by separately reacting the compound with a suitable organic or inorganic acid or base and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.,* 66, 1-19 (1977).

The compounds of the present invention may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g. hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons. For example, the pyrimidonr ring of this invention may also exist in its hydroxy pyrimidine form. Both such forms are included in the compounds of Formula I.

Certain compounds of the present invention may exist in different stable conformational forms which may be separable. Torsional asymmetry due to restricted rotation about an asymmetric single bond, for example, because of steric hindrance or ring strain, may permit separation of different conformers.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$, respectively.

Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$. are useful for positron emission tomography (PET) studies to examine substrate occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Certain compounds of the present invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the present invention followed by gradual or fast cooling. The presence of polymorphs may be determined by solid probe NMR spectroscopy, IR spectroscopy, differential scanning calorimetry, powder X-ray diffraction or such other techniques.

Compounds of the present invention are useful for treating diseases, conditions and/or disorders modulated by glucagon; therefore, another embodiment of the present invention is a pharmaceutical composition comprising a therapeutically effective amount of a compound of the present invention and a pharmaceutically acceptable excipient, diluent or carrier. The compounds of the present invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other no-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of Formula I. The term "solvate" refers to a molecular complex of a compound represented by Formula I (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by glucagon in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from the modulation of glucagon which include: eating disorders (e.g., binge eating disorder, anorexia, bulimia, weight loss or control and obesity), prevention of obesity and insulin resistance.

One aspect of the present invention is the treatment of obesity, and obesity-related disorders (e.g., overweight, weight gain, or weight maintenance).

Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Another aspect of the present invention is for the treatment or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, and diabetic complications (such as atherosclerosis, coronary heart disease, stroke, peripheral vascular disease, nephropathy, hypertension, neuropathy, and retinopathy).

Yet another aspect of the present invention is the treatment of diabetes- or obesity-related co-morbidities, such as metabolic syndrome. Metabolic syndrome includes diseases, conditions or disorders such as dyslipidemia, hypertension, insulin resistance, diabetes (e.g., Type 2 diabetes), weight gain, coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology*, 7(2), (2005); and Alberti, K. G., et al., "The Metabolic Syndrome—A New Worldwide Definition," *Lancet*, 366, 1059-62 (2005). Preferably, administration of the compounds of the present invention provides a statistically significant ($p<0.05$) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant ($p<0.05$) reduction in glucose serum levels.

In yet another aspect of the present invention, the condition treated is impaired glucose tolerance, hyperglycemia, diabetic complications such as sugar cataracts, diabetic neuropathy, diabetic nephropathy, diabetic retinopathy and diabetic cardiomyopathy, anorexia nervosa, bulimia, cachexia, hyperuricemia, hyperinsulinemia, hypercholesterolemia, hyperlipidemia, dyslipidemia, mixed dyslipidemia, hypertriglyceridemia, nonalcoholic fatty liver disease, atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, vascular stenosis, solid tumors, skin cancer, melanoma, lymphoma, breast cancer, lung cancer, colorectal cancer, stomach cancer, esophageal cancer, pancreatic cancer, prostate cancer, kidney cancer, liver cancer, bladder cancer, cervical cancer, uterine cancer, testicular cancer and ovarian cancer.

The present invention also relates to therapeutic methods for treating the above described conditions in a mammal, including a human, wherein a compound of Formula I of this invention is administered as part of an appropriate dosage regimen designed to obtain the benefits of the therapy. The appropriate dosage regimen, the amount of each dose administered and the intervals between doses of the compound will depend upon the compound of formula (I) of this invention being used, the type of pharmaceutical compositions being used, the characteristics of the subject being treated and the severity of the conditions.

In general, an effective dosage for the compounds of the present invention is in the range of 0.01 mg/kg/day to 30 mg/kg/day, preferably 0.01 mg/kg/day to 5 mg/kg/day of active compound in single or divided doses. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. Practitioners will appreciate that "kg" refers to the weight of the patient measured in kilograms.

The compounds or compositions of this invention may be administered in single (e.g., once daily) or multiple doses or via constant infusion. The compounds of this invention may also be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents.

The compounds or compositions of the present invention may be administered to a subject in need of treatment by a variety of conventional routes of administration, including orally and parenterally, (e.g., intravenously, subcutaneously or intramedullary). Further, the pharmaceutical compositions of this invention may be administered intranasally, as a suppository, or using a "flash" formulation, i.e., allowing the medication to dissolve in the mouth without the need to use water.

It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable anti-diabetic agents include an acetyl-CoA carboxylase-2 (ACC-2) inhibitor, a diacylglycerol O-acyltransferase 1 (DGAT-1) inhibitor, a phosphodiesterase (PDE)-10 inhibitor, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) agonist (e.g., exendin-3 and exendin-4), a protein tyrosine phosphatase-1B (PTP-1B) inhibitor (e.g., trodusquemine, hyrtiosal extract, and compounds disclosed by Zhang, S., et al., *Drug Discovery Today*, 12(9/10), 373-381 (2007)), SIRT-1 inhibitor (e.g., resveratrol), a dipeptidyl peptidase IV (DPP-IV) inhibitor (e.g., sitagliptin, vildagliptin, alogliptin and saxagliptin), an SGLT1 inhibitor, an SGLT2 inhibitor (e.g. dapagliflozin, remogliflozin, sergliflozin and AVE2268), an insulin secreatagogue, a fatty acid oxidation inhibitor, an A2 antagonist, a c-jun amino-terminal kinase (JNK) inhibitor, insulin, an insulin mimetic, a glycogen phosphorylase inhibitor, and a VPAC2 receptor agonist. Preferred anti-diabetic agents for the combination aspects are metformin, SGLT2 inhibitors (e.g. dapagliflozin, remogliflozin, sergliflozin and AVE2268) and DPP-IV inhibitors (e.g., sitagliptin, vildagliptin, alogliptin and saxagliptin). Preferred combinations include the instant compounds of Formula I with metformin and a DPP-IV inhibitor or with metformin and an SGLT2 inhibitor.

Suitable anti-obesity agents include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $\beta_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as pegleted $PYY_{3-36}$ e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, liraglutide, bromocriptine, odistat, exenatide (Byetta®), AOD-9604 (CAS No. 221231-10-3) and sibutramine. Preferably, compounds of the present invention and combination therapies are administered in conjunction with exercise and a sensible diet.

All of the above recited U.S. patents and publications are incorporated herein by reference.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairdawn, N.J.), May-bridge Chemical Company, Ltd. (Cornwall, England), Tyger Scientific (Princeton, N.J.), and AstraZeneca Pharmaceuticals (London, England).

General Experimental Procedures

NMR spectra were recorded on a Varian Unity™ 400 (available from Varian Inc., Palo Alto, Calif.) at room temperature at 400 MHz for proton. Chemical shifts are expressed in parts per million (δ) relative to residual solvent as an internal reference. The peak shapes are denoted as follows: s, singlet; d, doublet; dd, doublet of doublet; t, triplet, q, quartet m, multiplet; bs, broad singlet; 2s, two singlets. Atmospheric pressure chemical ionization mass spectra (APCI) were obtained on a Fisons™ Platform II Spectrometer (carrier gas: acetonitrile: available from Micromass Ltd, Manchester, UK). Chemical ionization mass spectra (CI) were obtained on a Hewlett-Packard™ 5989 instrument (ammonia ionization, PBMS: available from Hewlett-Packard Company, Palo Alto, Calif.). Electrospray ionization mass spectra (ES) were obtained on a Waters™ ZMD instrument (carrier gas: acetonitrile: available from Waters Corp., Milford, Mass.). High resolution mass spectra (HRMS) were obtained on an Agilent™ Model 6210 using time of flight method. Where the intensity of chlorine or bromine-containing ions are described, the expected intensity ratio was observed (approximately 3:1 for $^{35}Cl/^{37}Cl$ containing ions and 1:1 for $^{79}Br/^{81}Br$-containing ions) and the intensity of only the lower mass ion is given. In some cases only representative $^1H$ NMR peaks are given. Optical rotations were determined on a PerkinElmer™ 241 polarimeter (available from PerkinElmer Inc., Wellesley, Mass.) using the sodium D line (λ=589 nm) at the indicated temperature and are reported as follows $[\alpha]_D^{temp}$, concentration (c=g/100 ml), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.) or Biotage™ SNAP cartridge KPsil or Redisep Rf silica (from Teledyne™ Isco™) under low nitrogen pressure. Chiral SFC (supercritical fluid chromatography) was performed on the chiral columns as specified.

Certain solvents and reagents may be referred to using common abbreviations such as DCM for dichloromethane. DMF for dimethylformamide, EtOH for ethanol, EtOAc for ethyl acetate, and MeOH for methanol, for example.

Preparation of Starting Materials and Intermediates

The following starting materials are available from the corresponding sources: (Z)—N-(3-(dimethylamino)-2-(trifluoromethyl)allylidene)-N-methylmethanaminium hexafluorophosphate—Anichem LLC (North Brunswick, N.J., USA); 4-phenyl-1H-pyrazole—Anichem LLC (North Brunswick, N.J., USA); tert-butyl 3-(tert-butylamino)propanoate—Aurora Fine Chemicals LLC (San Diego, Calif., USA); 2,4,5,6-tetrahydrocyclopenta[c]pyrazole—Ambinter (Paris, France); methyl 6-formylnicotinate—Ark Pharm Inc. (Libertyville, Ill. USA): 4-(trifluoromethyl)-1H-pyrazole—Anichem LLC (North Brunswick, N.J., USA); 4-(trifluoromethyl)-1H-imidazole—Ark Pharm Inc. (Libertyville, Ill., USA); 4-methyl-3-(trifluoromethyl)-1H-pyrazole—ASDI Inc. (Newark. Del., USA); 3-methyl-4-(trifluoromethyl)-1H-pyrazole—Accel Pharmtech LLC (East Brunswick, N.J., USA); 3-(trifluoromethyl)-1H-1,2,4-triazole—Beta Pharma Inc. (Branford, Conn., USA); 2-methyl-4-(trifluoromethyl)-1H-imidazole—APAC Pharmaceutical LLC (Columbia, Mass. USA): ethyl 2-chloropyrimidine-5-carboxylate—Ark Pharm Inc. (Libertyville, Ill., USA); 2-cyclopropylacetaldehyde—Anichem LLC (North Brunswick, N.J., USA); 4-chloro-3-methyl-1H-pyrazole—Oakwood Products, Inc. (West Columbia, S.C., USA); 2-(1H-pyrazol-4-yl)pyridine—Oakwood Products, Inc. (West Columbia, S.C., USA); and 4-ethyl-3-methyl-1H-pyrazole—Aces Pharma, Inc. (Branford, Conn., USA).

Preparation of Intermediates

Intermediate (1): (4-(4-(trifluoromethyl)-1H-pyrazol-1-yl)phenyl)methanol

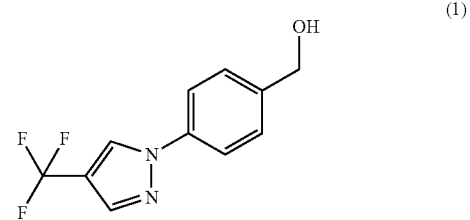 [SMILES: OCc1ccc(-n2cc(C(F)(F)F)cn2)cc1]

(1)

A mixture of (4-iodophenyl)methanol (1030 mg, 4.41 mmol), 4-(trifluoromethyl)-1H-pyrazole (600 mg, 4.41 mmol), copper(I) iodide (168 mg, 0.882 mmol), trans-4-hydroxy-L-proline (231 mg, 1.76 mmol) and cesium carbonate (2900 mg, 8.82 mmol) in dimethylsulfoxide (7.5 mL) was heated to 85° C. for 20 hours. The mixture was diluted with water and extracted with ethyl acetate twice. The combined organic layers were dried over sodium sulfate, filtered and concentrated. Purification by column chromatography (0-45% ethyl acetate in heptane), gave (4-(4-(trifluoromethyl)-1H-pyrazol-1-yl)phenyl)methanol. $^1H$ NMR (400 MHz, CDCl$_3$, δ): 8.16 (s, 1H), 7.89 (s, 1H), 7.65 (d, J=8.39 Hz, 2H), 7.47 (d, J=8.39 Hz, 2H), 4.74 (d, J=5.66 Hz, 2H), 1.85 (t, J=5.86 Hz, 1H).

Intermediate (2): 4-(4-(trifluoromethyl)-1H-pyrazol-1-yl)benzaldehyde

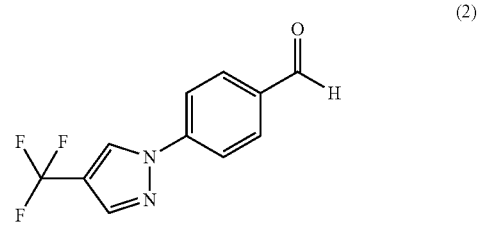 [SMILES: O=Cc1ccc(-n2cc(C(F)(F)F)cn2)cc1]

(2)

A mixture of Intermediate (1) (230 mg, 0.95 mmol), dimethylsulfoxide (1.35 mL) and triethylamine (0.662 mL, 4.75 mmol) in dichloromethane (3.5 mL) was cooled to 0° C. Sulfur trioxide pyridine complex (0.454 g, 2.85 mmol) was added in portions and the mixture stirred at 0° C. for 2 hours. The reaction was diluted with ethyl acetate, washed with saturated ammonium chloride and brine, dried over sodium sulfate, filtered and concentrated to give 4-(4-(trifluoromethyl)-1H-pyrazol-1-yl)benzaldehyde. $^1H$ NMR (400 MHz, CDCl$_3$, δ): 10.04 (s, 1H), 8.29 (s, 1H), 7.99-8.05 (m, 2H), 7.95 (s, 1H), 7.87-7.92 (m, 2H).

Intermediate (3): 1-(2-methyl-4-nitrophenyl)-4-(trifluoromethyl)-1H-imidazole

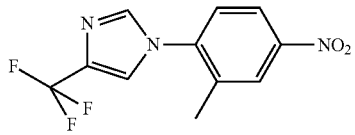

(3)

A mixture of 4-(trifluoromethyl)-1H-imidazole (198 mg, 1.46 mmol), 1-fluoro-2-methyl-4-nitrobenzene (216 mg, 1.53 mmol) and potassium carbonate (402 mg, 2.91 mmol) in acetonitrile (1.5 mL) was heated to 85° C. for 24 hours. The mixture was diluted with water and saturated ammonium chloride and was extracted with ethyl acetate twice. The combined organic layers were dried over sodium sulfate, filtered and concentrated. Purification by column chromatography (0-50% ethyl acetate in heptane), gave 1-(2-methyl-4-nitrophenyl)-4-(trifluoromethyl)-1H-imidazole. $^1$H NMR (500 MHz, CDCl$_3$, δ): 8.30 (d, J=2.44 Hz, 1H), 8.21-8.25 (m, 1H), 7.70 (s, 1H), 7.45-7.49 (m, 2H), 2.38 (s, 3H).

Intermediate (4): 3-methyl-4-(4-(trifluoromethyl)-1H-imidazol-1-yl)benzenamine

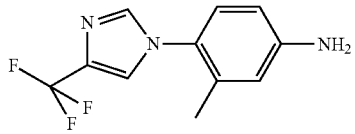

(4)

A mixture of Intermediate (3) (325 mg, 1.20 mmol) and 10 wt % palladium on carbon (40 mg) in ethanol (6 mL) was pressurized to 48 psi hydrogen and agitated for 6 hours. The mixture was filtered through celite, rinsing with ethyl acetate and methanol. The filtrate was concentrated to give 3-methyl-4-(4-(trifluoromethyl)-1H-imidazol-1-yl)benzenamine. $^1$H NMR (500 MHz, CDCl$_3$, δ): 7.56 (s, 1H), 7.32 (s, 1H), 7.01 (d, J=8.54 Hz, 1H), 6.62 (d, J=2.68 Hz, 1H), 6.57 (dd, J=8.29, 2.44 Hz, 1H), 3.85 (br. s., 2H), 2.08 (s, 3H). MS (M+1): 242.3.

Intermediate (5): Ethyl 4-butyrylbenzoate

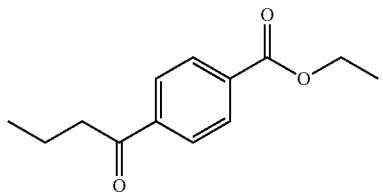

(5)

At –40° C., isopropylmagnesium chloride lithium chloride (15.3 mL, 1.3 M in THF, 19.9 mmol) was added dropwise to a solution of ethyl 4-iodobenzoate (5000 mg, 18.11 mmol) in tetrahydrofuran (30 mL). The solution was stirred at –40° C. for 40 minutes. Butyraldehyde (1830 mg, 25.4 mmol) was added. The mixture was allowed to warm to room temperature over 3 hours. The reaction was quenched with 1N HCl and extracted three times with ethyl acetate. The combined organic layers were dried over sodium sulfate, filtered and concentrated to give ethyl 4-(1-hydroxybutyl)benzoate. $^1$H NMR (400 MHz, CDCl$_3$, δ): 8.02 (d, J=8.6 Hz, 2H), 7.41 (d, J=8.0 Hz, 2H), 4.83-4.66 (m, 1H), 4.38 (q, J=7.2 Hz, 2H), 1.86 (d, J=3.7 Hz, 1H), 1.83-1.61 (m, 2H), 1.51-1.42 (m, 1H), 1.39 (t J=7.2 Hz, 3H), 1.36-1.23 (m, 1H), 0.94 (t, J=7.6 Hz, 3H).

A mixture of the crude alcohol (1.0 g, 4.5 mmol) in dichloromethane (16.7 mL), dimethylsulfoxide (4.79 mL) and triethylamine (2.28 g, 22.5 mmol) was cooled to 0° C. Sulfur trioxide pyridine complex (2.15 g, 13.5 mmol) was added in portions and the mixture stirred at 0° C. for 1 hour. The reaction was then allowed to warm to room temperature and stir for 2 hours. The reaction was quenched with brine and diluted with dichloromethane. The layers were separated and the aqueous was extracted again with dichloromethane. The combined organic layers were dried over sodium sulfate, filtered and concentrated. Purification by column chromatography (0-30% ethyl acetate in heptane) gave ethyl 4-butyrylbenzoate. $^1$H NMR (400 MHz, CDCl$_3$, δ): 8.05-8.17 (m, 2H), 8.04-7.92 (m, 2H), 4.40 (q, J=7.15 Hz, 2H), 2.96 (t, J=7.22 Hz, 2H), 1.86-1.69 (m, 2H), 1.40 (t, J=7.12 Hz, 3H), 1.00 (t, J=7.22 Hz, 3H).

Intermediate (6): 6-(4-(trifluoromethyl)-1H-imidazol-1-yl)pyridin-3-amine

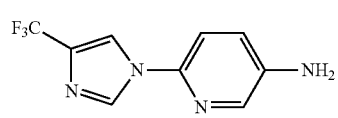

(6)

A mixture of 4-(trifluoromethyl)-1H-imidazole (2000 mg, 14.70 mmol), 2-chloro-5-nitropyridine (2330 mg, 14.70 mmol), and potassium carbonate (4060 mg, 29.4 mmol) in acetonitrile (14.7 mL) was heated at 85° C. overnight. The reaction was diluted with water and extracted three times with ethyl acetate. The combined organic layers were washed with brine, dried over sodium sulfate, filtered and concentrated. The crude residue was dissolved in ethanol (20 mL) and ethyl acetate (15 mL). 10 wt % Palladium on carbon (500 mg) was added to the solution. The mixture was pressurized to 50 psi hydrogen and was shaken for 5 hours. The reaction was filtered through celite, rinsing with methanol. The filtrate was concentrated to give 6-(4-(trifluoromethyl)-1H-imidazol-1-yl)pyridin-3-amine. $^1$H NMR (400 MHz, CDCl$_3$, δ): 8.15 (s, 1H), 7.93 (d, J=2.73 Hz, 1H), 7.85 (s, 1H), 7.20-7.15 (m, 1H), 7.14-7.09 (m, 1H), 3.13-2.30 (m, 2H). MS (M+HCO2$^-$): 273.0.

Intermediate (7A): (Z)—N-(3-(dimethylamino)-2-(trifluoromethyl)allylidene)-N-methylmethanaminium hexafluorophosphate(V)

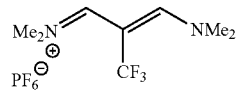

Phosphoryl chloride (18.0 mL, 200 mmol), was added in an addition funnel over 30 minutes to anhydrous dimethylformamide (40.0 ml) at 0° C. After completion of the addition, the light pink solution was warmed to room temperature and 3,3,3-trifluoropropionic acid (8.90 mL, 101 mmol) was added dropwise over 10 minutes. The solution was then warmed to 55° C. and stirred for 4 hours at 55° C. The bright yellow solution was cooled to room temperature and slowly added over 30 minutes to a 0° C. solution of sodium hexafluorophosphate (19.0 g, 110 mmol) in water (250 mL) while maintaining the internal temperature below 10° C. The yellow precipitate was collected by vacuum filtration and washed with ice cold water (3×150 mL). The yellow solid was dried in vacuo and then azeotrophed with toluene two times and dried again in vacuo to provide (Z)—N-(3-(dimethylamino)-2-(trifluoromethyl)allylidene)-N-methylmethanaminium hexafluorophosphate(V) as a yellow solid (22.0 g, 64%). $^1$H NMR (400 MHz, CD$_3$CN, δ): 7.72 (s, 2H), 3.41 (s, 6H), 3.23 (d, J=1.4 Hz, 6H).

Intermediate (7B): 1-(4-bromo-2,6-dimethylphenyl)hydrazine hydrochloride

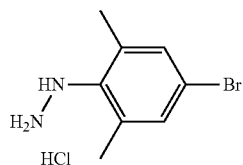

In a 3 L 3-neck round bottom flask equipped with a mechanical stirrer was added concentrated hydrochloric acid (125 mL) and water (250 mL). 4-Bromo-2,6-dimethylbenzenamine (100 g, 500 mmol) was added slowly at 0° C. Stirring was continued for an additional 15 minutes, resulting in a thick white slurry. A freshly prepared solution of sodium nitrite (34.5 g, 500 mmol) in water (100 mL) was added to the slurry dropwise maintaining the internal temperature below 5° C. After stirring for 30 minutes, a deep orange solution was formed. Tin(II) chloride dehydrate (282 g, 1250 mmol) in 1:1 concentrated hydrochloric acid:water (300 mL) was added dropwise while maintaining the internal temperature between 0-5° C. The resulting mixture was stirred at 0° C. for 1 hour and then warmed to room temperature and stirred for 15 hours. The reaction mixture was filtered and washed with diethyl ether. The solid was slowly added to an aqueous 10 M solution of sodium hydroxide (1 L) between 0-10° C. and extracted with ethyl acetate (3×800 mL). The organic layer was washed with brine twice, dried over anhydrous sodium sulfate, and concentrated to give 1-(4-bromo-2,6-dimethylphenyl)hydrazine (76.0 g, 353 mmol). The hydrazine was dissolved in ethyl acetate (800 mL) to which hydrochloric acid/methanol (88.2 mL) was added. The mixture was stirred for 25 minutes. The reaction was filtered, washed with ethyl acetate until the solid is white. The white solid was dried in vacuo to afford 1-(4-bromo-2,6-dimethylphenyl)hydrazine hydrochloride (80.0 g, 64%). $^1$H NMR (400 MHz, DMSO-d6, δ): 9.71 (s, 3H), 7.32 (s, 2H), 6.78 (s, 1H), 2.37 (s, 6H).

Intermediate (7): 1-(4-bromo-2,6-dimethylphenyl)-4-(trifluoromethyl)-1H-pyrazole

(Z)—N-(3-(dimethylamino-2-(trifluoromethyl)allylidene)-N-methyl methanaminium hexafluorophosphate (3000 mg, 8.819 mmol) and 1-(4-bromo-2,6-dimethylphenyl)hydrazine hydrochloride (2480 mg, 9.84 mmol) were suspended in tetrahydrofuran. The suspension was cooled to 0° C. Sodium methoxide (551 mg, 9.7 mmol) was added as a solid in one portion. The ice bath was removed and the mixture warmed to room temperature and stirred for 48 hours. Trifluoroacetic acid (3 mL) was then added at room temperature. The reaction was heated to 80° C. for 5 hours, diluted with ethyl acetate and washed with saturated sodium bicarbonate twice. The combined aqueous washings were extracted with ethyl acetate. The combined organic layers were washed with brine, dried over sodium sulfate, filtered and concentrated. Purification by column chromatography (0-20% ethyl acetate in heptane), gave 1-(4-bromo-2,6-dimethylphenyl-4-(trifluoromethyl)-1H-pyrazole as an oil. $^1$H NMR (400 MHz, CDCl$_3$, δ): 7.93 (s, 1H), 7.71 (s, 1H), 7.31 (s, 2H), 1.99 (s, 6H).

Intermediate (8): 3,5-dimethyl-4-(4-(trifluoromethyl)-1H-pyrazol-1-yl)benzenamine

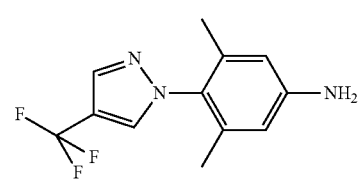

A vial containing Intermediate (7) (1200 mg, 3.76 mmol), copper(I) iodide (143 mg, 0.75 mmol), trans-4-hydroxy-L-proline (197 mg, 1.50 mmol) and potassium carbonate (1570 mg, 11.3 mmol) was purged with nitrogen. Dimethylsulfoxide (7.5 mL) was added followed by ammonia (3.73 mL, ~28% aqueous). The vial was sealed and heated to 75° C. for 20 hours. The reaction was cooled to room temperature, diluted with water, and extracted with ethyl acetate twice. The combined organic layers were dried over sodium sulfate, filtered and concentrated to give 3,5-dimethyl-4-(4-(trifluoromethyl)-1H-pyrazol-1-yl)benzenamine. $^1$H NMR (400

MHz, CDCl₃, δ): 7.84 (s, 1H), 7.65 (s, 1H), 6.37 (s, 2H), 3.82-3.47 (br s, 2H), 1.85 (s, 6H). MS (M+H+CH₃CN): 297.2.

Intermediate (9): (+/−)-methyl 4-(1-hydroxy-3-methylbutyl)benzoate

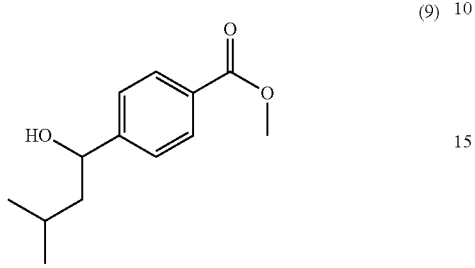

(9)

A solution of 4-formyl-benzoic acid methyl ester (1.56 g, 9.50 mmol) in tetrahydrofuran (53 mL) was cooled to 0° C. Isobutylmagnesium chloride (4.75 mL, 2M in THF) was then added dropwise over 15 minutes. The reaction was stirred at 0° C. for 1 hour. The ice bath was removed and the reaction was allowed to warm to room temperature and stir for 1 hour. The reaction was quenched by carefully adding 1N HCl. The reaction was diluted with water and diethylether and the layers were separated. The aqueous was extracted three more times with diethyl ether. The combined organics were dried over magnesium sulfate, filtered, and concentrated. Purification by column chromatography (0-40% ethyl acetate in heptane) gave (+/−)-methyl 4-(1-hydroxy-3-methylbutyl)benzoate (404.6 mg, 19%) as a clear, colorless oil. ¹H NMR (400 MHz, CDCl₃, δ): 7.99 (d, J=8.2 Hz, 2H), 7.40 (d, J=8.2 Hz, 2H), 4.79 (br. s., 1H), 3.89 (s, 3H), 1.94 (d, J=2.73, 1H), 1.65-1.78 (m, 2H), 1.42-1.52 (m, 1H), 0.91-0.97 (m, 6H).

Intermediate (10): methyl 4-(3-methylbutanoyl)benzoate (10)

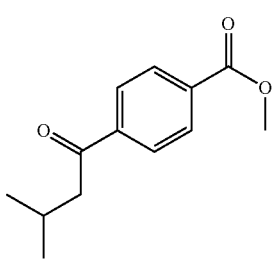

(10)

Intermediate (9) (404.6 mg, 1.820 mmol) was dissolved in dichloromethane (6.07 mL) and cooled to 0° C. Pyridinium chlorochromate (785 mg, 3.64 mmol) was added. The ice bath was removed and the reaction was allowed to warm to room temperature and stir for 48 hours. The reaction was diluted with dichloromethane and magnesium sulfate was added. This mixture was stirred for 10 minutes and was then filtered and concentrated. Purification by column chromatography (0-30% ethyl acetate in heptane) gave methyl 4-(3-methylbutanoyl)benzoate (363.7 mg, 91%) as a clear, colorless oil. ¹H NMR (400 MHz, CDCl₃, δ): 8.07-8.13 (m, 2H), 7.95-8.00 (m, 2H), 3.93 (s, 3H), 2.82-2.86 (m, 2H), 2.28 (dt, J=13.4, 6.8 Hz, 1H), 0.99 (d, 6H).

Intermediate (11): 4-fluoro-1-(4-nitrophenyl)-1H-pyrazole

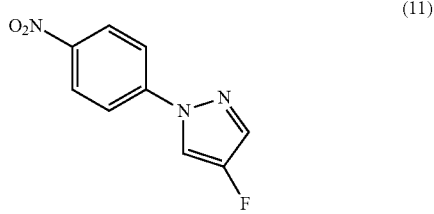 [SMILES: O=[N+]([O-])c1ccc(-n2cc(F)cn2)cc1]

(11)

To a solution of 4-fluoro-1H-pyrazole (250 mg, 2.90 mmol) and potassium carbonate (803 mg, 5.81 mmol) in acetonitrile (3 mL) was added 4-fluoronitrobenzene (430 mg, 3.05 mmol). The resulting mixture was stirred at 70° C. for 2 hours. The reaction was then filtered and concentrated. Purification by column chromatography gave 4-fluoro-1-(4-nitrophenyl)-1H-pyrazole (400 mg, 67%). ¹H NMR (400 MHz, CDCl₃, δ): 8.34 (d, 2H), 7.91 (d, 1H), 7.81 (d, 2H), 7.67 (d, 1H).

Intermediate (12): 4-(4-fluoro-1H-pyrazol-1-yl)aniline

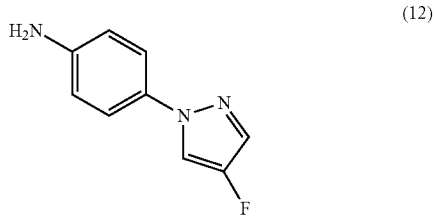

(12)

A mixture of Intermediate (11) (200 mg, 0.965 mmol) and 10 wt % palladium on carbon (100 mg) in ethanol (10 mL) was pressurized to 15 psi hydrogen and stirred at 35° C. overnight. The reaction was filtered and concentrated. Purification by column chromatography gave 4-(4-fluoro-1H-pyrazol-1-yl)aniline (150 mg, 88%). ¹HNMR (400 MHz, CDCl₃, δ): 7.65 (d, 1H), 7.50 (d, 1H), 7.37 (d, 2H), 6.72 (d, 2H), 3.76 (br s, 2H).

Intermediate (13): 4-(4-(trifluoromethyl)-1H-pyrazol-1-yl)benzonitrile

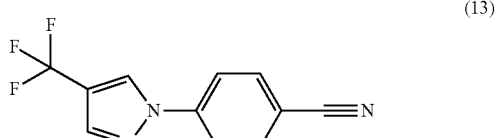

(13)

To a 0° C. solution of 4-(trifluoromethyl)-1H-pyrazole (1 g, 7 mmol) in N,N-dimethylformamide (10 mL) was added 60 wt % sodium hydride (132 mg, 3.31 mmol). The mixture was stirred at 0° C. for 30 minutes, 4-fluorobenzonitrile (979 mg, 8.08 mmol) was added and the reaction was heated to 80° C. overnight. Saturated ammonium chloride was added and the mixture extracted with ethyl acetate. The organic layer was dried over sodium sulfate, filtered and concentrated. Purification by column chromatography gave 4-(4-(trifluoromethyl)-1H-pyrazol-1-yl)benzonitrile (1.2 g, 72%). $^1$H NMR (400 MHz, CD$_3$OD, δ): 8.84 (s, 1H), 7.96 (s, 1H), 7.95 (d, 2H), 7.78 (d, 2H).

Intermediate (14): (+/−)-3-methyl-1-(4-(4-(trifluoromethyl)-1H-pyrazol-1-yl)phenyl)butan-1-amine

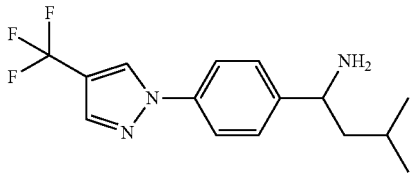

(14)

A microwave vial was charged with Intermediate (13) (300 mg, 1.26 mmol) and tetrahydrofuran (5 mL). Isobutylmagnesium bromide (1.90 mL, 2M in THF, 3.80 mmol) was added. The resulting mixture was heated to 100° C. under microwave irradiation for 1 hour. The mixture was carefully added to a solution of sodium borohydride (95.7 mg, 2.53 mmol) in methanol (5 mL) at room temperature. After stirring for 5 minutes, the reaction was concentrated to dryness. Purification by column chromatography gave (+/−)-3-methyl-1-(4-(4-(trifluoromethyl)-1H-pyrazol-1-yl)phenyl)butan-1-amine (250 mg, 67%). $^1$H NMR (400 MHz, CD$_3$OD, δ): 8.69 (s, 1H), 7.91 (s, 1H), 7.76 (d, 2H), 7.46 (d, 2H), 4.09-4.05 (m, 1H), 1.67-1.60 (m, 2H), 1.37-1.34 (m, 1H), 0.86 (d, 3H), 0.82 (d, 3H).

Intermediate (15): (+/−)-tert-butyl 3-(N-tert-butyl-4-(1-hydroxy-3-methylbutyl)benzamido)propanoate

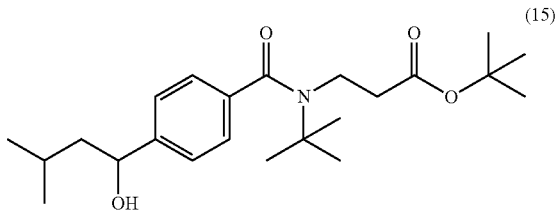 [SMILES: CC(C)CC(O)c1ccc(C(=O)N(CCC(=O)OC(C)(C)C)C(C)(C)C)cc1]

(15)

To a −20° C. solution of Intermediate 30 (1.28 g, 4.26 mmol) in tetrahydrofuran (20 mL) was added isobutylmagnesium bromide (2.13 mL, 2M in THF, 4.26 mmol). The reaction mixture was warmed to room temperature and stirred for 5 hours. Saturated ammonium chloride was added and the mixture was extracted with ethyl acetate. The combined organic layers were dried over magnesium sulfate, filtered and concentrated. Purification by column chromatography gave (+/−)-tert-butyl 3-(N-tert-butyl-4-(1-hydroxy-3-methylbutyl)benzamido)propanoate (400 mg, 24%). $^1$H NMR (400 MHz, CD$_3$OD, δ): 7.45-7.43 (m, 2H), 7.35-7.33 (m, 2H), 4.73 (m, 1H), 3.62-3.58 (m, 2H), 2.48-2.45 (m, 2H), 1.72-1.67 (m, 2H), 1.57 (s, 9H), 1.50-1.47 (m, 1H), 1.36 (s, 9H), 0.97-0.96 (m, 6H).

Intermediate (16): (+/−)-methyl 4-(2-cyclopropyl-1-hydroxyethyl)benzoate

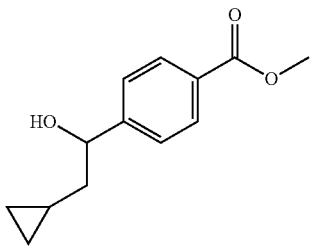

(16)

To a −40° C. solution of methyl 4-iodobenzoate (0.39 g, 1.5 mmol) in tetrahydrofuran (7.5 mL) was added isopropylmagnesium chloride-lithium chloride (1.5 mL, 1.3 M in THF, 1.95 mmol) dropwise. After stirring for 30 minutes at −40° C., 2-cyclopropylacetaldehyde (190 mg, 2.26 mmol) was added dropwise. The resulting mixture was then stirred at room temperature for 1 hour. The reaction mixture was quenched with saturated ammonium chloride and partitioned between water and ethyl acetate. The layers were separated and the aqueous was extracted again with ethyl acetate. The combined organic layers were dried over sodium sulfate, filtered and concentrated. Purification by column chromatography gave (+/−)-methyl 4-(2-cyclopropyl-1-hydroxyethyl)benzoate (150 mg, 45%). $^1$HNMR (400 MHz, CDCl$_3$, δ): 7.89 (d, 2H), 7.32 (d, 2H), 4.75-4.72 (m, 1H), 3.79 (s, 3H), 1.60-1.51 (m, 2H), 0.60-0.51 (m, 1H), 0.49-025 (m, 2H), 0.07-0.12 (m, 2H).

Intermediate (17): (+/−)-tert-butyl 3-(N-tert-butyl-4-(1-hydroxy-2-methylpropyl)benzamido)propanoate

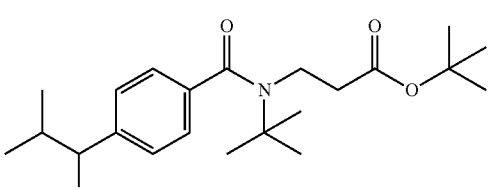

(17)

To a −20° C. solution of Intermediate (30) (100 mg, 0.3 mmol) in tetrahydrofuran (1 mL) was added isopropylmagnesium bromide (0.45 mL, 1M in THF, 0.45 mmol). The reaction mixture was stirred for 5 hours at room temperature. Saturated ammonium chloride was then added and the mixture was extracted three times with ethyl acetate. The combined organic layers were dried over magnesium sulfate, filtered and concentrated. Purification by column chromatography gave (+/−)-tert-butyl 3-(N-tert-butyl-4-(1-hydroxy-2-methylpropyl)benzamido)propanoate (45 mg, 40%). $^1$H NMR (400 MHz, CDCl$_3$, δ): 7.26-7.32 (m, 4H), 4.39-4.41 (m, 1H), 3.53-3.57 (m, 2H), 2.37-2.41 (m, 2H), 1.93-1.95 (m, 1H), 1.53 (s, 9H), 1.34 (s, 9H), 0.97 (m, 3H), 0.79 (m, 3H).

Intermediate (18): 1-azido-4-nitrobenzene

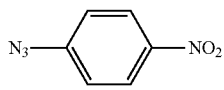

(18)

A solution of sodium nitrite (761 mg, 11 mmol) in water (5 mL) was added dropwise to a 0° C. solution of 4-nitroaniline (508 mg, 3.68 mmol) in trifluoroacetic acid (5 mL). After stirring for 10 minutes, a solution of sodium azide (1.55 g, 23.9 mmol) was added slowly. The resulting yellow suspension was stirred at room temperature for 5 hours. The reaction mixture was partitioned between water and ethyl acetate. The organic layer was dried over sodium sulfate, filtered and concentrated. Purification by column chromatography gave 1-azido-4-nitrobenzene (600 mg, 99%). $^1$H NMR (400 MHz, CDCl$_3$, δ): 8.16-8.19 (m, 2H), 7.05-7.09 (m, 2H).

Intermediate (19): (+/−)-methyl 4-(cyclopropyl(hydroxy)methyl)benzoate

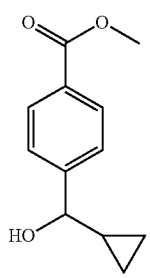

(19)

The title compound was prepared by a method analogous to that described for Intermediate (16) using cyclopropanecarbaldehyde. $^1$H NMR (400 MHz, CDCl$_3$, δ): 7.96 (d, J=6.8 Hz, 2H), 7.43 (d, J=8.4 Hz, 2H), 4.00 (d, J=8.4 Hz, 1H), 3.85 (s, 3H), 1.19-1.12 (m, 1H), 0.59-0.52 (m, 2H), 0.43-0.34 (m, 2H).

Intermediate (20): (+/−)-methyl 4-(1-hydroxybutyl)benzoate

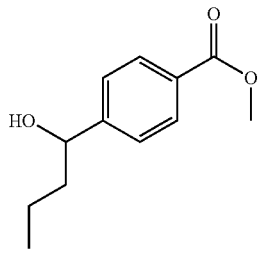

(20)

A solution of methyl 4-formylbenzoate (2.092 g, 12.74 mmol) in tetrahydrofuran (50 mL) was cooled to 0° C. To this solution was added n-propylmagnesium bromide (6.4 mL, 2.0M in THF) dropwise over 20 minutes. The reaction was stirred at 0° C. for 2 hours. The reaction was then quenched by addition of saturated ammonium chloride. This mixture was extracted with ethyl acetate twice. The organics were dried over magnesium sulfate, filtered and concentrated. Purification by column chromatography (0-40% ethyl acetate in heptanes) gave (+/−)-methyl 4-(1-hydroxybutyl)benzoate (1.252 g, 47%) as a colorless oil. $^1$H NMR (400 MHz, CDCl$_3$, δ): 7.97-8.02 (m, 2H), 7.40 (d, J=8.4 Hz, 2H), 4.74 (dd, J=7.8, 5.7 Hz, 1H), 3.90 (s, 3H), 1.61-1.82 (m, 2H), 1.23-1.49 (m, 2H), 0.92 (t, J=7.32 Hz, 3H).

Intermediate (21): methyl 4-butyrylbenzoate

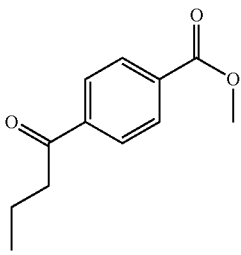

(21)

The title compound was prepared by a method analogous to that described for Intermediate (10) using Intermediate (20). $^1$H NMR (400 MHz, CDCl$_3$, δ): 8.08-8.13 (m, 2H), 7.97-8.01 (m, 2H), 3.94 (s, 3H), 2.96 (t, J=7.3 Hz, 2H), 1.77 (m, 2H), 1.00 (t, J=7.41 Hz, 3H).

Intermediate (22): 4-butyrylbenzoic acid

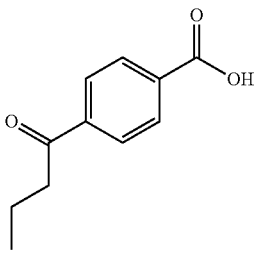

(22)

Intermediate (21) (256.1 mg, 1.242 mmol) was dissolved in tetrahydrofuran (3 mL) and methanol (3.0 mL). 1N NaOH (3.73 mL) was added and the reaction was heated to 50° C. for 3 hours. The reaction was then cooled to room temperature and concentrated. The crude residue was taken up in water and acidified to pH=5 with 1N HCl. A white precipitate formed. The solids were filtered off and dried under vacuum to give 4-butyrylbenzoic acid (155.4 mg, 65%) as a white solid. ¹H NMR (400 MHz, CDCl₃, δ): 8.16-8.21 (m, 2H), 8.01-8.05 (m, 2H), 2.98 (t, J=7.2 Hz, 2H), 1.78 (m, 2H), 1.01 (t, J=7.41 Hz, 3H).

Intermediate (23): methyl 3-(4-butyrylbenzamido)propanoate

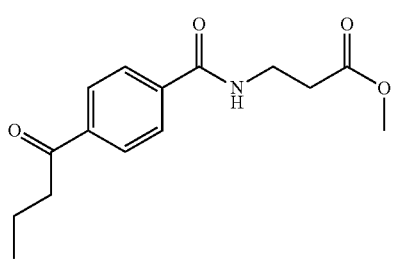

(23)

1-ethyl-3-(3-dimethylaminopropyl)carbodiimide hydrochloride (154 mg, 0.801 mmol) was added to a solution or Intermediate (22) (154 mg, 0.801 mmol), methyl 3-aminopropanoate hydrochloride (90.8 mg, 0.881 mmol), 1-hydroxy-7-azabenzotriazole (109 mg, 0.801 mmol), and triethylamine (120 µL, 0.86 mmol) in dichloromethane (8.0 mL). The reaction was stirred at room temperature for 19 hours. The reaction was diluted with dichloromethane and washed with water and brine. The organic layer was dried over magnesium sulfate, filtered, and concentrated. Purification by column chromatography (5-60% ethyl acetate in heptane) gave methyl 3-(4-butyrylbenzamido)propanoate (124.1 mg, 56%) as a white solid. ¹H NMR (400 MHz, CDCl₃, δ): 7.99 (d, J=8.4 Hz, 2H), 7.83 (d, J=8.2 Hz, 2H), 6.89 (br. s., 1H), 3.69-3.77 (m, 5H), 2.95 (t, J=7.2 Hz, 2H), 2.66 (t, J=5.8 Hz, 2H), 1.71-1.82 (m, 2H), 1.00 (t, J=7.43 Hz, 3H). MS (M+1): 278.2.

Intermediate (24): 5-iodo-2-(4-phenyl-1H-pyrazol-1-yl)pyridine

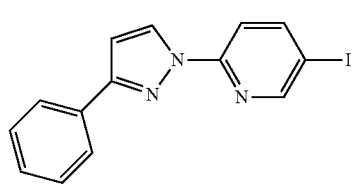

(24)

A mixture of 2-fluoro-5-iodopyridine (368.3 mg, 1.652 mmol), 4-phenyl-1H-pyrazole (238.2 mg, 1.652 mmol), and potassium carbonate (457 mg, 3.30 mmol) in N,N-dimethylformamide (3.30 mL) was heated to 85° C. for 21 hours. The reaction was then concentrated and the crude residue diluted with water and ethyl acetate. The layers were separated and the aqueous was extracted two more times with ethyl acetate. The combined organics were dried over magnesium sulfate, filtered, and concentrated to give 5-iodo-2-(4-phenyl-1H-pyrazol-1-yl)pyridine (537.2 mg, 94%) as a white solid. ¹H NMR (400 MHz, CDCl₃, δ): 8.76 (s, 1H), 8.61 (d, J=1.8 Hz, 1H), 8.09 (dd, J=8.7, 2.2 Hz, 1H), 8.01 (s, 1H), 7.82 (d, J=8.6 Hz, 1H), 7.55-7.61 (m, 2H), 7.36-7.43 (m, 2H), 7.25-7.31 (m, 1H). MS (M+1): 348.0.

Intermediate (25): 6-(4-phenyl-1H-pyrazol-1-yl)pyridin-3-amine

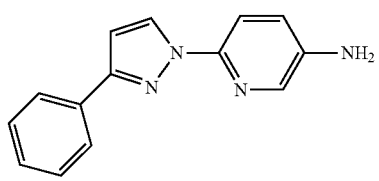

(25)

A reaction vial was oven-dried and cooled under nitrogen. To this vial was added Intermediate (24) (100.9 mg, 0.291 mmol), copper(I) iodide (11.0 mg, 0.058 mmol), trans-4-hydroxy-L-proline (15.2 mg, 0.116 mmol), potassium carbonate (122 mg, 0.873 mmol), and dimethylsulfoxide (0.58 mL). The vial was capped, evacuated, and back-filled with nitrogen 4 times. Ammonium hydroxide (28 wt %, 0.29 mL) was then added. The reaction was heated to 80° C. for 18 hours. The reaction was then cooled to room temperature and diluted with water and ethyl acetate. The layers were separated and the aqueous was extracted two more times with ethyl acetate. The combined organics were washed once with brine, dried over magnesium sulfate, filtered, and concentrated. Purification by column chromatography (5-60% ethyl acetate in heptane) gave 6-(4-phenyl-1H-pyrazol-1-yl)pyridin-3-amine (42.1 mg, 61%) as a pale yellow solid. ¹H NMR (400 MHz, CDCl₃, δ): 8.66 (s, 1H), 7.95 (s, 1H), 7.89 (d, J=2.9 Hz, 1H), 7.78 (d, J=8.8 Hz, 1H), 7.54-7.60 (m, 2H), 7.34-7.41 (m, 2H), 7.21-7.27 (m, 1H), 7.14 (dd, J=8.7, 2.8 Hz, 1H), 3.69 (br. s., 2H). MS (M+1): 237.2.

Intermediate (26): 3,5-dimethyl-4-(4-(trifluoromethyl)-1H-pyrazol-1-yl)phenol

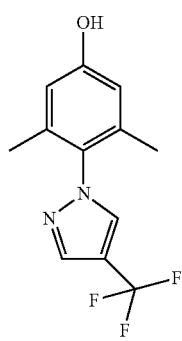

(26)

A microwave vial was charged with tris(dibenzylideneacetone)dipalladium(0) (75.9 mg, 0.13 mmol), 2-di-tert-butylphosphino-2',4',6'-triisopropylbiphenyl (22.1 mg, 0.051 mmol), and potassium hydroxide (113 mg, 1.92 mmol). The vial was capped, evacuated, and back-filled with nitrogen three times. A solution of Intermediate (7) (204 mg, 0.64 mmol) in 1,4-dioxane (0.38 mL) was added, followed by degassed water (0.38 mL). The reaction was heated at 100° C. for 2.5 hours. The reaction was quenched with 1 N HCl and extracted three times with ethyl acetate. The organics were dried over sodium sulfate, filtered and concentrated. Purification by column chromatography (0-15% ethyl acetate in heptane) provided 3,5-dimethyl-4-(4-(trifluoromethyl)-(1H-pyrazol-1-yl)phenol (120 mg, 73%) as a white solid. $^1$H NMR (400 MHz, CDCl$_3$, δ): 7.94 (s, 1H), 7.72 (s, 1H), 6.50 (s, 2H), 1.92 (s, 6H). MS (M+1): 257.

Alternatively, intermediate (26) can be prepared as follows. To a flask containing Intermediate (7) (15.0 g, 47.0 mmol) in 1,4-dioxane (28.1 mL) and degassed water (28.1 mL), was added tris(dibenzylideneacetone)dipalladium(0) (557 mg, 0.94 mmol), 2-di-tert-butylphosphino-2',4',6'-trisopropylbiphenyl (1.6 g, 3.76 mmol), and potassium hydroxide (3.3 g, 141.0 mmol). The reaction was purged with nitrogen and then heated at 95° C. for 1 hour. The reaction was quenched with 1 N HCl and extracted three times with ethyl acetate. The organics were dried over sodium sulfate, filtered and concentrated. The crude material was filtered through a plug of silica (5-10% ethyl acetate in heptane). The concentrated material was then triturated three times with heptanes to provide 3,5-dimethyl-4-(4-(trifluoromethyl)-(1H-pyrazol-1-yl)phenol (11 g, 91%) as a white solid. $^1$H NMR (400 MHz, CDCl$_3$, δ): 7.94 (s, 1H), 7.72 (s, 1H), 6.50 (s, 2H), 1.92 (s, 6H). MS (M+H): 257.

Intermediate (27): (+/−)-methyl 4-(1-(4-iodophenoxy)butyl)benzoate

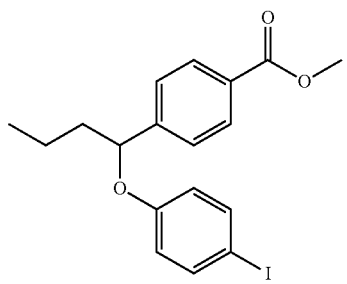

(27)

Diisopropyl azodicarboxylate (880 μL, 4.47 mmol) was added to a room temperature solution of Intermediate (20) (929 mg, 4.46 mmol), 4-iodophenol (987 mg, 4.49 mmol), and triphenylphosphine (1.17 g, 4.46 mmol) in tetrahydrofuran (22 mL). The reaction was stirred at room temperature overnight. The reaction was then diluted with diethylether (30 mL). The mixture was washed successively with 1N NaOH and saturated ammonium chloride. The organic layer was dried over magnesium sulfate, filtered and concentrated. Purification by column chromatography gave (+/−)-methyl 4-(1-(4-iodophenoxy)butyl)benzoate (1.38 g, 75%) as a colorless oil. $^1$H NMR (400 MHz, CDCl$_3$, δ): 7.95-8.00 (m, 2H), 7.39-7.45 (m, 2H), 7.32-7.38 (m, 2H), 6.52-6.59 (m, 2H), 5.03-5.10 (m, 1H), 3.88 (s, 3H), 1.89-2.01 (m, 1H), 1.70-1.82 (m, 1H), 1.33-1.52 (m, 2H), 0.89-0.95 (m, 3H).

Intermediate (28): Preparation of 1-(4-methoxyphenyl)-4-(trifluoromethyl)-1H-pyrazole

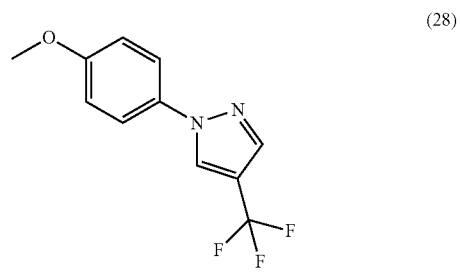 [SMILES: COc1ccc(-n2cc(C(F)(F)F)cn2)cc1]

(28)

(Z)—N-(3-(dimethylamino)-2-(trifluoromethyl)allylidene)-N-methyl methanaminium hexafluorophosphate (4.46 g, 13.1 mmol) and 4-methoxyphenyl hydrazine hydrochloride (2.55 g, 14.6 mmol) were suspended in tetrahydrofuran (50 mL) and cooled to 0° C. Sodium methoxide (820 mg, 14 mmol) was added as a solid in one portion. The mixture was stirred at 0° C. for 10 minutes. The ice bath was removed and the mixture was stirred at room temperature for 1 hour. The mixture was cooled again to 0° C. and trifluoroacetic acid (3 mL) was added. The ice bath was removed and the mixture heated to reflux. After 18 hours at reflux, the reaction was cooled to room temperature and diluted with ethyl acetate (50 mL). The mixture was washed successively with saturated sodium bicarbonate until the washings were basic. The combined aqueous washings were extracted with ethyl acetate. The combined organic layers were washed with brine, dried over magnesium sulfate, filtered and concentrated. The crude material was passed through a plug of silica gel (100 g), eluting with dichloromethane (600 mL). The filtrate was concentrated to give 1-(4-methoxyphenyl)-4-(trifluoromethyl)-1H-pyrazole (2.7 g, 85%). $^1$H NMR (400 MHz, CDCl$_3$, δ): 8.06 (s, 1H), 7.85 (s, 1H), 7.53-7.59 (m, 2H), 6.94-7.00 (m, 2H), 3.84 (s, 3H).

Intermediate (29): 4-(4-(trifluoromethyl)-1H-pyrazol-1-yl)phenol

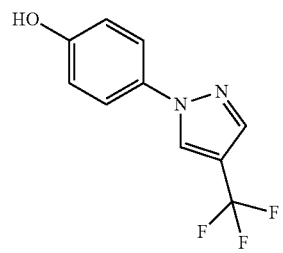

(29)

Intermediate (28) (2.63 g, 10.9 mmol) was dissolved in dichloromethane (50 mL). The solution was cooled to −78° C. Boron tribromide (2.0 mL, 21 mmol) was added dropwise over 10 minutes. Following the addition, the mixture was allowed to gradually warm to room temperature and stir overnight. The resulting clear red solution was cooled to 0° C. and additional boron tribromide (1 mL) was added. The ice bath was removed and the solution stirred at room temperature. After 6 hours the solution was cooled to 0° C. and quenched by slow addition of anhydrous methanol (15 mL). The resulting mixture was washed with water. The aqueous layer was extracted with ethyl acetate. The combined organic layers were washed with brine, dried over magnesium sulfate, filtered and concentrated to give 4-(4-(trifluoromethyl)-1H-pyrazol-1-yl)phenol (2.46 g, 99%). $^1$H NMR (400 MHz, CDCl$_3$, δ): 8.04 (s, 1H), 7.86 (s, 1H), 7.45-7.51 (m, 2H), 6.85-6.92 (m, 2H), 5.65-5.85 (br s, 1H).

Intermediate (30): tert-butyl 3-(N-tert-butyl-4-formylbenzamido)propanoate

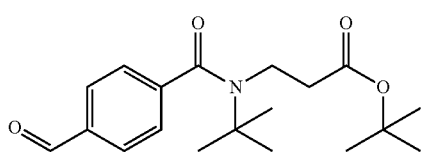

(30)

N,N-dimethylformamide (25 µL) was added to a room temperature suspension of 4-carboxybenzaldehyde (2.0 g, 13 mmol) and oxalyl chloride (1.14 mL, 13.3 mmol) in dichloromethane (50 mL). The reaction was stirred at room temperature 30 minutes, then heated to reflux for 5 hours. The reaction mixture was concentrated. A solution of tert-butyl 3-(tert-butylamino)propanoate (2.68 g, 13.3 mmol) and triethylamine (1.9 mL, 13 mmol) in dichloromethane (50 mL) was added to the crude acid chloride. The mixture was stirred at room temperature overnight. The reaction was washed with water, then brine. The organic layer was dried over magnesium sulfate, filtered and concentrated to give tert-butyl 3-(N-tert-butyl-4-formylbenzamido)propanoate (4.47 g, 100%). $^1$H NMR (400 MHz, CDCl$_3$, δ): 10.01 (s, 1H), 7.86-7.91 (m, 2H), 7.45-7.49 (m, 2H), 3.46-3.54 (m, 2H), 2.34-2.41 (m, 2H), 1.52 (s, 9H), 1.31 (s, 9H).

Intermediate (31): ethyl 4-(cyclopentanecarbonyl)benzoate

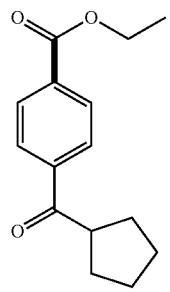

(31)

At −40° C., isopropylmagnesium chloride lithium chloride (13.9 mL, 1.3 M in THF) was added dropwise to a solution of ethyl 4-iodobenzoate (4971 mg, 18.01 mmol) in tetrahydrofuran (30 mL). The solution was stirred at −40° C. for 50 minutes. Copper(I) iodide (1.03 g, 5.4 mmol) was added. The mixture was allowed to warm to −15° C. and stir for 8 minutes. The solution was cooled back to −40° C. and cyclopentanecarbonyl chloride (3580 mg, 27.0 mmol) was added dropwise. The mixture was allowed to gradually warm to 0° C. over 3 hours. The mixture was quenched with 1 N HCl (20 mL) and diluted with ethyl acetate. The mixture was stirred at room temperature for 5 min. A white precipitate formed. The mixture was filtered through celite and the filtrate transferred to a separatory funnel. The layers were separated. The aqueous was extracted twice with ethyl acetate. The combined organics were washed with brine, dried over sodium sulfate, filtered and concentrated. Purification by column chromatography (0-20% ethyl acetate in heptane) gave ethyl 4-(cyclopentanecarbonyl)benzoate as an oil. $^1$H NMR (400 MHz, CDCl$_3$, δ): 8.13-8.08 (m, 2H), 8.02-7.97 (m, 2H), 4.39 (q, J=7.22 Hz, 2H), 3.77-3.65 (m, 1H), 1.99-1.79 (m, 4H), 1.77-1.60 (m, 4H), 1.40 (t, J=7.22 Hz, 3H).

Intermediate (32): 6-(4-(trifluoromethyl)-1H-pyrazol-1-yl)pyridin-3-amine

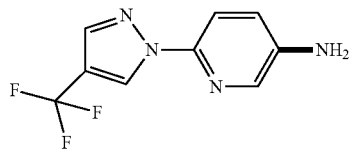

(32)

The title compound was prepared by a method analogous to that described for Intermediate (6) using 4-(trifluoromethyl)-1H-pyrazole. $^1$H NMR (400 MHz, CDCl$_3$, δ): 8.68 (s, 1H), 7.86 (d, J=2.73 Hz, 1H), 7.82 (s, 1H), 7.75 (d, J=8.58 Hz, 1H), 7.13 (dd, J=8.68, 2.83 Hz, 1H), 3.77 (br. s, 2H). MS (M+1): 229.1.

Intermediate (33): (+/−)-1-(4-bromophenyl)-3-methylbutan-1-ol

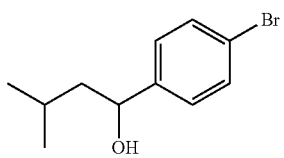

4-bromo-iodobenzene (1.42 g, 5.00 mmol) was dissolved in tetrahydrofuran (50 mL) and cooled to −40° C. A solution of isopropylmagnesium chloride lithium chloride (5 mL, 1.3 M in THF) was added dropwise over 5 minutes. The mixture was stirred at −40° C. for 30 minutes, then 3-methylbutanal (0.81 mL, 7.5 mmol) was added. The reaction was allowed to warm to room temperature and stir for 1 hour. The reaction was then quenched by addition of saturated ammonium chloride (10 mL) and water (40 mL). The mixture was diluted with ethyl acetate (50 mL), and the layers were separated. The organics were washed with water (50 mL) and brine (25 mL), dried over sodium sulfate, filtered and concentrated. Purification by column chromatography (0-50% ethyl acetate in heptane) gave (+/−)-1-(4-bromophenyl)-3-methylbutan-1-ol (958 mg, 79%) as a clear oil. $^1$H NMR (400 MHz, CDCl$_3$, δ):

7.47-7.41 (m, 2H), 7.22-7.17 (m, 2H), 4.68 (dd, J=8.1, 5.4 Hz, 1H), 1.97 (br.s, 1H), 1.71-1.61 (m, 2H), 1.49-1.39 (m, 1H), 0.94-0.90 (m, 6H).

Intermediate (34): (+/−)-methyl 4-(1-(4-bromophenyl)-3-methylbutoxy)benzoate

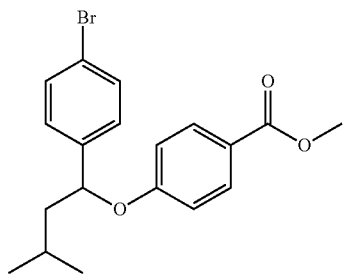
(34)

Methyl 4-hydroxybenzoate (609 mg, 4.00 mmol), 1-(4-bromophenyl)-3-methylbutan-1-ol (1.95 g, 8.00 mmol) and triphenylphosphine (2.10 g, 8.00 mmol) were dissolved in tetrahydrofuran (10 mL). Diisopropyl azodicarboxylate (1.58 mL, 8.00 mmol) was added. The resulting solution was stirred at room temperature overnight. The reaction was diluted with ethyl acetate (50 mL) and washed with 0.1M HCl (3×100 mL) and brine. The organics were dried over magnesium sulfate, filtered and concentrated. Purification by column chromatography (0-30% ethyl acetate in heptane) gave (+/−)-methyl 4-(1-(4-bromophenyl)-3-methylbutoxy)benzoate (1.4 g, 93%) as a clear oil. $^1$H NMR (400 MHz, CDCl$_3$, δ): 7.89-7.83 (m, 2H), 7.46-7.40 (m, 2H), 7.21-7.16 (m, 2H), 6.83-6.78 (m, 2H), 5.16 (dd, J=9, 4.7 Hz, 1H), 3.83 (s, 3H), 1.99-1.91 (m, 1H), 1.88-1.75 (m, 1H), 1.58-1.51 (m, 1H), 0.97 (d, J=6.6 Hz, 3H), 0.92 (d, J=6.6 Hz, 3H).

Intermediate (35): (+/−)-1-(5-bromopyridin-2-yl)butan-1-ol

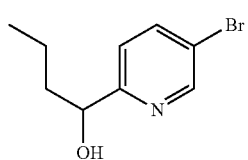
(35)

2,5-Dibromopyridine (1.08 g, 4.6 mmol) was azeotroped with toluene several times, then dissolved in anhydrous toluene (12 mL) under a nitrogen atmosphere. The resulting solution was cooled to −78° C. and n-butyl lithium (2.4 mL, 2.1 M in hexane, 5.0 mmol) was added dropwise, maintaining an internal temperature below −70° C. The resulting orange solution was stirred for 30 minutes at −78° C., then butyraldehyde was added. The resulting solution was stirred for 30 minutes at −78° C. then quenched by addition of saturated ammonium chloride. The resulting mixture was warmed to room temperature and diluted with ethyl acetate (25 mL) and water (25 mL). The layers were separated. The organics were washed with brine, dried over sodium sulfate, filtered and concentrated. Purification by column chromatography (0-50% ethyl acetate in heptane) gave (+/−)-1-(5-bromopyridin-2-yl)butan-1-ol (738 mg, 70%) as a clear oil. $^1$H NMR (400 MHz, CDCl$_3$, δ): 8.57 (d, J=2.3 Hz, 1H), 7.77 (dd, J=8.3, 2.2 Hz, 1H), 7.17 (d, J=8.4 Hz, 1H), 4.72-4.66 (m, 1H), 3.58 (d, J=5.7 Hz, 1H), 1.79-1.57 (m, 2H), 1.47-1.35 (m, 2H), 0.91 (t, J=7.4 Hz, 3H).

Intermediate (36): (+/−)-5-bromo-2-(1-(4-iodophenoxy)butyl)pyridine

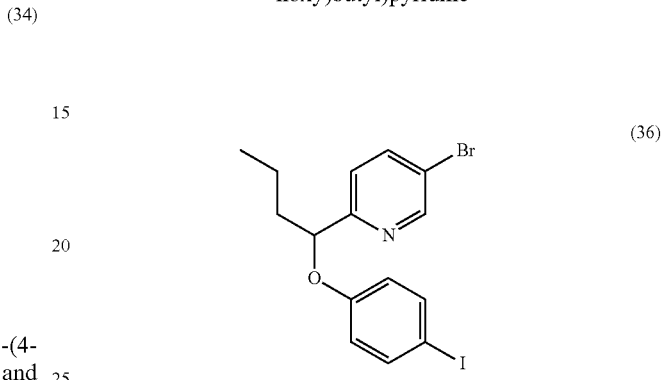
(36)

Intermediate (35) (738 mg, 3.21 mmol), 4-iodophenol (1.06 g, 4.81 mmol) and triphenylphosphine (1.68 g, 6.41 mmol) were dissolved in tetrahydrofuran (10 mL). Diisopropyl azodicarboxylate (1.34 mL, 6.41 mmol) was added. The resulting solution was allowed to stir at room temperature overnight. The reaction was heated to 50° C. and allowed to stir for 24 hours. The reaction was concentrated. Purification by column chromatography (0-100% ethyl acetate in heptane) gave (+/−)-5-bromo-2-(1-(4-iodophenoxy)butyl)pyridine (540 mg, 39%) as a clear oil. $^1$H NMR (400 MHz, CDCl$_3$, δ): 8.61 (d, J=2.3 Hz, 1H), 7.73 (dd, J=8.4, 2.3 Hz, 1H), 7.48-7.42 (m, 2H), 7.22 (d, J=8.4 Hz, 1H), 6.62-6.56 (m, 2H), 5.13 (dd, J=8.1, 4.8 Hz, 1H), 1.99-1.81 (m, 2H), 1.57-1.36 (m, 2H), 0.94 (t, J=7.4 Hz, 3H). MS (M+1): 432.0.

Intermediate (37): (+/−)-methyl 4-(cyclopentyl(hydroxy)methyl)benzoate

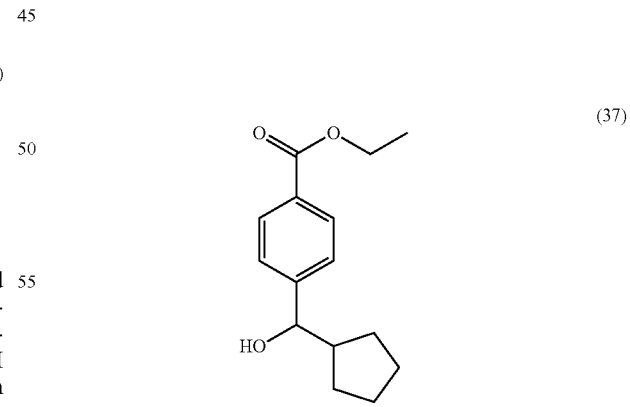
(37)

The title compound was prepared by a method analogous to that described for Intermediate (16) using cyclopentanecarbaldehyde. $^1$H NMR (400 MHz, CDCl$_3$, δ): 8.005 (m, 2H), 7.413 (m, 2H), 4.50 (m, 1H), 3.90 (s, 3H), 2.25-2.15 (m, 1H), 1.87-1.71 (m, 2H), 1.70-1.49 (m, 6H), 1.47-1.43 (m, 1H), 1.30-1.11 (m, 1H).

Intermediate (38): 6-(4-(trifluoromethyl)-1H-pyrazol-1-yl)pyridin-3-ol

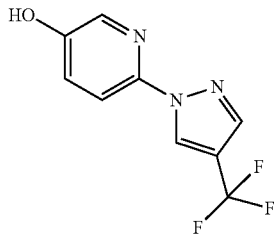
(38)

Concentrated sulfuric acid (5.5 mL) was added to water (20 mL) and cooled to 0° C. Intermediate (32) (500 mg, 2.19 mmol) was added, followed by the dropwise addition of a solution of sodium nitrite (133 mg, 1.93 mmol) in water (1.5 mL). The reaction was stirred at 0° C. for 30 minutes. The reaction was then poured into a boiling mixture of water (29 mL) and concentrated sulfuric acid (2.6 mL) and stirred for 30 minutes. The reaction was cooled to room temperature, poured onto ice, and extracted with ethyl acetate. The organic layer was dried over sodium sulfate, filtered and concentrated to give 6-(4-(trifluoromethyl)-1H-pyrazol-1-yl)pyridin-3-ol (220 mg, 44%). $^1$H NMR (400 MHz, CD$_3$OD, δ): 8.71 (s, 1H), 7.89 (m, 1H), 7.84 (s, 1H), 7.71 (m, 1H), 7.27-7.24 (m, 1H).

Intermediate (39): 1-benzyl-1H-pyrazol-4-ol

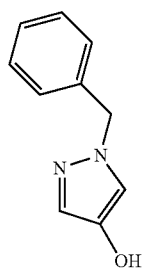
(39)

1-benzyl-4-(4,4,5,5-tetramethyl-1,3,2-dioxaborolan-2-yl)-1H-pyrazole (2.0 g, 7.03 mmol) was dissolved in tetrahydrofuran (18 mL) and cooled to 0° C. 2N NaOH (7.03 mL, 14.06 mmol) and 30% peroxide (14.07 mL) were added and the reaction was stirred at room temperature for 45 minutes. The reaction was acidified to pH=2 by addition of 2N HCl and extracted with dichloromethane. The organic layer was dried over sodium sulfate, filtered and concentrated to give 1-benzyl-1H-pyrazol-4-ol (1.54 g) as a yellow solid. $^1$H NMR (400 MHz, CDCl$_3$, δ): 7.25-7.21 (m, 3H), 7.08-7.07 (m, 3H), 6.91 (s, 1H), 5.06 (s, 2H).

Intermediate (40): 1-benzyl-4-methoxy-1H-pyrazole

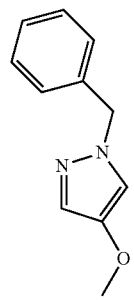
(40)

To a mixture of Intermediate (39) (588 mg, 3.38 mmol) and cesium carbonate (1540 mg, 4.73 mmol) in N,N-dimethylformamide (14.7 mL) was added iodomethane (672 mg, 4.73 mmol). The reaction mixture was stirred at room temperature for 1 hour. The reaction was diluted with water and extracted with ethyl acetate. The organic layer was dried over sodium sulfate, filtered and concentrated. Purification by column chromatography gave 1-benzyl-4-methoxy-1H-pyrazole (0.586 g, 92%) as a yellow oil. $^1$HNMR (400 MHz, CDCl$_3$, δ): 7.29-7.22 (m, 3H), 7.19 (s, 1H), 7.14 (m, 2H), 6.95 (s, 1H), 5.13 (s, 2H), 3.64 (s, 3H).

Intermediate (41): 4-methoxy-1H-pyrazole

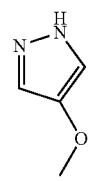
(41)

Intermediate (40) (586 mg, 3.11 mmol) was dissolved in methanol (70 mL) and 1N HCl (7.78 mL). Palladium hydroxide on carbon (0.734 g, 4.83 mmol) was added. The mixture was pressurized to 50 psi hydrogen and agitated at room temperature overnight. The reaction mixture was filtered through celite and the filtrate concentrated to give 4-methoxy-1H-pyrazole (110 mg, 36%) as a yellow oil. $^1$H NMR (400 MHz, CD$_3$OD, δ): 7.64 (br s, 2H), 3.64 (s, 3H).

Intermediate (42): (+/−)-methyl 4-(1-hydroxy-3,3-dimethylbutyl)benzoate

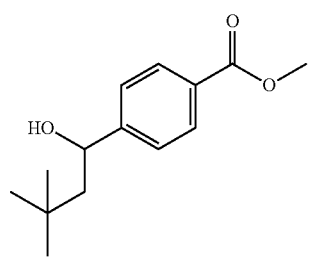
(42)

To a −40° C. solution of methyl 4-iodobenzoate (1 g, 4 mmol) in tetrahydrofuran (10 mL) was added isopropylmagnesium chloride lithium chloride (3.82 mL, 1.3 M in THF, 4.98 mmol). The mixture was stirred at −40° C. for 30 minutes, 3,3-Dimethylbutanal (573 mg, 2.86 mmol) was added. The reaction was stirred at room temperature for 4 hours. Water (10 mL) was added and the mixture was extracted with ethyl acetate. The organic layer was dried over sodium sulfate, filtered and concentrated. Purification by column chromatography gave (+/−)-methyl 4-(1-hydroxy-3,3-dimethylbutyl)benzoate (640 mg, 95%). ¹H NMR (400 MHz, CDCl₃, δ): 7.93 (d, 2H), 7.34 (d, 2H), 4.81-4.84 (m, 1H), 3.84 (s, 3H), 1.70-1.61 (m, 1H), 1.53-1.49 (m, 1H), 0.94 (s, 9H).

Intermediate (43): methyl 4-(3,3-dimethylbutanoyl)benzoate

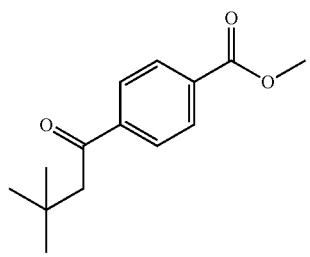

(43)

To a 0° C. solution of Intermediate (42) (0.300 g, 1.27 mmol) in tetrahydrofuran (10 mL) was added trifluoroacetic acid (261 mL, 2.29 mmol) followed by 1,1,1-Tris(acetyloxy)-1,1-dihydro-1,2-benziodoxol-3-(1H)-one (862 mg, 2.03 mmol). The reaction was stirred at room temperature for 2 hours. The reaction mixture was quenched by addition of 1M sodium hydrosulfite (10 mL) and extracted with ethyl acetate. The organic layer was dried over sodium sulfate, filtered and concentrated. Purification by column chromatography gave methyl 4-(3,3-dimethylbutanoyl)benzoate (220 mg, 74%). ¹H NMR (400 MHz, CDCl₃, δ): 8.04 (d, 2H), 7.90 (d, 2H), 3.88 (s, 3H), 2.82 (s, 2H), 0.99 (s, 9H).

Intermediate (44): methyl 4-(cyclohexanecarbonyl)benzoate

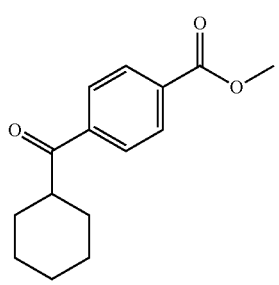

(44)

Magnesium turnings (324 mg, 13.5 mmol) were suspended in tetrahydrofuran (20 mL). A crystal of iodine was added. Bromocyclohexane (2.00 g, 12.26 mmol) was added dropwise. The mixture was refluxed for 2 hours. The mixture was then added to a −5° C. solution of methyl 4-(methoxy(methyl)carbamoyl)benzoate (456 mg, 2.04 mmol) in tetrahydrofuran (5 mL). The reaction was stirred 1 hour, maintaining an internal temperature below 0° C. The reaction was quenched with saturated ammonium chloride and extracted with ethyl acetate. The organic layer was dried over sodium sulfate, filtered, and concentrated. Purification by column chromatography gave methyl 4-(cyclohexanecarbonyl)benzoate (160 mg, 32%). ¹H NMR (400 MHz, CDCl₃, δ): 8.10-8.12 (m, 2H), 7.96-7.98 (m, 2H), 3.94 (s, 3H), 3.22-3.25 (m, 1H), 1.90-1.82 (m, 4H), 1.76-1.72 (m, 1H), 1.25-1.50 (m, 5H).

Intermediate (45): (+/−)-methyl 4-(cyclobutyl(hydroxy)benzoate

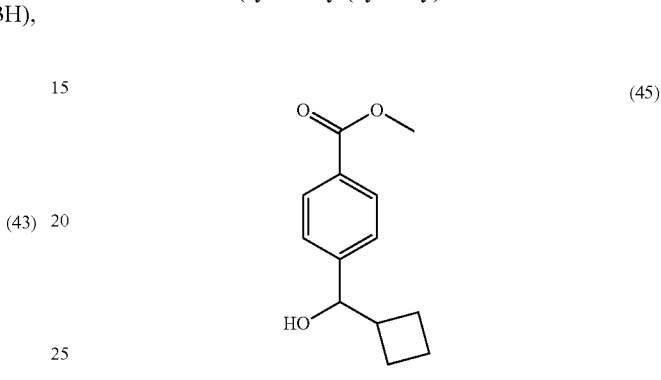

(45)

The title compound was prepared by a method analogous to that described for Intermediate (16) using cyclobutanecarbaldehyde. ¹H NMR (400 MHz, CDCl₃, δ): 7.93-8.00 (m, 2H), 7.35-7.39 (m, 2H), 4.64 (m, 1H), 3.90 (s, 3H), 2.57-2.65 (m, 1H), 1.95-2.08 (m, 2H), 1.80-1.91 (m, 4H).

Intermediate (46): (+/−)-tert-butyl 3-(N-tert-butyl-4-(1-hydroxypropyl)benzamido)propanoate

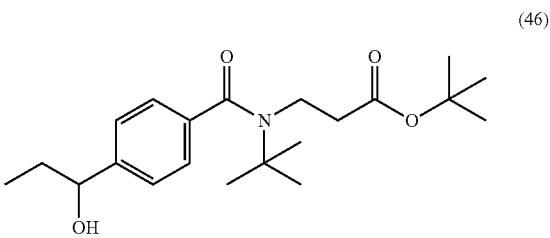 [SMILES: CCC(O)c1ccc(C(=O)N(CCC(=O)OC(C)(C)C)C(C)(C)C)cc1]

(46)

The title compound was prepared by a method analogous to that described for Intermediate (17), using ethylmagnesium bromide. ¹H NMR (400 MHz, CDCl₃, δ): 7.29-7.35 (m, 4H), 4.59-4.62 (m, 1H), 3.53-3.57 (m, 2H), 2.37-2.41 (m, 2H), 1.71-1.83 (m, 2H), 1.53 (s, 9H), 1.34 (s, 9H), 0.87-0.91 (m, 3H).

Intermediate (47): 4-(4-methyl-1H-1,2,3-triazol-1-yl)aniline

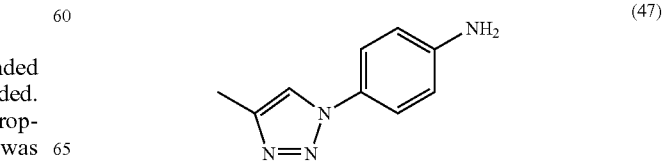

(47)

A solution of 1-azido-4-nitrobenzene (0.500 g, 3.05 mmol) and 3-bromoprop-1-yne (1.45 g, 12.2 mmol) in toluene (3 mL) was heated to 60° C. for 24 hours in a sealed tube. Additional 3-bromoprop-1-yne (1.45 g, 12.2 mmol) was added and the solution stirred at 60° C. overnight. The reaction mixture was concentrated to an orange solid. The crude residue was dissolved in ethanol (100 mL). 10 wt % Palladium on carbon (150 mg) was added and the mixture was pressurized to 50 psi hydrogen and stirred for 18 hours. The reaction mixture was filtered through celite and the filtrate was concentrated. The residue was slurried in ethyl acetate. The mixture was filtered, and the solid dried under vacuum to give 4-(4-methyl-1H-1,2,3-triazol-1-yl)aniline (300 mg). $^1$HNMR (400 MHz, CD$_3$OD, δ): 8.37 (s, 1H), 8.03 (m, 2H), 7.58 (m, 2H), 2.44 (s, 3H).

Intermediate (48): (+/−)-tert-butyl 3-(N-tert-butyl-4-(1-hydroxybutyl)benzamido) propanoate

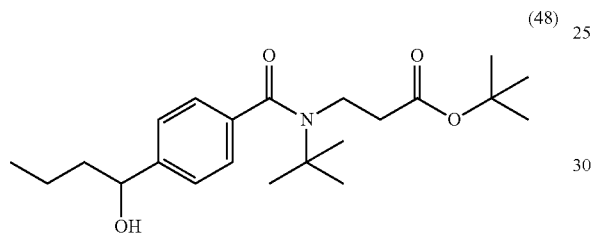
(48)

The title compound was prepared by a method analogous to that described for Intermediate (17) using n-propylmagnesium bromide. $^1$H NMR (400 MHz, CDCl$_3$, δ): 7.33 (m, 4H), 4.69 (m, 1H), 3.55 (m, 2H), 2.41 (m, 2H), 1.77 (m, 4H), 1.52 (s, 9H), 1.42 (s, 9H), 0.90 (m, 3H).

Intermediate (49): (+/−)-methyl 4-(1-(5-iodopyridin-2-yloxy)butyl)benzoate

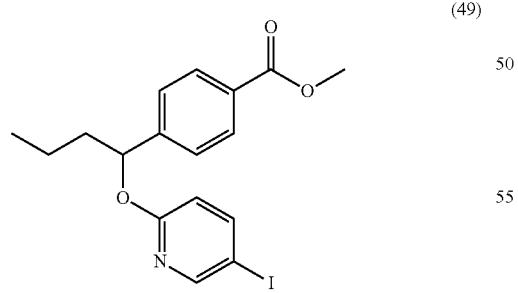
(49)

The title compound was prepared by a method analogous to that described for Intermediate (27) using 2-hydroxy-5-iodopyridine. $^1$H NMR (400 MHz, CDCl$_3$, δ): 8.19 (d, J=2.5 Hz, 1H), 7.99-7.94 (m, 2H), 7.73 (dd, J=8.7, 2.4 Hz, 1H), 7.44-7.39 (m, 2H), 6.61 (d, J=8.6 Hz, 1H), 6.00 (dd, J=7.8, 5.7 Hz, 1H), 3.87 (s, 3H), 2.03-1.92 (m, 1H), 1.85-1.74 (m, 1H), 1.49-1.27 (m, 2H), 0.92 (t, J=7.41 Hz, 3H). MS (M+1): 412.1.

Intermediate (50): 6-(4-(trifluoromethyl)-1H-imidazol-1-yl)pyridin-3-ol

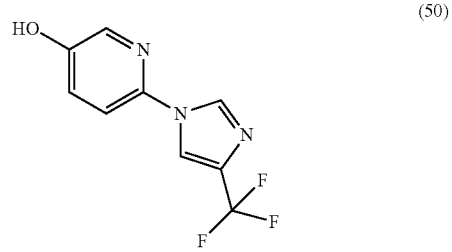 [SMILES: Oc1ccc(-n2cnc(C(F)(F)F)c2)nc1]
(50)

The title compound was prepared by a method analogous to that described for Intermediate (38) using Intermediate (6). $^1$H NMR (400 MHz, CD$_3$OD, δ): 8.71 (s, 1H), 7.89 (d, 1H), 7.84 (s, 1H), 7.71 (m, 1H), 7.27-7.24 (m, 1H).

Intermediate (51): 1-(4-nitrophenyl)-4-(trifluoromethyl)-1H-pyrazole

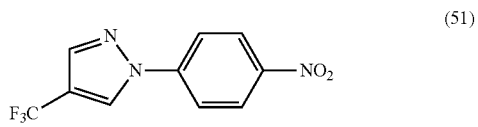
(51)

The title compound was prepared by a method analogous to that described for Intermediate (3), using 1-fluoro-4-nitrobenzene and 4-(trifluoromethyl)-1H-pyrazole. $^1$H NMR (400 MHz, CDCl$_3$, δ): 8.38 (m, 1H), 8.30 (m, 1H), 7.97 (s, 2H), 7.90 (m, 2H).

Intermediate (52): 4-[4-(trifluoromethyl)-1H-pyrazol-1-yl]aniline

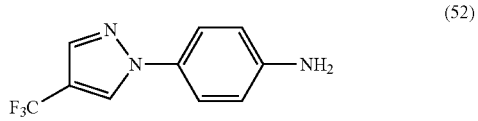 [SMILES: O=[N+]([O-])c1ccc(-n2cc(C(F)(F)F)cn2)cc1]
(52)

The title compound was prepared by a method analogous to that described for Intermediate (4) using Intermediate (51). $^1$H NMR (400 MHz, CDCl$_3$, δ): 8.03 (m, 1H), 7.85 (s, 1H), 7.43 (dt, J=9.0, 2.9 Hz, 2H), 6.75 (dt, J=9.0, 3.1 Hz, 2H).

Intermediate (53): 1-(4-nitrophenyl)-4-(trifluoromethyl)-1H-imidazole

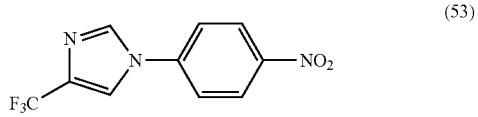 [SMILES: O=[N+]([O-])c1ccc(-n2cnc(C(F)(F)F)c2)cc1]
(53)

The title compound was prepared by a method analogous to that described for Intermediate (3) using 1-fluoro-4-nitrobenzene. The crude product was recrystallized from toluene and minimal ethyl acetate to afford the product as a white powder. MS (M+1): 257.0.

Intermediate (54):
4-[4-(trifluoromethyl)-1H-imidazol-1-yl]aniline

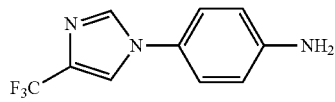

(54)

A solution of Intermediate (53) (3.02 g, 11.7 mmol) and di-tert-butyl dicarbonate (4.05 mL, 17.6 mmol) in ethanol (117 mL) was passed through an H-Cube reactor (50° C., 50 bar, 1 mL/min, 10% Pd/C cartridge). The reaction mixture was concentrated and the crude oil was heated at 40° C. overnight. The crude oil was then treated with trifluoroacetic acid (8.7 mL) in dicholoromethane (15.6 mL). The mixture was stirred for 30 min whereupon the reaction mixture was concentrated and the residual trifluoroacetic acid was removed via a toluene azeotrope. Purification via column chromatography (0-70% ethyl acetate in heptane) gave 4-[4-(trifluoromethyl)-1H-imidazol-1-yl]aniline (1.23 g, 46%) as a solid. $^1$H NMR (400 MHz, CD$_3$OD, δ): 8.15 (s, 1H), 8.02 (m, 1H), 7.48 (dd, J=8.8, 2.9 Hz, 2H), 7.10 (dd, J=8.6, 2.9 Hz, 2H).

Intermediate (55): 4-(2H-indazol-2-yl)phenol

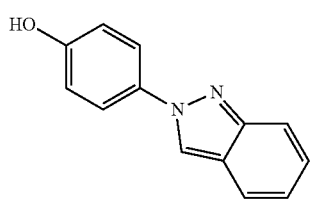

(55)

4-Bromophenol (2.00 g, 11.6 mmol) was combined with 1H-indazole (1.64 g, 13.9 mmol), copper(I) iodide (110 mg, 0.578 mmol), potassium phosphate (5.15 g, 24.3 mmol), trans-dimethylcyclohexane-1,2-diamine (0.365 mL, 2.31 mmol), and toluene (10 mL). The reaction was refluxed for 21 hours, then cooled to room temperature and partitioned between ethyl acetate and water/ammonium hydroxide. The organic layer was washed with 0.5 N HCl and brine, dried over magnesium sulfate, filtered and concentrated. Purification by column chromatography (0-40% ethyl acetate in heptane) gave 4-(2H-indazol-2-yl)phenol (0.479 g, 20%) as a tan solid. $^1$H NMR (400 MHz, (CD$_3$)$_2$SO, δ): 9.84 (s, 1H), 8.90 (s, 1H), 7.86 (d, J=8.8 Hz, 2H), 7.74 (d, J=8.4 Hz, 1H), 7.68 (d, J=8.8 Hz, 1H), 7.22-7.33 (m, 1H), 7.03-7.12 (m, 1H), 6.94 (d, J=8.8 Hz, 2H). MS (M+1): 211.2.

Intermediate (56): (R)-ethyl 4-(1-hydroxybutyl)benzoate

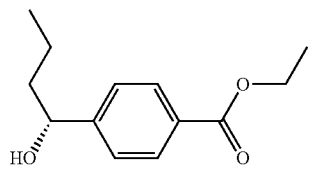

(56)

A mixture of Intermediate (5) (30.0 g, 140 mmol) and [N-[(1R,2R)-2-(amino-κN)-1,2-diphenylethyl]-4-methyl-benzenesulfonamidato-κN]chloro[(1,2,3,4,5,6-q)-1,3,5-trimethylbenzene]-ruthenium (2.12 g, 3.40 mmol) was suspended in a 5:2 azetropic mixture of formic acid and triethylamine (68.1 mL). The mixture was stirred at ambient temperature for 12 hours. The reaction was quenched with water and extracted three times with ethyl acetate. The combined organic layers were washed with concentrated sodium bicarbonate, dried over sodium sulfate, filtered, and concentrated in vacuo. The crude oil was dissolved in dichloromethane (1.0 L) and silacycle Si-Thiol (90 g) was added. The mixture was slurried for twelve hours at ambient temperature. The crude mixture was filtered and concentrated in vacuo to give primarily (R)-ethyl 4-(1-hydroxybutyl)benzoate (30.0 g, 100%). $^1$H NMR (400 MHz, CDCl$_3$, δ): 7.98 (d, J=8.4 Hz, 2H), 7.38 (d, J=8.0 Hz, 2H), 4.71 (dd, J=7.4, 5.7 Hz, 1H), 4.34 (q, J=7.0 Hz, 2H), 1.58-1.81 (m, 2H), 1.29-1.48 (m, 2H), 1.36 (t, J=7.1 Hz, 3H), 0.90 (t, J=7.3 Hz, 3H). Chiral HPLC: Chiralpak AD-H, 4.6 mm×25 cm; SFC Mobile Phase 80:20 CO$_2$/Methanol, 2.5 mL/min, Retention time: 3.13 min (R-ent, 92.9%), 3.41 min (S-ent, 7.1%), 86% ee. The (R)-enantiomer was further resolved by chiral SFC to give optically pure (R)-ethyl 4-(1-hydroxybutyl)benzoate. Column: Chiralpak AD-H. Dimensions: 21×250 mm. Mobile Phase: 80/20 CO$_2$/methanol. Flow Rate: 65 mL/min. Modifier: none. Retention time: 2.91 min.

Intermediate (57): ethyl 4-(3-methylbutanoyl)benzoate

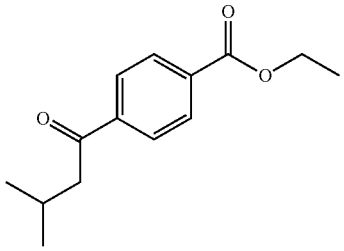 [SMILES: CCOC(=O)c1ccc(C(=O)CC(C)C)cc1]

Step A: (+/−)-ethyl 4-(1-hydroxy-3-methylbutyl)benzoate

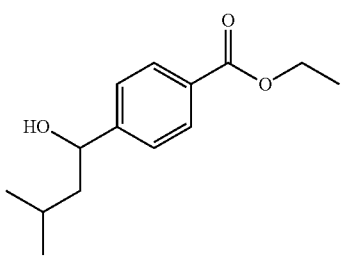 [SMILES: CCOC(=O)c1ccc(C(O)CC(C)C)cc1]

To a solution of ethyl 4-iodobenzoate (20 g, 72 mmol) in tetrahydrofuran (200 mL) at −40° C. was added isopropylmagnesium chloride lithium chloride (62 mL, 80 mmol, 1.3 M in THF) dropwise, maintaining the internal temperature below −30° C. The mixture was stirred for 30 minutes and 3-methylbutanal (8.68 g, 101 mmol) was then added dropwise, maintaining the internal temperature below −35° C. Following the addition, the reaction was allowed to stir for 15 minutes at −35° C. and was then allowed to warm to room temperature. The reaction was quenched with 1 N aqueous hydrochloric acid (400 mL), and the mixture was extracted with ethyl acetate (2×200 mL). The organics were washed with brine (200 mL) and water (200 mL), dried over sodium sulfate, filtered and concentrated to give ethyl 4-(1-hydroxy-3-methylbutyl)benzoate (16 g, 93%) as an oil. $^1$H NMR (400 MHz, CDCl$_3$, δ): 7.95 (d, J=8.4 Hz, 2H), 7.34 (d, J=8.4 Hz, 2H), 4.73-4.76 (m, 1H), 4.28-4.33 (m, 2H), 1.60-1.71 (m, 2H), 1.41-1.46 (m, 1H), 1.31-1.39 (m, 3H), 0.87-0.92 (m, 6H).

Step B: ethyl 4-(3-methylbutanoyl)benzoate

A mixture of ethyl 4-(1-hydroxy-3-methylbutyl)benzoate (15 g, 63 mmol), dichloromethane (150 mL), dimethylsulfoxide (198 g, 2540 mmol), and triethylamine (32 g, 317 mmol) was cooled to 0° C. Sulfur trioxide pyridine complex (30 g, 190 mmol) was added in portions, maintaining the internal temperature below 50° C. The mixture was stirred at 0° C. for 1 hour. The reaction was then allowed to warm to room temperature and stir for 36 hours. The reaction was diluted with brine (300 mL) and extracted with methyl tert-butylether (2×500 mL). The combined organics were washed with 1 N aqueous hydrochloric acid (500 mL), dried over sodium sulfate, filtered, and concentrated. Purification by flash column chromatography gave ethyl 4-(3-methylbutanoyl)benzoate (12 g, 80%) as a white solid. $^1$H NMR (400 MHz, CDCl$_3$, δ): 8.11 (dd, J=1.6, 6.8 Hz, 2H), 7.98 (d, J=6.8 Hz, 2H), 4.40 (q, J=7.2 Hz, 2H), 2.85 (d, J=6.8 Hz, 2H), 2.24-2.34 (m, 1H), 1.39-1.43 (t, J=7.2 Hz, 3H), 1.50 (d, J=6.8 Hz, 6H).

Intermediate (58): methyl 3-(4-(3-methylbutanoyl)benzamido)propenoate

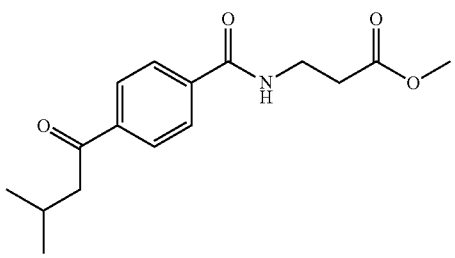 [SMILES: COC(=O)CCNC(=O)c1ccc(C(=O)CC(C)C)cc1]

Step A: 4-(3-methylbutanoyl)benzoic acid

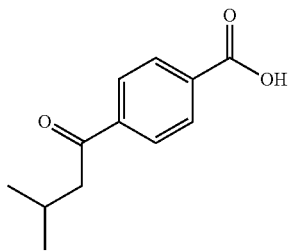

To a solution of Intermediate (57) (12 g, 51 mmol) in methanol (80 mL) was added 2 N aqueous sodium hydroxide (80 mL, 160 mmol). The reaction was stirred at room temperature for 40 minutes. The methanol was then removed in vacuo and the residue was extracted with dichloromethane. The aqueous phase was acidified to pH=4 with 3 N aqueous hydrochloric acid and extracted with ethyl acetate (2×200 mL). The combined organics were washed with brine, dried over sodium sulfate, filtered and concentrated to give 4-(3-methylbutanoyl)benzoic acid (9.5 g, 86%) as a white solid. $^1$H NMR (400 MHz, CDCl$_3$, δ): 8.13 (d, J=8.4 Hz, 2H), 7.96 (d, J=8.0 Hz, 2H), 2.81 (d, J=6.8 Hz, 2H), 2.19-2.29 (m, 1H), 0.96 (d, J=6.8 Hz, 6H).

Step B: methyl 3-(4-(3-methylbutanoyl)benzamido)propanoate

To a solution of 4-(3-methylbutanoyl)benzoic acid (9.5 g, 46 mmol) in N,N-dimethylformamide (80 mL) was added O-(7-Azabenzotriazol-1-yl)-N,N,N',N'-tetramethyluronium hexafluorophosphate (26.3 g, 69.1 mmol) at 0° C. The mixture was stirred for 40 minutes. Methyl 3-aminopropanoate hydrochloride (7.72 g, 55.3 mmol) and triethylamine (23.3 g, 230 mmol) were added and the reaction was allowed to warm to room temperature and stir for 16 hours. The reaction mixture was extracted with ethyl acetate (3×). The combined organics were washed with brine, dried over sodium sulfate, filtered, and concentrated. Purification by column chromatography gave methyl 3-(4-(3-methylbutanoyl)benzamido)propanoate (10 g, 77%) as a pale yellow solid. $^1$H NMR (400 MHz, CDCl$_3$, δ): 7.98 (d, J=8.0 Hz, 2H), 7.83 (d, J=8.4 Hz, 2H), 6.91 (s, 1H), 3.72-3.76 (m, 5H), 2.84 (d, J=6.0 Hz, 2H), 2.66-2.69 (t, J=6.0 Hz, 2H), 2.23-2.33 (m, 1H), 0.99 (d, J=6.4 Hz, 6H).

Intermediate (59): ethyl 4-(cyclobutanecarbonyl)benzoate

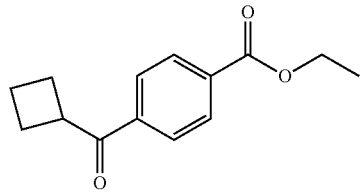 [SMILES: CCOC(=O)c1ccc(C(=O)C2CCC2)cc1]

Step A: (+/−)-ethyl 4-(cyclobutyl(hydroxy)methylbenzoate

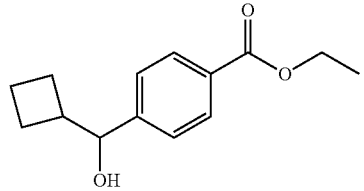 [SMILES: CCOC(=O)c1ccc(C(O)C2CCC2)cc1]

The title compound was prepared by a method analogous to that described for Intermediate (16), using ethyl 4-iodobenzoate and cyclobutanecarbaldehyde. $^1$H NMR (400 MHz, CDCl$_3$, δ): 7.93 (d, J=8.0 Hz, 2H), 7.31 (d, J=8.0 Hz, 2H), 4.58 (d, J=8.0 Hz, 1H), 4.29 (q, J=6.8 Hz, 2H), 2.50-2.58 (m, 1H), 1.70-2.02 (m, 6H), 1.34 (t, J=7.2 Hz, 3H).

Step B: ethyl 4-(cyclobutanecarbonyl)benzoate

Trifluoroacetic acid (613 mg, 5.38 mmol) was added dropwise to a 0° C. solution of ethyl 4-(cyclobutyl(hydroxy)methyl)benzoate (700 mg, 3 mmol) in dichloromethane (10 mL). Then Dess-Martin periodinane (2.03 g, 4.78 mmol) was added and the reaction was warmed to room temperature and stirred for 2 hours. The reaction was quenched with 1 N aqueous sodium hydrosulfite (10 mL) and extracted with ethyl acetate (3×30 mL). The combined organics were dried over sodium sulfate, filtered, and concentrated. Purification by flash column chromatography gave ethyl 4-(cyclobutanecarbonyl)benzoate (540 mg, 78%) as an oil. $^1$H NMR (400 MHz, CDCl$_3$, δ): 8.04 (d, J=8.4 Hz, 2H), 7.86 (d, J=8.4 Hz, 2H), 4.33 (q, J=7.2 Hz, 2H), 3.90-3.99 (m, 1H), 2.20-2.40 (m, 4H), 2.00-2.09 (m, 1H), 1.81-1.90 (m, 1H), 1.34 (t, J=7.2 Hz, 3H).

Intermediate (60): ethyl 4-(2-cyclopropylacetyl)benzoate

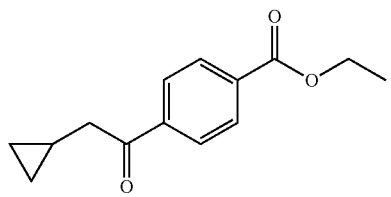 [SMILES: CCOC(=O)c1ccc(C(=O)CC2CC2)cc1]

The title compound was prepared by a method analogous to that described for Intermediate (59), using 2-cyclopropylacetaldehyde. $^1$H NMR (400 MHz, CDCl$_3$, δ): 8.15 (d, J=7.2 Hz, 2H), 8.01 (d, J=72 Hz, 2H), 4.44 (q, J=7.2 Hz, 2H), 2.94 (d, J=6.8 Hz, 2H), 1.45 (t, J=7.2 Hz, 3H), 1.10-1.22 (m, 1H), 0.59-0.68 (m, 2H), 0.21-0.26 (m, 2H).

Intermediate (61): 3-methyl-4-(4-(trifluoromethyl)-1H-pyrazol-1-yl)phenol

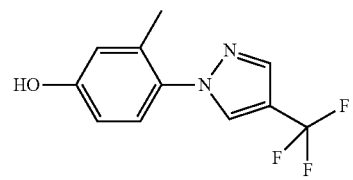 [SMILES: Cc1cc(O)ccc1-n1cc(C(F)(F)F)cn1]

Step A: 1-(4-methoxy-2-methylphenyl-4-(trifluoromethyl)-1H-pyrazole

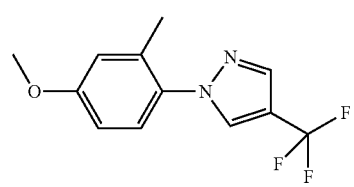 [SMILES: COc1ccc(-n2cc(C(F)(F)F)cn2)c(C)c1]

To a mixture of 1-bromo-4-methoxy-2-methylbenzene (1.5 g, 7.5 mmol) in N,N-dimethylformamide (15 mL) was added 4-(trifluoromethyl)-1H-pyrazole (1.12 g, 8.21 mmol), copper(II) oxide (107 mg, 0.746 mmol), and cesium carbonate (4.86 g, 14.9 mmol). The mixture was heated in a microwave to 120° C. for 1 hour. The mixture was diluted with water (20 mL) and extracted with ethyl acetate (3×30 mL). The combined organics were dried over sodium sulfate, filtered, and concentrated. Purification by column chromatography gave 1-(4-methoxy-2-methylphenyl)-4-(trifluoromethyl)-1H-pyrazole (550 mg, 29%) as a white solid. $^1$H NMR (400 MHz, CDCl$_3$, δ): 7.81 (s, 1H), 7.74 (s, 1H), 7.16 (m, 1H), 6.74 (m, 2H), 3.77 (s, 3H), 2.10 (s, 3H).

Step B: 3-methyl-4-(4-(trifluoromethyl)-1H-pyrazol-1-yl)phenol

To a 0° C. solution of 1-(4-methoxy-2-methylphenyl)-4-(trifluoromethyl)-1H-pyrazole (400 mg, 2 mmol) in dichloromethane (5 mL) was added boron tribromide (1 g, 6 mmol). The mixture was allowed to warm to room temperature and stir overnight. The reaction was quenched with methanol (2 mL), diluted with water (10 mL), and extracted with dichloromethane (3×10 mL). The combined organics were dried over sodium sulfate, filtered, and concentrated to give 3-methyl-4-(4-(trifluoromethyl)-1H-pyrazol-1-yl)phenol (390 mg, 99%) as a brown solid. $^1$H NMR (400 MHz, CDCl$_3$, δ): 7.83 (s, 1H), 7.74 (s, 1H), 7.08 (d, J=8.4 Hz, 1H), 6.65 (s, 1H), 6.62 (d, J=8.4 Hz, 1H), 5.57 (s, 1H), 2.05 (s, 3H).

Intermediate (62): methyl 4-butyryl-3-fluorobenzoate

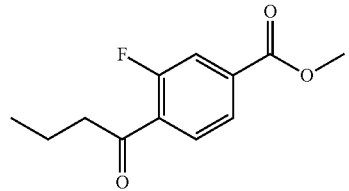 [SMILES: CCCC(=O)c1ccc(C(=O)OC)cc1F]

Step A: (+/−)-(4-bromo-2-fluorophenyl)butan-1-ol

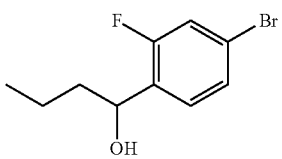

To a −78° C. solution of 4-bromo-2-fluorobenzaldehyde (600 mg, 3 mmol) in tetrahydrofuran (10 mL) was added n-propylmagnesium chloride (2.22 mL, 4.43 mmol) dropwise over 20 minutes. The reaction was warmed to 0° C. and stirred for 2 hours. The reaction was quenched with saturated aqueous ammonium chloride, extracted with ethyl acetate (3×), dried over sodium sulfate, filtered, and concentrated. Purification by preparatory thin layer chromatography gave (+/−)-1-(4-bromo-2-fluorophenyl)butan-1-ol (440 mg, 60%) as a colorless oil. $^1$H NMR (400 MHz, CDCl$_3$, δ): 7.26-7.30

(m, 1H), 7.21 (d, J=8.0 Hz 1H), 7.13 (d, J=8.0 Hz, 1H), 4.90 (t, J=5.6 Hz, 1H), 1.53-1.79 (m, 2H), 1.30-1.45 (m, 2H), 0.85 (s, J=5.6 Hz, 3H).

Step B: 1-(4-bromo-2-fluorophenyl)butan-1-one

Trifluoroacetic acid (366 mL, 3.21 mmol) was added dropwise to a 0° C. solution of 1-(4-bromo-2-fluorophenyl)butanol (440 mg, 1.8 mmol) in dichloromethane (10 mL). Added Dess-Martin periodinane (1.21 g, 2.85 mmol) and let reaction warm to room temperature and stir for 2 hours. The reaction was quenched with 1 N aqueous sodium hydrosulfite (10 mL) and extracted with ethyl acetate (3×20 mL). The combined organics were dried over sodium sulfate, filtered, and concentrated. Purification by flash column chromatography gave 1-(4-bromo-2-fluorophenyl)butan-1-one (330 mg, 75%) as a colorless oil. $^1$H NMR (400 MHz, CDCl$_3$, δ): 7.65-7.69 (m, 1H), 7.32-7.45 (m, 2H), 2.83-2.87 (m, 2H), 1.62-1.71 (m, 2H), 0.90 (m, 3H).

Step C: methyl 4-butyryl-3-fluorobenzoate

A mixture of 1-(4-bromo-2-fluorophenyl)butan-1-one (300 mg, 11.8 mmol), (1,1'-bis(diphenylphosphino)ferrocene)dichloropalladium (258 mg, 0.367 mmol), and diisopropylethylamine (790 mg, 6.1 mmol) in methanol (20 mL) was pressurized to 50 psi of carbon monoxide. The reaction was heated to 80° C. and stirred for 10 hours. The reaction was cooled to room temperature and filtered through Celite. The filtrate was concentrated and purified by flash column chromatography to give methyl 4-butyryl-3-fluorobenzoate (260 mg, 87%) as a pale yellow solid. $^1$H NMR (400 MHz, CDCl$_3$, δ): 7.81 (d, J=8.4 Hz, 1H), 7.79 (d, J=8.4 Hz, 1H), 7.73 (d, 1H), 3.88 (s, 3H), 2.88-2.92 (m, 2H), 1.64-1.73 (m, 2H), 0.92 (t, J=7.6 Hz, 3H).

Intermediate (63): methyl 4-butyryl-3-methylbenzoate

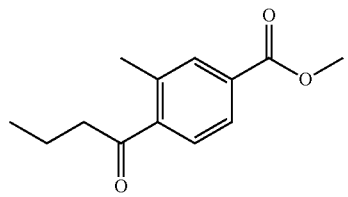 [SMILES: CCCC(=O)c1ccc(C(=O)OC)cc1C]

Step A: (+/−)-methyl 4-(1-hydroxybutyl)-3-methylbenzoate

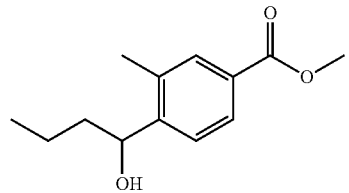 [SMILES: CCCC(O)c1ccc(C(=O)OC)cc1C]

The title compound was prepared by a method analogous to that described for Intermediate (16), using methyl 4-iodo-3-methylbenzoate and butyraldehyde. $^1$H NMR (400 MHz, CDCl$_3$, δ): 7.87 (d, J=8.4 Hz, 1H), 7.81 (s, 1H), 7.56 (d, J=8.4 Hz, 1H), 4.98 (q, J=4.4 Hz, 1H), 3.90 (s, 3H), 2.37 (s, 3H), 1.63-1.72 (m, 2H), 1.50-1.54 (m, 1H), 1.39-1.43 (m, 1H), 0.98 (t, J=7.6 Hz, 3H).

Step B: methyl 4-butyryl-3-methylbenzoate

To a solution of (+/−)-methyl 4-(1-hydroxybutyl)-3-methylbenzoate (0.8 g, 4 mmol) in dichloromethane (15 mL) was added manganese dioxide (3.13 g, 36.0 mmol). The reaction was stirred at 30° C. overnight. TLC showed starting material remained and the reaction was heated to reflux for 5 hours. The reaction was cooled to room temperature and filtered through Celite. The filtrate was concentrated and purified by flash column chromatography to give methyl 4-butyryl-3-methylbenzoate (290 mg) as an oil. $^1$H NMR (400 MHz, CDCl$_3$, δ): 7.90 (d, J=7.6 Hz, 2H), 7.59 (d, J=7.6 Hz, 1H), 3.93 (s, 3H), 2.86 (t, J=7.6 Hz, 2H), 2.49 (s, 3H), 1.69-1.78 (m, 2H), 0.99 (t, J=7.6 Hz, 3H).

Intermediate (64): 2-(4-(trifluoromethyl)-1H-pyrazol-1-yl)pyrimidin-5-amine

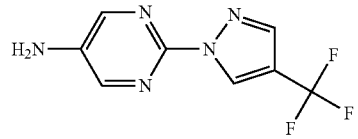 [SMILES: Nc1cnc(-n2cc(C(F)(F)F)cn2)nc1]

Step A: 5-nitro-2-(4-(trifluoromethyl)-1H-pyrazol-1-yl)pyrimidine

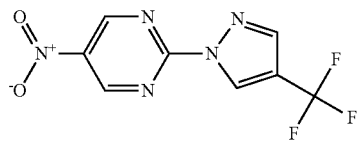

To a solution of 2-chloro-5-nitropyrimidine (1.5 g, 9.4 mmol) and 4-(trifluoromethyl)-1H-pyrazole (1.41 g, 10.3 mmol) in acetonitrile (40 mL) was added potassium carbonate (2.60 g, 18.8 mmol). The reaction was heated to 80° C. and stirred overnight. The reaction was concentrated and the residue was diluted with water and extracted with ethyl acetate (2×40 mL). The combined organics were washed with brine, dried over sodium sulfate, filtered, and concentrated. Purification by flash column chromatography gave 5-nitro-2-(4-(trifluoromethyl)-1H-pyrazol-1-yl)pyrimidine (1.5 g, 62%) as a yellow solid. $^1$H NMR (400 MHz, CDCl$_3$, δ): 9.48 (s, 2H), 8.92 (s, 1H), 8.05 (s, 1H).

Step B: 2-(4-(trifluoromethyl)-1H-pyrazol-1-yl)pyrimidin-5-amine

Glacial acetic acid (2.78 g, 46.3 mmol) was slowly added to a solution of 5-nitro-2-(4-(trifluoromethyl)-1H-pyrazol-1-yl)pyrimidine (1.5 g, 5.8 mmol) and iron powder (1.94 g, 34.7 mmol) in methanol (30 mL). The reaction was stirred at room temperature for 3 hours. The reaction was then diluted with ethyl acetate (50 mL) and filtered through Celite. The filtrate was neutralized with saturated aqueous potassium carbonate. The organic layer was separated and washed with water and brine, dried over sodium sulfate, filtered, and concentrated to give 2-(4-(trifluoromethyl)-1H-pyrazol-1-yl)pyrimidin-5-amine (850 mg, 64%) as a yellow solid. $^1$H NMR (400 MHz, CDCl$_3$, δ): 8.68 (s, 1H), 8.16 (s, 2H), 7.87 (s, 1H), 3.82 (s, 2H).

Intermediate (65): ethyl 4-(3,3-dimethylcyclobutanecarbonyl)benzoate

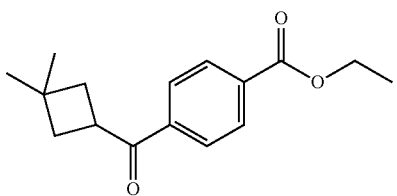 [SMILES: CCOC(=O)c1ccc(C(=O)C2CC(C)(C)C2)cc1]

To a 0° C. solution of 3,3-dimethylcyclobutanecarboxylic acid (1.35 g, 10.5 mmol) in dichloromethane (10 mL) was slowly added oxalyl chloride (4.01 g, 31.6 mmol) and 1 drop of N,N-dimethylformamide. The reaction was warmed to room temperature and stirred for 2 hours. The reaction was concentrated in vacuo to give crude 3,3-dimethylcyclobutanecarbonylchloride (1.54 g) as a yellow oil.

To a −40° C. solution of ethyl 4-iodobenzoate (2.30 g, 8.30 mmol) in tetrahydrofuran (20 mL) was added isopropylmagnesium chloride-lithium chloride (7.1 mL, 1.3 M in THF, 9.2 mmol) dropwise. The mixture was stirred for 1 hour at −40° C. Copper(I) iodide (476 mg, 2.50 mmol) was then added and the reaction was allowed to warm to −10° C. and stir for 20 minutes. The solution was cooled again to −40° C. and a solution of the previously prepared 3,3-dimethylcyclobutanecarbonylchloride (1.54 g, 10.5 mmol) in tetrahydrofuran (10 mL) was added dropwise. The reaction was allowed to warm to 0° C. and stir for 2 hours. The reaction was quenched with 1 N aqueous hydrochloric acid and extracted with ethyl acetate (3×15 mL). The combined organics were dried over sodium sulfate, filtered, and concentrated. Purification by flash column chromatography gave ethyl 4-(3,3-dimethylcyclobutanecarbonyl)benzoate (1.80 g, 83%) as a pale yellow solid. $^1$H NMR (400 MHz, CDCl$_3$, δ): 8.15 (d, J=8.4 Hz, 2H), 7.98 (d, J=8.4 Hz, 2H), 4.20-4.47 (m, 2H), 3.89-3.98 (m, 1H), 2.22-2.27 (m, 2H), 2.09-2.15 (m, 2H), 1.45 (t, J=7.2 Hz, 3H), 1.32 (s, 3H), 1.13 (s, 3H).

Intermediate (66): 4-(2H-indazol-2-yl)-3-methylphenol

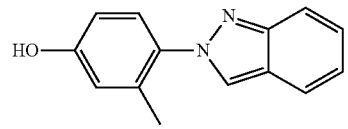 [SMILES: Cc1cc(O)ccc1-n1cc2ccccc2n1]

Step A: 2-(4-methoxy-2-methylphenyl)-2H-indazole

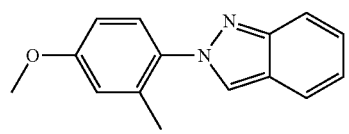 [SMILES: COc1ccc(-n2cc3ccccc3n2)c(C)c1]

A mixture of 4-methoxy-2-methylaniline (1.37 g, 10.0 mmol) and 2-nitrobenzaldehyde (1.51 g, 10.0 mmol) in tetrahydrofuran (30 mL) was stirred at reflux for 4 hours. The reaction was concentrated. To the residue was added triethyl phosphite (10 mL) and the mixture was stirred at reflux for 40 hours. The reaction was concentrated and purification by flash column chromatography gave 2-(4-methoxy-2-methylphenyl)-2H-indazole (1.5 g, 63%) as a white solid. $^1$H NMR (400 MHz, CDCl$_3$, δ): 8.05 (s, 1H), 7.80 (d, J=8.8 Hz, 1H), 7.74 (d, J=8.8 Hz, 1H), 7.31-7.35 (m, 2H), 7.12-7.16 (m, 1H), 6.82-6.88 (m, 2H), 3.87 (s, 3H), 2.20 (s, 3H).

Step B: 4-(2H-indazol-2-yl)-3-methylphenol

A solution of 2-(4-methoxy-2-methylphenyl)-2H-indazole (500 mg, 2.1 mmol) in dichloromethane (10 mL) was cooled to −78° C. Added boron tribromide (2.6 g, 10.5 mmol) and reaction was stirred at −78° C. for 1 hour. Reaction was warmed to room temperature are stirred overnight. The reaction was diluted with methanol and water, and extracted with ethyl acetate (3×30 mL). The combined organics were washed with water and brine, dried over sodium sulfate, filtered, and concentrated to give 4-(2H-indazol-2-yl)-3-methylphenol (350 mg, 74%) as a yellow solid. $^1$H NMR (400 MHz, DMSO-d$_6$, δ): 9.82 (s, 1H), 8.51 (s, 1H), 7.76 (d, J=8.4 Hz, 1H), 7.68 (d, J=8.8 Hz, 1H), 7.25-7.30 (m, 2H), 7.07-7.11 (m, 1H), 6.80 (d, J=2.4 Hz, 1H), 6.75 (dd, J=8.4, 2.4 Hz, 1H), 2.06 (s, 3H).

Intermediate (67): 2-methyl-4-(4-(trifluoromethyl)-1H-pyrazol-1-yl)benzonitrile

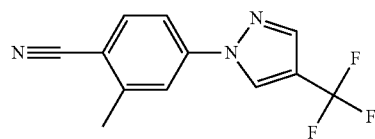

To a solution of 4-(trifluoromethyl)-1H-pyrazole (1.0 g, 7.0 mmol) and 4-fluoro-2-methylbenzonitrile (1.16 g, 8.50 mmol) in acetonitrile (8 mL) was slowly added potassium carbonate (1.96 g, 14.2 mmol) at room temperature. The reaction was heated to 80° C. and stirred overnight. The reaction was cooled to room temperature and poured into water. The layers were separated and the aqueous was extracted with ethyl acetate (3×15 mL). The combined organics were washed with water, dried over sodium sulfate, filtered, and concentrated. Purification by flash column chromatography gave 2-methyl-4-(4-(trifluoromethyl)-1H-pyrazol-1-yl)benzonitrile (710 mg, 40%) as a yellow solid. $^1$H NMR (400 MHz, CDCl$_3$, δ): 8.26 (s, 1H), 7.94 (s, 1H), 7.72-7.74 (m, 2H), 7.61-7.64 (m, 1H), 2.64 (s, 3H).

Intermediate (68): (+/−)-ethyl 4-(cyclopentyl(hydroxy)methyl)benzoate

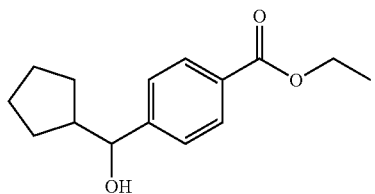 [SMILES: CCOC(=O)c1ccc(C(O)C2CCCC2)cc1]

The title compound was prepared by a method analogous to that described for Intermediate (16) using cyclopentanecarbaldehyde and ethyl 4-iodobenzoate. $^1$H NMR (400 MHz, CDCl$_3$, δ): 8.01 (d, J=8.4 Hz, 2H), 7.40-7.44 (m, 2H), 4.49 (d, J=8.0 Hz, 1H), 4.39 (q, J=7.2 Hz, 2H), 2.19-2.21 (m, 1H), 1.82-1.87 (m, 2H), 1.41-1.67 (m, 6H), 1.39 (t, J=7.2 Hz, 3H).

Intermediate (69): 6-(4-chloro-1H-imidazol-1-yl)pyridin-3-amine

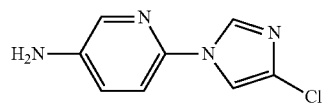

Step A: 4-chloro-1H-imidazole

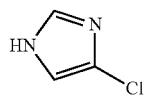

To a solution of 1H-imidazole (10.0 g, 0.15 mol) in chloroform (100 mL) was slowly added a solution of chlorine (2.08 g, 0.0294 mol) in chloroform (18.6 mL). The reaction was cooled to 0° C., then left stirring overnight, gradually warming to room temperature. Aqueous sodium bisulfite was added and the layers were separated. The aqueous was extracted with ethyl acetate (3×100 mL). The combined organic layers were dried over sodium sulfate, filtered, and concentrated. Purification by flash column chromatography (0-10% methanol/dichloromethane) gave 4-chloro-1H-imidazole (400 mg) as a light yellow solid. $^1$H NMR (400 MHz, CD$_3$OD, δ): 7.58 (s, 1H), 7.05 (s, 1H).

Step B: 2-(4-chloro-1H-imidazol-1-yl)-5-nitropyridine

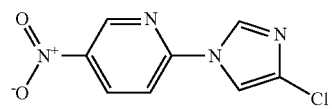

A vial was charged with 4-chloro-1H-imidazole (450 mg, 4.4 mmol), 2-chloro-5-nitropyridine (1.04 g, 6.58 mmol), potassium carbonate (1.21 g, 8.78 mmol), and acetonitrile (10 mL). The vial was capped and heated to 80° C. for 2 hours. The reaction was cooled to room temperature and poured into water (20 mL). The mixture was extracted with ethyl acetate (3×50 mL). The combined organics were dried over sodium sulfate, filtered, and concentrated. Purification by flash column chromatography gave 2-(4-chloro-1H-imidazol-1-yl)-5-nitropyridine (675 mg, 68%) as a white solid. $^1$H NMR (400 MHz, CD$_3$OD, δ): 9.35 (d, J=2.4 Hz, 1H), 8.78 (dd, J=9.0, 2.6 Hz, 1H), 8.64 (d, J=1.6 Hz, 1H), 8.05 (d, J=1.6 Hz, 1H), 7.95 (d, J=8.8 Hz, 1H).

Step C: 6-(4-chloro-1H-imidazol-1-yl)pyridin-3-amine

A vial was charged with 2-(4-chloro-1H-imidazol-1-yl)-5-nitropyridine (675 mg, 3.01 mmol), tin(II) chloride dihydrate (2.03 g, 9.02 mmol), and methanol (10 mL). The vial was sealed and heated to 90° C. and stirred for 16 hours. The reaction was cooled to room temperature and concentrated. The residue was taken up in water (20 mL) and neutralized with saturated aqueous sodium bicarbonate. The mixture was extracted with ethyl acetate (3×50 mL) and the combined organics were dried over sodium sulfate, filtered, and concentrated. Purification by flash column chromatography gave 6-(4-chloro-1H-imidazol-1-yl)pyridin-3-amine (380 mg, 65%) as a light yellow solid. $^1$H NMR (400 MHz, CD$_3$OD, δ): 8.20 (d, J=1.6 Hz, 1H), 7.89 (d, J=2.4 Hz, 1H), 7.68 (d, J=1.6 Hz, 1H), 7.38 (d, J=8.8 Hz, 1H), 7.21 (dd, J=8.8, 2.8 Hz, 1H).

Intermediate (70): 1-bromo-3,3-dimethylbutan-2-one

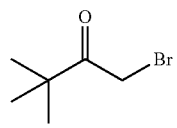

To a solution of 3,3-dimethylbutan-2-one (18 g, 180 mmol) in dichloromethane (400 mL) and methanol (160 mL) was added tetrabutylammonium tribromide (95.3 g, 198 mmol). The reaction mixture was stirred at room temperature for 2 h. The solution was concentrated under reduced pressure and the residue dissolved in methyl t-butyl ether (250 mL). The solution was washed with 1N aqueous HCl (250 mL*3) and brine (250 mL*2). The organic layer was dried over anhydrous Na$_2$SO$_4$ and concentrated under reduced pressure to give crude 1-bromo-3,3-dimethylbutan-2-one (28 g) as a colorless oil which was used without further purification. $^1$H NMR (400 MHz, CDCl$_3$) δ 4.17 (s, 2H), 1.23 (s, 9H).

Intermediate (71): 4-tert-butyl-1H-imidazole

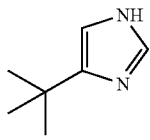

A solution or intermediate (70) (3 g, 20 mmol) in formamide (15 mL) was heated to 160° C. for 5 h. The mixture was poured into 10% aqueous sodium bicarbomate (30 mL). The solution was extracted with dichloromethane (30 mL*2). The combined organic layers were washed with 10% aqueous potassium carbonate, brine, dried over Na$_2$SO$_4$ and concentrated under reduced pressure to give 4-tert-butyl-1H-imidazole (1.1 g) as a brown oil. $^1$H NMR (400 MHz, CDCl$_3$) δ 7.57 (s, 1H), 6.76 (s, 1H), 1.31 (s, 9H).

Intermediate (72): 2-(4-tert-butyl-1H-imidazol-1-yl)-5-nitropyridine

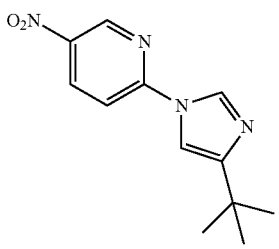 [SMILES: CC(C)(C)c1cn(-c2ccc(N)cn2)cn1]

To a solution 2-bromo-5-nitropyridine (2.2 g, 10 mmol) in acetonitrile (15 mL) was added Intermediate (71) (1.5 g, 12 mmol) and potassium carbonate (3 g, 20 mmol). The mixture was stirred at 80° C. for 12 h. The reaction mixture was diluted with water and extracted with ethyl acetate (10 mL*3). The organic layer was dried over anhydrous Na$_2$SO$_4$ and concentrated under reduced pressure. Purification by silica gel chromatography gave 2-(4-tert-butyl-1H-imidazol-1-yl)-5-nitropyridine (1.4 g) as a yellow solid. $^1$H NMR (400 MHz, CDCl$_3$) δ 9.23 (d, J=2.8 Hz, 1H), 8.53 (dd, J=9.2, 2.8 Hz, 1H), 8.33 (s, 1H), 7.39 (d, J=9.2 Hz, 1H), 7.19 (s, 1H), 1.28 (s, 9H).

Intermediate (73): 6-(4-tert-butyl-1H-imidazol-1-yl)pyridin-3-amine

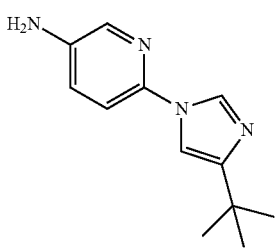

To a solution of Intermediate (72) (1.2 g, 4.9 mmol) in ethanol (40 mL) was added 10% Pd/C (500 mg). The mixture was stirred under a 40 psi hydrogen atmosphere for 24 h. The mixture was filtered and concentrated to give 6-(4-tert-butyl-1H-imidazol-1-yl)pyridin-3-amine (1.1 g) as a yellow solid which was used without further purification. $^1$H NMR (400 MHz, CD$_3$OD) δ 8.22 (s, 1H), 7.93 (d, J=2.8 Hz, 1H), 7.42-7.40 (m, 2H), 7.28 (d, J=2.4 Hz, 1H), 1.38 (s, 9H).

Intermediate (74): 4-isopropyl-1H-imidazole

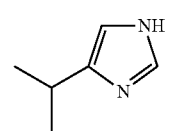

A solution of 1-bromo-3-methylbutan-2-one (15 g, 9.1 mmol) in formamide (60 mL) was refluxed for 4 h. The mixture was poured into 10% aqueous sodium bicarbonate (30 mL) and adjusted to pH=9.5. The solution was extracted with dichloromethane (30 mL*2). The combined organic layers were washed with 10% aqueous potassium carbonate, brine, dried over Na$_2$SO$_4$, and concentrated under reduced pressure to give 4-isopropyl-1H-imidazole (5.5 g) as a brown oil. $^1$H NMR (400 MHz, CDCl$_3$) δ 7.51 (s, 1H), 6.70 (s, 1H), 2.92-2.85 (m, 1H), 1.22 (d, 6H).

Intermediate (75): 2-(4-isopropyl-1H-imidazol-1-yl)-5-nitropyridine

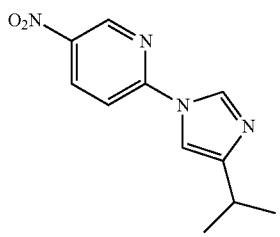

To a solution 2-chloro-5-nitropyridine (1 g, 9.1 mmol) in acetonitrile (15 mL) was added Intermediate (74) (1.3 g, 8.3 mmol) and potassium carbonate (2.27 g, 16.4 mmol). The mixture was stirred at 80° C. for 12 h. The reaction mixture was diluted with water and extracted with ethyl acetate (10 mL*3). The combined organic layers were dried over anhydrous Na$_2$SO$_4$ and concentrated under reduced pressure. Purification by silica gel chromatography gave 2-(4-isopropyl-1H-imidazol-1-yl)-5-nitropyridine (860 mg) as a yellow solid. $^1$H NMR (400 MHz, CDCl$_3$) δ 9.23 (d, J=2.4 Hz, 1H), 8.53 (dd, J=9.2, 2.8 Hz, 1H), 8.35 (d, J=0.8 Hz, 1H), 7.39 (d, J=9.2 Hz, 1H), 7.31 (s, 1H), 2.94-2.87 (m, 1H), 1.27 (d, J=6.8 Hz, 6H).

Intermediate (76): 6-(4-isopropyl-1H-imidazol-1-yl)pyridin-3-amine

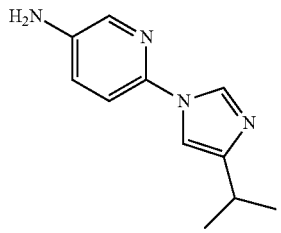

To a solution of Intermediate (75) (800 mg, 3.44 mmol) in methanol (20 mL) was added 10% Pd/C (400 mg). The mixture was stirred under a 40 psi hydrogen atmosphere 12 h. The mixture was filtered and the filtrate concentrated under reduced pressure to give 6-(4-isopropyl-1H-imidazol-1-yl)pyridin-3-amine (600 mg) as a yellow solid which was used without further purification. $^1$H NMR (400 MHz, CD$_3$OD) δ 8.04 (d, J=−1.2 Hz, 1H), 7.77 (d, J=2.8 Hz, 1H), 7.22-7.26 (m, 2H), 7.10 (dd, J=8.4, 2.8 Hz, 1H), 2.83-2.76 (m, 1H), 1.18 (d, J=7.2 Hz, 6H).

Intermediate (77): (+/−)-ethyl 4-(1-(4-bromophenoxy)butyl)benzoate

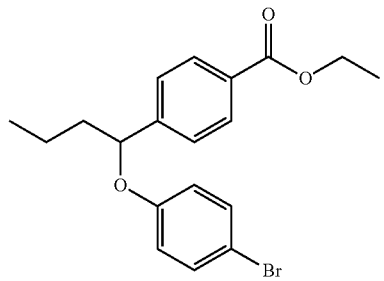 [SMILES: CCCC(Oc1ccc(Br)cc1)c1ccc(C(=O)OCC)cc1]

To a 0° C. solution of 4-bromophenol (1.87 g, 1.08 mmol), ethyl 4-(1-hydroxybutyl)benzoate (2 g, 0.9 mmol) and triphenylphosphine (2.83 g, 1.08 mmol) in THF (20 mL) was added DIAD (2.18 g, 1.08 mmol). The resulting mixture was stirred at 30° C. overnight. The reaction mixture was diluted with brine (20 mL) and extracted with ethyl acetate (3*25 mL). The combined organic layers were dried over Na$_2$SO$_4$, filtered, and concentrated under reduced pressure. The residue was purified by silica gel chromatography to give (+/−)-ethyl 4-(1-(4-bromophenoxy)butyl)benzoate (2.3 g, 67.7%) as a yellow oil. $^1$HNMR (400 MHz, CDCl$_3$) δ 8.00 (d, J=8.4 Hz, 2H), 7.37 (d, J=8.4 Hz, 2H), 7.25 (d, J=8.8 Hz, 2H), 6.67 (d, J=8.8 Hz, 2H), 5.08 (m, 1H), 4.35 (q, J=7.2 Hz, 2H), 1.98-1.94 (m, 1H), 1.80-1.74 (m, 1H), 1.52-1.50 (m, 1H), 1.43-1.39 (m, 1H), 1.37 (t, J=7.2 Hz, 3H), 0.94 (t, J=7.2 Hz, 3H).

Intermediate (78): 4-phenyl-1H-imidazole

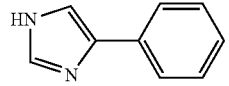

A solution or 2-bromo-1-phenylethanone (5.56 g, 30.38 mmol) in formamide (35.4 ml, 1.04 mol) was stirred at 185° C. for 3 h. After cooling to room temperature, the reaction was washed with saturated aqueous sodium chloride (100 mL) and extracted with ethyl acetate (100 mL*4). The combined organic extracts were dried over Na$_2$SO$_4$, filtered, and concentrated under reduced pressure. The residue was purified by silica gel chromatography to give 4-phenyl-1H-imidazole (4.6 g) as a yellow solid. $^1$H NMR (400 MHz, CDCl$_3$) δ 8.23 (d, J=13.6 Hz, 1H), 7.72-7.75 (m, 3H), 7.34-7.42 (m 2H), 7.26-7.29 (m, 1H).

Intermediate (79): 2-bromo-5-methoxy-1,3-dimethylbenzene

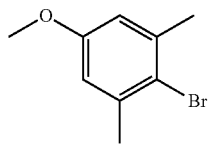

To a 0° C. solution of 4-bromo-3,5-dimethylphenol (1.00 g, 4.98 mmol) in DMF (10.0 mL) was added iodomethane (1.41 g, 9.96 mmol) and potassium carbonate (1.37 g, 9.96 mmol). The mixture was stirred for 5 h at room temperature. The mixture was poured into water and extracted with ethyl acetate (15 ml*3). The combined organic layers were dried over Na$_2$SO$_4$ and concentrated under reduced pressure. The crude material was purified by silica gel chromatography to give 2-bromo-5-methoxy-1,3-dimethylbenzene (1.00 g) as a yellow oil. $^1$H NMR (400 MHz, CDCl$_3$) δ 6.57 (s, 2H), 3.69 (s, 3H), 2.31 (s, 6H).

Intermediate (80): 4-chloro-1-(4-methoxy-2,6-dimethylphenyl)-1H-pyrazole

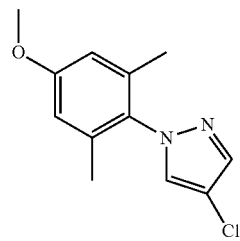 [SMILES: COc1cc(C)c(-n2cc(Cl)cn2)c(C)c1]

To a −78° C. solution of Intermediate (79) (500 mg, 2.34 mmol) in THF (10 mL) was added n-BuLi (0.98 mL of a 2.5M solution in hexanes, 2.45 mmol). The reaction mixture was stirred for 30 min at −78° C. Di-t-butyl diazene-1,2-dicarboxylate (565 mg, 2.45 mmol) was added in one portion. The reaction mixture was allowed to warm to room temperature and stirred for 30 min. A solution of 2-chloromalonaldehyde (260 mg, 2.45 mmol) in THF (2.0 mL) was added dropwise at 0° C. 4M HCl in dioxane (10 mL) was added. The reaction mixture was stirred at reflux overnight Saturated aqueous NaHCO₃ was added to bring the aqueous layer to pH=7. The mixture was extracted with ethyl acetate (10 ml×3). The combined organic layers were dried over Na₂SO₄ and concentrated under reduced pressure. The crude residue was purified by silica gel chromatography to give compound 4-chloro-1-(4-methoxy-2,6-dimethylphenyl)-1H-pyrazole (100 mg) as a pale yellow oil. ¹H NMR (400 MHz, CDCl₉) δ 7.57 (s, 1H), 7.35 (s, 1H), 6.57 (s, 2H), 3.74 (s, 3H), 1.92 (s, 6H).

Intermediate (81): 4-(4-chlor-1H-pyrazol-1-yl)-3,5-dimethylphenol

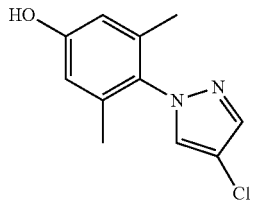

To a −10° C. solution of Intermediate (80) (850 mg, 3.60 mmol) in dichloromethane (15.0 mL) was added boron tribromide (2.72 mg, 10.8 mmol). The reaction mixture was allowed to warm to room temperature and stirred overnight. The resulting mixture was quenched by addition of methanol and concentrated under reduced pressure to give 4-(4-chloro-1H-pyrazol-1-yl)-3,5-dimethylphenol (795 mg) as a yellow solid. ¹H NMR (400 MHz, Methanol-d4) δ 7.83 (d, J=0.4 Hz, 1H), 7.72 (d, J=0.4 Hz, 1H), 6.60 (s, 2H), 1.94 (s, 6H).

Intermediate (82): 1-(2,6-dimethyl-4-nitrophenyl)-4-(trifluoromethyl)-1H-imidazole

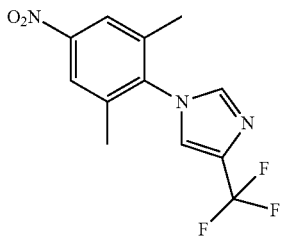 [SMILES: Cc1cc([N+](=O)[O-])cc(C)c1-n1cnc(C(F)(F)F)c1]

To a 0° C. solution of 2,6-dimethyl-4-nitrophenol (3 g, 17.9 mmol) and pyridine (4.25 g, 53.7 mmol) in dichloromethane (30 mL) was slowly added triflic anhydride (7.6 g, 26.8 mmol). The solution was stirred at room temperature for 2 h. The mixture was concentrated poured into water (50 mL) and extracted with ethyl acetate (50 mL×3). The organic layer was dried over anhydrous Na₂SO₄ and concentrated under reduced pressure to give crude 2,6-dimethyl-4-nitrophenyl trifluoromethanesulfonate (5.5 g) as a yellow solid.

To a 0° C. solution of 4-(trifluoromethyl)-1H-imidazole (1.82 g, 13.4 mmol) in DMF (20 mL) was added sodium hydride (0.81 g, 20.1 mmol). The mixture was stirred at room temperature for 1 h. The crude 2,6-dimethyl-4-nitrophenyl trifluoromethanesulfonate prepared above (4.0 g, 13.4 mmol) was added. The mixture was stirred at 80° C. for 12 h. The reaction was diluted with water and extracted with ethyl acetate (30 mL×3). The organic layer was dried over anhydrous Na₂SO₄ and concentrated under reduced pressure. The crude material was purified by silica gel chromatography to give 1-(2,6-dimethyl-4-nitrophenyl)-4-(trifluoromethyl)-1H-imidazole (805 mg, 21%) as a colorless solid. ¹H NMR (400 MHz, CDCl₃) δ 8.01 (s, 2H), 7.47 (s, 1H), 7.23 (s, 1H), 2.11 (s, 6H).

Intermediate (83): 3,5-dimethyl-4-(4-(trifluoromethyl)-1H-imidazol-1-yl)phenol

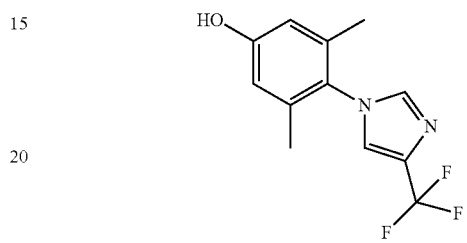

To a solution of Intermediate (82) (470 mg, 1.65 mmol) in ethanol (40 mL) was added 10% Pd/C (150 mg). The mixture was stirred under a 40 psi hydrogen atmosphere at 15° C. for 24 h. The mixture was filtered and concentrated under reduced pressure. The residue was added to a solution of concentrated H₂SO₄ (5.5 mL) in water (20 mL) and cooled to 0° C. A solution of sodium nitrite (146 mg, 2.12 mmol) in water (2 mL) was added dropwise. The mixture was stirred for at 0° C. 30 min. The reaction was poured into a boiling mixture of concentrated H₂SO₄ (2.9 mL) and water (26 mL) and refluxed for 2 h. The reaction mixture was then cooled to room temperature and slowly added into ice water. The mixture was extracted with ethyl acetate (30 mL×3). The combined organic layers were washed with brine, dried over Na₂SO₄, filtered, and then concentrated under reduced pressure. The crude material was purified by silica gel chromatography to give 3,5-dimethyl-4-(4-(trifluoromethyl)-1H-imidazol-1-yl)phenol (330 mg) as a yellow solid. ¹H NMR (400 MHz, CD₃OD) δ 7.80 (s, 1H), 7.68 (s, 1H), 6.64 (s, 2H), 2.03 (s, 6H).

Intermediate (84): 6-(4-phenyl-1H-pyrazol-1-yl)pyridin-3-ol

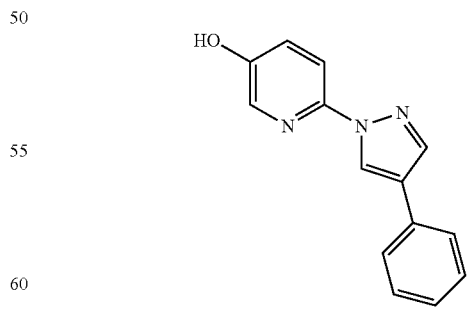

Intermediate 25 (400 mg, 1.69 mmol) was added to a 0° C. solution of concentrated H₂SO₄ (5.5 ml) in water (20 ml). A solution of sodium nitrite (128.5 mg, 1.86 mmol) in water (1.5 ml) was added dropwise. The reaction was stirred at 0° C. for 1 h. The reaction mixture was poured into a boiling mixture of water (29 ml) and concentrated H₂SO₄ (2.6 ml) and refluxed for 1 h. The mixture was cooled, poured into ice water and extracted with ethyl acetate (3×25 ml). The organic layer was dried over anhydrous Na₂SO₄ and concentrated under reduced pressure. The crude residue was purified by silica gel chromatography to afford 6-(4-phenyl-1H-pyrazol-1-yl)pyridin-3-ol (200 mg) as an orange solid. ¹H NMR (400 MHz, CDCl₃) δ 8.75 (s, 1H), 8.14 (d, J=2.8 Hz, 1H), 7.99 (s, 1H), 7.93 (d, J=8.8 Hz, 1H), 7.59 (d, J=7.6 Hz, 2H), 7.38-7.42 (m, 3H), 7.26-7.29 (m, 1H).

Intermediate (85): tert-butyl 4-tert-butyl-1H-pyrazole-1-carboxylate

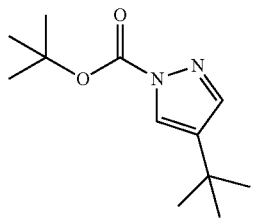 [SMILES: CC(C)(C)OC(=O)n1cc(C(C)(C)C)cn1]

A mixture of pyrazole (40 g, 0.587 mol) and 2-chloro-2-methylpropane (81.7 g, 0.881 mol) were heated at 220° C. for 6 h in an autoclave. The reaction mixture was cooled to room temperature and adjusted to ~pH 9 with saturated aqueous NaHCO₃. The mixture was extracted with dichloromethane (200 mL×3). The combined organic layers were dried over Na₂SO₄ and concentrated to dryness, providing a 50 g of mixture, consisting mostly of 4-tert-butyl-1H-pyrazole and 1,4-di-tert-butyl-1H-pyrazole. 500 mg of this crude mixture was dissolved in THF (8 mL). The solution was cooled to 0° C. LiHMDS (6 mL of a 1M solution in THF, 6.0 mmol) was added. The mixture was stirred at 0° C. for 45 min. Di-t-butyldicarbonate (967 mg, 4.43 mmol) was added. The resulting mixture was stirred at room temperature overnight. The reaction was quenched by addition of 1N aqueous HCl and extracted with dichloromethane (10 mL×3). The combined organic layers were washed with brine, dried over Na₂SO₄ and concentrated. The crude material was purified by silica gel chromatography to give tert-butyl 4-tert-butyl-1H-pyrazole-1-carboxylate (120 mg) as a yellow solid. ¹H NMR (400 MHz, CDCl₃) δ 7.82 (s, 1H), 7.63 (s, 1H), 1.64 (s, 9H), 1.26 (s, 9H).

Intermediate (86): 4-tert-butyl-1H-pyrazole

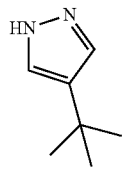

To a solution of Intermediate (85) (120 mg, 0.535 mmol) in dichloromethane (5 mL) was added trifluoroacetic acid (64 mg, 1.6 mmol). The mixture was stirred at room temperature overnight. Saturated aqueous NaHCO₃ was added and the mixture extracted with dichloromethane (10 mL×3). The combined organic layers were washed with brine, dried over Na₂SO₄, and concentrated to give 4-tert-butyl-1H-pyrazole (80 mg) as a yellow solid. ¹H NMR (400 MHz, CDCl₃) δ 11.98 (br s, 1H), 7.47 (br s, 2H), 1.20 (s, 9H).

Intermediate (87): 6-(4-tert-butyl-1H-pyrazol-1-yl)pyridin-3-amine

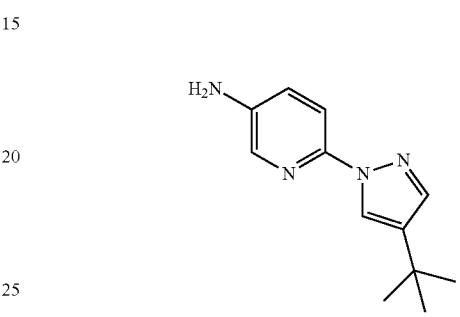

To a solution of 4-tert-butyl-1H-pyrazole (300 mg, 2.41 mmol) and 2-bromo-5-nitropyridine in acetonitrile (15 mL) was added potassium carbonate (833 mg, 6.04 mmol). The mixture was stirred at reflux overnight. The mixture was diluted with water and extracted with ethyl acetate (20 mL×3). The combined organic layers were washed with brine, dried over Na₂SO₄, and concentrated to give 350 mg yellow solid. The solid was dissolved in ethanol (10 mL). 10 wt % Pd/C (30 mg) was added. The mixture was stirred overnight at 30° C. under a 40 psi hydrogen atmosphere. The reaction mixture was filtered and concentrated. The residue was purified by silica gel chromatography to give 6-(4-tert-butyl-1H-pyrazol-1-yl)pyridin-3-amine (140 mg) as a yellow solid. ¹H NMR (400 MHz, CD₃OD) δ 8.04 (s, 1H), 7.72 (d, J=2.4 Hz, 1H), 7.43-7.47 (m, 2H), 7.09 (dd, J=8.8, 2.8 Hz, 2H), 1.19 (s, 9H).

Intermediate (88): 4-(5-chloro-2H-indazol-2-yl)phenol

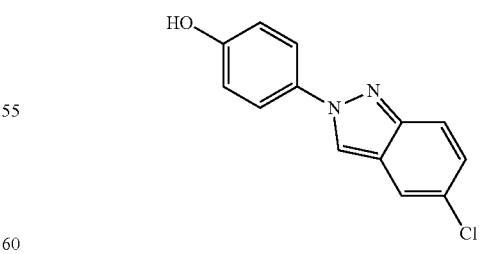

4-(5-chloro-2H-indazol-2-yl)phenol was prepared using a method analogous to that described for Intermediate (Q10), starting from 4-methoxyaniline and 5-chloro-2-nitrobenzaldehyde. Yellow solid. ¹HNMR (400 MHz Methanol-d₄) δ 8.60 (d, J=1.6 Hz, 1H), 7.71-7.75 (m, 3H), 7.65 (d, J=9.2 Hz, 1H), 727 (dd, J=9.2, 2.0 Hz, 1H), 6.95 (d, J=8.8 Hz, 2H).

Intermediate (89): 3-methyl-1-(6-(4-(trifluoromethyl)-1H-pyrazol-1-yl)pyridin-3-yl)butan-1-ol

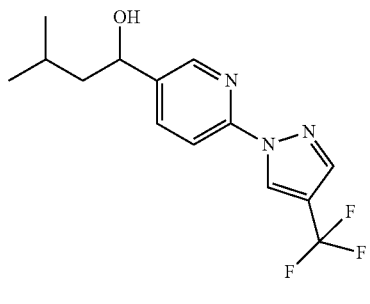 [SMILES: CC(C)CC(O)c1ccc(-n2cc(C(F)(F)F)cn2)nc1]

Step A: 6-chloro-N-methoxy-N-methylnicotinamide

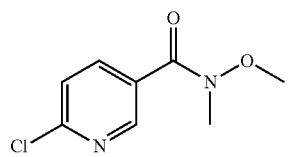

To a solution of 6-chloronicotinic acid (2.0 g, 12.7 mmol) in DMF (20 mL) was added TBTU (6.11 g, 19.0 mmol), di-iso-propylethylamine (4.9 g, 38.1 mmol), and N-methoxymethylamine hydrochloride (1.48 g, 15.2 mmol). The reaction mixture was stirred at 25° C. overnight. The reaction solution was poured into brine (40 mL) and extracted with ethyl acetate (40 mL*2). The organic layer was dried over Na$_2$SO$_4$ and concentrated under reduced pressure. The residue was purified by silica gel chromatography to give 6-chloro-N-methoxy-N-methylnicotinamide (2.3 g) as an oil. $^1$H NMR (400 MHz, CDCl$_3$) δ 8.70 (d, J=2.0 Hz, 1H), 7.95 (dd, J=2.4, 8.4 Hz, 1H), 7.32 (d, J=8.0 Hz, 1H), 3.49 (s, 3H), 3.32 (s, 3H).

Step B: 1-(6-chloropyridin-3-yl)-3-methylbutan-1-one

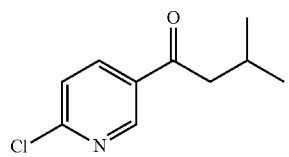

To a 0° C. solution of 6-chloro-N-methoxy-N-methylnicotinamide (2 g, 10 mmol) in THF (30 mL) was added the iso-butymagnesium bromide (15 mL of a 1.33M solution in THF, 20 mmol). The reaction mixture was stirred at 25° C. for 2 h. The reaction was quenched by addition of aqueous NH$_4$Cl (30 mL) and extracted with ethyl acetate (30 mL*2). The organic layer was washed with brine (50 mL) and water (50 mL), then dried over anhydrous Na$_2$SO$_4$ and concentrated under reduced pressure. The crude residue was purified by silica gel chromatography to give 1-(6-chloropyridin-3-yl)-3-methylbutan-1-one (1.8 g) as a colorless solid. $^1$H NMR (400 MHz, CDCl$_3$) δ 8.85 (d, J=2.0 Hz, 1H), 8.12 (dd, J=2.4, 8.4 Hz, 1H), 7.37 (d, J=8.0 Hz, 1H), 2.75 (d, J=6.8 Hz, 2H), 2.26-2.19 (m, 1H), 0.94 (d, J=6.8 Hz, 6H).

Step C: 3-methyl-1-(6-(4-(trifluoromethyl)-1H-pyrazol-1-yl)pyridin-3-yl)butan-1-one

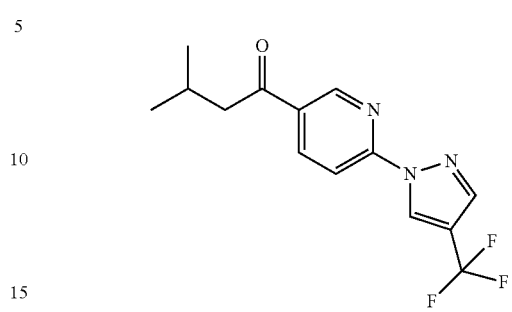

To a solution of 1-(6-chloropyridin-3-yl)-3-methylbutan-1-one (1.0 g, 5.1 mmol) and 4-(trifluoromethyl)-1H-pyrazole (766 mg, 5.62 mmol) in anhydrous DMF (20 mL) was added potassium carbonate (2.12 g, 15.3 mmol). The mixture was stirred at 50° C. for 6 h. The reaction mixture was poured into brine (30 mL) and extracted with ethyl acetate (30 mL*2). The combined organic layers were dried over anhydrous Na$_2$SO$_4$, filtered, and concentrated under reduced pressure. The crude residue was purified by silica gel chromatography to give 3-methyl-1-(6-(4-(trifluoromethyl)-1H-pyrazol-1-yl)pyridin-3-yl)butan-1-one (1.4 g) as a colorless solid. $^1$H NMR (400 MHz, CDCl$_3$) δ 8.92 (d, J=2.0 Hz, 1H), 8.85 (s, 1H), 8.33 (dd, J=2.0, 8.4 Hz, 1H), 8.02 (d, J=8.4 Hz, 1H), 7.88 (s, 1H), 2.79 (d, J=6.8 Hz, 2H), 2.31-2.21 (m, 1H), 0.96 (d, J=6.8 Hz, 6H).

Step D: 3-methyl-1-(6-(4-(trifluoromethyl)-1H-pyrazol-1-yl)pyridin-3-yl)butan-1-ol To a 0° C. solution of 3-methyl-1-(6-(4-(trifluoromethyl)-1H-pyrazol-1-yl)pyridin-3-yl)butan-1-one (1.4 g, 4.7 mmol) in methanol (20 mL) was added sodium borohydride (367 mg, 9.4 mmol). The resulting mixture was stirred at 20° C. for 1 hour. Water was added and the mixture was extracted with ethyl acetate (40 mL). The organic layer was dried over anhydrous Na$_2$SO$_4$, filtered, and concentrated to give 3-methyl-1-(6-(4-(trifluoromethyl)-1H-pyrazol-1-yl)pyridin-3-yl)butan-1-ol (1.4 g) as a colorless solid. $^1$H NMR (400 MHz, CDCl$_3$) δ 8.78 (s, 1H), 8.32 (d, J=2.0 Hz, 1H), 7.91 (d, J=8.4 Hz, 1H), 7.82-7.79 (m, 2H), 4.82-4.77 (m, 1H), 1.83 (s, 1H), 1.75-1.64 (m, 2H), 1.47-1.43 (m, 1H), 0.88-0.92 (m, 6H).

Intermediate (90): methyl 6-(tert-butoxycarbonylamino)nicotinate

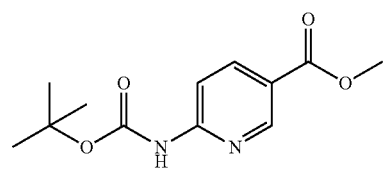 [SMILES: COC(=O)c1ccc(NC(=O)OC(C)(C)C)nc1]

Di-t-butyldicarbonate (5.0 g, 23 mmol) was added to a room temperature suspension of methyl 6-aminonicotinate (2.65 g, 17.4 mmol) and N,N-dimethylaminopyridine (109 mg, 0.86 mmol) in 40 mL acetonitrile. The resulting orange mixture was stirred at room temperature overnight. The suspension was filtered. The solid was washed with acetonitrile and air dried to give 2.64 g methyl 6-(tert-butoxycarbonylamino)nicotinate as a colorless solid. The filtrate was concentrated under reduced pressure. The residue was purified by silica gel chromatography to give an additional 1.50 g methyl 6-(tert-butoxycarbonylamino)nicotinate. $^1$H NMR (400 MHz, CDCl$_3$) δ 8.89-8.92 (m, 1H), 8.49-8.59 (br s, 1H), 8.24 (dd, J=8.0, 2.3 Hz, 1H), 8.04 (d, J=8.0 Hz), 3.89 (s, 3H), 1.54 (s, 9H).

Intermediate (91): (E)-N-(2-cyclopropyl-3-(dimethylamino)allylidene)-N-methylmethanaminium hexafluorophosphate(V)

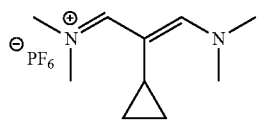

(E)-N-(2-cyclopropyl-3-(dimethylamino)allylidene)-N-methylmethanaminium hexafluorophosphate(V) was prepared using a method analogous to that described for the preparation of Intermediate (7A), starting from 2-cyclopropylacetic acid. Yellow solid. $^1$H NMR (400 MHz, DMSO-d$_6$) δ 7.38 (s, 2H), 3.42 (s, 6H), 3.25 (s, 6H), 1.80-1.78 (m, 1H), 0.89-0.85 (m, 2H), 0.47-0.43 (m, 2H).

Intermediate (92): 1-(4-bromo-2,6-dimethylphenyl)-4-cyclopropyl-1H-pyrazole

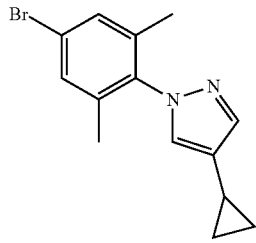 [SMILES: Cc1cc(Br)cc(C)c1-n1cc(C2CC2)cn1]

1-(4-bromo-2,6-dimethylphenyl)-4-cyclopropyl-1H-pyrazole was prepared using a method analogous to that described for the preparation of Intermediate (7), starting from Intermediate (7B) and Intermediate (91). Brown oil. $^1$H NMR (400 MHz, CDCl$_3$) δ 7.42 (s, 1H), 7.19 (s, 2H), 7.10 (s, 1H), 1.91 (s, 6H), 1.72-1.67 (m, 1H), 0.85-0.80 (m, 2H), 0.52-0.48 (m, 2H).

Intermediate (93): 4-(4-cyclopropyl-1H-pyrazol-1-yl)-3,5-dimethylphenol

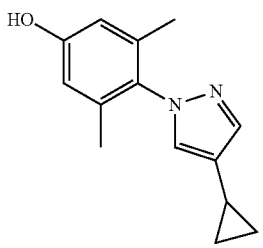 [SMILES: Cc1cc(O)cc(C)c1-n1cc(C2CC2)cn1]

4-(4-cyclopropyl-1H-pyrazol-1-yl)-3,5-dimethylphenol was prepared using a method analogous to that described for Intermediate (26), starting from Intermediate (92). Yellow solid. $^1$H NMR (400 MHz, CDCl$_3$) δ 7.55 (br, 1H), 7.42 (s, 1H), 7.10 (s, 1H), 6.30 (s, 1H), 1.79 (s, 6H), 1.71-1.67 (m, 1H), 0.85-0.80 (m, 2H), 0.52-0.48 (m, 2H).

Intermediate (94): 1-(4-bromo-2,6-dimethylphenyl)-4-(trifluoromethyl)-1H-1,2,3-triazole

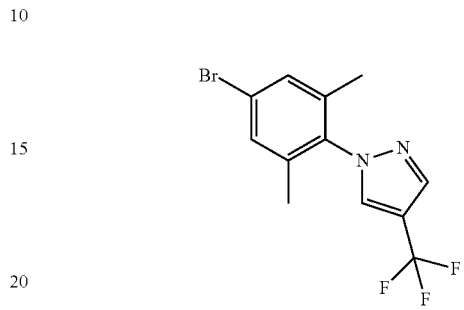

4-bromo-2,6-dimethylaniline (302 mg, 1.51 mmol) was suspended in 4 mL 18% aqueous HCl. The mixture was cooled to 0° C. A solution of sodium nitrite (125 mg, 1.81 mmol) in 500 µL water was added dropwise over 5 min. During addition, the suspension begins to clear, giving a yellow solution. The solution was stirred at 0° C. 1 h. A solution of sodium acetate (2.50 g, 30.5 mmol) and sodium azide (201 mg, 3.1 mmol) in 5 mL water was added dropwise. The mixture was stirred at 0° C. for 30 min and then warmed to room temperature. The mixture was extracted with 3×20 mL ethyl acetate. The combined organic layers were dried over MgSO$_4$, filtered and concentrated under reduced pressure, without heating, to give 520 mg brown oil. The residue was dissolved in 15 mL ethanol in a heavy walled sealable glass tube. The solution was cooled to −78° C. 3,3,3-trifluoromethylpropyne was bubbled through the solution for 5 min. A solution of copper (I) iodide (14 mg, 0.074 mmol) and sodium ascorbate (30 mg, 0.15 mmol) in 500 µL water was added. The reaction vessel was sealed and allowed to warm to room temperature. After 15 h at, the reaction mixture was cooled to −78° C. The vessel was opened at this temperature and then allowed to warm to room temperature. The reaction mixture was concentrated to give 1-(4-bromo-2,6-dimethylphenyl)-4-(trifluoromethyl)-1H-1,2,3-triazole (447 mg) as a pale yellow solid. Recrystallization from heptane gave fine, colorless needles. $^1$H NMR (400 MHz, CDCl$_3$) δ 7.89-7.92 (m, 1H), 7.38 (s, 2H), 1.98 (s, 6H).

Intermediate (95): 3,5-dimethyl-4-(4-(trifluoromethyl)-1H-1,2,3-triazol-1-yl)phenol

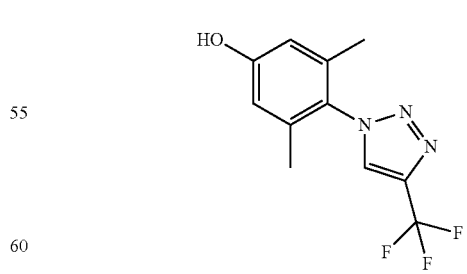

3,5-dimethyl-4-(4-(trifluoromethyl)-1H-1,2,3-triazol-1-yl)phenol was prepared using a method analogous to that described for Intermediate (26), starting from Intermediate (94). Colorless solid. $^1$H NMR (400 MHz, CDCl$_3$) δ 7.87-7.90 (m, 1H), 6.65 (s, 2H), 5.09 (s, 1H), 1.93 (s, 6H).

Intermediate (96): ethyl 3-(4-(1-hydroxybutyl)benzamido)propanoate

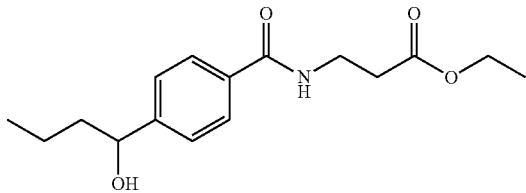 [SMILES: CCCC(O)c1ccc(C(=O)NCCC(=O)OCC)cc1]

Step (A): 4-(1-hydroxybutyl)benzoic acid

The alcohol corresponding to intermediate 5 (1.0 g, 4.5 mmol) was charged with tetrahydrofuran (10.0 mL), water (10.0 mL), and methanol (10.0 mL). Lithium hydroxide monohydrate (944 mg, 22.5 mmol) was then added. The suspension was stirred at room temperature for 18 hours. The reaction was quenched with 1 N hydrochloric acid to pH 3 and extracted three times with ethyl acetate. The combined organic layers were dried over sodium sulfate, filtered, and concentrated to give 1.4 g of crude material. Purification by silica gel flash chromatography (0-30% ethyl acetate in heptane) afforded 4-(1-hydroxybutyl)benzoic acid (730 mg, 83% yield) as a white solid. $^1$H NMR (400 MHz, CDCl$_3$) δ 8.09 (d, J=8.0 Hz, 2H), 7.46 (d, J=8.2 Hz, 2H), 4.79 (dd, J=7.6, 5.5 Hz, 1H), 1.86-1.75 (m, 1H), 1.75-1.64 (m, 1H), 1.52-1.24 (m, 2H), 0.95 (t, J=7.4 Hz, 3H).

Step (B): ethyl 3-(4-(1-hydroxybutyl)benzamido)propanoate

N,N-dimethylformamide (8.60 mL) was added to a vial containing 4-(1-hydroxybutyl)benzoic acid (250 mg, 1.29 mmol), ethyl 3-aminopropanoate hydrochloride (395 mg, 2.57 mmol) and O-(7-azabenzotriazol-1-yl)-N,N,N',N'-tetramethyluronium hexafluorophosphate (979 mg, 2.57 mmol). Diisopropylethylamine (1.12 mL, 6.44 mmol) was then added. The reaction was stirred for 16 h, and was then concentrated. Purification by column chromatography (0-50% ethyl acetate in heptane) afforded ethyl 3-(4-(1-hydroxybutyl)benzamido)propanoate (350 mg, 93% yield) as an oil. $^1$H NMR (400 MHz, CDCl$_3$) δ 7.73 (d, J=8.2 Hz, 2H), 7.40 (d, J=8.0 Hz, 2H), 6.84 (br.s., 1H), 4.74 (t, J=6.5 Hz, 1H), 4.23-4.07 (m, 2H), 3.72 (q, J=5.9 Hz, 2H), 2.64 (t, J=5.9 Hz, 2H), 1.85-1.72 (m, 1H), 1.72-1.58 (m, 1H), 1.52-1.37 (m, 1H), 1.37-1.30 (m, 1H), 1.28 (t, J=7.2 Hz, 3H), 0.93 (t, J=7.3 Hz, 3H). MS (M+1) 294.3.

Intermediate (97): 5-methyl-6-(4-(trifluoromethyl)-1H-pyrazol-1-yl)pyridin-3-ol

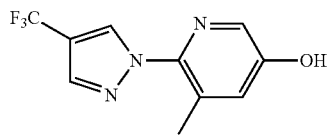 [SMILES: Cc1cc(O)cnc1-n1cc(C(F)(F)F)cn1]

Step (A): 5-bromo-3-methyl-2-(4-(trifluormethyl)-1H-pyrazol-1-yl)pyridine

A flask was charged with 5-bromo-2-chloro-3-methylpyridine (250 mg, 1.21 mmol), 4-(trifluoromethyl)-1H-pyrazole (165 mg, 1.21 mmol), potassium carbonate (512 mg, 3.63 mmol), and anhydrous dimethylformamide (1.21 mL). The reaction was heated at 85 to 130° C. for 36 h. The reaction was concentrated to give 690 mg of crude material. Purification by silica gel flash chromatography (0-5% ethyl acetate in heptane) afforded 5-bromo-3-methyl-2-(4-(trifluoromethyl)-1H-pyrazol-1-yl)pyridine (containing approximately 30% starting material) was carried forth to the next reaction. MS (M+1) 308.1.

Step (B): 5-methyl-6-(4-(trifluoromethyl)-1H-pyrazol-1-yl)pyridin-3-ol

To a flask containing 5-bromo-3-methyl-2-(4-(trifluoromethyl)-1H-pyrazol-1-yl)pyridine (55.0 mg, 0.180 mmol) in 1,4-dioxane (0.100 mL) and degassed water (0.100 mL), was added tris(dibenzylideneacetone)dipalladium(0) (21.3 mg, 0.0360 mmol), 2-di-tert-butylphosphino-2',4',6'-triisopropylbiphenyl (6.10 mg, 0.014 mmol), and potassium hydroxide (31.9 mg, 0.0540 mmol). The reaction was purged with nitrogen and then heated at 100° C. for 2 hour. The reaction was quenched with 1 N HCl and extracted three times with ethyl acetate. The organics were dried over sodium sulfate, filtered and concentrated. Purification by silica gel flash chromatography (0-25% ethyl acetate in heptane) afforded impure 5-methyl-6-(4-(trifluoromethyl)-1H-pyrazol-1-yl)pyridin-3-ol (containing approximately 30% impurity as a solid. MS (M+H): 244.2.

Intermediate (98): ethyl 3-(4-(cyclobutyl(hydroxy)methyl)benzamido)propanoate

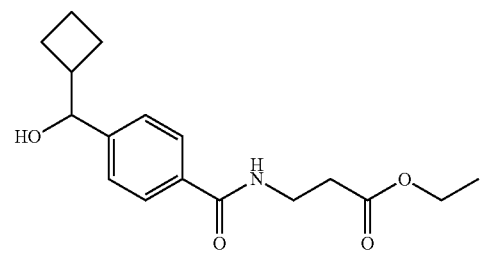 [SMILES: CCOC(=O)CCNC(=O)c1ccc(C(O)C2CCC2)cc1]

Step (A): cyclobutanecarbaldehyde

A flask was charged with oxalyl chloride (1.12 mL, 12.8 mmol) and anhydrous methylene chloride (21.0 mL). The solution was cooled to −78° C. and dimethylsulfoxide (1.82 mL, 25.5 mL) was added dropwise and the reaction was stirred for 30 min. at −78° C. A solution of cyclobutylmethanol (1.10 mL 11.6 mmol) in methylene chloride (8.0 mL) was added dropwise and the reaction was aged for 1 h at the same temperature. Triethylamine (8.20 mL, 58.0 mL) was then added dropwise and the reaction was warmed to room temperature and aged for 18 h. The reaction was quenched with water and extracted three times with methylene chloride. The combined organic layers were dried over magnesium sulfate, filtered, and concentrated to give cyclobutanecarbaldehyde (2.00 g) as a crude oil containing approximately 1.0 g triethylamine. ¹H NMR (400 MHz, CDCl₃) δ 9.73 (d, J=2.0 Hz, 1H), 3.18 (s, 1H), 2.34-2.22 (m, 2H), 2.22-2.11 (m, 2H), 2.11-1.99 (m, 1H), 1.99-1.84 (m, 1H).

Step (B): ethyl 4-(cyclobutyl(hydroxymethyl)benzoate

To a solution of ethyl 4-iodobenzoate (1.45 mL, 8.69 mmol) in anhydrous tetrahydrofuran (14.5 mL) at −40° C. was added isopropyl magnesium chloride lithium chloride complex (8.0 mL, 10.4 mmol) dropwise. The resulting brown solution was stirred for 40 min at −40° C. The crude cyclobutanecarbaldehyde (1.8 g, approximately 10.5 mmol pure) was added and the reaction was warmed to room temperature and stirred for 18 h. The reaction is then quenched with 1 N hydrochloric acid and extracted three times with ethyl acetate. The combined organic layers were dried over sodium sulfate, filtered, and concentrated to give 2.0 g of crude material. Purification by silica gel flash chromatography (0-20% ethyl acetate in heptane) afforded ethyl 4-(cyclobutyl(hydroxy)methyl)benzoate (1.05 g) as an oil. ¹H NMR (400 MHz, CDCl₃) δ 8.01 (d, J=8.4 Hz, 2H), 7.39 (d, J=8.2 Hz, 2H), 4.64 (d, J=7.6 Hz, 1H), 4.47-4.25 (m, 2H), 2.73-2.47 (m, 1H), 2.13-1.94 (m, 2H), 1.95-1.70 (m, 4H), 1.55 (br. s., 1H), 1.38 (t, J=7.0 Hz, 3H).

Step (C): 4-(cyclobutyl(hydroxymethyl)benzoic acid

To a flask containing ethyl 4-(cyclobutyl(hydroxy)methyl) benzoate (530 mg, 2.26 mmol) was added tetrahydrofuran (5.60 mL), water (5.60 mL), and methanol (5.60 mL). Lithium hydroxide monohydrate (475 mg, 11.3 mmol) was then added. The suspension was stirred at room temperature for 18 hours. The reaction was quenched with 1 N hydrochloric acid to pH 3 and extracted three times with ethyl acetate. The combined organic layers were dried over sodium sulfate, filtered, and concentrated to give 490 mg of crude material. Purification by silica gel flash chromatography (0-20% ethyl acetate in heptane) afforded 4-(cyclobutyl(hydroxy)methyl) benzoic acid (360 mg, 77%) as a white solid. ¹H NMR (400 MHz, CDCl₃) δ 8.07 (d, J=8.2 Hz, 2H), 7.43 (dd, J=8.0, 1.0 Hz, 2H), 4.67 (d, J=7.6 Hz, 1H), 2.62 (d, J=8.0 Hz, 1H), 2.09-1.98 (m, 2H), 1.91-1.80 (m, 4H). MS (M−1): 205.2.

Step (D): ethyl 3-(4-(cyclobutyl(hydroxy)methyl) benzamido)propanoate

N,N-dimethylformamide (9.00 mL) was added to a vial containing 4-(cyclobutyl(hydroxy)methyl)benzoic acid (370 mg, 1.79 mmol), ethyl 3-aminopropanoate hydrochloride (551 mg, 3.59 mmol) and O-(7-azabenzotriazol-1-yl)-N,N,N',N'-tetramethyluronium hexafluorophosphate (1.36 g, 3.59 mmol). Diisopropylethylamine (1.56 mL, 8.97 mmol) was then added. The reaction was stirred for 1.5 h, and was then concentrated. Purification by column chromatography (0-50% ethyl acetate in heptane) afforded ethyl 3-(4-(cyclobutyl(hydroxy)methyl)benzamido)propanoate (570 mg, 100% yield) as a white solid. ¹H NMR (400 MHz, CDCl₃) δ 7.73 (d, J=8.2 Hz, 2H), 7.38 (d, J=8.2 Hz, 2H), 4.63 (d, J=7.8 Hz, 1H), 4.17 (q, J=7.2 Hz, 2H), 3.72 (q, J=6.0 Hz, 2H), 2.64 (t, J=5.9 Hz, 2H), 2.61-2.54 (m, 1H), 2.08-1.95 (m, 2H), 1.88-1.75 (m, 4H), 1.27 (t, J=7.1 Hz, 3H). MS (M+1): 306.3.

Intermediate (99): ethyl 4-(3,3-dimethylcyclobutanecarbonyl)benzoate

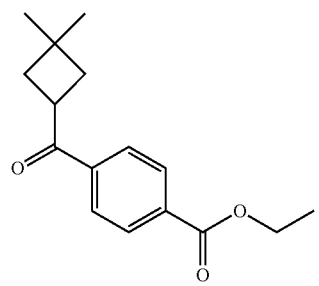 [SMILES: CCOC(=O)c1ccc(C(=O)C2CC(C)(C)C2)cc1]

Step (A)-3,3-dimethylcyclobutanecarbonyl chloride 3,3-Dimethyl-cyclobutanecarboxylic acid (Parkway Scientific, New York, N.Y., USA) (500 mg, 3.90 mmol) was dissolved in dichloromethane (3 mL) and oxalyl chloride (1.02 mL, 11.7 mmol) was added. The solution was stirred at room temperature for 4 h before concentrating in vacuo to provide 3,3-dimethylcyclobutanecarbonyl chloride which was carried on without purification. ¹H NMR (400 MHz, CDCl₃) δ 3.49 (quin, J=8.9 Hz, 1H) 2.27-2.15 (m, 2H) 2.14-2.06 (m, 2H) 1.18 (s, 3H) 1.12 (s, 3H).

Step (B): ethyl 4-(3,3-dimethylcyclobutanecarbonyl)benzoate

In a 3-neck flask at −30° C. (monitored with thermalcouple) containing ethyl 4-iodobenzoate (25.0 g, 89.0 mmol) in anhydrous tetrahydrofuran (148 mL) was added isopropylmagnesium chloride (51.0 mL, 20.4 mmol) dropwise over 30 min. and then stirred at the same temperature for another 105 min. Copper iodide (5.07 g, 26.6 mmol) was then added quickly in one portion. The mixture was brought to −20° C. for 25 min. to ensure the solid has dissolved. The reaction is then brought back to −40° C. 3,3-dimethylcyclobutane carbonyl chloride (15.6 g, 106 mmol) was then added over 5 min. the reaction was then warmed to 0° C. over 4 h. The mixture was then diluted with 1 N HCl and extracted three times with ethyl acetate. The combined organic layers were then washed two times with brine and then dried over sodium sulfate, filtered, and concentrated to provide 26.6 g of crude brown oil. Purification by silica gel flash chromatography twice (0-5% ethyl acetate in heptane) afforded ethyl 4-(3,3-dimethylcyclobutanecarbonyl)benzoate (17.2 g, 74% yield) as an oil. ¹H NMR (400 MHz, CDCl₃) δ 8.11 (d, J=8.2 Hz, 2H), 7.93 (d, J=8.2 Hz, 2H), 4.40 (q, J=7.2 Hz, 2H), 3.89 (quin, J=8.8 Hz, 1H), 2.27-2.14 (m, 2H), 2.12-2.02 (m, 2H), 1.41 (t, J=7.1 Hz, 3H), 1.27 (s, 3H), 1.08 (s, 3H). MS (M+1): 261.2.

Intermediate (100): ethyl 4-((3,3-dimethylcyclobutyl)(hydroxy)methyl)benzoate

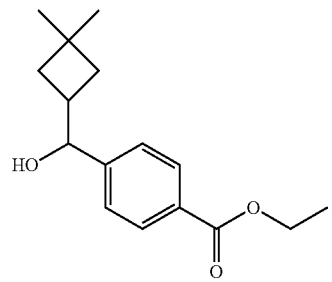 [SMILES: CCOC(=O)c1ccc(C(O)C2CC(C)(C)C2)cc1]

To a flask containing Intermediate (99) (350 mg, 1.34 mmol) was added anhydrous methanol (6.70 mL). The solution was cooled to 0° C. and sodium borohydride (152 mg, 4.00 mmol) was added. After 20 min., the reaction was quenched with saturated aqueous ammonium chloride and extracted three times with ethyl acetate. The combined organic layers were dried over sodium sulfate, filtered, and concentrated to give 420 mg of crude material. Purification by silica gel flash chromatography (0-15% ethyl acetate in heptane) afforded impure ethyl 4-((3,3-dimethylcyclobutyl)(hydroxy)methyl)benzoate (260 mg, 73.8%) as a solid. $^1$H NMR (400 MHz, CDCl$_3$) δ 8.00 (d, J=8.6 Hz, 2H), 7.38 (d, J=8.0 Hz, 2H), 4.60 (d, J=7.8 Hz, 1H), 4.37 (q, J=7.0 Hz, 2H), 2.61-2.39 (m, 1H), 1.89-1.71 (m, 2H), 1.66-1.51 (m, 2H), 1.38 (t, J=7.2 Hz, 3H), 1.11 (s, 3H), 1.07 (s, 3H).

Intermediate (101): ethyl 3-(4-(3,3-dimethylcyclobutanecarbonyl)benzamido)propanoate

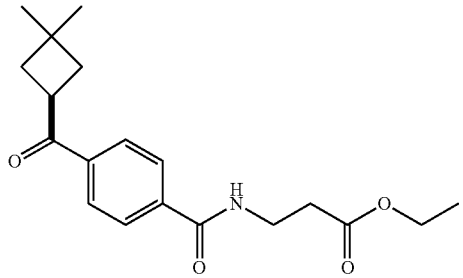

Step (A): 4-(3,3-dimethylcyclobutanecarbonyl)benzoic acid

To a flask containing Intermediate (99) (3.00 g, 12.0 mmol) was added anhydrous tetrahydrofuran (28.8 mL), methanol (28.8 mL), and 1 N sodium hydroxide (28.8 mL, 28.8 mmol). After 1 h, the reaction was concentrated to a white solid. The solid was the redissolved in 700 mL of water. With vigorous stirring, 1 N HCl (29.0 mL) was added dropwise and the suspension was stirred for 30 min. at room temperature. The solid was then collected with a Buchner funnel and the solid was washed two times with water. The solid was then azeotrophed with toluene to give 4-(3,3-dimethylcyclobutanecarbonyl)benzoic acid (2.15 g, 92% yield) as a white solid. $^1$H NMR (400 MHz, CDCl$_3$) δ 8.21-8.15 (m, 2H), 8.01-7.94 (m, 2H), 3.91 (quin, J=8.9 Hz, 1H), 2.28-2.17 (m, 2H), 2.15-2.04 (m, 2H), 1.28 (s, 3H), 1.09 (s, 3H). MS (M−1): 231.4.

Step (B): ethyl 3-(4-(3,3-dimethylcyclobutanecarbonyl)benzamido)propanoate

Tetrahydrofuran (138 mL) was added to a vial containing 4-(3,3-dimethylcyclobutanecarbonyl)benzoic acid (3.20 g, 14.0 mmol), ethyl 3-aminopropanoate hydrochloride (3.17 g, 20.7 mmol) and 1,2,3-benzotriazol-1-ol monohydrate (2.22 g, 14.5 mmol). Triethylamine (9.11 mL, 4.75 mmol) was then added. The reaction was stirred for 16 h, and was then concentrated. Purification by column chromatography (0-35% ethyl acetate in heptane) afforded impure ethyl 3-(4-(3,3-dimethylcyclobutanecarbonyl)benzamido)propanoate (4.22 g, approximately 8.90 mmol pure) as an oil. MS (M+1) 332.2.

Intermediate (102): ethyl 3-(4-((3,3-dimethylcyclobutyl)(hydroxyl)methyl)benzamido)propanoate

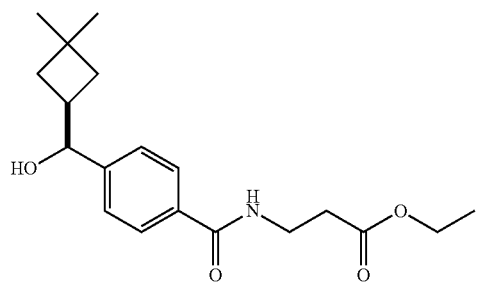

To a flask containing ethyl 3-(4-(3,3-dimethylcyclobutanecarbonyl)benzamido) propanoate (1.21 g, approximately 2.55 mmol pure) was added anhydrous methanol (18.3 mL). The solution was cooled to 0° C. and sodium borohydride (414 mg, 11.0 mmol) was added. After 15 min., the reaction was quenched with saturated aqueous ammonium chloride and extracted three times with ethyl acetate. The combined organic layers were dried over sodium sulfate, filtered, and concentrated to give 1.10 g of crude material. Purification by silica gel flash chromatography (0-50% ethyl acetate in heptane) afforded impure ethyl 3-(4-((3,3-dimethylcyclobutyl (hydroxy)methyl)benzamido)propanoate (750 mg, approximately 1.8 mmol pure) as an oil. MS (M+1): 334.3.

Intermediate (103): 3-methoxy-5-methyl-(4-(trifluoromethyl)-1H-pyrazol-1-yl)phenol

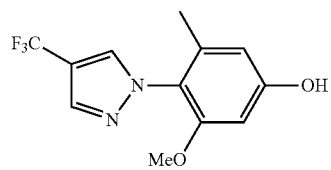 [SMILES: COc1cc(O)cc(C)c1-n1cc(C(F)(F)F)cn1]

Step (A): 1-(2-methoxy-6-methylphenyl)-4-(trifluoromethyl)-1H-pyrazole

Intermediate 7A (1.77 g, 5.20 mmol) and 1-(2-methoxy-6-methylphenyl)hydrazine hydrochloride (Shanghai Chempartner Co. Ltd.) (1.00 g, 5.20 mmol) were suspended in tetrahydrofuran (20.8 mL). The suspension was cooled to 0° C. Sodium methoxide (325 mg, 5.72 mmol) was added as a solid in one portion. The ice bath was removed and the mixture warmed to room temperature and stirred for 18 hours. Trifluoroacetic acid (1.77 mL) was then added at room temperature. The reaction was heated to 80° C. for 5 hours, diluted with ethyl acetate and washed with saturated sodium bicarbonate twice. The combined aqueous washings were extracted with ethyl acetate. The combined organic layers were washed with brine, dried over sodium sulfate, filtered and concentrated. Purification by column chromatography (0-10% ethyl acetate in heptane), gave 1-(2-methoxy-6-methylphenyl)-4-(trifluoromethyl)-1H-pyrazole (810 mg, 61%) as a solid. $^1$H NMR (400 MHz, CDCl$_3$) δ 7.93 (s, 1H), 7.81-7.71 (m, 1H), 7.33 (t, J=8.1 Hz, 1H), 6.96-6.81 (m, 2H), 3.76 (s, 3H), 2.07 (s, 3H). MS (M+1): 257.2.

Step (B): 3-methoxy-5-methyl-4-(4-(trifluoromethyl)-1H-pyrazol-1-yl)phenol

To a flask containing 1-(2-methoxy-6-methylphenyl)-4-(trifluoromethyl)-1H-pyrazole (75.0 mg, 0.290 mmol) was added di-μ-methoxobis(1,5-cyclooctadiene)diiridium(I) (2.00 mg, 0.003 mmol), bis(pinacolato)diboron (75.2 mg, 0.290 mmol), 4,4'di-tert-butyl-2,2'-dipyridyl (1.60 mg, 0.006 mmol) and degassed methyl tert-butyl ether (1.50 mL). The resulting red solution was heated to 80° C. for 18 h and then at room temperature for 3 d. The reaction was concentrated. Acetone (0.980 mL) was added to provide a homogenous solution followed by an aqueous solution of oxone (180 mg, 0.290 mmol), 0.98 mL of water) dropwise over 2 min. The reaction was stirred at room temperature for 18 h. The reaction was then quenched with aqueous sodium bisulfate and extracted three times with methylene chloride. The combined organic layers were washed with brine and water. The organic layer was then dried over sodium sulfate, filtered, and concentrated. Purification by column chromatography (0-25% ethyl acetate in heptane), gave 3-methoxy-5-methyl-4-(4-(trifluoromethyl)-1H-pyrazol-1-yl)phenol (26.0 mg, 33%) as a solid. $^1$H NMR (400 MHz, CDCl$_3$) δ 7.93 (s, 1H), 7.75-7.70 (m, 1H), 6.27 (dd, J=15.8, 2.5 Hz, 2H), 3.68 (s, 3H), 1.96 (s, 3H). MS (M+1): 273.2.

Intermediate (104): ethyl 4-(3,3-difluorocyclobutanecarbonyl)benzoate

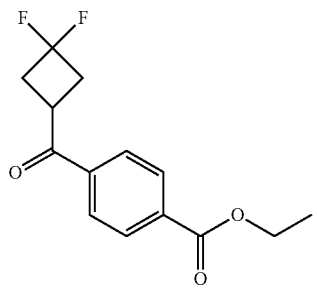 [SMILES: CCOC(=O)c1ccc(C(=O)C2CC(F)(F)C2)cc1]

Step (A): 3,3-difluorocyclobutanecarbonyl chloride 3,3-Difluorocyclobutanecarboxylic acid (Parkway Scientific, New York, N.Y., USA) (531 mg, 3.90 mmol) was dissolved in dichloromethane (3.00 mL) and oxalyl chloride (1.02 mL, 11.7 mmol) was added. The solution was stirred at room temperature for 4 h before concentrating in vacuo to provide 3,3-difluorocyclobutanecarbonyl chloride (ca. 50% pure), which was carried on without purification.

Step (B): ethyl 4-(3,3-difluorocyclobutanecarbonyl)benzoate

In a 3-neck flask at −30° C. containing ethyl 4-iodobenzoate (600 mg, 2.17 mmol) in anhydrous tetrahydrofuran (6.00 mL) was added isopropylmagnesium chloride lithium chloride complex (1.84 mL, 2.39 mmol) dropwise and then stirred at the same temperature for another 40 min. Copper iodide (124 mg, 0.650 mmol) was then added quickly in one portion. The mixture was brought to −15° C. for 20 min. to ensure the solid has dissolved. The reaction is then brought back to −40° C. Crude 3,3-difluorocyclobutanecarbonyl chloride (470 mg, 1.50 mmol pure) was then added and the reaction was then warmed to 0° C. over 1 h and then stirred at room temperature for 18 h. The mixture was then diluted with 1 N HCl and extracted three times with ethyl acetate. The combined organic layers were then washed with brine and then dried over sodium sulfate, filtered, and concentrated to provide 680 mg of crude oil. Purification by silica gel flash chromatography (0-10% ethyl acetate in heptane) afforded impure ethyl 4-(3,3-difluorocyclobutanecarbonyl)benzoate (130 mg, approximately 0.24 mmol pure) as a solid. $^1$H NMR (400 MHz, CDCl$_3$) δ 8.09 (d, J=9.0 Hz, 2H), 7.18 (d, J=9.2 Hz, 2H), 4.39 (q, J=7.4 Hz, 2H), 3.34-3.15 (m, 1H), 3.12-2.78 (m, 4H), 1.40 (t, J=7.4 Hz, 3H).

Intermediate (105): 2-(4-(trifluoromethyl)-1H-pyrazol-1-yl)pyrimidin-5-ol

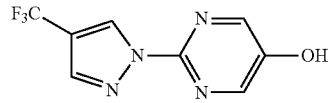

Step (A): 5-bromo-2-(4-(trifluoromethyl)-1H-pyrazol-1-yl)pyrimidine

To a mixture of 5-bromo-2-chloropyrimidine (4.32 g, 21.5 mmol), 4-(trifluoromethyl)-1H-pyrazole (2.92 g, 21.5 mmol), and dried potassium carbonate (8.90 g, 64.4 mmol) was added anhydrous dimethylformamide (31.5 mL). The resulting suspension was heated at 85° C. for 4 h. The reaction was diluted with water and extracted with ethyl acetate three times. The combined organic layers were dried over sodium sulfate, filtered, and concentrated to give 12.4 g of crude yellow solid. The crude material was put through a plug of silica eluting with 15% ethyl acetate in heptanes to give 5-bromo-2-(4-(trifluoromethyl)-1H-pyrazol-1-yl)pyrimidine (6.2 g, 99%) as a solid. $^1$H NMR (400 MHz, CDCl$_3$) δ 8.87 (s, 1H), 8.83 (s, 2H), 8.02 (s, 1H).

Step (B): 5-(4,4,5,5-tetramethyl-1,3,2-dioxaborolan-2-yl)-2-(4-(trifluoromethyl)-1H-pyrazol-1-yl)pyrimidine To a flask containing 5-bromo-2-(4-(trifluoromethyl)-1H-pyrazol-1-yl)pyrimidine (2.90 g, 9.9 mmol) was added bis(dipinacolato)borane (3.00 g, 11.9 mmol), potassium acetate (2.90 g, 29.7 mmol), and 1,1'-bis(diphenylphosphino)ferrocenepalladium(II)dichloride (366 mg, 0.500 mmol). After purging with nitrogen, anhydrous dimethylforamide (12.4 mL) was added. The reaction was heated at 80° C. After 2 h, the reaction was cooled to room temperature and partitioned between ethyl acetate and brine. The mixture was filtered through celite and eluted with ethyl acetate. The filtrate was washed twice with brine. The organic layer was dried over sodium sulfate, filtered, and concentrated to give 5.30 g of crude material. Purification by silica gel flash chromatography (0-50% ethyl acetate in heptane) afforded 5-(4,4,5,5-tetramethyl-1,3,2-dioxaborolan-2-yl)-2-(4-(trifluoromethyl)-1H-pyrazol-1-yl)pyrimidine (3.22 g, 96% yield) as a yellow solid. $^1$H NMR (400 MHz, CDCl$_3$) δ 9.05 (s, 2H), 9.00-8.89 (m, 1H), 8.02 (s, 1H), 1.38 (s, 12H).

Step (C): 2-(4-(trifluoromethyl)-1H-pyrazol-1-yl)pyrimidin-5-ol

To a flask containing 5-(4,4,5,5-tetramethyl-1,3,2-dioxaborolan-2-yl)-2-(4-(trifluoromethyl)-1H-pyrazol-1-yl)pyrimidine (3.20 g, 9.40 mmol) was added methanol (72.4 mL) and 50% aqueous hydrogen peroxide (1.71 mL). After 2 h, the reaction was carefully concentrated and the solid was dissolved in diethyl ether and washed twice with water then brine. The organic layer was dried over sodium sulfate, filtered, and concentrated to give 880 mg of crude solid. The brown solid was suspended in water and filtered through a Buchner funnel and washed with ethyl acetate to give a white solid (580 mg). The above aqueous layer was also filtered through a Buchner funnel to provide 926 mg of white solid. The combined batches provided pure 2-(4-(trifluoromethyl)-1H-pyrazol-1-yl)pyrimidin-5-ol (1.50 g, 69%) as a white solid. $^1$H NMR (400 MHz, CDCl$_3$) δ: 8.79 (s, 1H), 8.43 (s, 2H), 7.96 (s, 1H). MS (M+1) 231.1.

Intermediate (106): 2-(4-(trifluoromethyl)-1H-pyrazol-1-yl)pyrimidin-5-amine

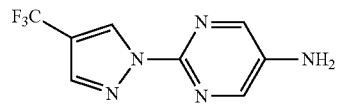

Step (A): 5-nitro-2-(4-(trifluoromethyl)-1H-pyrazol-1-yl)pyrimidine

A round bottom flask was charged with 2-chloro-5-nitropyrimidine (2.50 g, 15.7 mmol), 4-(trifluoromethyl)-1H-pyrazole (2.35 g, 17.2 mmol), K$_2$CO$_3$ (4.33 g, 31.3 mmol) and acetonitrile (39 mL). The reaction was heated at 80° C. for 2 hours. Potassium carbonate filtered off with a büchner funnel and acetonitrile removed under reduced pressure. The crude material was dissolved in ethyl acetate and transferred to a separatory funnel. Organics washed with water (3×), with brine (1×), dried over sodium sulfate, filtered and concentrated to afford the raw material. Purification by silica gel flash chromatography (ethyl acetate/heptane) provide 5-nitro-2-(4-(trifluoromethyl)-1H-pyrazol-1-yl)pyrimidine (1.95 g, 49%) as a yellow solid. MS (M+1): 259.2.

Step (B): 2-(4-(trifluoromethyl)-1H-pyrazol-1-yl)pyrimidin-5-amine

A Parr Shaker bottle was charged with Pd/C (10% wet; degussa type; 300 mg) and the 5-nitro-2-(4-(trifluoromethyl)-1H-pyrazol-1-yl)pyrimidine (1.18 g, 4.55 mmol) in ethyl acetate (91 mL). Shaked at 40 psi of H$_2$ (g) for 8 hours. Crude mixture filtered through celite and concentrated under reduced pressure to afford 2-(4-(trifluoromethyl)-1H-pyrazol-1-yl)pyrimidin-5-amine (1.78 g, 98%) as an orange solid.

$^1$H NMR (400 MHz, DMSO-d6) δ 5.85 (s, 2H) 8.15 (s, 1H) 8.18 (s, 2H) 8.95 (s, 1H); MS (M+1): 230.2.

Intermediate (107): 6-(4-phenyl-1H-imidazol-1-yl)pyridin-3-amine

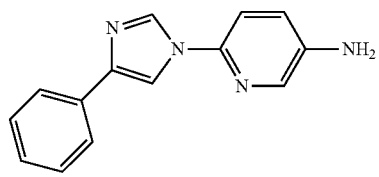 [SMILES: Nc1ccc(-n2cnc(-c3ccccc3)c2)nc1]

Step A: 5-iodo-2-(4-phenyl-1H-imidazol-1-yl)pyridine

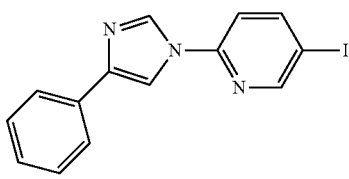 [SMILES: Ic1ccc(-n2cnc(-c3ccccc3)c2)nc1]

The title compound was prepared by a method analogous to that described for Intermediate (24), using 4-phenyl-1H-imidazole. $^1$H NMR (400 MHz, CDCl$_3$, δ): 8.69 (d, J=2.1 Hz, 1H), 8.40 (s, 1H), 8.11 (dd, J=8.5, 2.2 Hz, 1H), 7.89 (s, 1H), 7.85 (d, J=7.2 Hz, 2H), 7.41 (t, J=7.7 Hz, 2H), 7.22-7.32 (m, 2H). MS (M+1) 348.1.

Step B: 6-(4-phenyl-1H-imidazol-1-yl)pyridin-3-amine

The title compound was prepared by a method analogous to that described for Intermediate (25), using 5-iodo-2-(4-phenyl-1H-imidazol-1-yl)pyridine. $^1$H NMR (400 MHz, CDCl$_3$, δ): 8.20 (s, 1H), 7.94 (d, J=2.7 Hz, 1H), 7.79-7.87 (m, 3H), 7.38 (t, J=7.6 Hz, 2H), 7.22-7.28 (m, 1H), 7.16-7.21 (m, 1H), 7.08-7.12 (m, 1H), 3.72 (br. s., 2H). MS (M+1) 237.3.

Intermediate (108): 6-(4-chloro-3-methyl-1H-pyrazol-1-yl)pyridin-3-amine

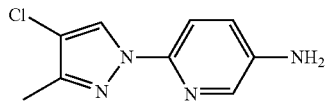

The title compound was prepared by a method analogous to that described for Intermediate (107), using 4-chloro-3-methyl-1H-pyrazole. $^1$H NMR (400 MHz, CDCl$_3$, δ): 8.28 (s, 1H), 7.82 (d, J=2.9 Hz, 1H), 7.62-7.66 (m, 1H), 7.07-7.11 (m, 1H), 3.68 (br. s., 2H), 2.30 (s, 3H). MS (M+1) 209.2.

Intermediate (109): 6-(4-(pyridin-2-yl)-1H-pyrazol-1-yl)pyridin-3-amine

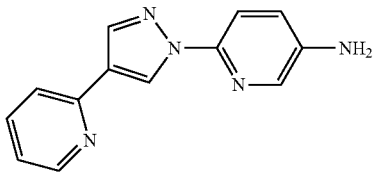 [SMILES: Nc1ccc(-n2cc(-c3ccccn3)cn2)nc1]

The title compound was prepared by a method analogous to that described for Intermediate (107) using 2-(1H-pyrazol-4-yl)pyridine. ¹H NMR (400 MHz, CDCl₃, δ): 8.88-8.90 (m, 1H), 8.56-8.59 (m, 1H), 8.19 (s, 1H), 7.88 (d, J=2.7 Hz, 1H), 7.77 (d, J=8.6 Hz, 1H), 7.62-7.68 (m, 1H), 7.50-7.55 (m, 1H), 7.08-7.14 (m, 2H), 3.73 (br. s., 2H). MS (M+1) 238.3.

Intermediate (110): 6-(4-ethyl-3-methyl-1H-pyrazol-1-yl)pyridin-3-amine

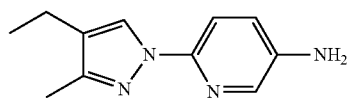

The title compound was prepared by a method analogous to that described for Intermediate (107), using 4-ethyl-3-methyl-1H-pyrazole. ¹H NMR (400 MHz, CDCl₃, δ): 8.07 (s, 1H), 7.82 (d, J=2.3 Hz, 1H), 7.65 (d, J=8.6 Hz, 1H), 7.08 (dd, J=8.7, 2.8 Hz, 1H), 3.56 (br. s., 2H), 2.44 (q, J=7.6 Hz, 2H), 2.26 (s, 3H), 1.20 (t, J=7.5 Hz, 3H). MS (M+1) 203.3.

Intermediate (111): 3,5-dimethyl-4-(4-(trifluoromethyl)-1H-pyrazol-1-yl)benzonitrile

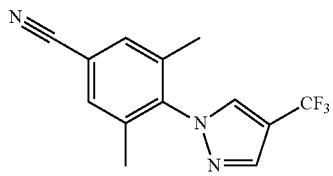 [SMILES: Cc1cc(C#N)cc(C)c1-n1cc(C(F)(F)F)cn1]

A microwave vial was charged with Intermediate (7) (1.00 g, 3.10 mmol), zinc cyanide (199 mg, 1.69 mmol), zinc acetate (22.9 mg, 0.125 mmol), zinc dust (8.2 mg, 0.13 mmol), bis(dibenzylideneacetone)palladium(0) (17.8 mg, 0.0310 mmol), and 1,1'-bis(diphenylphosphino)ferrocene (52.6 mg, 0.0940 mmol). The solids were purged with dry nitrogen, and then dissolved in N,N-dimethylformamide (3.13 mL) and water (0.31 mL). The reaction was sealed and heated to 100° C. for 3 hours. The mixture was cooled to room temperature, quenched by addition of sat. aq ammonium chloride, and extracted with ethyl acetate (3×). The combined organics were dried (Na₂SO₄) and filtered, and the filtrate was concentrated under reduced pressure. Purification by column chromatography (ethyl acetate/heptane) gave 3,5-dimethyl-4-(4-(trifluoromethyl)-1H-pyrazol-1-yl)benzonitrile. ¹H NMR (400 MHz, CDCl₃, δ): 8.00 (s, 1H), 7.77 (s, 1H), 7.50 (s, 2H), 2.09 (s, 6H). MS (M+1): 266.1.

Intermediate (112): 3,5-dimethyl-4-(4-(trifluoromethyl)-1H-pyrazol-1-yl)benzaldehyde

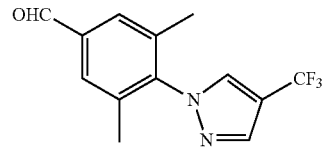 [SMILES: Cc1cc(C=O)cc(C)c1-n1cc(C(F)(F)F)cn1]

A solution of Intermediate (111) (250 mg, 0.943 mmol) in tetrahydrofuran (8.57 mL) was cooled to −78° C. Diisobutylaluminum hydride (1.5 M in toluene, 1.57 mL, 2.36 mmol) was added dropwise. After 2 hours, the reaction was warmed to 0° C. After 30 minutes, the mixture was quenched by addition of sat aq ammonium chloride, allowed to warm to room temperature, and extracted with ethyl acetate (3×). The combined organics were dried (Na₂SO₄) and filtered, and the filtrate was concentrated under reduced pressure. Purification by column chromatography (ethyl acetate/heptane) gave 3,5-dimethyl-4-(4-(trifluoromethyl)-1H-pyrazol-1-yl)benzaldehyde. ¹H NMR (400 MHz, CDCl₃, δ): 10.04 (s, 1H), 8.00 (s, 1H), 7.79 (s, 1H), 7.70 (s, 2H), 2.13 (s, 6H). MS (M+1): 269.2.

Intermediate (113): (+/−)-N-(3,5-dimethyl-4-(4-(trifluoromethyl)-1H-pyrazol-1-yl)benzylidene)-2-methylpropane-2-sulfinamide

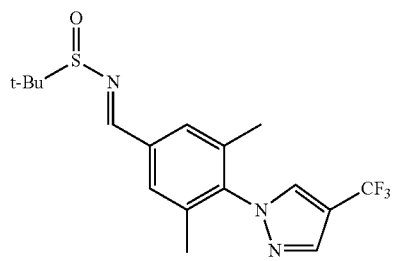 [SMILES: Cc1cc(/C=N/S(=O)C(C)(C)C)cc(C)c1-n1cc(C(F)(F)F)cn1]

To a solution of Intermediate (112) (526 mg, 1.96 mmol) and (+/−)-2-methyl-2-propanesulfinamide (245 mg, 1.96 mmol) in dichloromethane (19.6 mL) was added titanium (IV) ethoxide (0.822 mL, 3.92 mmol). Reaction was refluxed for 1 hour then cooled to room temperature. Methanol (2 mL) was added followed by sat. aq sodium bicarbonate (1 mL). The resulting slurry was stirred for 1 hour, then concentrated under reduced pressure. After diluting with ethyl acetate (40 mL), the slurry was dried (Na₂SO₄) and filtered through celite (ethyl acetate eluent). The filtrate was concentrated under reduced pressure to provide (+/−)-N-(3,5-dimethyl-4-(4-(trifluoromethyl)-1H-pyrazol-1-yl)benzylidene)-2-methylpropane-2-sulfinamide. ¹H NMR (400 MHz, CDCl₃, δ): 8.59 (s, 1H), 7.99 (s, 1H), 7.78 (s, 1H), 7.66 (s, 2H), 2.10 (s, 6H), 1.30 (s, 9H).

Intermediate (114): (+/−)-N-(1-(3,5-dimethyl-4-(4-(trifluoromethyl)-1H-pyrazol-1-yl)phenyl)-3-methylbutyl)-2-methylpropane-2-sulfinamide

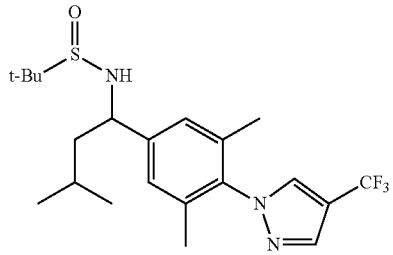 [SMILES: Cc1cc(C(CC(C)C)NS(=O)C(C)(C)C)cc(C)c1-n1cc(C(F)(F)F)cn1]

A suspension of Intermediate (113) (186 mg, 0.501 mmol) in tetrahydrofuran (5.01 mL) was cooled to −78° C. Isobutyllithium (1.7 M in heptane, 0.353 mL, 0.600 mmol) was added dropwise. After 2 hours, additional isobutyllithium (1.7 M in heptane, 0.353 mL, 0.600 mmol) was added. After 1 hour, the solution was quenched at −78° C. by addition of sat. aq ammonium chloride (6 mL). The resulting slurry was allowed to warm to room temperature. The mixture was diluted with 20 mL sat. aq ammonium chloride then extracted with ethyl acetate (3×25 mL). The combined organics were dried (Na₂SO₄) and filtered, and the filtrate was concentrated under reduced pressure. Purification by column chromatography (ethyl acetate/heptane) gave (+/−)-N-(1-(3,5-dimethyl-4-(4-(trifluoromethyl)-1H-pyrazol-1-yl)phenyl)-3-methylbutyl)-2-methylpropane-2-sulfinamide. ¹H NMR (400 MHz, CDCl₃, δ): 7.94 (s, 1H), 7.75 (s, 1H), 7.12 (s, 2H), 4.37 (t, J=7.4 Hz, 1H), 2.03 (s, 6H), 1.89-1.79 (m, 1H), 1.68-1.45 (m, 4H), 1.24 (s, 9H), 0.95 (d, J=6.6 Hz, 3H), 0.91 (d, J=6.6 Hz, 3H). MS (M+1): 430.5.

Intermediate (115): (+/−)-1-(3,5-dimethyl-4-(4-(trifluoromethyl)-1-pyrazol-1-yl)phenyl)-3-methylbutan-1-amine hydrochloride

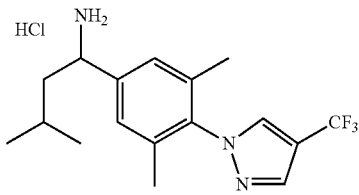 [SMILES: Cc1cc(C(N)CC(C)C)cc(C)c1-n1cc(C(F)(F)F)cn1 ; Cl]

To a solution of Intermediate (114) (226 mg, 0.525 mmol) in methanol (2.62 mL) was added hydrogen chloride (4 M in dioxane, 0.524 mL, 2.10 mmol) dropwise. The reaction was concentrated under reduced pressure to provide (+/−)-1-(3,5-dimethyl-4-(trifluoromethyl)-1H-pyrazol-1-yl)phenyl)-3-methylbutan-1-amine hydrochloride. ¹H NMR (400 MHz, CD₃OD, δ): 8.33 (s, 1H), 8.08 (s, 1H), 7.32 (s, 2H), 4.35 (dd, J=9.8, 5.9 Hz, 1H), 2.06 (s, 6H), 1.99-1.87 (m, 1H), 1.84-1.74 (m, 1H), 1.50-1.37 (m, 1H), 0.99 (d, J=6.4 Hz, 3H), 0.95 (d, J=6.6 Hz, 3H).

Intermediate (116): methyl (+/−)-6-((1-(3,5-dimethyl-4-(4-(trifluoromethyl)-1H-pyrazol-1-yl)phenyl)-3-methylbutyl)amino)nicotinate

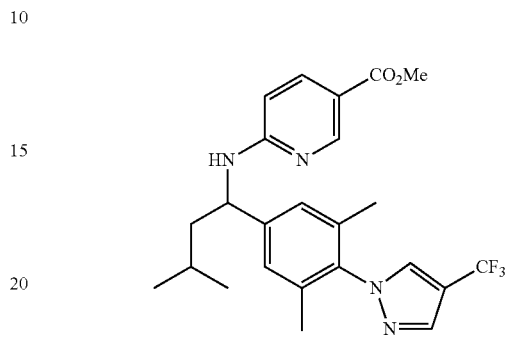

To a mixture of Intermediate (115) (190 mg, 0.525 mmol) and potassium carbonate (296 mg, 2.10 mmol) in N,N-dimethylformamide (1.05 mL) was added methyl 6-fluoronicotinate (88.1 mg, 0.551 mmol). The reaction was heated to 85° C. After 19 h, the reaction was cooled to room temperature, diluted with water (25 mL), and extracted with ethyl acetate (3×25 mL). The combined organics were dried (Na₂SO₄) and filtered, and the filtrate was concentrated under reduced pressure. Purification by column chromatography (ethyl acetate/heptane) gave methyl (+/−)-6-((1-(3,5-dimethyl-4-(4-(trifluoromethyl)-1H-pyrazol-1-yl)phenyl)-3-methylbutyl)amino)nicotinate. ¹H NMR (400 MHz, CDCl₃, δ): 8.67 (d, J=1.8 Hz, 1H), 8.03 (dd, J=8.8, 2.0 Hz, 1H), 7.94 (s, 1H), 7.74 (s, 1H), 7.12 (s, 2H), 6.33 (d, J=9.0 Hz, 1H), 4.67-4.61 (m, 1H), 3.88 (s, 3H), 2.01 (s, 6H), 1.89-1.71 (m, 2H), 1.71-1.61 (m, 1H), 1.02 (d, J=6.4 Hz, 3H), 0.98 (d, J=6.4 Hz, 3H). MS (M+1): 461.5.

Intermediate (117): (+/−)-6-((1-(3,5-dimethyl-4-(4-(trifluoromethyl)-1H-pyrazol-1-yl)phenyl)-3-methylbutyl)amino)nicotinic acid

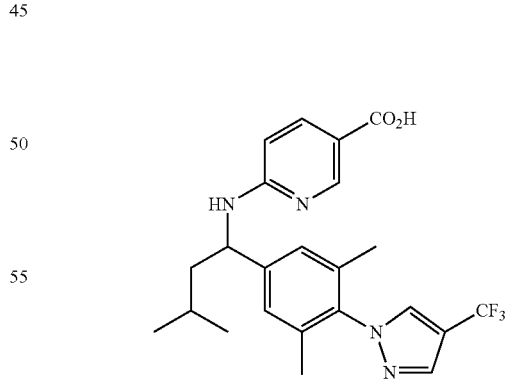

To a solution of Intermediate (116) (197 mg, 0.428 mmol) in tetrahydrofuran (2.14 mL) and methanol (2.14 mL) was added 1 N aq sodium hydroxide (2.14 mL, 2.14 mmol). After 22 h, the solution was concentrated under reduced pressure to remove tetrahydrofuran and methanol. 1 N aq hydrochloric acid was added until the mixture was at pH 3.5. The mixture was diluted with sat aq sodium chloride (10 mL) and extracted with ethyl acetate (3×20 mL). The combined organics were dried (Na₂SO₄) and filtered, and the filtrate was concentrated under reduced pressure to provide (+/−)-6-((1-(3,5-dimethyl-4-(4-(trifluoromethyl)-1H-pyrazol-1-yl)phenyl)-3-methylbutyl)amino)nicotinic acid. ¹H NMR (400 MHz, CDCl₃, δ): 8.71 (s, 1H), 8.16 (d, J=9.0 Hz, 1H), 7.94 (s, 1H), 7.75 (s, 1H), 7.14 (s, 2H), 6.40 (d, J=9.2 Hz, 1H), 4.55-4.48 (m, 1H), 2.02 (s, 6H), 1.99-1.91 (m, 1H), 1.89-1.77 (m, 1H), 1.71-1.60 (m, 1H), 1.03 (d, J=6.6 Hz, 3H), 0.98 (d, J=6.6 Hz, 3H). MS (M+1): 447.5.

Intermediate (118): ethyl (R)-3-(6-((1-(3,5-dimethyl-4-(4-(trifluoromethyl)-1H-pyrazol-1-yl)phenyl)-3-methylbutyl)amino)nicotinamido)propanoate and Intermediate (119): ethyl (S)-3-(6-((1-(3,5-dimethyl-4-(4-(trifluoromethyl)-1H-pyrazol-1-yl)phenyl-3-methylbutyl)amino)nicotinamido)propanoate

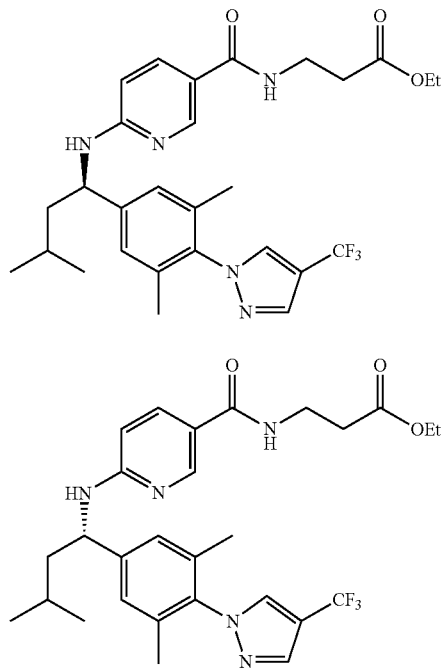

To a mixture of Intermediate (117) (183 mg, 0.410 mmol), β-alanine ethyl ester hydrochloride (99.4 mg, 0.615), and 1-hydroxy-7-azabenzotriazole (69.0 mg, 0.492 mmol) in dichloromethane (4.10 mL) was added triethylamine (0.172 mL, 1.23 mmol) followed by N-(3-dimethylaminopropyl)-N'-ethylcarbodiimide hydrochloride (95.8 mg, 0.492 mmol). After 20 hours, additional β-alanine ethyl ester hydrochloride (99.4 mg, 0.615), 1-hydroxy-7-azabenzotriazole (69.0 mg, 0.492 mmol), triethylamine (0.172 mL, 1.23 mmol), N-(3-dimethylaminopropyl)-N'-ethylcarbodiimide hydrochloride (95.8 mg, 0.492 mmol), and dichloromethane (2.10 mL) were added. After 7 hours, the mixture was diluted with dichloromethane (20 mL) and washed with water (3×20 mL) and sat aq sodium chloride (20 mL). The organic layer was dried (Na₂SO₄) and filtered, and the filtrate was concentrated under reduced pressure. Purification by column chromatography (ethyl acetate/heptane) followed by SFC (Chiralpak OD-H column, 10 mm×250 mm, 15% 2-propanol/carbon dioxide eluent) gave ethyl (R)-3-(6-((1-(3,5-dimethyl-4-(4-(trifluoromethyl)-1H-pyrazol-1-yl)phenyl)-3-methylbutyl)amino) nicotinamido) propanoate (SFC retention time 4.54 min) and ethyl (S)-3-(6-((1-(3,5-dimethyl-4-(4-(trifluoromethyl)-1H-pyrazol-1-yl)phenyl)-3-methylbutyl)amino)nicotinamido) propanoate (SFC retention time 6.94 min). ¹H NMR (400 MHz, CDCl₃, δ): 8.49 (d, J=1.6 Hz, 1H), 7.92 (s, 1H), 7.77 (dd, J=8.8, 2.3 Hz, 1H), 7.74 (s, 1H), 7.09 (s, 2H), 6.71 (t, J=5.9 Hz, 1H), 6.24 (d, J=8.8 Hz, 1H), 5.55 (br. s., 1H), 4.68 (d, J=6.4 Hz, 1H), 4.16 (q, J=7.0 Hz, 2H), 3.67 (q, J=5.9 Hz, 2H), 2.60 (t, J=5.9 Hz, 2H), 1.98 (s, 6H), 1.80-1.67 (m, 2H), 1.67-1.56 (m, 1H), 126 (t, J=7.1 Hz, 3H), 0.99 (d, J=6.2 Hz, 3H), 0.96 (d, J=6.2 Hz, 3H). MS (M+1): 546.4.

An asymmetric synthesis of ethyl (R)-3-(6-((1-(3,5-dimethyl-4-(4-(trifluoromethyl)-1H-pyrazol-1-yl)phenyl)-3-methylbutyl)amino)nicotinamido) propanoate may also be achieved by utilizing (S)-(−)-2-methyl-2-propanesulfinamide and Intermediate (112), analogous to that described for the preparation of Intermediate (113). Ethyl (R)-3-(6-((1-(3, 5-dimethyl-4-(4-(trifluoromethyl)-1H-pyrazol-1-yl)phenyl)-3-methylbutyl)amino)nicotinamido) propanoate may then be prepared analogous to the racemic route.

Intermediate (120): methyl 4-(tetrahydro-2H-pyran-4-carbonyl)benzoate

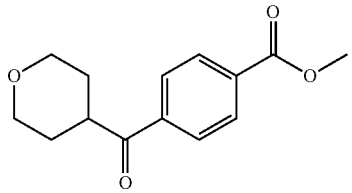 [SMILES: COC(=O)c1ccc(C(=O)C2CCOCC2)cc1]

Step A:

To a solution of methyl 4-iodobenzoate (1.21 mL, 7.24 mmol) in THF (12 ml) at −40° C. was added TurboGrignard (1.3 M in THF, 6.13 ml, 7.97 mmol) dropwise. The mixture was stirred for approximately 60 minutes whereupon, tetrahydro-2H-pyran-4-carbaldehyde (0.761 ml, 0.724 mmol) was added dropwise. The mixture was stirred for 15 minutes and slowly warmed to rt over 12 hours. The reaction was quenched with HCl (1N, aq.) and the aq. layer was extracted with EtOAc (3×75 mL). The combined organic layers were washed with brine, dried over Na₂SO₄, filtered, and concentrated in vacuo to provide ethyl 4-(hydroxy(tetrahydro-2H-pyran-4-yl)methyl)benzoate. Crude mixture used into the next step without any further purification. Step B: A round bottom flask was charged with ethyl 4-(hydroxy(tetrahydro-2H-pyran-4-yl)methyl)benzoate (1.9 g, 72 mmol), the Dess-Martin reagent (3.66 g, 8.63 mmol) and DCM (15 mL). The reaction was stirred at room temperature overnight. Reaction diluted with DCM and solid filtered off. The mother liquor concentrated and loaded onto a silica gel column. Purification by silica gel flash chromatography (ethyl acetate/DCM) provide methyl 4-(tetrahydro-2H-pyran-4-carbonyl)benzoate (290 mg, mmol) as a white solid. ¹H NMR (400 MHz, CDCl₃) δ 1.75-1.96 (m, 4H) 3.45-3.62 (m, 3H) 3.97 (s, 3H) 4.07 (dt, J=11.88, 325 Hz, 2H) 7.98-8.02 (m, 2H) 8.12-8.17 (m, 2H); MS (M−1): 246.8.

Intermediate (121): (±)-methyl 4-((tetrahydro-2H-pyran-4-yl)((6-(4-(trifluoromethyl)-1H-pyrazol-1-yl)pyridin-3-yl)amino)methyl)benzoate

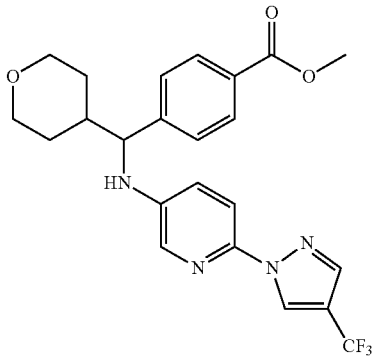 [SMILES: COC(=O)c1ccc(C(Nc2ccc(-n3cc(C(F)(F)F)cn3)nc2)C2CCOCC2)cc1]

A round bottom flask was charged with methyl 4-(tetrahydro-2H-pyran-4-carbonyl)benzoate (150 mg, 572 mmol), 6-(4-(trifluoromethyl)-1H-pyrazol-1-yl)pyridin-3-amine (130 mg, 572 mmol) and MeOH (1.2 mL). Decaborane reagent (26.4 mg, 229 mmol) was added in one portion and the reaction stirred over the week-end. The reaction mixture was quenched with HCl solution (1N, aq.) and extracted with EtOAc twice. The combined organic layers were washed with brine, dried over $Na_2SO_4$ and concentrated under reduced pressure. Purification by slica gel flash chromatography (ethyl acetate/heptane) provide (±)-methyl 4-((tetrahydro-2H-pyran-4-yl)((6-(4-(trifluoromethyl)-1H-pyrazol-1-yl)pyridin-3-yl)amino)methyl)benzoate (206 mg, 78%) as a colorless gum. MS (M+1): 461.3.

Intermediate (122): ethyl 3-(4-pivaloylbenzamido)propanoate

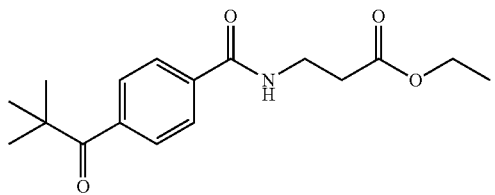 [SMILES: CCOC(=O)CCNC(=O)c1ccc(C(=O)C(C)(C)C)cc1]

Step A:
A round bottom flask was charged with the ethyl 4-iodobenzoate (10 g, 36 mmol) and THF (45 mL). Solution cooled down to 0° C. Turbo Grignard 1.3 M in THF (30.6 mL, 39.8 mmol) was then added in one portion and the reaction stirred for 30 minutes at 0° C. Pivaloyl chloride (5.35 mL, 43.5 mmol) was then charged in a second flask in THF (10 mL) and the preformed anion transferred via canula to the acyl chloride. The reaction was then slowly warmed to room temperature and stirred overnight. The reaction was quenched with ammonium chloride solution (sat. aq.) and extracted with ethyl acetate (2×), washed with brine (1×), dried over sodium sulfate, filtered and concentrated to provide ethyl 4-pivaloylbenzoate as a crude yellow gum (8.50 g). Used without further purification. $^1$H NMR (400 MHz, $CDCl_3$) δ 1.30-1.36 (m, 9H) 1.42 (t, J=7.04 Hz, 3H) 4.40 (q, J=-7.24 Hz, 2H) 7.61-7.69 (m, 2H) 8.04-8.12 (m, 2H); MS (M): 234.

Step B:
A round bottom flask was charged with ethyl 4-pivaloylbenzoate (7.67 g, 32.7 mmol), THF (100 mL) and MeOH (100 mL). Sodium hydroxide 1N, aq. (65.5 mL, 65.5 mmol) was then added in one portion. Reaction stirred at 40° C. for 1 hour. Organic solvent removed under reduced pressure and water (150 mL) added to the flask. Acidification with HCl 1N aq. to ca. pH 1 followed by filtration of the solid formed over a büchner funnel provide 4-pivaloylbenzoic acid as a light yellow solid (9.25 g). $^1$H NMR (400 MHz, DMSO-$d_6$) δ 1.25-1.27 (m, 9H) 7.70-7.74 (m, 2H) 7.97-8.01 (m, 2H) 13.00 (br. s., 1H); MS (M−1): 205.3.

Step C:
A round bottom flask was charged with 4-pivaloylbenzoic acid (7.67 g, 37.2 mmol), ethyl 3-aminopropanoate hydrochloride (6.86 g, 44.6 mmol), HOAT (5.57 g, 40.9 mmol), DCM (93 mL) and TEA (7.80 mL, 55.8 mmol). EDC hydrochloride (7.92 g, 40.9 mmol) was then added in one portion and the reaction allowed to stir at room temperature for 2 hours. DCM added to the reaction mixture and organics washed with an ammonium chloride solution (sat. aq.; 1×), water (2×), brine (1×), dried over sodium sulfate, filtered and concentrated under reduced pressure to afford the crude material. Purification by silica gel flash chromatography (ethyl acetate/heptane) provide ethyl 3-(4-pivaloylbenzamido)propanoate as a yellow oil (4.25 g, 37.4%; over 3 steps). $^1$H NMR (400 MHz, $CDCl_3$) δ 1.26 (m, J=7.02, 7.02 Hz, 3H) 1.32 (s, 9H) 2.63 (t, J=5.95 Hz, 2H) 3.72 (m, J=6.05, 6.05, 6.05 Hz, 2H) 4.16 (m, J=7.22, 7.22, 7.22 Hz, 2H) 6.92 (br. s., 1H) 7.64-7.68 (m, 2H) 7.75-7.79 (m, 2H); MS (M+1): 306.3.

Intermediate (123) (±)-ethyl 3-(4-(2,2-dimethyl-1-((6-(4-(trifluoromethyl)-1H-pyrazol-1-yl)pyridin-3-yl)amino)propyl)benzamido)propanoate

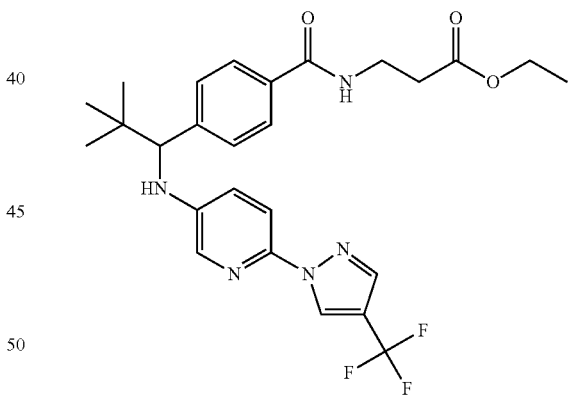

A round bottom flask was charged with Intermediate (32) (1.12 g, 4.91 mmol), ethyl 3-(4-pivaloylbenzamido)propanoate (1.50 g, 4.91 mmol), decaborane (309 mg, 2.46 mmol) and MeOH (12 mL). Reaction mixture stirred overnight at room temperature. The mixture was quenched with 1N HCl and extracted with EtOAc (2×). The combined organic layers were washed with brine (1×), dried over $Na_2SO_4$, filtered and concentrated under reduced pressure to afford the crude material. Purification by silica gel flash chromatography (ethyl acetate/heptane) provide (±)-ethyl 3-(4-(2,2-dimethyl-1-((6-(4-(trifluoromethyl)-1H-pyrazol-1-yl)pyridin-3-yl)amino)propyl)benzamido)propanoate as an orange gum (1.97 g, 77.5%). $^1$H NMR (400 MHz, $CDCl_3$) δ 1.05 (s, 9H) 1.27 (t, J=7.12 Hz, 3H) 2.59-2.67 (m, 2H) 3.72 (q, J=6.18 Hz, 2H) 4.12-4.21 (m, 3H) 6.83 (t, J=5.95 Hz, 1H) 6.90 (dd, J=8.78, 2.34 Hz, 1H) 7.37 (d, J=8.00 Hz, 2H) 7.65 (d, J=8.78 Hz, 1H) 7.71 (d, J=8.58 Hz, 2H) 7.76 (br. s., 1H) 7.79 (s, 1H) 8.67 (s, 1H); MS (M+1): 518.4.

Intermediate (124) (±)-ethyl 3-(4-(2,2-dimethyl-1-((6-(4-(trifluoromethyl)-1H-imidazol-1-yl)pyridin-3-yl)amino)propyl)benzamido)propanoate

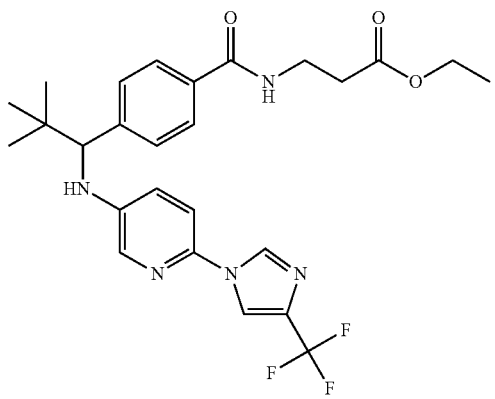 [SMILES: CCOC(=O)CCNC(=O)c1ccc(C(Nc2ccc(-n3cnc(C(F)(F)F)c3)nc2)C(C)(C)C)cc1]

A round bottom flask was charged with Intermediate (6) (747 mg, 3.28 mmol), 3-(4-pivaloylbenzamido)propanoate (1.00 g, 3.28 mmol), decaborane (206 mg, 1.64 mmol) and MeOH (8 mL). Reaction mixture stirred overnight at room temperature. The mixture was quenched with 1N HCl and extracted with EtOAc (2×). The combined organic layers were washed with brine (1×), dried over Na₂SO₄, filtered and concentrated under reduced pressure to afford the crude material. Purification by silica gel flash chromatography (ethyl acetate/DCM) provide (±)-ethyl 3-(4-(2,2-dimethyl-1-((6-(4-(trifluoromethyl)-1H-imidazol-1-yl)pyridin-3-yl)amino)propyl)benzamido)propanoate as an orange oil. ¹H NMR (400 MHz, DMSO-d₆) δ 0.99 (s, 9H) 1.16 (m, J=6.83, 6.83 Hz, 3H) 2.54 (t, J=6.93 Hz, 2H) 3.42-3.50 (m, 2H) 4.00-4.08 (m, 2H) 4.34 (d, J=8.39 Hz, 1H) 6.55 (d, J=8.39 Hz, 1H) 7.11 (dd, J=8.88, 2.83 Hz, 1H) 7.42-7.48 (m, 3H) 7.71-7.77 (m, 2H) 7.89 (d, J=2.73 Hz, 1H) 8.26-8.30 (m, 1H) 8.38 (s, 1H) 8.46 (t, J=5.56 Hz, 1H); MS (M+1): 518.4.

Intermediate (125): 4-(5-fluoro-indazol-2-yl)-phenol

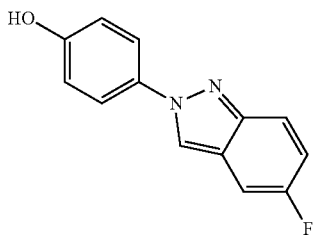 [SMILES: Oc1ccc(-n2cc3cc(F)ccc3n2)cc1]

4-bromophenol (1.27 g, 7.35 mmol) was combined with 5-fluoro-1H-indazole (1.000 g, 7.35 mmol), CuI (69.9 mg, 0.367 mmol), K₃PO₄ (3.282 g, 15.4 mmol), toluene (15 mL), and dimethylethylenediamine (0.158 mL, 1.47 mmol). This was refluxed as a mixture for 3 d. The reaction was cooled and partitioned between ethyl acetate and sat. NH₄Cl. The aqueous was extracted with ethyl acetate and the combined organics were dried over MgSO₄. Purification by silica gel flash chromatography (ethyl acetate in heptane) gave 4-(5-fluoro-indazol-2-yl)-phenol (0.114 g) impure with the indazole starting material. Used as is. The other regioisomer was also observed but was separated by chromatography. MS (M+1): 229.2.

Intermediate (126): 4-(6-fluoro-indazol-2-yl)-phenol

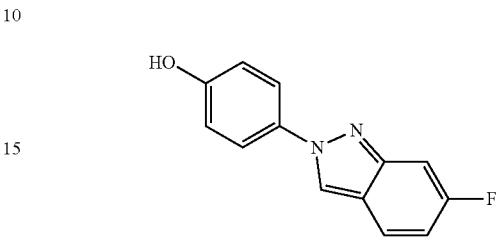

4-bromophenol (1.27 g, 7.3 mmol) was combined with 6-fluoro-1H-indazole (1.000 g, 7.35 mmol), CuI (69.9 mg, 0.367 mmol), K₃PO₄ (3.282 g, 15.4 mmol), toluene (15 mL), and dimethylethylenediamine (0.158 mL, 1.47 mmol). This was refluxed as a mixture for 3 d. The reaction was cooled and partitioned between ethyl acetate and sat. NH₄Cl. The aqueous was extracted with ethyl acetate and the combined organics were dried over MgSO₄. Purification by silica gel flash chromatography (ethyl acetate in heptane) gave 4-(6-fluoro-indazol-2-yl)-phenol (0.129 g, 8%) as a tan solid. The other regioisomer was also observed but was separated by chromatography. ¹H NMR (400 MHz, DMSO-d₆, δ): 9.86 (s, 1H) 8.96 (s, 1H) 7.75-7.91 (m, 3H) 7.41 (d, J=10.6 Hz, 1H) 6.99 (td, J=9.3, 2.2 Hz, 1H) 6.93 (d, J=8.8 Hz, 2H); MS (M+1): 229.2.

Intermediate (127): 4-(2H-indazol-2-yl)-3,5-dimethylphenol

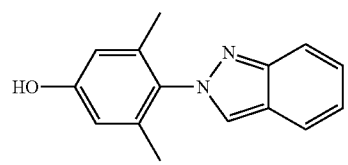 [SMILES: Cc1cc(O)cc(C)c1-n1cc2ccccc2n1]

Step A: (E)-4-((2-(hydroxymethyl)phenyl)diazenyl)-3,5-dimethylphenol

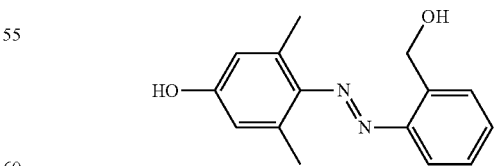

(2-aminophenyl)methanol (4000 mg, 32.48 mmol) was dissolved in water (25 mL) with concentrated HCl (6 N, 7.00 mL, 42.2 mmol) and the solution was cooled in an ice/NaCl bath to −5° C., afterward sodium nitrite (2420 mg, 39 mmol) in 20 mL of water was added dropwise over 20 minutes. Solids precipitated out. The organic mixture/suspension was stirred at −5° C.→0° C. for 25 minutes, 5 mL CH₃CN was added. The solution of 3,5-dimethylphenol (3970 mg, 32.5 mmol) in CH₃CN (10 mL) was mixed with a solution of Na₂CO₃ (13.8 g, 130 mmol) in H₂O (20 mL). The mixed solution was added to the above diazonium solution slowly at −5° C.→0° C. The mixture was stirred at −5° C.→0° C. for 2 hours. Brownish solids precipitated out.

The mixture was neutralized with conc. HCl (12 N) and diluted with EtOAc. The suspension filtered through celite and washed with EtOAc which was used for extraction. After four extractions, the combine dark brownish organic layers were washed with brine, dried over Na₂SO₄ and concentrated, leading to dark brownish solids. The crude was dissolved in EtOAc and loaded to the column and purified by ISCO (120 g silica gel, EtOAc/Heptane: 0→45%), leading the desired product as orange solids. $^1$H NMR (400 MHz, DMSO-d₆) δ ppm 2.42 (s, 6H) 4.96 (d, J=5.66 Hz, 2H) 5.14-5.25 (m, 1H) 6.58 (s, 2H) 7.29-7.36 (m, 1H) 7.41-7.50 (m, 2H) 7.65 (d, J=0.78 Hz, 1H) 9.92 (s, 1H). LCMS: m/z=257.3 [M+H].

Step B: 4-(2H-indazol-2-yl)-3,5-dimethylphenol

Iodine (3980 mg, 15.7 mmol) was added to the orange solution of (E)-4-((2-(hydroxymethyl)phenyl)diazenyl)-3,5-dimethyphenol (2680 mg, 10.46 mmol), triphenylphosphine (4110 mg, 15.7 mmol) and imidazole (2140 mg, 31.4 mmol) in tetrahydrofuran (30 mL) at room temperature. The mixture was stirred for 40 minutes. The solvent was evaporated. The crude was dissolved in EtOAc/MeOH and loaded to the column and purified by ISCO (40 g silica gel, EtOAc/heptane: 0→50%), leading to the desired product as a white/pale yellow solid. $^1$H NMR (400 MHz, CDCl₃) δ ppm 1.85 (s, 6H) 6.49 (s, 2H) 7.07-7.21 (m, 1H) 7.32-7.42 (m, 1H) 7.75 (d, J=8.58 Hz, 1H) 7.80 (dd, J=8.78, 0.98 Hz, 1H) 7.96 (d, J=0.78 Hz, 1H) 7.99 (s, 1H). LCMS: m/z=239.2 [M+H].

Intermediate (128): 1-(6-(4-(trifluoromethyl)-1H-pyrazol-1-yl)pyridin-3-yl)butan-1-ol

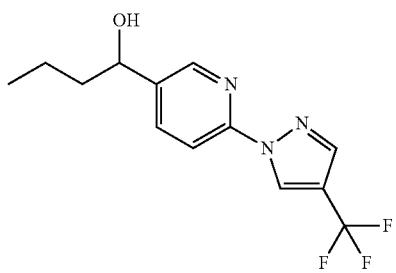 [SMILES: CCCC(O)c1ccc(-n2cc(C(F)(F)F)cn2)nc1]

Step A: 1-(6-chloropyridin-3-yl)butan-1-ol

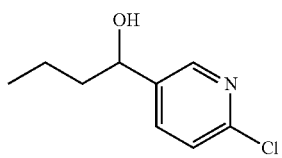

To a −10° C. solution of 6-chloronicotinaldehyde (553 mg, 3.91 mmol) in 3.5 mL THF was added n-propylmagnesium bromide (2.34 mL of a 2.0 M solution in THF, 4.69 mmol). The solution was stirred at −10° C. for 10 min, and was then allowed to warm to room temperature. The reaction mixture was quenched by addition of saturated aqueous ammonium chloride. The mixture was extracted with ethyl acetate. The organic layer was concentrated. The crude residue was purified by silica gel chromatography to give 1-(6-chloropyridin-3-yl)butan-1-ol (400 mg) as a yellow oil. $^1$H NMR (400 MHz, CDCl₃) δ 8.24-8.31 (m, 1H), 7.61-7.67 (m, 1H), 7.25-7.30 (m, 1H), 4.68-4.74 (m, 1H), 2.05-2.26 (br s, 1H), 1.69-1.82 (m, 1H), 1.57-1.68 (m, 1H), 1.19-1.49 (m, 2H), 0.91 (t, J=7.43 Hz, 3H).

Step B: 1-(6-chloropyridin-3-yl)butan-1-one

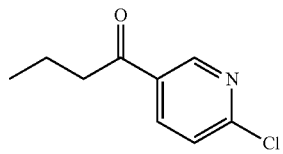

To a solution of 1-(6-chloropyridin-3-yl)butan-1-ol (210 mg, 1.13 mmol) in 10 mL dichloromethane was added 2 g of silica gel, followed by pyridinium chlorochromate (488 mg, 2.26 mmol) The mixture was stirred at room temperature 5 h. The mixture was filtered through a plug of silica gel, eluting with 100 mL dichloromethane. The eluent was concentrated to give 1-(6-chloropyridin-3-yl)butan-1-one (210 mg). $^1$H NMR (400 MHz, CDCl₃) δ 8.88-8.96 (m, 1H), 8.14-8.20 (m, 1H), 7.42 (d, J=8.4 Hz, 1H), 2.92 (t, J=7.2 Hz, 2H), 1.70-1.82 (m, 2H), 0.99 (t, J=7.4 Hz, 3H).

Step C: 1-(6-(4-(trifluoromethyl)-1H-pyrazol-1-yl)pyridin-3-yl)butan-1-one

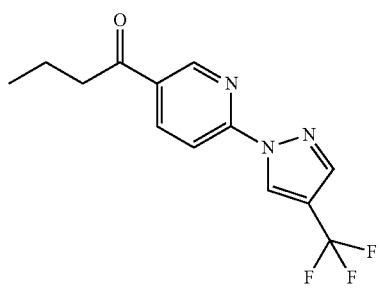 [SMILES: CCCC(=O)c1ccc(-n2cc(C(F)(F)F)cn2)nc1]

A mixture of 4-(trifluoromethyl)pyrazole (116 mg, 0.85 mmol), 1-(6-chloropyridin-3-yl)butan-1-one (130 mg, 0.71 mmol), and potassium carbonate (294 mg, 2.12 mmol) was stirred 4 h at 50° C. The mixture was cooled to room temperature and stirred overnight. The mixture was partitioned between ethyl acetate and water. The organic layer was dried over MgSO₄ and concentrated under reduced pressure. The residue was purified by silica gel chromatography to give 1-(6-(4-(trifluoromethyl)-1H-pyrazol-1-yl)pyridin-3-yl)butan-1-one (200 mg) as a colorless solid. $^1$H NMR (400 MHz, CDCl₃) δ 8.97-8.99 (m, 1H), 8.90-8.91 (m, 1H), 8.39 (dd, J=8.5, 2.4 Hz, 1H), 8.08 (dd, J=8.58, 0.78 Hz, 1H), 7.93 (s, 1H), 2.94 (t, J=7.4 Hz, 2H), 1.74-1.85 (m, 2H), 1.02 (t, J=7.4 Hz, 3H).

Step D: 1-(6-(4-(trifluoromethyl)-1H-pyrazol-1-yl)pyridin-3-yl)butan-1-ol 1-(6-(4-(trifluoromethyl)-1H-pyrazol-1-yl)pyridin-3-yl)butan-1-one (140 mg, 0.49 mmol) was dissolved in 5 mL methanol. Sodium borohydride (18.7 mg, 0.494 mmol) was added. The reaction mixture was concentrated and the residue partitioned between water and ethyl acetate. The organic layer was concentrated to give 1-(6-(4-(trifluoromethyl)-1H-pyrazol-1-yl)pyridin-3-yl)butan-1-ol (140 mg). $^1$H NMR (400 MHz, CDCl$_3$) δ 8.84 (s, 1H), 8.34-8.40 (m, 1H), 7.96 (d, J=8.4 Hz, 1H), 7.82-7.90 (m, 2H), 4.75-4.82 (m, 1H), 1.64-1.89 (m, 2H), 1.27-1.53 (m, 2H), 0.94 (t, J=7.4 Hz, 3H).

Intermediate (129): 2-(4-(trifluoromethyl)-1H-imidazol-1-yl)pyrimidin-5-amine

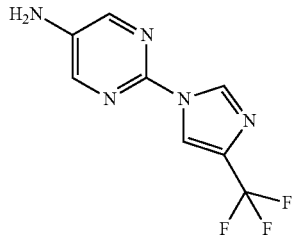 [SMILES: Nc1cnc(-n2cnc(C(F)(F)F)c2)nc1]

A mixture of 4-(trifluoromethyl)-1H-imidazole (572 mg, 4.2 mmol) 5-bromo-2-chloropyrimidine (813 mg, 4.20 mmol) and potassium carbonate (1740 mg, 12.6 mmol) in DMF (5 mL) was heated at 85° C. for 2 h. The reaction mixture was diluted with water and extracted with ethyl acetate. The combined organic layers were dried over sodium sulfate and concentrated under reduced pressure. A mixture of this crude residue (376 mg), copper(I) iodide (61.1 mg, 0.32 mmol), 4-hydroxy-L-proline (84.1 mg, 0.64 mmol) and potassium carbonate (537 mg, 3.85 mmol) was purged with nitrogen. Dimethyl sulfoxide (2.5 mL) was added followed by ammonium hydroxide (1.40 mL, 28% aqueous solution). The mixture was heated at 75° C. for 20 hours. The mixture was diluted with 1 N HCl and extracted with ethyl acetate. The combined organic layers were dried over sodium sulfate and concentrated under reduced pressure. The crude residue was purified by silica gel chromatography to the provide 2-(4-(trifluoromethyl)-1H-imidazol-1-yl)pyrimidin-5-amine. $^1$H NMR (400 MHz, CDCl$_3$) δ 3.86 (br s, 2H), 8.13-8.15 (m, 1H), 8.15 (s, 2H), 8.50 (s, 1H). LCMS: m/z=230.1 [M+H].

Preparation of Compounds of Formula I

Example 1

(+/−)-3-(4-(1-(3-methy-4-(4-(trifluoromethyl)-1H-imidazol-1-yl)phenylamino)butyl)benzamido)propanoic acid

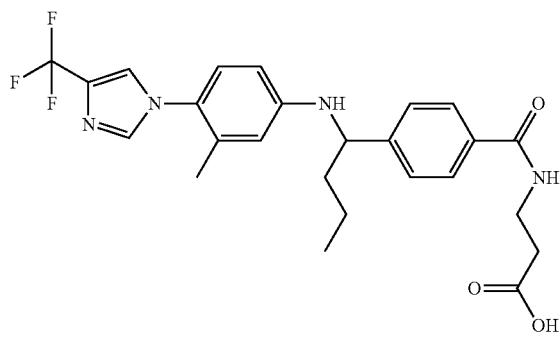 [SMILES: CCCC(Nc1ccc(-n2cnc(C(F)(F)F)c2)c(C)c1)c1ccc(C(=O)NCCC(=O)O)cc1]

Step A: (+/−)-methyl-4-(1-(methyl-4-(4-(trifluoromethyl)-1H-imidazol-1-yl)phenylamino)butyl)benzoate

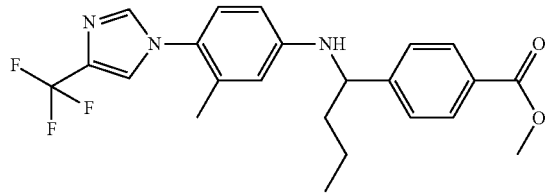 [SMILES: CCCC(Nc1ccc(-n2cnc(C(F)(F)F)c2)c(C)c1)c1ccc(C(=O)OC)cc1]

To a solution of Intermediate (21) (248 mg, 1.2 mmol) and Intermediate (4) (290 mg, 1.2 mmol) in methanol (12 mL) was added decaborane (44.1 mg, 0.36 mmol) at room temperature under nitrogen. The resulting solution was stirred at room temperature overnight. The reaction was concentrated and purification by column chromatography (0-35% ethyl acetate in heptane), gave (+/−)-methyl-4-(1-(3-methyl-4-(4-(trifluoromethyl)-1H-imidazol-1-yl)phenylamino)butyl)benzoate as a foam. $^1$H NMR (500 MHz, CDCl$_3$, δ): 8.02 (d, J=8.29 Hz, 2H), 7.48 (s, 1H), 7.42 (d, J=8.29 Hz, 2H), 7.25 (s, 1H), 6.90 (d, J=8.54 Hz, 1H), 6.41 (m, 1H), 6.34 (m, 1H), 4.40 (m, 2H), 3.91 (s, 3H), 1.98 (s, 3H), 1.72-1.87 (m, 2H), 1.34-1.52 (m, 2H), 0.96 (t, J=7.32 Hz 3H). MS (M+1): 432.4.

Step B: (+/−)-tert-butyl 3-(4-(1-(3-methyl-4-(4-(trifluoromethyl)-1H-imidazol-1-yl)phenylamino)butyl)benzamido)propanoate

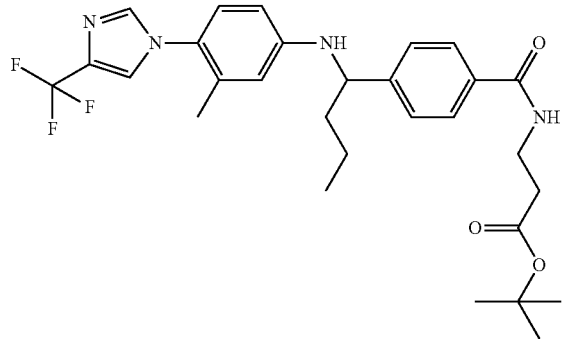 [SMILES: CCCC(Nc1ccc(-n2cnc(C(F)(F)F)c2)c(C)c1)c1ccc(C(=O)NCCC(=O)OC(C)(C)C)cc1]

To a solution of (+/−)-methyl-4-(1-(3-methyl-4-(4-(trifluoromethyl)-1H-imidazol-1-yl)phenylamino)butyl)benzoate (0.100 g, 0.232 mmol) in methanol (1 mL), tetrahydrofuran (1 mL), and water (1 mL) was added lithium hydroxide (0.40 g, 9.2 mmol). The reaction was stirred at room temperature for 60 hours. The mixture was acidified with 1N HCl and extracted three times with ethyl acetate. The combined organic layers were dried over sodium sulfate, filtered and concentrated.

To the crude residue was added N,N-dimethylformamide (2 mL), beta-alanine tert-butyl ester hydrochloride (69.8 mg, 0.384 mmol) and O-(7-Azabenzotriazol-1-yl)-N,N,N',N'-tetramethyluronium hexafluorophosphate (146 mg, 0.384 mmol). Diisopropylethylamine (99.3 mg, 0.768 mmol) was then added and the reaction was stirred at room temperature for 4 hours. The reaction was concentrated and purification by column chromatography (0-70% ethyl acetate in heptane), gave (+/−)-tert-butyl 3-(4-(1-(3-methyl-4-(4-(trifluoromethyl)-1H-imidazol-1-yl)phenylamino)butyl)benzamido)

propanoate (92 mg, 88%). ¹H NMR (500 MHz, CDCl₃, δ): 7.73 (d, J=8.29 Hz, 2H), 7.46 (s, 1H), 7.39 (d, J=8.05 Hz, 2H), 7.24 (s, 1H), 6.99-6.93 (m, 1H), 6.89-6.85 (m, 1H), 6.41-6.39 (m, 1H), 6.34-6.30 (m, 1H), 4.54-4.43 (m, 1H), 4.41-4.31 (m, 1H), 3.70-3.62 (m, 2H), 2.57-2.50 (m, 2H), 1.96 (s, 3H), 1.85-1.70 (m, 2H), 1.45 (s, 9H), 1.43-1.27 (m, 2H), 0.94 (t, J=7.44 Hz, 3H). MS (M+1): 545.2.

Step C: (+/−)-3-(4-(1-(3-methyl-4-(4-(trifluoromethyl)-1H-imidazol-1-yl)phenylamino)butyl)benzamido)propanoic acid Trifluoroacetic acid (0.4 mL) was added to a solution of (+/−)-tert-butyl 3-(4-(1-(3-methyl-4-(4-(trifluoromethyl)-1H-imidazol-1-yl)phenylamino)butyl)benzamido)propanoate (58 mg, 0.11 mmol) in dichloromethane (0.6 mL). The mixture was stirred at room temperature overnight. The reaction was concentrated and successively evaporated from dichloromethane, ethyl acetate and toluene, to give (+/−)-3-(4-(1-(3 nm ethyl-4-(4-(trifluoromethyl)-1H-imidazol-1-yl) phenylamino)butyl)benzamido)propanoic acid (10 mg, 16%) as a solid. ¹H NMR (400 MHz, CDCl₃, δ): 7.77-7.72 (m, 1H), 7.72-7.68 (m, 2H), 7.40-7.35 (m, 2H), 7.30-7.25 (m, 1H), 6.90-6.84 (m, 2H), 6.40-6.36 (m, 1H), 6.33-6.28 (m, 1H), 4.41-4.32 (m, 1H), 3.82-3.67 (m, 2H), 2.75-2.66 (m, 2H), 1.97 (s, 3H), 1.89-1.73 (m, 2H), 1.49-1.31 (m, 2H), 0.94 (t, J=7.44 Hz, 3H). MS (M+1): 489.2.

Example 2

(+/−)-3-(4-(3-methyl-1-(4-(4-(trifluoromethyl)-1H-imidazol-1-yl)phenyl)butoxy)benzamido)propanoic acid

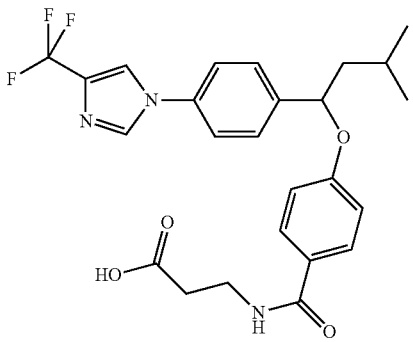 [SMILES: CC(C)CC(Oc1ccc(C(=O)NCCC(=O)O)cc1)c1ccc(-n2cnc(C(F)(F)F)c2)cc1]

Step A: (+/−)-methyl 4-(3-methyl-1-(4-(4-(trifluoromethyl)-1H-imidazol-1-yl)phenyl)butoxy)benzoate

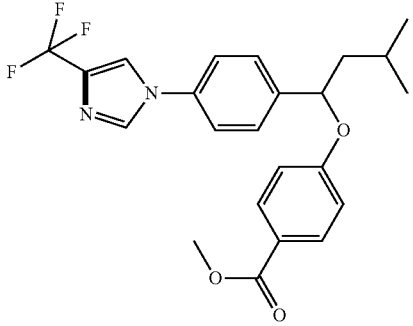

Dimethylsulfoxide (1.5 mL) was added to a screw-top reaction vial charged with Intermediate (34) (128 mg, 0.339 mmol), 4-(trifluoromethyl)imidazole (55 mg, 0.406 mmol), copper(I) iodide (13 mg, 0.068 mmol), quinolin-8-d (9.9 mg, 0.068 mmol), and potassium carbonate (92 mg, 0.67 mmol). The vial was evacuated and back-filled with nitrogen repeatedly then heated with stirring to 100° C. overnight. After 18 hours the reaction was diluted with saturated ammonium chloride (20 mL) and ethyl acetate (20 mL). The phases were separated and the organic layer was washed with water (2×20 mL) and brine (5 mL). The organics were dried over magnesium sulfate, filtered and concentrated. Purification by column chromatography (0-50% ethyl acetate in heptanes) gave (+/−)-methyl 4-(3-methyl-1-(4-(4-(trifluoromethyl)-1H-imidazol-1-yl)phenyl)butoxy)benzoate (65 mg, 44%) as a clear oil. ¹H NMR (400 MHz, CDCl₃, δ): 7.94-7.89 (m, 2H), 7.84 (s, 1H), 7.58 (s, 1H), 7.53-7.48 (m, 2H), 7.40-7.36 (m, 2H), 6.89-6.84 (m, 2H), 5.31 (dd, J=9, 4.6 Hz, 1H), 3.86 (s, 3H), 2.04 (m, 1H), 1.96-1.83 (m, 1H), 1.67-1.59 (m, 1H), 1.04 (d, J=6.6 Hz, 3H), 0.99 (d, J=6.6 Hz, 3H). MS (M+1): 433.0.

Step B: (+/−)-4-(3-methyl-1-(4-(4-(trifluoromethyl)-1H-imidazol-1-yl)phenyl)butoxy)benzoic acid

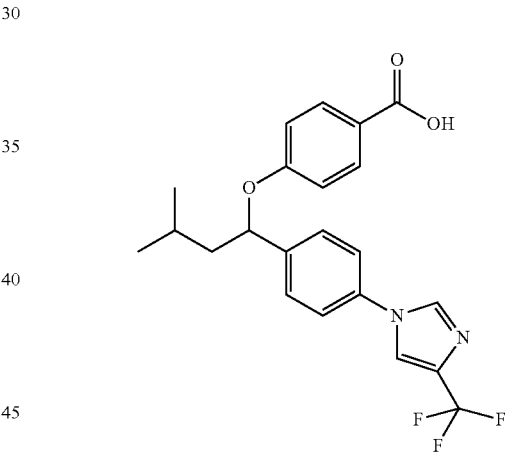

Methyl 4-(3-methyl-1-(4-(4-(trifluoromethyl)-1H-imidazol-1-yl)phenyl)butoxy)benzoate (65 mg, 0.15 mmol) was dissolved in methanol (1.5 mL) and 1M NaOH (0.75 mL) was added at room temperature. The resulting mixture was stirred overnight. The reaction mixture was diluted with water (10 mL), acidified with 1M HCl (1 mL) and extracted with ethyl acetate (2×10 mL). The combined organics were washed with brine, dried over sodium sulfate, filtered and concentrated to give (+/−)-4-(3-methyl-1-(4-(4-(trifluoromethyl)-1H-imidazol-1-yl)phenyl)butoxy)benzoic acid (65 mg, 100%) as a gum. ¹H NMR (400 MHz, CDCl₃, δ): 7.98 (d, J=9 Hz, 2H), 7.88 (s, 1H), 7.59 (d, J=8.5 Hz, 2H), 7.58 (s, 1H), 7.39 (d, J=8.5 Hz, 2H), 6.89 (d, J=8.8 Hz, 2H), 5.33 (dd, J=9, 4.6 Hz, 1H), 2.05 (m, 1H), 1.96-1.83 (m, 1H), 1.67-1.60 (m, 1H), 1.04 (d, J=6.6 Hz, 3H), 0.99 (d, J=6.6 Hz, 3H). MS (M+1): 419.0.

Step C: (+/−)-methyl 3-(4-(3-methyl-1-(4-(trifluoromethyl)-1H-imidazol-1-yl)phenyl)butoxy)benzamido)propanoate

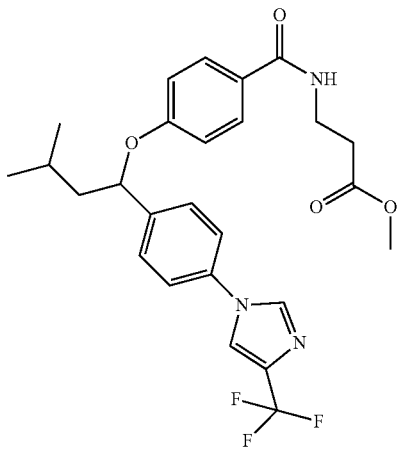 [SMILES: COC(=O)CCNC(=O)c1ccc(OC(CC(C)C)c2ccc(-n3cnc(C(F)(F)F)c3)cc2)cc1]

4-(3-Methyl-1-(4-(4-(trifluoromethyl)-1H-imidazol-1-yl)phenyl)butoxy)benzoic acid (65 mg, 0.16 mmol), methyl beta-alanine hydrochloride (31 mg, 0.16 mmol), and triethylamine (0.031 mL) were dissolved in dichloromethane (1 mL). 1-Ethyl-3-(3-dimethylaminopropyl)carbodiimide hydrochloride (34 mg, 0.18 mmol) was added. The solution was stirred at room temperature for 15 minutes, and 1-hydroxy-7-azabenzotriazole (34 mg, 0.25 mmol) was then added. The resulting yellow solution was stirred overnight. After 18 hours, the reaction was diluted with ethyl acetate (20 mL) and washed with water (25 mL) and brine (10 mL). The organics were dried over magnesium sulfate, filtered and concentrated. Purification by column chromatography (0-100% ethyl acetate in heptane) gave (+/−)-methyl 3-(4-(3-methyl-1-(4-(4-(trifluoromethyl)-1H-imidazol-1-yl)phenyl)butoxy)benzamido) propanoate (70 mg, 90%). $^1$H NMR (400 MHz, CDCl$_3$, δ): 7.84 (s, 1H), 7.67-7.62 (m, 2H), 7.58 (s, 1H), 7.53-7.46 (m, 2H), 7.39-7.34 (m 2H), 6.89-6.84 (m, 2H), 6.72 (t, J=5.9 Hz, 1H), 5.29 (dd, J=8.9, 4.5 Hz, 1H), 3.72-3.65 (m, 5H), 2.63 (m, 2H), 2.03 (m, 1H), 1.95-1.83 (m, 1H), 1.65-1.58 (m, 1H), 1.03 (d, J=6.6 Hz, 3H), 0.99 (d, J=6.3 Hz, 3H). MS (M+1): 504.0.

Step D: (+/−)-3-(4-(3-methyl-1-(4-(4-(trifluoromethyl)-1H-imidazol-1-yl)phenyl)butoxy)benzamido)propanoic acid Methyl 3-(4-(3-methyl-1-(4-(4-(trifluoromethyl)-1H-imidazol-1-yl)phenyl)butoxy)benzamido)propanoate (70 mg, 0.14 mmol) was dissolved in methanol (2 mL) and 1M lithium hydroxide (1 mL) was added. The reaction was stirred at room temperature for 1 hour. The methanol was removed under reduced pressure and the residue was diluted with water (2 mL). Upon stirring a precipitate forms. The solution was further diluted with water (15 mL) and 1M NaOH (3 mL). The solution was extracted with ether (20 mL). The organics were washed with water (10 mL) and the aqueous layers were combined. The aqueous solution was acidified with 1M HCl to give a cloudy solution. The solution was extracted with ethyl acetate (2×15 mL). The combined organics were dried over sodium sulfate, filtered and concentrated to give (+/−)-3-(4-(3-methyl-1-(4-(4-(trifluoromethyl)-1H-imidazol-1-yl)phenyl)butoxy)benzamido)propanoic acid (53.1 mg, 78%) as an off-white solid. $^1$H NMR (400 MHz, CDCl$_3$, δ): 7.89 (s, 1H), 7.66-7.60 (m, 2H), 7.58 (s, 1H), 7.49 (d, J=8.5 Hz, 2H), 7.36 (d, J=8.5 Hz, 2H), 6.97-6.92 (m, 2H), 6.77 (t, J=6 Hz, 1H), 5.29 (dd, J=9, 4.4 Hz, 1H), 3.73-3.63 (m, 2H), 2.66-2.64 (m, 2H), 2.06-2.00 (m, 1H), 1.95-1.83 (m, 1H), 1.62 (m, 1H), 1.03 (d, J=6.6 Hz, 3H), 0.99 (d, J=6.6 Hz, 3H). MS (M+1): 490.2.

Example 3

(+/−)-3-(6-(1-(4-(4-(trifluoromethyl)-1H-pyrazol-1-yl)phenoxy)butyl)nicotinamido)propanoic acid

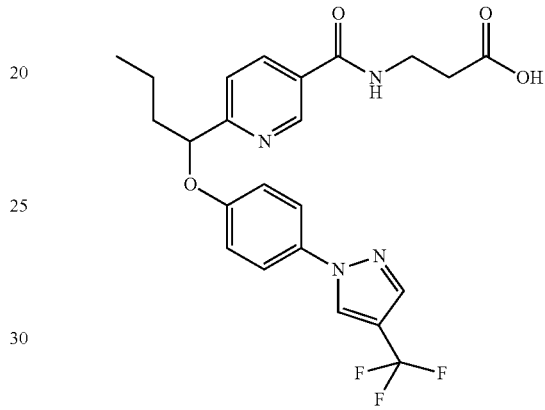

Step A: (+/−)-5-bromo-2-(1-(4-(4-(trifluoromethyl)-1H-pyrazol-1-yl)phenoxy)butyl)pyridine

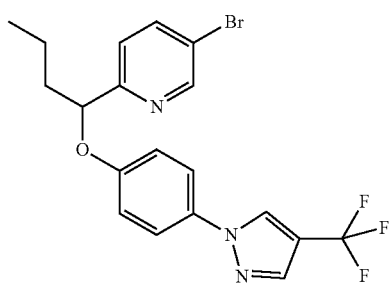 [SMILES: CCCC(Oc1ccc(-n2cc(C(F)(F)F)cn2)cc1)c1ccc(Br)cn1]

Intermediate (36) (216 mg, 0.50 mmol), 4-trifluoromethylpyrazole (68 mg, 0.50 mmol), copper(I) iodide (19 mg, 0.10 mmol), trans-4-hydroxy-L-proline (26.2 mg, 0.20 mmol) and cesium carbonate (329 mg, 1.00 mmol) were suspended in dimethylsulfoxide and heated to 85° C. with stirring for 18 hours. The reaction was diluted with ethyl acetate (25 mL) and washed with water (2×25 mL) and brine (20 mL). The organics were dried over magnesium sulfate, filtered and concentrated. Purification by column chromatography (0-50% ethyl acetate in heptanes) gave 5-bromo-2-(1-(4-(4-(trifluoromethyl)-1H-pyrazol-1-yl)phenoxy)butyl)pyridine (81 mg, 37%) as a clear oil. $^1$H NMR (400 MHz, CDCl$_3$, δ): 8.63 (d, J=2.3 Hz, 1H), 8.00 (br. s, 1H), 7.82 (br. s, 1H), 7.75 (dd, J=8.4, 2.3 Hz, 1H), 7.49-7.43 (m, 2H), 7.26 (d, overlaps Step B: (+/−)-ethyl 3-(6-(1-(4-(4-(trifluoromethyl)-1H-pyrazol-1-yl)phenoxy)butyl)nicotinamido)propanoate

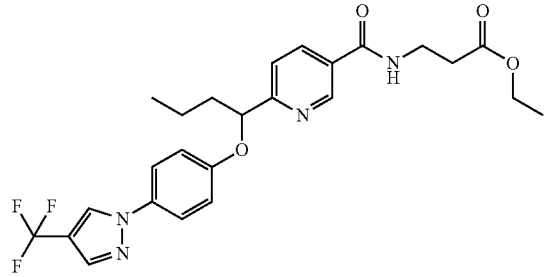 [SMILES: CCCC(Oc1ccc(-n2cc(C(F)(F)F)cn2)cc1)c1ccc(C(=O)NCCC(=O)OCC)cn1]

5-Bromo-2-(1-(4-(4-(trifluoromethyl)-1H-pyrazol-1-yl)phenoxy)butyl)pyridine (81 mg, 0.180 mmol), ethyl 3-aminopropanoate hydrochloride (85 mg, 0.55 mmol), molybdenumhexacarbonyl (50 mg, 0.18 mmol), tri-tert-butylphosphonium tetrafluoroborate (8.4 mg, 0.028 mmol), palladium(II) acetate (2 mg, 9 μmol), and 1,8-diazabicycloundec-7-ene (150 μL, 1.1 mmol) were placed in a microwave vial and suspended in dry acetonitrile (2 mL). The vial was capped and heated by a Biotage Initiator microwave to 170° C. for 2 minutes. The resulting dark amber mixture was filtered through a 1" plug of silica gel, and eluted with ethyl acetate. The residue was concentrated and purification by column chromatography (0-100% ethyl acetate in heptane) gave (+/−)-ethyl 3-(6-(1-(4-(4-(trifluoromethyl)-1H-pyrazol-1-yl)phenoxy)butyl)nicotinamido)propanoate (42 mg, 45%) as a pale amber glass. $^1$H NMR (400 MHz, CDCl$_3$, δ): 8.63 (dd, J=2.2, 0.9 Hz, 1H), 8.01-7.97 (m, 2H), 7.82 (s, 1H), 7.48-7.40 (m, 3H), 6.94-6.85 (m, 3H), 5.30 (dd, J=7.90, 4.8 Hz, 1H), 4.15 (q, J=7.2 Hz, 2H), 3.74-3.68 (m, 2H), 2.65-2.60 (m, 2H), 2.05-1.87 (m, 2H), 1.63-1.39 (m, 2H), 1.28-1.23 (m, 3H), 0.96 (t, J=7.4 Hz, 3H). MS (M+1): 505.4.

Step C: (+/−)-3-(6-(1-(4-(4-(trifluoromethyl)-1H-pyrazol-1-yl)phenoxy)butyl)nicotinamido)propanoic acid (+/−)-Ethyl 3-(6-(1-(4-(4-(trifluoromethyl)-1H-pyrazol-1-yl)phenoxy)butyl)nicotinamido)propanoate (45 mg, 0.089 mmol) was dissolved in methanol (2 mL). 1 M NaOH (2 mL) was added with stirring at room temperature. After stirring for 6 hours, 1M HCl (2 mL) was added. The pH was adjusted to approximately 4, using 1M HCl and 1M NaOH. The resulting cloudy solution was extracted with ethyl acetate (2×15 mL). The combined organic extracts were dried over sodium sulfate, filtered and concentrated to give (+/−)-3-(6-(1-(4-(4-(trifluoromethyl)-1H-pyrazol-1-yl)phenoxy)butyl)nicotinamido)propanoic acid (42 mg, 100%) as a foamy solid. $^1$H NMR (400 MHz, CDCl$_3$, δ): 9.23 (d, J=1.6 Hz, 1H), 8.38 (dd, J=8.2, 2.1 Hz, 1H), 7.99 (s, 1H), 7.85-7.80 (m, 2H), 7.55 (d, 1H), 7.49-7.42 (m, 2H), 6.92-6.85 (m, 2H), 5.31 (dd, J=7.7, 4.8 Hz, 1H), 3.83-3.76 (m, 2H), 2.75-2.69 (m, 2H), 2.09-1.85 (m, 2H), 1.60-1.39 (m, 2H), 0.96 (t, J=7.3 Hz, 3H). MS (M+1): 477.3.

Example 4

(+/−)-3-(4-(4-methyl-1-(4-(4-(trifluoromethyl)-1H-pyrazol-1-yl)phenyl)pentan-2-yl)benzamido)propanoic acid

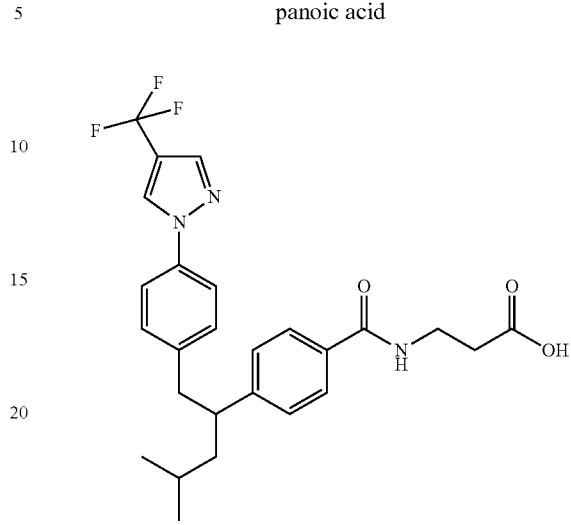

Step A: methyl 4-(1-(4-bromophenyl)-4-methylpent-1-en-2-yl)benzoate

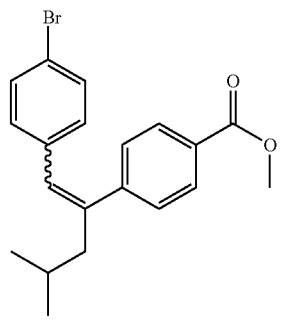 [SMILES: COC(=O)c1ccc(C(=Cc2ccc(Br)cc2)CC(C)C)cc1]

4-Bromobenzyltriphenylphosphonium bromide (2.07 g, 4.40 mmol) was suspended in toluene (4.0 mL) and cooled to 0° C. Lithium bis(trimethylsilyl)amide (4.04 mL, 1.0 M in toluene) was added. The ice bath was removed and the reaction was allowed to warm to room temperature and stir for 1 hour. A solution of Intermediate (10) (180 mg, 0.817 mmol) in toluene (0.8 mL) was then added drop-wise, and the reaction was allowed to stir for 18 hours. The reaction was diluted with water and ethyl acetate. The layers were separated and the aqueous was extracted three times with ethyl acetate. The combined organics were washed twice with 1N HCl and once with brine, then dried over magnesium sulfate, filtered, and concentrated. The crude solid was taken up in heptane and the remaining solids (triphenylphospine oxide) were filtered off. The filtrate was concentrated and purified by column chromatography (0-10% ethyl acetate in heptane) to give methyl 4-(1-(4-bromophenyl)-4-methylpent-1-en-2-yl)benzoate (184.7 mg, 61%) as an approximate 1:1 mixture of E/Z isomers. $^1$H NMR (400 MHz, CDCl$_3$, δ): 8.04-8.00 (m, 2H), 7.97-7.92 (m, 2H), 7.50-7.46 (m, 4H), 7.22-7.16 (m, 6H), 6.77-6.72 (m, 2H), 6.69 (s, 1H), 6.39 (s, 1H), 3.92 (s, 3H), 3.90 (s, 3H), 2.58 (d, J=7.4 Hz, 2H), 2.37 (dd, J=7.2, 1.2 Hz, 2H), 1.68-1.57 (m, 1H), 1.51 (dt, J=13.5, 6.8 Hz, 1H), 0.88 (d, J=6.6 Hz, 6H), 0.78 (d, J=6.6 Hz, 6H).

Step B: methyl 4-(4-methyl-1-(4-(4-(trifluoromethyl)-1H-pyrazol-1-yl)phenyl)pent-1-en-2-yl)benzoate

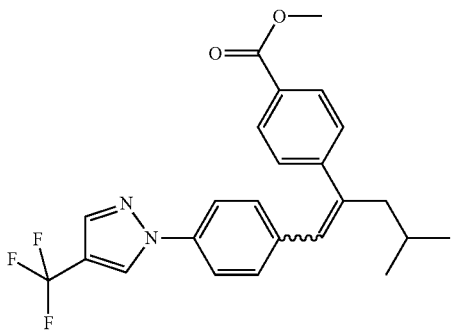 [SMILES: COC(=O)c1ccc(C(=Cc2ccc(-n3cc(C(F)(F)F)cn3)cc2)CC(C)C)cc1]

An oven-dried and nitrogen-cooled vial was charged with 4-trifluoromethyl pyrazole (77.0 mg, 0.56 mmol), quinolin-8-ol (10 mg, 0.07 mmol), copper(I) iodide (14 mg, 0.073 mmol), and potassium carbonate (140 mg, 1.0 mmol). A solution of methyl 4-(1-(4-bromophenyl)-4-methylpent-1-en-2-yl)benzoate (182.7 mg, 0.489 mmol) in dimethylsulfoxide (2.5 mL) was then added. The vial was capped and evacuated and back-filled with nitrogen four times. The reaction was then heated to 90° C. for 18 hours. The reaction was cooled to room temperature and partitioned between saturated ammonium chloride and ethyl acetate. The aqueous layer was extracted again with ethyl acetate, and the combined organics were dried over magnesium sulfate, filtered, and concentrated. Column chromatography (0-10% ethyl acetate in heptane) provided methyl 4-(4-methyl-1-(4-(4-(trifluoromethyl)-1H-pyrazol-1-yl)phenyl)pent-1-en-2-yl)benzoate (19.8 mg, 9.5%) as an approximate 1:1 mixture of E/Z isomers. $^1$H NMR (400 MHz, CDCl$_3$, δ): 8.20 (s, 1H), 8.06 (s, 1H), 8.05-8.01 (m, 2H), 7.98-7.93 (m, 2H), 7.91 (s, 1H), 7.83 (s, 1H), 7.71-7.66 (m, 2H), 7.53-7.49 (m, 2H), 7.46-7.42 (m, 2H), 7.41-7.36 (m, 2H), 7.24-7.20 (m, 2H), 7.01-6.96 (m, 2H), 6.78 (s, 1H), 6.49 (s, 1H), 3.92 (s, 3H), 3.90 (s, 3H), 2.62 (d, J=7.2 Hz, 2H), 2.41 (dd, J=7.2, 1.0 Hz, 2H), 1.70-1.48 (m, 2H), 0.90 (d, J=6.6 Hz, 6H), 0.80 (d, J=6.6 Hz, 6H). MS (M+1): 429.3.

Step C: 4-(4-methyl-1-(4-(4-(trifluoromethyl)-1H-pyrazol-1-yl)phenyl)pent-1-en-2-yl)benzoic acid

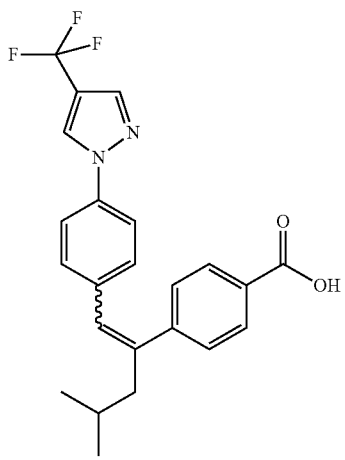 [SMILES: CC(C)CC(=Cc1ccc(-n2cc(C(F)(F)F)cn2)cc1)c1ccc(C(=O)O)cc1]

Methyl 4-(4-methyl-1-(4-(4-(trifluoromethyl)-1H-pyrazol-1-yl)phenyl)pent-1-en-2-yl)benzoate (19.8 mg, 0.0460 mmol) was dissolved in methanol (0.5 mL) and tetrahydrofuran (0.5 mL). 1 N Sodium hydroxide (0.092 mL) was added and the reaction was stirred at room temperature for 60 hours. The reaction was concentrated. The crude residue was taken up in water and acidified to pH=2 with 1N HCl. This solution was extracted four times with ethyl acetate, dried over magnesium sulfate, filtered, and concentrated to provide 4-(4-methyl-1-(4-(4-(trifluoromethyl)-1H-pyrazol-1-yl)phenyl)pent-1-en-2-yl)benzoic acid (18.3 mg, 96%) as an approximate 1:1 mixture of E/Z isomers. $^1$H NMR (400 MHz, CD$_3$OD, δ): 8.76 (s, 1H), 8.62 (s, 1H), 8.02 (d, J=8.4 Hz, 2H), 7.98 (s, 1H), 7.97-7.93 (m, 2H), 7.90 (s, 1H), 7.85-7.79 (m, 2H), 7.58 (d, J=8.4 Hz, 2H), 7.54-7.47 (m, 4H), 7.30-7.24 (m, 2H), 7.06-7.00 (m, 2H), 6.84 (s, 1H), 6.56 (s, 1H), 2.70 (d, J=7.2 Hz, 2H), 2.46 (dd, J=7.2, 1.0 Hz, 2H), 1.63 (dt, J=13.5, 6.7 Hz, 1H), 1.57-1.46 (m, 1H), 0.92 (d, J=6.6 Hz, 6H), 0.80 (d, J=6.6 Hz, 6H).

Step D: (+/−)-methyl 3-(4-(4-methyl-1-(4-(4-(trifluoromethyl)-1H-pyrazol-1-yl)phenyl)pentan-2-yl)benzamido)propanoate

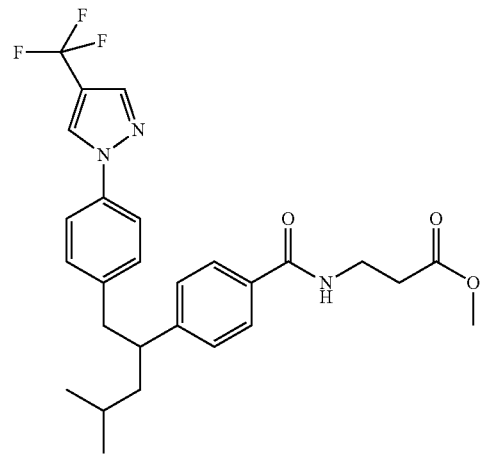 [SMILES: COC(=O)CCNC(=O)c1ccc(C(Cc2ccc(-n3cc(C(F)(F)F)cn3)cc2)CC(C)C)cc1]

To a solution of 4-(4-methyl-1-(4-(4-(trifluoromethyl)-1H-pyrazol-1-yl)phenyl)pent-1-en-2-yl)benzoic acid (18.3 mg, 0.0440 mmol), methyl 3-aminopropanoate hydrochloride (6.70 mg, 0.0480 mmol), 1-hydroxy-7-aza benzotriazole (6.00 mg, 0.0440 mmol), and triethylamine (6.6 µL, 0.047 mmol) in dichloromethane (0.5 mL), was added 1-ethyl-3-(3-dimethylaminopropyl)carbodiimide hydrochloride (8.50 mg, 0.0440 mmol). The reaction was stirred at room temperature for 18 hours. The reaction was diluted with dichloromethane and was washed with water and brine. The organic layer was dried over magnesium sulfate, filtered and concentrated.

This crude material was dissolved in methanol (15 mL) and was cycled through a THALES Nano H-cube (10% Pd/C catalyst cartridge, 50° C., full hydrogen setting, 1 mL/min) for 2 hours. The crude reaction was concentrated. Purification by column chromatography (0-40% ethyl acetate in heptane) gave methyl 3-(4-(4-methyl-1-(4-(4-(trifluoromethyl)-1H-pyrazol-1-yl)phenyl)pentan-2-yl)benzamido)propanoate (4.2 mg, 19%). $^1$H NMR (400 MHz, CDCl$_3$, δ): 8.10 (s, 1H), 7.85 (s, 1H), 7.65-7.60 (m, 2H), 7.48-7.42 (m, 2H), 7.14-7.09 (m, 2H), 7.06-7.00 (m, 2H), 6.79-6.72 (m, 1H), 3.73-3.67 (m, 5H), 3.00-2.91 (m, 2H), 2.86-2.78 (m, 1H), 2.66-2.61 (m, 2H), 1.67 (m, 1H), 1.52-1.43 (m, 1H), 1.38-1.27 (m, 1H), 0.82 (dd, J=6.5, 2.4 Hz, 6H). MS (M+1): 502.4.

Step E: (+/−)-3-(4-(4-methyl-1-(4-(4-(trifluoromethyl)-1H-pyrazol-1-yl)phenyl)pentan-2-yl)benzamido)propanoic acid Methyl 3-(4-(4-methyl-1-(4-(4-(trifluoromethyl)-1H-pyrazol-yl)phenyl)pentan-2-yl)benzamido)propanoate (4.2 mg, 0.0080 mmol) was dissolved in 1:1 methanol:tetrahydrofuran (0.50 mL). 1N NaOH (0.024 mL) was added and the reaction was stirred at room temperature for 18 hours. The reaction was concentrated to dryness. The crude residue was taken up in water and acidified to pH=2 with 1N HCl. This solution was extracted three times with ethyl acetate. The combined organics were dried over magnesium sulfate, filtered, and concentrated to give (+/−)-3-(4-(4-methyl-1-(4-(4-(trifluoromethyl)-1H-pyrazol-1-yl)phenyl)pentan-2-yl)benzamido)propanoic acid (4.0 mg, 100%), as a white solid. $^1$H NMR (400 MHz, CD$_3$OD, δ): 8.62 (s, 1H), 7.91 (s, 1H), 7.69-7.64 (m, 2H), 7.58-7.53 (m, 2H), 7.22-7.17 (m, 2H), 7.14-7.09 (m, 2H), 3.62-3.55 (m, 2H), 3.09-2.96 (m, 2H), 2.90-2.81 (m, 1H), 2.60 (t, J=6.9 Hz, 2H), 1.78-1.68 (m, 1H), 1.52 (ddd, J=13.7, 9.2, 4.9 Hz, 1H), 1.39-1.25 (m, 1H), 0.83 (dd, J=6.4, 4.7 Hz, 6H). MS (M+1): 488.4.

Example 5

(+/−)-3-(4-(1-(6-(4-(trifluoromethyl)-1H-pyrazol-1-yl)pyridine-3-ylamino)butyl)benzamido)propanoic acid

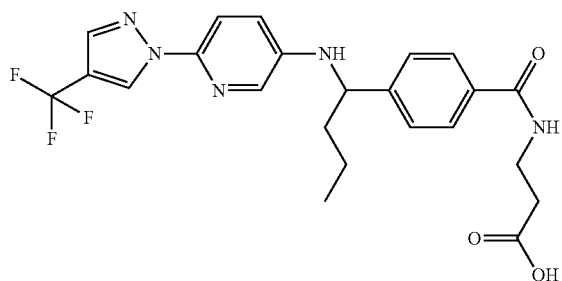

The title compound was prepared by a method analogous to that described for Example 1 using Intermediate (32). $^1$H NMR (400 MHz, CDCl$_3$, δ): 8.54 (s, 1H), 7.83 (s, 1H), 7.81 (d, J=2.8 Hz, 1H), 7.69 (d, J=8.4 Hz, 2H), 7.62 (d, J=8.97 Hz, 1H), 7.38 (d, J=8.4 Hz, 2H), 7.06 (t, J=5.95 Hz, 1H), 6.98 (dd, J=8.97, 2.8 Hz, 1H), 4.37 (t, J=6.83 Hz, 1H), 3.71 (m, 2H), 2.70 (t, J=5.85 Hz, 2H), 1.92-1.72 (m, 2H), 1.50-1.26 (m, 2H), 0.93 (t, J=7.32 Hz, 3H). MS (M+1): 476.3.

Example 6

3-(4-(1-(6-(4-(trifluoromethyl)-1H-pyrazol-1-yl)pyridine-3-ylamino)butyl)benzamido)propanoic acid, Isomer 1

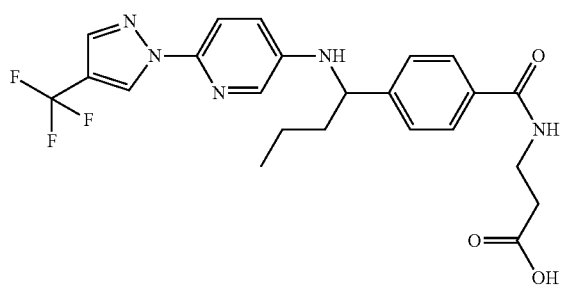

The title compound is obtained by resolving racemic 3-(4-(1-(6-(4-(trifluoromethyl)-1H-pyrazol-1-yl)pyridine-3-ylamino)butyl)benzamido)propanoic acid Example 5, by chiral SFC. Column: Chiralpak AD-H. Dimensions: 4.6 mm×25 cm. Mobile Phase: 70/30 CO$_2$/methanol. Flow Rate: 2.5 mL/min. Modifier none. Retention time: 4.05 minutes.

Example 7

3-(4-(1-(6-(4-(trifluoromethyl)-1H-pyrazol-1-yl)pyridine-3-ylamino)butyl)benzamido)propanoic acid, Isomer 2

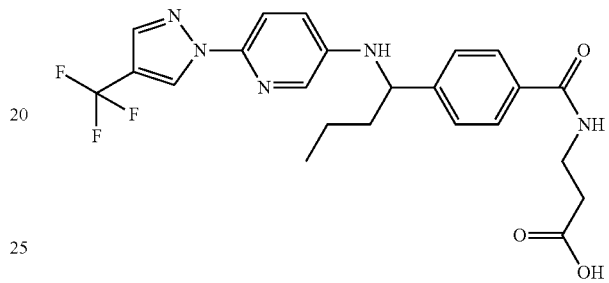

The title compound is obtained by resolving racemic 3-(4-(1-(6-(4-(trifluoromethyl)-1H-pyrazol-1-yl)pyridine-3-ylamino)butyl)benzamido)propanoic acid, the compound of Example 5, by chiral SFC. Column: Chiralpak AD-H. Dimensions: 4.6 mm×25 cm. Mobile Phase: 70/30 CO$_2$/methanol. Flow Rate: 2.5 mL/min. Modifier: none. Retention time: 6.40 minutes.

Example 8

(+/−)-3-(4-(cyclopentyl(6-(4-(trifluoromethyl)-1H-imidazol-1-yl)pyridine-3-ylamino)methyl)benzamido)propanoic acid

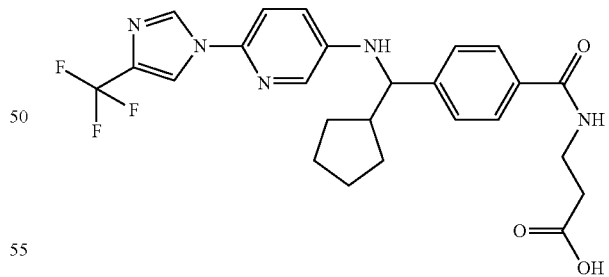

The title compound was prepared by a method analogous to that described for Example 1 using Intermediate (31) and Intermediate (6). $^1$H NMR (400 MHz. CDCl$_3$, δ): 8.29 (s, 1H), 7.81 (s, 1H), 7.76 (d, J=2.73 Hz, 1H), 7.69 (d, J=8.19 Hz, 2H), 7.37 (d, J=8.19 Hz, 2H), 7.09-7.05 (m, 1H), 6.96-6.90 (m, 1H), 6.85-6.80 (m, 1H), 4.14 (d, J=8.39 Hz, 1H), 3.73-3.66 (m, 2H), 2.72-2.64 (m, 2H), 2.24-2.14 (m, 1H), 2.00-1.88 (m, 1H), 1.75-1.20 (m, 7H). MS (M+1): 502.2.

Example 9

(+/−)-3-(4-(1-(6-(4-(trifluoromethyl)-1H-imidazol-1-yl)yridine-3-ylamino)butyl)benzamido)propanoic acid

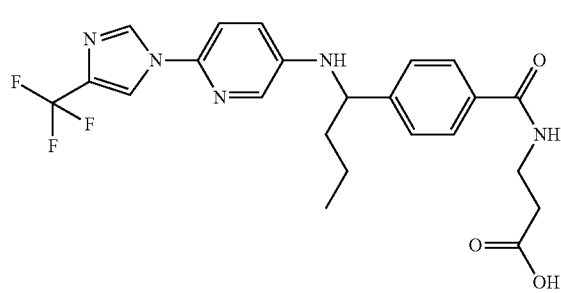

The title compound was prepared by a method analogous to that described for Example 1 using Intermediate (6). Column: Waters Atlantis dC18 4.6×50 mm, 5 µm. Modifier TFA 0.05%. Gradient 95% H$_2$O/5% MeCN linear to 5% H$_2$O/95% MeCN over 4.0 min, HOLD at 5% H$_2$O/95% MeCN to 5.0 min. Flow: 2.0 mL/min.

Retention time: 2.83 min. MS (M+1): 476.4.

Example 10

3-(4-(1-(6-(4-(trifluoromethyl)-1H-imidazol-1-yl)yridine-3-ylamino)butyl)benzamido)propanoic acid, Isomer 1

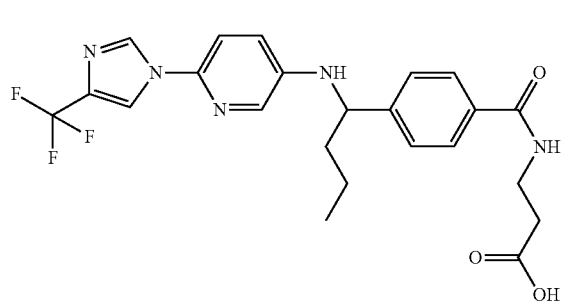

The title compound is obtained by resolving racemic 3-(4-(1-(6-(4-(trifluoromethyl)-1H-imidazol-1-yl)yridine-3-ylamino)butyl)benzamido)propanoic acid Example 9, by chiral SFC. Column: Chiralpak AD-H. Dimensions: 4.6 mm×25 cm. Mobile Phase: 65/35 CO$_2$/ethanol. Flow Rate: 2.5 mL/min. Modifier: none. Retention time: 4.990 minutes.

Example 11

3-(4-(1-(6-(4-(trifluoromethyl)-1H-imidazol-1-yl)yridine-3-ylamino)butyl)benzamido)propanoic acid, Isomer 2

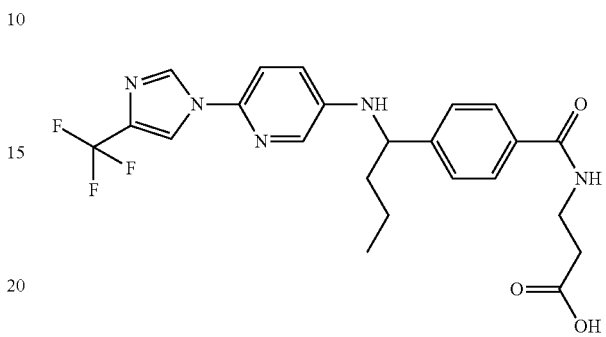

The title compound is obtained by resolving racemic 3-(4-(1-(6-(4-(trifluoromethyl)-1H-imidazol-1-yl)pyridine-3-ylamino)butyl)benzamido)propanoic acid Example 9, by chiral SFC. Column: Chiralpak AD-H. Dimensions: 4.6 mm×25 cm. Mobile Phase: 65/35 CO$_2$/ethanol. Flow Rate: 2.5 mL/min. Modifier: none. Retention time: 7.410 minutes.

Example 12

(+/−)-3-(4-(1-(4-(4-(trifluoromethyl)-1H-pyrazol-1-yl)phenylamino)butyl)benzamido)propanoic acid

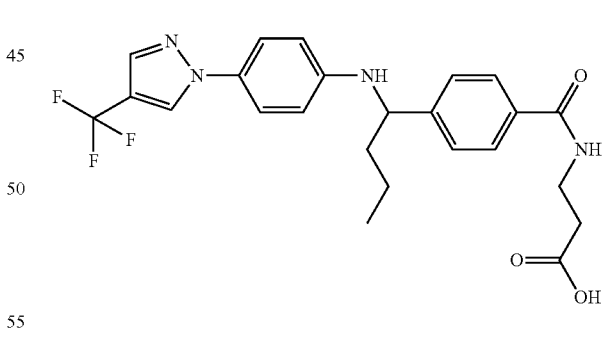

The title compound was prepared by a method analogous to that described for Example 1 using Intermediate (5) and Intermediate (52). $^1$H NMR (400 MHz, CDCl$_3$, δ): 7.91 (s, 1H), 7.78 (s, 1H), 7.67 (d, J=7.6 Hz, 2H), 7.35 (d, J=6.8 Hz, 2H), 7.27 (d, J=7.2 Hz, 2H), 7.03-6.88 (m, 1H), 6.60-6.42 (m, 2H), 4.33 (t, J=156.3 Hz, 1H), 3.64 (s, 2H), 2.72-2.54 (m, 2H), 1.87-1.65 (m, 2H), 1.51-1.22 (m, 2H), 0.90 (t, J=7.0 Hz, 3H). MS (M+1): 475.2.

Example 13

(+/−)-3-(4-(1-(3,5-dimethyl-4-(4-(trifluoromethyl)-1H-pyrazol-1-yl)phenylamino)butyl)benzamido)propanoic acid

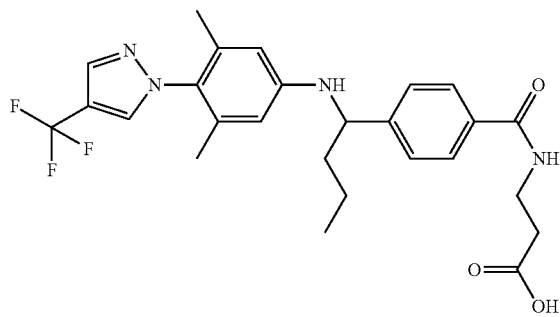 [SMILES: CCCC(Nc1cc(C)c(-n2cc(C(F)(F)F)cn2)c(C)c1)c1ccc(C(=O)NCCC(=O)O)cc1]

The title compound was prepared by a method analogous to that described for Example 1 using Intermediate (8). $^1$H NMR (400 MHz, CDCl$_3$, δ): 7.91 (s, 1H), 7.72-7.61 (m, 3H), 7.39 (d, J=8.00 Hz, 2H), 7.21-7.12 (br. t, J=5.6 Hz, 1H), 6.49 (s, 2H), 4.36 (m, 1H), 3.75-3.59 (m, 2H), 2.71-2.57 (m, 2H), 1.91-1.76 (m, 2H), 1.84 (s, 6H), 1.40-1.16 (m, 2H), 0.88 (t, J=7.32 Hz, 3H). MS (M+1): 503.2.

Example 14

3-(4-(1-(3,5-dimethyl-4-(4-(trifluoromethyl)-1H-pyrazol-1-yl)phenylamino)butyl)benzamido)propanoic acid, Isomer 1

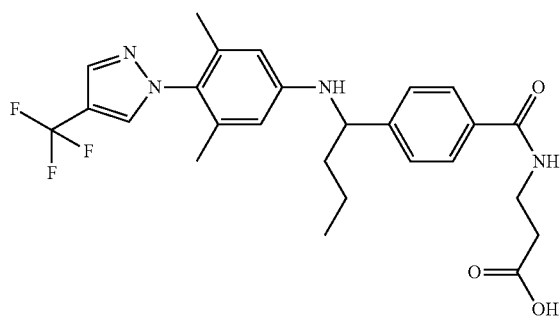 [SMILES: CCCC(Nc1cc(C)c(-n2cc(C(F)(F)F)cn2)c(C)c1)c1ccc(C(=O)NCCC(=O)O)cc1]

The title compound is obtained by resolving racemic 3-(4-(1-(3,5-dimethyl-4-(4-(trifluoromethyl)-1H-pyrazol-1-yl)phenylamino)butyl)benzamido)propanoic acid Example 13, by chiral SFC. Column: Chiralpak AD-H. Dimensions: 4.6 mm×25 cm. Mobile Phase: 75/25 CO$_2$/2-propanol. Flow Rate: 2.5 mL/min. Modifier: none. Retention time: 3.77 minutes.

Example 15

3-(4-(1-(3,5-dimethyl-4-(4-(trifluoromethyl)-1H-pyrazol-1-yl)phenylamino)butyl)benzamido)propanoic acid, Isomer 2

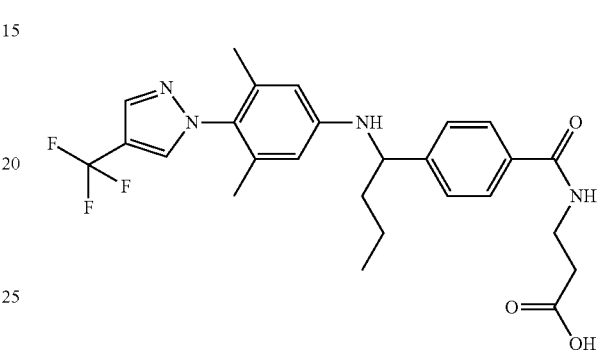

The title compound is obtained by resolving racemic 3-(4-(1-(3,5-dimethyl-4-(4-(trifluoromethyl)-1H-pyrazol-1-yl)phenylamino)butyl)benzamido)propanoic acid Example 13, by chiral SFC. Column: Chiralpak AD-H. Dimensions: 4.6 mm×25 cm. Mobile Phase: 75/25 CO$_2$/2-propanol. Flow Rate: 2.5 mL/min. Modifier: none. Retention time: 4.62 minutes.

Example 16

(+/−)-3-(4-(1-(4-(4-(trifluoromethyl)-1H-imidazol-1-yl)phenylamino)butyl)benzamido)propanoic acid

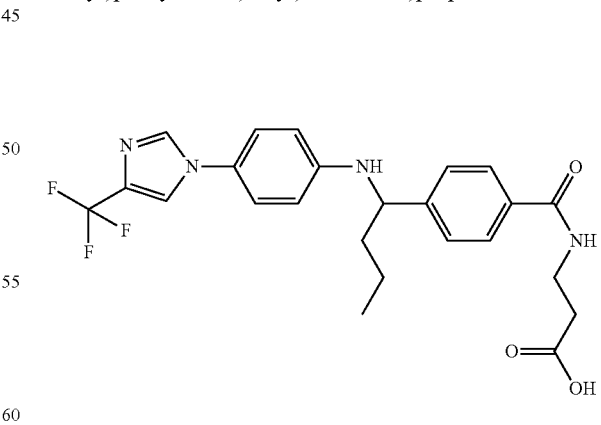

The title compound was prepared by a method analogous to that described for Example 1 using Intermediate (5) and Intermediate (54). $^1$H NMR (400 MHz, CDCl$_3$, δ): 7.77 (s, 1H), 7.73 (d, J=8.2 Hz, 2H), 7.43 (s, 1H), 7.39 (d, J=8.4 Hz, 2H), 7.06 (dt, J=8.8, 3.5 Hz, 2H), 6.83 (t, J=6.1 Hz, 1H), 6.53 (dt, J=8.8, 3.3 Hz, 2H), 4.38 (t, J=6.7 Hz, 1H), 3.73 (q, J=6.0 Hz, 2H), 2.71 (t, J=5.8 Hz, 2H), 1.88-1.73 (m, 2H), 1.53-1.31 (m, 2H), 0.97 (t, J=7.3 Hz, 3H). MS (M+1): 475.2.

Example 17

3-(4-(1-(4-(4-(trifluoromethyl)-1H-imidazol-1-yl)phenylamino)butyl)benzamido)propanoic acid, Isomer 1

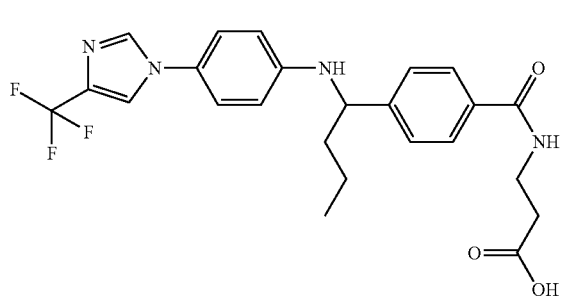 [SMILES: CCCC(Nc1ccc(-n2cnc(C(F)(F)F)c2)cc1)c1ccc(C(=O)NCCC(=O)O)cc1]

The title compound is obtained by resolving racemic 3-(4-(1-(4-(4-(trifluoromethyl)-1H-imidazol-1-yl)phenylamino)butyl)benzamido)propanoic acid Example 16, by chiral SFC. Column: Chiralpak AD-H. Dimensions: 10 mm×250 mm. Mobile Phase: 70/30 CO$_2$/methanol. Flow Rate: 10.0 mL/min. Modifier: none. Retention time: 7.25 minutes.

Example 18

3-(4-(1-(4-(4-(trifluoromethyl)-1H-imidazol-1-yl)phenylamino)butyl)benzamido)propanoic acid, Isomer 2

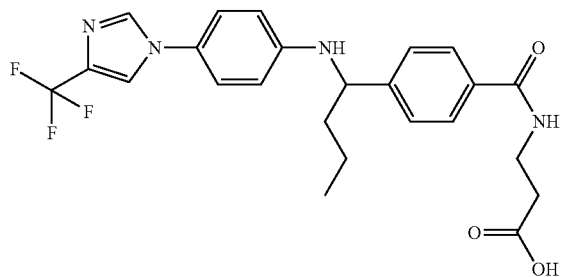 [SMILES: CCCC(Nc1ccc(-n2cnc(C(F)(F)F)c2)cc1)c1ccc(C(=O)NCCC(=O)O)cc1]

The title compound is obtained by resolving racemic 3-(4-(1-(4-(4-(trifluoromethyl)-1H-imidazol-1-yl)phenylamino)butyl)benzamido)propanoic acid Example 16, by chiral SFC. Column: Chiralpak AD-H. Dimensions: 10 mm×250 mm. Mobile Phase: 70/30 CO$_2$/methanol. Flow Rate: 10.0 mL/min. Modifier: none. Retention time: 8.80 minutes.

Example 19

(+/−)-3-(4-(1-(4-(4-(trifluoromethyl)-1H-imidazol-1-yl)phenoxy)butyl)benzamido)propanoic acid

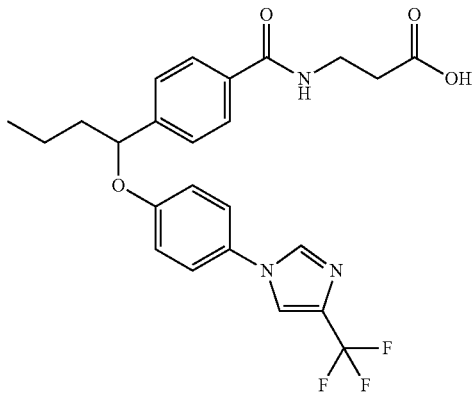 [SMILES: CCCC(Oc1ccc(-n2cnc(C(F)(F)F)c2)cc1)c1ccc(C(=O)NCCC(=O)O)cc1]

Step A: (+/−)-methyl 4-(1-(4-(4-(trifluoromethyl)-1H-imidazol-1-yl)phenoxy)butyl)benzoate

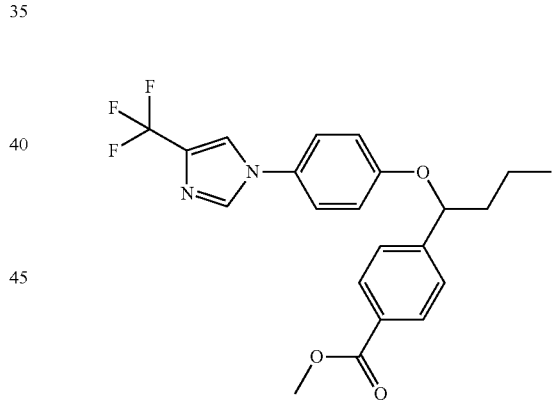

A mixture of Intermediate (27) (130 mg, 0.32 mmol), 4-(trifluoromethyl)-1H-imidazole (50 mg, 0.37 mmol), quinolin-8-ol (7.0 mg, 0.048 mmol), copper(I) iodide (9.1 mg, 0.048 mmol), and potassium carbonate (90.0 mg, 0.65 mmol) in dimethylsulfoxide (1.5 mL) was stirred under nitrogen at 100° C. overnight. The reaction mixture was cooled to ambient temperature and partitioned between ethyl acetate and saturated ammonium chloride. The organic layer was dried over magnesium sulfate, filtered and concentrated. Purification by column chromatography gave (+/−)-methyl 4-(1-(4-(4-(trifluoromethyl)-1H-imidazol-1-yl)phenoxy)butyl)benzoate (95 mg, 71%). $^1$H NMR (400 MHz, CDCl$_3$, δ): 8.02-7.98 (m, 2H), 7.68 (s, 1H), 7.44-7.42 (m, 1H), 7.41-7.37 (m, 2H), 7.18-7.14 (m, 2H), 6.91-6.86 (m, 2H), 5.18-5.12 (m, 1H), 3.88 (s, 3H), 2.07-1.94 (m, 1H), 1.87-1.75 (m, 1H), 1.60-1.36 (m, 2H), 0.98-0.91 (m, 3H).

Step B: (+/−)-(4-(1-(4-(4-(trifluoromethyl)-1H-imidazol-yl)phenoxy)butyl)benzoic acid

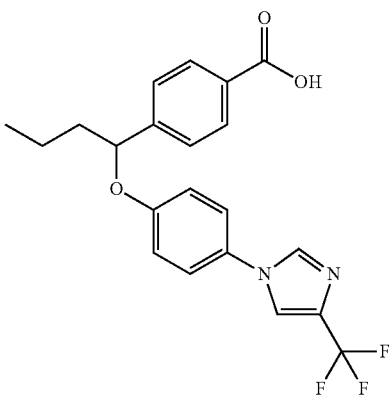 [SMILES: CCCC(Oc1ccc(-n2cnc(C(F)(F)F)c2)cc1)c1ccc(C(=O)O)cc1]

Lithium hydroxide (1.0 mL, 1N in water, 1.0 mmol) was added to a room temperature solution of methyl 4-(1-(4-(4-(trifluoromethyl)-1H-imidazol-1-yl)phenoxy)butyl)benzoate (95 mg, 0.23 mmol) in tetrahydrofuran (2 mL). The solution was stirred at ambient temperature for 18 hours, then at reflux for 2 hours. The mixture was cooled to room temperature and acidified to pH=2 with 1N HCl. The mixture was extracted with ethyl acetate. The organic layer was dried over magnesium sulfate, filtered and concentrated to give (+/−)-4-(1-(4-(4-(trifluoromethyl)-1H-imidazol-1-yl)phenoxy)butyl)benzoic acid (80 mg, 87%). $^1$H NMR (400 MHz, CDCl$_3$, δ): 8.09-8.04 (m, 2H), 7.71 (s, 1H), 7.46-7.41 (m, 3H), 7.20-7.14 (m, 2H), 6.92-6.87 (m, 2H), 5.20-5.14 (m, 1H), 2.08-1.95 (m, 1H), 1.88-1.76 (m, 1H), 1.62-1.36 (m, 2H), 1.01-0.92 (m, 3H).

Step C: (+/−)-methyl 3-(4-(1-(4-(4-(trifluoromethyl)-1H-imidazol-1-yl)phenoxy)butyl)benzamido)propanoate

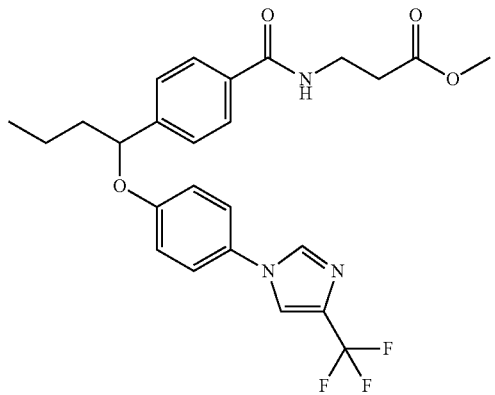 [SMILES: CCCC(Oc1ccc(-n2cnc(C(F)(F)F)c2)cc1)c1ccc(C(=O)NCCC(=O)OC)cc1]

1-Ethyl-3-(3-dimethylaminopropyl)carbodiimide hydrochloride (40 mg, 0.21 mmol) was added to a room temperature solution of (+/−)-4-(1-(4-(4-(trifluoromethyl)-1H-imidazol-1-yl)phenoxy)butyl)benzoic acid (80 mg, 0.20 mmol), methyl 3-aminopropanoate hydrochloride (28 mg, 0.20 mmol), 1-hydroxy-7-azabenzotriazole (30 mg, 0.22 mmol), and triethylamine (31 μL, 0.22 mmol) in dichloromethane (2 mL). The solution was stirred at room temperature overnight. The reaction mixture was diluted with dichloromethane (20 mL) and washed with water, then brine. The organic layer was dried over magnesium sulfate, filtered and concentrated to give (+/−)-methyl 3-(4-(1-(4-(4-(trifluoromethyl)-1H-imidazol-1-yl)phenoxy)butyl)benzamido)propanoate (89 mg, 90%). $^1$H NMR (400 MHz, CDCl$_3$, δ): 7.74-7.70 (m, 2H), 7.69-7.66 (s, 1H), 7.44-7.41 (m, 1H), 7.40-7.36 (m, 2H), 7.18-7.13 (m, 2H), 6.91-6.86 (m, 2H), 6.83-6.75 (m, 1H), 5.16-5.12 (m, 1H), 3.72-3.66 (m, 5H), 2.66-2.60 (m, 2H), 2.06-1.93 (m, 1H), 1.86-1.74 (m, 1H), 1.55-1.35 (m, 2H), 0.99-0.91 (m, 3H).

Step D: (+/−)-3-(4-(1-(4-(4-(trifluoromethyl)-1H-imidazol-1-yl)phenoxy)butyl)benzamido)propanoic acid Lithium hydroxide (1.0 mL, 1N in water, 1.0 mmol) was added to a room temperature solution of (+/−)-methyl 3-(4-(1-(4-(4-(trifluoromethyl)-1H-imidazol-1-yl)phenoxy)butyl)benzamido)propanoate (89 mg, 0.18 mmol) in tetrahydrofuran (2 mL). The solution was stirred at room temperature 5 hours. The mixture was acidified to pH=2 with 1N HCl, and extracted with ethyl acetate. The organic layer was dried over magnesium sulfate, filtered and concentrated to give (+/−)-3-(4-(1-(4-(4-(trifluoromethyl)-1H-imidazol-1-yl)phenoxy)butyl)benzamido)propanoic acid (84 mg, 98%). $^1$H NMR (400 MHz, CDCl$_3$, δ): 7.74-7.68 (m, 3H), 7.45-7.41 (m, 1H), 7.39-7.34 (m, 2H), 7.18-7.12 (m, 2H), 6.91-6.85 (m, 2H), 6.84-6.77 (m, 1H), 5.17-5.11 (m, 1H), 3.73-3.65 (m, 2H), 2.71-2.64 (m, 2H), 2.03-1.94 (m, 1H), 1.86-1.74 (m, 1H), 1.60-1.35 (m, 2H), 0.99-0.91 (m, 3H). MS (M+1): 475.9.

Example 20

(+/−)-3-(4-(1-(4-(4-(methylthio)-1H-pyrazol-1-yl)phenoxy)butyl)benzamido)propanoic acid

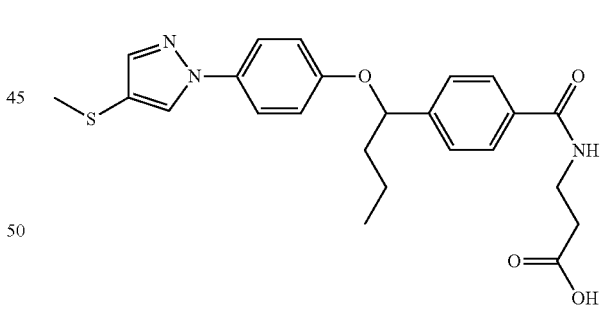

Copper iodide (1.31 g, 6.87 mmol), quinolin-8-ol (1.00 g, 6.87 mmol), and potassium carbonate (10.5 g, 76.0 mmol) were combined and pulverized. 78 mg of this mixture was added to 4-(methylthio)-1H-pyrazole (0.400 mmol) in a two dram vial. A solution of Intermediate (27) (123 mg, 0.300 mmol) in dimethylsulfoxide (0.500 mL) was added to the vial under a stream of dry nitrogen. The vial was capped and agitated on an orbital shaker at 120° C. for 12 hours. The reaction mixture was concentrated in vacuo.

To the crude residue was added methanol (2.0 mL), tetrahydrofuran (1.0 mL), and aqueous lithium hydroxide (2.0 M, 2.0 mL). The reaction was agitated on an orbital shaker at 60° C. for 12 hours. The reaction mixture was concentrated in vacuo and the remaining crude residue was carefully acidified with 1.0M aqueous hydrochloric acid (5.0 mL). The resulting acidified mixture was concentrated in vacuo.

A mixture of tert-butyl 3-aminopropanoate hydrochloride (12.3 g, 67.7 mmol), 1-hydroxybenzotriazole (6.89 g, 45 mmol) and 1-ethyl-3-(3-dimethylamino propyl)carbodiimide hydrochloride (12.9 g, 67.3 mmol) was suspended in tetrahydrofuran (450 mL). A 3.0 mL aliquot of this solution was transferred to the crude acid from the previous transformation. Triethylamine (0.167 mL, 1.20 mmol) was added and the mixture was agitated on an orbital shaker overnight. The reaction mixture was treated with Si-diamine scavenger (ca. 5.0 eq) and was agitated for 12 hours on an orbital shaker. The reaction was filtered through a silica gel plug, washing with tetrahydrofuran (three times). The combined organic filtrate was concentrated in vacuo.

To the crude residue was added dichloromethane (4.0 mL), followed by trifluoroacetic acid (2.0 mL). The reaction was agitated on an orbital shaker for 12 hours. The reaction mixture was concentrated in vacuo. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(4-(methylthio)-1H-pyrazol-1-yl)phenoxy)butyl)benzamido)propanoic acid (39.7 mg, 23% over 4 steps). Analytical LCMS: retention time 3.25 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier, flow rate 2.0 mL/minute); MS (M+1): 454.0.

Example 21

(+/−)-3-(4-(1-(4-(3-tert-butyl-1H-pyrazol-1-yl)phenoxy)butyl)benzamido)propanoic acid

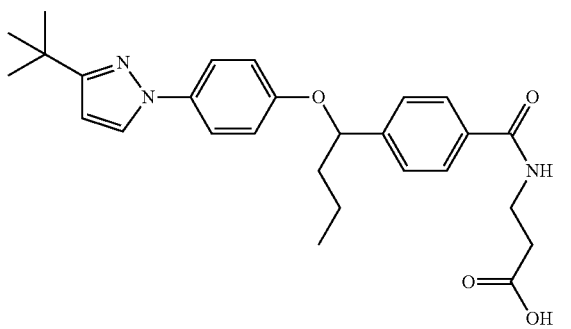 [SMILES: CCCC(Oc1ccc(-n2ccc(C(C)(C)C)n2)cc1)c1ccc(C(=O)NCCC(=O)O)cc1]

The title compound was prepared by a method analogous to that described for Example 20 using 3-tert-butyl-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(3-tert-butyl-1H-pyrazol-1-yl)phenoxy)butyl)benzamido)propanoic acid (50.3 mg, 29% over 4 steps). Analytical LCMS: retention time 3.71 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier, flow rate 2.0 mL/minute); MS (M+1): 464.0.

Example 22

(+/−)-3-(4-(1-(4-(4-chloro-3-methyl-1H-pyrazol-1-yl)phenoxy)butyl)benzamido)propanoic acid

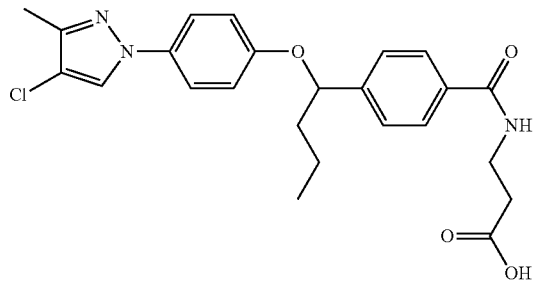 [SMILES: CCCC(Oc1ccc(-n2cc(Cl)c(C)n2)cc1)c1ccc(C(=O)NCCC(=O)O)cc1]

The title compound was prepared by a method analogous to that described for Example 20 using 4-chloro-3-methyl-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(4-chloro-3-methyl-1H-pyrazol-1-yl)phenoxy)butyl)benzamido)propanoic acid (31.4 mg, 18% over 4 steps). Analytical LCMS: retention time 3.44 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 456.0.

Example 23

(+/−)-3-(4-(1-(4-(4-chloro-1H-pyrazol-1-yl)phenoxy)butyl)benzamido)propanoic acid

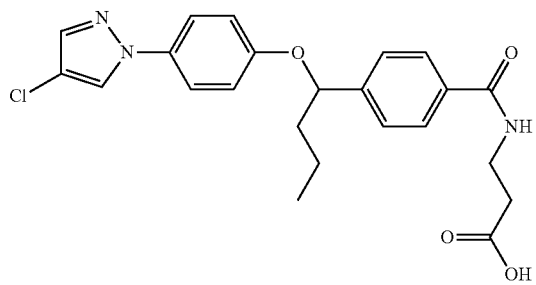 [SMILES: CCCC(Oc1ccc(-n2cc(Cl)cn2)cc1)c1ccc(C(=O)NCCC(=O)O)cc1]

The title compound was prepared by a method analogous to that described for Example 20 using 4-chloro-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(4-chloro-1H-pyrazol-1-yl)phenoxy)butyl)benzamido)propanoic acid (40.1 mg, 24% over 4 steps). Analytical LCMS: retention time 3.31 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier: flow rate 2.0 mL/minute); MS (M+1): 441.0.

Example 24

(+/−)-3-(4-(1-(4-(4-ethyl-3-methyl-1H-pyrazol-1-yl)phenoxy)butyl)benzamido)propanoic acid

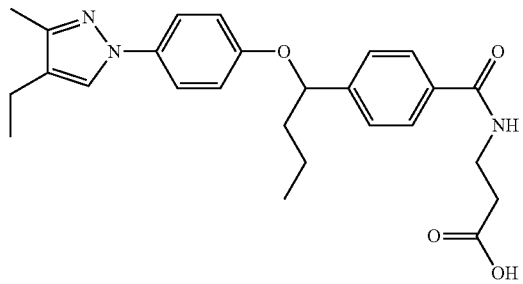 [SMILES: CCCC(Oc1ccc(-n2cc(CC)c(C)n2)cc1)c1ccc(C(=O)NCCC(=O)O)cc1]

The title compound was prepared by a method analogous to that described for Example 20 using 4-ethyl-3-methyl-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(4-ethyl-3-methyl-1H-pyrazol-1-yl)phenoxy)butyl)benzamido)propanoic acid (15.2 mg, 9% over 4 steps). Analytical LCMS: retention time 3.19 minutes (Atlantis $C_{18}$ 4.6×50 mm, 5 µM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 450.0.

Example 25

(+/−)-3-(4-(1-(4-(3,5-diethyl-1H-pyrazol-1-yl)phenoxy)butyl)benzamido)propanoic acid

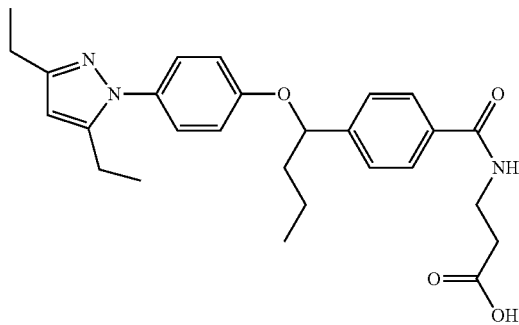 [SMILES: CCCC(Oc1ccc(-n2nc(CC)cc2CC)cc1)c1ccc(C(=O)NCCC(=O)O)cc1]

The title compound was prepared by a method analogous to that described for Example 20 using 3,5-diethyl-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(3,5-diethyl-1H-pyrazol-1-yl)phenoxy)butyl)benzamido)propanoic acid (24.4 mg, 14.1%). Analytical LCMS: retention time 3.31 minutes (Atlantis $C_{18}$ 4.6×50 mm, 5 µM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 464.1.

Example 26

(+/−)-3-(4-(1-(4-(4-methyl-1H-pyrazol-1-yl)phenoxy)butyl-benzamido)propanoic acid

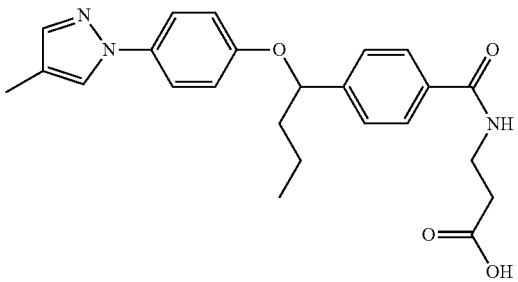 [SMILES: CCCC(Oc1ccc(-n2cc(C)cn2)cc1)c1ccc(C(=O)NCCC(=O)O)cc1]

The title compound was prepared by a method analogous to that described for Example 20 using 4-methyl-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(4-methyl-1H-pyrazol-1-yl)phenoxy)butyl)benzamido)propanoic acid (57.5 mg, 36% over 4 steps). Analytical LCMS: retention time 3.10 minutes (Atlantis $C_{18}$ 4.6×50 mm, 5 µM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 422.0.

Example 27

(+/−)-3-(4-(1-(4-(3-isopropyl-1H-pyrazol-1-yl)phenoxy)butyl)benzamido)propanoic acid

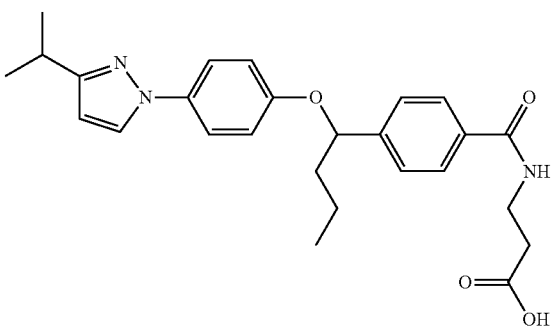 [SMILES: CCCC(Oc1ccc(-n2ccc(C(C)C)n2)cc1)c1ccc(C(=O)NCCC(=O)O)cc1]

The title compound was prepared by a method analogous to that described for Example 20 using 3-isopropyl-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(3-isopropyl-1H-pyrazol-1-yl)phenoxy)butyl)benzamido)propanoic acid (38.6 mg, 23% over 4 steps). Analytical LCMS: retention time 3.43 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier, flow rate 2.0 mL/minute); MS (M+1): 450.0.

Example 28

(+/−)-3-(4-(1-(4-(4-fluoro-1H-pyrazol-1-yl)phenoxy)butyl)benzamido)propanoic acid

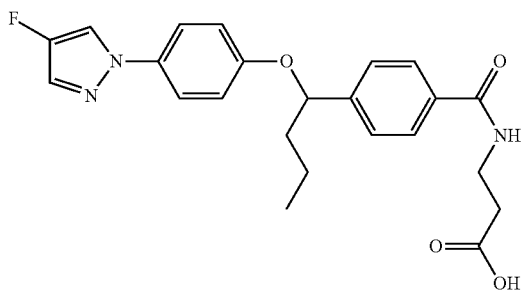 [SMILES: CCCC(Oc1ccc(-n2cc(F)cn2)cc1)c1ccc(C(=O)NCCC(=O)O)cc1]

The title compound was prepared by a method analogous to that described for Example 20 using 4-fluoro-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(4-fluoro-1H-pyrazol-1-yl)phenoxy)buty)benzamido)propanoic acid (34.4 mg, 23% over 4 steps). Analytical LCMS: retention time 3.25 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier: flow rate 2.0 mL/minute); MS (M+1): 454.0.

Example 29

(+/−)-3-(4-(1-(4-(3-methyl-1H-pyrazol-1-yl)phenoxy)butyl)benzamido)propanoic acid

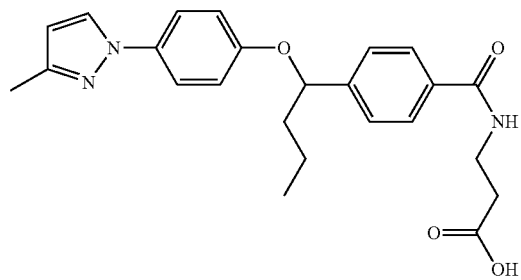 [SMILES: CCCC(Oc1ccc(-n2ccc(C)n2)cc1)c1ccc(C(=O)NCCC(=O)O)cc1]

The title compound was prepared by a method analogous to that described for Example 20 using 3-methyl-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(3-methyl-1H-pyrazol-1-yl)phenoxy)butyl)benzamido)propanoic acid (52 mg, 32% over 4 steps). Analytical LCMS: retention time 3.02 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 422.0.

Example 30

(+/−)-3-(4-(1-(4-(2H-1,2,3-triazol-2-yl)phenoxy)butyl)benzamido)propanoic acid

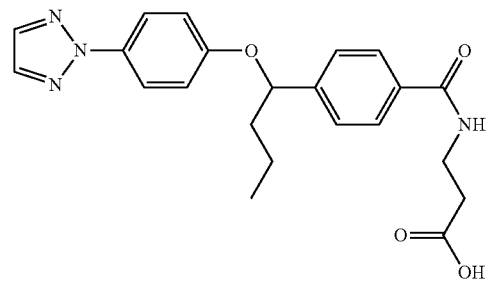 [SMILES: CCCC(Oc1ccc(-n2nccn2)cc1)c1ccc(C(=O)NCCC(=O)O)cc1]

The title compound was prepared by a method analogous to that described for Example 20 using 2H-1,2,3-triazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(2H-1,2,3-triazol-2-yl)phenoxy)butyl)benzamido)propanoic acid (18.7 mg, 12% over 4 steps). Analytical LCMS: retention time 3.07 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 409.0.

Example 31

(+/−)-3-(4-(1-(4-(3-butyl-1H-pyrazol-1-yl)phenoxy)butyl)benzamido)propanoic acid

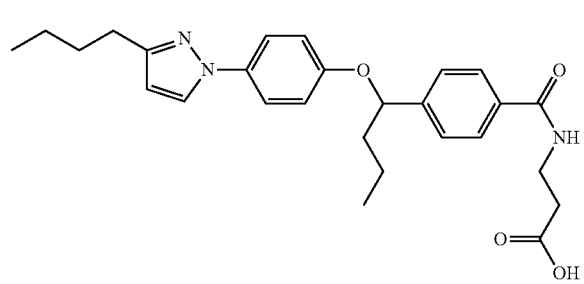 [SMILES: CCCCc1ccn(-c2ccc(OC(CCC)c3ccc(C(=O)NCCC(=O)O)cc3)cc2)n1]

The title compound was prepared by a method analogous to that described for Example 20 using 3-buty-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(3-butyl-1H-pyrazol-1-yl)phenoxy)butyl)benzamido)propanoic acid (15.3 mg, 9% over 4 steps). Analytical LCMS: retention time 3.4 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier, flow rate 2.0 mL/minute); MS (M+1): 464.0.

Example 32

(+/−)-3-(4-(1-(4-(5-ethoxy-3-methyl-1H-pyrazol-1-yl)phenoxy)butyl)benzamido)propanoic acid

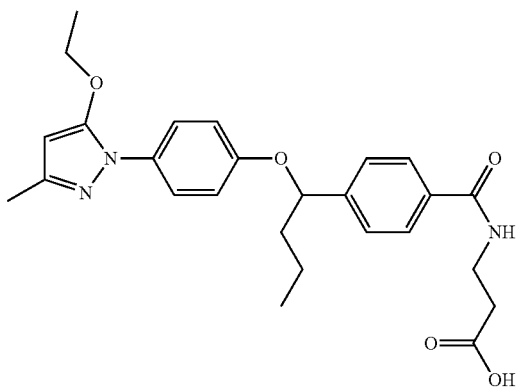 [SMILES: CCCC(Oc1ccc(-n2nc(C)cc2OCC)cc1)c1ccc(C(=O)NCCC(=O)O)cc1]

The title compound was prepared by a method analogous to that described for Example 20 using 5-ethoxy-3-methyl-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(5-ethoxy-3-methyl-1H-pyrazol-1-yl)phenoxy)butyl)benzamido)propanoic acid (33.3 mg, 19% over 4 steps). Analytical LCMS: retention time 3.23 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 466.0.

Example 33

(+/−)-3-(4-(1-(4-(5-methoxy-3-methyl-1H-pyrazol-1-yl)phenoxy)butyl)benzamido)propanoic acid

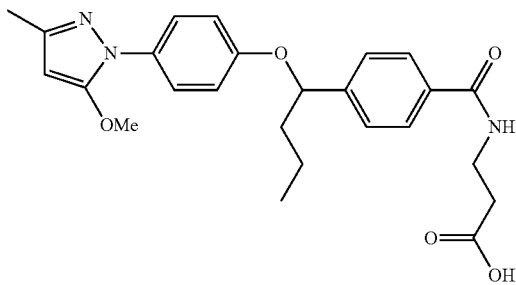 [SMILES: CCCC(Oc1ccc(-n2nc(C)cc2OC)cc1)c1ccc(C(=O)NCCC(=O)O)cc1]

The title compound was prepared by a method analogous to that described for Example 20 using 5-methoxy-3-methyl-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(5-methoxy-3-methyl-1H-pyrazol-1-yl)phenoxy)butyl)benzamido)propanoic acid (36.3 mg, 21% over 4 steps). Analytical LCMS: retention time 3.07 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 452.0.

Example 34

(+/−)-3-(4-(1-(4-(4-butyl-1H-imidazol-1-yl)phenoxy)butyl)benzamido)propanoic acid

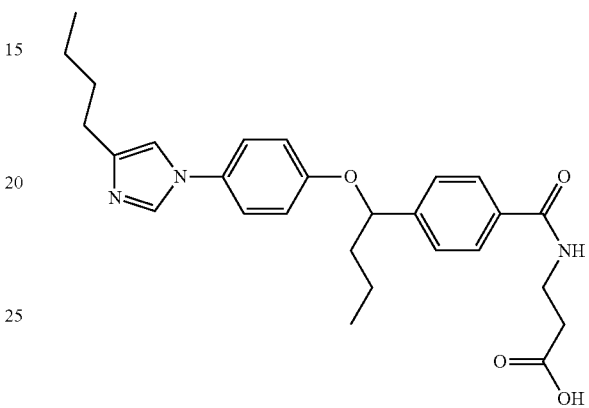

The title compound was prepared by a method analogous to that described for Example 20 using 4-butyl-1H-imidazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(4-butyl-1H-imidazol-1-yl)phenoxy)butyl)benzamido)propanoic acid (5.9 mg, 3% over 4 steps). Analytical LCMS: retention time 2.45 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier, flow rate 2.0 mL/minute); MS (M+1): 464.1.

Example 35

(+/−)-3-(4-(1-(4-(2-cyano-3,4,5-trimethyl-1H-pyrrol-1-yl)phenoxy)butyl)benzamido)propanoic acid

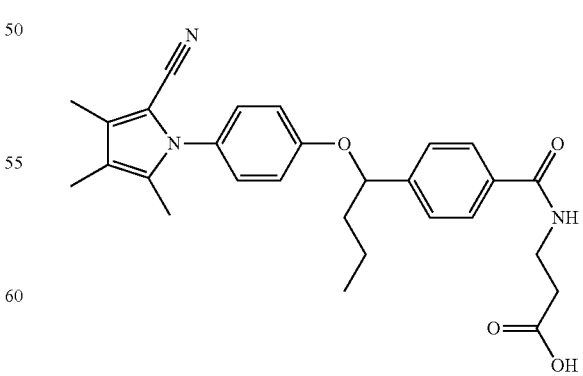

The title compound was prepared by a method analogous to that described for Example 20 using 3,4,5-trimethyl-1H-pyrrole-2-carbonitrile. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(2-cyano-3,4,5-trimethyl-1H-pyrrol-1-yl)phenoxy)butyl)benzamido)propanoic acid (31.9 mg, 18% over 4 steps). Analytical LCMS: retention time 3.6 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 474.0.

Example 36

(+/−)-3-(4-(1-(4-(3-cyano-2,4-dimethyl-1H-pyrrol-1-yl)phenoxy)butyl)benzamido)propanoic acid

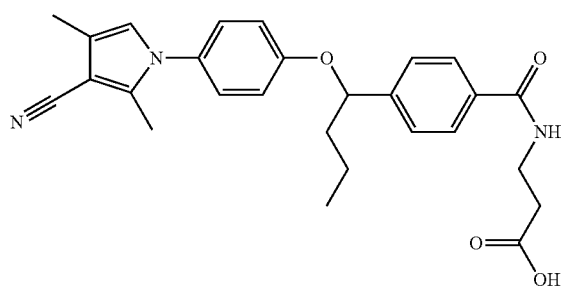 [SMILES: CCCC(Oc1ccc(-n2cc(C)c(C#N)c2C)cc1)c1ccc(C(=O)NCCC(=O)O)cc1]

The title compound was prepared by a method analogous to that described for Example 20 using 2,4-dimethyl-1H-pyrrole-3-carbonitrile. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(3-cyano-2,4-dimethyl-1H-pyrrol-1-yl)phenoxy)butyl)benzamido)propanoic acid (19.9 mg, 12% over 4 steps). Analytical LCMS: retention time 3.4 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 460.0.

Example 37

(+/−)-3-(4-(1-(4-(2-cyano-3-methyl-1H-pyrrol-1-yl)phenoxy)butyl)benzamido)propanoic acid

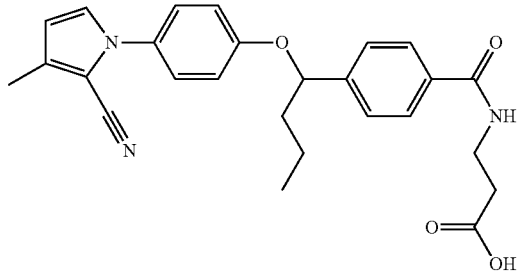 [SMILES: CCCC(Oc1ccc(-n2ccc(C)c2C#N)cc1)c1ccc(C(=O)NCCC(=O)O)cc1]

The title compound was prepared by a method analogous to that described for Example 20 using 3-methyl-1H-pyrrole-2-carbonitrile. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(2-cyano-3-methyl-1H-pyrrol-1-yl)phenoxy)butyl)benzamido)propanoic acid (37.1 mg, 22% over 4 steps). Analytical LCMS: retention time 3.36 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 446.0.

Example 38

(+/−)-3-(6-(1-(4-(3-propyl-1H-pyrazol-1-yl)phenoxy)butyl)nicotinamido)propanoic acid

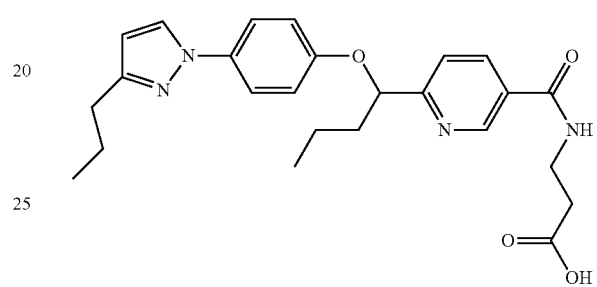

The title compound was prepared by a method analogous to that described for Example 20 using 3-propyl-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(6-(1-(4-(3-propyl-1H-pyrazol-1-yl)phenoxy)butyl)nicotinamido)propanoic acid (4.4 mg, 3% over 4 steps). Analytical LCMS: retention time 3.24 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 450.0.

Example 39

(+/−)-3-(4-(1-(4-(3,4-dimethyl-1H-pyrazol-1-yl)phenoxy)butyl)benzamido)propanoic acid

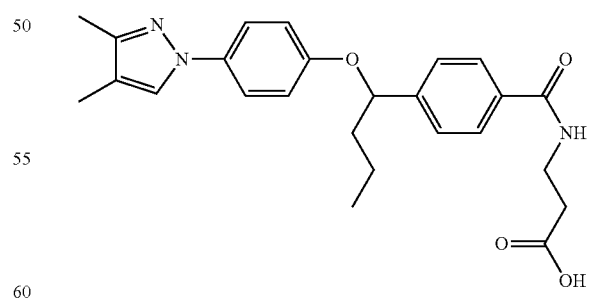

The title compound was prepared by a method analogous to that described for Example 20 using 3,4-dimethyl-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(3,4-dimethyl-1H-pyrazol- 1-yl)phenoxy)butyl)benzamido)propanoic acid (22.8 mg, 14% over 4 steps). Analytical LCMS: retention time 3.07 minutes (Atlantis $C_{18}$ 4.6×50 mm, 5 µM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 436.

Example 40

(+/−)-3-(4-(1-(4-(1H-pyrazol-1-yl)phenoxy)butyl)benzamido)propanoic

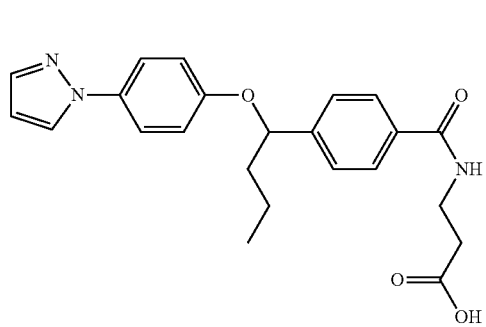 [SMILES: CCCC(Oc1ccc(-n2cccn2)cc1)c1ccc(C(=O)NCCC(=O)O)cc1]

The title compound was prepared by a method analogous to that described for Example 20 using 1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(1H-pyrazol-1-yl)phenoxy)butyl)benzamido)propanoic acid (46.1 mg, 29% over 4 steps). Analytical LCMS: retention time 2.93 minutes (Atlantis $C_{18}$ 4.6×50 mm, 5 µM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 408.0.

Example 41

(+/−)-3-(4-(1-(4-(1H-imidazo[1,2-b]pyrazol-1-yl)phenoxy)butyl)benzamido)propanoic acid

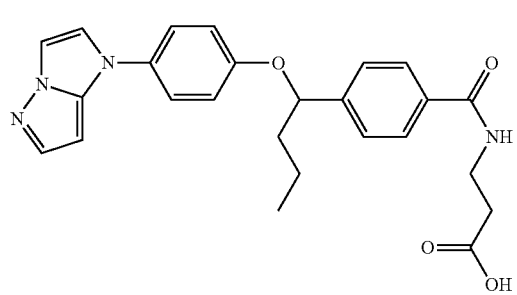 [SMILES: CCCC(Oc1ccc(-n2ccn3nccc23)cc1)c1ccc(C(=O)NCCC(=O)O)cc1]

The title compound was prepared by a method analogous to that described for Example 20 using 1H-imidazo[1,2-b]pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(1H-imidazo[1,2-b]pyrazol-1-yl)phenoxy)butyl)benzamido)propanoic acid (29.6 mg, 18% over 4 steps). Analytical LCMS: retention time 2.74 minutes (Atlantis $C_{18}$ 4.6×50 mm, 5 µM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 447.0.

Example 42

(+/−)-3-(4-(1-(4-(3-ethyl-1H-pyrazol-1-yl)phenoxy)butyl)benzamido)propanoic acid

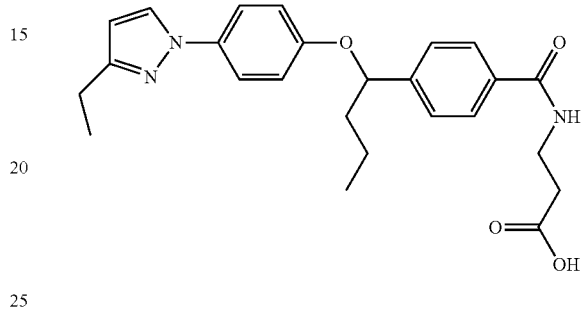

The title compound was prepared by a method analogous to that described for Example 20 using 3-ethyl-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(3-ethyl-1H-pyrazol-1-yl)phenoxy)butyl)benzamido)propanoic acid (10.0 mg, 6% over 4 steps). Analytical LCMS: retention time 3.07 minutes (Atlantis $C_{18}$ 4.6×50 mm, 5 µM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 436.0.

Example 43

(+/−)-3-(4-(1-(4-(4-chloro-5-methyl-1H-imidazol-1-yl)phenoxy)butyl)benzamido)propanoic acid

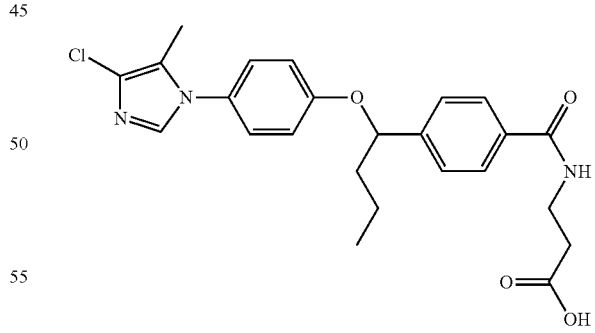

The title compound was prepared by a method analogous to that described for Example 20 using 4-chloro-5-methyl-1H-imidazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(4-chloro-5-methyl-1H-imidazol-1-yl)phenoxy)butyl)benzamido)propanoic acid (5.1 mg, 3% over 4 steps). Analytical LCMS: retention time 2.48 minutes (Atlantis $C_{18}$ 4.6×50 mm, 5 µM column; 95% water/ acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 456.0.

Example 44

(+/−)-3-(4-(1-(4-(4,5-diethyl-1H-imidazol-1-yl)phenoxy)butyl)benzamido)propanoic acid

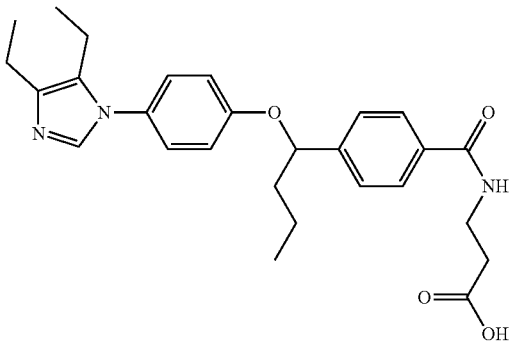 [SMILES: CCCC(Oc1ccc(-n2cnc(CC)c2CC)cc1)c1ccc(C(=O)NCCC(=O)O)cc1]

The title compound was prepared by a method analogous to that described for Example 20 using 4,5-diethyl-1H-imidazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(4,5-diethyl-1H-imidazol-1-yl)phenoxy)butyl)benzamido)propanoic acid (56.1 mg, 32% over 4 steps). Analytical LCMS: retention time 2.50 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 464.0.

Example 45

(+/−)-3-(4-(1-(4-(3,5-dimethyl-1H-pyrazol-1-yl)phenoxy)butyl)benzamido)propanoic acid

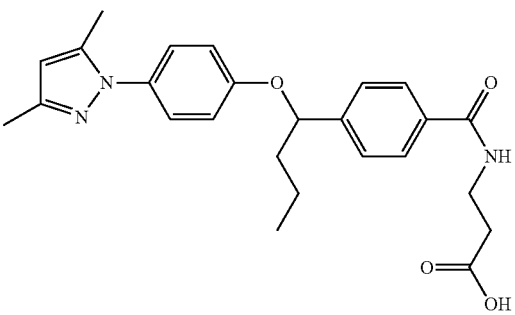 [SMILES: CCCC(Oc1ccc(-n2nc(C)cc2C)cc1)c1ccc(C(=O)NCCC(=O)O)cc1]

The title compound was prepared by a method analogous to that described for Example 20 using 3,5-dimethyl-1H-pyrazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(3,5-dimethyl-1H-pyrazol-1-yl)phenoxy)butyl)benzamido)propanoic acid (42.0 mg, 25% over 4 steps). Analytical LCMS: retention time 2.97 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 436.0.

Example 46

(+/−)-3-(4-(1-(4-(4-(3-methyl-1H-1,2,4-triazol-1-yl)phenoxy)butyl)benzamido)propanoic acid

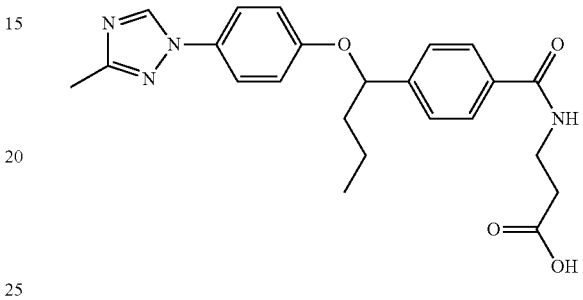

The title compound was prepared by a method analogous to that described for Example 20 using 3-methyl-1H-1,2,4-triazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(4-(3-methyl-1H-1,2,4-triazol-1-yl)phenoxy)butyl)benzamido)propanoic acid (30.3 mg, 19% over 4 steps). Analytical LCMS: retention time 2.58 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 423.0.

Example 47

(+/−)-3-(4-(1-(4-(1H-1,2,4-triazol-1-yl)phenoxy)butyl)benzamido)propanoic acid

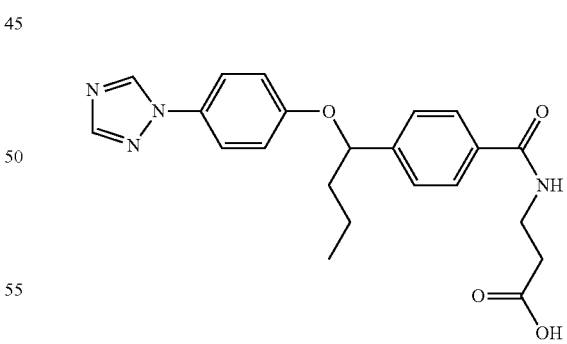

The title compound was prepared by a method analogous to that described for Example 20 using 1H-1,2,4-triazole. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(1H-1,2,4-triazol-1-yl)phenoxy)butyl)benzamido)propanoic acid (44.2 mg, 28% over 4 steps). Analytical LCMS: retention time 2.59 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier, flow rate 2.0 mL/minute); MS (M+1): 409.0.

Example 48

(+/−)-3-(4-(1-(4-(2-butyl-1H-imidazol-1-yl)phenoxy)butyl)benzamido)propanoic acid

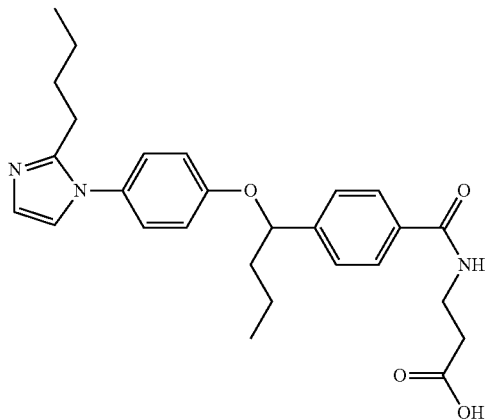 [SMILES: CCCCc1nccn1-c1ccc(OC(CCC)c2ccc(C(=O)NCCC(=O)O)cc2)cc1]

The title compound was prepared by a method analogous to that described for Example 20 using 2-butyl-1H-imidazole. Purification by reversed-phase HPLC on a Waters Sunfire C$_{18}$ 19×100 mm, 0.005 mm column eluting with a gradient of water in acetonitrile (0.05% trifluoroacetic acid modifier) gave (+/−)-3-(4-(1-(4-(2-butyl-1H-imidazol-1-yl)phenoxy)butyl)benzamido)propanoic acid (82 mg, 47% over 4 steps). Analytical LCMS: retention time 2.36 minutes (Atlantis C$_{18}$ 4.6×50 mm, 5 µM column; 95% water/acetonitrile linear gradient to 5% water/acetonitrile over 4.0 minutes, hold at 5% water/acetonitrile to 5.0 minutes; 0.05% trifluoroacetic acid modifier: flow rate 2.0 mL/minute); MS (M+1): 464.1.

Example 49

(+/−)-3-(4-(1-(4-(4,5-dimethyl-1H-imidazol-1-yl)phenoxy)butyl)benzamido)propanoic acid

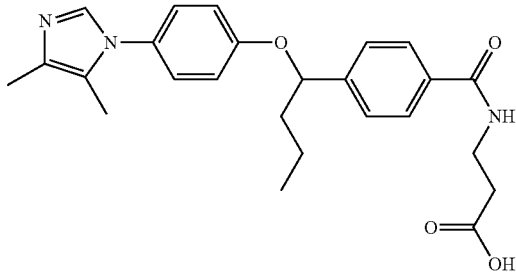 [SMILES: CCCC(Oc1ccc(-n2cnc(C)c2C)cc1)c1ccc(C(=O)NCCC(=O)O)cc1]

The title compound was prepared by a method analogous to that described for Example 20 using 4,5-dimethyl-1H-imidazole. Purification by reversed-phase HPLC on a Waters Sunfire C$_{18}$ 19×100 mm, 0.005 mm column eluting with a gradient of water in acetonitrile (0.05% trifluoroacetic acid modifier) gave (+/−)-3-(4-(1-(4-(4,5-dimethyl-1H-imidazol-1-yl)phenoxy)butyl)benzamido)propanoic acid (43.1 mg, 26% over 4 steps). Analytical LCMS: retention time 2.19 minutes (Atlantis C$_{18}$ 4.6×50 mm, 5 µM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 436.0.

Example 50

(+/−)-3-(4-(1-(4-(1-propyl-1H-pyrazol-4-yl)phenoxy)butyl)benzamido)propanoic acid

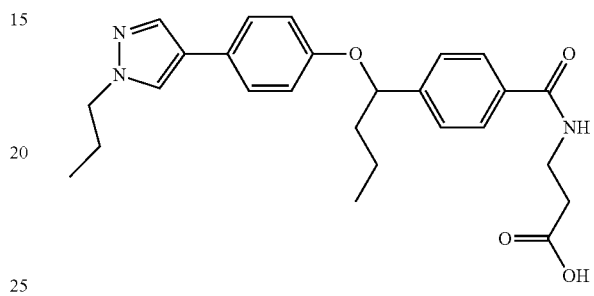

To 1-propyl-4-(4,4,5,5-tetramethyl-1,3,2-dioxaborolan-2-yl)-1H-pyrazole (95.2 mg, 0.400 mmol) and PS—PPh$_3$-Pd (0.170 g, 0.017 mmol) in a microwave vial was added a solution of Intermediate (27) (123 mg, 0.300 mmol) in dimethoxyethane (3.3 mL), followed by an aqueous solution of potassium carbonate (2.0M, 1.7 mL). The vial was capped and heated to 100° C. for 1 hour. The reaction mixture was filtered, the resin was washed with tetrahydrofuran (2×1.0 mL), and the combined organic filtrate was concentrated in vacuo.

To the crude residue was added methanol (2.0 mL), tetrahydrofuran (1.0 mL), and aqueous lithium hydroxide (2.0 mL, 2.0M). The reaction was agitated on an orbital shaker at 60° C. for 12 hours. The reaction mixture was concentrated in vacuo and the remaining crude residue was carefully acidified with 1.0M aqueous hydrochloric acid (5.0 mL). The resulting acidified mixture was concentrated in vacuo.

A mixture of tert-butyl 3-aminopropanoate hydrochloride (12.3 g, 67.7 mmol), 1-hydroxybenzotriazole (6.89 g, 45 mmol) and 1-ethyl-3-(3-dimethylamino propyl)carbodiimide hydrochloride (12.9 g, 67.3 mmol) was suspended in tetrahydrofuran (450 mL). A 3.0 mL aliquot of this solution was transferred to the crude acid from the previous transformation. Triethylamine (0.167 mL, 1.20 mmol) was added and the mixture was agitated on an orbital shaker overnight. The reaction mixture was treated with Si-diamine scavenger (ca. 5.0 eq) and the mixture was agitated for 12 hours on an orbital shaker. The reaction was filtered through a plug of silica gel, rinsing with tetrahydrofuran (3 times). The combined organic filtrate was concentrated in vacuo.

To the crude residue was added dichloromethane (4.0 mL), followed by trifluoroacetic acid (2.0 mL). The reaction was agitated on an orbital shaker for 12 hours at ambient temperature. The crude reaction mixture was concentrated in vacuo. The crude material was purified by reversed-phase HPLC on a Waters Sunfire C$_{18}$ 19×100 mm, 0.005 mm column eluting with a gradient of water in acetonitrile (0.05% trifluoroacetic acid modifier) to give (+/−)-3-(4-(1-(4-(1-propyl-1H-pyrazol-4-yl)phenoxy)butyl)benzamido)propanoic acid (56.1 mg, 33% over 4 steps). Analytical LCMS: retention time 3.11 minutes (Atlantis C$_{18}$ 4.6×50 mm, 5 µM column; 95% water/ acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 450.0.

Example 51

(+/−)-3-(4-(1-(4-(1H-pyrazol-3-yl)phenoxy)butyl)benzamido)propanoic acid

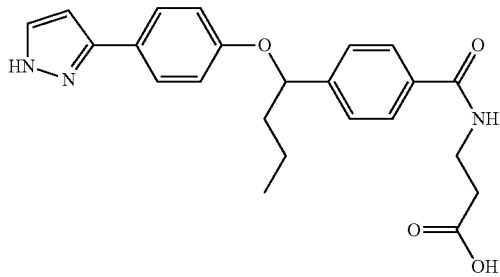 [SMILES: CCCC(Oc1ccc(-c2cc[nH]n2)cc1)c1ccc(C(=O)NCCC(=O)O)cc1]

The title compound was prepared by a method analogous to that described for Example 50. Purification by reversed-phase HPLC on a Waters Sunfire $C_{18}$ 19×100 mm, 0.005 mm column eluting with a gradient of water in acetonitrile (0.05% trifluoroacetic acid modifier) gave the desired product (3.8 mg, 2% over 4 steps). Analytical LCMS: retention time 2.65 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier, flow rate 2.0 mL/minute); MS (M+1): 408.0.

Example 52

(+/−)-3-(4-(1-(4-(3,5-dimethylisoxazol-4-yl)phenoxy)butyl)benzamido)propanoic acid

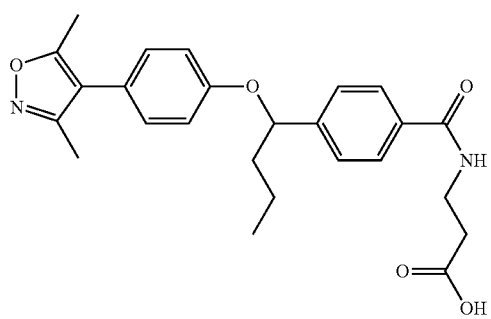 [SMILES: CCCC(Oc1ccc(-c2c(C)noc2C)cc1)c1ccc(C(=O)NCCC(=O)O)cc1]

The title compound was prepared by a method analogous to that described for Example 50. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(3,5-dimethylisoxazol-4-yl)phenoxy)butyl)benzamido)propanoic acid (40.3 mg, 24% over 4 steps). Analytical LCMS: retention time 3.14 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 437.0.

Example 53

(+/−)-3-(4-(1-(4-(1-methyl-3-(trifluoromethyl)-1H-pyrazol-5-yl)phenoxy)butyl)benzamido)propanoic acid

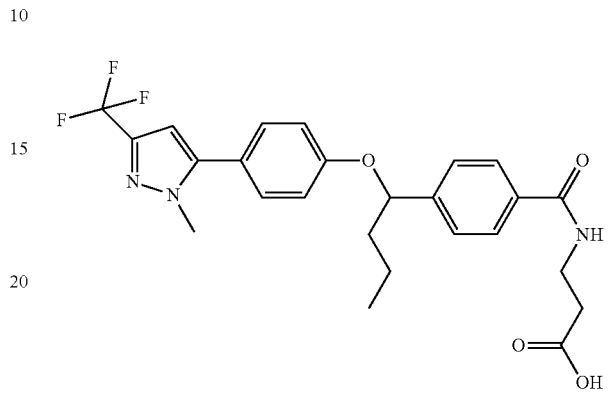

The title compound was prepared by a method analogous to that described for Example 50. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-(4-(1-(4-(1-methyl-3-(trifluoromethyl)-1H-pyrazol-5-yl)phenoxy)butyl)benzamido)propenoic acid (53.5 mg, 30% over 4 steps). Analytical LCMS: retention time 3.42 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier flow rate 2.0 mL/minute); MS (M+1): 490.0.

Example 54

(+/−)-3-(4-(1-(4-(1-methyl-1H-pyrazol-4-yl)phenoxy)butyl)benzamido)propanoic acid

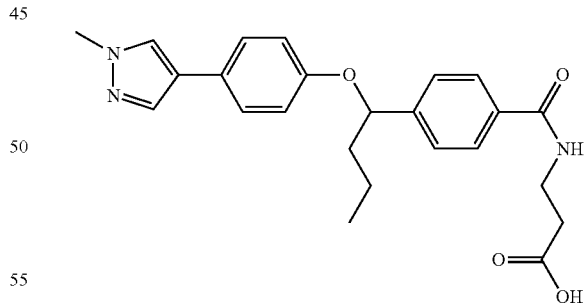

The title compound was prepared by a method analogous to that described for Example 50. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(1-methyl-1H-pyrazol-4-yl)phenoxy)butyl)benzamido)propanoic acid (2.5 mg, 2% over 4 steps). Analytical LCMS: retention time 2.85 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0

Example 55

(+/−)-3-(4-(1-(4-(1,5-dimethyl-1H-pyrazol-4-yl)phenoxy)butyl)benzamido)propanoic acid

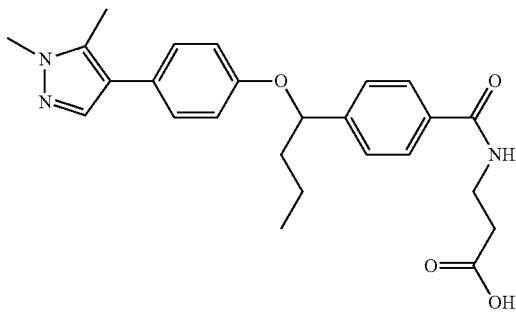 [SMILES: CCCC(Oc1ccc(-c2cnn(C)c2C)cc1)c1ccc(C(=O)NCCC(=O)O)cc1]

The title compound was prepared by a method analogous to that described for Example 50. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(1,5-dimethyl-1H-pyrazol-4-yl)phenoxy)butyl)benzamido)propanoic acid (7.0 mg, 4% over 4 steps). Analytical LCMS: retention time 2.86 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 436.0.

Example 56

(+/−)-3-(4-(1-(4-(1H-pyrazol-4-yl)phenoxy)butyl)benzamido)propanoic acid

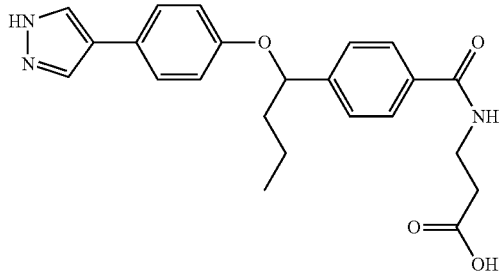 [SMILES: CCCC(Oc1ccc(-c2cn[nH]c2)cc1)c1ccc(C(=O)NCCC(=O)O)cc1]

The title compound was prepared by a method analogous to that described for Example 50. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(1H-pyrazol-4-yl)phenoxy)butyl)benzamido)propanoic acid (1.8 mg, 1% over 4 steps). Analytical LCMS: retention time 2.62 minutes (Atlantis $C_{18}$ 4.6×50 mm, 5 μM column; 95% water/acetonitrile linear gradient to 5% water/acetonitrile over 4.0 minutes; 0.05% trifluoroacetic acid modifier; flow rate 2.0 mL/minute); MS (M+1): 422.0.

Example 57

(+/−)-3-(4-(1-(4-(1-methyl-1H-pyrazol-5-yl)phenoxy)butyl)benzamido)propanoic acid

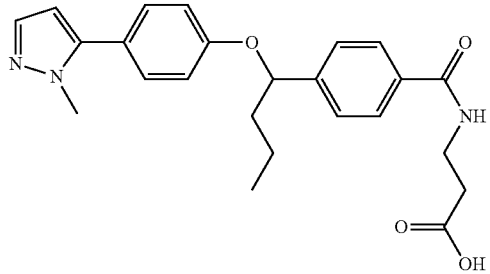 [SMILES: CCCC(Oc1ccc(-c2ccnn2C)cc1)c1ccc(C(=O)NCCC(=O)O)cc1]

The title compound was prepared by a method analogous to that described for Example 50. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(1-methyl-1H-pyrazol-5-yl)phenoxy)butyl)benzamido)propanoic acid (8.1 mg, 5% over 4 steps). Analytical LCMS: retention time 2.85 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 422.0.

Example 58

(+/−)-3-(4-(1-(4-(1,3,5-trimethyl-1H-pyrazol-4-yl)phenoxy)butyl)benzamido)propanoic acid

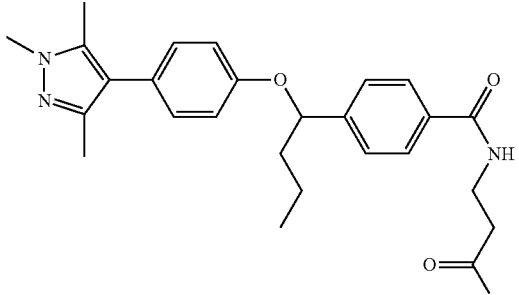

The title compound was prepared by a method analogous to that described for Example 50. Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(1-(4-(1,3,5-trimethyl-1H-pyrazol-4-yl)phenoxy)butyl)benzamido)propanoic acid (21 mg, 12% over 4 steps). Analytical LCMS: retention time 2.81 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 450.0.

Example 59

(+/−)-3-(4-(1-(4-(4-(trifluoromethyl)-1H-pyrazol-1-yl)phenoxy)butyl)benzamido)propanoic acid

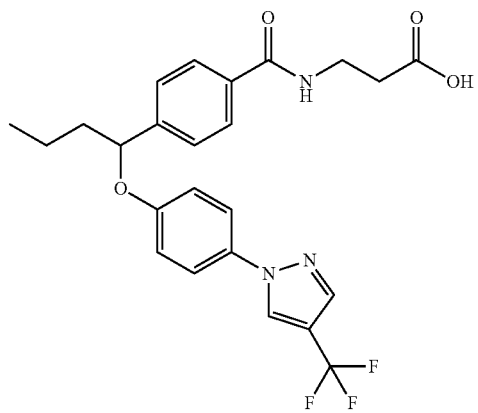 [SMILES: CCCC(Oc1ccc(-n2cc(C(F)(F)F)cn2)cc1)c1ccc(C(=O)NCCC(=O)O)cc1]

The title compound was prepared by a method analogous to that described for Example 19, using 4-(trifluoromethyl)-1H-pyrazole. $^1$H NMR (400 MHz, CDCl$_3$, δ): 8.00-7.97 (m, 1H), 7.84-7.80 (m, 1H), 7.73-7.68 (m, 2H), 7.46-7.36 (m, 4H), 6.90-6.84 (m, 2H), 6.77-6.70 (m, 1H), 5.18-5.11 (m, 1H), 3.74-3.66 (m, 2H), 2.72-2.66 (m, 2H), 2.02-1.93 (m, 1H), 1.85-1.74 (m, 1H), 1.59-1.36 (m, 2H), 0.99-0.91 (m, 3H). MS (M−1): 474.0.

Example 60

3-(4-(1-(4-(4-(trifluoromethyl)-1H-pyrazol-1-yl)phenoxy)butyl)benzamido)propanoic acid, Isomer 1

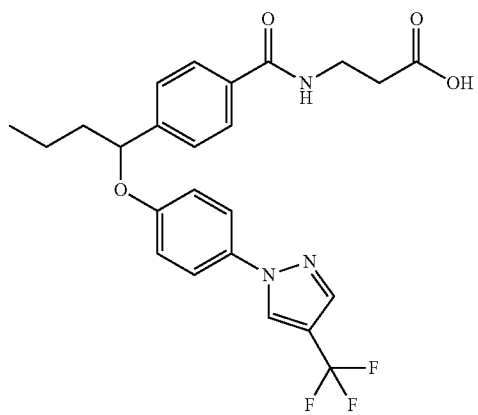 [SMILES: CCCC(Oc1ccc(-n2cc(C(F)(F)F)cn2)cc1)c1ccc(C(=O)NCCC(=O)O)cc1]

The title compound is obtained by resolving racemic 3-(4-(1-(4-(4-(trifluoromethyl)-1H-pyrazol-1-yl)phenoxy)butyl)benzamido)propanoic acid Example 59, by chiral SFC. Column: Chiracel OJ-H. Dimensions: 10 mm×250 mm. Mobile Phase: 80/20 CO$_2$/methanol. Flow Rate: 10.0 mL/min. Modifier: none. Retention time: 3.66 minutes.

Example 61

3-(4-(1-(4-(4-(trifluoromethyl)-1H-pyrazol-1-yl)phenoxy)butyl)benzamido)propanoic acid, Isomer 2

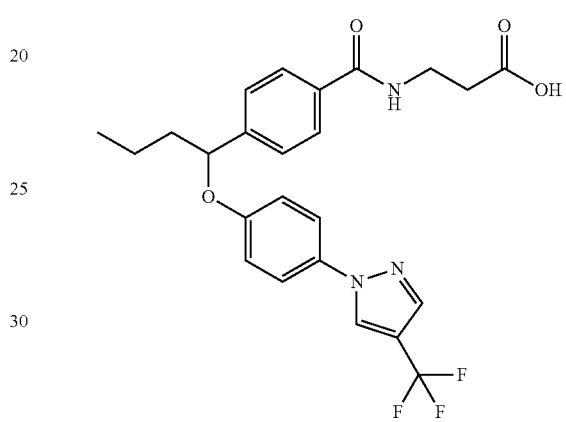

The title compound is obtained by resolving racemic 3-(4-(1-(4-(4-(trifluoromethyl)-1H-pyrazol-1-yl)phenoxy)butyl)benzamido)propenoic acid Example 59, by chiral SFC. Column: Chiracel OJ-H. Dimensions: 10 mm×250 mm. Mobile Phase: 80/20 CO$_2$/methanol. Flow Rate: 10.0 mL/min. Modifier: none. Retention time: 4.81 minutes.

Example 62

(+/−)-3-(4-(1-(6-(4-phenyl-1H-pyrazol-1-yl)pyridine-3-ylamino)butyl)benzamido)propanoic acid

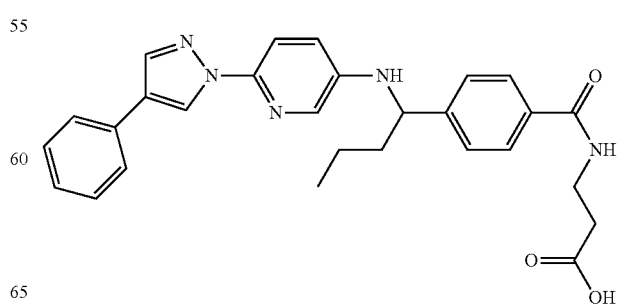

141

Step A: (+/−)-methyl 3-(4-(1-(6-(4-phenyl-1H-pyrazol-1-yl)pyridine-3-ylamino)butyl)benzamido)propanoate

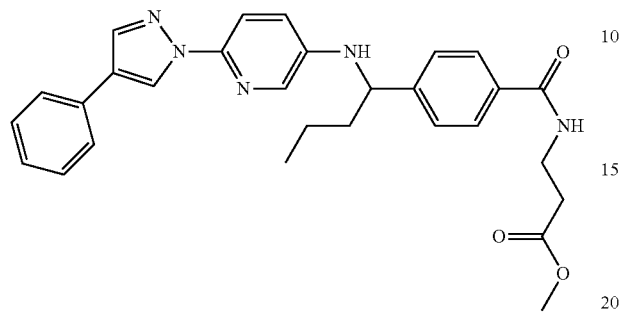

Intermediate (25) (42.1 mg, 0.178 mmol) was dissolved in methanol (0.8 mL). Intermediate (23) (54.4 mg, 0.196 mmol) was added, followed by decaborane (13.1 mg, 0.107 mmol). The reaction was stirred at room temperature for 18 hours and was then concentrated. Purification by column chromatography (20-100% ethyl acetate in heptane) gave (+/−)-methyl 3-(4-(1-(6-(4-phenyl-1H-pyrazol-1-yl)pyridine-3-ylamino) butyl)benzamido)propanoate (81.3 mg, 92%) as a white solid. $^1$H NMR (400 MHz, CDCl$_3$, δ): 8.61 (s, 1H), 7.90 (s, 1H), 7.76-7.66 (m, 4H), 7.53 (d, J=7.2 Hz, 2H), 7.42-7.31 (m, 4H), 7.26-7.19 (m, 1H), 6.94 (m, 1H), 6.81-6.74 (m, 1H), 4.41-4.34 (m, 1H), 3.73-3.66 (m, 5H), 2.66-2.60 (m, 2H), 1.94-1.72 (m, 2H), 1.50-1.29 (m, 2H), 0.98-0.90 (m, 3H). MS (M+1): 498.4.

Step B: (+/−)-3-(4-(1-(6-(4-phenyl-1H-pyrazol-1-yl)pyridine-3-ylamino)butyl)benzamido)propanoic acid Methyl 3-(4-(1-(6-(4-phenyl-1H-pyrazol-1-yl)pyridine-3-ylamino)butyl)benzamido)propanoate (82.1 mg, 0.165 mmol) was dissolved in methanol (0.5 mL) and tetrahydrofuran (0.5 mL). 1N Sodium hydroxide (0.33 mL) was added and the reaction was stirred at room temperature for 24 hours. The reaction was then concentrated. The crude residue was taken up in water and acidified with 1N hydrochloric acid to pH=3. A white precipitate formed. The solids were filtered off and dried under vacuum to give (+/−)-3-(4-(1-(6-(4-phenyl-1H-pyrazol-1-yl)pyridine-3-ylamino)butyl)benzamido)propanoic acid (61.6 mg, 77%) as an off-white solid. $^1$H NMR (400 MHz, CD$_3$OD, δ): 8.57 (d, J=1.0 Hz, 1H), 7.96 (d, J=0.8 Hz, 1H), 7.78-7.69 (m, 3H), 7.61-7.50 (m, 3H), 7.47 (d, J=8.4 Hz, 2H), 7.38-7.31 (m, 2H), 7.24-7.16 (m, 1H), 7.05 (dd, J=8.9, 3.0 Hz, 1H), 4.48-4.41 (m, 1H), 3.63-3.55 (m, 2H), 2.60 (t, J=6.9 Hz, 2H), 1.94-1.69 (m, 2H), 1.58-1.33 (m, 2H), 0.96 (t, J=7.4 Hz, 3H). MS (M+1): 484.4.

142

Example 63

(+/−)-3-(4-(1-(4-(4-fluoro-1H-pyrazol-1-yl)phenylamino)butyl)benzamido)propanoic acid

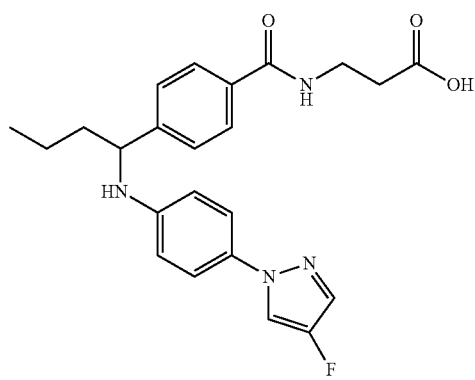 [SMILES: CCCC(Nc1ccc(-n2cc(F)cn2)cc1)c1ccc(C(=O)NCCC(=O)O)cc1]

The title compound was prepared by a method analogous to that described for Example 62 using Intermediate (12). $^1$HNMR (400 MHz CD$_3$OD, δ): 7.91 (d, 1H), 7.72 (d, 2H), 7.48 (d, 1H), 7.44 (d, 2H), 7.23 (d, 2H), 6.58 (d, 2H), 4.39 (m, 1H), 3.59 (m, 2H), 2.60 (m, 2H), 1.84-1.80 (m, 1H), 1.74-1.68 (m, 1H), 1.50-1.48 (m, 1H), 1.40-1.35 (m, 1H), 0.94 (m, 3H). MS (M+1): 425.3.

Example 64

(+/−)-3-(6-(3-methyl-1-(4-(4-(trifluoromethyl)-1H-pyrazol-1-yl)phenyl)butylamino)nicotinamido)propanoic acid

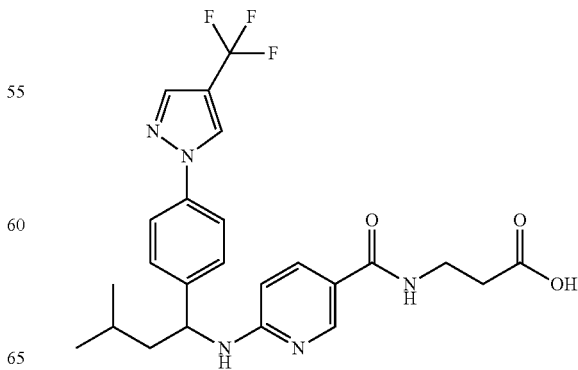

Step A: (+/−)-6-(3-methyl-4-(4-(trifluoromethyl)-1H-pyrazol-1-yl)phenyl)butylamino)nicotinic acid

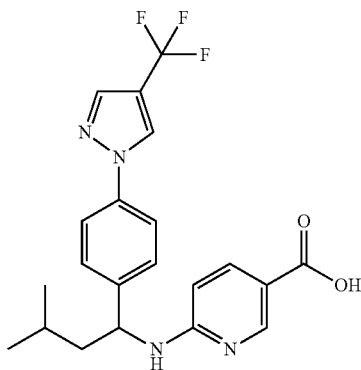 [SMILES: CC(C)CC(Nc1ccc(C(=O)O)cn1)c1ccc(-n2cc(C(F)(F)F)cn2)cc1]

A microwave reaction vial was charged with Intermediate (14) (180 mg, 0.605 mmol) and isopropanol (5 mL). Methyl 6-chloronicotinate (114 mg, 0.665 mmol) and diisopropylethylamine (313 mg, 2.42 mmol) were added. The resulting mixture was heated to 130° C. for 15 hours under microwave irradiation. The mixture was concentrated and the crude residue was purified by column chromatography to give (+/−)-methyl 6-(3-methyl-1-(4-(4-(trifluoromethyl)-1H-pyrazol-1-yl)phenyl)butylamino)nicotinate (30 mg).

To a solution of (+/−)-methyl 6-(3-methyl-1-(4-(4-(trifluoromethyl)-1H-pyrazol-1-yl)phenyl)butylamino)nicotinate (30 mg, 0.069 mmol) in tetrahydrofuran (3 mL) was added lithium hydroxide (0.103 mL, 2N in water, 0.207 mmol). The mixture was stirred at 50° C. overnight. The mixture was neutralized with 1N aqueous hydrochloric acid and extracted with ethyl acetate. The organic layer was dried over sodium sulfate, filtered and concentrated to give 6-(3-methyl-1-(4-(4-(trifluoromethyl)-1H-pyrazol-1-yl)phenyl)butylamino)nicotinic acid (25 mg, 87%) as a white solid. MS (M+1): 419.1.

Step B: (+/−)-methyl 3-(6-(3-methy-1-(4-(4-(trifluoromethyl)-1H-pyrazol-1-yl)phenyl)butylamino)nicotinamido)propanoate

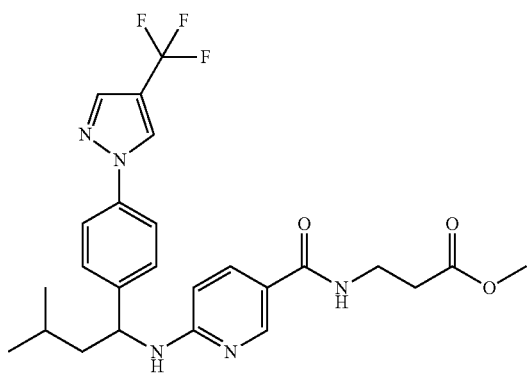 [SMILES: COC(=O)CCNC(=O)c1ccc(NC(CC(C)C)c2ccc(-n3cc(C(F)(F)F)cn3)cc2)nc1]

To a solution of (+/−)-6-(3-methyl-1-(4-(4-(trifluoromethyl)-1H-pyrazol-1-yl)phenyl)butylamino)nicotinic acid (50 mg, 0.12 mmol) in N,N-dimethylformamide (5 mL) was added O-(7-Azabenzotriazol-1-yl)-N,N,N',N'-tetramethyluronium hexafluorophosphate (67.7 mg, 0.178 mmol). The mixture was stirred for 45 minutes. Methyl 3-aminopropionate hydrochloride (24.6 mg, 0.178 mmol) and diisopropylethylamine (61.5 mg, 0.476 mmol) were added. The resulting mixture was stirred at room temperature for 2 hours. The mixture was diluted with saturated ammonium chloride. The solution was extracted three times with ethyl acetate. The combined organics were washed with water, dried over sodium sulfate, filtered and concentrated to give methyl-6-(3-methyl-1-(4-(4-(trifluoromethyl)-1H-pyrazol-1-yl)phenyl)butylamino)nicotinamido)propenoate (50 mg, 83%) as a brown oil. MS (M+1): 504.1.

Step C: (+/−)-3-(6-(3-methyl-1-(4-(4-(trifluoromethyl)-1H-pyrazol-1-yl)phenyl)butylamino)nicotinamido)propanoic acid Methyl 3-(6-(3-methyl-1-(4-(4-(trifluoromethyl)-1H-pyrazol-1-yl)phenyl)butylamino)nicotinamido)propanoate (50 mg, 0.099 mmol) was dissolved in water (5 mL) and tetrahydrofuran (5 mL). Lithium hydroxide (0.387 mL, 2N in water, 0.774 mmol) was added. The mixture was stirred at room temperature for 2 hours. The mixture was neutralized with 1N aqueous hydrochloric acid and extracted with ethyl acetate. The organic layer was dried over sodium sulfate, filtered and concentrated. Purification by HPLC (column: Boston Analytics Symmetrix ODS-H 150×30 mm, 5 μm; modifier: formic acid 0.225%; gradient 10 to 80% acetonitrile in water) gave (+/−)-3-(6-(3-methyl-1-(4-(4-(trifluoromethyl)-1H-pyrazol-1-yl)phenyl)butylamino)nicotinamido) propanoic acid (25 mg, 52%). $^1$H NMR (400 MHz, CD$_3$OD, δ): 8.70 (s, 1H), 8.40 (s, 1H), 7.97 (s, 1H), 7.82 (d, 1H), 7.74 (d, 2H), 7.53 (d, 2H), 6.59 (d, 1H), 5.12-5.02 (m, 1H), 3.57 (m, 2H), 2.59 (m, 2H), 1.89-1.69 (m, 2H), 1.68-1.58 (m, 1H), 1.02 (d, 3H), 0.98 (d, 3H). MS (M+1): 490.5.

Example 65

(+/−)-3-(4-(2-cyclopropyl-1-(4-(4-(trifluoromethyl)-1H-pyrazol-1-yl)phenoxy)ethyl)benzamido)propanoic acid

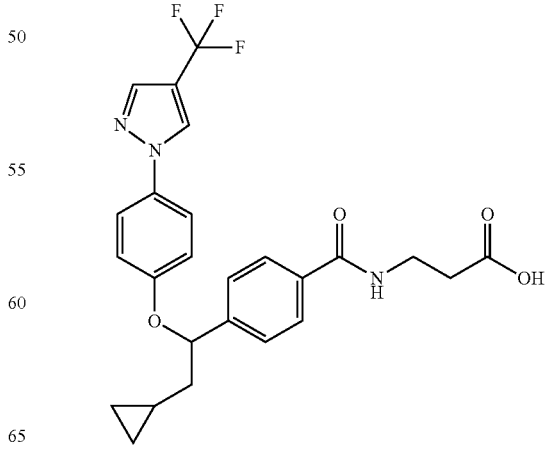

Step A: (+/−)-methyl 4-(2-cyclopropyl-1-(4-(4-(trifluoromethyl)-1H-pyrazol-1-yl)phenoxy)ethyl)benzoate

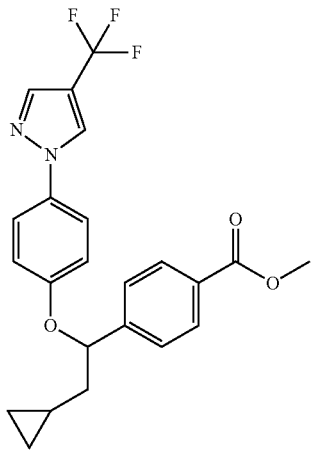 [SMILES: COC(=O)c1ccc(C(CC2CC2)Oc2ccc(-n3cc(C(F)(F)F)cn3)cc2)cc1]

To a solution of Intermediate (16) (50.0 mg, 0.227 mmol), Intermediate (29) (62.2 mg, 0.272 mmol) and triphenylphosphine (120 mg, 0.454 mmol) in tetrahydrofuran (0.5 mL) was added diethylazodicarboxylate (79.1 mg, 0.454 mmol). The resulting mixture was stirred at room temperature overnight. The reaction mixture was partitioned between water and ethyl acetate. The aqueous layer was extracted with ethyl acetate. The combined organic layers were dried over sodium sulfate, filtered, and concentrated. Purification by column chromatography gave (+/−)-methyl 4-(2-cyclopropyl-1-(4-(4-(trifluoromethyl)-1H-pyrazol-1-yl)phenoxy)ethyl)benzoate (32 mg, 33%). ¹HNMR (400 MHz, CDCl₃, δ): 7.95-7.93 (m, 3H), 7.79 (s, 1H), 7.45-7.33 (m, 4H), 6.84 (d, 2H), 5.19 (m, 1H), 3.83 (s, 3H), 1.99-1.94 (m, 1H), 1.64-1.55 (m, 1H), 0.79-0.69 (m, 1H), 0.46-0.42 (m, 2H), 0.10-0.10 (m, 2H).

Step B: (+/−)-methyl 3-(4-(2-cyclopropyl-1-(4-(4-(trifluoromethyl)-1H-pyrazol-1-yl)phenoxy)ethyl)benzamido)propanoate

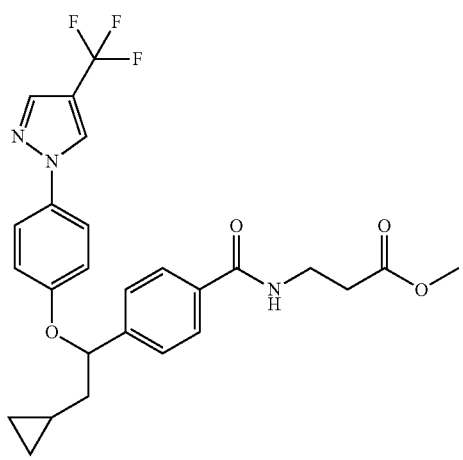 [SMILES: COC(=O)CCNC(=O)c1ccc(C(CC2CC2)Oc2ccc(-n3cc(C(F)(F)F)cn3)cc2)cc1]

To a mixture of (+/−)-methyl 4-(2-cyclopropyl-1-(4-(4-(trifluoromethyl)-1H-pyrazol-1-yl)phenoxy)ethyl)benzoate (104 mg, 0.242 mmol) in methanol (1.2 mL) and water (0.2 L) was added lithium hydroxide monohydrate (50.08 mg, 1.21 mmol) at room temperature. The resulting mixture was stirred overnight. The reaction mixture was poured into water and acidified to pH=6 with 1N hydrochloric acid. The solution was extracted with dichloromethane. The organic layer was dried over sodium sulfate, filtered, and concentrated. The residue was dissolved in N,N-dimethylformamide (0.84 mL) and O-(7-Azabenzotriazol-1-yl)-N,N,N',N'-tetramethyluronium hexafluorophosphate (95.8 mg, 0.252 mmol) was added, followed by N-methylmorpholine (50.9 mg, 0.504 mmol). The reaction mixture was stirred for 30 minutes at room temperature. Methyl 3-aminopropionate (23.4 mg, 0.168 mmol) was then added and the reaction was stirred for 48 hours. The reaction mixture was partitioned between brine and ethyl acetate. The aqueous layer was extracted with ethyl acetate. The combined extracts were dried over sodium sulfate, filtered and concentrated. Purification by column chromatography gave (+/−)-methyl 3-(4-(2-cyclopropyl-1-(4-(4-(trifluoromethyl)-1H-pyrazol-1-yl)phenoxy)ethyl)benzamido)propanoate (92 mg, 76%). MS (M+Na): 524.1.

Step C: (+/−)-3-(4-(2-cyclopropyl-1-(4-(4-(trifluoromethyl)-1H-pyrazol-1-yl)phenoxy)ethyl)benzamido)propanoic acid To a mixture of methyl 3-(4-(2-cyclopropyl-1-(4-(4-(trifluoromethyl)-1H-pyrazol-1-yl)phenoxy)ethyl)benzamido)propanoate (92 mg, 0.18 mmol) in methanol (0.9 mL) and water (0.2 mL) was added lithium hydroxide monohydrate (38.4 mg, 0.92 mmol). The resulting mixture was stirred at room temperature overnight. The reaction mixture was poured into water and acidified with 1N hydrochloric acid to pH=6. The mixture was extracted with dichloromethane. The organic layer was dried over sodium sulfate, filtered, and concentrated. Purification by column chromatography gave (+/−)-3-(4-(2-cyclopropyl-1-(4-(4-(trifluoromethyl)-1H-pyrazol-1-yl)phenoxy)ethyl)benzamido)propanoic acid (52 mg, 59%). ¹HNMR (400 MHz, CD₃OD, δ): 8.47 (s, 1H), 7.82 (s, 1H), 7.70 (d, 2H), 7.50 (d, 2H), 7.42 (d, 2H), 6.92 (d, 2H), 5.34 (m, 1H), 3.53 (m, 2H), 2.48 (m, 2H), 1.98-1.94 (m, 1H), 1.60-1.58 (m, 1H), 0.75-0.77 (m, 1H), 0.42-0.33 (m, 2H), 0.08-0.01 (m, 2H). MS (M+Na): 510.3.

Example 66

(+/−)-3-(4-(cyclopentyl(4-(4-(trifluoromethyl)-1H-pyrazol-1-yl)phenoxy)methyl)benzamido)propanoic acid

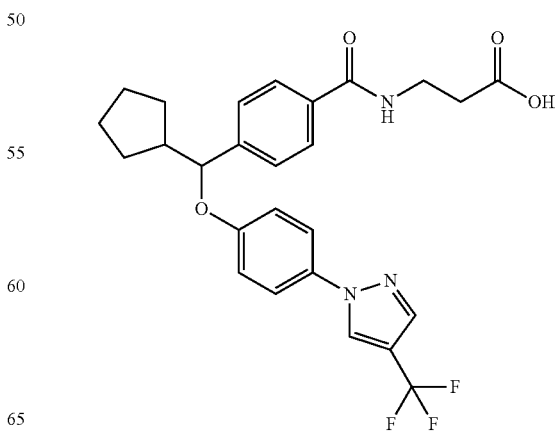

The title compound was prepared by a method analogous to that described for Example 65 using Intermediate (37). ¹H NMR (400 MHz, CD₃OD, δ): 8.55 (s, 1H), 7.92 (s, 1H), 7.78 (d, 2H), 7.57 (d, 2H), 7.51 (d, 2H), 6.99 (d, 2H), 5.15 (d, 1H), 3.64-3.60 (m, 2H), 2.65-2.61 (m, 2H), 2.50-2.41 (m, 1H), 1.97-1.90 (m, 1H), 1.80-1.38 (m, 7H). MS (M+1): 502.3.

Example 67

3-(4-(cyclopentyl(4-(4-(trifluoromethyl)-1H-pyrazol-1-yl)phenoxy)methyl)benzamido)propanoic acid, Isomer 1

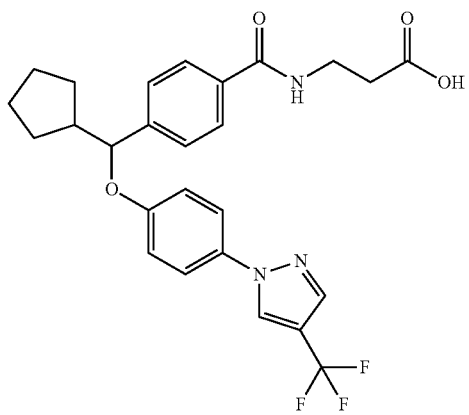 [SMILES: O=C(O)CCNC(=O)c1ccc(C(Oc2ccc(-n3cc(C(F)(F)F)cn3)cc2)C2CCCC2)cc1]

The title compound is obtained by resolving racemic 3-(4-(cyclopentyl(4-(4-(trifluoromethyl)-1H-pyrazol-1-yl)phenoxy)methyl)benzamido)propanoic acid Example 66, by chiral SFC. Column: Chiralpak AD-H. Dimensions: 10×250 mm. Mobile Phase: 70/30 CO₂/2-propanol. Flow Rate: 10.0 mL/min. Modifier: none. Retention time: 4.24 minutes.

Example 68

3-(4-(cyclopentyl(4-(4-(trifluoromethyl)-1H-pyrazol-1-yl)phenoxy)methyl)benzamido)propanoic acid, Isomer 2

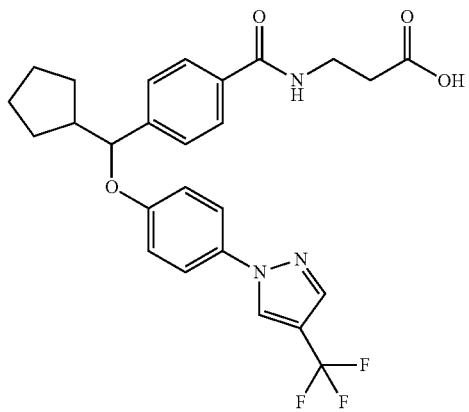 [SMILES: O=C(O)CCNC(=O)c1ccc(C(Oc2ccc(-n3cc(C(F)(F)F)cn3)cc2)C2CCCC2)cc1]

The title compound is obtained by resolving racemic 3-(4-(cyclopentyl(4-(4-(trifluoromethyl)-1H-pyrazol-1-yl)phe-noxy)methyl)benzamido)propanoic acid Example 66, by chiral SFC. Column: Chiralpak AD-H. Dimensions: 10×250 mm. Mobile Phase: 70/30 CO₂/2-propanol. Flow Rate: 10.0 mL/min. Modifier: none. Retention time: 6.00 minutes.

Example 69

(+/−)-3-(4-(cyclobutyl(4-(4-(trifluoromethyl)-1H-pyrazol-1-yl)phenoxy)methyl)benzamido)propanoic acid

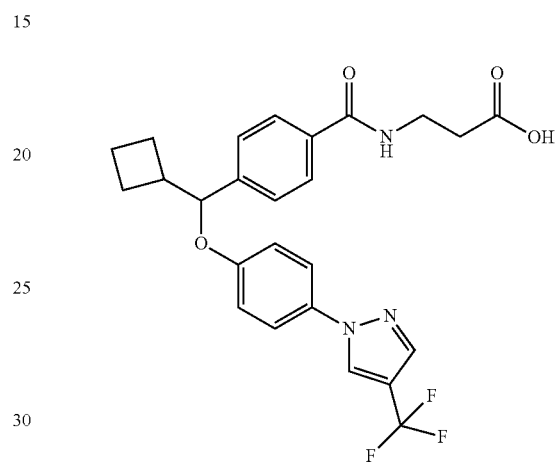

The title compound was prepared by a method analogous to that described for Example 65 using Intermediate (45). ¹H NMR (400 MHz, CD₃OD, δ): 8.56 (s, 1H), 7.92 (s, 1H), 7.77 (d, 2H), 7.58 (d, 2H), 7.48 (d, 2H), 7.01 (d, 2H), 5.27-5.25 (m, 1H), 3.63-3.60 (m, 2H), 2.88-2.78 (m, 1H), 2.65-2.59 (m, 2H), 2.21-2.00 (m, 3H), 2.00-1.70 (m, 3H). MS (M+1): 488.5.

Example 70

(+/−)-3-(4-(1-(4-(3-(trifluoromethyl)-1H-pyrazol-1-yl)phenoxy)butyl)benzamido)propanoic acid

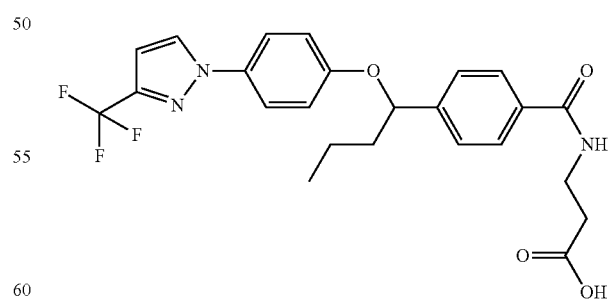

The title compound was prepared by a method analogous to that described for Example 19 using 3-(trifluoromethyl)-1H-pyrazole. Analytical LCMS: retention time 3.48 minutes (Waters Atlantis dC18 4.6×50 mm, 5 μm column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 475.98.

Example 71

(+/−)-3-(4-(3,3-dimethyl-1-(4-(4-(trifluoromethyl)-1H-pyrazol-1-yl)phenoxy)butyl)benzamido)propanoic acid

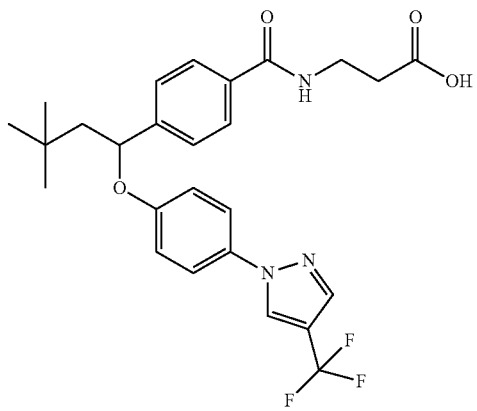 [SMILES: CC(C)(C)CC(Oc1ccc(-n2cc(C(F)(F)F)cn2)cc1)c1ccc(C(=O)NCCC(=O)O)cc1]

The title compound was prepared by a method analogous to that described for Example 65 using Intermediate (42). $^1$H NMR (400 MHz, CD$_3$OD, δ): 8.57 (s, 1H), 7.93 (s, 1H), 7.79 (d, 2H), 7.60 (d, 2H), 7.49 (d, 2H), 6.99 (d, 2H), 5.47-5.45 (m, 1H), 3.64-3.60 (m, 2H), 2.65-2.61 (m, 2H), 2.12-2.05 (m, 1H), 1.66-1.63 (m, 1H), 1.08 (s, 9H). MS (M+1): 504.4.

Example 72

(+/−)-3-(4-(1-(4-(4-methyl-3-(trifluoromethyl)-1H-pyrazol-1-yl)phenoxy)butyl)benzamido)propanoic acid

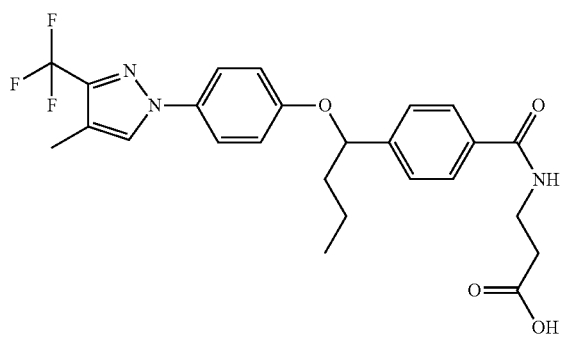 [SMILES: CCCC(Oc1ccc(-n2cc(C)c(C(F)(F)F)n2)cc1)c1ccc(C(=O)NCCC(=O)O)cc1]

The title compound was prepared by a method analogous to that described for Example 19 using 4-methyl-3-(trifluoromethyl)-1H-pyrazole. Analytical LCMS: retention time 3.63 minutes (Waters Atlantis dC$_{18}$ 4.6×50 mm, 5 μm column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 489.98.

Example 73

(+/−)-3-(4-(1-(4-(3-(trifluoromethyl)-1H-1,2,4-triazol-1-yl)phenoxy)butyl)benzamido)propanoic acid

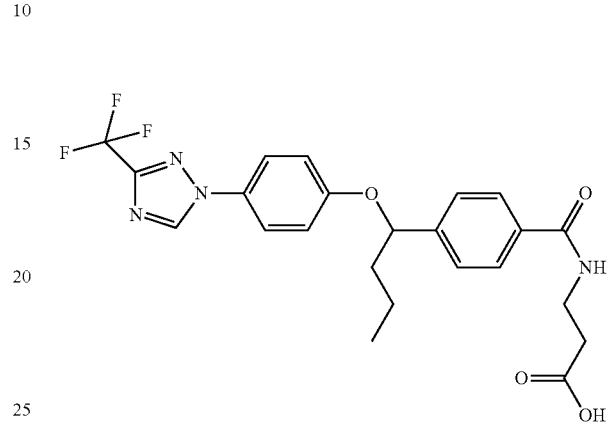

The title compound was prepared by a method analogous to that described for Example 19 using 3-(trifluoromethyl)-1H-1,2,4-triazole. $^1$H NMR (400 MHz, CD$_3$OD, δ): 8.99 (s, 1H), 7.76 (d, J=8.2 Hz, 2H), 7.57-7.63 (m, 2H), 7.46 (d, J=8.4 Hz, 2H), 6.99-7.05 (m, 2H), 5.35 (dd, J=7.8, 5.1 Hz, 1H), 3.55-3.62 (m, 2H), 2.59 (t, J=6.9 Hz, 2H), 1.94-2.05 (m, 1H), 1.76-1.87 (m, 1H), 1.36-1.61 (m, 2H), 0.96 (t, 3H). MS (M+1): 477.1.

Example 74

(+/−)-3-(4-(1-(4-(3-methyl-4-(trifluoromethyl)-1H-pyrazol-1-yl)phenoxy)butyl)benzamido)propanoic acid

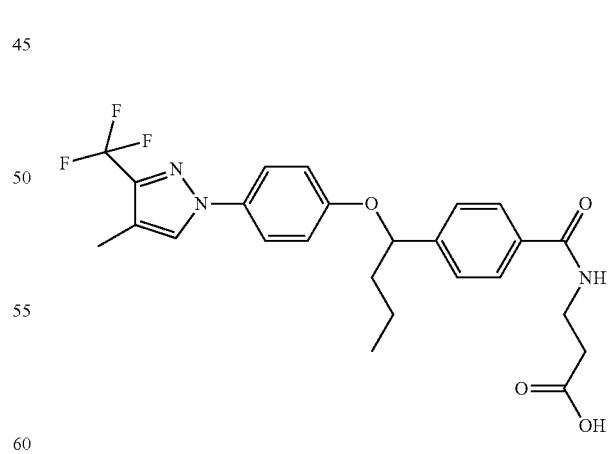

The title compound was prepared by a method analogous to that described for Example 19 using 3-methyl-4-(trifluoromethyl)-1H-pyrazole. Analytical LCMS: retention time 3.57 minutes (Waters Atlantis dC$_{18}$ 4.6×50 mm, 5 μm column; 95% water/acetonitrile linear gradient to 5% water/acetonitrile over 4.0 minutes, hold at 5% water/acetonitrile to 5.0

Example 75

(+/−)-3-(4-(1-(4-(2-methyl-4-(trifluoromethyl)-1H-imidazol-1-yl)phenoxy)butyl)benzamido)propanoic acid

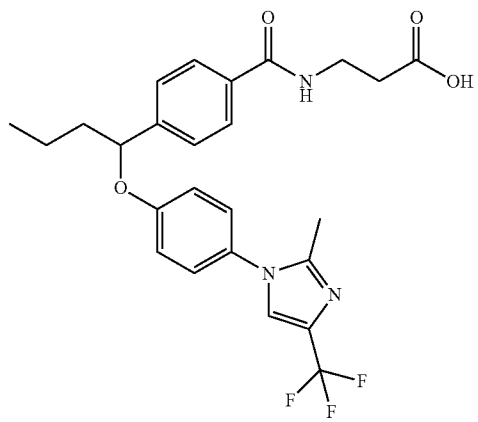 [SMILES: CCCC(Oc1ccc(-n2cc(C(F)(F)F)nc2C)cc1)c1ccc(C(=O)NCCC(=O)O)cc1]

The title compound was prepared by a method analogous to that described for Example 19 using 2-methyl-4-(trifluoromethyl)-1H-imidazole. $^1$H NMR (400 MHz, CDCl$_3$, δ): 7.75-7.70 (m, 2H), 7.40-7.35 (m, 2H), 7.23 (s, 1H), 7.11-7.05 (m, 2H), 6.93-6.85 (m, 3H), 5.16-5.11 (m, 1H), 3.73-3.67 (m, 2H), 2.71-2.65 (m, 2H), 2.31 (s, 3H), 2.03-1.94 (m, 1H), 1.84-1.74 (m, 1H), 1.58-1.48 (m, 1H), 1.47-1.37 (m, 1H), 0.98-0.92 (m, 3H). MS (M+1): 490.3.

Example 76

(+/−)-3-(4-(cyclopropyl(4-(4-(trifluoromethyl)-1H-pyrazol-1-yl)phenoxy)methyl)benzamido)propanoic acid

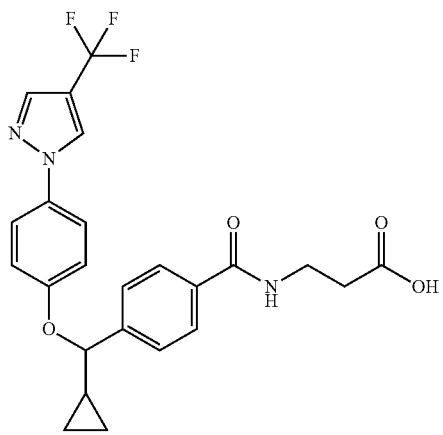 [SMILES: O=C(O)CCNC(=O)c1ccc(C(Oc2ccc(-n3cc(C(F)(F)F)cn3)cc2)C2CC2)cc1]

The title compound was prepared by a method analogous to that described for Example 65 using Intermediate (19). $^1$H NMR (400 MHz, CDCl$_3$, δ): 8.00 (s, 1H), 7.83 (s, 1H), 7.73 (m, 2H), 7.44-7.42 (m, 4H), 6.89-6.87 (m, 2H), 6.77-6.76 (m, 1H), 4.69-4.67 (m, 1H), 3.74-3.70 (m, 2H), 2.71-2.69 (m, 2H), 1.38-1.34 (m, 1H), 0.73-0.68 (m, 1H), 0.63-0.46 (m, 3H). MS (M+1): 474.4, MS (M+23): 496.3.

Example 77

(+/−)-3-(4-(2-methyl-1-(4-(4-(trifluoromethyl)-1H-pyrazol-1-yl)phenoxy)propyl)benzamido)propanoic acid

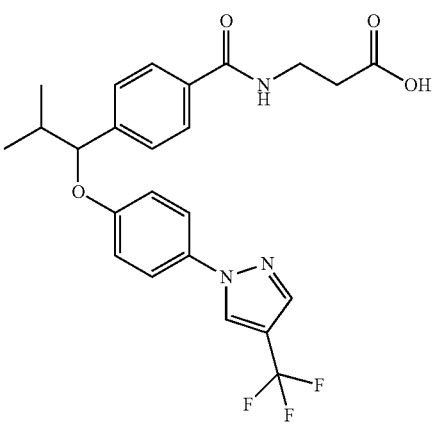 [SMILES: CC(C)C(Oc1ccc(-n2cc(C(F)(F)F)cn2)cc1)c1ccc(C(=O)NCCC(=O)O)cc1]

Step A: (+/−)-tert-butyl 3-(N-tert-butyl-4-(2-methyl-1-(4-(4-(trifluoromethyl)-1H-pyrazol-1-yl)phenoxy)propyl)benzamido)propanoate

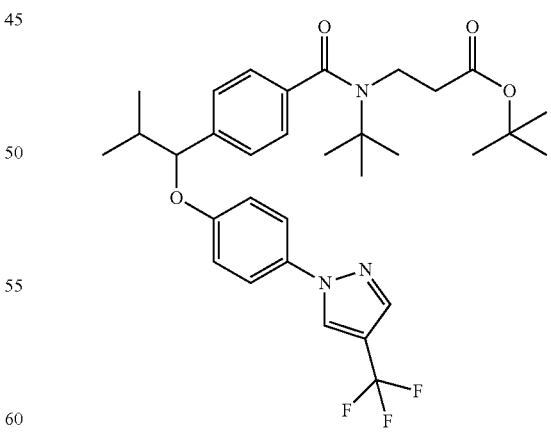

To a 0° C. solution of Intermediate (17) (120 mg, 0.32 mmol) and Intermediate (29) (103 mg, 0.48 mmol) in toluene (2 mL) was added tributylphosphine (129 mg, 0.64 mmol)

followed by 1,1'-(azodicarbonyl)dipiperidine (134 mg, 0.64 mmol). The reaction was warmed to ambient temperature and stirred overnight. Brine (20 mL) was added and the mixture was extracted twice with ethyl acetate. The combined organic layers were dried over magnesium sulfate, filtered and concentrated. Purification by column chromatography gave tert-butyl 3-(N-tert-butyl-4-(2-methyl-1-(4-(4-(trifluoromethyl)-1H-pyrazol-1-yl)phenoxy)propyl)benzamido)propanoate (60 mg, 32%). $^1$H NMR (400 MHz, CDCl$_3$, δ): 7.93 (s, 1H), 7.75 (s, 1H), 7.37-7.32 (m, 2H), 7.30-7.20 (m, 4H), 6.81-6.79 (m, 2H), 4.78 (d, 1H), 3.47-3.43 (m, 2H), 2.31-2.27 (m, 2H), 2.10-2.05 (m, 1H), 1.44 (s, 9H), 1.21 (s, 9H), 0.97 (d, 3H), 0.85 (d, 3H).

Step B: (+/−)-3-(4-(2-methyl-1-(4-(4-(trifluoromethyl)-1H-pyrazol-1-yl)phenoxy)propyl)benzamido)propanoic acid To a room temperature solution of tert-butyl 3-(N-tert-butyl-4-(2-methyl-1-(4-(4-(trifluoromethyl)-1H-pyrazol-1-yl)phenoxy)propyl)benzamido)propanoate (60 mg, 0.10 mmol) in dichloromethane (6 mL) was added trifluoroacetic acid (2.0 mL). The mixture was stirred at room temperature for 3 hours. The reaction mixture was concentrated and purification by HPLC gave (+/−)-3-(4-(2-methyl-1-(4-(4-(trifluoromethyl)-1H-pyrazol-1-yl)phenoxy)propyl)benzamido)propanoic acid (11.4 mg, 24%). $^1$H NMR (400 MHz, CD$_3$OD, δ): 8.53 (s, 1H), 7.89 (s, 1H), 7.76 (d, 2H), 7.55 (d, 2H), 7.45 (d, 2H), 6.97 (d, 2H), 5.06 (d, 1H), 3.61-3.58 (m, 2H), 2.62-2.59 (m, 2H), 2.21-2.11 (m, 1H), 1.08 (d, 3H), 0.93 (d, 3H). MS (M+1): 476.4.

Example 78

(+/−)-3-(4-(1-(4-(4-(trifluoromethyl)-1H-pyrazol-1-yl)phenoxy)propyl)benzamido)propanoic acid

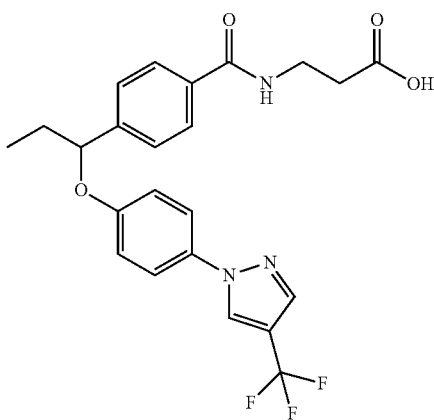 [SMILES: CCC(Oc1ccc(-n2cc(C(F)(F)F)cn2)cc1)c1ccc(C(=O)NCCC(=O)O)cc1]

The title compound was prepared by a method analogous to that described for Example 77 using Intermediate (46). $^1$H NMR (400 MHz, (CD$_3$)$_2$SO, δ): 8.97 (s, 1H), 8.49-8.47 (m, 1H), 8.11 (s, 1H), 7.80-7.78 (d, 2H), 7.69-7.65 (m, 2H), 7.49-7.47 (m, 2H), 7.05-7.01 (m, 2H), 5.40-5.37 (m, 1H), 3.51-3.40 (m, 2H), 2.50-2.46 (m, 2H), 2.00-1.81 (m, 2H), 0.96-0.92 (m, 3H). MS (M+1): 462.5.

Example 79

(+/−)-3-(4-(3-methyl-1-(4-(4-(trifluoromethyl)-1H-imidazol-1-yl)phenyl)butoxy)benzamido)propanoic acid

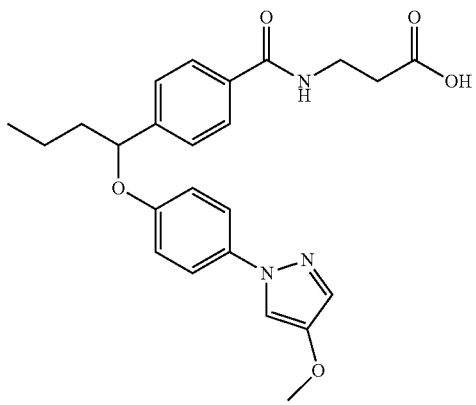 [SMILES: CCCC(Oc1ccc(-n2cc(OC)cn2)cc1)c1ccc(C(=O)NCCC(=O)O)cc1]

The title compound was prepared by a method analogous to that described for Example 19 using Intermediate (41). $^1$H NMR (400 MHz, CD$_3$OD, δ): 7.78-7.77 (m, 3H), 7.50-7.44 (m, 4H), 7.39 (s, 1H), 6.96-6.92 (m, 2H), 5.33-5.31 (m, 1H), 3.75 (s, 3H), 3.67-3.59 (m, 2H), 2.64-2.60 (m, 2H), 2.05-1.95 (m, 1H), 1.87-1.61 (m, 1H), 1.61-1.41 (m, 2H), 0.98-0.94 (m, 3H). MS (M+1): 438.1.

Example 80

(+/−)-3-(4-(3-methyl-1-(4-(4-(trifluoromethyl)-1H-pyrazol-1-yl)phenoxy)butyl)benzamido)propanoic acid

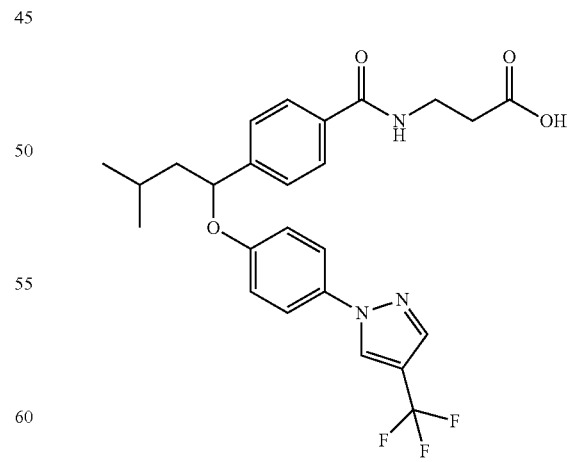

The title compound was prepared by a method analogous to that described for Example 77 using Intermediate (15). $^1$H NMR (400 MHz, CD$_3$OD, δ): 8.52 (s, 1H), 7.89 (s, 1H), 7.76 (d, 2H), 7.57 (d, 2H), 7.47 (d, 2H), 6.97 (d, 2H), 5.39-5.36 (m, 1H), 3.61-3.57 (m, 2H), 2.62-2.58 (m, 2H), 2.00-1.92 (m, 1H), 1.89-1.82 (m, 1H), 1.63-1.57 (m, 1H), 1.02-0.97 (m, 6H). MS (M+1): 490.5.

Example 81

3-(4-(3-methyl-1-(4-(4-(trifluoromethyl)-1H-pyrazol-1-yl)phenoxy)butyl)benzamido)propanoic acid, Isomer 2

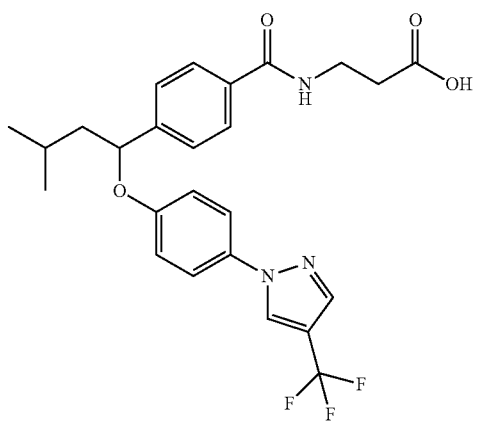 [SMILES: CC(C)CC(Oc1ccc(-n2cc(C(F)(F)F)cn2)cc1)c1ccc(C(=O)NCCC(=O)O)cc1]

The title compound is obtained by resolving racemic 3-(4-(3-methyl-1-(4-(4-(trifluoromethyl)-1H-pyrazol-1-yl)phenoxy)butyl)benzamido)propanoic acid, the compound of Example 80, by chiral SFC. Column: Chiralpak AD-H. Dimensions: 10×250 mm. Mobile Phase: 70/30 CO$_2$/2-propanol. Flow Rate: 10.0 mL/min. Modifier: none. Retention time: 3.39 minutes (second peak eluted).

Example 82

(+/−)-3-(4-(1-(3,5-dimethyl-4-(4-(trifluoromethyl)-1H-pyrazol-1-yl)phenoxy)butyl)benzamido)propanoic acid

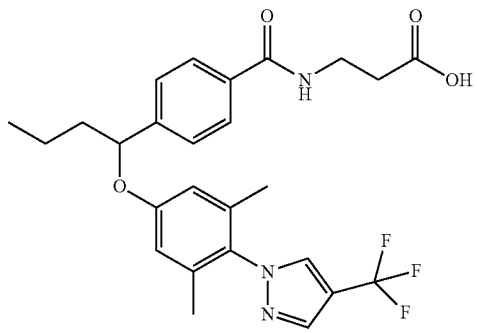 [SMILES: CCCC(Oc1cc(C)c(-n2cc(C(F)(F)F)cn2)c(C)c1)c1ccc(C(=O)NCCC(=O)O)cc1]

Step A: (+/−)-ethyl 4-(1-(3,5-dimethyl-4-(4-(trifluoromethyl)-1H-pyrazol-1-yl)phenoxy)butyl benzoate

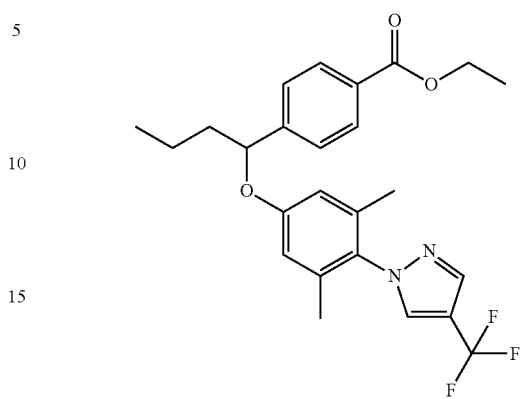

Diisopropyl azodicarboxylate (0.14 mL, 0.67 mmol) was added dropwise to a solution of Intermediate (26) (119.9 mg, 0.47 mmol), ethyl 4-(1-hydroxybutyl)benzoate (98.0 mg, 0.44 mmol), and triphenylphosphine (178 mg, 0.67 mmol) in tetrahydrofuran (4.4 mL). After 18 hours, the reaction was concentrated and purification by column chromatography (0-40% ethyl acetate in heptanes) gave (+/−)-ethyl 4-(1-(3,5-dimethyl-4-(4-(trifluoromethyl)-1H-pyrazol-1-yl)phenoxy)butyl)benzoate (140 mg, 69%) as an oil. $^1$H NMR (400 MHz, CDCl$_3$, δ): 8.02 (d, J=8.8 Hz, 2H), 7.88 (s, 1H), 7.65 (s, 1H), 7.40 (d, J=8.2 Hz, 2H), 6.57 (s, 2H), 5.16 (dd, J=7.9, 5.0 Hz, 1H), 4.37 (q, J=7.0 Hz, 2H), 2.06-1.91 (m, 1H), 1.88 (s, 6H), 1.86-1.74 (m, 1H), 1.54-1.41 (m, 2H), 1.38 (t, J=7.1 Hz, 3H), 0.96 (t, J=7.3 Hz, 3H). MS (M+1): 461.

Step B: (+/−)-4-(1-(3,5-dimethyl-4-(trifluoromethyl)-1H-pyrazol-1-yl)phenoxy)butyl)benzoic acid

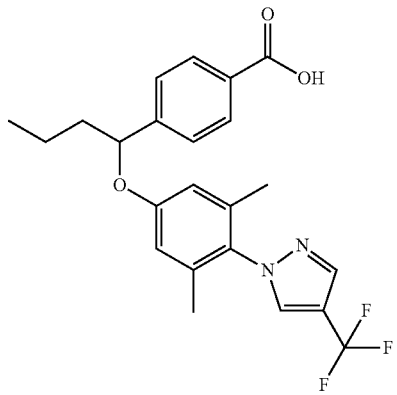 [SMILES: CCCC(Oc1cc(C)c(-n2cc(C(F)(F)F)cn2)c(C)c1)c1ccc(C(=O)O)cc1]

To a vial containing ethyl 4-(1-(3,5-dimethyl-4-(4-(trifluoromethyl)-1H-pyrazol-1-yl)phenoxy)butyl)benzoate (135 mg, 0.29 mmol) was added water (0.59 mL), tetrahydrofuran (0.591 mL), and methanol (0.59 mL). Lithium hydroxide monohydrate (615.0 mg, 14.6 mmol) was then added. The suspension was stirred at room temperature for 18 hours. The reaction was concentrated in vacuo. The residue was acidified to pH=3 with citric acid (5%). The mixture was extracted three times with ethyl acetate. The organics were dried over sodium sulfate, filtered and concentrated to give (+/−)-4-(1-(3,5-dimethyl-4-(4-(trifluoromethyl)-1H-pyrazol-1-yl)phenoxy)butyl)benzoic acid (120 mg, 95%) as a white solid. $^1$H NMR (400 MHz, CDCl₃, δ): 8.07 (d, J=8.4 Hz, 2H), 7.88 (s, 1H), 7.65 (s, 1H), 7.45 (d, J=8.2 Hz, 2H), 6.58 (s, 2H), 5.18 (dd, J=8.0, 4.9 Hz, 1H), 2.04-1.92 (m, 1H), 1.89 (s, 6H), 1.87-1.75 (m, 1H), 1.61-1.36 (m, 2H), 0.97 (t, J=7.4 Hz, 3H). MS (M+1): 433.

Step C: (+/−)-ethyl 3-(4-(1-(3,5-dimethyl-4-(4-(trifluoromethyl)-1H-pyrazol-1-yl)phenoxy)butyl)benzamido)propanoic

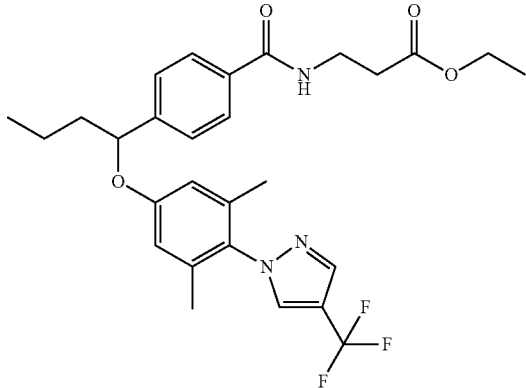 [SMILES: CCCC(Oc1cc(C)c(-n2cc(C(F)(F)F)cn2)c(C)c1)c1ccc(C(=O)NCCC(=O)OCC)cc1]

N,N-dimethylformamide (1.88 mL) was added to a vial containing 4-(1-(3,5-dimethyl-4-(4-(trifluoromethyl)-1H-pyrazol-1-yl)phenoxy)butyl)benzoic acid (122.0 mg, 0.28 mmol), ethyl 3-aminopropanoate hydrochloride (86.6 mg, 0.56 mmol) and O-(7-azabenzotriazol-1-yl)-N,N,N',N'-tetramethyluronium hexafluorophosphate (214.0 mg, 0.56 mmol). Diisopropylethylamine (0.25 mL, 1.41 mmol) was then added. After stirring for 4 hours, the reaction was diluted with saturated ammonium chloride and extracted three times with diethyl ether. The combined organics were dried over sodium sulfate, filtered and concentrated. Purification by column chromatography (0-25% ethyl acetate in heptane) afforded (+/−)-ethyl 3-(4-(1-(3,5-dimethyl-4-(4-(trifluoromethyl)-1H-pyrazol-1-yl)phenoxy)butyl)benzamido) propanoate (117 mg, 78% yield). ¹H NMR (400 MHz, CDCl₃, δ): 7.87 (s, 1H), 7.73 (d, J=8.0 Hz, 2H), 7.65 (s, 1H), 7.39 (d, J=8.2 Hz, 2H), 6.84 (d, J=5.9 Hz, 1H), 6.57 (s, 2H), 5.15 (dd, J=7.8, 5.1 Hz, 1H), 4.17 (q, J=7.1 Hz, 2H), 3.71 (q, J=6.0 Hz, 2H), 2.63 (t, J=5.7 Hz, 2H), 2.04-1.91 (m, 1H), 1.88 (s, 6H), 1.86-1.71 (m, 1H), 1.58-1.33 (m, 2H), 1.26 (t, J=7.0 Hz, 3H), 0.96 (t, J=7.4 Hz, 3H). MS (M+1): 532.

Step D: (+/−)-3-(4-(1-(3,5-dimethyl-4-(4-(trifluoromethyl)-1H-pyrazol-1-yl)phenoxy)butyl)benzamido)propanoic acid To a flask containing ethyl 3-(4-(1-(3,5-dimethyl-4-(4-(trifluoromethyl)-1H-pyrazol-1-yl)phenoxy)butyl)benzamido) propanoate (117 mg, 0.22 mmol) was added water (0.55 mL), tetrahydrofuran (0.55 mL), and methanol (0.55 mL). Lithium hydroxide monohydrate (508 mg, 12.1 mmol) was then added. The suspension was stirred at room temperature for 18 hours. The reaction was concentrated and acidified to pH=3 with citric acid (10%). A white precipitate formed. The solid was filtered, rinsed with water, and dried under vacuum to give (+/−)-3-(4-(1-(3,5-dimethyl-4-(4-(trifluoromethyl)-1H-pyrazol-1-yl)phenoxy)butyl)benzamido)propanoic acid (90 mg, 81%) as a white solid. ¹H NMR (400 MHz, CDCl₃, δ): 7.88 (s, 1H), 7.73 (d, J=8.2 Hz, 2H), 7.65 (s, 1H), 7.39 (d, J=8.4 Hz, 2H), 6.80 (t, J=5.9 Hz, 1H), 6.56 (s, 2H), 5.16 (dd, J=7.8, 5.1 Hz, 1H), 3.71 (q, J=5.9 Hz, 2H), 2.69 (t, J=5.8 Hz, 2H), 2.04-1.91 (m, 1H), 1.88 (s, 6H), 1.86-1.67 (m, 1H), 1.63-1.31 (m, 2H), 0.96 (t, J=7.3 Hz, 3H). MS (M+1): 504.

Example 83

(S)-3-(4-(1-(3,5-dimethyl-4-(4-(trifluoromethyl)-1H-pyrazol-1-yl)phenoxy)butyl)benzamido)propanoic acid

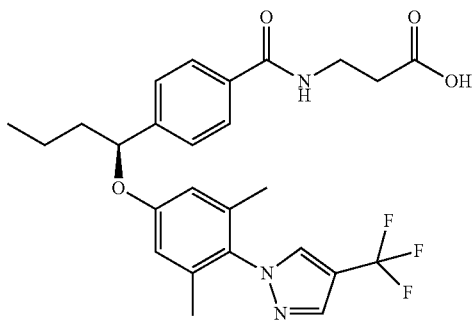 [SMILES: CCC[C@H](Oc1cc(C)c(-n2cc(C(F)(F)F)cn2)c(C)c1)c1ccc(C(=O)NCCC(=O)O)cc1]

The title compound is obtained by resolving racemic 3-(4-(1-(3,5-dimethyl-4-(4-(trifluoromethyl)-1H-pyrazol-1-yl)phenoxy)butyl)benzamido)propenoic acid, the compound of Example 82, by chiral SFC. Column: Chiralpak AD-H. Dimensions: 10×250 mm. Mobile Phase: 80/20 CO₂/2-propanol. Flow Rate: 10.0 mL/min. Modifier: 0.2% isopropylamine. Retention time: 3.23 minutes.

Alternatively (S)-3-(4-(1-(3,5-dimethyl-4-(4-(trifluoromethyl)-1H-pyrazol-1-yl)phenoxy)butyl)benzamido)propanoic acid, the compound of Example 83 can be prepared by chiral synthesis as follows.

Step A: (S)-ethyl 4-(1-(3,5-dimethyl-4-(4-(trifluoromethyl)-1H-pyrazol-1-yl)phenoxyl)butyl)benzoate

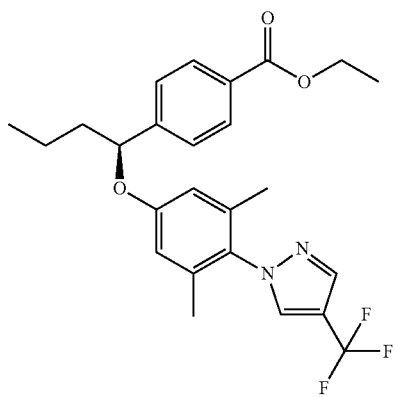 [SMILES: CCC[C@H](Oc1cc(C)c(-n2cc(C(F)(F)F)cn2)c(C)c1)c1ccc(C(=O)OCC)cc1]

To a solution of Intermediate (56) (4.51 g, 20.3 mmol) and Intermediate (26) (5.2 g, 20.0 mmol) in tetrahydrofuran (100 mL) was added diisopropyl azodicarboxylate (13.1 mL, 30.4 mmol). Tributylphosphine (7.86 mL, 31.5 mmol) was added dropwise at room temperature, maintaining the internal temperature below 30° C. The mixture was stirred at room temperature for 2 hours. The reaction was then concentrated. The resulting solid was diluted with dichloromethane and hydrochloric acid (1N). The mixture was extracted twice with dichloromethane. The combined organic layers were dried over sodium sulfate, filtered, and concentrated.

Purification by column chromatography (0-8% ethyl acetate in heptanes) afforded (S)-ethyl 4-(1-(3,5-dimethyl-4-(4-(trifluoromethyl)-1H-pyrazol-1-yl)phenoxy)butyl) benzoate (6.9 g, 74%) as an oil: $^{1}$H NMR (400 MHz, CDCl$_{3}$, δ): 8.02 (d, J=8.8 Hz, 2H), 7.88 (s, 1H), 7.65 (s, 1H), 7.40 (d, J=8.2 Hz, 2H), 6.57 (s, 2H), 5.16 (dd, J=7.9, 5.0 Hz, 1H), 4.37 (q, J=7.0 Hz, 2H), 2.06-1.91 (m, 1H), 1.88 (s, 6H), 1.86-1.74 (m, 1H), 1.54-1.41 (m, 2H), 1.38 (t, J=7.1 Hz, 3H), 0.96 (t, J=7.3 Hz, 3H). MS (M+1): 461.

Step B: (S)-4-(1-(3,5-dimethyl-4-(4-(trifluoromethyl)-1H-pyrazol-1-yl)phenoxy)butyl)benzoic acid

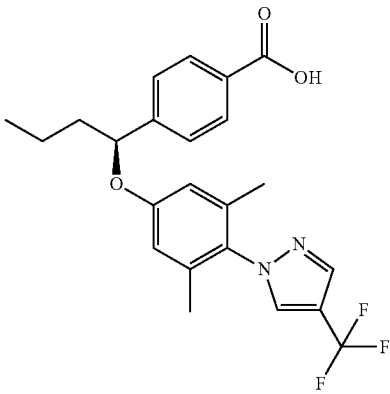 [SMILES: CCC[C@H](Oc1cc(C)c(-n2cc(C(F)(F)F)cn2)c(C)c1)c1ccc(C(=O)O)cc1]

To a flask containing (S)-ethyl 4-(1-(3,5-dimethyl-4-(4-(trifluoromethyl)-1H-pyrazol-1-yl)phenoxy)butyl)benzoate (11.8 g, 25.6 mmol) was added water (32.0 mL), tetrahydrofuran (32.0 mL), and methanol (32.0 mL). Lithium hydroxide monohydrate (2.15 g, 51.2 mmol) was then added. The suspension was stirred at room temperature. After 1.5 h, another (1.07 g, 25.6 mmol) of lithium hydroxide monohydrate was added. After 2 h, the reaction was concentrated. The crude residue was dissolved in water and the solution was acidified to pH=3 with 1N hydrochloric acid. A white precipitate formed. The solid was filtered, rinsed with water, and dried under vacuum to give (S)-4-(1-(3,5-dimethyl-(4-(trifluoromethyl)-1H-pyrazol-1-yl)phenoxy)butyl)benzoic acid (11.1 g, 100%) as a white gum. $^{1}$H NMR (400 MHz, CDCl$_{3}$, δ): 8.07 (d, J=8.4 Hz, 2H), 7.88 (s, 1H), 7.65 (s, 1H), 7.45 (d, J=8.2 Hz, 2H), 6.58 (s, 2H), 5.18 (dd, J=8.0, 4.9 Hz, 1H), 2.04-1.92 (m, 1H), 1.89 (s, 6H), 1.87-1.75 (m, 1H), 1.61-1.36 (m, 2H), 0.97 (t, J=7.4 Hz, 3H). MS (M+1): 433.

Step C: (S)-ethyl 3-(4-(1-(3,5-dimethyl-4-(4-(trifluoromethyl)-1H-pyrazol-1-yl)phenoxy)butyl)benzamido)propanoic

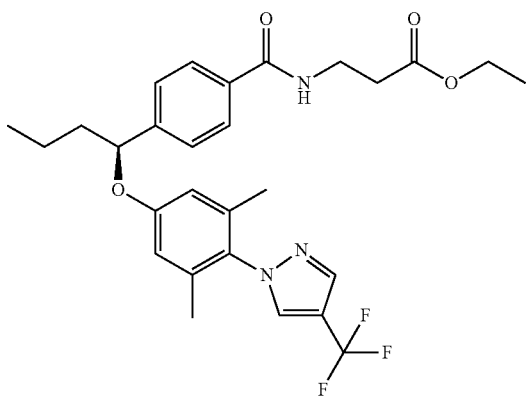 [SMILES: CCC[C@H](Oc1cc(C)c(-n2cc(C(F)(F)F)cn2)c(C)c1)c1ccc(C(=O)NCCC(=O)OCC)cc1]

N,N-dimethylformamide (17.6 mL) was added to a vial containing (S)-4-(1-(3,5-dimethyl-4-(4-(trifluoromethyl)-1H-pyrazol-1-yl)phenoxy)butyl)benzoic acid (6.1 g, 14.1 mmol), ethyl 3-aminopropanoate hydrochloride (4.33 g, 28.2 mmol) and O-(7-azabenzotriazol-1-yl-N,N,N',N'-tetramethyluronium hexafluorophosphate (10.7 g, 28.2 mmol). Diisopropylethylamine (12.3 mL, 70.5 mmol) was then added. The reaction was stirred for 1 h, and was then concentrated. Purification by column chromatography (0-30% ethyl acetate in heptane) afforded (S)-ethyl 3-(4-(1-(3,5-dimethyl-4-(4-(trifluoromethyl)-1H-pyrazol-1-yl)phenoxy)butyl)benzamido) propanoate (7.07 g, 94% yield) as a colorless gum. $^{1}$H NMR (400 MHz, CDCl$_{3}$, δ): 7.87 (s, 1H), 7.73 (d, J=8.0 Hz, 2H), 7.65 (s, 1H), 7.39 (d, J=8.2 Hz, 2H), 6.84 (d, J=5.9 Hz, 1H), 6.57 (s, 2H), 5.15 (dd, J=7.8, 5.1 Hz, 1H), 4.17 (q, J=7.1 Hz, 2H), 3.71 (q, J=6.0 Hz, 2H), 2.63 (t, J=5.7 Hz, 2H), 2.04-1.91 (m, 1H), 1.88 (s, 6H), 1.86-1.71 (m, 1H), 1.58-1.33 (m, 2H), 1.26 (t, J=7.0 Hz, 3H), 0.96 (t, J=7.4 Hz, 3H). MS (M+1): 532.

Step D: (S)-3-(4-(1-(3,5-dimethyl-4-(4-(trifluoromethyl)-1H-pyrazol-1-yl)phenoxy)butyl)benzamido) propanoic acid To a flask containing ethyl (S)-ethyl 3-(4-(1-(3,5-dimethyl-4-(4-(trifluoromethyl)-1H-pyrazol-1-yl)phenoxy)butyl)benzamido)propanoate (6.95 g, 13.1 mmol) was added water (33.0 mL), tetrahydrofuran (33.0 mL), and methanol (33.0 mL). Lithium hydroxide monohydrate (1.1 g, 26.1 mmol) was then added. The suspension was stirred at room temperature for 13 hours. The reaction was concentrated. The crude residue was dissolved in water, and the solution was acidified to pH=4 with 1N hydrochloric acid. A white precipitate formed. The solid was filtered, rinsed with water, and dried under vacuum to give (S)-3-(4-(1-(3,5-dimethyl-4-(4-(trifluoromethyl)-1H-pyrazol-1-yl)phenoxy)butyl)benzamido) propanoic acid (5.7 g, 87%) as a white solid. $^{1}$H NMR (400 MHz, CDCl$_{3}$, δ): 7.88 (s, 1H), 7.73 (d, J=8.2 Hz, 2H), 7.65 (s, 1H), 7.39 (d, J=8.4 Hz, 2H), 6.80 (t, J=5.9 Hz, 1H), 6.56 (s, 2H), 5.16 (dd, J=7.8, 5.1 Hz, 1H), 3.71 (q, J=5.9 Hz, 2H), 2.69 (t, J=5.8 Hz, 2H), 2.04-1.91 (m, 1H), 1.88 (s, 6H), 1.86-1.67 (m, 1H), 1.63-1.31 (m, 2H), 0.96 (t, J=7.3 Hz, 3H). MS (M+1): 504.

Another alternative synthesis of (S)-3-(4-(1-(3,5-dimethyl-4-(4-(trifluoromethyl)-pyrazol-1-yl)phenoxy)butyl) benzamido)propanoic acid, the compound of Example 83 is provided by chiral synthesis as follows.

Step A: (R)-4-(1-hydroxybutyl)benzoic acid

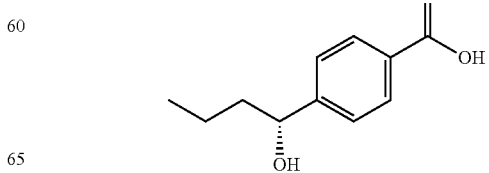

To a solution of Intermediate (56) (3.25 g, 14.6 mmol), was added water (25.0 mL), tetrahydrofuran (25.0 mL), and methanol (25.0 mL). Lithium hydroxide monohydrate (1.23 g, 29.2 mmol) was then added. The suspension was stirred at room temperature. After 2.5 h. the reaction was concentrated. The crude residue was dissolved in ethyl acetate and the solution was acidified to pH=3 with 1N hydrochloric acid. The mixture was extracted three times with ethyl acetate. The combined organics were dried over sodium sulfate, filtered and concentrated to give (R)-4-(1-hydroxybutyl)benzoic acid (2.63 g, 93%) as a white solid. $^1$H NMR (400 MHz, CDCl$_3$, δ): 8.09 (d, J=8.2 Hz, 2H), 7.46 (d, J=8.2 Hz, 2H), 4.79 (dd, J=7.6, 5.5 Hz, 1H), 1.86-1.76 (m, 1H), 1.76-1.64 (m, 1H), 1.54-1.40 (m, 1H), 1.40-1.27 (m, 1H), 0.95 (t, J=7.3 Hz, 3H). MS (M−1): 193.

Step B: (R)-ethyl 3-(4-(1-hydroxybutyl)benzamido)propanoate

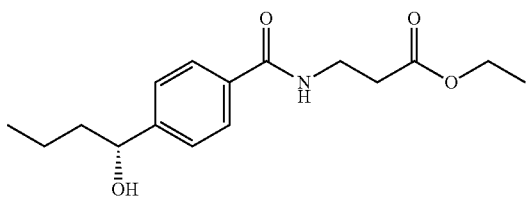 [SMILES: CCC[C@@H](O)c1ccc(C(=O)NCCC(=O)OCC)cc1]

N,N-dimethylformamide (16.9 mL) was added to a vial containing (R)-4-(1-hydroxybutyl)benzoic acid (2.6 g, 13.5 mmol), ethyl 3-aminopropanoate hydrochloride (4.16 g, 27.1 mmol) and O-(7-azabenzotriazol-1-yl)-N,N,N',N'-tetramethyluronium hexafluorophosphate (10.3 g, 27.1 mmol). Diisopropylethylamine (11.8 mL, 67.7 mmol) was then added. The reaction was stirred for 1 h, and was then concentrated. Purification by column chromatography (0-50% ethyl acetate in heptane) afforded (R)-ethyl 3-(4-(1-hydroxybutyl)benzamido)propenoate (3.97 g, 100% yield) as an oil. $^1$H NMR (400 MHz, CDCl$_3$, δ): 7.75 (d, J=8.2 Hz, 2H), 7.40 (d, J=8.0 Hz, 2H), 6.83 (br. s., 1H), 4.74 (t, J=8.2 Hz, 1H), 4.18 (q, J=7.1 Hz, 2H), 3.73 (q, J=5.9 Hz, 2H), 2.64 (t, J=6.4 Hz, 2H), 1.87 (br. s., 1H), 1.84-1.62 (m, 2H), 1.49-1.30 (m, 2H), 1.28 (t, J=107.1 Hz, 3H), 0.93 (t, J=7.3 Hz, 3H). MS (M+1): 294.

Step C: (S)-ethyl 3-(4-(1-(3,5-dimethyl-4-(4-(trifluoromethyl)-1H-pyrazol-1-yl)phenoxy)butyl)benzamido)propanoic

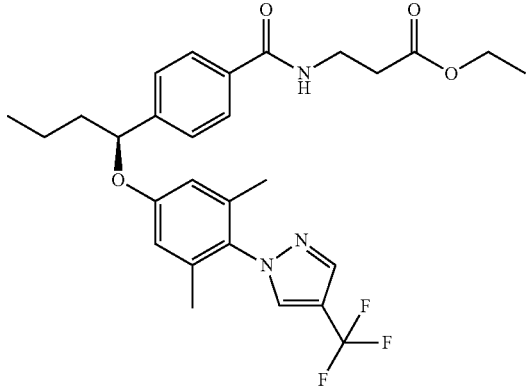 [SMILES: CCC[C@H](Oc1cc(C)c(-n2cc(C(F)(F)F)cn2)c(C)c1)c1ccc(C(=O)NCCC(=O)OCC)cc1]

To a solution of azeotropically dried (R)-ethyl 3-(4-(1-hydroxybutyl)benzamido)propanoate (2.6 g, 8.9 mmol) and azodicarboxylic acid dipiperidine (3.8 g, 15.1 mmol) (with toluene) in tetrahydrofuran (49.2 mL) was added tributylphosphine (3.9 mL, 16.0 mmol) dropwise at room temperature. Intermediate (26) (2.3 g, 8.9 mmol) was then added portionwise. The mixture was stirred at room temperature for 16 hours. The reaction was diluted with ethyl acetate and then extracted twice with sodium hydroxide (1N), once with water, once with hydrochloric acid (1N), and finally once with brine. The organic layer was dried over sodium sulfate, filtered, and concentrated. Purification by column chromatography (0-30% ethyl acetate in heptanes) afforded (S)-ethyl 4-(1-(3,5-dimethyl-4-(4-(trifluoromethyl)-1H-pyrazol-1-yl)phenoxy)butyl)benzoate (3.53 g, 75%) as colorless gum: $^1$H NMR (400 MHz, CDCl$_3$, δ): 7.87 (s, 1H), 7.73 (d, J=8.0 Hz, 2H), 7.65 (s, 1H), 7.39 (d, J=8.2 Hz, 2H), 6.84 (d, J=5.9 Hz, 1H), 6.57 (s, 2H), 5.15 (dd, J=7.8, 5.1 Hz, 1H), 4.17 (q, J=7.1 Hz, 2H), 3.71 (q, J=6.0 Hz, 2H), 2.63 (t, J=5.7 Hz, 2H), 2.04-1.91 (m, 1H), 1.88 (s, 6H), 1.86-1.71 (m, 1H), 1.58-1.33 (m, 2H), 1.26 (t, J=7.0 Hz, 3H), 0.96 (t, J=7.4 Hz, 3H). MS (M+1): 532. Chiral SFC. Column: Chiralpak AD-H. Dimensions: 4.6×250 mm. Mobile Phase: 80/20 CO$_2$/ethanol. Flow Rate: 2.5 mL/min. Modifier: None. Retention time: 3.05 minutes.

Step D: (S)-3-(4-(1-(3,5-dimethyl-4-(4-(trifluoromethyl)-1H-pyrazol-1-yl)phenoxy)butyl)benzamido) propanoic acid To a flask containing ethyl (S)-ethyl 3-(4-(1-(3,5-dimethyl-4-(4-(trifluoromethyl)-1H-pyrazol-1-yl)phenoxy)butyl)benzamido)propanoate (3.5 g, 6.6 mmol) was added tetrahydrofuran (16.5 mL), methanol (16.5 mL), and sodium hydroxide (1N) (16.5 mL, 16.5 mmol). The suspension was stirred at room temperature for 18 hours. The reaction was concentrated. The crude residue was dissolved in water, and the solution was acidified to pH=3 with 1N hydrochloric acid. A white precipitate formed. The solid was filtered, rinsed with water, and dried under vacuum to give (S)-3-(4-(1-(3,5-dimethyl-4-(4-(trifluoromethyl)-1H-pyrazol-1-yl)phenoxy)butyl)benzamido)propanoic acid (2.87 g, 87%) as a white solid. Recrystallization was performed using methyl tert-butyl ether to provide a crystalline compound. The crystalline compound can be characterized by powder X-ray diffraction to provide the spectrum substantially as shown in FIG. 1. $^1$H NMR (400 MHz, CDCl$_3$, δ): 7.88 (s, 1H), 7.73 (d, J=8.2 Hz, 2H), 7.65 (s, 1H), 7.39 (d, J=8.4 Hz, 2H), 6.80 (t, J=5.9 Hz, 1H), 6.56 (s, 2H), 5.16 (dd, J=7.8, 5.1 Hz, 1H), 3.71 (q, J=5.9 Hz, 2H), 2.69 (t, J=5.8 Hz, 2H), 2.04-1.91 (m, 1H), 1.88 (s, 6H), 1.86-1.67 (m, 1H), 1.63-1.31 (m, 2H), 0.96 (t, J=7.3 Hz, 3H). MS (M+1): 504. Mp 157-159° C. [α]$_D$=−43.8 (c=1; CHCl$_3$).

A further synthesis of the compound of Example 83 is provided below.

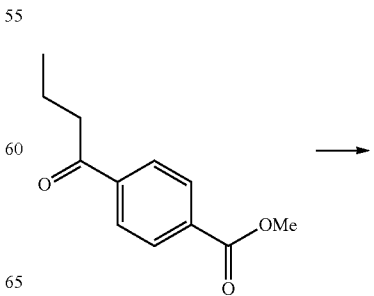

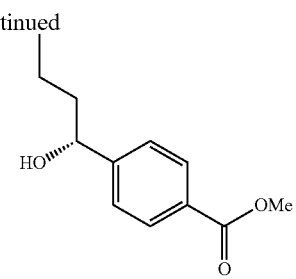

Step (1): (R)-methyl 4-(1-hydroxybutyl)benzoate

To a solution of borane diethylaniline complex (20.6 g, 25.2 mL, 126 mmol) in tetrahydrofuran (130 mL) at 20° C. was added (s)-methyl oxazaborilidine (6.3 mL, 6.3 mmol). A solution of ketone (26.0 g, 126 mmol) in tetrahydrofuran (130 mL) was added over 2.5 h. The reaction was stirred 10 min before quenching with methanol (15.3 mL). To the quenched solution was added 1 M HCl (125 mL) and the product was extracted with heptane (2×130 mL). The combined organic solution was washed with 1 M HCl (125 mL) and concentrated to a final volume of 250 mL. The solution was cooled to −10° C. the product filtered and washed with cold heptanes to give (R)-methyl 4-(1-hydroxybutyl)benzoate as a white solid (23.3 g, 89% yield). $^1$H NMR (400 MHz, CDCl$_3$) δ: 7.99 (d, J=8.4 Hz, 2H), 7.39 (d, J=8.4 Hz, 2H), 4.73 (dd, J=7.4, 5.9 Hz, 1H), 3.89 (s, 3H), 1.81-1.61 (m, 2H), 1.47-1.26 (m, 2H), 0.92 (t, J=7.4 Hz, 3H).

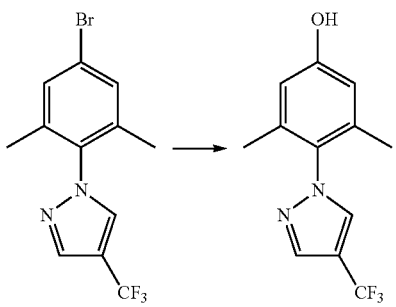

Step (1s): 3,5-dimethyl-4-(4-(trifluoromethyl)-1H-pyrazol-1-yl)phenol

To a solution of the aryl bromide (intermediate 7) (15.3 g, 49 mmol) and potassium hydroxide (9.50 g, 144 mmol) in N-methylpyrrolidone (38 mL) and water (38 mL) was added tris(dibenzylidineacetone)dipalladium (0.44 g, 0.48 mol) and t-butyl X-Phos (0.41 g, 0.96 mmol). The solution was heated to 90° C. After 30 min the reaction was cooled to room temperature and ethyl acetate (75 mL) was added. The solution was acidified with conc. HCl (9 mL). The aq. phase was split and the organic layer washed with a 0.5 M potassium phosphate, tribasic solution (75 mL). The solvent was removed and toluene (75 mL) added. The toluene solution was cooled to 0° C. and filtered to give 3,5-dimethyl-4-(4-(trifluoromethyl)-1H-pyrazol-1-yl)phenol (921 g, 75% yield) as an off-white solid. $^1$H NMR (400 MHz, DMSO-d6) δ: 9.71 (s, 1H), 8.52 (s, 1H), 8.09 (s, 1H), 6.57 (s, 1H), 1.82 (s, 6H).

Step (2,3,4): (S)-4-(1-(3,5-dimethyl-4-(4-(trifluoromethyl)-1H-pyrazol-1-yl)phenoxy)butyl)benzoic acid tromethamine salt

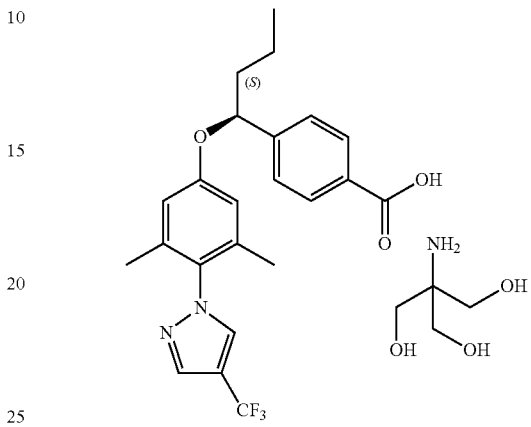

Step (2): (R)-methyl 4-(1-(methylsulfonyloxy)butyl)benzoate

To a solution of (R)-methyl 4-(1-hydroxybutyl)benzoate, intermediate (26) (10 g, 48 mmol) in methyl t-butyl ether (80 mL) containing triethylamine (6.32 g, 62 mmol) was added methanesulfonyl chloride (6.05 g, 53 mmol) slowly at 20° C. The solution was filtered to remove triethylamine salts and the solution used in the next step without isolation.

Step (3): (S)-methyl 4-(1-(3,5-dimethyl-4-(4-(trifluoromethyl)-1H-pyrazol-1-yl)phenoxy)butyl)benzoate To a solution of 3,5-dimethyl-4-(4-(trifluoromethyl)-1H-pyrazol-1-yl)phenol (intermediate 26) (12.6 g, 49 mmol) in 2-methyltetrahydrofuran (70 mL) was added cesium carbonate (23.5 g, 72 mmol) and the solution of mesylate from step 2. The reaction was heated to 65° C. for 5 h. The reaction was then cooled to room temperature and water (80 mL) was added. The aq. layer was split and the organic solution was used in the next step without isolation.

Step (4): (S)-4-(1-(3,5-dimethyl-4-(4-(trifluoromethyl)-1H-pyrazol-1-yl)phenoxy)butyl)benzoic acid tromethamine salt To the solution from step 3 was added 5 M sodium hydroxide solution (29 mL, 145 mmol) and methanol (30 mL). The solution was heated to 35° C. for 6 h. After cooling to room temperature, the solution was acidified with conc. HCl (12.4 mL). The reaction was washed with water (30 mL). The organic solution was concentrated and the residue taken up in acetonitrile (100 mL). A solution of tris(hydroxymethyl)aminomethane (5.82 g, 48 mmol) in water (5 mL) was added slowly. The resulting slurry was cooled to 0° C. The product was filtered and washed with acetonitrile to give the desired salt as a white solid (20.5 g, 77% yield) $^1$H NMR (400 MHz, DMSO-d6) δ: 8.53 (s, 1H), 8.09 (s, 1H), 7.80 (d, J=8.2 Hz, 2H), 7.35 (d, J=8.2 Hz, 2H), 6.74 (s, 2H), 5.38 (dd, J=7.4, 5.1

Hz, 1H), 3.37 (s, 6H), 1.94-1.85 (m, 1H), 1.79 (s, 6H), 1.76-1.68 (m, 1H), 1.45-1.29 (m, 2H), 0.89 (t, J=7.5 Hz, 3H).

Step (5-6): (S)-3-(4-(1-(3,5-dimethyl-4-(4-(trifluoromethyl)-1H-pyrazol-1-yl)phenoxy)butyl)benzamido)propanoic acid

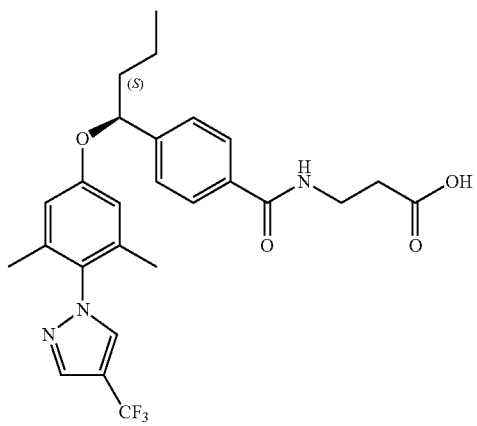

Step (5): (S)-methyl 3-(4-(1-(3,5-dimethyl-4-(4-(trifluoromethyl)-1H-pyrazol-1-yl)phenoxy)butyl)benzamido)propanoate To a solution of the tromethamine salt (20 g, 36 mmol) in 2-methyltetrahydrofuran (200 mL) was added f-alanine ethyl ester (7.08 g, 45 mmol), 2-chloro-4,6-dimethoxy-1,3,5-triazine (8.25 g, 47 mmol) and N-methylmorpholine (7.31 g, 72 mmol). The reaction was stirred at 20° C. for 2 h. The reaction was washed with water (2×72 ml) and the organic solution used in the next step without isolation.

Step (6): (S)-3-(4-(1-(3,5-dimethyl-4-(4-(trifluoromethyl)-1H-pyrazol-1-yl)phenoxy)butyl)benzamido) propanoic acid To the solution from step 5 was added methanol (40 mL), water (54 mL) and sodium hydroxide (4.34 g, 108 mmol). The reaction was stirred 1 h at 30° C. The solution was acidified with conc. HCl (9.33 mL) and the aq. phase split. The organic solution was washed with 1 N HCl (40 mL). The organic phase was concentrated and the residue taken up in acetonitrile (300 mL). The solution was cooled to 0° C. and stirred 5 h. The solid product was filtered and washed with cold acetonitrile, giving the desired compound as a white solid (14.6 g, 80% yield). $^1$H NMR (400 MHz, CDCl$_3$) δ: 7.88 (s, 1H), 7.72 (d, J=8.3 Hz, 2H), 7.65 (s, 1H), 7.38 (d, J=8.3 Hz, 2H), 6.89 (t, J=6.2 Hz, 1H), 6.55 (s, 2H), 5.15 (dd, J=7.8, 4.6 Hz, 1H), 3.68 (q, J=6.2 Hz, 2H), 2.65 (t, J=6.2 Hz, 2H), 1.95 (m, 1H), 1.86 (s, 6H), 1.78 (m, 1H), 1.55-1.38 (m, 2H), 0.94 (t, J=7.4 Hz, 3H). The final compound was recrystallized from acetonitrile (5 vol). The compound was heated to 80° C. and then cooled to 0° C. to provide a purity of 99.01%.

Example 84

(R)-3-(4-(1-(3,5-dimethyl-4-(4-(trifluoromethyl)-1H-pyrazol-1-yl)phenoxy)butyl)benzamido)propanoic acid

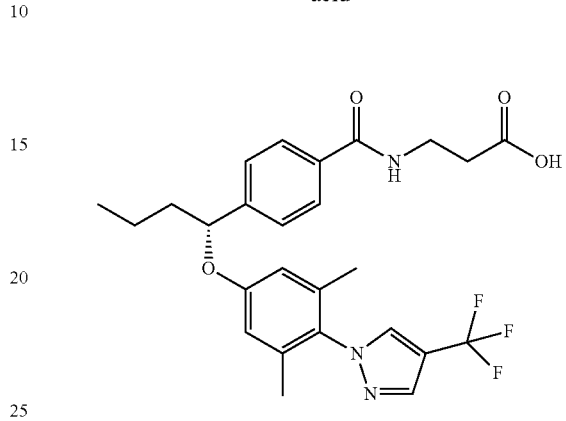

The title compound is obtained by resolving racemic 3-(4-(1-(3,5-dimethyl-4-(4-(trifluoromethyl)-1H-pyrazol-1-yl) phenoxy)butyl)benzamido)propanoic acid, the compound of Example 82, by chiral SFC. Column: Chiralpak AD-H. Dimensions: 10×250 mm. Mobile Phase: 80/20 CO$_2$/2-propanol. Flow Rate: 10.0 mL/min. Modifier 0.2% isopropylamine. Retention time: 3.65 minutes.

Example 85

(+/−)-3-(4-(1-(5-(4-(trifluoromethyl)-1H-pyrazol-1-yl)pyridine-2-yloxy)butyl)benzamido)propanoic acid

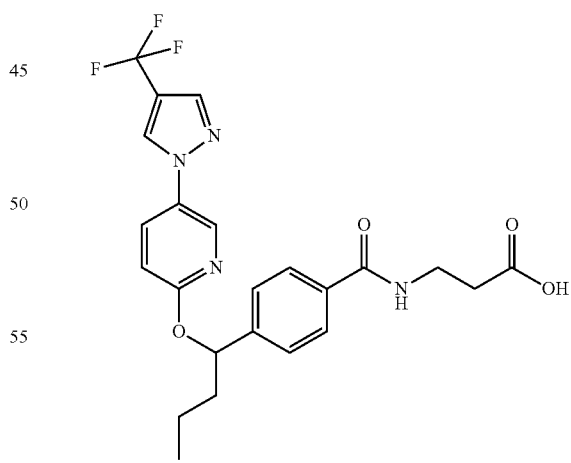

The title compound was prepared by a method analogous to that described for Example 19 using Intermediate (49) and 4-(trifluoromethyl)-1H-pyrazole. $^1$H NMR (400 MHz, CD$_3$OD, δ): 8.62 (s, 1H), 8.42 (d, J=2.3 Hz, 1H), 8.03 (dd, J=9.0, 2.9 Hz, 1H), 7.94 (s, 1H), 7.76-7.72 (m, 2H), 7.49-7.44 (m, 2H), 6.99-6.93 (m, 1H), 6.09 (dd, J=7.9, 5.6 Hz, 1H), 3.63-3.55 (m, 2H), 2.60 (t, J=6.9 Hz, 2H), 2.08-1.96 (m, 1H), 1.90-1.78 (m, 1H), 1.54-1.33 (m, 2H), 0.98-0.92 (m, 3H). MS (M+1): 477.3.

Example 86

(+/−)-3-(4-(1-(6-(4-(trifluoromethyl)-1H-pyrazol-1-yl)pyridine-3-yloxy)butyl)benzamido)propanoic acid

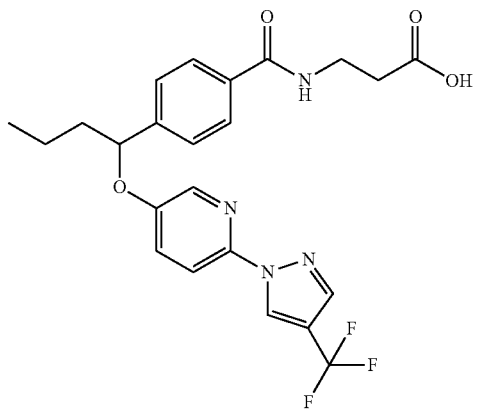 [SMILES: CCCC(Oc1ccc(-n2cc(C(F)(F)F)cn2)nc1)c1ccc(C(=O)NCCC(=O)O)cc1]

Step A: (+/−)-methyl 4-(1-(6-(4-(trifluoromethyl)-1H-pyrazol-1-yl)pyridine-3-yloxy)butyl)benzoate

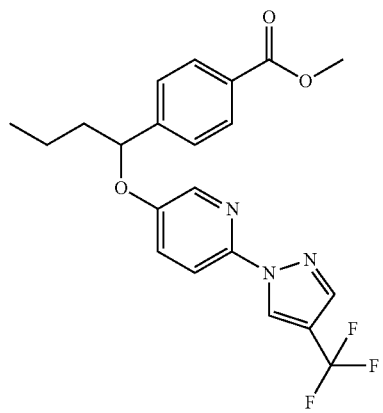 [SMILES: CCCC(Oc1ccc(-n2cc(C(F)(F)F)cn2)nc1)c1ccc(C(=O)OC)cc1]

To a 0° C. mixture of Intermediate (20) (150 mg, 0.72 mmol) and Intermediate (38) (110 mg, 0.48 mmol) in tetrahydrofuran (5.0 mL) was added triphenylphosphine (252 mg, 0.96 mmol) followed by diethylazodicarboxylate (167 mg, 0.96 mmol). The mixture was stirred at 40° C. overnight. The reaction mixture was partitioned between water and ethyl acetate. The organic layer was dried over sodium sulfate, filtered and concentrated. Purification by column chromatography gave (+/−)-methyl 4-(1-(6-(4-(trifluoromethyl)-1H-pyrazol-1-yl)pyridine-3-yloxy)butyl)benzoate (170 mg, 84%). $^1$H NMR (400 MHz, CDCl$_3$, δ): 8.60 (s, 1H), 7.97-7.93 (m, 3H), 7.75 (s, 1H), 7.72 (d, 1H), 7.34 (d, 2H), 7.20-7.17 (m, 1H), 5.13-5.10 (m, 1H), 3.83 (s, 3H), 2.01-1.95 (m, 1H), 1.81-1.78 (m, 1H), 1.48-1.47 (m, 1H), 1.38-1.36 (m, 1H), 0.92-0.89 (m, 3H).

Step B: (+/−)-3-(4-(1-(6-(4-(trifluoromethyl)-1H-pyrazol-1-yl)pyridine-3-yloxy)butyl)benzamido) propanoic acid To a 0° C. solution of methyl 4-(1-(6-(4-(trifluoromethyl)-1H-pyrazol-1-yl)pyridine-3-yloxy)butyl)benzoate (170.0 mg, 0.405 mmol) in tetrahydrofuran (3 mL) was added 2N lithium hydroxide (610 μL, 1.22 mmol). The mixture was stirred at 50° C. overnight. The reaction was neutralized with 1N hydrochloric acid and extracted with ethyl acetate. The organic layer was dried over sodium sulfate, filtered and concentrated, to give 164 mg of a colorless solid. To a solution of 100 mg of the crude residue in N,N-dimethylformamide (5 mL) was added O-(7-azabenzotriazol-1-yl)-N,N,N',N'-tetramethyluronium hexafluorophosphate (141 mg, 0.37 mmol). The mixture was stirred for 45 minutes and then methyl 3-aminopropionate hydrochloride (51.1 mg, 0.37 mmol) and diisopropylethylamine (128 mg, 0.988 mmol) were added. The resulting mixture was stirred at room temperature for 2 hours. The mixture was diluted with saturated ammonium chloride, and the layers were separated. The organic layer was washed with water, dried over sodium sulfate, filtered and concentrated. The crude residue was dissolved in water (5 mL) and tetrahydrofuran (5 mL). 2N lithium hydroxide (330 μL, 0.66 mmol) was added. The mixture was stirred at room temperature for 2 hours. The mixture was neutralized with 1N hydrochloric acid and extracted with ethyl acetate. The organic layer was dried over sodium sulfate, filtered and concentrated. Purification by HPLC (column: Boston Analytics Symmetrix ODS-H 150×30 mm, 5 μm; modifier formic acid 0.225%; gradient: 47 to 67% acetonitrile in water) gave (+/−)-3-(4-(1-(6-(4-(trifluoromethyl)-1H-pyrazol-1-yl)pyridine-3-yloxy)butyl)benzamido)propanoic acid (90 mg) as a colorless solid. $^1$H NMR (400 MHz, CD$_3$OD, δ): 8.71 (s, 1H), 7.98 (m, 1H), 7.84 (s, 1H), 7.71-7.69 (m, 3H), 7.42-7.35 (m, 3H), 5.33-5.30 (m, 1H), 3.53-3.50 (m, 2H), 2.54-2.51 (m, 2H), 1.97-1.92 (m, 1H), 1.79-1.73 (m, 1H), 1.49-1.38 (m, 1H), 1.37-1.34 (m, 1H), 0.90 (t, 3H). MS (M+1): 477.5.

Example 87

(+/−)-3-(4-(1-(6-(4-(trifluoromethyl)-1H-imidazol-1-yl)pyridine-3-yloxy)butyl)benzamido)propanoic acid

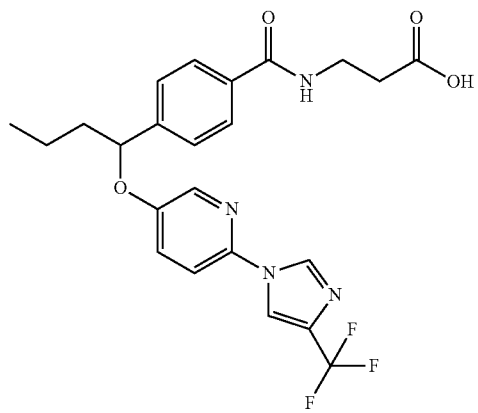 [SMILES: CCCC(Oc1ccc(-n2cnc(C(F)(F)F)c2)nc1)c1ccc(C(=O)NCCC(=O)O)cc1]

The title compound was prepared by a method analogous to that described for Example 86 using Intermediate (50). $^1$H NMR (400 MHz, CD$_3$OD, δ): 8.43 (s, 1H), 8.22 (s, 1H), 8.14

(d, 1H), 7.80-7.78 (m, 2H), 7.57-7.55 (m, 1H), 7.47-7.44 (m, 3H), 5.44-5.41 (m, 1H), 3.61-3.57 (m, 2H), 2.62-2.58 (m, 2H), 2.06-2.03 (m, 1H), 1.89-1.85 (m, 1H), 1.57-1.55 (m, 1H), 1.47-1.43 (m, 1H), 1.00-0.96 (m, 3H). MS (M+1): 477.2.

Example 88

(+/−)-3-(4-(1-(4-(4-cyano-1H-pyrazol-1-yl)phenoxy)butyl)benzamido)propanoic acid

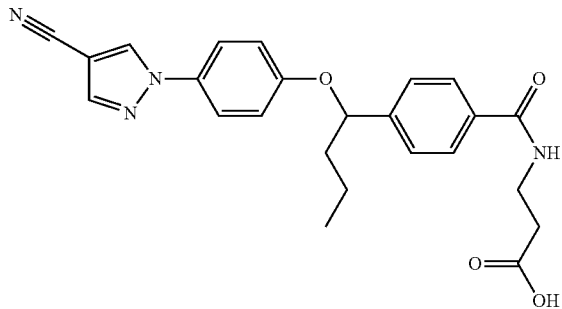 [SMILES: CCCC(Oc1ccc(-n2cc(C#N)cn2)cc1)c1ccc(C(=O)NCCC(=O)O)cc1]

Step A: 1-(4-methoxyphenyl)-1H-pyrazole

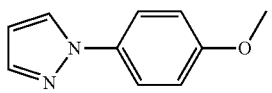

A mixture of (4-methoxyphenyl)hydrazine hydrochloride (8.0 g, 0.046 mol) and 1,1,3,3-tetramethoxypropane (8.3 g, 0.05 mol) in ethanol (120 mL) was heated to reflux for 1 hour. The reaction was then cooled to room temperature and concentrated. The residue was diluted with saturated sodium bicarbonate (50 mL) and ethyl acetate (100 mL). The phases were separated and the aqueous was extracted with ethyl acetate (2×20 mL). The combined organics were washed with brine (50 mL), dried over sodium sulfate, filtered and concentrated. Purification by column chromatography gave 1-(4-methoxyphenyl)-1H-pyrazole (7.7 g, 97%) as a yellow oil. $^1$H NMR (400 MHz, CDCl$_3$, δ): 7.82 (m, 1H), 7.69 (m, 1H), 7.59 (d, J=9.2 Hz, 2H), 6.97 (d, J=9.2 Hz, 2H), 6.43 (m, 1H), 3.83 (s, 3H).

Step B: 4-bromo-1-(4-methoxyphenyl)-1H-pyrazol

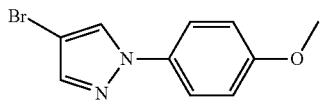

To a solution of 1-(4-methoxyphenyl)-1H-pyrazole (7.2 g, 0.042 mol) in tetrahydrofuran (100 mL) was added N-bromosuccinimide (7.3 g, 0.042 mol). The reaction was stirred at room temperature for 3 hours. The reaction was concentrated and purification by column chromatography gave 4-bromo-1-(4-methoxyphenyl)-1H-pyrazole (8.9 g, 84%) as a white solid. $^1$H NMR (400 MHz, CDCl$_3$, δ): 7.83 (s, 1H), 7.63 (s, 1H), 7.52 (d, J=8.8 Hz, 2H), 6.97 (d, J=8.8 Hz, 2H), 3.84 (s, 3H).

Step C:
1-(4-methoxyphenyl)-1H-pyrazole-4-carbaldehyde

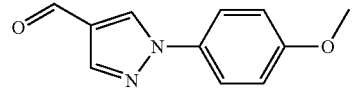

To a −78° C. solution of 4-bromo-1-(4-methoxyphenyl)-1H-pyrazole (506 mg, 2.0 mmol) in anhydrous tetrahydrofuran (20 mL) was added n-butyllithium in hexane (0.95 mL, 2.4 mmol). The reaction was stirred for 2 h at −78° C. N,N-dimethylformamide (292 mg, 4 mmol) was added and the reaction continued to stir at −78° C. for 1 h, then at room temperature for 2 h. The reaction was quenched with saturated ammonium chloride (20 mL) and extracted with ethyl acetate (3×30 mL). The combined organics were washed with brine (30 mL), dried over sodium sulfate, filtered and concentrated. Purification by column chromatography gave 1-(4-methoxyphenyl)-1H-pyrazole-4-carbaldehyde (80 mg, 20%) as a yellow oil. $^1$H NMR (400 MHz, CDCl$_3$, δ): 9.95 (s, 1H), 8.33 (s, 1H), 8.13 (s, 1H), 7.62 (d, J=9.2 Hz, 2H), 7.01 (d, J=9.2 Hz, 2H), 3.86 (s, 3H).

Step D:
1-(4-methoxyphenyl)-1H-pyrazole-4-carbonitrile

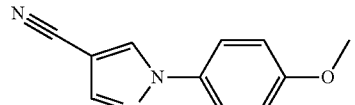

To a mixture of 1-(4-methoxyphenyl)-1H-pyrazole-4-carbaldehyde (80 mg, 0.54 mmol) in tetrahydrofuran (3 mL) and ammonium hydroxide (3 mL) was added iodine (138 mg, 0.54 mmol). The reaction was stirred at room temperature for 5 hours. The reaction was diluted with saturated sodium thiosulphate (5 mL) and extracted with ethyl acetate (3×10 mL). The combined organics were washed with brine, dried over sodium sulfate, filtered and concentrated to give 1-(4-methoxyphenyl)-1H-pyrazole-4-carbonitrile (78 mg, 100%) as a yellow solid. $^1$H NMR (400 MHz, CDCl$_3$, δ): 8.19 (s, 1H), 7.96 (s, 1H), 7.56 (d, J=9.2 Hz, 2H), 7.01 (d, J=9.2 Hz, 2H), 3.86 (s, 3H).

Step E:
1-(4-hydroxyphenyl)-1H-pyrazole-4-carbonitrile

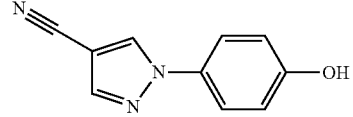

To a solution of 1-(4-methoxyphenyl)-1H-pyrazole-4-carbonitrile (115 mg, 0.575 mmol) in dichloromethane (5 mL)

was added boron tribromide (431 mg, 1.73 mmol) at −10° C. The reaction was then warmed to room temperature and stirred for 16 hours. The reaction was quenched with methanol (0.5 mL) and water (5 mL), and extracted with ethyl acetate (3×15 mL). The combined organics were washed with brine (15 mL), dried over sodium sulfate, filtered and concentrated to give 1-(4-hydroxyphenyl)-1H-pyrazole-4-carbonitrile (46 mg, 43%) as a yellow solid. $^1$H NMR (400 MHz, CDCl$_3$, δ): 9.89 (s, 1H), 9.12 (s, 1H), 8.27 (s, 1H), 7.62 (d, J=9.2 Hz, 2H), 6.90 (d, J=9.2 Hz, 2H).

Step F: (+/−)-3-(4-(1-(4-(4-cyano-1H-pyrazol-1-yl)phenoxy)butyl)benzamido)propanoic acid The title compound was prepared by a method analogous to that described for Example 77 using Intermediate (48), 1-(4-hydroxyphenyl)-1H-pyrazole-4-carbonitrile, triphenylphosphine, and diethylazodicarboxylate. Analytical LCMS: retention time 1.310 minutes (Atlantis C$_{18}$ 4.6×50 mm, 5 µM column; 95% water/acetonitrile linear gradient to 5% water/acetonitrile over 4.0 minutes, hold at 5% water/acetonitrile to 5.0 minutes; 0.05% trifluoroacetic acid modifier, flow rate 2.0 mL/minute); MS (M+1): 433.2.

Example 89

(+/−)-3-(4-(1-(4-(4,5,6,7-tetrahydro-2H-indazol-2-yl)phenoxy)butyl)benzamido)propanoic acid

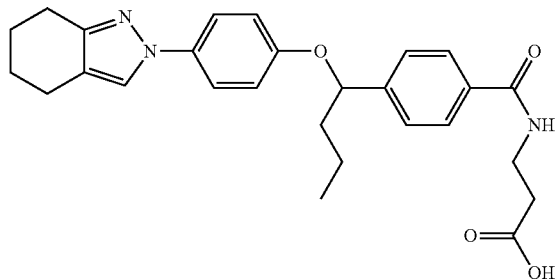 [SMILES: CCCC(Oc1ccc(-n2cc3c(n2)CCCC3)cc1)c1ccc(C(=O)NCCC(=O)O)cc1]

Step A: (+/−)-methyl 4-(1-(4-(4,5,6,7-tetrahydro-2H-indazol-2-yl)phenoxy)butyl)benzoate

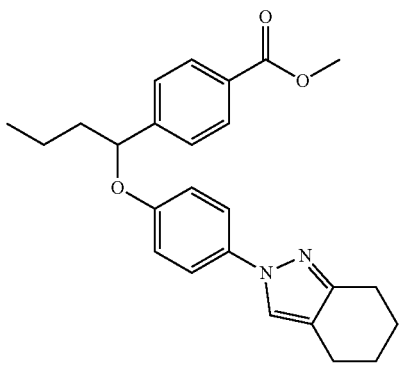 [SMILES: CCCC(Oc1ccc(-n2cc3c(n2)CCCC3)cc1)c1ccc(C(=O)OC)cc1]

Intermediate (27) (111 mg, 0.271 mmol) was combined with 4,5,6,7-tetrahydro-2H-indazole (39.4 mg, 0.323 mmol), copper(I) iodide (2.7 mg, 0.014 mmol), potassium carbonate (78.6 mg, 0.569 mmol), trans-dimethylcyclohexane-1,2-diamine (9.0 µL, 0.054 mmol), and toluene (2 mL). The reaction was refluxed for 16 hours, then cooled to room temperature, and partitioned between ethyl acetate and water/ammonium hydroxide. The organic layer was washed with 0.5N HCl and brine, dried over magnesium sulfate, filtered and concentrated. Purification by column chromatography (0-30% ethyl acetate in heptane) gave (+/−)-methyl 4-(1-(4-(4,5,6,7-tetrahydro-2H-indazol-2-yl)phenoxy)butyl)benzoate (0.056 g, 51%) as a clear oil. $^1$H NMR (400 MHz, CDCl$_3$, δ): 8.01 (d, J=8.2 Hz, 2H), 7.35-7.48 (m, 5H), 6.84 (d, J=9.0 Hz, 2H), 5.15 (dd, J=7.6, 5.1 Hz, 1H), 3.91 (s, 3H), 2.74 (t, J=6.2 Hz, 2H), 2.58 (t, J=6.1 Hz, 2H), 1.94-2.04 (m, 1H), 1.70-1.90 (m, 5H), 1.37-1.56 (m, 2H), 0.96 (t, 3H). MS (M+1): 405.2.

Step B: (+/−)-3-(4-(1-(4-(4,5,6,7-tetrahydro-2H-indazol-2-yl)phenoxy)butyl)benzamido)propanoic acid The title compound was prepared by a method analogous to that described for Example 20 using methyl 4-(1-(4-(4,5,6,7-tetrahydro-2H-indazol-2-yl)phenoxy)butyl)benzoate. Column: Waters Atlantis C18 4.6×50 mm, 5 µm; Modifier: TFA 0.05%; Gradient 95% H$_2$O/5% acetonitrile linear to 5% H$_2$O/95% acetonitrile over 4.0 min, hold at 5% H$_2$O/95% acetonitrile to 5.0 min. Flow: 2.0 mL/min.; Retention time: 3.39 minutes. MS (M+1): 462.2.

Example 90

(+/−)-3-(4-(1-(4-(5,6-dihydrocyclopenta[c]pyrazol-2(4H)-yl)phenoxy)butyl)benzamido)propanoic acid

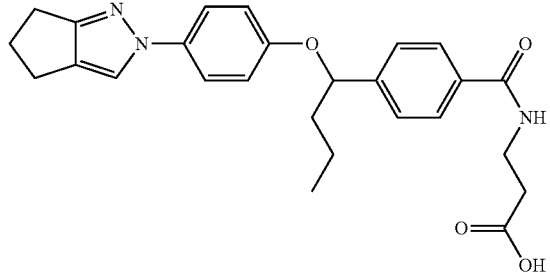 [SMILES: CCCC(Oc1ccc(-n2cc3c(n2)CCC3)cc1)c1ccc(C(=O)NCCC(=O)O)cc1]

Step A: (+/−)-methyl 4-(1-(4-(5,6-dihydrocyclopenta[c]pyrazol-2(4H)-yl)phenoxy)butyl)benzoate

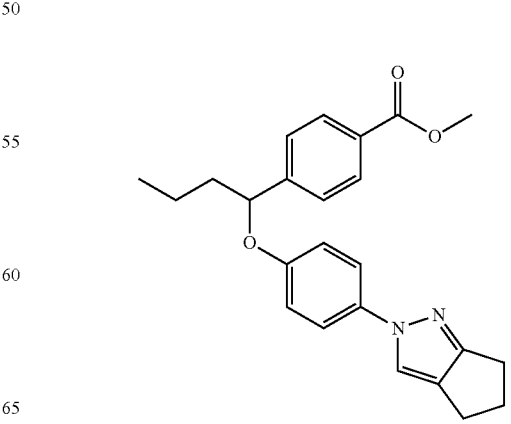

The title compound was prepared by a method analogous to that described for Example 89, Step A, using 1,4,5,6-tetrahydro-cyclopenta[c]pyrazole hydrochloride. The product obtained was a 4:1 mixture of regioisomers. $^1$H NMR (500 MHz, CDCl$_3$, δ): 8.01 (d, J=8.1 Hz, 2H), 7.46-7.29 (m, 5H), 6.88-6.79 (m, 2H), 5.19-5.11 (m, 1H), 3.91 (s, 3H), 2.93-2.36 (m, 6H), 2.04-1.94 (m, 1H), 1.87-1.75 (m, 1H), 1.56-1.38 (m, 2H), 0.97 (t, 3H). MS (M+1): 391.3.

Step B: (+/−)-3-(4-(1-(4-(5,6-dihydrocyclopenta[c]pyrazol-2(4H)-yl)phenoxy)butyl)benzamido)propanoic acid The title compound was prepared by a method analogous to that described for Example 20 using methyl 4-(1-(4-(5,6-dihydrocyclopenta[c]pyrazol-2(4H)-yl)phenoxy)butyl)benzoate. $^1$H NMR (400 MHz, CDCl$_3$, δ): 7.72 (d, J=8.2 Hz, 2H), 7.45-7.30 (m, 5H), 6.90-6.76 (m, 3H), 5.13 (dd, J=7.5, 5.4 Hz, 1H), 3.76-3.64 (m, 2H), 2.94-2.73 (m, 2H), 2.73-2.35 (m, 6H), 2.10-1.93 (m, 1H), 1.88-1.74 (m, 1H), 1.64-1.36 (m, 2H), 0.96 (t, 3H). MS (M+1): 448.4.

Example 91

(+/−)-3-(4-(1-(4-(2H-indazol-2-yl)phenoxy)butyl)benzamido)propanoic acid

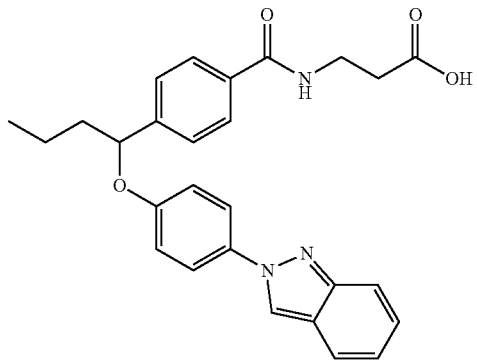

Step A: (+/−)-methyl 4-(1-(4-(2H-indazol-2-yl)phenoxy)butyl)benzoate

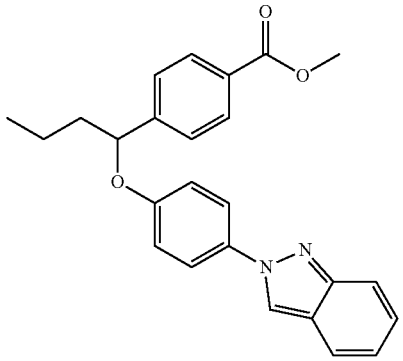 [SMILES: CCCC(Oc1ccc(-n2cc3ccccc3n2)cc1)c1ccc(C(=O)OC)cc1]

The title compound was prepared by a method analogous to that described for Intermediate (27), using Intermediate (55). $^1$H NMR (400 MHz, CDCl$_3$, δ): 8.26 (s, 1H), 8.03 (d, J=8.4 Hz, 2H), 7.75 (d, J=9.0 Hz, 1H), 7.72-7.64 (m, 3H), 7.44 (d, J=8.2 Hz, 2H), 7.31 (d, J=7.4 Hz, 1H), 7.14-7.05 (m, 1H), 6.95 (d, J=9.0 Hz, 2H), 5.21 (dd, J=7.6, 5.3 Hz, 1H), 3.91 (s, 3H), 2.11-1.97 (m, 1H), 1.91-1.77 (m, 1H), 1.65-1.37 (m, 2H), 0.98 (t, J=7.3 Hz, 3H). MS (M+1): 211.2.

Step B: (+/−)-3-(4-(1-(4-(2H-indazol-2-yl)phenoxy)butyl)benzamido)propanoic acid The title compound was prepared by a method analogous to that described for Example 20 using methyl 4-(1-(4-(2H-indazol-2-yl)phenoxy)butyl)benzoate. Column: Waters Atlantis C18 4.6×50 mm, 5 μm; Modifier: TFA 0.05%; Gradient 95% H$_2$0/5% acetonitrile linear to 5% H$_2$0/95% acetonitrile over 4.0 min, hold at 5% H$_2$0/95% acetonitrile to 5.0 min. Flow: 2.0 mL/min.; Retention time: 3.23 minutes. MS (M+1): 458.2.

Example 92

(+/−)-3-(4-(1-(4-(4-methyl-1H-1,2,3-triazol-1-yl)phenylamino)butyl)benzamido)propanoic acid

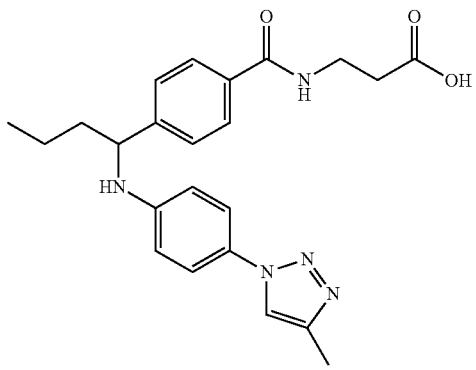 [SMILES: CCCC(Nc1ccc(-n2cc(C)nn2)cc1)c1ccc(C(=O)NCCC(=O)O)cc1]

The title compound was prepared by a method analogous to that described for Example 62 using Intermediate (47) and Intermediate (23). $^1$HNMR (400 MHz, CD$_3$OD, δ): 8.0 (s, 1H), 7.76 (d, 2H), 7.48 (d, 2H), 7.37 (d, 2H), 6.65 (d, 2H), 4.47 (m, 1H), 3.62 (m, 2H), 2.63 (m, 2H), 2.36 (s, 3H), 1.89-1.84 (m, 1H), 1.79-1.72 (m, 1H), 1.57-1.45 (m, 1H), 1.44-1.38 (m, 1H), 1.00 (m, 3H). MS (M+1): 422.4.

Example 93

(+/−)-3-(2-(3-methyl-1-(4-(4-(trifluoromethyl)-1H-pyrazol-1-yl)phenyl)butylamino)pyrimidine-5-carboxamido)propanoic acid

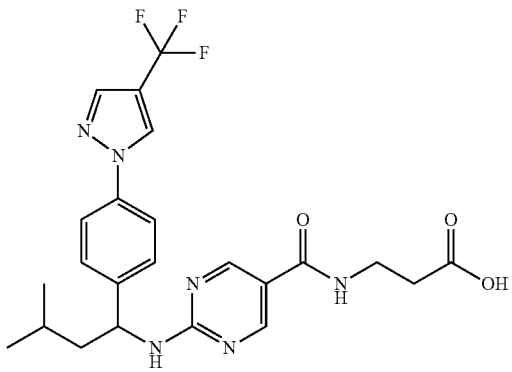 [SMILES: CC(C)CC(Nc1ncc(C(=O)NCCC(=O)O)cn1)c1ccc(-n2cc(C(F)(F)F)cn2)cc1]

Step A: (+/−)-ethyl 2-(3-methyl-1-(4-(4-(trifluoromethyl)-1H-pyrazol-1-yl)phenyl)butylamino)pyrimidine-5-carboxylate

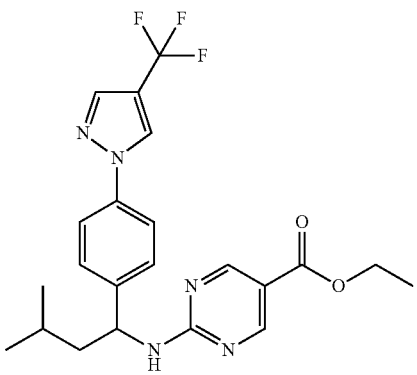 [SMILES: CCOC(=O)c1cnc(NC(CC(C)C)c2ccc(-n3cc(C(F)(F)F)cn3)cc2)nc1]

A vial was charged with Intermediate (14) (180 mg, 0.605 mmol), ethanol (5 mL), ethyl 2-chloropyrimidine-5-carboxylate (115 mg, 0.665 mmol), and diisopropylamine (156 mg, 1.21 mmol). The resulting mixture was heated under microwave irradiation at 100° C. for 20 minutes. The reaction mixture was diluted with water and extracted with ethyl acetate. The organic layer was dried over sodium sulfate, filtered and concentrated. Purification by column chromatography gave (+/−)-ethyl 2-(3-methyl-1-(4-(4-(trifluoromethyl)-1H-pyrazol-1-yl)phenyl)butylamino)pyrimidine-5-carboxylate (120 mg, 44%). $^1$H NMR (400 MHz, CDCl$_3$, δ): 8.80 (s, 2H), 8.13 (s, 1H), 7.88 (s, 1H), 7.62 (d, 2H), 7.46 (d, 2H), 5.97-5.95 (m, 1H), 5.29-5.22 (m, 1H), 4.34-4.29 (m, 2H), 1.82-1.78 (m, 1H), 1.70-1.66 (m, 2H), 1.35-1.32 (m, 3H), 0.99-0.95 (m, 6H).

Step B: (+/−)-3-(2-(3-methyl-1-(4-(4-trifluoromethyl)-pyrazol-1-yl)phenyl)butylamino)pyrimidine-5-carboxamido)propanoic acid To a solution of ethyl 2-(3-methyl-1-(4-(4-(trifluoromethyl)-1H-pyrazol-1-yl)phenyl)butylamino)pyrimidine-5-carboxylate (120 mg, 0.268 mmol) in anhydrous tetrahydrofuran (3 mL) was added 1N lithium hydroxide (0.83 mL, 0.83 mmol). The mixture was stirred at 50° C. overnight. The mixture was neutralized with 1N aqueous hydrochloric acid and extracted with ethyl acetate. The organic layer was dried over sodium sulfate, filtered and concentrated. The residue was dissolved in N,N-dimethylformamide (5 mL). O-(7-Azabenzotriazol-1-yl)-N,N,N',N'-tetramethyluronium hexafluorophosphate (149 mg, 0.393 mmol) was added. The mixture was stirred for 45 minutes at room temperature. Methyl 3-aminopropionate hydrochloride (54.3 mg, 0.393 mmol) and diisopropylethylamine (136 mg, 1.05 mmol) were added. The resulting mixture was stirred at room temperature for 2 hours. The mixture was diluted with aqueous ammonium chloride and ethyl acetate. The layers were separated and the organic layer was washed with water, dried over sodium sulfate, filtered and concentrated.

The residue was dissolved in water (5 mL) and tetrahydrofuran (5 mL). 1N Lithium hydroxide (0.774 mL, 0.774 mmol) was added. The mixture was stirred at room temperature for 2 hours. The mixture was neutralized with 1N aqueous hydrochloric acid and extracted with ethyl acetate. The organic layer was dried over sodium sulfate, filtered and concentrated. Purification by HPLC (column: Kromasil Eternity-5-C18 150×30 mm, 5 μm; modifier: formic acid 0.225%; gradient: 36 to 56% acetonitrile in water) gave (+/−)-3-(2-(3-methyl-1-(4-(4-(trifluoromethyl)-1H-pyrazol-1-yl)phenyl)butylamino)pyrimidine-5-carboxamido)propanoic acid (50 mg). $^1$H NMR (400 MHz, CD$_3$OD, δ): 8.70 (s, 1H), 8.64 (s, 2H), 7.96 (s, 1H), 7.73 (d, 2H), 7.53 (d, 2H), 5.27-5.21 (m, 1H), 3.62-3.53 (m, 2H), 2.68-2.53 (m, 2H), 1.94-1.82 (m, 1H), 1.79-1.68 (m, 1H), 1.68-1.58 (m, 1H), 1.06-0.91 (m, 6H). MS (M+1): 491.4.

Example 94

(+/−)-3-(4-(cyclopentyl(6-(4-(trifluoromethyl)-1H-pyrazol-1-yl)pyridine-3-ylamino)methyl)benzamido)propanoic acid

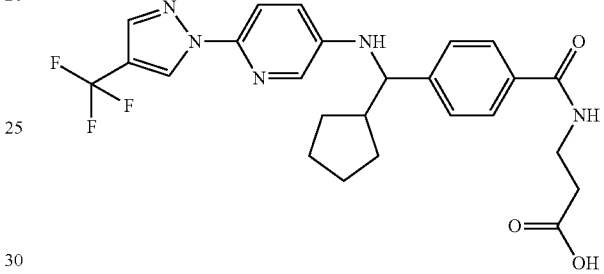

The title compound was prepared by a method analogous to that described for Example 1 using Intermediate (31) and Intermediate (32). $^1$H NMR (400 MHz, CDCl$_3$, δ): 8.54 (s, 1H), 7.82 (s, 1H), 7.77 (d, J=2.73 Hz, 1H), 7.69 (d, J=8.19 Hz, 2H), 7.60 (d, J=8.97 Hz, 1H), 7.40 (d, J=8.19 Hz, 2H), 7.01-6.95 (m, 1H), 6.93 (dd, J=8.88, 2.83 Hz, 1H), 4.15 (d, J=8.58 Hz, 1H), 3.77-3.66 (m, 2H), 2.76-2.65 (m, 2H), 2.25-2.12 (m, 1H), 2.00-1.87 (m, 1H), 1.73-1.16 (m, 7H). MS (M+1): 5022.

Example 95

3-(4-(cyclopentyl(6-(4-(trifluoromethyl)-1H-pyrazol-1-yl)pyridine-3-ylamino)methyl)benzamido)propanoic acid, Isomer 1

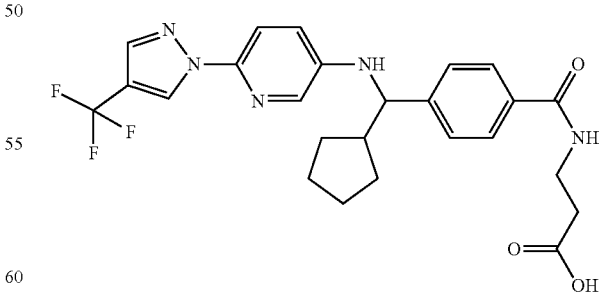

The title compound is obtained by resolving racemic 3-(4-(cyclopentyl(6-(4-(trifluoromethyl)-1H-pyrazol-1-yl)pyridine-3-ylamino)methyl)benzamido)propenoic acid, the compound of Example 94, by chiral SFC. Column: Chiralpak AD-H. Dimensions: 4.6 mm×25 cm. Mobile Phase: 80/20

CO₂/methanol. Flow Rate: 2.5 mL/min. Modifier: 0.2% isopropylamine. Retention time: 3.49 minutes.

Example 96

3-(4-(cyclopentyl(6-(4-(trifluoromethyl)-1H-pyrazol-1-yl)pyridine-3-ylamino)methyl)benzamido)propanoic acid, Isomer 2

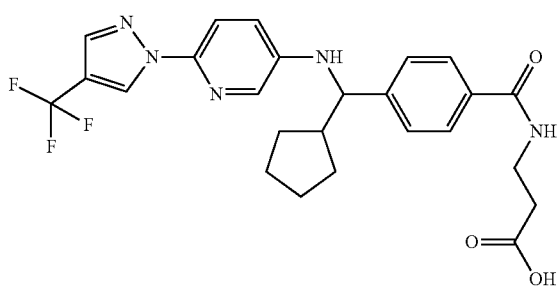 [SMILES: O=C(O)CCNC(=O)c1ccc(C(Nc2ccc(-n3cc(C(F)(F)F)cn3)nc2)C2CCCC2)cc1]

The title compound is obtained by resolving racemic 3-(4-(cyclopentyl(6-(4-(trifluoromethyl)-1H-pyrazol-1-yl)pyridine-3-ylamino)methyl)benzamido)propanoic acid, the compound of Example 94, by chiral SFC. Column: Chiralpak AD-H. Dimensions: 4.6 mm×25 cm. Mobile Phase: 80/20 CO₂/methanol. Flow Rate: 2.5 mL/min. Modifier: 0.2% isopropylamine. Retention time: 4.38 minutes.

Example 97

3-(4-(cyclopentyl(6-(4-(trifluoromethyl)-1H-imidazol-1-yl)pyridin-3-ylamino)methyl)benzamido)propanoic acid, Isomer 1

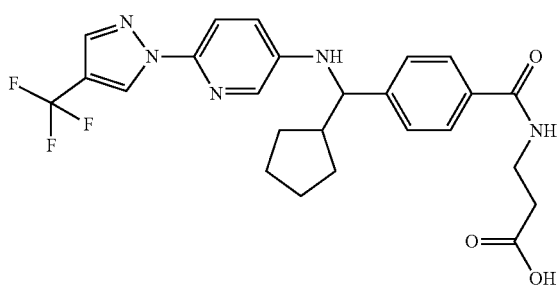 [SMILES: O=C(O)CCNC(=O)c1ccc(C(Nc2ccc(-n3cc(C(F)(F)F)cn3)nc2)C2CCCC2)cc1]

The title compound is obtained by resolving racemic 3-(4-(cyclopentyl(6-(4-(trifluoromethyl)-1H-imidazol-1-yl)pyridin-3-ylamino)methyl)benzamido)propanoic acid, the compound of Example 8, by chiral SFC. Column: Chiralpak AD-H. Dimensions: 4.6 mm×25 cm. Mobile Phase: 65/35 CO₂/2-propanol. Flow Rate: 2.5 mL/min. Modifier: none. Retention time: 3.92 minutes.

Example 98

3-(4-(cyclopentyl(6-(4-(trifluormethyl)-1H-imidazol-1-yl)pyridin-3-ylamino)methyl)benzamido)propanoic acid, Isomer 2

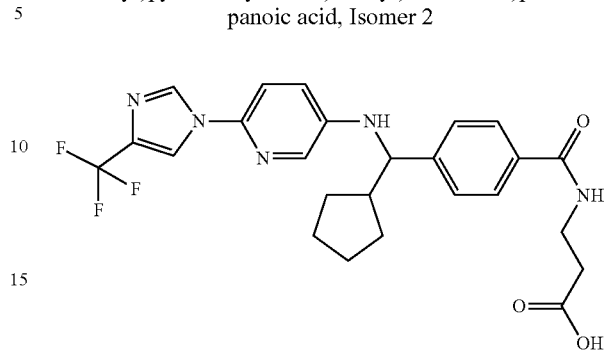

The title compound is obtained by resolving racemic 3-(4-(cyclopentyl(6-(4-(trifluoromethyl)-1H-imidazol-1-yl)pyridin-3-ylamino)methyl)benzamido)propenoic acid, the compound of Example 8, by chiral SFC. Column: Chiralpak AD-H. Dimensions: 4.6 mm×25 cm. Mobile Phase: 65/35 CO₂/2-propanol. Flow Rate: 2.5 mL/min. Modifier: none. Retention time: 4.91 minutes.

Example 99

(+/−)-3-(2-(cyclohexyl(6-(4-(trifluoromethyl)-1H-imidazol-1-yl)pyridine-3-yl)methylamino)nicotinamido)propanoic acid

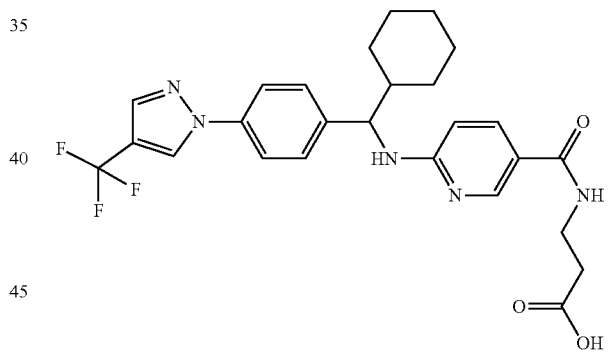

Step A: (+/−)-methyl 6-(cyclohexyl(4-(4-(trifluoromethyl)-1H-pyrazol-1-yl)phenyl)methylamino)nicotinate

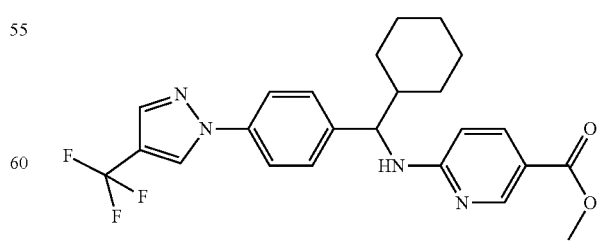

A round bottom flask equipped with a condenser was charged with Intermediate (2) (230 mg, 0.958 mmol) and 2-methyl-2-propane-sulfinamide (120 mg, 0.958 mmol) in dichloromethane (5 mL). Titanium(IV) ethoxide (437 mg, 1.92 mmol) was added in one portion and the mixture was stirred at reflux for 2 hours. Then methanol (1.5 mL) and saturated sodium bicarbonate (1.5 mL) were added to the reaction. A precipitate formed. The mixture was diluted with ethyl acetate and the slurry was filtered through celite, rinsing with ethyl acetate. The organics were dried over sodium sulfate, filtered and concentrated to give (E)-N-(4-(4-(trifluoromethyl)-1H-pyrazol-1-yl)benzylidene)-2-methylpropane-2-sulfinamide (290 mg, 0.845 mmol).

This crude residue was diluted in tetrahydrofuran (3 mL) and cooled to −78° C. Cyclohexyl magnesium chloride (1.27 mL, 2M in diethyl ether, 2.54 mmol) was then added dropwise. The reaction mixture was warmed to room temperature and stirred for 3 hours. The mixture was quenched with saturated aqueous ammonium chloride and extracted three times with ethyl acetate. The combined organic layers were washed with brine, dried over sodium sulfate, filtered and concentrated. The crude material was dissolved in methanol (4.2 mL). Hydrogen chloride (4M in dioxane) was added. The mixture was stirred at room temperature for 3 hours. The reaction was then concentrated. To this crude residue was added N,N-dimethylformamide (1 mL), methyl 6-fluoronicotinate (155 mg, 1.0 mmol) and potassium carbonate (207 mg, 1.5 mmol). The reaction was heated to 120° C. for 2 hours. The mixture was diluted with water and extracted three times with ethyl acetate. The combined organic layers were washed with brine, dried over sodium sulfate, filtered and concentrated. Purification by column chromatography (0-45% ethyl acetate in heptane) gave (+/−)-methyl 6-(cyclohexyl(4-(4-(trifluoromethyl)-1H-pyrazol-1-yl)phenyl)methylamino)nicotinate. $^1$H NMR (400 MHz, CDCl$_3$, δ): 8.69 (d, J=1.56 Hz, 1H), 8.13 (s, 1H), 7.93-7.82 (m, 2H), 7.67-7.53 (m, 2H), 7.45-7.33 (m, 2H), 6.16 (d, J=8.78 Hz, 1H), 5.67-5.51 (m, 1H), 4.61-4.41 (m, 1H), 3.81 (s, 3H), 1.94-0.98 (m, 11H). MS (M+1): 459.1.

Step B: (+/−)-tert-butyl 3-(2-(cyclohexyl(4-(4-(trifluoromethyl)-1H-pyrazol-1-yl)phenyl)methylamino)nicotinamido)propanoate

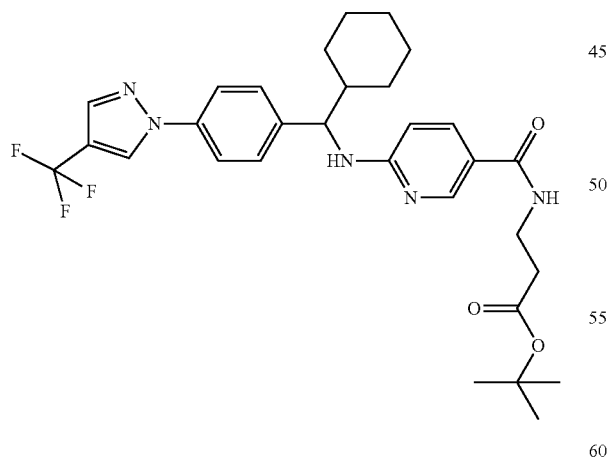

Lithium hydroxide (800 mg) was added to a solution of methyl 6-(cyclohexyl(4-(4-(trifluoromethyl)-1H-pyrazol-1-yl)phenyl)methylamino)nicotinate (129 mg, 0.281 mmol) in methanol (1.67 mL), tetrahydrofuran (1.67 mL), and water (1.67 mL). The mixture was stirred at room temperature for 4 hours. The mixture was acidified with 4N hydrochloric acid and extracted with three times with ethyl acetate. The combined organic layers were washed with brine, dried over sodium sulfate, filtered and concentrated.

To the crude acid was added N,N-dimethylformamide (2 mL), tert-butyl 3-aminopropanoate hydrochloride (94.1 mg, 0.518 mmol), O-(7-azabenzotriazol-1-yl)-N,N,N', N'-tetramethyluronium hexafluorophosphate) (197 mg, 0.518 mmol), and diisopropylethylamine (251 μL, 1.44 mmol). The mixture was stirred at room temperature overnight and was then concentrated. Purification by column chromatography (0-45% ethyl acetate in heptane), gave (+/−)-tert-butyl 3-(2-(cyclohexyl(4-(4-(trifluoromethyl)-1H-pyrazol-1-yl)phenyl)methylamino)nicotinamido) propanoate. $^1$H NMR (400 MHz, CDCl$_3$, δ): 8.49-8.40 (m, 1H), 8.12 (s, 1H), 7.85 (s, 1H), 7.75-7.66 (m, 1H), 7.59 (d, J=8.41 Hz, 2H), 7.36 (d, J=8.41 Hz, 2H), 6.73-6.58 (m, 1H), 6.24-6.10 (m, 1H), 5.58-5.41 (m, 1H), 4.57-4.38 (m, 1H), 3.66-3.50 (m, 2H), 2.53-2.40 (m, 2H), 2.08-0.95 (m, 11H), 1.41 (s, 9H). MS (M+1): 572.3.

Step C: (+/−)-3-(2-(cyclohexyl(4-(4-(trifluoromethyl)-1H-pyrazol-1-yl)phenyl)methylamino)nicotinamido)propanoic acid Trifluoroacetic acid (0.30 mL) was added to a solution of tert-butyl 3-(2-(cyclohexyl(6-(4-(trifluoromethyl)-1H-pyrazol-1-yl)pyridine-3-yl)methylamino)nicotinamido)propanoate (30 mg, 0.052 mmol) in dichloromethane (0.4 mL). The mixture was stirred at room temperature for 2 hours. The reaction was concentrated and the residue was co-evaporated with dichloromethane, ethyl acetate and toluene several times, to give (+/−)-3-(2-(cyclohexyl(4-(4-(trifluoromethyl)-1H-pyrazol-1-yl)phenyl)methylamino)nicotinamido)propenoic acid, as a solid. $^1$H NMR (400 MHz, CDCl$_3$, δ): 9.81 (br. s, 1H), 8.94 (hr. s, 1H), 8.31-8.21 (m, 1H), 8.15 (s, 1H), 7.87 (s, 1H), 7.66 (d, J=8.58 Hz, 2H), 7.61-7.51 (m, 1H), 7.39 (d, J=8.39 Hz, 2H), 6.70-6.58 (m, 1H), 4.29-4.17 (m, 1H), 3.69-3.53 (m, 2H), 2.76-2.65 (m, 2H), 2.00-0.91 (m, 11H). MS (M+1): 516.2.

Example 100

(+/−)-3-(4-(3,3-dimethyl-1-(6-(4-(trifluoromethyl)-1H-imidazol-1-yl)pyridine-3-ylamino)butyl)benzamido)propanoic acid

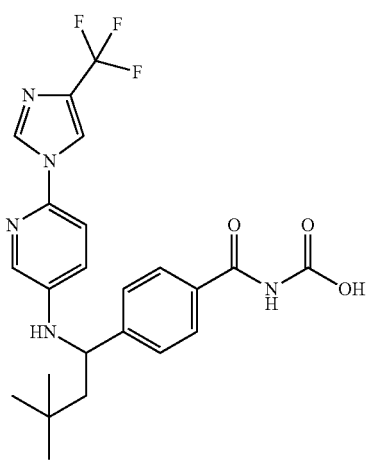 [SMILES: CC(C)(C)CC(Nc1ccc(-n2cnc(C(F)(F)F)c2)nc1)c1ccc(C(=O)NC(=O)O)cc1]

Step A: (+/−)-methyl 4-(3,3-dimethyl-1-(6-(4-(trifluoromethyl)-1H-imidazol-1-yl)pyridine-3-ylamino)butyl)benzoate

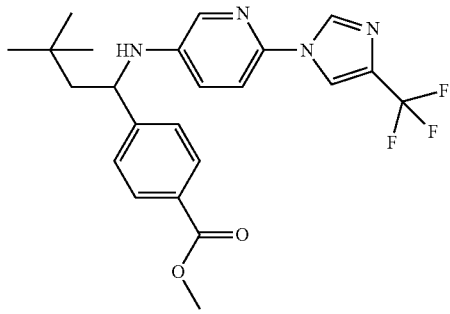 [SMILES: COC(=O)c1ccc(C(CC(C)(C)C)Nc2ccc(-n3cnc(C(F)(F)F)c3)nc2)cc1]

To a solution of Intermediate (43) (220 mg, 0.939 mmol) and Intermediate (6) (214 mg, 0.939 mmol) in methanol (48 mL) was added decaborane (57.3 mg, 0.469 mmol). The mixture was stirred at room temperature for 48 hours. The reaction mixture was concentrated and purification by preparative TLC gave methyl 4-(3,3-dimethyl-1-(6-(4-(trifluoromethyl)-1H-imidazol-1-yl)pyridine-3-ylamino)butyl)benzoate (50 mg, 12%). $^1$H NMR (400 MHz, CDCl$_3$, δ): 8.03 (s, 1H), 7.94 (d, 2H), 7.71 (m, 2H), 7.32 (d, 2H), 7.01 (d, 1H), 6.78-6.75 (m, 1H), 4.41-4.34 (m, 1H), 3.83 (s, 3H), 1.71-1.68 (m, 2H), 0.95 (s, 9H).

Step B: (+/−)-3-(4-(3,3-dimethyl-1-(6-(4-(trifluoromethyl)-1H-imidazol-1-yl)pyridine-3-ylamino)butyl)benzamido)propanoic acid To a solution of methyl 4-(3,3-dimethyl-1-(6-(4-(trifluoromethyl)-1H-imidazol-1-yl)pyridine-3-ylamino)butyl)benzoate (50 mg, 0.11 mmol) in tetrahydrofuran (5 mL) was added 2N lithium hydroxide (5 mL, 10 mmol). The reaction mixture was heated to 70° C. for 12 hours. The mixture was adjusted to pH=2 by addition of 1N aqueous hydrochloric acid and the resulting solution extracted with ethyl acetate. The organic layer was dried over sodium sulfate, filtered and concentrated. The residue was dissolved in N,N-dimethylformamide (5 mL). O-(7-Azabenzotriazol-1-yl)-N,N,N',N'-tetramethyluronium hexafluorophosphate (70.0 mg, 0.184 mmol) was added and the solution stirred at room temperature for 30 minutes. Methyl 3-aminopropionate hydrochloride (19.3 mg, 0.138 mmol) was added followed by diisopropylamine (47.6 mg, 0.37 mmol). The resulting mixture was stirred at room temperature for 1 hour. Saturated aqueous ammonium chloride was added and the mixture was extracted with ethyl acetate. The organic layer was dried over sodium sulfate, filtered and concentrated. The residue was dissolved in tetrahydrofuran (4 mL) and 2N Lithium hydroxide (4 mL, 8 mmol) was added. The mixture was stirred at room temperature for 1 hour. 1N Aqueous hydrochloric acid was added to adjust the pH=2 and the solution was extracted with ethyl acetate. The organic layer was dried over sodium sulfate, filtered and concentrated. Purification by HPLC (column: Boston Analytics Symmetrix ODS-H 150×30 mm, 5 μm; modifier: formic acid 0.225%; gradient: 39 to 59% acetonitrile in water) gave (+/−)-3-(4-(3,3-dimethyl-1-(6-(4-(trifluoromethyl)-1H-imidazol-1-yl)pyridine-3-ylamino)butyl)benzamido) propanoic acid (22.7 mg, 41%). $^1$H NMR (400 MHz, CD$_3$OD, δ): 8.21 (s, 1H), 8.01 (s, 1H), 7.72 (s, 1H), 7.65 (d, 2H), 7.36 (d, 2H), 7.26 (d, 1H), 6.94 (m, 1H), 4.48-4.45 (m, 1H), 3.51-3.48 (m, 2H), 2.53-2.49 (m, 2H), 1.81-1.75 (m, 1H), 1.58-1.53 (m, 1H), 0.94 (s, 9H). MS (M+1): 504.3.

Example 101

(+/−)-3-(4-(cyclohexyl(6-(4-(trifluoromethyl)-1H-pyrazol-1-yl)pyridine-3-ylamino)methyl)benzamido) propanoic acid

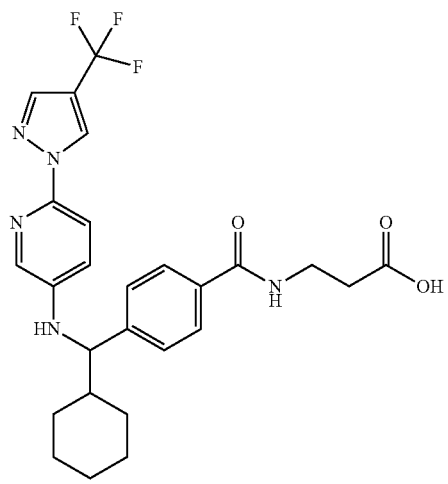 [SMILES: O=C(O)CCNC(=O)c1ccc(C(Nc2ccc(-n3cc(C(F)(F)F)cn3)nc2)C2CCCCC2)cc1]

The title compound was prepared by a method analogous to that described for Example 100 using Intermediate (44) and Intermediate (32). $^1$HNMR (400 MHz, CD$_3$OD, δ): 8.64 (s, 1H), 7.86 (s, 1H), 7.74-7.72 (m, 3H), 7.55 (d, 1H), 7.42 (d, 2H), 7.04 (m, 1H), 4.19 (m, 1H), 3.59 (m, 2H), 2.60 (m, 2H), 2.07-2.04 (m, 1H), 1.79-1.66 (m, 4H), 1.43-1.40 (m, 1H), 1.30-1.04 (m, 5H). MS (M+1): 516.2.

Example 102

(+/−)-3-(6-(3-methyl-1-(5-methy-6-(4-(trifluoromethyl)-1H-pyrazol-1-yl)pyridin-3-ylamino)butyl) nicotinamido)propanoic acid

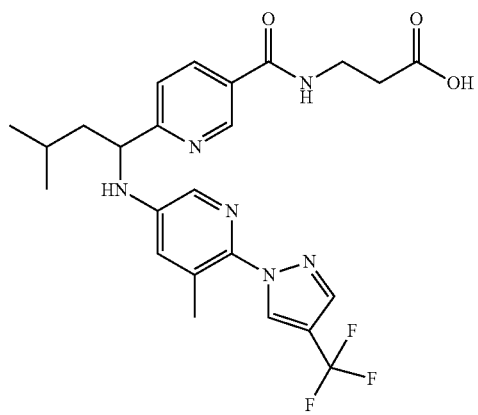 [SMILES: Cc1cc(NC(CC(C)C)c2ccc(C(=O)NCCC(=O)O)cn2)cnc1-n1cc(C(F)(F)F)cn1]

Step A: 5-methyl-6-(4-(trifluoromethyl)-1H-pyrazol-1-yl)pyridin-3-amine

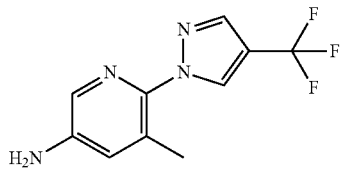

The title compound was prepared by a method analogous to that described for Intermediate (6) using 4-trifluoromethyl-1H-pyrazole and 2-chloro-3-methyl-5-nitro-pyridine. $^1$H NMR (400 MHz, CDCl$_3$, δ): 8.21 (s, 1H), 7.85 (s, 1H), 7.75 (d, J=2.4 Hz, 1H), 6.93 (d, J=2.4 Hz, 1H), 3.85 (s, 2H), 2.32 (s, 3H).

Step B: methyl 6-((5-methyl-6-(4-(trifluoromethyl)-1H-pyrazol-1-yl)pyridin-3-ylimino)methyl)nicotinate

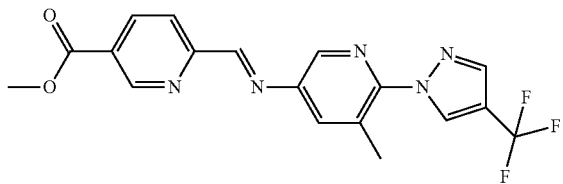 [SMILES: COC(=O)c1ccc(/C=N/c2cnc(-n3cc(C(F)(F)F)cn3)c(C)c2)nc1]

A mixture of methyl 6-formylnicotinate (251.3 mg, 1.52 mmol) and 5-methyl-6-(4-(trifluoromethyl)-1H-pyrazol-1-yl)pyridin-3-amine (369 mg, 1.52 mmol) in toluene (8 mL) was heated at reflux under nitrogen overnight. The reaction mixture was concentrated to give methyl 6-((5-methyl-6-(4-(trifluoromethyl)-1H-pyrazol-1-yl)pyridin-3-ylimino)methyl)nicotinate (592 mg, 100%). $^1$H NMR (400 MHz, (CD$_3$)$_2$SO, δ): 9.09 (d, 1H), 8.83 (s, 1H), 8.72 (s, 1H), 8.35-8.30 (m, 2H), 8.20-8.17 (m, 1H), 8.11 (s, 1H), 7.90 (d, 1H), 3.79 (s, 3H), 2.32 (s, 3H).

Step C: (+/−)-methyl 6-(3-methyl-1-(5-methy-6-(4-(trifluoromethyl)-1H-pyrazol-1-yl)pyridin-3-ylamino)butyl)nicotinate

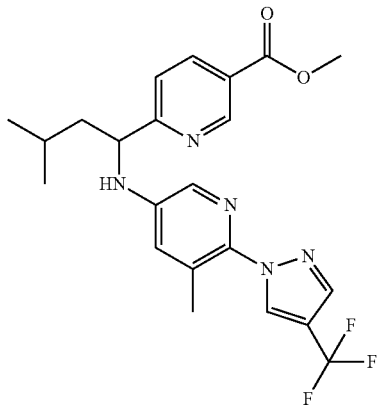 [SMILES: COC(=O)c1ccc(C(CC(C)C)Nc2cnc(-n3cc(C(F)(F)F)cn3)c(C)c2)nc1]

To a 0° C. solution of methyl 6-((5-methyl-6-(4-(trifluoromethyl)-1H-pyrazol-1-yl)pyridin-3-ylimino)methyl)nicotinate (592 mg, 1.52 mmol) in anhydrous tetrahydrofuran (8 mL) was added isobutylmagnesium bromide (1.0 mL, 2.0M in THF, 2.0 mmol). The reaction mixture was allowed to warm to room temperature and stir for 3 hours. Saturated aqueous ammonium chloride (10 mL) was added and the mixture extracted with ethyl acetate. The organic layer was washed with brine, dried over sodium sulfate, filtered and concentrated. Purification by preparative TLC gave methyl 6-(3-methyl-1-(5-methyl-6-(4-(trifluoromethyl)-1H-pyrazol-1-yl)pyridin-3-ylamino)butyl)nicotinate (250 mg). $^1$H NMR (400 MHz, CDCl$_3$, δ): 9.18-9.17 (m, 1H), 8.26-8.23 (m, 1H), 8.16 (s, 1H), 7.81 (s, 1H), 7.69-7.68 (m, 1H), 7.40-7.38 (m, 1H), 6.79-6.78 (m, 1H), 4.65-4.58 (m, 1H), 4.00 (s, 3H), 2.27 (s, 3H), 1.78-1.66 (m, 3H), 1.02 (d, 3H), 0.96 (d, 3H).

Step D: (+/−)-3-(6-(3-methyl-1-(5-methyl-6-(4-(trifluoromethyl)-1H-pyrazol-1-yl)pyridin-3-ylamino)butyl)nicotinamido)propanoic acid The title compound was prepared by a method analogous to that described for Example 100 step B using methyl 6-(3-methyl-1-(5-methyl-6-(4-(trifluoromethyl)-1H-pyrazol-1-yl)pyridin-3-ylamino)butyl)nicotinate. $^1$H NMR (400 MHz, CD$_3$OD, δ): 8.91 (d, 1H), 8.32 (s, 1H), 8.14-8.11 (m, 1H), 7.91 (s, 1H), 7.65-7.64 (d, 1H), 7.55-7.53 (m, 1H), 6.90-6.89 (m, 1H), 4.63-4.60 (m, 1H), 3.62-3.59 (m, 2H), 2.63-2.59 (m, 2H), 2.08 (s, 3H), 1.81-1.78 (m, 2H), 1.70-1.65 (m, 1H), 1.01 (d, 3H), 0.97 (d, 3H). MS (M+1): 505.3.

Example 103

3-(4-(1-(4-(4-(trifluoromethyl)-1H-pyrazol-1-yl)phenylamino)butyl)benzamido)propanoic acid, Isomer 1

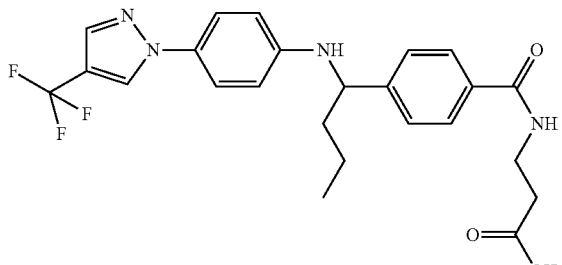

Step A: 4-(1-(4-(4-(trifluoromethyl)-1H-pyrazol-1-yl)phenylamino)butyl)benzoic acid

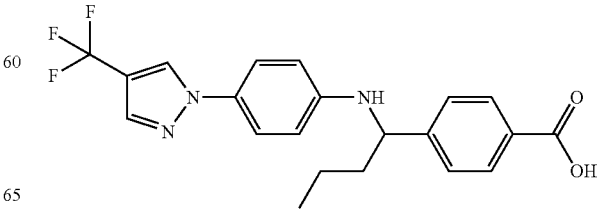

The title compound was prepared by a method analogous to that described for Example 1 using Intermediate (5) and Intermediate (52). MS (M−1): 402.0.

Step B: ethyl 3-(4-(1-(4-(4-(trifluoromethyl)-1H-pyrazol-1-yl)phenylamino)butyl)benzamido)propanoate, Isomers 1 and 2

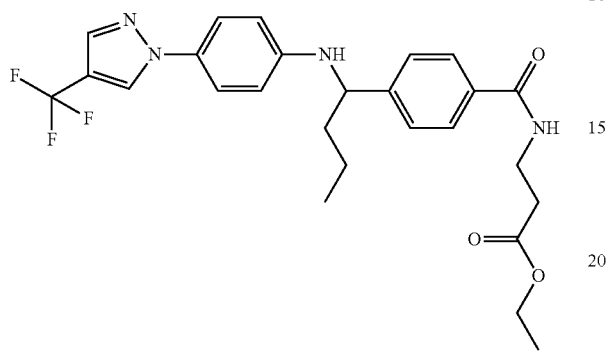

To a mixture of ethyl 3-aminopropanoate hydrochloride (418 mg, 2.72 mmol), 4-(1-(4-(4-(trifluoromethyl)-1H-pyrazol-1-yl)phenylamino)butyl)benzoic acid (732 mg, 1.82 mmol), 1-hydroxybenzotriazole hydrate (292 mg, 1.91 mmol), and N,N-diisopropylethylamine (1.20 mL, 7.26 mmol) in tetrahydrofuran (18.2 mL) was added 1-ethyl-3-(3-dimethylaminopropyl)carbodiimide (557 mg, 2.90 mmol). The mixture was stirred for 48 hours at ambient temperature. The reaction mixture was concentrated and the crude material was purified by column chromatography (0-100% ethyl acetate in heptane) to afford racemic ethyl 3-(4-(1-(4-(4-(trifluoromethyl)-1H-pyrazol-1-yl)phenylamino)butyl)benzamido)propanoate (684 mg, 85%) as a solid. The racemate was further purified via chiral SFC to afford 300 mg of Isomer 1 and 300 mg of Isomer 2, which were used in conversion to the final enatiopure products. $^1$H NMR (400 MHz, CDCl$_3$, δ): 7.94 (q, J=0.8 Hz, 1H), 7.81 (s, 1H), 7.73 (d, J=8.2 Hz, 2H), 7.39 (d, J=8.2 Hz, 2H), 7.32 (d, J=9.0 Hz, 2H), 6.84 (t, J=5.8 Hz, 1H), 6.53 (d, J=8.8 Hz, 2H), 4.42-4.34 (m, 1H), 4.31 (d, J=4.7 Hz, 1H), 4.16 (q, J=7.2 Hz, 2H), 3.71 (q, J=6.1 Hz, 2H), 2.63 (t, J=5.9 Hz, 2H), 1.88-1.71 (m, 2H), 1.53-1.31 (m, 2H), 1.27 (t, J=7.0 Hz, 3H), 0.95 (t, J=7.3 Hz, 3H). Chiral SFC: Chiralpak AD-H, 10×250 mm; Mobile Phase 65:35 CO$_2$/methanol, 65 mL/min, Retention time: 3.95 min (Isomer 1), 6.81 min (Isomer 2).

Step C: 3-(4-(1-(4-(4-(trifluoromethyl)-1H-pyrazol-1-yl)phenylamino)butyl)benzamido)propanoic acid, Isomer 1

Isomer 1 of ethyl 3-(4-(1-(4-(4-(trifluoromethyl)-1H-pyrazol-1-yl)phenylamino)butyl)benzamido)propenoate (0.300 g, 0.597 mmol) was dissolved in methanol (8.0 mL) and tetrahydrofuran (4.2 mL) and treated with 2N aqueous lithium hydroxide (4.2 mL, 8.4 mmol). The mixture was stirred at ambient temperature for 4 hours. The crude reaction mixture was concentrated and the residual solid was dissolved in water and acidified to pH=4 with 1.0M aqueous hydrochloric acid. A brown precipitate formed. The precipitate was collected by filtration, washed with water, and dried in vacuo to afford 3-(4-(1-(4-(4-(trifluoromethyl)-1H-pyrazol-1-yl)phenylamino)butyl)benzamido)propanoic acid, Isomer 1 (0.220 g, 78%) as a solid. $^1$H NMR (400 MHz, CDCl$_3$, δ): 7.91 (s, 1H), 7.78 (s, 1H), 7.67 (d, J=7.6 Hz, 2H), 7.35 (d, J=6.8 Hz, 2H), 7.27 (d, J=7.2 Hz, 2H), 7.03-6.88 (m, 1H), 6.60-6.42 (m, 2H), 4.33 (t, J=6.3 Hz, 1H), 3.64 (s, 2H), 2.72-2.54 (m, 2H), 1.87-1.65 (m, 2H), 1.51-1.22 (m, 2H), 0.90 (t, J=7.0 Hz, 3H). MS (M+1): 475.2.

Example 104

3-(4-(1-(4-(4-(trifluoromethyl)-1H-pyrazol-1-yl)phenylamino)butyl)benzamido)propanoic acid, Isomer 2

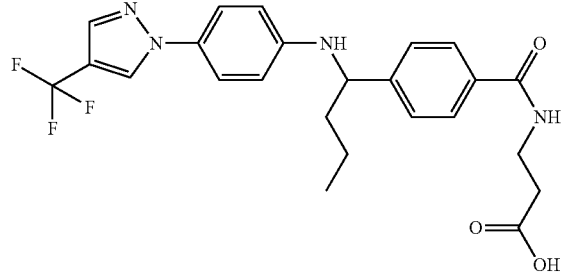 [SMILES: CCCC(Nc1ccc(-n2cc(C(F)(F)F)cn2)cc1)c1ccc(C(=O)NCCC(=O)O)cc1]

The title compound was prepared by a method analogous to that described for Example 103 using Isomer 2 of ethyl 3-(4-(1-(4-(4-(trifluoromethyl)-1H-pyrazol-1-yl)phenylamino)butyl)benzamido)propanoate. $^1$H NMR (400 MHz, CDCl$_3$, δ): 7.91 (s, 1H), 7.78 (s, 1H), 7.67 (d, J=7.6 Hz, 2H), 7.35 (d, J=6.8 Hz, 2H), 7.27 (d, J=7.2 Hz, 2H), 7.03-6.88 (m, 1H), 6.60-6.42 (m, 2H), 4.33 (t, J=6.3 Hz, 1H), 3.64 (s, 2H), 2.72-2.54 (m, 2H), 1.87-1.65 (m, 2H), 1.51-1.22 (m, 2H), 0.90 (t, J=7.0 Hz, 3H). MS (M+1): 475.2.

Example 105

(+/−)-3-(4-(3-methyl-1-(5-methyl-6-(4-(trifluoromethyl)-1H-pyrazol-1-yl)pyridin-3-ylamino)butyl)benzamido)propanoic acid

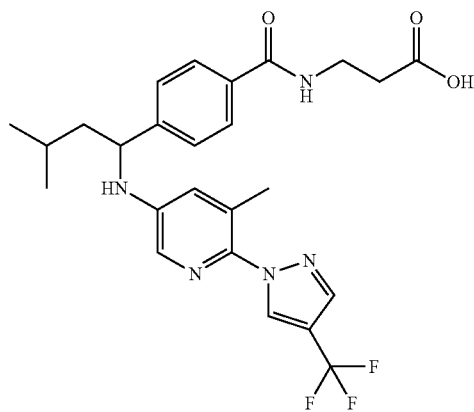 [SMILES: Cc1cc(NC(CC(C)C)c2ccc(C(=O)NCCC(=O)O)cc2)cnc1-n1cc(C(F)(F)F)cn1]

The title compound was prepared by a method analogous to that described for Example 62, using Intermediate (58) and 5-methyl-6-(4-(trifluoromethyl)-1H-pyrazol-1-yl)pyridin-3-amine (Step A of Example 102). $^1$H NMR (400 MHz, CD$_3$OD, δ): 8.32 (s, 1H), 7.92 (s, 1H), 7.77 (dd, J=2.4, 8.4 Hz, 2H), 7.65 (d, J=2.4 Hz, 1H), 7.48 (dd, J=2.0, 8.4 Hz, 2H), 6.91 (s, 1H), 4.54-4.58 (m, 1H), 3.61 (t, J=4.8 Hz, 2H), 2.60-2.64 (m, 2H), 2.08 (d, J=2.0 Hz, 3H), 1.72-1.86 (m, 2H), 1.53-1.61 (m, 1H), 0.97-1.04 (m, 6H). MS (M+1): 504.3.

Example 106

(+/−)-3-(4-(cyclobutyl(6-(4-(trifluoromethyl)-1H-pyrazol-1-yl)pyridin-3-ylamino)methyl)benzamido)propanoic acid

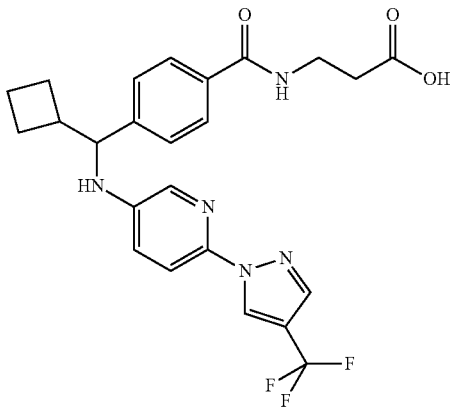 [SMILES: O=C(O)CCNC(=O)c1ccc(C(Nc2ccc(-n3cc(C(F)(F)F)cn3)nc2)C2CCC2)cc1]

The title compound was prepared by a method analogous to that described for Example 100, using Intermediate (59) and Intermediate (32). ¹H NMR (400 MHz, CDCl₃, δ): 8.66 (s, 1H), 7.88 (s, 1H), 7.76 (d, J=1.6 Hz, 1H), 7.75 (s, 2H), 7.58 (d, J=8.8 Hz, 1H), 7.48 (d, J=1.6 Hz, 1H), 7.47 (s, 1H), 7.05 (dd, J=2.8, 8.8 Hz, 1H), 4.36 (d, J=8.4 Hz, 1H), 3.60 (t, J=6.0 Hz, 2H), 2.59-2.68 (m, 3H), 2.24 (s, 1H), 1.75-2.00 (m, 5H). MS (M+1): 510.2.

Example 107

(+/−)-3-(4-(2-cyclopropyl-1-(6-(4-(trifluoromethyl)-1H-pyrazol-1-yl)pyridin-3-ylamino)ethyl)benzamido)propanoic acid

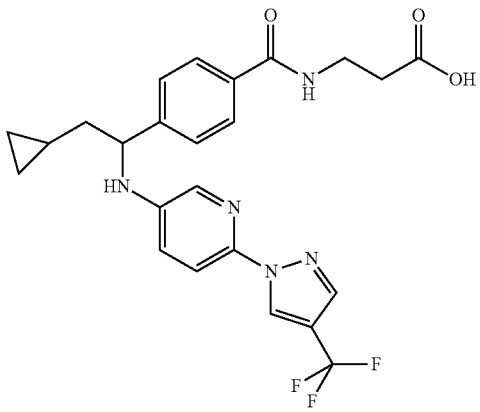 [SMILES: O=C(O)CCNC(=O)c1ccc(C(CC2CC2)Nc2ccc(-n3cc(C(F)(F)F)cn3)nc2)cc1]

The title compound was prepared by a method analogous to that described for Example 100, using Intermediate (60) and Intermediate (32). ¹H NMR (400 MHz, CD₃OD, δ): 8.61 (s, 1H), 7.83 (s, 1H), 7.70-7.72 (m, 3H), 7.54 (d, J=6.4 Hz, 1H), 7.46 (d, J=6.4 Hz, 2H), 7.01 (d, J=6.4 Hz, 1H), 4.48-4.52 (m, 1H), 3.55 (t, J=6.8 Hz, 2H), 2.56 (t, J=6.8 Hz, 2H), 1.78-1.89 (m, 1H), 1.52-1.61 (m, 1H), 0.67-0.79 (m, 1H), 0.31-0.49 (m, 2H), 0.00-0.14 (m, 2H). MS (M+1) 488.4.

Example 108

(+/−)-3-(4-(1-(3-methyl-4-(4-(trifluoromethyl)-1H-pyrazol-1-yl)phenoxy)butyl)benzamido)propanoic acid

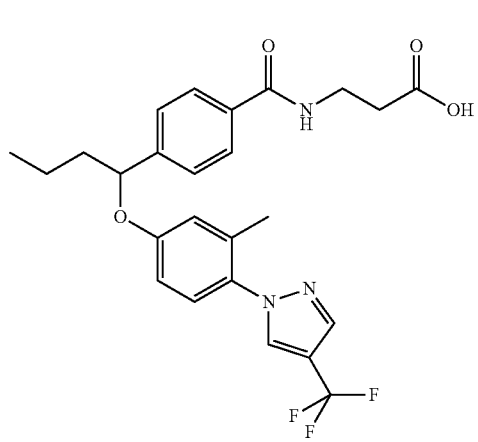 [SMILES: CCCC(Oc1ccc(-n2cc(C(F)(F)F)cn2)c(C)c1)c1ccc(C(=O)NCCC(=O)O)cc1]

The title compound was prepared by a method analogous to that described for Example 86, using Intermediate (61). ¹H NMR (400 MHz, CD₃OD, δ): 8.23 (s, 1H), 7.95 (s, 1H), 7.79 (d, J=8.0 Hz, 2H), 7.49 (d, J=8.0 Hz, 2H), 7.16 (d, J=8.8 Hz, 1H), 7.90 (s, 1H), 6.82 (d, J=8.8 Hz, 1H), 5.36-5.39 (m, 1H), 3.61-3.64 (m, 2H), 2.62-2.65 (m, 2H), 2.06 (s, 3H), 1.98-2.05 (m, 1H), 1.81-1.86 (m, 1H) 1.54-1.58 (m, 1H), 1.45-1.51 (m, 1H), 0.97-1.01 (m, 3H). MS (M+1) 490.4.

Example 109

3-(3-fluoro-4-(1-(6-(4-(trifluoromethyl)-1H-pyrazol-1-yl)pyridin-3-ylamino)butyl)benzamido)propanoic acid, Isomer 1

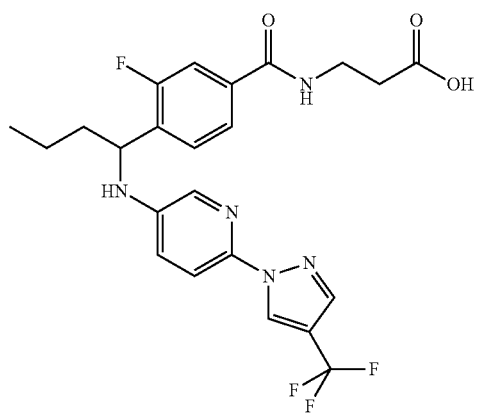 [SMILES: CCCC(Nc1ccc(-n2cc(C(F)(F)F)cn2)nc1)c1ccc(C(=O)NCCC(=O)O)cc1F]

Step A: (+/−)-methyl 3-fluoro-4-(1-(6-(4-(trifluoromethyl)-1H-pyrazol-1-yl)pyridin-3-ylamino)butyl)benzoate

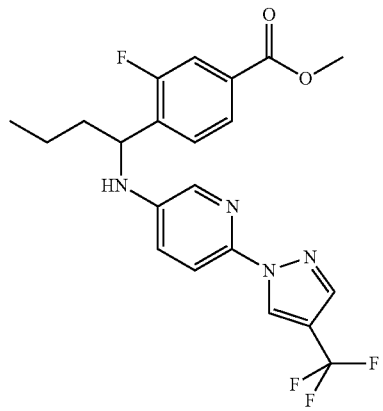 [SMILES: CCCC(Nc1ccc(-n2cc(C(F)(F)F)cn2)nc1)c1ccc(C(=O)OC)cc1F]

Decaborane (65.4 mg, 0.535 mmol) was added to a solution of Intermediate (32) (244 mg, 1.07 mmol) and Intermediate (62) (240 mg, 1.07 mmol) in methanol (8 mL). The reaction was heated to 60° C. for 24 hours. The reaction was cooled to 35° C. and stirred for another 24 hours. The reaction was concentrated and purified by flash column chromatography to give (+/−)-methyl 3-fluoro-4-(1-(6-(4-(trifluoromethyl)-1H-pyrazol-1-yl)pyridin-3-ylamino)butyl)benzoate (400 mg, 86%) as a yellow oil. $^1$H NMR (400 MHz, CDCl$_3$, δ): 8.55 (s, 1H), 7.60-7.90 (m, 5H), 7.29-7.33 (m, 1H), 6.86 (dd, J=8.8, 2.8 Hz, 1H), 4.64-4.69 (m, 1H), 4.16 (d, J=6.8 Hz, 1H), 3.83 (s, 3H), 1.75-1.98 (m, 2H), 1.21-1.45 (m, 2H), 0.90 (t, J=7.2 Hz, 3H).

Step B: methyl 3-(3-fluoro-4-(1-(6-(trifluoromethyl)-1H-pyrazol-1-yl)pyridin-3-ylamino)butyl)benzamido)propanoate, Isomers 1 and 2

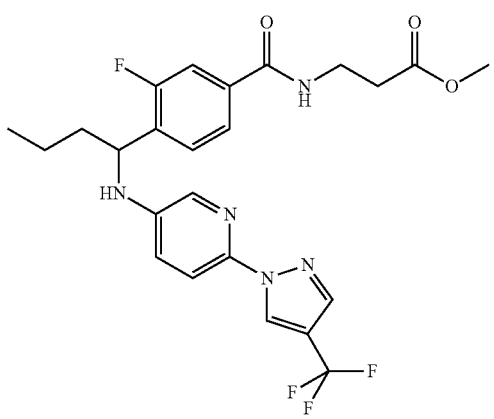 [SMILES: CCCC(Nc1ccc(-n2cc(C(F)(F)F)cn2)nc1)c1ccc(C(=O)NCCC(=O)OC)cc1F]

2 N Aqueous lithium hydroxide (15 mL, 30 mmol) was added to (+/−)-methyl 3-fluoro-4-(1-(6-(4-(trifluoromethyl)-1H-pyrazol-1-yl)pyridin-3-ylamino)butyl)benzoate (400 mg, 0.9 mmol) in tetrahydrofuran (15 mL). The reaction was heated to 80° C. for 12 hours. The reaction was cooled to room temperature and acidified to pH ~2 with 1 N aqueous hydrochloric acid. The mixture was extracted with ethyl acetate (3×10 mL) and the combined organics were dried over sodium sulfate, filtered, and concentrated to give a yellow solid (380 mg). The solid was taken up in N,N-dimethylformamide (30 mL) and O-(7-azabenzotriazol-1-yl)-N,N,N',N'-tetramethyluronium hexafluorophosphate (1.86 g, 4.88 mmol) was added. The mixture was stirred at room temperature for 30 minutes. Methyl 3-aminopropanoate hydrochloride (511 mg, 3.66 mmol) and diisopropylethylamine (1.26 g, 9.76 mmol) were added, and the reaction was stirred for 1 hour. The reaction was diluted with saturated aqueous ammonium chloride and extracted with ethyl acetate (3×30 mL). The combined organics were dried over sodium sulfate, filtered, and concentrated. Purification by flash column chromatography gave racemic methyl 3-(3-fluoro-4-(1-(6-(4-(trifluoromethyl)-1H-pyrazol-1-yl)pyridin-3-ylamino)butyl)benzamido)propanoate (450 mg, 96%) as a yellow solid. The racemate was further purified via chiral SFC to afford 180 mg of Isomer 1 and 150 mg of Isomer 2, which were used in conversion to the final enantiopure products. Chiral SFC: Chiralpak AD-3, 4.6×50 mm, 3 μm. Modifier: 0.05% DEA. Gradient: 95% CO$_2$/5% ethanol linear to 60% CO$_2$/40% ethanol over 3.0 minutes. Flow: 4 mL/min. Retention time: 1.44 minutes (Isomer 1), 1.75 minutes (Isomer 2).

Step C: 3-(3-fluoro-4-(1-(6-(4-(trifluoromethyl)-1H-pyrazol-1-yl)pyridin-3-ylamino)butyl)benzamido)propanoic acid, Isomer 1

To a solution of Isomer 1 of methyl 3-(3-fluoro-4-(1-(6-(4-(trifluoromethyl)-1H-pyrazol-1-yl)pyridin-3-ylamino)butyl)benzamido)propanoate (180 mg, 0.36 mmol) in tetrahydrofuran (8 mL) was added 2 N aqueous lithium hydroxide (8 mL, 16 mmol). The reaction was stirred at room temperature for 1 hour. The reaction mixture was acidified to pH ~2 with 1 N aqueous hydrochloric acid and extracted with ethyl acetate (3×5 mL). The combined organics were dried over sodium sulfate, filtered, and concentrated to give 3-(3-fluoro-4-(1-(6-(4-(trifluoromethyl)-1H-pyrazol-1-yl)pyridin-3-ylamino)butyl)benzamido)propanoic acid, Isomer 1 (104 mg, 59%) as a white solid. $^1$H NMR (400 MHz, CD$_3$OD, δ): 8.57 (s, 1H), 7.77 (s, 1H), 7.63 (s, 1H), 7.50 (d, J=8.8 Hz, 1H), 7.43-7.46 (m, 2H), 7.34-7.38 (m, 1H), 6.93 (d, J=8.8 Hz, 1H), 4.66 (t, J=6.8 Hz, 1H), 3.48 (t, J=6.8 Hz, 2H), 2.50 (t, J=6.8 Hz, 2H), 1.65-1.82 (m, 2H), 1.17-1.49 (m, 2H), 0.89 (t, J=6.8 Hz, 3H). MS (M+1) 494.2. Chiral SFC: Chiralpak AD-3, 4.6×50 mm, 3 μm. Modifier: 0.05% DEA. Gradient: 95% CO$_2$/5% ethanol linear to 60% CO$_2$/40% ethanol over 3.0 minutes. Flow: 4 mL/min. Retention time: 1.74 minutes, 100% ee (Isomer 1).

Example 110

3-(3-fluoro-4-(1-(6-(4-(trifluoromethyl)-1H-pyrazol-1-yl)pyridin-3-ylamino)butyl)benzamido)propanoic acid, Isomer 2

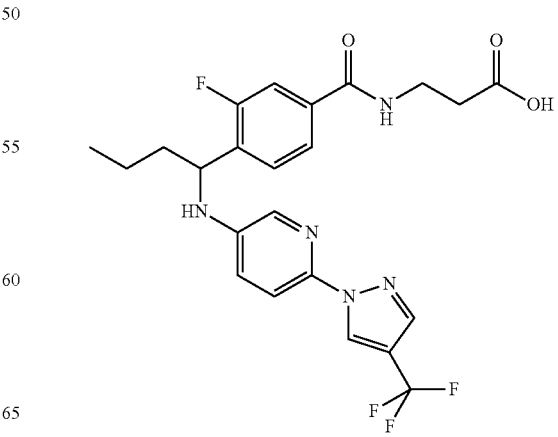

The title compound was prepared by a method analogous to that described for Example 109, using Isomer 2 of methyl 3-(3-fluoro-4-(1-(6-(4-(trifluoromethyl)-1H-pyrazol-1-yl)pyridin-3-ylamino)butyl)benzamido)propanoate in Step C. ¹H NMR (400 MHz, CD₃OD, δ): 8.57 (s, 1H), 7.77 (s, 1H), 7.63 (s, 1H), 7.50 (d, J=8.4 Hz, 1H), 7.43-7.46 (m, 2H), 7.34-7.38 (m, 1H), 6.94 (d, J=8.4 Hz, 1H), 4.66 (t, J=7.2 Hz, 1H), 3.48 (t, J=7.2 Hz, 2H), 2.50 (t J=6.8 Hz, 2H), 1.67-1.82 (m, 2H), 1.29-1.48 (m, 2H), 0.89 (t, J=7.6 Hz, 3H). MS (M+1) 494.2. Chiral SFC: Chiralpak AD-3, 4.6×50 mm, 3 μm. Modifier: 0.05% DEA. Gradient: 95% CO₂/5% ethanol linear to 60% CO₂/40% ethanol over 3.0 minutes. Flow: 4 mL/min. Retention time: 1.42 minutes, 99% ee (Isomer 2).

Example 111

3-(3-methyl-4-(1-(6-(4-(trifluoromethyl)-1H-pyrazol-1-yl)pyridin-3-ylamino)butyl)benzamido)propanoic acid, Isomer 1

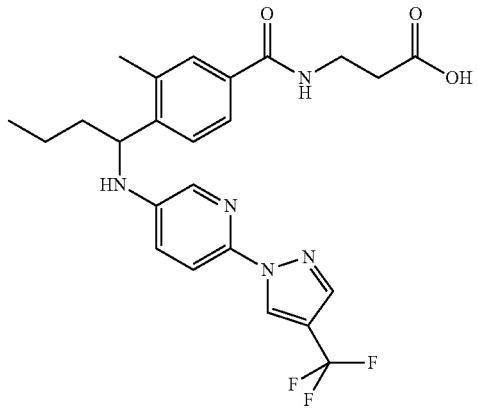 [SMILES: CCCC(Nc1ccc(-n2cc(C(F)(F)F)cn2)nc1)c1ccc(C(=O)NCCC(=O)O)cc1C]

Step A: methyl 3-(3-methyl-4-(1-(6-(4-(trifluoromethyl)-1H-pyrazol-1-yl)pyridin-3-ylamino)butyl)benzamido)propanoate, Isomers 1 and 2

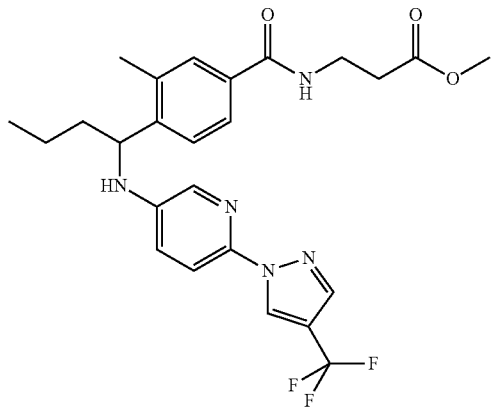 [SMILES: CCCC(Nc1ccc(-n2cc(C(F)(F)F)cn2)nc1)c1ccc(C(=O)NCCC(=O)OC)cc1C]

The title compounds were prepared by a method analogous to that described in Steps A-B of Example 109, using Intermediate (63). Purification of racemic methyl 3-(3-methyl-4-(1-(6-(4-(trifluoromethyl)-1H-pyrazol-1-yl)pyridin-3-ylamino)butyl)benzamido) propanoate via chiral SFC afforded 140 mg of Isomer 1 and 140 mg of Isomer 2, which were used in conversion to the final enantiopure products. ¹H NMR (400 MHz, CDCl₃, δ): 8.60 (s, 1H), 7.79 (s, 1H), 7.59-7.66 (m, 3H), 7.49 (d, J=8.0 Hz, 1H), 7.36 (d, J=8.4 Hz, 1H), 6.75-6.82 (m, 2H), 4.56-4.61 (m, 1H), 4.26 (d, J=4.8 Hz, 1H), 3.66-3.72 (m, 5H), 2.64 (t, J=5.8 Hz, 2H), 2.50 (s, 3H), 1.73-1.78 (m, 2H), 1.40-1.57 (m, 2H), 0.99 (t, J=7.2 Hz, 3H). Chiral SFC: Chiralpak AD-2, 30×50 mm, 3 μm. Modifier: none. Mobile Phase: 60/40 CO₂/ethanol. Flow rate: 80 mL/min. Retention time: 1.46 minutes (Isomer 1) and 2.13 minutes (Isomer 2).

Step B: 3-(3-methyl-4-(1-(6-(4-(trifluoromethyl)-1H-pyrazol-1-yl)pyridin-3-ylamino)butyl)benzamido) propanoic acid, Isomer 1

The title compound was prepared by a method analogous to that described in Step C of Example 109, using Isomer 1 of methyl 3-(3-methyl-4-(1-(6-(4-(trifluoromethyl)-1H-pyrazol-1-yl)pyridin-3-ylamino)butyl)benzamido)propanoate. ¹H NMR (400 MHz, CD₃OD, δ): 8.65 (s, 1H), 7.86 (s, 1H), 7.63 (d, J=2.8 Hz, 2H), 7.53-7.58 (m, 2H), 7.40 (d, J=8.0 Hz, 1H), 6.92 (dd, J=8.8, 2.8 Hz, 1H), 4.60-4.64 (m, 1H), 3.58 (t, J=6.4 Hz, 2H), 2.59 (t, J=7.0 Hz, 2H), 2.52 (s, 3H), 1.70-1.79 (m, 2H), 1.61-1.67 (m, 1H), 1.46-1.51 (m, 1H), 0.99 (t J=7.2 Hz, 3H). MS (M+1) 490.1. Chiral SFC: Chiralpak AD-H, 4.6×250 mm, 5 μm. Modifier: 0.05% DEA. Mobile Phase: 75/25 CO₂/ethanol. Flow rate: 35 mL/min. Retention time: 3.92 minutes, 99.9% ee (Isomer 1).

Example 112

3-(3-methyl-4-(1-(6-(4-(trifluoromethyl)-1H-pyrazol-1-yl)pyridin-3-ylamino)butyl)benzamido)propanoic acid, Isomer 2

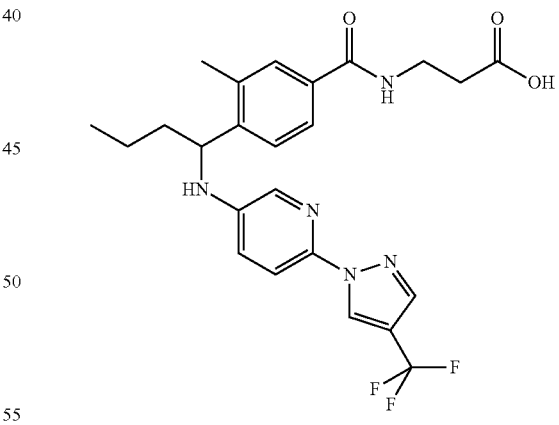

The title compound was prepared by a method analogous to that described for Example 111, using Isomer 2 of methyl 3-(3-methyl-4-(1-(6-(4-(trifluoromethyl)-1H-pyrazol-1-yl)pyridin-3-ylamino)butyl)benzamido)propanoate. ¹H NMR (400 MHz, CD₃OD, δ): 8.65 (s, 1H), 7.86 (s, 1H), 7.63 (d, J=2.8 Hz, 2H), 7.53-7.58 (m, 2H), 7.40 (d, J=8.0 Hz, 1H), 6.92 (dd, J=8.8, 2.8 Hz, 1H), 4.60-4.64 (m, 1H), 3.58 (t, J=6.4 Hz, 2H), 2.59 (t, J=7.0 Hz, 2H), 2.52 (s, 3H), 1.70-1.79 (m, 2H), 1.61-1.67 (m, 1H), 1.46-1.51 (m, 1H), 0.99 (t, J=7.2 Hz, 3H). MS (M+1) 490.1. Chiral SFC: Chiralpak AD-H, 4.6×250 mm, 5 μm. Modifier: 0.05% DEA. Mobile Phase: 75/25

CO₂/ethanol. Flow rate: 35 mL/min. Retention time: 5.38 minutes, 99.7% ee (Isomer 2).

Example 113

3-(4-(1-(2-(4-(trifluoromethyl)-1H-pyrazol-1-yl)pyrimidin-5-ylamino)butyl)benzamido)propanoic acid, Isomer 1

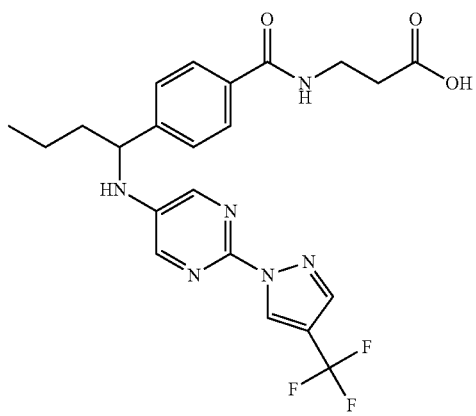 [SMILES: CCCC(Nc1cnc(-n2cc(C(F)(F)F)cn2)nc1)c1ccc(C(=O)NCCC(=O)O)cc1]

Step A: methyl 3-(4-(1-(2-(4-(trifluoromethyl)-1H-pyrazol-1-yl)pyrimidin-5-ylamino)butyl)benzamido)propanoate, Isomer 1 and 2

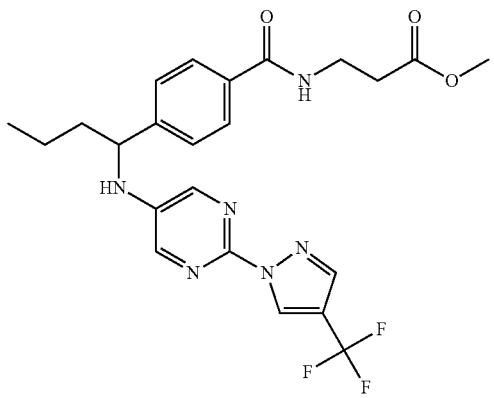 [SMILES: CCCC(Nc1cnc(-n2cc(C(F)(F)F)cn2)nc1)c1ccc(C(=O)NCCC(=O)OC)cc1]

The title compound was prepared by a method analogous to that described in Step A of Example 62, using Intermediate (64). Purification of racemic methyl 3-(4-(1-(2-(4-(trifluoromethyl)-1H-pyrazol-1-yl)pyrimidin-5-ylamino)butyl)benzamido)propanoate via chiral SFC afforded 400 mg of Isomer 1 and 420 mg of Isomer 2, which were used in conversion to the final enantiopure products. ¹H NMR (400 MHz, CD₃OD, δ): 8.84 (s, 1H), 8.08 (s, 2H), 7.99 (s, 1H), 7.79 (d, J=8.4 Hz, 2H), 7.50 (d, J=8.4 Hz, 2H), 4.52 (t, J=7.0 Hz, 1H), 3.69 (s, 3H), 3.63 (t, J=6.8 Hz, 2H), 2.66 (t, J=6.8 Hz, 2H), 1.75-1.99 (m, 2H), 1.39-1.60 (m, 2H), 1.00 (t, J=7.2 Hz, 3H). Chiral SFC: Chiralpak AD, 50×250 mm, 10 µm. Modifier: 0.05% DEA. Mobile Phase: 70/30 CO₂/methanol. Flow rate: 200 mL/min. Retention time: 8.65 minutes (Isomer 1) and 10.5 minutes (Isomer 2).

Step B: 3-(4-(1-(2-(4-(trifluoromethyl)-1H-pyrazol-1-yl)pyrimidin-5-ylamino)butyl)benzamido)propanoic acid, Isomer 1

The title compound was prepared by a method analogous to that described in Step C of Example 109, using Isomer 2 of methyl 3-(4-(1-(2-(4-(trifluoromethyl)-1H-pyrazol-1-yl)pyrimidin-5-ylamino)butyl)benzamido)propanoate. ¹H NMR (400 MHz, CD₃OD, δ): 8.73 (s, 1H), 7.97 (s, 2H), 7.89 (s, 1H), 7.68 (d, J=8.4 Hz, 2H), 7.38 (d, J=8.4 Hz, 2H), 4.40 (t, J=6.8 Hz, 1H), 3.50 (t, J=6.8 Hz, 2H), 2.52 (t, J=6.4 Hz, 2H), 1.67-1.82 (m, 2H), 1.20-1.50 (m, 2H), 0.87 (t, J=7.2 Hz, 3H). MS (M+1) 477.2. Chiral SFC: Chiralpak AD-3, 4.6×150 mm, 3 µm. Modifier: 0.05% DEA. Gradient: 95% CO₂/5% methanol linear to 60% CO₂/40% methanol over 16.0 minutes. Flow rate: 2.5 mL/min. Retention time: 7.69 minutes, 99.8% ee (Isomer 1).

Example 114

3-(4-((3,3-dimethylcyclobutyl)(6-(4-(trifluoromethyl)-1H-pyrazol-1-yl)pyridin-3-ylamino)methyl)benzamido)propanoic acid, Isomer 1

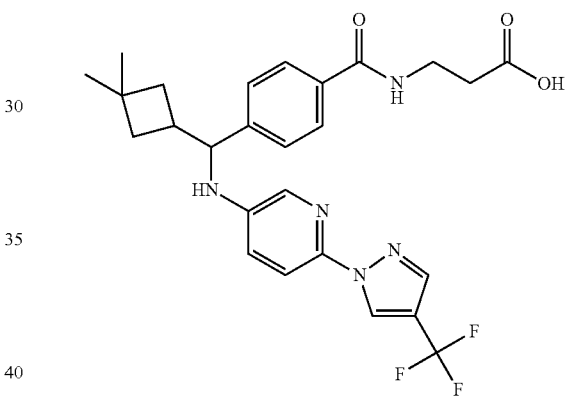

Step A: (+/−)-ethyl 4-((3,3-dimethylcyclobutyl)(6-(4-(trifluoromethyl)-1H-pyrazol-1-yl)pyridin-3-ylamino)methyl)benzoate

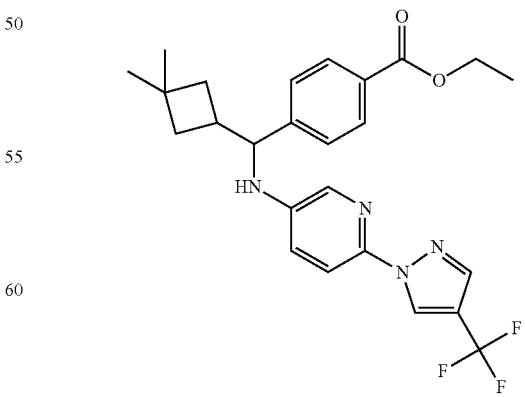

The title compound was prepared by a method analogous to that described in Step A of Example 1, using Intermediate

(65) and Intermediate (32). ¹H NMR (400 MHz, CDCl₃, δ): 8.54 (s, 1H), 7.93 (d, J=8.00 Hz, 2H), 7.72 (s, 1H), 7.55-7.60 (m, 2H), 7.31 (d, J=8.00 Hz, 2H), 6.79 (d, J=8.80 Hz, 1H), 4.26-4.31 (m, 2H), 4.14 (d, J=8.80 Hz, 1H), 2.38-2.43 (m, 1H), 1.92-1.98 (m, 1H), 1.50-1.67 (m, 3H), 1.30 (t, J=7.20 Hz, 3H), 1.06 (s, 3H), 1.01 (s, 3H). MS (M+1) 473.2.

Step B: 3-(4-((3,3-dimethylcyclobutyl)(6-(4-(trifluoromethyl)-1H-pyrazol-1-yl)pyridin-3-ylamino)methyl)benzamido)propanoic acid, Isomer 1

The title compound was prepared by a method analogous to that described in Steps B-C of Example 99, using (+/−)-ethyl 4-((3,3-dimethylcyclobutyl)(6-(4-(trifluoromethyl)-1H-pyrazol-1-yl)pyridin-3-ylamino)methyl)benzoate. Purification of racemic 3-(4-((3,3-dimethylcyclobutyl)(6-(4-(trifluoromethyl)-1H-pyrazol-1-yl)pyridin-3-ylamino)methyl)benzamido)propanoic acid via chiral SFC afforded the single enantiomer product. ¹H NMR (400 MHz, CDCl₃, δ): 8.53 (s, 1H), 7.84 (s, 1H), 7.80 (d, J=2.7 Hz, 1H), 7.68 (d, J=8.4 Hz, 2H), 7.61 (d, J=9.0 Hz, 1H), 7.38 (d, J=8.2 Hz, 2H), 6.98-7.05 (m, 1H), 6.95 (dd, J=8.9, 2.8 Hz, 1H), 4.21 (d, J=9.4 Hz, 1H), 3.72 (q, J=5.9 Hz, 2H), 2.72 (t, J=5.9 Hz, 2H), 2.42-2.56 (m, 1H), 1.99 (m, 1H), 1.53-1.73 (m, 3H), 1.11 (s, 3H), 1.07 (s, 3H). MS (M+1) 516.1. Chiral SFC: MiniGram-2, 20×250 mm. Modifier: None. Mobile Phase: 60/40 CO₂/ethanol. Flow rate: 10.0 mL/min. Retention time: 2.37 minutes (Isomer 1).

Example 115

3-(4-((3,3-dimethylcyclobutyl)(6-(4-(trifluoromethyl)-1H-pyrazol-1-yl)pyridin-3-ylamino)methyl)benzamido)propanoic acid, Isomer 2

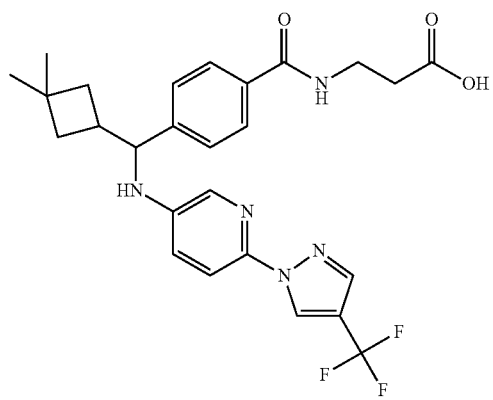 [SMILES: CC1(C)CC(C(Nc2ccc(-n3cc(C(F)(F)F)cn3)nc2)c2ccc(C(=O)NCCC(=O)O)cc2)C1]

The title compound was prepared by a method analogous to that described in Steps B-C of Example 99, using (+/−)-ethyl 4-((3,3-dimethylcyclobutyl)(6-(4-(trifluoromethyl)-1H-pyrazol-1-yl)pyridin-3-ylamino)methyl)benzoate. Purification of racemic 3-(4-((3,3-dimethylcyclobutyl)(6-(4-(trifluoromethyl)-1H-pyrazol-1-yl)pyridin-3-ylamino)methyl)benzamido)propanoic acid via chiral SFC afforded the single enantiomer product. ¹H NMR (400 MHz, CDCl₃, δ): 8.53 (s, 1H), 7.84 (s, 1H), 7.80 (d, J=2.7 Hz, 1H), 7.68 (d, J=8.4 Hz, 2H), 7.61 (d, J=9.0 Hz, 1H), 7.38 (d, J=8.2 Hz, 2H), 6.98-7.05 (m, 1H), 6.95 (dd, J=8.9, 2.8 Hz, 1H), 4.21 (d, J=9.4 Hz, 1H), 3.72 (q, J=5.9 Hz, 2H), 2.72 (t, J=5.9 Hz, 2H), 2.42-2.56 (m, 1H), 1.99 (m, 1H), 1.53-1.73 (m, 3H), 1.11 (s, 3H), 1.07 (s, 3H). MS (M+1) 516.1. Chiral SFC: MiniGram-2, 20×250 mm. Modifier: None. Mobile Phase: 60/40 CO₂/ethanol. Flow rate: 10.0 mL/min. Retention time: 4.12 minutes (Isomer 2).

Example 116

3-(4-(1-(4-(2H-indazol-2-yl)-3-methylphenoxy)butyl)benzamido)propanoic acid, Isomer 2

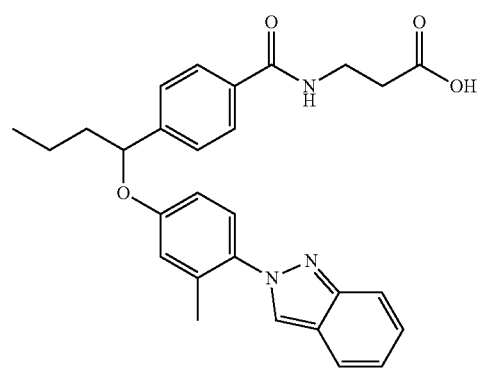 [SMILES: CCCC(Oc1ccc(-n2cc3ccccc3n2)c(C)c1)c1ccc(C(=O)NCCC(=O)O)cc1]

Step A: methyl 3-(4-(1-(4-(2H-indazol-2-yl)-3-methylphenoxy)butyl)benzamido)propanoate, Isomers 1 and 2

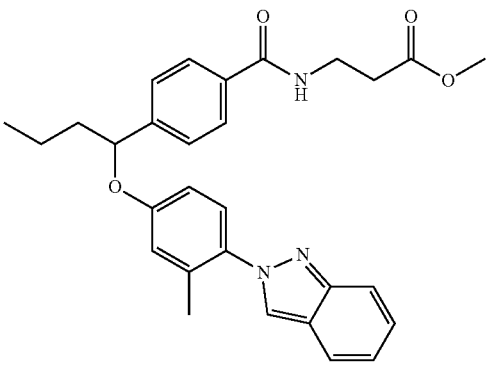 [SMILES: CCCC(Oc1ccc(-n2cc3ccccc3n2)c(C)c1)c1ccc(C(=O)NCCC(=O)OC)cc1]

The title compound was prepared by a method analogous to that described in Steps A-C of Example 82, using Intermediate (66) in Step A and methyl 3-aminopropanoate hydrochloride in Step C. Racemic methyl 3-(4-(1-(4-(2H-indazol-2-yl)-3-methylphenoxy)butyl)benzamido)propanoate was purified via chiral SFC to afford Isomer 1 and Isomer 2, which were used in conversion to the final enantiopure products. Chiral SFC: Berger MultiGram SFC, Mettler Toledo Co Ltd., OD 30×250 mm, 5 µm. Modifier: none. Mobile Phase: 60/40 CO₂/methanol. Flow rate: 50 nm/min. Retention time: 8.89 minutes (Isomer 1) and 9.42 minutes (Isomer 2).

Step B: 3-(4-(1-(4-(2H-indazol-2-yl)-3-methylphenoxy)butyl)benzamido)propanoic acid, Isomer 2

The title compound was prepared by a method analogous to that described in Step D of Example 82, using Isomer 2 of methyl 3-(4-(1-(4-(2H-indazol-2-yl)-3-methylphenoxy)butyl)benzamido)propanoate. ¹H NMR (400 MHz, CD₃OD, δ):

8.25 (s, 1H), 7.78 (d, J=8.4 Hz, 2H), 7.74 (d, J=8.4 Hz, 1H), 7.62 (d, J=8.8 Hz, 1H), 7.49 (d, J=8.4 Hz, 2H), 7.30-7.35 (m, 1H), 7.23 (d, J=8.4 Hz, 1H), 7.09-7.13 (m, 1H), 6.92 (d, J=2.4 Hz, 1H), 6.83 (dd, J=8.4, 2.8 Hz, 1H), 5.37-5.40 (m, 1H), 3.60 (t, J=6.4 Hz 2H), 2.61 (t, J=6.8 Hz, 2H), 1.96-2.02 (m, 4H), 1.80-1.86 (m, 1H), 1.44-1.57 (m, 2H), 1.00 (t, J=6.4 Hz, 3H). MS (M+1) 472.3. Chiral SFC: Chiralpak AD-3, 4.6×50 mm, 3 μm. Modifier: 0.05% DEA. Gradient 95% $CO_2$/5% methanol linear to 60% $CO_2$/40% methanol over 3 minutes. Flow rate: 4 mL/min. Retention time: 1.94 minutes, 96.1% ee (Isomer 2).

Example 117

3-(6-(cyclohexyl(2-methyl-4-(4-(trifluoromethyl)-1H-pyrazol-1-yl)phenyl)methylamino)nicotinamido)propanoic acid, Isomer 1

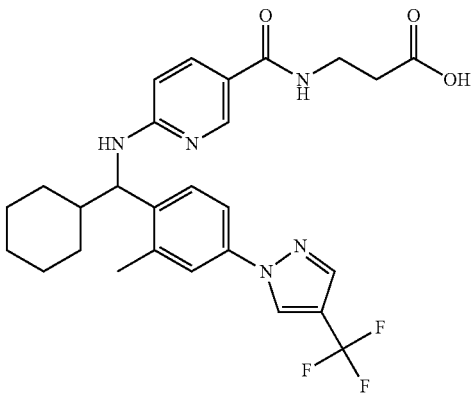 [SMILES: Cc1cc(-n2cc(C(F)(F)F)cn2)ccc1C(Nc1ccc(C(=O)NCCC(=O)O)cn1)C1CCCCC1]

Step A: (+/−)-cyclohexyl(2-methyl-4-(4-(trifluoromethyl)-1H-pyrazol-1-yl)phenyl)methanamine

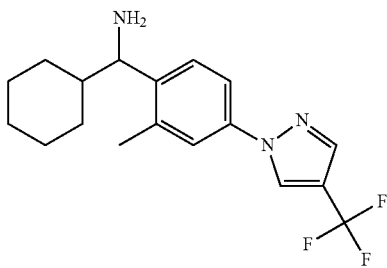 [SMILES: Cc1cc(-n2cc(C(F)(F)F)cn2)ccc1C(N)C1CCCCC1]

To a solution of Intermediate (67) (300.0 mg, 1.19 mmol) in tetrahydrofuran (3 mL) was added cyclohexylmagnesium bromide (1.79 mL, 3.58 mmol, 2 M in THF). The reaction vessel was sealed and heated to 120° C. in a microwave for 20 minutes. The reaction was cooled to 0° C. and methanol (1 mL) was added, followed by sodium borohydride (90.4 mg, 2.39 mmol). The reaction was stirred at 0° C. for 10 minutes. The reaction was quenched with water and extracted with ethyl acetate (3×10 mL). The combined organics were dried over sodium sulfate, filtered, and concentrated. Purification by flash column chromatography gave (+/−)-cyclohexyl(2-methyl-4-(4-(trifluoromethyl)-1H-pyrazol-1-yl)phenyl)methanamine (80 mg, 20%) as a brown solid. $^1$H NMR (400 MHz, CDCl$_3$, δ): 8.09 (s, 1H), 7.82 (s, 1H), 7.41-7.45 (m, 3H), 3.87 (d, J=8.00 Hz, 1H), 2.34 (s, 3H), 1.94-1.98 (m, 1H), 0.98-1.85 (m, 10H).

Step B: (+/−)-methyl 6-(cyclohexyl(2-methyl-4-(4-(trifluoromethyl)-1H-pyrazol-1-yl)phenyl)methylamino)nicotinate

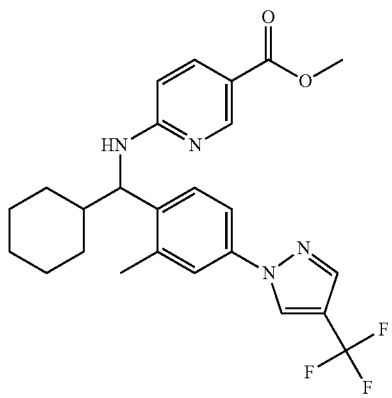 [SMILES: COC(=O)c1ccc(NC(c2ccc(-n3cc(C(F)(F)F)cn3)cc2C)C2CCCCC2)nc1]

To a solution of (+/−)-cyclohexyl(2-methyl-4-(4-(trifluoromethyl)-1H-pyrazol-1-yl)phenyl)methanamine (80.0 mg, 0.237 mmol) in N,N-dimethylformamide (3 mL) was added methyl 6-fluoronicotinate (55.2 mg, 0.356 mmol) and potassium carbonate (98.4 mg, 0.712 mmol). The reaction was heated to 110° C. and stirred overnight. The reaction was cooled to room temperature, diluted with water, and extracted with ethyl acetate (3×5 mL). The combined organics were dried over sodium sulfate, filtered, and concentrated. Purification by flash column chromatography gave (+/−)-methyl 6-(cyclohexyl(2-methyl-4-(4-(trifluoromethyl)-1H-pyrazol-1-yl)phenyl)methylamino)nicotinate (20 mg, 15%) as a yellow solid. $^1$H NMR (400 MHz, CDCl$_3$, δ): 8.63 (s, 1H), 8.06 (s, 1H), 7.79-7.82 (m, 2H), 7.43 (s, 1H), 7.33-7.36 (m, 1H), 7.25 (d, J=8.4 Hz, 1H), 6.03 (d, J=8.8 Hz, 1H), 5.39 (d, J=6.8 Hz, 1H), 4.74 (m, 1H), 3.75 (s, 3H), 2.49 (s, 3H), 1.85-1.88 (m, 1H), 1.58-1.72 (m, 5H), 1.05-1.19 (m, 5H).

Step C: methyl 3-(6-(cyclohexyl(2-methyl-4-(4-(trifluoromethyl)-1H-pyrazol-1-yl)phenyl)methylamino)nicotinamido)propanoate, Isomers 1 and 2

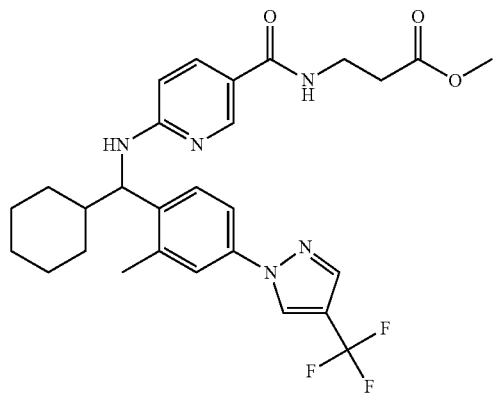 [SMILES: COC(=O)CCNC(=O)c1ccc(NC(c2ccc(-n3cc(C(F)(F)F)cn3)cc2C)C2CCCCC2)nc1]

The title compound was prepared by a method analogous to that described in Steps B-C of Example 82, using (+/−)-methyl 6-(cyclohexyl(2-methyl-4-(4-(trifluoromethyl)-1H-pyrazol-1-yl)phenyl)methylamino)nicotinate in Step B and methyl 3-aminopropanoate hydrochloride in Step C. Racemic methyl 3-(6-(cyclohexyl(2-methyl-4-(4-(trifluoromethyl)-1H-pyrazol-1-yl)phenyl)methylamino)nicotinamido)propanoate was purified by chiral SFC to afford Isomer 1 and Isomer 2, which were used in conversion to the final enantiopure products. Chiral SFC: Chiralpak AD-H, 4.6×250 mm, 5 μm. Modifier 0.05% DEA. Mobile Phase: 60/40 CO/ethanol. Flow: 2.35 mL/min. Retention time: 5.19 minutes (Isomer 1) and 7.83 minutes (Isomer 2).

Step D: 3-(6-(cyclohexyl(2-methyl-4-(4-(trifluoromethyl)-1H-pyrazol-1-yl)phenyl)methylamino)nicotinamido)propanoic acid, Isomer 1

The title compound was prepared by a method analogous to that described in Step D of Example 82, using Isomer 1 of methyl 3-(6-(cyclohexyl(2-methyl-4-(4-(trifluoromethyl)-1H-pyrazol-1-yl)phenyl)methylamino)nicotinamido)propanoate. $^1$H NMR (400 MHz, CD$_3$OD, δ): 8.68 (s, 1H), 8.41 (d, 1H), 7.95 (s, 1H), 7.72-7.75 (m, 1H), 7.54-7.57 (m, 2H), 7.45 (d, 1H), 6.49 (d, 1H), 5.08 (d, 1H), 3.55 (t, 2H), 2.56-2.60 (m, 5H), 2.08 (m, 1H), 1.68-1.79 (m, 4H), 1.40-1.50 (m, 1H), 1.00-1.35 (m, 5H). MS (M+1) 530.1. Chiral SFC: Chiralpak AD-3, 4.6×50 mm, 3 μm. Modifier: 0.05% DEA. Mobile Phase: 60/40 CO$_2$/2-propanol. Flow: 4 mL/min. Retention time: 0.78 minutes, 99.7% ee (Isomer 1).

Example 118

3-(6-(cyclohexyl(2-methyl-4-(4-(trifluoromethyl)-1H-pyrazol-1-yl)phenyl)methylamino)nicotinamido)propanoic acid, Isomer 2

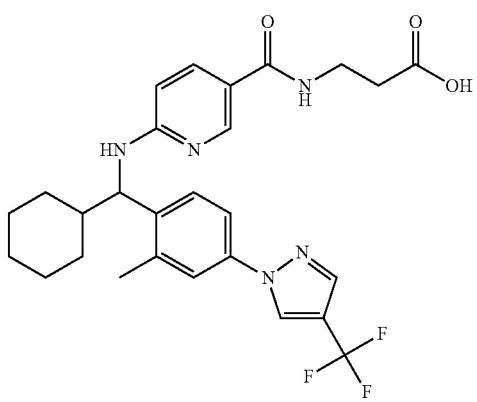 [SMILES: Cc1cc(-n2cc(C(F)(F)F)cn2)ccc1C(Nc1ccc(C(=O)NCCC(=O)O)cn1)C1CCCCC1]

The title compound was prepared by a method analogous to that described in Step D of Example 82, using Isomer 2 of methyl 3-(6-(cyclohexyl(2-methyl-4-(4-(trifluoromethyl)-1H-pyrazol-1-yl)phenyl)methylamino)nicotinamido)propanoate. $^1$H NMR (400 MHz, CD$_3$OD, δ): 8.68 (s, 1H), 8.41 (d, 1H), 7.95 (s, 1H), 7.72-7.75 (m, 1H), 7.54-7.57 (m, 2H), 7.45 (d, 1H), 6.49 (d, 1H), 5.08 (d, 1H), 3.55 (t, 2H), 2.56-2.60 (m, 5H), 2.08 (m, 1H), 1.68-1.79 (m, 4H), 1.40-1.50 (m, 1H), 1.00-1.35 (m, 5H). MS (M+1) 530.1. Chiral SFC: Chiralpak AD-3, 4.6×50 mm, 3 μm. Modifier: 0.05% DEA. Mobile Phase: 60/40 CO$_2$/2-propanol. Flow: 4 mL/min. Retention time: 1.46 minutes, 100% ee (Isomer 2).

Example 119

(+/−)-3-(4-((4-(2H-indazol-2-yl)phenoxy)cyclopentyl)methyl)benzamido)propanoic acid

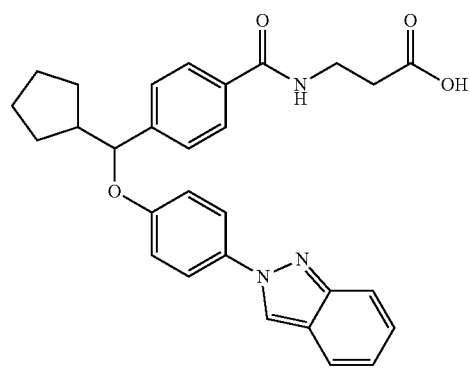 [SMILES: O=C(O)CCNC(=O)c1ccc(C(Oc2ccc(-n3cc4ccccc4n3)cc2)C2CCCC2)cc1]

The title compound was prepared by a method analogous to that described for Example 86, using Intermediate (55) and Intermediate (68), and heating the reaction in toluene to 110° C. for 18 hours in Step A. $^1$H NMR (400 MHz, CD$_3$OD, δ): 8.64 (s, 1H), 7.84 (d, J=8.4 Hz, 2H), 7.79 (dd, J=9.2, 2.8 Hz, 3H), 7.70 (d, J=8.8 Hz, 1H), 7.59 (d, J=8.0 Hz, 2H), 7.38 (t, J=7.2 Hz, 1H), 7.16 (t, J=8.0 Hz, 1H), 7.10 (d, 2H), 5.24 (d, J=7.6 Hz, 1H), 3.67 (t, J=6.8 Hz, 2H), 2.68 (t, J=6.8 Hz, 2H), 1.99-2.10 (m, 1H), 1.62-1.80 (m, 6H), 1.49-1.56 (m, 2H). MS (M+1) 484.4.

Example 120

3-(4-((6-(4-chloro-1-imidazol-1-yl)pyridin-3-ylamino)(cyclopentyl)methyl)benzamido)propanoic acid, Isomer 1

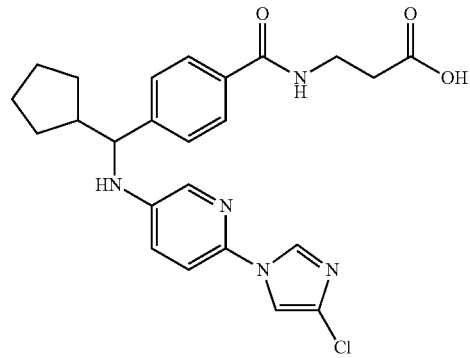 [SMILES: O=C(O)CCNC(=O)c1ccc(C(Nc2ccc(-n3cnc(Cl)c3)nc2)C2CCCC2)cc1]

201

Step A: ethyl 4-((6-(4-chloro-1H-imidazol-1-yl)pyridin-3-ylamino)(cyclopentyl)methyl)benzoate

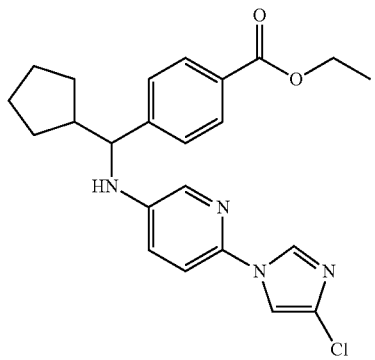 [SMILES: CCOC(=O)c1ccc(C(Nc2ccc(-n3cnc(Cl)c3)nc2)C2CCCC2)cc1]

The title compound was prepared by a method analogous to that described in Step A of Example 1, using Intermediate (31) and Intermediate (69). $^1$H NMR (400 MHz, CD$_3$OD, δ): 8.11 (d, J=1.6 Hz, 1H), 7.97 (d, J=8.4 Hz, 2H), 7.80 (d, J=2.8 Hz, 1H), 7.59 (d, J=1.6 Hz, 1H), 7.52 (d, J=8.0 Hz, 2H), 7.26 (d, J=8.8 Hz, 1H), 7.04 (dd, J=8.8, 2.8 Hz, 1H), 4.35 (q, J=7.2 Hz, 2H), 4.22 (d, J=8.8 Hz, 1H), 2.21-2.32 (m, 1H), 2.03-2.11 (m, 1H), 1.68-1.78 (m, 3H), 1.48-1.66 (m, 2H), 1.25-1.45 (m, 5H).

Step B: 3-(4-((6-(4-chloro-1H-imidazol-1-yl)pyridin-3-ylamino)(cyclopentyl)methyl)benzamido)propanoic acid, Isomer 1

The title compound was prepared by a method analogous to that described in Example 65, Steps B-C, using ethyl 4-((6-(4-chloro-1H-imidazol-1-yl)pyridin-3-ylamino)(cyclopentyl)methyl)benzoate. Racemic 3-(4-((6-(4-chloro-1H-imidazol-1-yl)pyridin-3-ylamino)(cyclopentyl)methyl)benzamido)propanoic acid was resolved by chiral SFC to afford the single enantiomer product. $^1$H NMR (400 MHz, CD$_3$OD, δ): 7.99 (d, J=1.2 Hz, 1H), 7.68 (d, J=2.8 Hz, 1H), 7.65 (d, J=8.4 Hz, 2H), 7.47 (d, J=1.6 Hz, 1H), 7.38 (d, J=8.4 Hz, 2H), 7.14 (d, J=8.8 Hz, 1H), 6.92 (dd, J=8.8, 2.8 Hz, 1H), 4.09 (d, J=9.2 Hz, 1H), 3.50 (t, J=6.8 Hz, 2H), 2.50 (t, J=6.8 Hz, 2H), 2.11-2.18 (m, 1H), 1.91-1.97 (m, 1H), 1.51-1.63 (m, 3H), 1.37-1.43 (m, 2H), 1.17-1.28 (m, 2H). MS (M+1) 468.1. Chiral SFC: Chiralcel AD-3, 4.6×50 mm, 3 μm. Modifier: 0.05% DEA. Mobile Phase: 40/60 CO$_2$/methanol. Flow rate: 3 mL/min. Retention time: 0.81 minutes, 100% ee (Isomer 1).

Example 121

(+/−)-3-(4-(2,2,2-trifluoro-1-(6-(4-(trifluoromethyl)-1H-imidazol-1-yl)pyridin-3-ylamino)ethyl)benzamido)propanoic acid

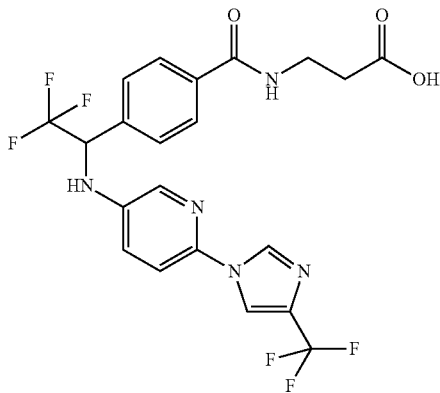 [SMILES: O=C(O)CCNC(=O)c1ccc(C(Nc2ccc(-n3cnc(C(F)(F)F)c3)nc2)C(F)(F)F)cc1]

202

Step A: (+/−)-N-(1-(4-bomophenyl)-2,2,2-trifluoroethyl)-6-(4-(trifluoromethyl)-1H-imidazol-1-yl)pyridin-3-amine

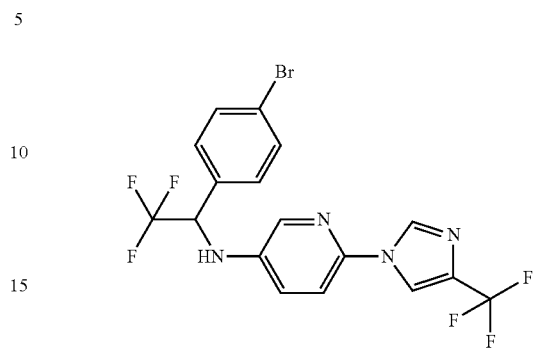

A solution of 1-(4-bromophenyl)-2,2,2-trifluoroethanone (253 mg, 1.00 mmol) in dichloromethane (10 mL) was cooled to 0° C. Added Intermediate (6) (228 mg, 1.00 mmol), titanium(IV) isopropoxide (1.1 g, 4.0 mmol), and diisopropylethylamine (0.7 mL, 4 mmol). The reaction was warmed to 30° C. and stirred for 18 hours. The reaction was cooled to 0° C. and sodium borohydride (80 mg, 2 mmol) was added. The reaction was allowed to warm to 30° C. and stir for 2 hours. The reaction was concentrated and purification by flash column chromatography gave (+/−)-N-(1-(4-bromophenyl)-2,2,2-trifluoroethyl)-6-(4-(trifluoromethyl)-1H-imidazol-1-yl)pyridin-3-amine (100 mg, 21%) as an oil. $^1$H NMR (400 MHz, CDCl$_3$, δ): 8.09 (s, 1H), 7.84 (d, J=2.8 Hz, 1H), 7.77 (s, 1H), 7.51 (d, J=8.4 Hz, 2H), 728 (d, J=8.4 Hz, 2H), 7.11 (d, J=9.2 Hz, 1H), 6.97 (dd, J=6.0, 8.8 Hz, 1H), 4.82 (m, 1H).

Step B: (+/−)-3-(4-(2,2,2-trifluoro-1-(6-(4-(trifluoromethyl)-1H-imidazol-1-yl)pyridin-3-ylamino)ethyl)benzamido)propenoic acid A mixture of (+/−)-N-(1-(4-bromophenyl)-2,2,2-trifluoroethyl)-6-(4-(trifluoromethyl)-1H-imidazol-1-yl)pyridin-3-amine (100 mg, 0.2 mmol), ethyl 3-aminopropanoate hydrochloride (90 mg, 0.6 mmol), molybdenum hexacarbonyl (57 mg, 0.21 mmol), 1,8-diazabicyclo[5.4.0]undec-7-ene (165 mg, 1.07 mmol), palladium(II) acetate (2.4 mg, 0.01 mmol), and tri-tert-butylphosphine tetrafluoroborate (9.4 mg, 0.03 mmol) in acetonitrile (2 mL) was heated to 170° C. for 5 minutes in a microwave. The reaction was diluted with water (20 mL) and extracted with ethyl acetate (2×20 mL). The combined organics were dried over sodium sulfate, filtered, and concentrated. The residue (40 mg) was taken up in tetrahydrofuran (2 mL) and cooled to 0° C. 2 N Aqueous lithium hydroxide (0.4 mL, 0.8 mmol) was added and the mixture was allowed to warm to room temperature and stir for 1 hour. The pH was adjusted to 4 with 1 N aqueous hydrochloric acid. The mixture was extracted with dichloromethane (2×20 mL). The combined organics were washed with water (30 mL) and brine (30 mL), dried over sodium sulfate, filtered, and concentrated. Purification by reversed-phase HPLC gave (+/−)-3-(4-(2,2,2-trifluoro-1-(6-(4-(trifluoromethyl)-1H-imidazol-1-yl)pyridin-3-ylamino)ethyl)benzamido)propanoic acid (12 mg, 31%) as a white solid. $^1$H NMR (400 MHz, CD$_3$OD, δ): 8.29 (s, 1H), 8.08 (s, 1H), 7.94 (d, J=2.8 Hz, 1H), 7.75 (d, J=8.4 Hz, 2H), 7.58 (d, J=8.0 Hz, 2H), 7.38 (d, J=9.2 Hz, 1H), 7.23 (dd, J=2.8, 8.8 Hz, 1H), 5.40 (m, 1H), 3.51 (t, J=6.8 Hz, 2H), 2.53 (t, J=6.8 Hz, 2H). MS (M+1) 502.0.

Example 122

3-(4-((6-(4-tert-butyl-1H-imidazol-1-yl)pyridin-3-ylamino)cyclopentyl)methyl)benzamido)propanoic acid

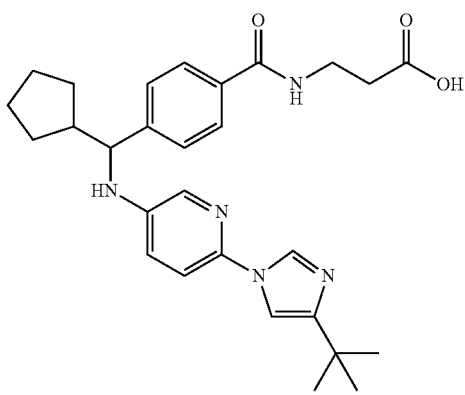 [SMILES: CC(C)(C)c1cn(-c2ccc(NC(c3ccc(C(=O)NCCC(=O)O)cc3)C3CCCC3)cn2)cn1]

To a 0° C. solution of Intermediate (68) (5 g, 20 mmol) in anhydrous dichloromethane (30 mL) was added triethylamine (6 g, 60 mmol) and methanesulfonyl chloride (2.54 g, 22 mmol). The solution was stirred at 20° C. for 4 h. The mixture was diluted with water and extracted with ethyl acetate (10 mL×3). The combined organic layers were dried over anhydrous $Na_2SO_4$, filtered, and concentrated under reduced pressure to afford crude ethyl 4-(cyclopentyl(methylsulfonyloxy)methyl)benzoate (6 g) as a yellow oil. To a solution of crude ethyl 4-(cyclopentyl(methylsulfonyloxy)methyl)benzoate (1.43 g, 4.58 mmol) and Intermediate (73) (900 mg, 3.92 mmol) in acetonitrile (15 mL) was added potassium carbonate (1.15 g, 8.33 mmol). The mixture was stirred at 80° C. for 12 h. The reaction was diluted with water and extracted with ethyl acetate (10 mL×3). The organic layer was dried over anhydrous $Na_2SO_4$ and concentrated under reduced pressure. Purification by silica gel chromatography gave impure ethyl 4-((6-(4-tert-butyl-1H-imidazol-1-yl)pyridin-3-ylamino)(cyclopentyl)methyl)benzoate (250 mg) as a colorless solid, which was dissolved in THF (8 mL). 8 mL 2N aqueous lithium hydroxide was added. The mixture was refluxed for 2 h. The mixture was adjusted to pH 1-2 by addition of 1N aqueous HCl and extracted with ethyl acetate (5 mL×3). The combined organic layers were dried over $Na_2SO_4$ and concentrated under reduced pressure to give a yellow solid which was dissolved in DMF (5 mL). HATU (425.7 mg, 1.12 mmol) was added. After 30 min methyl 3-aminopropanoate hydrochloride (116.13 mg, 0.84 mmol) was added followed by addition of diisopropylethelamine (361.78 mg, 2.8 mmol). The resulting mixture was stirred at room temperature for 2 h. The reaction mixture was diluted with saturated aqueous ammonium chloride and extracted with ethyl acetate (30 mL×3). The combined organic layers were dried over $Na_2SO_4$ and concentrated under reduced pressure to give a yellow solid which was dissolved in THF (5 mL). 5 mL 2N aqueous lithium hydroxide was added. The mixture was stirred at 25° C. for 2 h. The mixture was adjusted to pH 1-2 by addition of 1N aqueous HCl and extracted with ethyl acetate (5 mL×3). The combined organic layers were dried over $Na_2SO_4$ and concentrated under reduced pressure. HPLC purification using a Kromasil Eternity-5-$C_{18}$ 150×30 mm×5 μm column eluting with 23 to 43% acetonitrile in water (0.225% formic acid modifier) gave (+/−)-3-(4-((6-(4-tert-butyl-1H-imidazol-1-yl)pyridin-3-ylamino)(cyclopentyl)methyl)benzamido)propanoic acid (34 mg) as a colorless solid. $^1$H NMR (400 MHz, $CD_3OD$) δ 8.96 (s, 1H), 8.46-8.50 (m, 1H), 7.84 (d, J=2.8 Hz, 1H), 7.76 (d, J=8.0 Hz, 2H), 7.66 (d, J=1.2 Hz, 1H), 7.49 (d, J=8.4 Hz, 2H), 7.39 (d, J=9.2 Hz, 1H), 7.07 (dd, J=8.8, 3.2 Hz, 1H), 4.22 (d, J=9.2 Hz, 1H), 3.59-3.63 (m, 2H), 2.60-2.64 (m, 2H), 2.30-2.24 (m, 1H), 2.08-2.04 (m, 1H), 1.75-1.65 (m, 3H), 1.55-1.51 (m, 2H), 1.29-1.49 (m, 11H). MS (M+1)=490.2

Example 123

3-(4-(cyclopentyl(6-(4-isopropyl-1H-imidazol-1-yl)pyridin-3-ylamino)methyl)benzamido)propanoic acid

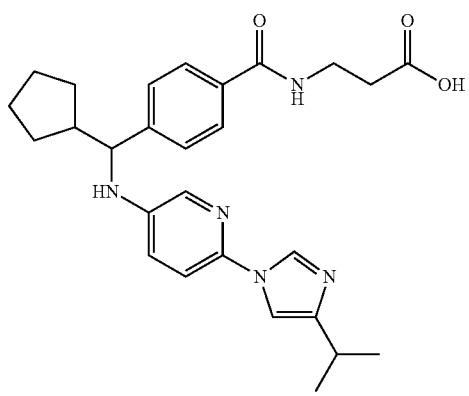 [SMILES: CC(C)c1cn(-c2ccc(NC(c3ccc(C(=O)NCCC(=O)O)cc3)C3CCCC3)cn2)cn1]

The title compound was prepared using a method analogous to that describe in Example 122, starting from Intermediate (76) and Intermediate (68). Colorless solid. $^1$H NMR (400 MHz, $CD_3OD$) δ 9.23 (d, J=1.6 Hz, 1H), 7.88 (d, J=2.8 Hz, 1H), 7.82 (s, 1H), 7.77 (d, J=8.4 Hz, 2H), 7.50 (d, J=8.4 Hz, 2H), 7.44 (d, J=8.8 Hz, 1H), 7.09 (dd, J=8.8 Hz, J=3.2 Hz, 1H), 4.24 (d, J=9.2 Hz, 1H), 3.60-3.64 (m, 2H), 3.12-3.02 (m, 1H), 2.61-2.65 (m, 2H), 2.48-2.25 (m, 1H), 2.13-2.02 (m, 1H), 1.81-1.62 (m, 3H), 1.59-1.49 (m, 2H), 1.48-1.30 (m, 1H), 1.36 (d, J=6.8 Hz, 6H). MS (M+1)=476.3.

Example 124

3-(4-(1-(4-(2-indazol-2-yl)phenoxy)butyl)benzamido)propanoic acid, Isomer 1

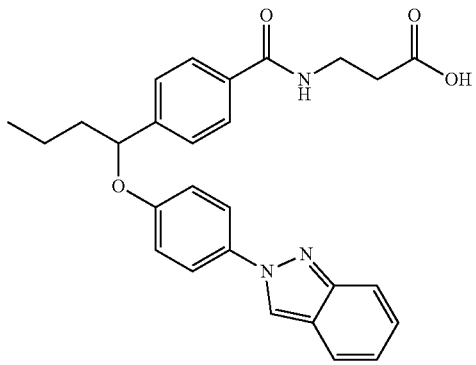 [SMILES: CCCC(Oc1ccc(-n2cc3ccccc3n2)cc1)c1ccc(C(=O)NCCC(=O)O)cc1]

Step A: (+/−)-3-(4-(1-(4-(2-indazol-2-yl)phenoxy)butyl)benzamido)propanoic acid Racemic 3-(4-(1-(4-(2-indazol-2-yl)phenoxy)butyl)benzamido)propanoic acid was prepared using a method analogous to that described for Example 86 using Intermediate 55 and ethyl 4-(1-hydroxybutyl)benzoate (prepared as described in preparation of Intermediate 5). $^1$H NMR (400 MHz, CD$_3$OD) δ 8.57 (s, 1H), 7.78 (d, J=8.4 Hz, 2H), 7.73-7.70 (m, 3H), 7.63 (d, J=8.8 Hz, 1H), 7.50 (d, J=8.4 Hz, 2H), 7.32-7.28 (m, 1H), 7.10-7.01 (m, 3H), 5.39-5.36 (m, 1H), 3.59 (m, 2H), 2.60 (m, 2H), 2.02-1.99 (m, 1H), 1.86-1.83 (m, 1H), 1.58-1.45 (m, 2H), 0.98 (t, J=7.2 Hz, 3H). MS (M+1)=458.2

Step B: 3-(4-(1-(4-(2-indazol-2-yl)phenoxy)butyl)benzamido)propanoic acid, Isomer 1

Racemic 3-(4-(1-(4-(2-indazol-2-yl)phenoxy)butyl)benzamido)propanoic acid was resolved by SFC (Column: OJ 300×50 mm×10 μm; Eluent: 60:40 CO$_2$:methanol; Flow rate: 200 mL/min; Modifier: none) to provide 3-(4-(1-(4-(2-indazol-2-yl)phenoxy)butyl)benzamido)propanoic acid, Isomer 1 (retention time: 1.38 min) and 3-(4-(1-(4-(2-indazol-2-yl)phenoxy)butyl)benzamido)propanoic acid, Isomer 2 (retention time 0.75 min) as colorless solids. Spectral data for isomer 1: $^1$H NMR (400 MHz, CD$_3$OD) δ 8.57 (s, 1H), 7.78 (d, J=8.4 Hz, 2H), 7.73-7.70 (m, 3H), 7.63 (d, J=8.8 Hz, 1H), 7.50 (d, J=8.4 Hz, 2H), 7.32-7.28 (m, 1H), 7.10-7.01 (m, 3H), 5.39-5.36 (m, 1H), 3.59 (m, 2H), 2.60 (m, 2H), 2.02-1.99 (m, 1H), 1.86-1.83 (m, 1H), 1.58-1.45 (m, 2H), 0.98 (t, J=7.2 Hz, 3H). MS (M+1)=458.2

Example 125

3-(4-(1-(4-(7-methyl-2H-indazol-2-yl)phenoxy)butyl)benzamido)propanoic acid

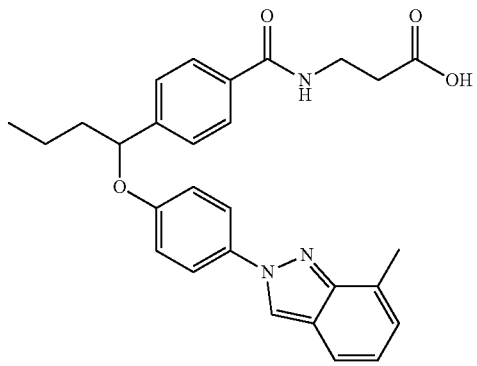

A suspension of Intermediate (77) (300 mg, 0.795 mmol), 7-methylindazole (126 mg, 0.954 mmol), copper(I) iodide (7.5 mg, 0.0397 mmol), K$_3$PO$_4$ (354 mg, 1.67 mmol) and N,N-dimethylcyclohexane-1,2-diamine (22.7 mg 0.159 mmol) in toluene (3 mL) was stirred at 48 h at 110° C. under a nitrogen atmosphere. The mixture was concentrated and the residue purified by preparative TLC to give 110 mg impure ethyl 4-(1-(4-(7-methyl-2H-indazol-2-yl)phenoxy)butyl)benzoate as an oil. This material was dissolved in THF (5 mL). 5 mL aqueous 2N sodium hydroxide was added. The resulting mixture was stirred at 30° C. overnight. The mixture was acidified to pH 3 by addition of 1N aqueous HCl. The mixture was extracted with ethyl acetate (3×5 mL). The combined organic layers were dried over anhydrous Na$_2$SO$_4$ and concentrated under reduced pressure. The residue was dissolved in DMF (2 mL). HATU (128.3 mg, 1.95 mmol) was added. The mixture was stirred for 20 min. Methyl 3-aminopropanoate hydrochloride (46.8 mg, 0.338 mmol), and diisopropylethylamine (145.4 mg, 1.125 mmol) were added. The resulting mixture was stirred at room temperature for 30 min. The mixture was poured into water (10 mL) and extracted with ethyl acetate (2×15 mL). The combined organic layers were washed with brine (20 mL), dried over anhydrous Na$_2$SO$_4$ and concentrated under reduced pressure. The residue was dissolved in THF (5 mL). 5 mL 2N aqueous lithium hydroxide was added. The resulting mixture was stirred at room temperature for 1 h. The mixture was adjusted to pH 5 by addition of 1N aqueous HCl. The mixture was extracted with ethyl acetate (2×10 mL). The combined organic layers were dried over anhydrous Na$_2$SO$_4$ and concentrated under reduced pressure. Preparative HPLC purification using a Kromasil Eternity-5-C$_{18}$ 150×30 mm×5 μm column eluting with 52 to 68% acetonitrile in water (0.225% formic acid modifier) gave 3-(4-(1-(4-(7-methyl-2H-indazol-2-yl)phenoxy)butyl)benzamido)propanoic acid (19.1 mg) as a colorless solid. $^1$H NMR (400 MHz, CD$_3$OD) δ 8.46 (s, 1H), 7.76 (d, J=8.4 Hz, 2H), 7.68 (d, J=8.8 Hz, 2H), 7.45-7.51 (m, 3H), 7.04-6.94 (m, 4H), 5.32-5.35 (m, 1H), 3.57-3.61 (m, 2H), 2.58-2.62 (m, 2H), 2.55 (s, 3H), 2.01-1.97 (m, 1H), 1.84-1.80 (m, 1H), 1.56-1.53 (m, 1H), 1.46-1.42 (m, 1H), 0.96 (t, J=7.2 Hz, 3H). MS (M+1)=472.1.

Example 126

3-(4-(1-(4-(6-methyl-2H-indazol-2-yl)phenoxy)butyl)benzamido)propanoic acid

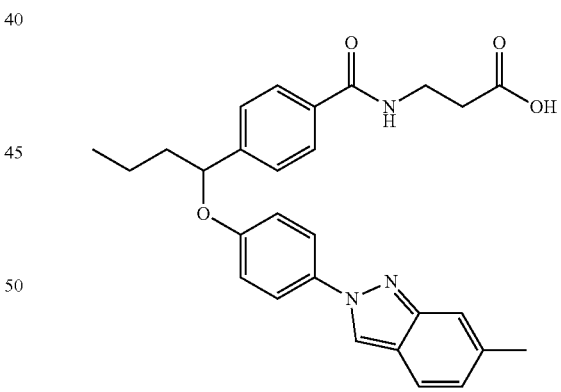

The title compound was prepared using a method analogous to that described for Example 125 using Intermediate (77) and 6-methylindazole. Colorless solid. $^1$H NMR (400 MHz, CD$_3$OD) δ 8.47 (d, J=12 Hz, 1H), 7.77 (d, J=8.4 Hz, 2H), 7.67 (d, J=8.8 Hz, 2H), 7.58 (d, J=8.8 Hz, 1H), 7.47 (d, J=8.4 Hz, 2H), 7.37 (s, 1H), 7.01 (d, J=8.8 Hz, 2H), 6.93 (dd, J=8.8, 1.2 Hz, 1H), 5.33-5.36 (m, 1H), 3.56-5.59 (m, 2H), 2.50-2.54 (m, 2H), 2.41 (s, 3H), 2.04-1.96 (m, 1H), 1.85-1.79 (m, 1H), 1.60-1.52 (m, 1H), 1.50-1.42 (m, 1H), 0.97 (t, J=7.2 Hz, 3H). MS (M+1)=472.4.

Example 127

3-(4-(1-(4-(4-methyl-2H-indazol-2-yl)phenoxy)butyl)benzamido)propanoic acid

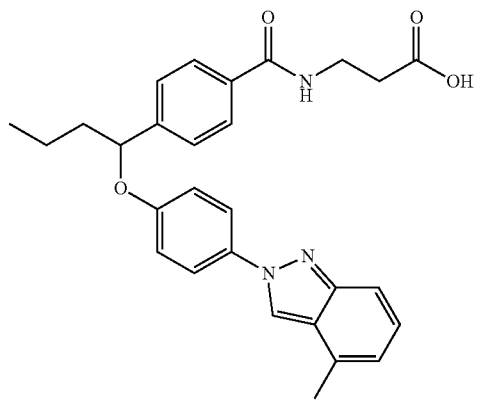 [SMILES: CCCC(Oc1ccc(-n2cc3c(C)cccc3n2)cc1)c1ccc(C(=O)NCCC(=O)O)cc1]

The title compound was prepared using a method analogous to that described for Example 126 using Intermediate (77) and 4-methylindazole. Colorless solid. $^1$H NMR (400 MHz CD$_3$OD) δ 8.63 (s, 1H), 7.77 (d, J=8.4 Hz, 2H), 7.72 (d, J=8.8 Hz, 2H), 7.49 (d, J=8.4 Hz, 2H), 7.43 (d, J=8.8 Hz, 1H), 7.20 (dd, J=8.8, 6.8 Hz, 1H), 7.03 (d, J=8.8 Hz, 2H), 6.84 (d, J=6.8 Hz, 1H), 5.35-5.38 (m, 1H), 3.57-3.61 (m, 2H), 2.59-2.62 (m, 2H), 2.54 (s, 3H), 2.02-1.98 (m, 1H), 1.85-1.82 (m, 1H), 1.56-1.55 (m, 1H), 1.48-1.44 (m, 1H), 0.98 (t, J=7.2 Hz, 3H). MS (M+1)=472.1.

Example 128

3-(4-(1-(4-(5-methyl-2H-indazol-2-yl)phenoxy)butyl)benzamido)propanoic acid

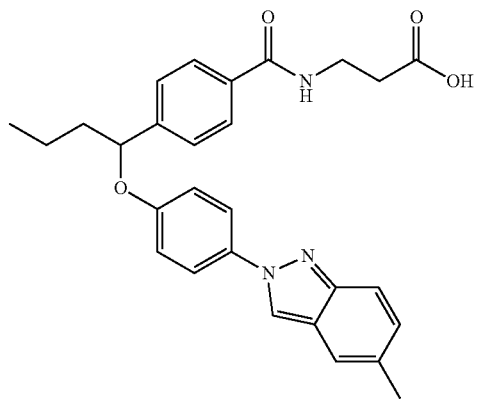 [SMILES: CCCC(Oc1ccc(-n2cc3cc(C)ccc3n2)cc1)c1ccc(C(=O)NCCC(=O)O)cc1]

The title compound was prepared using a method analogous to that described in Example 126 using Intermediate (77) and 5-methylindazole. Colorless solid. $^1$H NMR (400 MHz, CD$_3$OD) δ 8.42 (s, 1H), 7.77 (d. J=8.4 Hz, 2H), 7.67 (d, J=8.8 Hz, 2H), 7.44-7.52 (m, 4H), 7.15 (dd, J=8.8, 1.2 Hz, 1H), 7.00 (d, J=8.8 Hz, 2H), 5.33-5.36 (m, 1H), 3.57-3.60 (m, 2H), 2.53-2.56 (m, 2H), 2.38 (s, 3H), 2.04-1.96 (m, 1H), 1.85-1.78 (m, 1H), 1.61-1.52 (m, 1H), 1.50-1.40 (m, 1H), 0.97 (t, J=7.2 Hz, 3H). MS (M+1)=472.1.

Example 129

3-(4-(1-(6-(4-phenyl-1H-imidazol-1-yl)pyridin-3-ylamino)butyl)benzamido)propanoic acid, Isomer 1

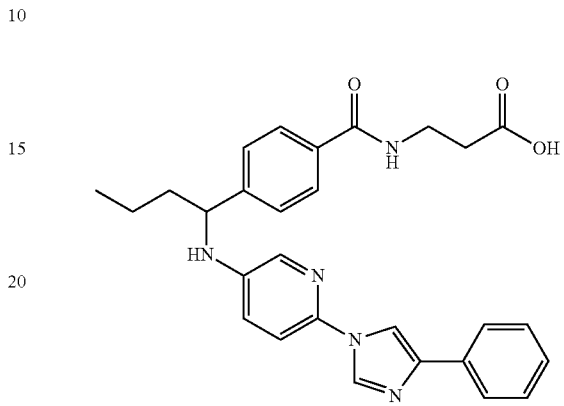

To a solution of Intermediate (78) (3.9 g, 27.1 mmol) 5-nitro-2-chloropyridine (5.15 g, 32.5 mmol) in acetonitrile (30 mL) was added potassium carbonate (7.47 g, 54.2 mmol). The resulting mixture was stirred at 85° C. overnight. The reaction mixture was washed with water (200 ml), and extracted with ethyl acetate (150 mL×4). The combined organic extracts were dried over Na$_2$SO$_4$, filtered, and concentrated under reduced pressure. The residue was dissolved in MeOH (20 mL). 10% Pd/C (800 mg) was added. The mixture was stirred overnight at 35° C. under a 40 psi atmosphere of hydrogen. The reaction mixture was filtered and concentrated under reduced pressure to give a yellow solid. The solid was dissolved in methanol (15 mL). Intermediate (23) (3.52 g, 12.71 mmol) was added followed by decaborane (776.6 mg, 6.35 mmol). The resulting mixture was stirred at 35° C. for 72 h. The reaction was concentrated and purified by silica gel chromatography to give methyl 3-(4-(1-(6-(4-phenyl-1H-imidazol-1-yl)pyridin-3-ylamino)butyl)benzamido)propanoate (1.1 g) as a yellow solid. The solid was dissolved in THF (8 mL). 8 mL 2N aqueous lithium hydroxide was added. The mixture was stirred at room temperature for 2 h. The mixture was acidified to pH 4 with 1 N aqueous HCl, and extracted with ethyl acetate (4×100 mL). The combined organic layers were dried over Na$_2$SO$_4$ and concentrated. Purification by silica gel chromatography gave racemic 3-(4-(1-(6-(4-phenyl-1H-imidazol-1-yl)pyridin-3-ylamino)butyl)benzamido)propanoic acid as a colorless solid. Resolution of this material by SFC (Column: Chiralcel AD 250×30 mm×20 μm, mobile phase: 45:55 CO$_2$:methanol, flow rate: 80 mL/min) gave 3-(4-(1-(6-(4-phenyl-1H-imidazol-1-yl)pyridin-3-ylamino)butyl)benzamido)propanoic acid, Isomer 1 (retention time: 2.63 min) and 3-(4-(1-(6-(4-phenyl-1H-imidazol-1-yl)pyridin-3-ylamino)butyl)benzamido)propanoic acid, Isomer 2 (retention time 0.85 min). Spectral data for isomer 1: $^1$H NMR (400 MHz, CD$_3$OD) δ 8.29 (s, 1H), 7.99 (s, 1H), 7.81 (d, J=2.4 Hz, 1H), 7.78 (d, J=5.6 Hz, 4H), 7.49 (d, J=8.0 Hz, 2H), 7.40-7.35 (m, 3H), 7.26 (t, J=7.0 Hz, 1H), 7.06 (dd, J=8.8, 2.0 Hz, 1H), 4.47 (t, J=7.0 Hz, 1H), 3.61 (t, J=7.0 Hz, 2H), 2.62 (t, J=6.8 Hz, 2H), 1.95-1.86 (m, 1H), 1.83-1.76 (m, 1H), 1.59-1.56 (m, 1H), 1.46-1.39 (m, 1H), 0.99 (t, J=7.4 Hz, 3H). MS (M+1)=484.2.

Example 130

(+\-)-3-(4-(1-(4-(4-chloro-1H-pyrazol-1-yl)-3,5-dimethylphenoxy)butyl)benzamido)propanoic acid

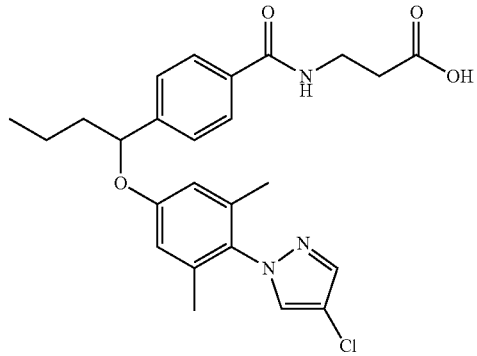 [SMILES: CCCC(Oc1cc(C)c(-n2cc(Cl)cn2)c(C)c1)c1ccc(C(=O)NCCC(=O)O)cc1]

(+\-)-3-(4-(1-(4-(4-chloro-1H-pyrazol-1-yl)-3,5-dimethylphenoxy)butyl)benzamido)propanoic acid was prepared using a method analogous to that described in Example 86 starting from Intermediate (81) and ethyl 4-(1-hydroxybutyl)benzoate (prepared as described in preparation of Intermediate 5). Colorless solid. $^1$H NMR (400 MHz, Methanol-d4) δ 8.50-8.60 (m, 1H), 7.77-7.81 (m, 3H) 7.68 (s, 1H), 7.48 (d, J=8.0 Hz, 2H), 6.70 (s, 2H), 5.35-5.38 (m, 1H), 3.61-3.64 (m, 2H), 2.62-2.68 (m, 2H), 2.00-1.96 (m, 2H), 1.89 (s, 6H), 1.87-1.79 (m, 1H), 1.57-1.44 (m, 2H), 0.99 (t, J=7.2 Hz, 3H). MS (M+23)=492.2.

Example 131

(+\-)-3-(4-(cyclopentyl(3,5-dimethyl-4-(4-(trifluoromethyl)-1H-imidazol-1-yl)phenoxy)methyl)benzamido)propanoic acid

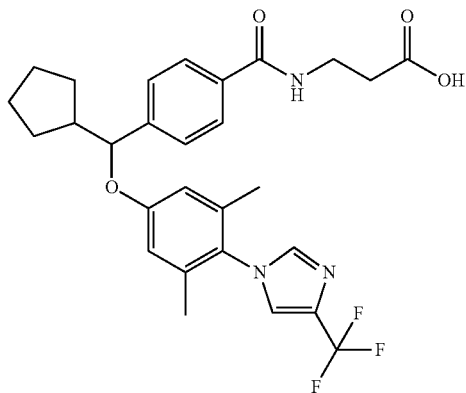 [SMILES: Cc1cc(OC(c2ccc(C(=O)NCCC(=O)O)cc2)C2CCCC2)cc(C)c1-n1cnc(C(F)(F)F)c1]

(+\-)-3-(4-(cyclopentyl(3,5-dimethyl-4-(4-(trifluoromethyl)-1H-imidazol-1-yl)phenoxy)methyl)benzamido)propanoic acid was prepared using a method analogous to that described in Example 86 starting from Intermediate (83) and Intermediate (68). Colorless solid. $^1$H NMR (400 MHz, CD$_3$OD) δ 7.74-7.78 (m, 3H), 7.62 (s, 1H), 7.49 (d, J=8.4 Hz, 2H), 6.73 (s, 2H), 5.15 (d, J=7.6 Hz, 1H), 3.60-3.63 (m, 2H), 2.60-2.64 (m, 2H), 2.42-2.38 (m, 1H), 1.92 (s, 6H), 1.89-1.87 (m, 1H), 1.67-1.54 (m, 5H), 1.47-1.40 (m, 2H). MS (M+1)=530.2.

Example 132

(+\-)-3-(6-(1-(6-(4-phenyl-1H-pyrazol-1-yl)pyridin-3-ylamino/butyl)nicotinamido)propanoic acid

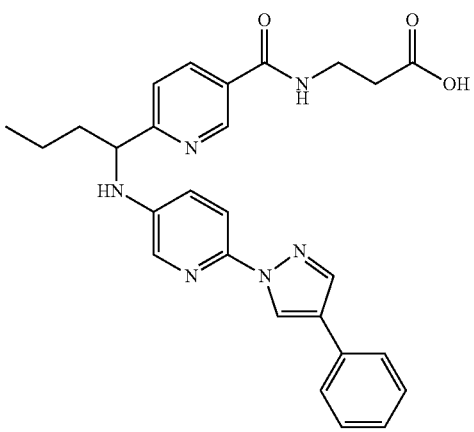 [SMILES: CCCC(Nc1ccc(-n2cc(-c3ccccc3)cn2)nc1)c1ccc(C(=O)NCCC(=O)O)cn1]

(+\-)-3-(6-(1-(6-(4-phenyl-1H-pyrazol-1-yl)pyridin-3-ylamino)butyl)nicotinamido)propanoic acid was prepared using a method analogous to that described for Example 102 starting from Intermediate 25 and methyl 6-formylnicotinate using n-propylmagnesium chloride in Step C. Colorless solid. $^1$H NMR (400 MHz, CD$_3$OD) δ 8.88 (d, J=1.2 Hz, 1H), 8.54 (s, 1H), 8.23 (d, J=7.6 Hz, 1H), 7.92 (s, 1H), 7.67-7.63 (m, 2H), 7.55-7.50 (m, 3H), 7.28-7.25 (m 2H), 7.15-7.11 (m 1H), 7.03-7.06 (m, 1H), 4.54-4.58 (m, 1H), 3.52-3.55 (m, 1H), 2.52-2.55 (m, 1H), 1.84-1.80 (m, 2H), 1.52-1.37 (m, 2H), 0.90 (t, J=6.8 Hz, 3H). MS (M+1)=485.3.

Example 133

(+\-)-3-(6-(1-(6-(4-phenyl-1H-pyrazol-1-yl)pyridin-3-yloxy)butyl)benzamido)propanoic acid

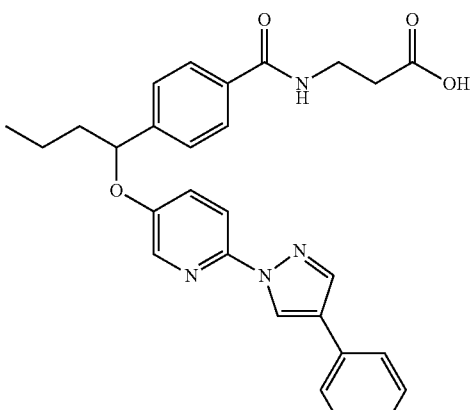

(+\-)-3-(6-(1-(6-(4-phenyl-1H-pyrazol-1-yl)pyridin-3-yloxy)butyl)benzamido)propanoic acid was prepared using a method analogous to that described in Example 86, starting from Intermediate (20) and Intermediate (84). Colorless solid. ¹H NMR (400 MHz, CD₃OD) δ 8.71 (s, 1H), 8.04 (d, J=2.8 Hz, 1H), 8.02 (s, 1H), 7.73-7.79 (m, 3H), 7.60 (d, J=7.6 Hz, 2H), 7.49 (d, J=8.4 Hz, 2H), 7.43-7.46 (m, 1H), 7.35 (t, J=7.6 Hz, 2H), 7.22 (t, J=7.6 Hz, 1H), 5.37-5.40 (m, 1H), 3.57-3.61 (m, 2H), 2.58-2.62 (m, 2H), 2.05-2.02 (m, 1H), 1.87-1.84 (m, 1H), 1.57-1.55 (m, 1H), 1.47-1.43 (m, 1H), 0.98 (t, J=7.2 Hz, 3H). MS (M+1)=485.2.

Example 134

3-(4-((3,3-dimethylcyclobutyl)(6-(4-(trifluoromethyl)-1H-imidazol-1-yl)pyridin-3-ylamino)methyl)benzamido)propanoic acid, Isomer 1 and Example 135

3-(4-((3,3-dimethylcyclobutyl)(6-(4-(trifluoroethyl)-1H-imidazol-1-yl)pyridin-3-ylamino)methyl)benzamido)propanoic acid, Isomer 2

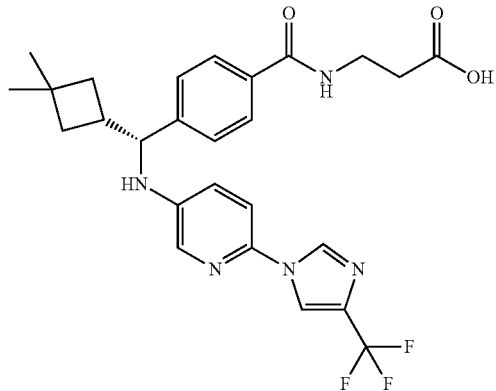

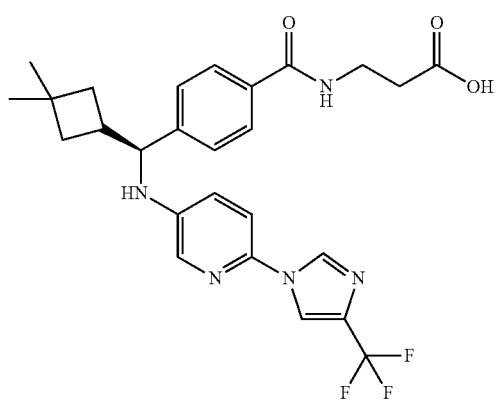

Step A: methyl 3-(4-((3,3-dimethylcyclobutyl)(6-(4-(trifluoromethyl)-1H-imidazol-1-yl)pyridin-3-ylamino)methyl)benzamido)propanoate, Isomer 1 and Isomer 2

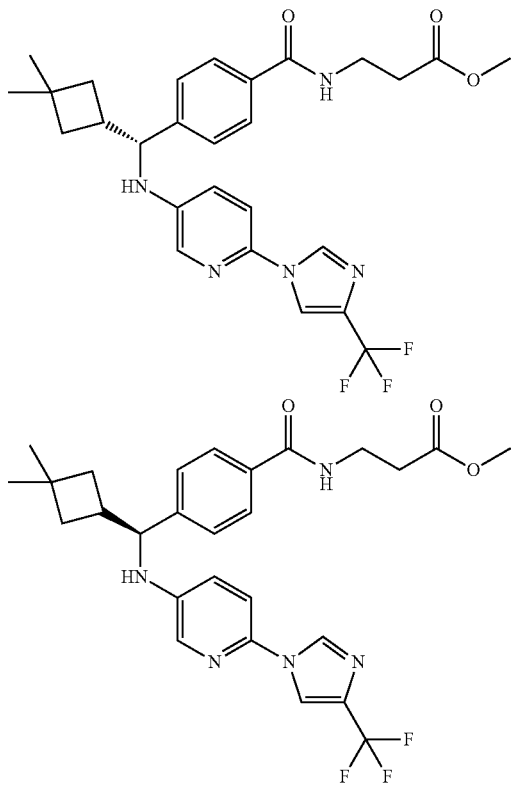

(+\-)-methyl 3-(4-((3,3-dimethylcyclobutyl)(6-(4-(trifluoromethyl)-1H-imidazol-1-yl)pyridin-3-ylamino)methyl)benzamido)propanoate was prepared using a method analogous to that described in Example 1, using appropriately substituted Intermediates such as Intermediate 6 in Step A and methyl 3-aminopropanoate hydrochloride in Step B. Yellow solid. (+\-)-methyl 3-(4-((3,3-dimethylcyclobutyl)(6-(4-(trifluoromethyl)-1H-imidazol-1-yl)pyridin-3-ylamino)methyl)benzamido)propanoate was resolved by SFC (column: Chiralpak AS-H 250×4.6 mm×5 μm; mobile phase: 5% to 40% methanol in CO₂; modifier: 0.05% diethylamine; flow rate: 2.35 mL/min) to give methyl 3-(4-((3,3-dimethylcyclobutyl)(6-(4-(trifluoromethyl)-1H-imidazol-1-yl)pyridin-3-ylamino)methyl)benzamido)propanoate, Isomer 1 (retention time: 8.26 min) and methyl 3-(4-((3,3-dimethylcyclobutyl)(6-(4-(trifluoromethyl)-1H-imidazol-1-yl)pyridin-3-ylamino)methyl)benzamido)propanoate, Isomer 2 (retention time: 7.43 min).

Step B: 3-(4-((3,3-dimethylcyclobutyl)(6-(4-(trifluoromethyl)-1H-imidazol-1-yl)pyridin-3-ylamino)methyl)benzamido)propanoic acid, Isomer 1

To a solution of methyl 3-(4-((3,3-dimethylcyclobutyl)(6-(4-(trifluoromethyl)-1H-imidazol-1-yl)pyridin-3-ylamino)methyl)benzamido)propanoate, Isomer 1 (550 mg, 1.10 mmol) in THF (5 mL) was added 2N aqueous lithium hydroxide (5.00 mL, 10 mmol). The reaction mixture was stirred for 1 h at room temperature. The mixture was acidified to pH 3 by addition of 1N aqueous HCl. The mixture was extracted with ethyl acetate (10 mL×3) The combined organic layers were washed with water, brine, dried over Na₂SO₄ and concentrated to dryness. The crude residue was purified by silica gel chromatography to give 3-(4-((3,3-dimethylcyclobutyl)(6-(4-(trifluoromethyl)-1H-imidazol-1-yl)pyridin-3-ylamino)methyl)benzamido)propanoic acid, Isomer 1 (255.8 mg) as an off-white solid. $^1$H NMR (400 MHz, Methanol-d$_4$) δ 8.33 (s, 1H), 8.12 (s, 1H), 7.82-7.76 (m, 3H), 7.48 (d, J=8.40 Hz, 2H), 7.35 (d, J=8.80 Hz, 1H), 7.04 (d, J=8.80 Hz, 1H), 4.31 (d, J=8.80 Hz, 1H), 3.62 (t, J=6.80 Hz, 2H), 2.64-2.55 (m, 3H), 2.11-2.03 (m, 1H), 1.77-1.68 (m, 2H), 1.59-1.50 (m, 1H), 1.16 (s, 3H), 1.11 (s, 3H). MS (M+1)=516.1.

Step C: 3-(4-((3,3-dimethylcyclobutyl)(6-(4-(trifluoromethyl)-1H-imidazol-1-yl)pyridin-3-ylamino)methyl)benzamido)propanoic acid, Isomer 2

To a solution of methyl 3-(4-((3,3-dimethylcyclobutyl)(6-(4-(trifluoromethyl)-1H-imidazol-1-yl)pyridin-3-ylamino)methyl)benzamido)propanoate, Isomer 2 (550 mg, 1.10 mmol) in THF (5 mL) was added 2N aqueous lithium hydroxide (5.00 mL, 10 mmol). The reaction mixture was stirred for 1 h at room temperature. The mixture was acidified to pH 3 by addition of 1N aqueous HCl. The mixture was extracted with ethyl acetate (10 mL×3) The combined organic layers were washed with water, brine, dried over Na$_2$SO$_4$ and concentrated to dryness. The crude residue was purified by silica gel chromatography to give 3-(4-((3,3-dimethylcyclobutyl)(6-(4-(trifluoromethyl)-1H-imidazol-1-yl)pyridin-3-ylamino)methyl)benzamido)propanoic acid, Isomer 2 (255.8 mg) as an off-white solid. $^1$H NMR (400 MHz, Methanol-d$_4$) δ 8.33 (s, 1H), 8.12 (s, 1H), 7.82-7.76 (m, 3H), 7.48 (d, J=8.40 Hz, 2H), 7.35 (d, J=8.80 Hz, 1H), 7.04 (d, J=8.80 Hz, 1H), 4.31 (d, J=8.80 Hz, 1H), 3.62 (t, J=6.80 Hz, 2H), 2.64-2.55 (m, 3H), 2.11-2.03 (m, 1H), 1.77-1.68 (m, 2H), 1.59-1.50 (m, 1H), 1.16 (s, 3H), 1.11 (s, 3H). MS (M+1)=516.1.

Example 136

3-(4-(1-(6-(4-tert-butyl-1H-pyrazol-1-yl)pyridin-3-ylamino)butyl)benzamido)propanoic acid, Isomer 1 and

Example 137

3-(4-(1-(6-(4-tert-butyl-1H-pyrazol-1-yl)pyridin-3-ylamino)butyl)benzamido)propanoic acid, Isomer 2

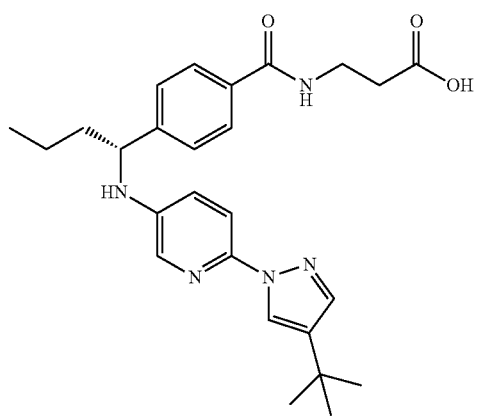

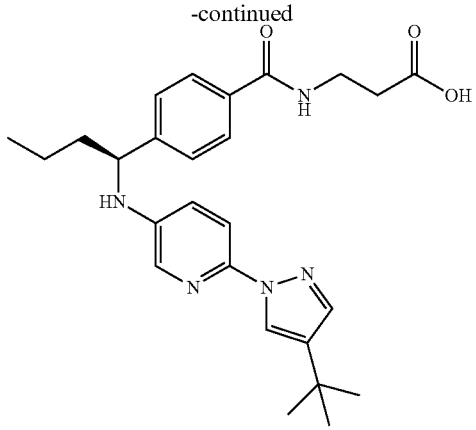

Step A: methyl 3-(4-(1-(6-(4-tert-butyl-1H-pyrazol-1-yl)pyridin-3-ylamino)butyl)benzamido)propanoate, Isomer 1 and methyl 3-(4-(1-(6-(4-tert-butyl-1H-pyrazol-1-yl)pyridin-3-ylamino)butyl)benzamido)propanoate, Isomer 2

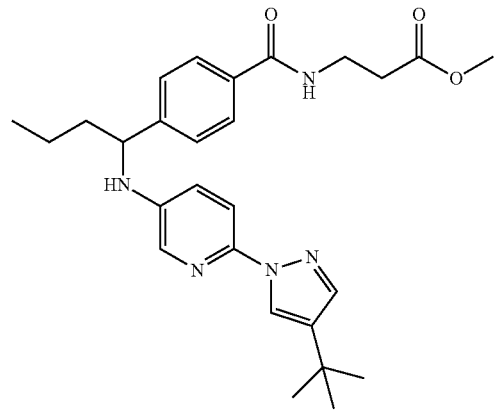 [SMILES: CCCC(Nc1ccc(-n2cc(C(C)(C)C)cn2)nc1)c1ccc(C(=O)NCCC(=O)OC)cc1]

To a solution of intermediate (87) (1.2 g, 5.5 mmol) and Intermediate (23) (1.54 g, 5.55 mmol) in anhydrous methanol (15 mL) was added decaborane (340 mg, 2.78 mmol). The solution as stirred at 30° C. overnight. The solution was concentrated under reduced pressure. The residue was purified by silica gel chromatography to give (+\−)-methyl 3-(4-(1-(6-(4-tert-butyl-1H-pyrazol-1-yl)pyridin-3-ylamino)butyl)benzamido)propanoate (1.6 g) as a colorless solid. $^1$H NMR (400 MHz, CD$_3$OD) δ 8.06 (d, J=0.8 Hz, 1H), 7.74 (d, J=8.4 Hz, 1H), 7.68 (d, J=2.8 Hz, 1H), 7.48 (s, 1H), 7.44-7.47 (m, 3H), 7.01-7.04 (m, 1H), 4.43 (t, 1H), 3.67 (s, 3H), 3.59-3.62 (m, 2H), 2.61-2.65 (m, 2H), 1.95-1.70 (m, 2H), 1.60-1.35 (m, 2H), 1.29 (s, 9H), 0.97 (t, J=7.2 Hz, 3H), (+\−)-methyl 3-(4-(1-(6-(4-tert-butyl-1H-pyrazol-1-yl)pyridin-3-ylamino)butyl)benzamido)propanoate was resolved by SFC (Column: Chiralpak OJ-H 250×4.6 mm×5 μm; mobile phase: 5 to 40% methanol in CO$_2$; modifier: 0.05% diethylamine; flow rate: 2.35 mL/min) to give methyl 3-(4-(1-(6-(4-tert-butyl-1H-pyrazol-1-yl)pyridin-3-ylamino)butyl)benzamido)propanoate, Isomer 1 (retention time 6.43 min) and methyl 3-(4-(1-(6-(4-tert-butyl-1H-pyrazol-1-yl)pyridin-3-ylamino)butyl)benzamido) propanoate, Isomer 2 (retention time, 7.37 min).

Step B: 3-(4-(1-(6-(4-tert-butyl-1H-pyrazol-1-yl)pyridin-3-ylamino)butyl)benzamido)propanoic acid, Isomer 1

To a solution of methyl 3-(4-(1-(6-(4-tert-butyl-1H-pyrazol-1-yl)pyridin-3-ylamino)butyl)benzamido)propenoate, Isomer 1 (500 mg, 1.05 mmol) in THF (5 mL) was added 2M aqueous lithium hydroxude (5 mL, 10 mmol). The mixture was stirred at room temperature for 1 h. The mixture was neutralized with 1N aqueous HCl and extracted with ethyl acetate (10 mL×3). The combined organic layer was dried over Na₂SO₄ and concentrated to dryness. The crude residue was purified by silica gel chromatography to give 3-(4-(1-(6-(4-tert-butyl-1H-pyrazol-1-yl)pyridin-3-ylamino)butyl)benzamido)propanoic acid, Isomer 1 (261.5 mg) as a colorless solid. $^1$H NMR (400 MHz, MeOD): δ8.06 (s, 1H), 7.74 (d, J=8.4 Hz, 1H), 7.68 (d, J=2.8 Hz, 1H), 7.48 (s, 1H), 7.46 (m, 3H), 7.03 (dd, J=8.8 Hz, 1H), 4.43 (t, 1H), 3.61 (t, J=6.8 Hz, 2H), 2.64 (t, J=6.8 Hz, 2H), 1.95-1.70 (m, 2H), 1.60-1.35 (m, 2H), 1.29 (s, 9H), 0.97 (t, J=7.2 Hz, 3H). MS (M+1)=464.2

Step C: 3-(4-(1-(6-(4-tert-butyl-1H-pyrazol-1-yl)pyridin-3-ylamino)butyl)benzamido)propanoic acid, Isomer 2

To a solution of methyl 3-(4-(1-(6-(4-tert-butyl-1H-pyrazol-1-yl)pyridin-3-ylamino)butyl)benzamido)propenoate, Isomer 2 (500 mg, 1.05 mmol) in THF (5 mL) was added 2M aqueous lithium hydroxude (5 mL, 10 mmol). The mixture was stirred at room temperature for 1 h. The mixture was neutralized with 1N aqueous HCl and extracted with ethyl acetate (10 mL×3). The combined organic layer was dried over Na₂SO₄ and concentrated to dryness. The crude residue was purified by silica gel chromatography to give 3-(4-(1-(6-(4-tert-butyl-1H-pyrazol-1-yl)pyridin-3-ylamino)butyl)benzamido)propanoic acid, Isomer 2 (271.3 mg) as a colorless solid. $^1$H NMR (400 MHz, MeOD): δ8.06 (s, 1H), 7.74 (d, J=8.4 Hz, 1H), 7.68 (d, J=2.8 Hz, 1H), 7.48 (s, 1H), 7.46 (m, 3H), 7.03 (dd, J=8.8 Hz, 1H), 4.43 (t, 1H), 3.61 (t, J=6.8 Hz, 2H), 2.64 (t, J=6.8 Hz, 2H), 1.95-1.70 (m, 2H), 1.60-1.35 (m, 2H), 1.29 (s, 9H), 0.97 (t, J=7.2 Hz, 3H). MS (M+1)=464.2

Example 138

3-(4-(cyclobutyl(3,5-dimethyl-4-(4-(trifluoromethyl)-1H-pyrazol-1-yl)phenoxy)methyl)benzamido)propanoic acid, Isomer 1

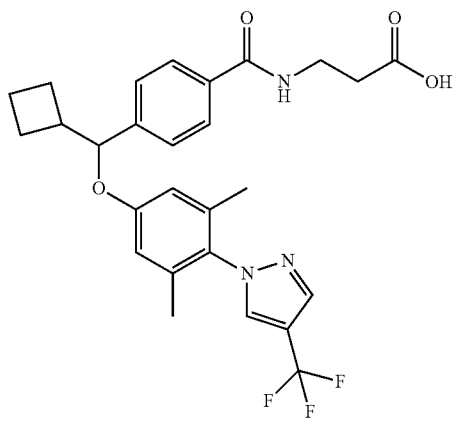 [SMILES: Cc1cc(OC(c2ccc(C(=O)NCCC(=O)O)cc2)C2CCC2)cc(C)c1-n1cc(C(F)(F)F)cn1]

Step A: methyl 3-(4-(cyclobutyl(3,5-dimethyl-4-(4-trifluoromethyl)-1H-pyrazol-1-yl)phenoxy)methyl)benzamido)propanoate, Isomer 1

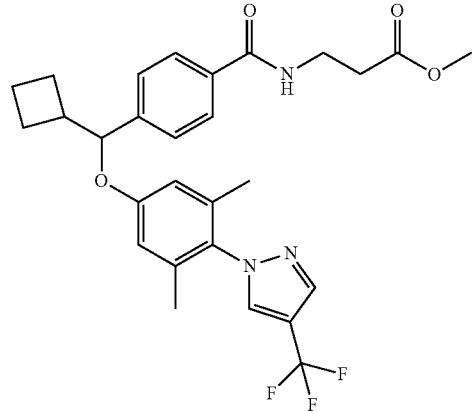 [SMILES: COC(=O)CCNC(=O)c1ccc(C(Oc2cc(C)c(-n3cc(C(F)(F)F)cn3)c(C)c2)C2CCC2)cc1]

(+/−)-methyl 3-(4-(cyclobutyl(3,5-dimethyl-4-(4-(trifluoromethyl)-1H-pyrazol-1-yl)phenoxy)methyl)benzamido)propanoate was prepared using a method analogous to that described in Example 65, Steps A-B, starting from Intermediate (26) and Intermediate (45). Resolution of the racemic material by SFC (column: Chiralpak AD-3 50×4.6 mm×3 μm; mobile phase: gradient 5 to 40% methanol in CO₂; modifier: 0.05% diethylamine; flow rate: 2.5 mL/min) gave methyl 3-(4-(cyclobutyl(3,5-dimethyl-4-(4-(trifluoromethyl)-1H-pyrazol-1-yl)phenoxy)methyl)benzamido)propenoate, Isomer 1 (retention time: 5.14 min) and methyl 3-(4-(cyclobutyl(3,5-dimethyl-4-(4-(trifluoromethyl)-1H-pyrazol-1-yl)phenoxy)methyl)benzamido)propanoate, Isomer 2 (retention time: 5.74 min) as colorless solids. Spectral data for Isomer 1: $^1$H NMR (400 MHz, CDCl₃) δ 7.80 (s, 1H), 7.65 (d, J=8.4 Hz, 2H), 7.58 (s, 1H), 7.30 (d, J=8.0 Hz, 2H), 6.73 (t, J=6.0 Hz, 1H), 6.51 (s, 2H), 4.97 (d, J=7.2 Hz, 1H), 3.67-3.63 (m, 5H), 2.71-2.65 (m, 1H), 2.58-2.60 (m, 2H), 2.02-1.91 (m, 3H), 1.91-1.76 (m, 9H).

Step B: 3-(4-(cyclobutyl(3,5-dimethyl-4-(4-(trifluoromethyl)-1H-pyrazol-1-yl)phenoxy)methyl)benzamido)propanoic acid, Isomer 1

To a solution of methyl 3-(4-(cyclobutyl(3,5-dimethyl-4-(4-(trifluoromethyl)-1H-pyrazol-1-yl)phenoxy)methyl)benzamido)propenoate, Isomer 1 (450 mg, 0.85 mmol) in THF (4 mL) was added 2N aqueous lithium hydroxide (4 mL, 8.0 mmol). The resulting mixture was stirred at 20° C. for 1 h. THF was removed under reduced pressure. The residue was acidified by addition of 1N aqueous HCl to pH 3-4 and extracted with dichloromethane (20 mL*2). The organic layer was concentrated to give 3-(4-(cyclobutyl(3,5-dimethyl-4-(4-(trifluoromethyl)-1H-pyrazol-1-yl)phenoxy)methyl)benzamido)propenoic acid, Isomer 1 (330 mg) as a colorless solid. $^1$H NMR (400 MHz, Methanol-d4) δ 8.08 (s, 1H), 7.88 (s, 1H), 7.65 (d, J=8.0 Hz, 2H), 7.35 (d, J=8.0 Hz, 2H), 6.61 (s, 2H), 5.15 (d, J=7.2 Hz, 1H), 3.50 (t, J=6.8 Hz, 2H), 2.70-2.67 (m, 1H), 2.52 (t, J=6.8 Hz, 2H), 2.04-1.94 (m, 3H), 1.82-1.72 (m, 9H). MS (M+1)=516.1.

Example 139

(+\-)-3-(4-(1-(4-(7-chloro-2H-indazol-2-yl)phenoxy)butyl)benzamido)propanoic acid

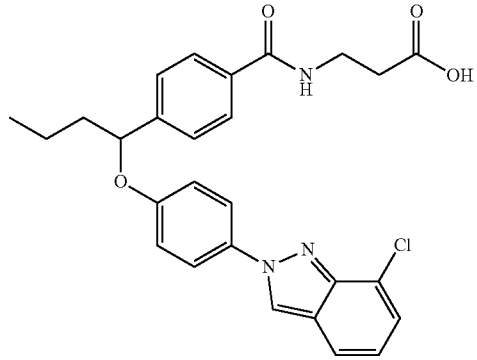 [SMILES: CCCC(Oc1ccc(-n2cc3cccc(Cl)c3n2)cc1)c1ccc(C(=O)NCCC(=O)O)cc1]

(+\-)-3-(4-(1-(4-(7-chloro-2H-indazol-2-yl)phenoxy)butyl)benzamido)propanoic acid was prepared using a method analogous to that described in Example 125, starting from Intermediate (77) and 7-chloroindazole. Colorless solid. $^1$HNMR (400 MHz Methanol-d4) δ 8.67 (s, 1H), 7.74-7.78 (m, 4H) 7.66 (d, J=8.4 Hz, 1H), 7.49 (d, J=8.4 Hz, 2H), 7.33 (d, J=7.2 Hz, 1H), 7.01-7.05 (m, 3H), 5.36-5.39 (m, 1H), 3.59 (t, J=6.8 Hz, 2H), 2.60 (t, J=6.8 Hz, 2H), 2.02-1.98 (m, 1H), 1.87-1.81 (m, 1H), 1.58-1.53 (m, 1H), 1.50-1.44 (m, 1H), 0.98 (t, J=7.2 Hz, 3H). MS (M+1)=492.2.

Example 140

(+\-)-3-(4-(1-(4-(5-chloro-2H-indazol-2-yl)phenoxy)butyl)benzamido)propanoic acid

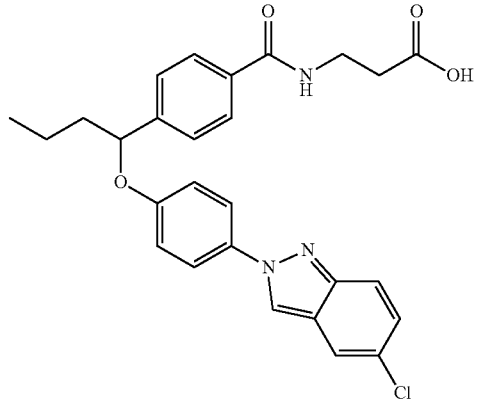 [SMILES: CCCC(Oc1ccc(-n2cc3cc(Cl)ccc3n2)cc1)c1ccc(C(=O)NCCC(=O)O)cc1]

(+\-)-3-(4-(1-(4-(5-cloro-2H-indazol-2-yl)phenoxy)butyl)benzamido)propanoic acid was prepared using a method analogous to that described in Example 82, starting from Intermediate (88) and ethyl 4-(1-hydroxybutyl)benzoate (prepared as described in preparation of Intermediate 5). Colorless solid. $^1$H NMR (400 MHz, Methanol-d$_4$) δ 8.56 (s, 1H), 7.77 (d, J=8.4 Hz, 2H), 7.70-7.72 (m, 3H), 7.62 (d, J=8.4 Hz, 1H), 7.48 (d, J=8.4 Hz, 2H), 7.24 (dd, J=9.2, 2.0 Hz, 1H), 7.03 (d, J=9.2 Hz, 2H), 5.35-5.38 (m, 1H), 3.59 (t, J=6.8 Hz, 2H), 2.59 (t, J=6.8 Hz, 2H), 2.02-1.98 (m, 1H), 1.86-1.82 (m, 1H), 1.57-1.54 (m, 1H), 1.48-1.44 (m, 1H), 0.97 (t, J=7.2 Hz, 3H). MS (M+1)=492.2.

Example 141

(+\-)-3-(4-(1-(3,5-dimethyl-4-(4-(trifluoromethyl)-1H-imidazol-1-yl)phenoxy)butyl)benzamido)propanoic acid

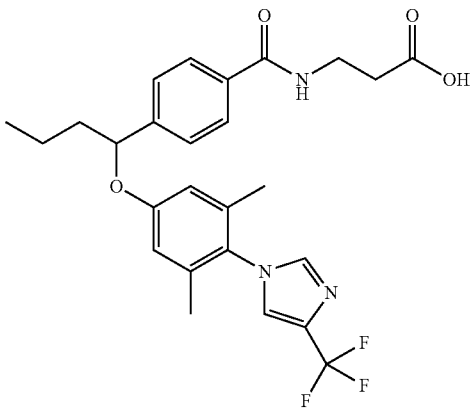 [SMILES: CCCC(Oc1cc(C)c(-n2cnc(C(F)(F)F)c2)c(C)c1)c1ccc(C(=O)NCCC(=O)O)cc1]

(+\-)-3-(4-(1-(3,5-dimethyl-4-(4-(trifluoromethyl)-1H-imidazol-1-yl)phenoxy)butyl)benzamido)propanoic acid was prepared using a method analogous to that described in Example 86 starting from Intermediate (83) and ethyl 4-(1-hydroxybutyl)benzoate (prepared as described in preparation of Intermediate 5). Colorless solid. $^1$H NMR (400 MHz, CD$_3$OD) δ 7.78-7.80 (m, 3H), 7.65 (s, 1H), 7.49 (d, J=8.4 Hz, 2H), 6.76 (s, 2H), 5.36-5.39 (m, 1H), 3.64 (t, J=6.8 Hz, 1H), 2.65 (t, J=6.8 Hz, 2H), 2.03-1.97 (m, 1H), 1.94 (s, 6H), 1.87-1.79 (m, 1H), 1.58-1.43 (m, 2H), 0.99 (t, J=7.2 Hz, 3H). MS (M+1)=504.2.

Example 142

3-(6-(3-methyl-1-(6-(4-(trifluoromethyl)-1H-pyrazol-1-yl)pyridin-3-yl)butylamino)nicotinamido)propanoic acid, Isomer 1 and

Example 143

3-(6-(3-methyl-1-(6-(4-(trifluoromethyl)-1H-pyrazol-1-yl)pyridin-3-yl)butylamino)nicotinamido)propanoic acid, Isomer 2

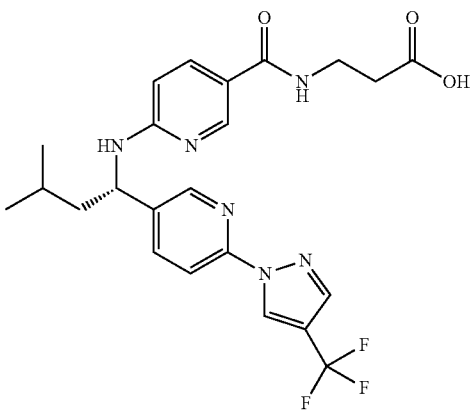

Step A: (+\−)-methyl 6-(tert-butoxycarbonyl(3-methyl-1-(6-(4-(trifluoromethyl)-1H-pyrazol-1-yl)pyridin-3-yl)butyl)amino)nicotinate

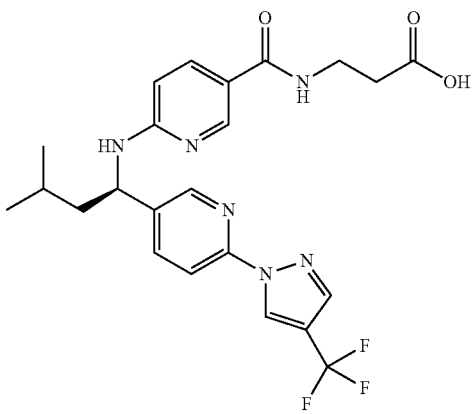

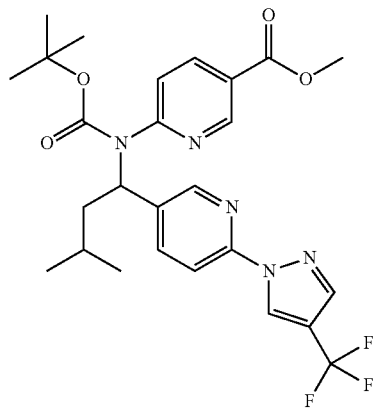 [SMILES: COC(=O)c1ccc(N(C(=O)OC(C)(C)C)C(CC(C)C)c2ccc(-n3cc(C(F)(F)F)cn3)nc2)nc1]

To a 0° C. solution of Intermediate (89) (1.40 mg, 4.67 mmol), Intermediate (90) (1.18 mg, 4.67 mmol), and triphenylphosphine (2.05 mg, 7.81 mmol) in THF (20 mL) was added di-iso-propyl azodicarboxylate (1.58 g, 7.8 mmol). The reaction was allowed to warm to 25° C. and stirred overnight. The mixture was diluted with water (30 mL) and extracted with ethyl acetate (30 mL×2). The combined organic layers were dried over anhydrous $Na_2SO_4$ and concentrated under reduced pressure. The residue was purified by silica gel chromatography to give (+\−)-methyl 6-(tert-butoxycarbonyl(3-methyl-1-(6-(4-(trifluoromethyl)-1H-pyrazol-1-yl)pyridin-3-yl)butyl)amino)nicotinate (1.10 g) as an oil. $^1$H NMR (400 MHz, $CDCl_3$) δ 8.95 (d, J=1.6 Hz, 1H), 8.78 (s, 1H), 8.47 (d, J=2.4 Hz, 1H), 8.15 (dd, J=2.0, 8.4 Hz, 1H), 7.95 (dd, J=2.4, 8.8 Hz, 1H), 7.86-7.82 (m, 2H), 7.50 (d, J=8.4 Hz, 1H), 5.95-5.92 (m, 1H), 3.87 (s, 3H), 2.27-2.20 (m, 1H), 1.91-1.84 (m, 1H), 1.57-1.54 (m, 1H), 1.19 (s, 9H), 0.88 (d, J=6.8 Hz, 3H), 0.79 (d, J=6.8 Hz, 3H).

Step B: (+\−)-methyl 6-(3-methyl-1-(6-(4-(trifluoromethyl)-1H-pyrazol-1-yl)pyridin-3-yl)butylamino)nicotinate

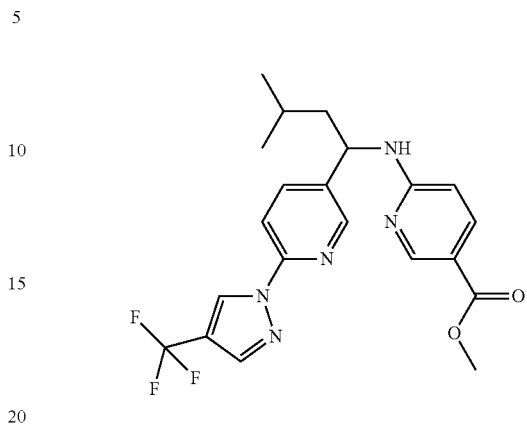

To a 0° C. solution of (+\−)-methyl 6-(tert-butoxycarbonyl (3-methyl-1-(6-(4-(trifluoromethyl)-1H-pyrazol-1-yl)pyridin-3-yl)butyl)amino)nicotinate (110 mg, 4.7 mmol) in dichloromethane (20 mL) was added trifluoroacetic acid (10 mL). The solution was stirred at 20° C. for 2 h. The solvent was removed under reduced pressure. The residue was dissolved in dichloromethane (20 mL) and washed with water (20 mL). The organic layer was dried over anhydrous $Na_2SO_4$, filtered, and concentrated to give (+\−)-methyl 6-(3-methyl-1-(6-(4-(trifluoromethyl)-1H-pyrazol-1-yl)pyridin-3-yl)butylamino)nicotinate (800 mg) as a colorless solid. $^1$H NMR (400 MHz, $CDCl_3$) δ 11.11 (d, J=4.0 Hz, 1H), 8.76 (s, 1H), 8.45 (d, J=1.6 Hz, 1H), 8.36 (d, J=1.6 Hz, 1H), 8.17 (d, J=9.2 Hz, 1H), 7.96 (d, J=8.4 Hz, 1H), 7.86-7.82 (m, 2H), 6.59 (d, J=9.6 Hz, 1H), 4.54-4.49 (m, 1H), 3.83 (s, 3H), 2.06-1.97 (m, 1H), 1.72-1.58 (m, 2H), 0.96 (d, J=6.4 Hz, 3H), 0.89 (d, J=6.4 Hz, 3H).

Step C: methyl 3-(6-(3-methyl-1-(6-(4-(trifluoromethyl)-1H-pyrazol-1-yl)pyridin-3-yl)butylamino) nicotinamido)propanoate, Isomer 1 and methyl 36-(3-methyl-1-(6-(4-(trifluoromethyl)-1H-pyrazol-1-yl)pyridin-3-yl)butylamino)nicotinamido) propanoate, Isomer 2

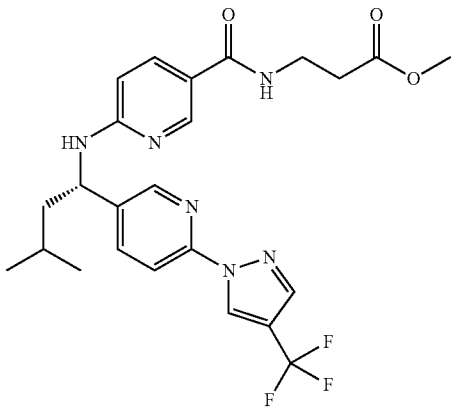

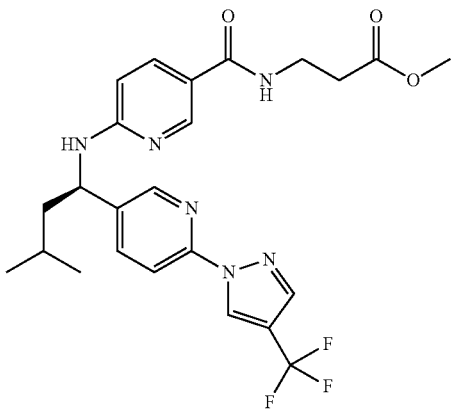

To a solution of (+\−)-methyl 6-(3-methyl-(6-(4-(trifluoromethyl)-1H-pyrazol-1-yl)pyridin-3-yl)butylamino)nicotinate (800 mg, 1.85 mmol) in methanol (5 mL) was added 2N aqueous sodium hydroxide (9.2 mL, 18.4 mmol). The resulting mixture was stirred at 20° C. for 2 h. Methanol was removed under reduced pressure and the residue was acidified by addition of 1N aqueous HCl to pH 3-4 and extracted with dichloromethane (30 mL×2). The combined organic layers were concentrated under reduced pressure. The residue was dissolved in DMF (10 mL). HATU (1.36 mg, 3.58 mmol) and N,N-di-iso-propylethylamine (1.15 mg, 8.95 mmol) were added. Methyl 3-aminopropanoate hydrochloride (370 mg, 2.68 mmol) was added. The resulting mixture was stirred at 30° C. for 1 h. The mixture was poured into brine (30 mL) and extracted with ethyl acetate (30 mL×2). The combined organic layers were washed with 1N aqueous HCl (30 mL), dried over anhydrous $Na_2SO_4$ and concentrated to dryness. The crude residue was purified silica gel chromatography to give (+\−)-methyl 3-(6-(3-methyl-1-(6-(4-(trifluoromethyl)-1H-pyrazol-1-yl)pyridin-3-yl)butylamino)nicotinamido)propanoate (850 mg) as an oil. $^1$H NMR (400 MHz, $CDCl_3$) δ 8.75 (s, 1H), 8.37 (d, J=12.0 Hz, 2H), 7.87 (d, J=8.4 Hz, 1H), 7.80 (s, 1H), 7.76-7.70 (m, 2H), 6.52 (s, 1H), 6.22 (d, J=8.4 Hz, 1H), 5.07 (d, J=4.0 Hz, 1H), 4.86 (d, J=9.2 Hz, 1H), 3.62-3.58 (m, 5H), 2.54 (t, J=5.6 Hz, 2H), 1.77-1.59 (m, 3H), 1.75-1.63 (m, 2H), 0.95 (d, J=6.0 Hz, 3H), 0.91 (d, J=6.0 Hz, 3H). (+\−)-methyl 3-(6-(3-methyl-1-(6-(4-(trifluoromethyl)-1H-pyrazol-1-yl)pyridin-3-yl)butylamino)nicotinamido)propanoate was resolved by SFC (column: Chiralpak AD-3, 50×4.6 mm×3 µm; mobile phase: 40% methanol in $CO_2$; modifier: 0.05% diethylamine; flow rate: 4 mL/min) to give methyl 3-(6-(3-methyl-1-(6-(4-(trifluoromethyl)-1H-pyrazol-1-yl)pyridin-3-yl)butylamino)nicotinamido)propanoate, Isomer 1 (450 mg, retention time: 0.62 min) and methyl 3-(6-(3-methyl-1-(6-(4-(trifluoromethyl)-1H-pyrazol-1-yl)pyridin-3-yl)butylamino)nicotinamido)propanoate, isomer 2 (400 mg, retention time: 1.30 min).

Step D: 3-(6-(3-methyl-1-(6-(4-(trifluoromethyl)-1H-pyrazol-1-yl)pyridin-3-yl)butylamino)nicotinamido)propanoic acid, Isomer 1

To a solution of methyl 3-(6-(3-methyl-1-(6-(4-(trifluoromethyl)-1H-pyrazol-1-yl)pyridin-3-yl)butylamino)nicotinamido)propenoate, Isomer 1 (450 mg, 0.89 mmol) in THF (4 mL) was added 2N aqueous lithium hydroxide (4.5 mL, 9.0 mmol). The resulting mixture was stirred at 20° C. for 1 hour. Methanol was removed under reduced pressure. The residue was acidified by addition of 1N aqueous HCl to pH 3-4 and extracted with dichloromethane (20 mL*2). The organic layer was concentrated to give 3-(6-(3-methyl-1-(6-(4-(trifluoromethyl)-1H-pyrazol-1-yl)pyridin-3-yl)butylamino)nicotinamido)propanoic acid, Isomer 1 (400 mg) as a colorless solid. $^1$H NMR (400 MHz, Methanol-d4) δ 8.87 (s, 1H), 8.45 (s, 1H), 8.22 (d, J=1.2 Hz, 1H), 8.10 (dd, J=2.0, 9.2 Hz, 1H), 7.94-7.90 (m, 3H), 7.01 (d, J=9.6 Hz, 1H), 5.00-4.97 (m, 1H), 3.47 (t, J=6.8 Hz, 2H), 2.49 (t, J=6.8 Hz, 2H), 1.92-1.82 (m, 1H), 1.75-1.63 (m, 2H), 0.90-0.95 (m, 6H). MS (M+1)=491.1.

Step E: 3-(6-(3-methyl-1-(6-(4-(trifluoromethyl)-1H-pyrazol-1-yl)pyridin-3-yl)butylamino)nicotinamido)propanoic acid, Isomer 2

To a solution of methyl 3-(6-(3-methyl-1-(6-(4-(trifluoromethyl)-1H-pyrazol-1-yl)pyridin-3-yl)butylamino)nicotinamido)propanoate, Isomer 2 (400 mg, 0.79 mmol) in THF (4 mL) was added 2N aqueous lithium hydroxide (4 mL, 8.0 mmol). The resulting mixture was stirred at 20° C. for 1 h. Methanol was removed under reduced pressure. The residue was acidified by addition of 1N aqueous HCl to pH 3-4 and extracted with dichloromethane (20 mL×2). The organic layer was concentrated to give 3-(6-(3-methyl-1-(6-(4-(trifluoromethyl)-1H-pyrazol-1-yl)pyridin-3-yl)butylamino)nicotinamido)propanoic acid, Isomer 2 (330 mg) as a colorless solid. $^1$H NMR (400 MHz, Methanol-d4) δ 8.87 (s, 1H), 8.45 (s, 1H), 8.22 (d, J=1.2 Hz, 1H), 8.10 (dd, J=2.0, 9.2 Hz, 1H), 7.94-7.90 (m, 3H), 7.01 (d, J=9.6 Hz, 1H), 5.00-4.97 (m, 1H), 3.47 (t, J=6.8 Hz, 2H), 2.49 (t, J=6.8 Hz, 2H), 1.92-1.82 (m, 1H), 1.75-1.63 (m, 2H), 0.90-0.95 (m, 6H). MS (M+1)=491.1.

Example 144

(+\−)-3-(4-(1-(4-(4-cyclopropyl-1H-pyrazol-1-yl)-3,5-dimethylphenoxy)butyl)benzamido)propanoic acid

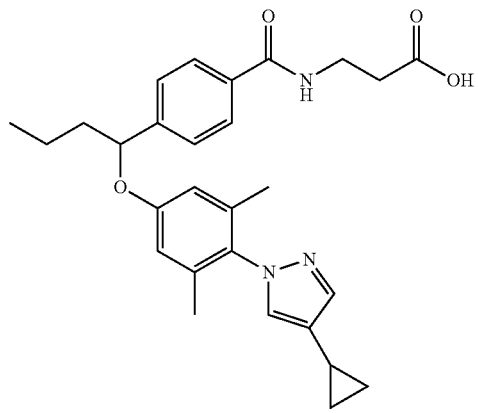 [SMILES: CCCC(Oc1cc(C)c(-n2cc(C3CC3)cn2)c(C)c1)c1ccc(C(=O)NCCC(=O)O)cc1]

(+\−)-3-(4-(1-(4-(4-cyclopropyl-1H-pyrazol-1-yl)-3,5-dimethylphenoxy)butyl)benzamido)propanoic acid was prepared using a method analogous to that describe for Example 82, starting from Intermediate (93) and ethyl 4-(1-hydroxybutyl)benzoate. Colorless solid. ¹H NMR (400 MHz, CD₃OD) δ 7.75 (d, J=8.0 Hz, 2H), 7.44 (s, J=8.0 Hz, 2H), 7.36 (s, 1H), 6.64 (s, 2H), 5.33-5.30 (m, 1H), 3.59 (t, J=6.8 Hz, 2H), 2.63 (t, J=6.8 Hz, 2H), 1.98-1.92 (m, 1H), 1.81 (s, 6H), 1.81-1.72 (m, 2H), 159-1.35 (m, 2H), 096 (t, J=7.6 Hz, 3H), 0.88-0.84 (m, 2H), 0.56-0.52 (m, 2H). MS (M+1)=476.3.

Example 145

3-(4-(1-(4-(4-chloro-1H-pyrazol-1-yl)-3,5-dimethylphenoxy)butyl)benzamido)propanoic acid, Isomer 1

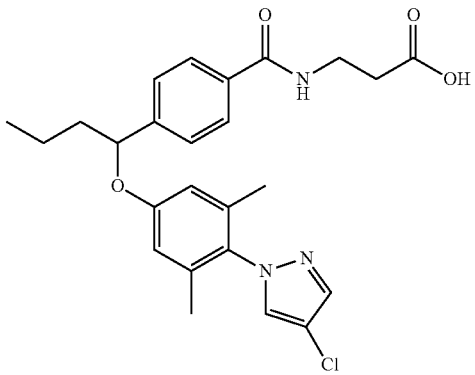 [SMILES: CCCC(Oc1cc(C)c(-n2cc(Cl)cn2)c(C)c1)c1ccc(C(=O)NCCC(=O)O)cc1]

(+\-)-ethyl 3-(4-(1-(4-(4-chloro-1H-pyrazol-1-yl)-3,5-dimethylphenoxy)butyl)benzamido) propanoate was prepared using a method analogous to that described in Example 82, Steps A-C, using Intermediate (81) in Step A and methyl 3-aminopropanoate hydrochloride in Step C. (+\-)-methyl 3-(4-(1-(4-(4-chloro-1H-pyrazol-1-yl)-3,5-dimethylphenoxy)butyl)benzamido)propanoate was resolved by SFC (column: Chiralpak AD-3 50×4.6 mm, 3 μm; mobile phase: gradient elution 5% to 40% methanol in CO₂; modifier: 0.05% diethylamine; flow rate: 4 mL/min) to give methyl 3-(4-(1-(4-(4-chloro-1H-pyrazol-1-yl)-3,5-dimethylphenoxy)butyl)benzamido)propanoate, Isomer 1 (retention time: 1.32 min) and methyl 3-(4-(1-(4-(4-chloro-1H-pyrazol-1-yl-3,5-dimethylphenoxy)butyl)benzamido) propanoate, Isomer 2 (retention time: 1.49 min), methyl 3-(4-(1-(4-(4-chloro-1H-pyrazol-1-yl)-3,5-dimethylphenoxy)butyl)benzamido)propanoate, Isomer 1 (70.0 mg, 0.145 mmol) was dissolved in THF (1.5 mL). 1N aqueous lithium hydroxide (1.50 mL, 1.50) was added. The reaction mixture was stirred for 1 h at room temperature. The mixture was acidified to pH 3 by addition of 1N aqueous HCl. The mixture was extracted with ethyl acetate (10 mL×3). The combined organic layers were washed with water, brine, dried over Na₂SO₄ and concentrated under reduced pressure. The residue was purified by silica gel chromatography to give 3-(4-(1-(4-(4-chloro-1H-pyrazol-1-yl)-3,5-dimethylphenoxy)butyl)benzamido)propanoic acid, Isomer 1 (23.9 mg) as an off-white solid. ¹H NMR (400 MHz, Methanol-d₄) δ 7.77-7.81 (m, 3H) 7.68 (s, 1H), 7.48 (d, J=8.0 Hz, 2H), 6.70 (s, 2H), 5.35-5.38 (m, 1H), 3.61-3.64 (m, 2H), 2.62-2.68 (m, 2H), 2.00-1.96 (m, 1H), 1.89 (s, 6H), 1.87-1.79 (m, 1H), 1.57-1.44 (m, 2H), 0.99 (t, J=7.2 Hz, 3H). MS (M+23)=492.2.

Example 146

3-(4-(cyclohexyl(6-(4-(trifluoromethyl)-1H-pyrazol-1-yl)pyridine-3-ylamino)methyl)benzamido)propanoic acid, Isomer 1 and Example 147

3-(4-(cyclohexyl(6-(4-(trifluoromethyl)-1H-pyrazol-1-yl)pyridine-3-ylamino)methyl)benzamido)propanoic acid, Isomer 2

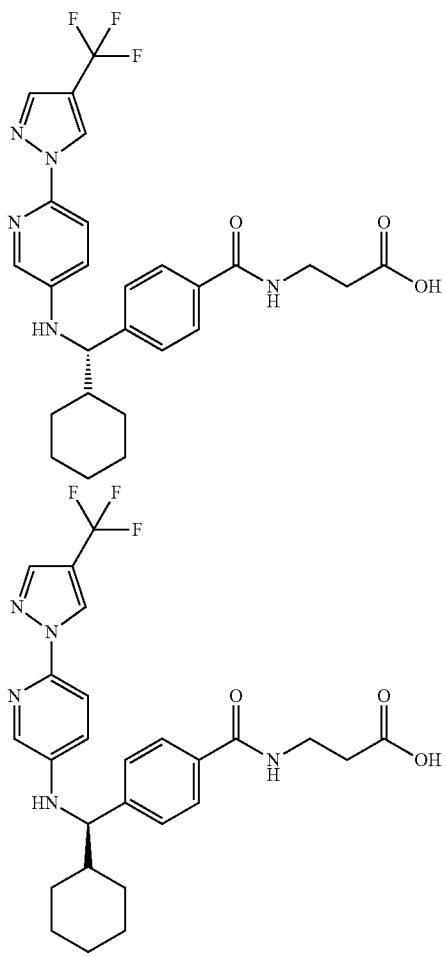

(+\)-3-(4-(cyclohexyl(6-(4-(trifluoromethyl)-1H-pyrazol-1-yl)pyridine-3-ylamino)methyl)benzamido)propanoic acid (Example 101) was resolved by SFC (Column: Chiralpak AD-H 25×4.6 mm; mobile phase: 25% ethanol in CO₂; modifier: 0.2% isopropylamine; flow rate: 2.5 mL/min) to provide 3-(4-(cyclohexyl(6-(4-(trifluoromethyl)-1H-pyrazol-1-yl)pyridine-3-ylamino)methyl)benzamido)propanoic acid, Isomer 1 (retention time: 6.93 min) and 3-(4-(cyclohexyl(6-(4-(trifluoromethyl)-1H-pyrazol-1-yl)pyridine-3-ylamino)methyl)benzamido)propanoic acid, Isomer 2 (retention time: 9.58 min) as their isopropylammonium salts. The salts were dissolved in water and the pH adjusted to 3.5 by addition of 1N aqueous HCl. The mixtures were extracted with dichloromethane. The organic layers were dried over MgSO₄ and concentrated to provide 3-(4-(cyclohexyl(6-(4-(trifluoromethyl)-1H-pyrazol-1-yl)pyridine-3-ylamino)methyl)benzamido)propanoic acid, Isomer 1 and 3-(4-(cyclohexyl(6-(4-(trifluoromethyl)-1H-pyrazol-1-yl)pyridine-3-ylamino)methyl)benzamido)propanoic acid, Isomer 2. Spectral data for Isomer 1: ¹H NMR (400 MHz, CDCl₃) δ 8.58 (s, 1H), 7.77 (s, 1H), 7.65-7.72 (m, 3H), 7.60 (d, J=8.8 Hz), 7.32 (d, J=8.2

Hz, 2H), 6.82-6.88 (m, 1H), 6.71-6.78 (m, 1H), 4.15 (d, J=6.2 Hz, 1H), 3.65-3.73 (m, 2H), 2.63-2.73 (m, 2H), 1.83-1.93 (m, 1H), 1.59-1.82 (m, 4H), 1.46-1.56 (m, 1H), 0.94-1.28 (m, 6H). MS (M+H)=516.2.

Example 148

(+\−)-3-(4-(1-(3,5-dimethyl-4-(4-(trifluoromethyl)-1H-1,2,3-triazol-1-yl)phenoxy)butyl)benzamido)propanoic acid

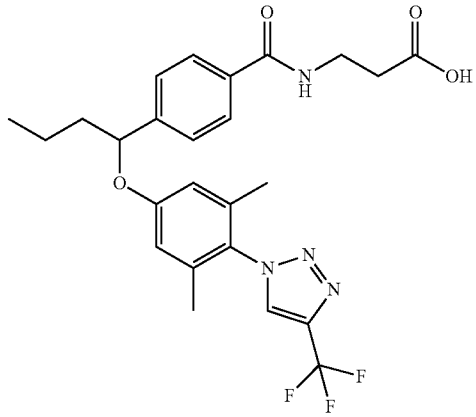 [SMILES: CCCC(Oc1cc(C)c(-n2cc(C(F)(F)F)nn2)c(C)c1)c1ccc(C(=O)NCCC(=O)O)cc1]

(+\−)-3-(4-(1-(3,5-dimethyl-4-(4-(trifluoromethyl)-1H-1,2,3-triazol-1-yl)phenoxy)butyl)benzamido)propanoic acid was prepared using a method analogous to that described in Example 82, starting from Intermediate (95). Colorless solid. $^1$H NMR (400 MHz, CDCl$_3$) δ 7.84 (s, 1H), 7.72 (d, J=8.4 Hz, 2H), 7.37 (d, J=8.4 Hz, 2H), 6.82-6.91 (m, 1H), 6.59 (s, 1H), 5.12-5.20 (m, 1H), 3.64-3.74 (m, 2H), 2.63-2.72 (m, 2H), 1.90-2.01 (m, 1H), 1.84 (s, 6H), 1.71-1.82 (m, 1H), 1.34-1.57 (m, 2H), 0.94 (t, J=7.2 Hz, 3H). MS (M+H)=505.0.

Example 149

(+/−)-3-(4-(1-(2-(4-(trifluoromethyl)-1H-pyrazol-1-yl)pyrimidin-5-yloxy)butyl)benzamido)propanoic acid

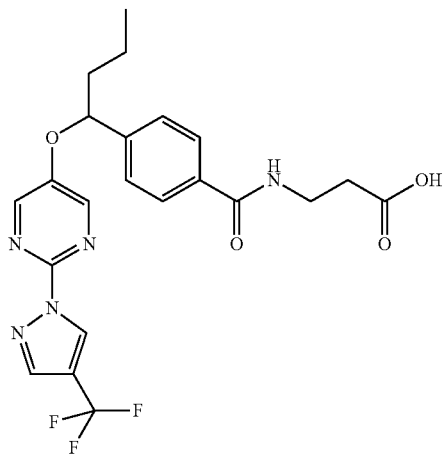 [SMILES: CCCC(Oc1cnc(-n2cc(C(F)(F)F)cn2)nc1)c1ccc(C(=O)NCCC(=O)O)cc1]

The title compound was prepared by a method analogous to that described for Example 82—Steps A and D using Intermediate (105) and Intermediate (96). Purification by reversed-phase HPLC on a Waters Sunfire C$_{18}$ 19×100 mm, 0.005 mm column eluting with a gradient of water in acetonitrile (0.05% trifluoroacetic acid modifier) gave (+/−)-3-(4-(1-(2-(4-(trifluoromethyl)-1H-pyrazol-1-yl)pyrimidin-5-yloxy)butyl)benzamido)propanoic acid. Analytical LCMS: retention time 2.95 minutes (Atlantis C$_{18}$ 4.6×50 mm, 51M column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 478.2.

Example 150

(+/−)-3-(4-(1-(5-methyl-6-(4-(trifluoromethyl)-1H-pyrazol-1-yl)pyridin-3-yloxy)butyl)benzamido)propanoic acid

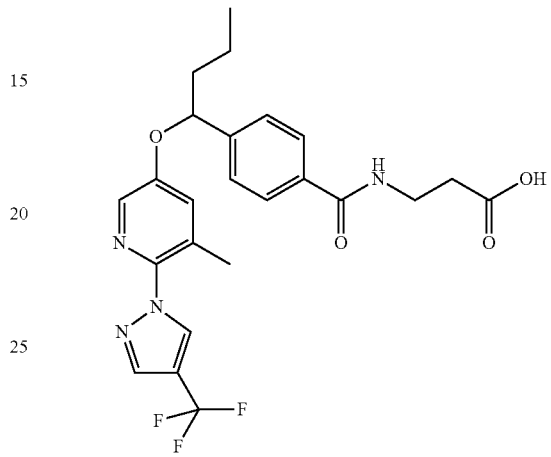

The title compound was prepared by a method analogous to that described for Example 82—Steps A and D using Intermediate (97) and Intermediate (96). Purification by reversed-phase HPLC on a Waters Sunfire C$_{18}$ 19×100 mm, 0.005 mm column eluting with a gradient of water in acetonitrile (0.05% trifluoroacetic acid modifier) gave (+/−)-3-(4-(1-(5-methyl-6-(4-(trifluoromethyl)-1H-pyrazol-1-yl)pyridin-3-yloxy)butyl)benzamido)propanoic acid. Analytical LCMS: retention time 3.27 minutes (Atlantis C$_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 491.2.

Example 151

(+/−)-3-(4-(cyclobutyl(3,5-dimethyl-4-(4-(trifluoromethyl)-1H-pyrazol-1-yl)phenoxy)methyl)benzamido)propanoic acid

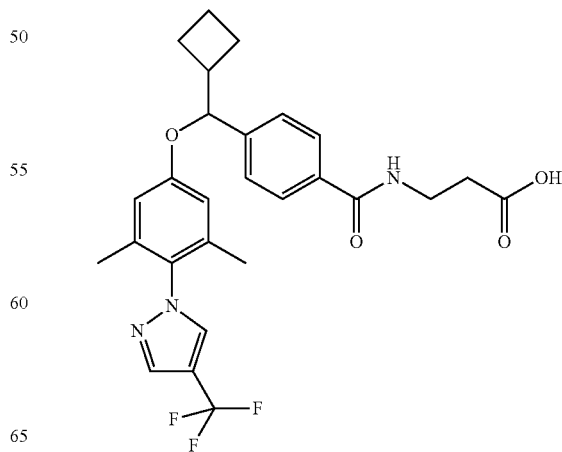

The title compound was prepared by a method analogous to that described for Example 82-Steps A and D using Intermediate (98) and Intermediate (26). Purification by reversed-phase HPLC on a Waters Sunfire $C_{18}$ 19×100 mm, 0.005 mm column eluting with a gradient of water in acetonitrile (0.05% trifluoroacetic acid modifier) gave (+/−)-3-(4-(cyclobutyl(3,5-dimethyl-4-(4-(trifluoromethyl)-1H-pyrazol-1-yl)phenoxy)methyl)benzamido)propanoic acid. Analytical LCMS: retention time 3.46 minutes (Atlantis $C_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 516.2.

Example 152

(+/−)-3-(4-((3,5-dimethyl-4-(4-(trifluoromethyl)-1H-pyrazol-1-yl)phenoxy)(3,3-dimethylcyclobutyl)methyl)benzamido)propanoic acid

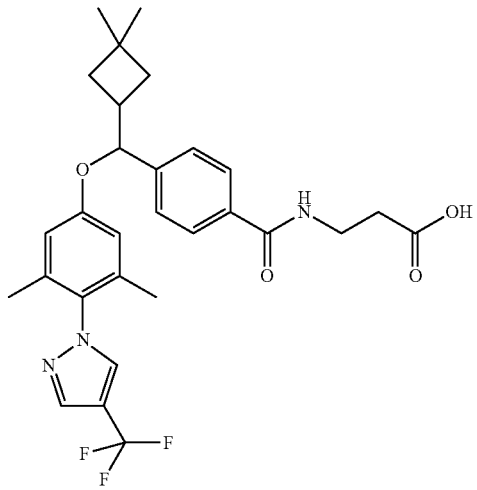 [SMILES: Cc1cc(OC(c2ccc(C(=O)NCCC(=O)O)cc2)C2CC(C)(C)C2)cc(C)c1-n1cc(C(F)(F)F)cn1]

Step (A): ethyl 4-((3,5-dimethyl-4-(4-(trifluoromethyl)-1H-pyrazol-1-yl)phenoxy)(3,3-dimethylcyclobutyl)methyl)benzoate

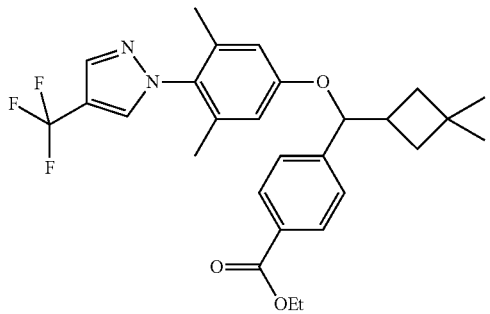

Diisopropyl azodicarboxylate (0.310 mL, 0.730 mmol) was added dropwise to a solution of Intermediate 26 (120 mg, 0.490 mmol), Intermediate (100) (128 mg, 0.490 mmol), and tributylphosphine (0.190 mL, 0.760 mmol) in tetrahydrofuran (2.20 mL). After 18 hours, another 0.5 equiv. of both diisopropyl azodicarboxylate and tributylphosphine were added. After an additional 3 h, the reaction was concentrated. The mixture was diluted with methylene chloride and acidified with 1 N hydrochloric acid. The mixture was then extracted twice with methylene chloride. The combined organic layers were dried over sodium sulfate, filtered, and concentrated to give 1.00 g of crude material. The crude material was purified by column chromatography (0-8% ethyl acetate in heptanes) gave ethyl 4-((3,5-dimethyl-4-(4-(trifluoromethyl)-1H-pyrazol-1-yl)phenoxy)(3,3-dimethylcyclobutyl)methyl)benzoate (134 mg, 54%) as an oil. $^1$H NMR (400 MHz, CDCl$_3$) δ 8.00 (d, J=8.2 Hz, 2H), 7.87 (s, 1H), 7.64 (s, 1H), 7.37 (d, J=8.2 Hz, 2H), 6.57 (s, 2H), 5.01 (d, J=6.8 Hz, 1H), 4.36 (q, J=7.0 Hz, 2H), 2.67 (d, J=7.0 Hz, 1H), 1.88 (s, 6H), 1.87-1.74 (m, 3H), 1.69-1.59 (m, 1H), 1.38 (t, J=7.4 Hz, 3H), 1.14 (s, 3H), 1.10 (s, 3H). MS (M+1): 501.4.

Step (B): 4-((3,5-dimethyl-4-(4-(trifluoromethyl)-1H-pyrazol-1-yl)phenoxy)(3,3-dimethylcyclobutyl)methyl)benzoic acid

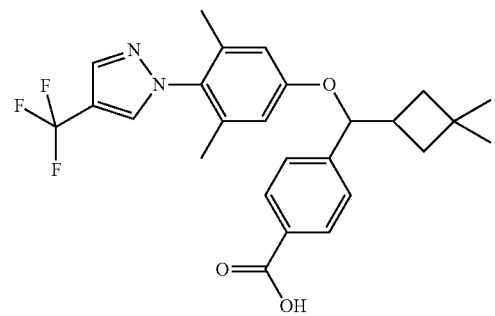 [SMILES: Cc1cc(OC(c2ccc(C(=O)O)cc2)C2CC(C)(C)C2)cc(C)c1-n1cc(C(F)(F)F)cn1]

To a flask containing ethyl 4-((3,5-dimethyl-4-(4-(trifluoromethyl)-1H-pyrazol-1-yl)phenoxy)(3,3-dimethylcyclobutyl)methyl)benzoate (135 mg, 0.270 mmol) was added anhydrous tetrahydrofuran (0.680 mL), methanol (0.680 mL), water (0.680 mL) and sodium hydroxide (55.7 mg, 1.35 mmol). After 8 h, the reaction was concentrated and dissolved in ethyl acetate and water. 1 N hydrochloric acid was added to pH 3 and the mixture was extracted three times with ethyl acetate. The combined organic layers were dried over sodium sulfate, filtered, and concentrated to give 4-((3,5-dimethyl-4-(4-(trifluoromethyl)-1H-pyrazol-1-yl)phenoxy)(3,3-dimethylcyclobutyl)methyl)benzoic acid (110 mg, 86% yield) as an oil. $^1$H NMR (400 MHz, CDCl$_3$) δ 8.06 (d, J=8.2 Hz, 2H), 7.88 (s, 1H), 7.65 (s, 1H), 7.41 (d, J=8.4 Hz, 2H), 6.58 (s, 2H), 5.03 (d, J=6.8 Hz, 1H), 2.80-2.55 (m, 1H), 2.07-1.72 (m, 9H), 1.67 (dd, J=8.2, 3.5 Hz, 1H), 1.14 (s, 3H), 1.10 (s, 3H). MS (M+1): 473.5.

Step (C): ethyl 3-(4-((3,5-dimethyl-4-(4-(trifluoromethyl)-1H-pyrazol-1-yl)phenoxy)(3,3-dimethylcyclobutyl)methyl)benzamido)propanoate

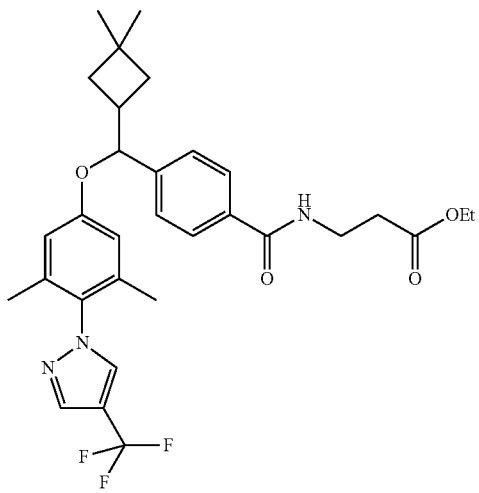 [SMILES: CCOC(=O)CCNC(=O)c1ccc(C(Oc2cc(C)c(-n3cc(C(F)(F)F)cn3)c(C)c2)C2CC(C)(C)C2)cc1]

Tetrahydrofuran (1.2 mL) was added to a vial containing 4-((3,5-dimethyl-4-(4-(trifluoromethyl)-1H-pyrazol-1-yl)phenoxy)(3,3-dimethylcyclobutyl)methyl)benzoic acid (115 mg, 0.240 mmol), ethyl 3-aminopropanoate hydrochloride (74.7 mg, 0.490 mmol) and O-(7-azabenzotriazol-1-yl)-N,N,N',N'-tetramethyluronium hexafluorophosphate (185 mg, 0.490 mmol). Diisopropylethylamine (0.210 mL, 1.22 mmol) was then added. The reaction was stirred for 1 h, and was then concentrated. Purification by column chromatography (0-50% ethyl acetate in heptane) afforded ethyl 3-(4-((3,5-dimethyl-4-(4-(trifluoromethyl)-1H-pyrazol-1-yl)phenoxy)(3,3-dimethylcyclobutyl)methyl)benzamido)propanoate (110 mg, 39% yield) as an oil. $^1$H NMR (400 MHz, CDCl$_3$) δ 7.87 (s, 1H), 7.71 (d, J=8.6 Hz, 2H), 7.64 (s, 1H), 7.36 (d, J=8.2 Hz, 2H), 6.81 (t, J=4.8 Hz, 1H), 6.57 (s, 2H), 5.00 (d, J=6.8 Hz, 1H), 4.17 (q, J=7.2 Hz, 2H), 3.71 (q, J=6.1 Hz, 2H), 2.57-2.74 (m, 3H), 1.87-1.92 (m, 7H), 1.80-1.87 (m, 1H), 1.72-1.80 (m, 1H), 1.59-1.68 (m, 1H), 1.21-1.35 (m, 3H), 1.13 (s, 3H), 1.10 (s, 3H). MS (M+1): 572.3.

Step (D): (+/−)-3-(4-((3,5-dimethyl-4-(4-(trifluoromethyl)-1H-pyrazol-1-yl)phenoxy)(3,3-dimethylcyclobutyl)methyl)benzamido)propanoic acid To a flask containing ethyl 3-(4-((3,5-dimethyl-4-(4-(trifluoromethyl)-1H-pyrazol-1-yl)phenoxy)(3,3-dimethylcyclobutyl)methyl)benzamido)propanoate (100 mg, 0.180 mmol) was added water (0.437 mL), tetrahydrofuran (0.437 mL), and methanol (0.437 mL). Sodium hydroxide (36.1 mg, 0.880 mmol) was then added. The suspension was stirred at room temperature for 18 hours. The reaction was quenched with 1 N hydrochloric acid to pH 3 and extracted three times with ethyl acetate. The combined organic layers were dried over sodium sulfate, filtered, and concentrated to give 108 mg of crude material. The crude material was azeotrophed three times with toluene and three times with methylene chloride and then dried in vacuo for 18 h to provide (+/−)-3-(4-((3,5-dimethyl-4-(4-(trifluoromethyl)-1H-pyrazol-1-yl)phenoxy)(3,3-dimethylcyclobutyl)methyl)benzamido)propanoic acid (99.0 mg, 100%) as a solid. $^1$H NMR (400 MHz, CDCl$_3$) δ 7.88 (s, 1H), 7.71 (d, J=8.2 Hz, 2H), 7.65 (s, 1H), 7.36 (d, J=8.4 Hz, 2H), 6.76 (t, J=6.2 Hz, 1H), 6.56 (s, 2H), 5.01 (d, J=7.0 Hz, 1H), 3.72 (q, J=5.9 Hz, 2H), 2.74-2.59 (m, 3H), 1.88 (s, 6H), 1.87-1.68 (m, 3H), 1.68-1.58 (m, 1H), 1.13 (s, 3H), 1.10 (s, 3H). MS (M+1): 544.3.

Example 153

(+/−)-3-(4-(1-(3-methoxy-5-methyl-4-(4-(trifluoromethyl)-1H-pyrazol-1-yl)phenoxy)butyl)benzamido)propanoic acid

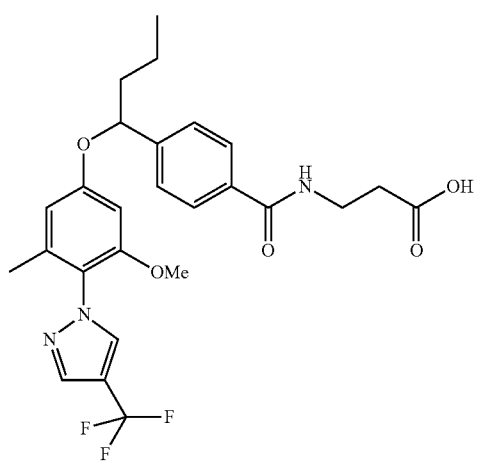 [SMILES: CCCC(Oc1cc(C)c(-n2cc(C(F)(F)F)cn2)c(OC)c1)c1ccc(C(=O)NCCC(=O)O)cc1]

Step (A): ethyl 3-(4-(1-(3-methoxy-5-methyl-4-(4-(trifluoromethyl)-1H-pyrazol-1-yl)phenoxy)butyl)benzamido)propanoate

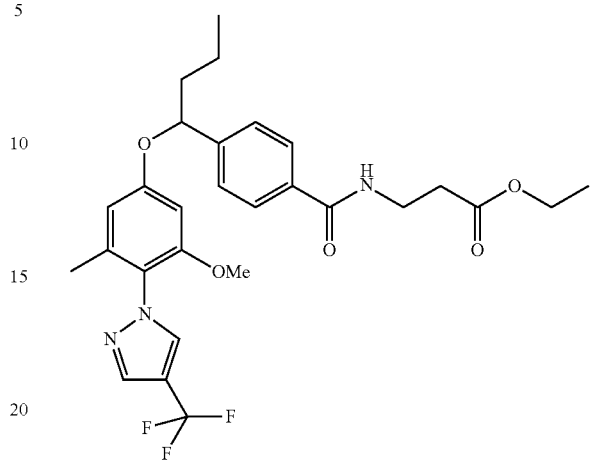

Tetrahydrofuran (0.450 mL) was added to azodicarboxylic acid dipiperidine (34.2 mg, 0.130 mmol), Intermediate (96) (26.0 mg, 0.0900 mmol) and Intermediate (103) (24.2 mg, 0.0900 mmol). Tributylphosphine (0.035 mL, 0.142 mmol) was added dropwise at room temperature. Another 0.450 mL of tetrahydrofuran was added. The mixture was stirred at room temperature for 16 hours. The reaction was diluted with ethyl acetate and then extracted twice with sodium hydroxide (1N), once with water, once with hydrochloric acid (1N), and finally once with brine. The organic layer was dried over sodium sulfate, filtered, and concentrated. Purification by column chromatography (0-30% ethyl acetate in heptanes) afforded ethyl 3-(4-(1-(3-methoxy-5-methyl-4-(4-(trifluoromethyl)-1H-pyrazol-1-yl)phenoxy)butyl)benzamido)propanoate (39.5 g, 81%) as an oil: $^1$H NMR (400 MHz, CDCl$_3$) δ 7.86 (s, 1H), 7.74 (d, J=8.2 Hz, 2H), 7.66 (s, 1H), 7.40 (d, J=8.4 Hz, 2H), 6.84 (t, J=6.0 Hz, 1H), 6.35 (d, J=2.5 Hz, 1H), 6.26 (d, J=2.5 Hz, 1H), 5.16 (dd, J=7.7, 5.2 Hz, 1H), 4.17 (q, J=7.2 Hz, 2H), 3.77-3.67 (m, 2H), 3.64 (s, 3H), 2.70-2.54 (m, 2H), 2.08-1.93 (m, 1H), 1.91 (s, 3H), 1.87-1.72 (m, 1H), 1.60-1.36 (m, 2H), 1.36-1.18 (m, 3H), 0.97 (t, J=7.4 Hz, 3H). MS (M+1): 548.4.

Step (B): (+/−)-3-(4-(1-(3-methoxy-5-methyl-4-(4-(trifluoromethyl)-1H-pyrazol-1-yl)phenoxy)butyl)benzamido)propanoic acid To a flask containing ethyl 3-(4-(1-(3-methoxy-5-methyl-4-(4-(trifluoromethyl)-1H-pyrazol-1-yl)phenoxy)butyl)benzamido)propanoate (37.0 mg, 0.0700 mmol) was added tetrahydrofuran (0.170 mL), methanol (0.170 mL), and 1 N sodium hydroxide (0.170 mL, 0.170 mmol) was then added. The suspension was stirred at room temperature for 18 hours. The reaction was quenched with 1 N hydrochloric acid to pH 2 and extracted three times with ethyl acetate. The combined organic layers were dried over sodium sulfate, filtered, and concentrated to give crude material. The crude material was azeotrophed three times with methylene chloride and then dried in vacuo for 18 h to provide (+/−)-3-(4-(1-(3-methoxy-5-methyl-4-(4-(trifluoromethyl)-1H-pyrazol-1-yl)phenoxy)butyl)benzamido) propanoic acid (26.0 mg, 74%) as a solid. $^1$H NMR (400 MHz, CDCl$_3$) δ 7.87 (s, 1H), 7.73 (d, J=8.4 Hz, 2H), 7.66 (s, 1H), 7.39 (d, J=82 Hz, 2H), 6.88 (t, J=6.0 Hz, 1H), 6.41-6.21 (m, 2H), 5.17 (dd, J=7.7, 5.2 Hz, 1H), 3.75-3.65 (m, 2H), 3.63 (s, 3H), 2.66 (t, J=5.9 Hz, 2H), 2.04-1.93 (m, 1H), 1.89 (s, 3H), 1.86-1.74 (m, 1H), 1.62-1.35 (m, 2H), 0.96 (t, J=7.4 Hz, 3H). MS (M+1): 520.4.

Example 154

(+/−)-3-(4-((3,3-difluorocyclobutyl)(6-(4-(trifluoromethyl)-1H-imidazol-1-yl)pyridin-3-ylamino)methyl)benzamido)propanoic acid

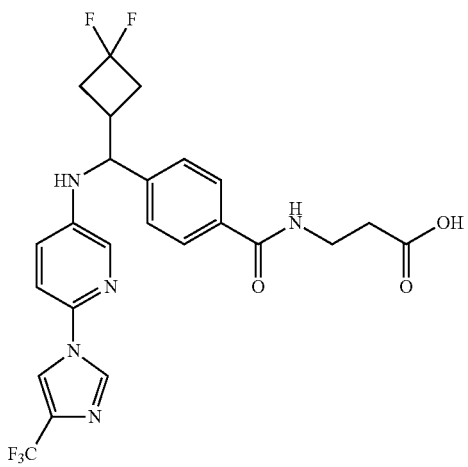 [SMILES: O=C(O)CCNC(=O)c1ccc(C(Nc2ccc(-n3cnc(C(F)(F)F)c3)nc2)C2CC(F)(F)C2)cc1]

Step (A): ethyl 4-((3,3-difluorocyclobutyl)(6-(4-(trifluoromethyl)-1H-imidazol-1-yl)pyridin-3-ylamino)methyl)benzoate

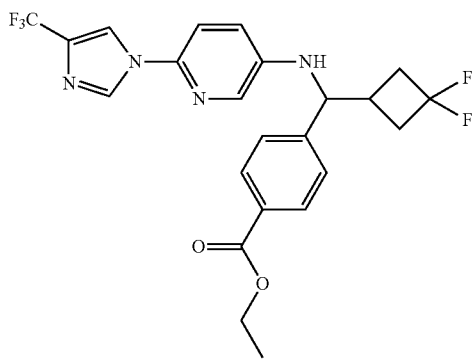 [SMILES: CCOC(=O)c1ccc(C(Nc2ccc(-n3cnc(C(F)(F)F)c3)nc2)C2CC(F)(F)C2)cc1]

To a solution of impure Intermediate (104) (72.0 mg, approximately 0.214 mmol pure) and intermediate 6 (61.2 mg, 0.270 mmol) in methanol (0.670 ml) was added decaborane (19.7 mg, 0.160 mmol). The reaction was stirred for 16 hours at ambient temperature. The reaction mixture was quenched with aqueous 1.0M hydrochloric acid and extracted three times with ethyl acetate. The combined organic layers were dried over sodium sulfate, filtered, and concentrated. Purification by silica gel flash chromatography (0-50% ethyl acetate in heptane) afforded impure ethyl 4-((3,3-difluorocyclobutyl)(6-(4-(trifluoromethyl)-1H-imidazol-1-yl)pyridin-3-ylamino)methyl)benzoate (30.0 mg, approximately 0.050 mmol pure) as a solid. MS (M+1): 481.1.

Step (B): 4-((3,3-difluorocyclobutyl)(6-(4-(trifluoromethyl)-1H-imidazol-1-yl)pyridin-3-ylamino)methyl)benzoic acid

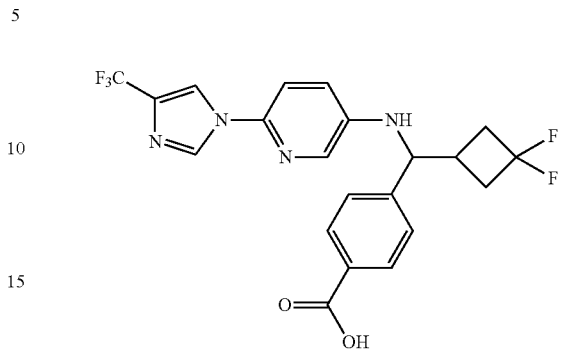

To a flask containing impure ethyl 4-((3,3-difluorocyclobutyl)(6-(4-(trifluoromethyl)-1H-imidazol-1-yl)pyridin-3-ylamino)methyl)benzoate (35.0 mg, 0.073 mmol) was added tetrahydrofuran (0.180 mL), methanol (0.180 mL), and 1 N sodium hydroxide (0.180 mL, 0.180 mmol) was then added. After 2 h, another 5 equiv. of aqueous sodium hydroxide was added. The suspension was stirred at room temperature for 18 hours. Another 5 equiv. of aqueous sodium hydroxide was added and the reaction was heated to 50° C. After 2 h, the reaction was quenched with 1 N hydrochloric acid to pH 3 and extracted three times with ethyl acetate. The combined organic layers were dried over sodium sulfate, filtered, and concentrated to give crude material. The crude material was azeotrophed three times with methylene chloride and then dried in vacuo for 18 h to provide crude 4-((3,3-difluorocyclobutyl)(6-(4-(trifluoromethyl)-1H-imidazol-1-yl)pyridin-3-ylamino)methyl)benzoic acid (24.0 mg). MS (M+1): 453.2.

Step (C): ethyl 3-(4-((3,3-difluorocyclobutyl)(6-(4-(trifluoromethyl)-1H-imidazol-1-yl)pyridin-3-ylamino)methyl)benzamido)propanoate

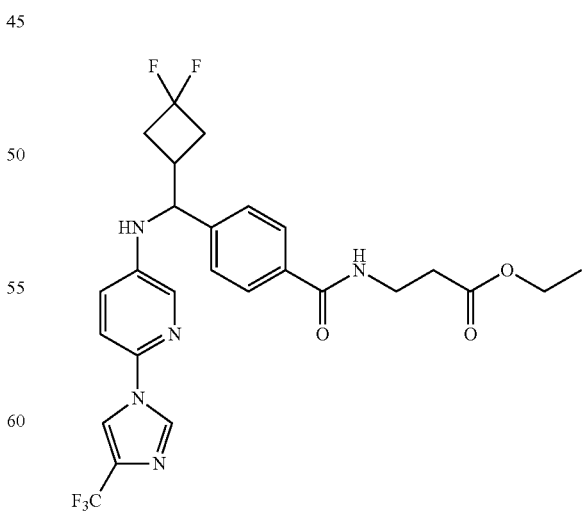

Dimethylformamide (0.270 mL) was added to a vial containing crude 4-((3,3-difluorocyclobutyl)(6-(4-(trifluoromethyl)-1H-imidazol-1-yl)pyridin-3-ylamino)methyl)benzoic acid (24.0 mg, approximately 0.120 mmol pure), ethyl 3-aminopropanoate hydrochloride (16.3 mg, 0.110 mmol) and O-(7-azabenzotriazol-1-yl)-N,N,N',N'-tetramethyluronium hexafluorophosphate (40.3 mg, 0.110 mmol).

Diisopropylethylamine (0.046 mL, 0.270 mmol) was then added. The reaction was stirred for 16 h, and was then concentrated. Purification by column chromatography (0-60% ethyl acetate in heptane) afforded ethyl 3-(4-((3,3-difluorocyclobutyl)(6-(4-(trifluoromethyl)-1H-imidazol-1-yl)pyridin-3-ylamino)methyl)benzamido)propanoate (7.00 mg) as an oil. MS (M+1): 552.3.

Step (D): (+/−)-3-(4-((3,3-difluorocyclobutyl)(6-(4-(trifluoromethyl)-1H-imidazol-1-yl)pyridin-3-ylamino)methyl)benzamido)propanoic acid To a flask containing 3-(4-((3,3-difluorocyclobutyl)(6-(4-(4-(trifluoromethyl)-1H-imidazol-1-yl)pyridin-3-ylamino)methyl)benzamido)propanoate (7.00 mg, 0.0100 mmol) was added water (0.0650 mL), tetrahydrofuran (0.0650 mL), and methanol (0.0650 mL). Lithium hydroxide monohydrate (27.3 mg, 0.650 mmol) was then added. The suspension was stirred at room temperature for 2 hours. The reaction was quenched with 1 N hydrochloric acid to pH 3 and extracted three times with ethyl acetate. The combined organic layers were dried over sodium sulfate, filtered, and concentrated to give (+/−)-3-(4-((3,3-difluorocyclobutyl)(6-(4-(trifluoromethyl)-1H-imidazol-1-yl)pyridin-3-ylamino)methyl)benzamido)propanoic acid (4.5 mg, 70%) of a glass-like material. $^1$H NMR (400 MHz, CDCl$_3$) δ 8.36-8.34 (m, 1H), 8.16-8.12 (m, 1H), 7.86 (d, J=2.9 Hz, 1H), 7.84-7.77 (m, 2H), 7.58-7.51 (m, 2H), 7.39 (dd, J=8.8, 0.6 Hz, 1H), 7.10 (dd, J=8.8, 2.9 Hz, 1H), 4.48 (d, J=8.8 Hz, 1H), 3.63 (t, J=6.9 Hz, 2H), 2.94-2.73 (m, 1H), 2.64 (t J=6.9 Hz, 2H), 2.61-2.49 (m, 2H), 2.49-2.33 (m, 2H). MS (M+1): 524.3.

Example 155

3-(4-((3,3-dimethylcyclobutyl)(2-(4-(trifluoromethyl)-1H-pyrazol-1-yl)pyrimidin-5-yloxy)methyl)benzamido)propanoic acid, Isomer 1 and Example 156

3-(4-((3,3-dimethylcyclobutyl)(2-(4-(trifluoromethyl)-1H-pyrazol-1-yl)pyrimidin-5-yloxy)methyl)benzamido)propanoic acid, Isomer 1

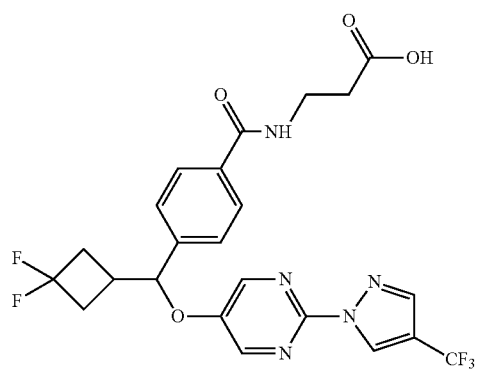 [SMILES: O=C(O)CCNC(=O)c1ccc(C(Oc2cnc(-n3cc(C(F)(F)F)cn3)nc2)C2CC(F)(F)C2)cc1]

Step (A): ethyl 3-(4-((3,3-dimethylcyclobutyl)(2-(4-(trifluoromethyl)-1H-pyrazol-1-yl)pyrimidin-5-yloxy)methyl)benzamido)propanoate, Isomer 1 and Isomer 2

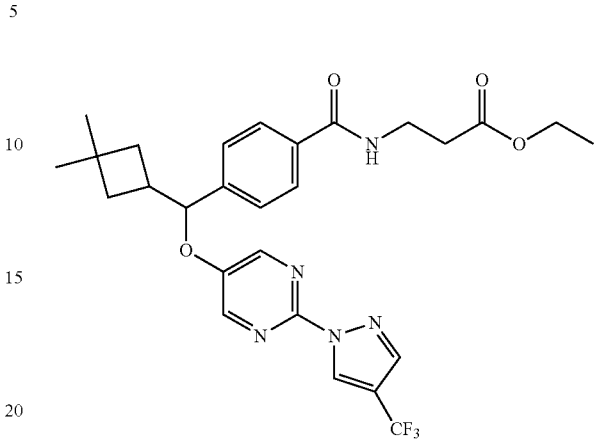

Azodicarboxylic acid dipiperidine (814 mg, 3.19 mmol) and Intermediate (102) (781 mg, 2.34 mmol) were azeotrophed twice with toluene. To this mixture was added anhydrous tetrahydrofuran (10.6 mL). Tributylphosphine (0.840 mL, 3.41 mmol) was then added dropwise. Intermediate (105) (490 mg, 2.13 mmol) was then added as a solid in one portion. After 18 hours, the reaction was not complete so another 0.5 equiv. of Azodicarboxylic acid dipiperidine and tributylphosphine were added. After another 4 h, the reaction was diluted with ethyl acetate to fully dissolve the solid. The mixture was washed twice with 1.0 M sodium hydroxide, water, 1.0 M hydrochloric acid, and brine. The organic layer was dried over magnesium sulfate, filtered, and concentrated to a viscous oil. Purification by silica gel flash chromatography (0-30% ethyl acetate in heptane) afforded ethyl 3-(4-((3,3-dimethylcyclobutyl)(2-(4-(trifluoromethyl)-1H-pyrazol-1-yl)pyrimidin-5-yloxy)methyl)benzamido)propanoate (520 mg, 45% yield) as a white solid.

Isomer 1 is obtained by resolving (+/−)-ethyl 3-(4-((3,3-dimethylcyclobutyl)(2-(4-(trifluoromethyl)-1H-pyrazol-1-yl)pyrimidin-5-yloxy)methyl)benzamido)propenoate by chiral SFC. Column: Chiralcel OJ-H. Dimensions: 21 mm×25 cm. Mobile Phase: 70/30 CO$_2$/methanol. Flow Rate: 65.0 mL/min. Modifier none. Retention time: 2.05 minutes, isomer 1, 2.71 minutes, isomer 2. Isomer 1: $^1$H NMR (400 MHz, CDCl$_3$) δ 8.71 (is, 1H), 8.29 (s, 2H), 7.92 (is, 1H), 7.74 (d, J=8.4 Hz, 2H), 7.35 (d, J=8.2 Hz, 2H), 6.81 (t, J=6.2 Hz, 1H), 5.08 (d, J=7.4 Hz, 1H), 4.27-4.02 (m, 2H), 3.70 (q, J=6.0 Hz, 2H), 2.85-2.66 (m, 1H), 2.62 (t, J=5.9 Hz, 2H), 1.96-1.82 (m, 2H), 1.79-1.69 (m, 1H), 1.69-1.59 (m, 1H), 1.30-1.21 (m, 3H), 1.15 (s, 3H), 1.11 (s, 3H). MS (M+1): 546.4. Isomer 2:) $^1$H NMR (400 MHz, CDCl$_3$) δ 8.72 (s, 1H), 8.29 (s, 2H), 7.92 (s, 1H), 7.74 (d, J=8.2 Hz, 2H), 7.35 (d, J=8.2 Hz, 2H), 6.81 (t, J=6.1 Hz, 1H), 5.08 (d, J=7.4 Hz, 1H), 4.23-4.03 (m, 2H), 3.71 (q, J=6.0 Hz, 2H), 2.84-2.67 (m, 1H), 2.62 (t, J=5.8 Hz, 2H), 1.97-1.84 (m, 2H), 1.78-1.69 (m, 1H), 1.69-1.58 (m, 1H), 1.31-1.22 (m, 3H), 1.15 (s, 3H), 1.11 (s, 3H). MS (M+1): 546.4.

Step (B): 3-(4-((3,3-dimethylcyclobutyl)(2-(4-(trifluoromethyl)-1H-pyrazol-1-yl)pyrimidin-5-yloxy)methyl)benzamido)propanoic acid, Isomer 1

The title compound is obtained by hydrolyzing ethyl 3-(4-((3,3-dimethylcyclobutyl)(2-(4-(trifluoromethyl)-1H-pyrazol-1-yl)pyrimidin-5-yloxy)methyl)benzamido)propanoate, isomer 1 using the conditions in Example 152, Step D. $^1$H NMR (400 MHz, CDCl$_3$) δ 8.71 (is, 1H), 8.29 (s, 2H), 7.92 (s, 1H), 7.80-7.68 (m, 2H), 7.42-7.31 (m, 2H), 6.74 (t, J=6.1 Hz, 1H), 5.08 (d, J=7.2 Hz, 1H), 3.72 (q, J=6.0 Hz, 2H), 2.82-2.74 (m, 1H), 2.71 (t, J=6.0 Hz, 2H), 1.97-1.82 (m, 2H), 1.80-1.68 (m, 1H), 1.68-1.58 (m, 1H), 1.15 (s, 3H), 1.11 (s, 3H). MS (M+1): 518.2. Chiral SFC. Column: Chiralpak AD-H. Dimensions: 4.6×250 mm. Mobile Phase: 60/40 CO$_2$/methanol. Flow Rate: 2.5 mL/min. Modifier: None. Retention time: 3.80 minutes.

Step (B): 3-(4-((3,3-dimethylcyclobutyl)(2-(4-(trifluoromethyl)-1H-pyrazol-1-yl)pyrimidin-5-yloxy)methyl)benzamido)propanoic acid, Isomer 2

The title compound is obtained by hydrolyzing ethyl 3-(4-((3,3-dimethylcyclobutyl)(2-(4-(trifluoromethyl)-1H-pyrazol-1-yl)pyrimidin-5-yloxy)methyl)benzamido)propanoate, isomer 2 using the conditions in Example 152, Step D. $^1$H NMR (400 MHz, CDCl$_3$) δ 8.71 (s, 1H), 8.29 (s, 2H), 7.92 (s, 1H), 7.77-7.67 (m, 2H), 7.42-7.32 (m, 2H), 6.75 (t, J=6.3 Hz, 1H), 5.08 (d, J=7.4 Hz, 1H), 3.72 (q, J=6.2 Hz, 2H), 2.82-2.73 (m, 1H), 2.71 (t, J=6.0 Hz, 2H), 1.96-1.83 (m, 2H), 1.80-1.69 (m, 1H), 1.69-1.58 (m, 1H), 1.15 (s, 3H), 1.11 (s, 3H). MS (M+1): 518.2. Chiral SFC. Column: Chiralpak AD-H. Dimensions: 4.6×250 mm. Mobile Phase: 60/40 CO$_2$/methanol. Flow Rate: 2.5 mL/min. Modifier: None. Retention time: 5.93 minutes.

Example 157

3-(4-((3,3-dimethylcyclobutyl)(2-(4-(trifluoromethyl)-1H-pyrazol-1-yl)pyrimidin-5-ylamino)methyl)benzamido)propanoic acid, Isomer 1 and Example 158

3-(4-((3,3-dimethylcyclobutyl)(2-(4-(trifluoromethyl)-1H-pyrazol-1-yl)pyrimidin-5-ylamino)methyl)benzamido)propanoic acid, Isomer 2

Step (A): ethyl 3-(4-((3,3-dimethylcyclobutyl)(2-(4-(trifluoromethyl)-1H-pyrazol-1-yl)pyrimidin-5-ylamino)methyl)benzamido)propanoate

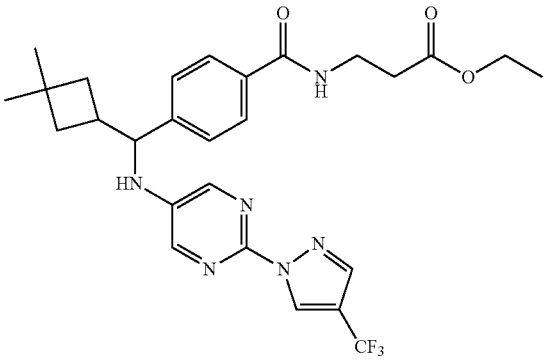 [SMILES: CCOC(=O)CCNC(=O)c1ccc(C(Nc2cnc(-n3cc(C(F)(F)F)cn3)nc2)C2CC(C)(C)C2)cc1]

To a solution of Intermediate (101) (1.19 g, 3.60 mmol) and Intermediate (106) (750 mg, 3.27 mmol) in methanol (10.9 ml) was added decaborane (240 mg, 1.96 mmol). The reaction was stirred for 12 hours at ambient temperature. The reaction mixture was quenched with aqueous 1.0M hydrochloric acid and extracted three times with ethyl acetate. The combined organic layers were dried over sodium sulfate, filtered, and concentrated. Purification by silica gel flash chromatography (0-70% ethyl acetate in heptane) afforded ethyl 3-(4-((3,3-dimethylcyclobutyl)(2-(4-(trifluoromethyl)-1H-pyrazol-1-yl)pyrimidin-5-ylamino)methyl)benzamido)propenoate (842 mg, 47% yield) as a yellow solid.

(+/−)-ethyl 3-(4-((3,3-dimethylcyclobutyl)(2-(4-(trifluoromethyl)-1H-pyrazol-1-yl)pyrimidin-5-ylamino)methyl)benzamido)propanoate was resolved by chiral SFC (Column: Chiralpak IA. Dimensions: 10 mm×25 cm. Mobile Phase: 65/35 CO$_2$/methanol. Flow Rate: 10.0 mL/min. Modifier: none) to give ethyl 3-(4-((3,3-dimethylcyclobutyl)(2-(4-(trifluoromethyl)-1H-pyrazol-1-yl)pyrimidin-5-ylamino)methyl)benzamido)propenoate Isomer 1 (retention time: 3.42 min) and ethyl 3-(4-((3,3-dimethylcyclobutyl)(2-(4-(trifluoromethyl)-1H-pyrazol-1-yl)pyrimidin-5-ylamino)methyl)benzamido)propanoate, Isomer 2 (retention time: 4.55 min). Isomer 1: $^1$H NMR (400 MHz, CDCl$_3$) δ 8.64 (s, 1H), 7.97 (s, 2H), 7.88 (s, 1H), 7.79-7.64 (m, 2H), 7.41-7.31 (m, 2H), 6.82 (t, J=5.9 Hz, 1H), 4.22 (d, J=9.4 Hz, 1H), 4.16 (q, J=7.0 Hz, 2H), 3.80-3.64 (m, 2H), 2.61 (t, J=5.9 Hz, 2H), 2.58-2.45 (m, 1H), 2.05-1.97 (m, 1H), 1.75-1.63 (m, 2H), 1.63-1.55 (m, 1H), 1.26 (t, J=7.2 Hz, 3H), 1.13 (s, 3H), 1.09 (s, 3H). MS (M+1): 545.4. Isomer 2: $^1$H NMR (400 MHz, CDCl$_3$) δ 8.64 (s, 1H), 7.97 (s, 2H), 7.88 (s, 1H), 7.80-7.67 (m, 2H), 7.43-7.30 (m, 2H), 6.82 (t, J=6.0 Hz, 1H), 4.22 (d, J=9.4 Hz, 1H), 4.16 (q, J=7.2 Hz, 2H), 3.77-3.64 (m, 2H), 2.63 (t, J=5.7 Hz, 2H), 2.58-2.40 (m, 1H), 2.05-1.97 (m, 1H), 1.76-1.64 (m, 2H), 1.64-1.52 (m, 1H), 1.26 (t, J=7.1 Hz, 3H), 1.13 (s, 3H), 1.09 (s, 3H). MS (M+1): 545.4.

Step (B): 3-(4-((3,3-dimethylcyclobutyl)(2-(4-(trifluoromethyl)-1H-pyrazol-1-yl)pyrimidin-5-ylamino)methyl)benzamido)propanoic acid, Isomer 1

The title compound is obtained by hydrolyzing ethyl 3-(4-((3,3-dimethylcyclobutyl)(2-(4-(trifluoromethyl)-1H-pyrazol-1-yl)pyrimidin-5-ylamino)methyl)benzamido)propanoate, isomer 1 using the conditions in Example 152, Step D. $^1$H NMR (400 MHz, CDCl$_3$) δ 8.80-8.53 (m, 1H), 8.01 (br.

s., 2H), 7.89 (br. s., 1H), 7.78-7.67 (m, 2H), 7.41-7.30 (m, 2H), 6.84 (s, 1H), 4.22 (d, J=9.4 Hz, 1H), 3.71 (q, J=4.7 Hz, 2H), 2.70 (t, J=5.7 Hz, 2H), 2.64-2.40 (m, 1H), 2.12-1.90 (m, 1H), 1.77-1.47 (m, 3H), 1.12 (s, 3H), 1.08 (s, 3H). MS (M+1): 517.3.

Step (C): 3-(4-((3,3-dimethylcyclobutyl)-2-(4-(trifluoromethyl)-1H-pyrazol-1-yl)pyrimidin-5-ylamino)methyl)benzamido)propanoic acid, Isomer 2

The title compound is obtained by hydrolyzing ethyl 3-(4-((3,3-dimethylcyclobutyl)(2-(4-(trifluoromethyl)-1H-pyrazol-1-yl)pyrimidin-5-ylamino)methyl)benzamido)propanoate, isomer 2 using the conditions in Example 152, Step D. ¹H NMR (400 MHz, CDCl₃) δ 8.72-8.58 (m, 1H), 8.00 (br. s., 2H), 7.89 (br. s., 1H), 7.76-7.65 (m, 2H), 7.40-7.29 (m, 2H), 6.87 (br. s, 1H), 4.22 (d, J=9.4 Hz, 1H), 3.78-3.66 (m, 2H), 2.70 (t, J=5.5 Hz, 2H), 2.62-2.42 (m, 1H), 2.08-1.93 (m, 1H), 1.77-1.51 (m, 3H), 1.12 (s, 3H), 1.08 (s, 3H). MS (M+1): 517.3.

Example 159

3-(4-(1-(2-methyl-4-(4-(trifluoromethyl)-1H-pyrazol-1-yl)phenoxyl)butyl)benzamido)propanoic acid

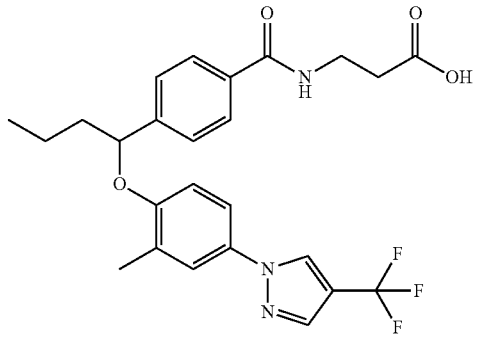 [SMILES: CCCC(Oc1ccc(-n2cc(C(F)(F)F)cn2)cc1C)c1ccc(C(=O)NCCC(=O)O)cc1]

Step A: 1-(benzyloxy)-4-iodo-2-methylbenzene

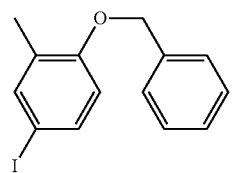 [SMILES: Cc1cc(I)ccc1OCc1ccccc1]

A mixture of 4-iodo-2-methylphenol (700 mg, 3.0 mmol), benzyl bromide (563 mg, 3.3 mmol), potassium carbonate (620 mg, 4.5 mmol), and acetonitrile (15 ml) was stirred at the ambient temperature for three days. The reaction was concentrated in vacuum and the residue was partitioned between water and ethyl acetate. The organic extract was washed with brine, dried over anhydrous magnesium sulfate, and loaded on silica gel. Chromatography on a silica gel column, eluting with a gradient from 5% to 30% of ethyl acetate in heptane gave the target product as a colorless solid (950 mg, 98%). ¹H NMR (500 MHz, CDCl₃) δ 7.48 (d, 1H), 7.38-7.45 (m, 5H), 7.33-7.37 (m, 1H), 6.66 (d, J=8.54 Hz, 1H), 5.07 (s, 2H), 2.25 (s, 3H).

Step B: 1-(4-(benzyloxy)-3-methylphenyl)-4-(trifluoromethyl)-1H-pyrazole

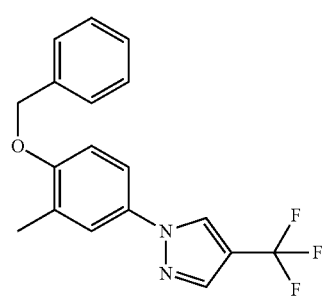 [SMILES: Cc1cc(-n2cc(C(F)(F)F)cn2)ccc1OCc1ccccc1]

A mixture of 1-(benzyloxy)-4-iodo-2-methylbenzene (850 mg, 2.6 mmol), 4-(trifluoromethyl)-1H-pyrazole (535 mg, 3.9 mmol), copper iodide (100 mg, 0.52 mmol), dimethylglycine (54 mg, 0.52 mmol), potassium carbonate (906 mg, 6.6 mmol), and DMSO (10 ml) was stirred at +1200 for 20 hours. The reaction was cooled to the ambient temperature, diluted with 10 ml of 5% aqueous ammonia and 10 ml of ethyl acetate and vigorously stirred for 20 min. The mixture was extracted with ethyl acetate (2×20 ml). The combined organic extract was washed with brine, dried over anhydrous magnesium sulfate, and loaded on silica gel. Chromatography on a silica gel column, eluting with a gradient from 5% to 30% of ethyl acetate in heptane gave the target product as an oil, which crystallized upon standing to a colorless solid (670 mg, 77%). MS (M+1): 333.1.

Step C: 2-methy-4-(4-(trifluoromethyl)-1H-pyrazol-1-yl)phenol

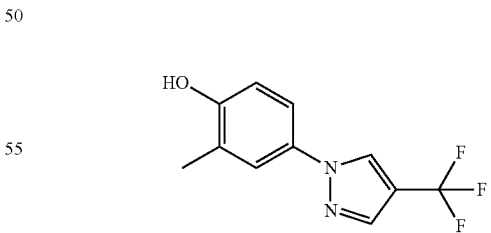

A mixture of 1-(4-(benzyloxy)-3-methylphenyl)-4-(trifluoromethyl)-1H-pyrazole (670 mg, 2.0 mmol), 20% palladium hydroxide on activated carbon (50 mg), ethanol (20 ml), and THF (20 ml) was shaken under 40 psi of hydrogen gas at the ambient temperature for 3 days and at +50° for 1 day, to drive reaction to completion. The reaction was filtered Step D: ethyl 4-(1-(2-methyl-4-(trifluoromethyl)-1H-pyrazol-1-yl)phenoxy)butyl)benzoate

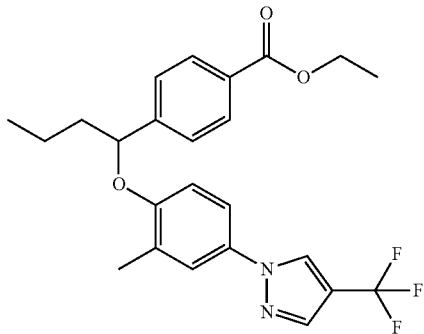 [SMILES: CCCC(Oc1ccc(-n2cc(C(F)(F)F)cn2)cc1C)c1ccc(C(=O)OCC)cc1]

2-Methyl-4-(4-(trifluoromethyl)-1H-pyrazol-1-yl)phenol (200 mg, 0.83 mmol) was combined with ethyl 4-(1-hydroxybutyl)benzoate (see Intermediate 5) (19 mg, 0.87 mmol) and dissolved in anhydrous tetrahydrofuran (5 mL). Triphenylphosphine (347 mg, 1.3 mmol) was added at 0° under stirring followed by 0.83 ml of 1.5 M solution of diazoethyl azodicarboxylate (1.24 mmol). The reaction was stirred at room temperature as a yellow solution. At 17 hours, the reaction was concentrated and 10 ml of ethyl acetate and 5 ml of heptanes were added. Solid was filtered off and the mother liquor was loaded on silica gel. Chromatography on a silica gel column (gradient from 5% to 40% of ethyl acetate in heptane) gave the target product as a colorless glass (90 mg, 24%). MS (M+1): 447.2.

Step E: 4-(1-(2-methyl-4-(4-(trifluoromethyl)-1H-pyrazol-1-yl)phenoxy)butyl)benzoic acid

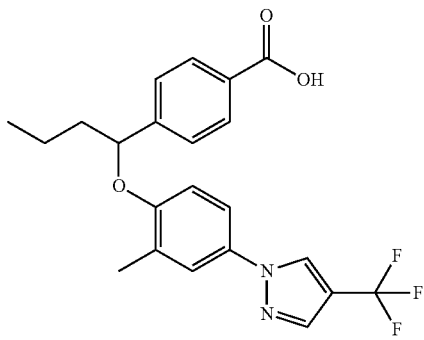 [SMILES: CCCC(Oc1ccc(-n2cc(C(F)(F)F)cn2)cc1C)c1ccc(C(=O)O)cc1]

A mixture of ethyl 4-(1-(2-methyl-4-(4-(trifluoromethyl)-1H-pyrazol-1-yl)phenoxy)butyl)benzoate (90 mg, 0.2 mmol), lithium hydroxide monohydrate (24 mg, 1.0 mmol), methanol (2 ml), THF (3 ml), and water (1 ml) was stirred at +450 for 18 hours. The mixture was concentrated, diluted with 8 ml of water and 2 ml of 1 M potassium hydrogen sulfate. The mixture was extracted with ethyl acetate-heptane (1:1), extract was washed with brine, dried over anhydrous magnesium sulfate and concentrated to obtain the target product as a white solid (84 mg, 99%). MS (M+1): 419.2.

Step F: ethyl 3-(4-(1-(2-methyl-4-(4-(trifluoromethyl)-1H-pyrazol-1-yl)phenoxy)butyl)benzamido)propanoate

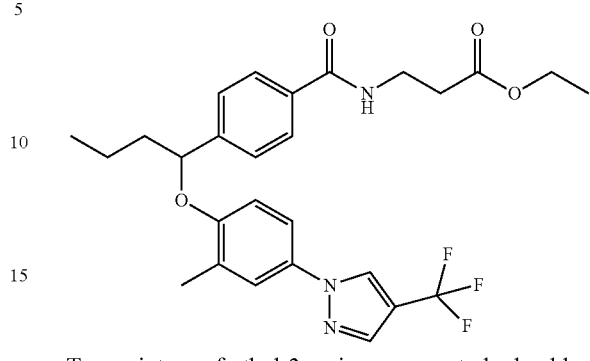

To a mixture of ethyl 3-aminopropanoate hydrochloride (46 mg, 0.3 mmol), 4-(1-(2-methyl-4-(4-(trifluoromethyl)-1H-pyrazol-1-yl)phenoxy)butyl)benzoic acid (84 mg, 0.2 mmol), HOBt hydrate (34 mg, 0.22 mmol), and DIPEA (0.133 ml, 0.8 mmol), and THF (3 ml) was added EDCl hydrochloride (62 mg, 0.32 mmol) in one portion at the ambient temperature and the reaction was stirred at the same temperature for three days. The mixture was diluted with 3 ml of ethyl acetate, 3 ml of heptanes, and washed successively with saturated aqueous sodium bicarbonate and brine, dried over anhydrous magnesium sulfate, and loaded on silica gel. Chromatography on a silica gel column, eluting with a gradient from 10% to 50% of ethyl acetate in heptane gave the target product as a colorless gum (55 mg, 53%). $^1$H NMR (500 MHz, CDCl$_3$) δ 8.01 (s, 1H), 7.84 (s, 1H), 7.75 (d, J=8.29 Hz, 2H), 7.45 (d, J=2.68 Hz, 1H), 7.40 (d, J=8.05 Hz, 2H), 7.20 (dd, J=2.68, 8.78 Hz, 1H), 6.81-6.87 (m, 1H), 6.61 (d, J=8.78 Hz, 1H), 5.21 (dd, J=5.12, 7.56 Hz, 1H), 4.18 (q, J=7.16 Hz, 2H), 3.73 (q, J=6.02 Hz, 2H), 2.64 (t, J=5.85 Hz, 2H), 2.40 (s, 3H), 2.00-2.10 (m, 1H), 1.81-1.90 (m, 1H), 1.52-1.61 (m, 1H), 1.44-1.51 (m, 1H), 1.28 (t, J=7.20 Hz, 3H), 0.98 (t, J=7.44 Hz, 3H). MS (M+1): 5182.

Step G: 3-(4-(1-(2-methyl-4-(4-(trifluoromethyl)-1H-pyrazol-1-yl)phenoxy)butyl)benzamido)propanoic acid

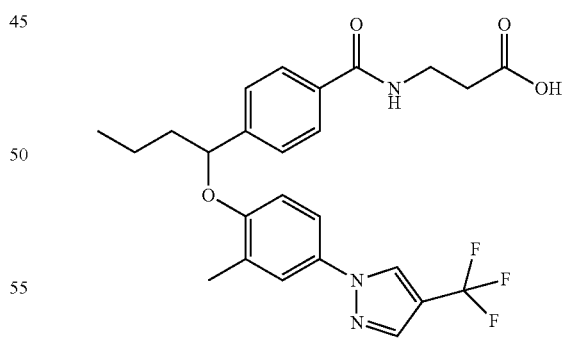

A mixture of ethyl 3-(4-(1-(2-methyl-4-(4-(trifluoromethyl)-1H-pyrazol-1-yl)phenoxy)butyl)-benzamido)propanoate (55 mg, 0.11 mmol), lithium hydroxide monohydrate (7.2 mg, 0.3 mmol), methanol (2 ml), THF (2 ml), and water (0.3 ml) was stirred at 220 for 3 days. The mixture was concentrated, diluted with 8 ml of water and 0.35 ml of 1 M potassium hydrogen sulfate. The mixture was extracted with ethyl acetate, the extract was washed with brine, dried over anhydrous magnesium sulfate and concentrated to obtain 3-(4-(1-(2-methyl-4-(4-(trifluoromethyl)-1H-pyrazol-1-yl)phenoxy)butyl)benzamido)-propanoic acid as a white solid (50 mg, 96%). $^1$H NMR (500 MHz, CDCl$_3$) δ 8.00 (s, 1H), 7.84 (s, 1H), 7.73 (d, J=8.29 Hz, 2H), 7.43 (d, J=2.68 Hz, 1H), 7.39 (d, J=8.29 Hz, 2H), 7.18 (dd, J=2.68, 8.78 Hz, 1H), 6.84-6.90 (m, 1H), 6.59 (d, J=8.78 Hz, 1H), 5.20 (dd, J=5.12, 7.56 Hz, 1H), 3.71 (q, J=5.94 Hz, 2H), 2.69 (t, J=5.85 Hz, 2H), 2.39 (s, 3H), 1.99-2.09 (m, 1H), 1.80-1.89 (m, 1H), 1.51-1.61 (m, 1H), 1.42-1.50 (m, 1H), 0.98 (t, J=7.32 Hz, 3H). MS (M+1): 4902.

Example 160

3-(4-(1-(6-(4-phenyl-1H-pyrazol-1-yl)pyridine-3-ylamino)butyl)benzamido)propanoic acid, Isomer 1

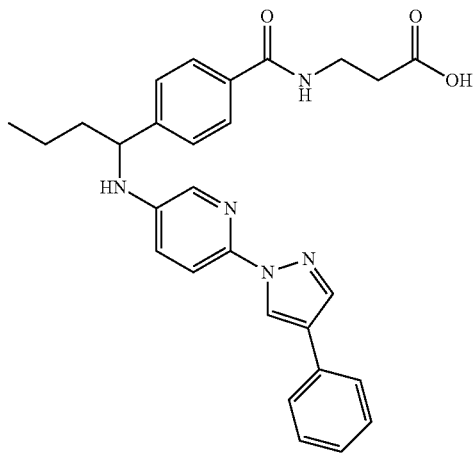 [SMILES: CCCC(Nc1ccc(-n2cc(-c3ccccc3)cn2)nc1)c1ccc(C(=O)NCCC(=O)O)cc1]

The title compound is obtained by resolving racemic 3-(4-(1-(6-(4-phenyl-1H-pyrazol-1-yl)pyridine-3-ylamino)butyl)benzamido)propanoic acid Example 62, by chiral SFC. Column: Chiralcel AS-H. Dimensions: 4.6 mm×250 mm. Mobile Phase: 60/40 CO$_2$/isopropanol. Flow Rate: 2.5 mL/min. Modifier: 0.2% isopropylamine. Retention time: 5.33 minutes.

Example 161

3-(4-(1-(6-(4-phenyl-1H-pyrazol-1-yl)pyridine-3-ylamino)butyl)benzamido)propanoic acid, Isomer 2

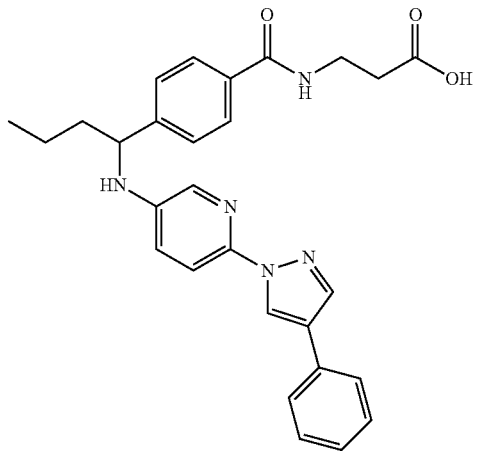 [SMILES: CCCC(Nc1ccc(-n2cc(-c3ccccc3)cn2)nc1)c1ccc(C(=O)NCCC(=O)O)cc1]

The title compound is obtained by resolving racemic 3-(4-(1-(6-(4-phenyl-1H-pyrazol-1-yl)pyridine-3-ylamino)butyl)benzamido)propanoic acid Example 62, by chiral SFC. Column: Chiralcel AS-H. Dimensions: 4.6 mm×250 mm. Mobile Phase: 60/40 CO$_2$/isopropanol. Flow Rate: 2.5 mL/min. Modifier: 0.2% isopropylamine. Retention time: 6.25 minutes.

Example 162

(+/−)-3-(4-(1-(6-(4-phenyl-1-imidazol-1-yl)pyridin-3-ylamino)butyl)benzamido)propanoic acid

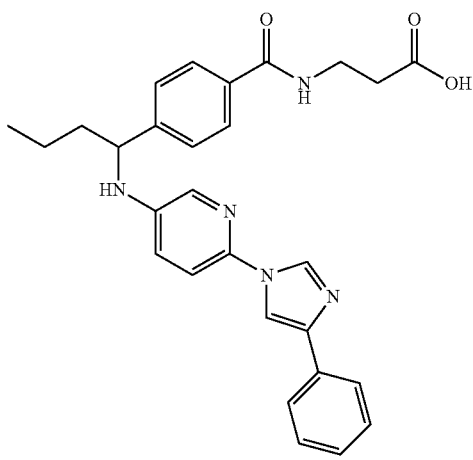 [SMILES: CCCC(Nc1ccc(-n2cnc(-c3ccccc3)c2)nc1)c1ccc(C(=O)NCCC(=O)O)cc1]

The title compound was prepared by a method analogous to that described for Example 62, using 6-(4-phenyl-1H-imidazol-1-yl)pyridin-3-amine. Column: Waters Atlantis dC18 4.6×50 mm, 5 μm. Modifier TFA 0.05%. Gradient: 95% H$_2$0/5% MeCN linear to 5% H$_2$0/95% MeCN over 4.0 min, Hold at 5% H$_2$0/95% MeCN to 5.0 min. Flow: 2.0 mL/min. Retention time: 2.38 min. MS (M+1): 484.0.

Example 163

(+/−)-3-(4-((6-(4-chloro-3-methyl-1H-pyrazol-1-yl)pyridin-3-ylamino(cyclopentyl)methyl)benzamido)propanoic acid

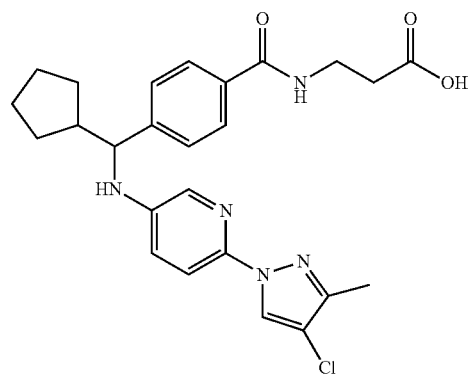 [SMILES: Cc1nn(-c2ccc(NC(c3ccc(C(=O)NCCC(=O)O)cc3)C3CCCC3)cn2)cc1Cl]

243

Step A: (+/−)-ethyl 4-((6-(4-chloro-3-methyl-1H-pyrazol-1-yl)pyridin-3-ylamino)(cyclopentyl)methyl)benzoate

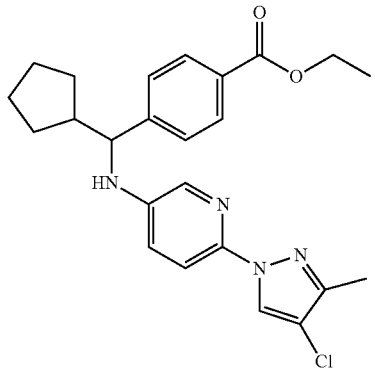 [SMILES: CCOC(=O)c1ccc(C(Nc2ccc(-n3cc(Cl)c(C)n3)nc2)C2CCCC2)cc1]

The title compound was prepared by a method analogous to that described in Step A of Example 1, using Intermediate (31) and Intermediate (108). $^1$H NMR (400 MHz, CDCl$_3$, δ): 8.18 (s, 1H), 7.96-8.00 (m, 2H), 7.62 (d, J=2.7 Hz, 1H), 7.52 (d, J=8.8 Hz, 1H), 7.36-7.40 (m, 2H), 6.85 (dd, J=8.9, 2.8 Hz, 1H), 4.34 (q, J=7.0 Hz, 2H), 4.13 (d, J=8.4 Hz, 1H), 2.26 (s, 3H), 2.13-2.22 (m, 1H), 1.87-1.96 (m, 1H), 1.38-1.72 (m, 6H), 1.33-1.38 (m, 3H), 1.22-1.32 (m, 2H). MS (M+1) 439.3.

Step B: (+/−)-4-((6-(4-chloro-3-methyl-1H-pyrazol-1-yl)pyridin-3-ylamino)(cyclopentyl)methyl)benzoic acid

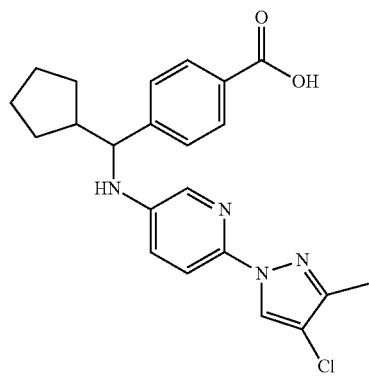 [SMILES: Cc1nn(-c2ccc(NC(c3ccc(C(=O)O)cc3)C3CCCC3)cn2)cc1Cl]

To a solution of (+/−)-ethyl 4-((6-(4-chloro-3-methyl-1H-pyrazol-1-yl)pyridin-3-ylamino)(cyclopentyl)methyl)benzoate (78.6 mg, 0.179 mmol) in methanol (1 mL) and tetrahydrofuran (1 mL) was added 1 N aqueous sodium hydroxide (0.36 mL, 0.36 mmol). The reaction was heated to 50° C. for 10 minutes. The heat was removed and the reaction was allowed to stir at room temperature for 1 hour. The reaction was concentrated. The residue was taken up in water and acidified to pH=4 with 1 N aqueous hydrochloric acid. The resulting precipitate was collected by filtration and dried under vacuum to give the title compound (68.3 mg, 93%) as a white solid. $^1$H NMR (400 MHz, CD$_3$OD, δ): 8.19 (s, 1H), 7.92-7.96 (m, 2H), 7.66-7.69 (m, 1H), 7.48 (d, J=8.4 Hz, 2H), 7.42-7.45 (m, 1H), 7.03 (dd, J=8.9, 2.8 Hz, 1H), 4.18 (d, J=9.2 Hz, 1H), 2.22 (s, 3H), 1.98-2.07 (m, 1H), 1.43-1.74 (m, 6H), 1.23-1.38 (m, 2H). MS (M+1) 411.3.

244

Step C: (+/−)-methyl 3-(4-((6-(4-chloro-3-methyl-1H-pyrazol-1-yl)pyridin-3-ylamino)(cyclopentyl)methyl)benzamido)propanoate

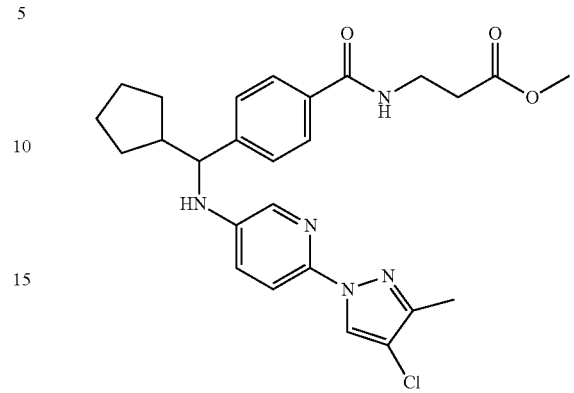

The title compound was prepared by a method analogous to that described in Step C of Example 2, using (+/−)-4-((6-(4-chlor-3-methyl-1H-pyrazol-1-yl)pyridin-3-ylamino)(cyclopentyl)methyl)benzoic acid. $^1$H NMR (400 MHz, CDCl$_3$, δ): 8.18 (s, 1H), 7.66-7.72 (m, 2H), 7.61 (d, J=2.7 Hz, 1H), 7.49-7.54 (m, 1H), 7.37 (d, J=8.4 Hz, 2H), 6.85 (dd, J=8.8, 2.9 Hz, 1H), 6.78 (t, J=6.0 Hz, 1H), 4.09-4.14 (m, 1H), 3.65-3.73 (m, 5H), 2.59-2.65 (m, 2H), 2.25 (s, 3H), 1.86-1.96 (m, 1H), 1.35-1.73 (m, 6H), 1.19-1.32 (m, 2H). MS (M+1) 496.4.

Step D: (+/−)-3-(4-((6-(4-chloro-3-methyl-1H-pyrazol-1-yl)pyridin-3-ylamino)(cyclopentyl)methyl)benzamido)propanoic acid The title compound was prepared by a method analogous to that described in Step E of Example 4, using (+/−)-methyl 3-(4-((6-(4-chloro-3-methyl-1H-pyrazol-1-yl)pyridin-3-ylamino)cyclopentyl)methyl)benzamido)propanoate. $^1$H NMR (400 MHz, CD$_3$OD, δ): 8.19 (s, 1H), 7.70-7.75 (m, 2H), 7.66 (d, J=2.5 Hz, 1H), 7.41-7.49 (m, 3H), 7.05 (dd, J=9.0, 2.9 Hz, 1H), 4.17 (d, J=9.2 Hz, 1H), 3.58 (t, J=6.9 Hz, 2H), 2.59 (t, J=6.9 Hz, 2H), 2.22 (s, 3H), 1.97-2.08 (m, 1H), 1.42-1.75 (m, 5H), 1.23-1.39 (m, 3H). MS (M+1) 482.4.

Example 164

(+/−)-3-(4-(1-(6-(4-(pyridin-2-yl-1H-pyrazol-1-yl)pyridin-3-ylamino)butyl)benzamido)propanoic acid

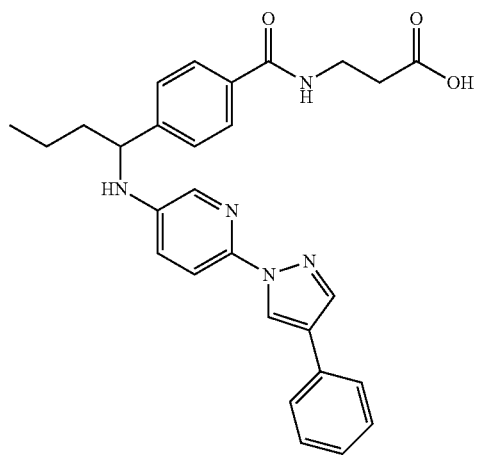 [SMILES: CCCC(Nc1ccc(-n2cc(-c3ccccc3)cn2)nc1)c1ccc(C(=O)NCCC(=O)O)cc1]

245

Step A: (+/−)-ethyl 4-(1-(6-(4-(pyridin-2-yl-1H-pyrazol-1-yl)pyridin-3-ylamino)butyl)benzoate

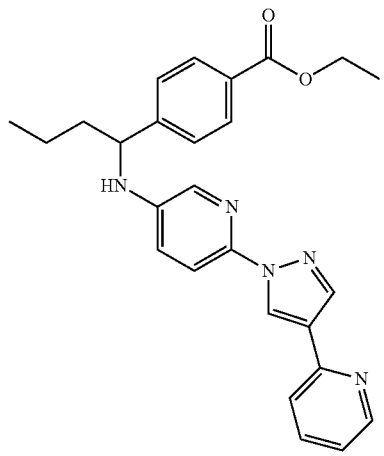 [SMILES: CCCC(Nc1ccc(-n2cc(-c3ccccn3)cn2)nc1)c1ccc(C(=O)OCC)cc1]

To a solution of Intermediate (109) (42.3 mg, 0.178 mmol) in methanol (1.8 mL) was added glacial acetic acid (20 μL, 0.4 mmol) and Intermediate (5) (43.0 mg, 0.195 mmol). Lastly, added decaborane (13 mg, 0.11 mmol) and let reaction stir at room temperature for 65 hours. The reaction was concentrated. The crude residue was taken up in ethyl acetate, washed with saturated aqueous sodium bicarbonate (3×) and brine, dried over magnesium sulfate, filtered, and concentrated. Purification by flash column chromatography (10-70% ethyl acetate/heptanes) gave ethyl 4-(1-(6-(4-(pyridin-2-yl)-1H-pyrazol-1-yl)pyridin-3-ylamino)butyl)benzoate (19.6 mg, 25%). $^1$H NMR (400 MHz, CDCl$_3$, δ): 8.82 (s, 1H), 8.56 (dd, J=4.9, 1.0 Hz, 1H), 8.16 (s, 1H), 8.00 (d, J=8.2 Hz, 2H), 7.61-7.72 (m, 3H), 7.50 (d, J=8.0 Hz, 1H), 7.39 (d, J=8.2 Hz, 2H), 7.10 (ddd, J=7.5, 5.0, 1.0 Hz, 1H), 6.88 (dd, J=8.9, 2.8 Hz, 1H), 4.34 (q, J=7.2 Hz, 2H), 4.23 (d, J=5.5 Hz, 1H), 1.71-1.90 (m, 2H), 1.31-1.54 (m, 5H), 0.94 (t, J=7.3 Hz, 3H). MS (M+1) 442.4.

Step B: (+/−)-3-(4-(1-(6-(4-(pyridin-2-yl)-1H-pyrazol-1-yl)pyridin-3-ylamino)butyl)benzamido)propanoic acid The title compound was prepared by a method analogous to that described for Example 163, Steps B-D, using (+/−)-ethyl 4-(1-(6-(4-(pyridin-2-yl)-1H-pyrazol-1-yl)pyridin-3-ylamino)butyl)benzoate. Column: Waters Atlantis dC18 4.6× 50 mm, 5 μm. Modifier TFA 0.05%. Gradient 95% H$_2$O/5% MeCN linear to 5% H$_2$O/95% MeCN over 4.0 min, Hold at 5% H$_2$O/95% MeCN to 5.0 min. Flow: 2.0 mL/min. Retention time: 2.20 min. MS (M+1): 485.0.

246

Example 165

(+/−)-3-(N-methyl-4-(1-(6-(4-phenyl-1H-pyrazol-1-yl)pyridin-3-ylamino)butyl)benzamido)propanoic acid

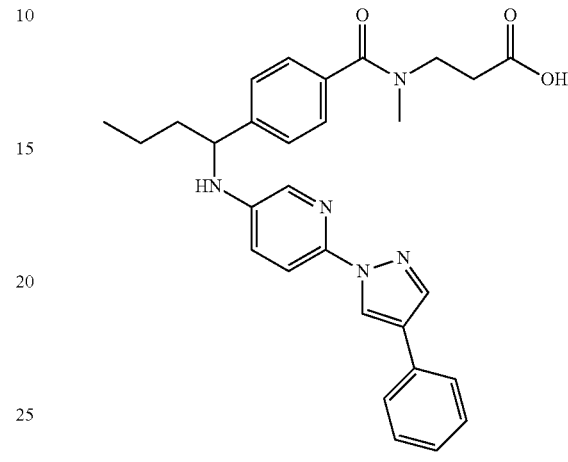

Step A: (+/−)-ethyl 4-(1-(6-(4-phenyl-1H-pyrazol-1-yl)pyridin-3-ylamino)butyl)benzoate The title compound was prepared by a method analogous to that described in Step A of Example 62, using Intermediate (5). $^1$H NMR (400 MHz, CDCl$_3$, δ): 8.59 (s, 1H), 7.98-8.03 (m, 2H), 7.90 (s, 1H), 7.65-7.71 (m, 2H), 7.51-7.56 (m, 2H), 7.32-7.43 (m, 4H), 7.20-7.25 (m, 1H), 6.90 (dd, J=8.8, 2.9 Hz, 1H), 4.31-4.41 (m, 3H), 1.73-1.90 (m, 2H), 1.32-1.51 (m, 5H), 0.92-0.98 (m, 3H). MS (M+1) 441.4.

Step B: (+/−)-tert-butyl 3-(N-methyl-4-(1-(6-(4-phenyl-1H-pyrazol-1-yl)pyridin-3-ylamino)butyl)benzamido)propanoate

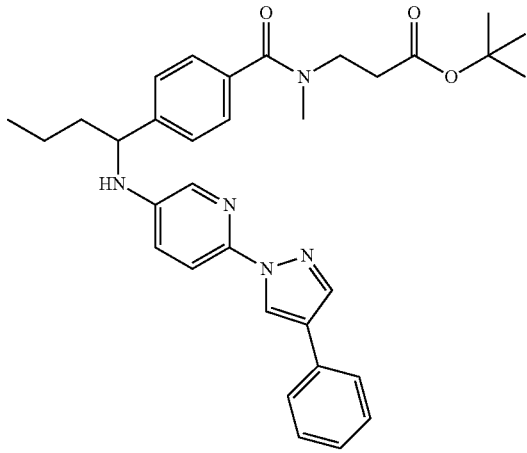 [SMILES: CCCC(Nc1ccc(-n2cc(-c3ccccc3)cn2)nc1)c1ccc(C(=O)N(C)CCC(=O)OC(C)(C)C)cc1]

The title compound was prepared by a method analogous to that described in Steps B and C of Example 2, using ethyl 4-(1-(6-(4-phenyl-1H-pyrazol-1-yl)pyridin-3-ylamino)butyl)benzoate and tert-butyl 3-(methylamino)propanoate. MS (M+1) 554.5.

Step C: (+/−)-3-(N-methyl-4-(1-(6-(4-phenyl-1H-pyrazol-1-yl)pyridin-3-ylamino)butyl)benzamido) propanoic acid The title compound was prepared by a method analogous to that described in Step C of Example 1, using (+/−)-tert-butyl 3-(N-methyl-4-(1-(6-(4-phenyl-1H-pyrazol-1-yl)pyridin-3-ylamino)butyl)benzamido)propanoate. Column: Waters Atlantis dC18 4.6×50 mm, 5 μm. Modifier: TFA 0.05%. Gradient: 95% H$_2$O/5% MeCN linear to 5% H$_2$O/95% MeCN over 4.0 min, Hold at 5% H$_2$O/95% MeCN to 5.0 min. Flow: 2.0 mL/min. Retention time: 3.27 min. MS (M+1): 498.1.

Example 166

3-(4-(1-(6-(4-ethyl-3-methyl-1H-pyrazol-1-yl)pyridin-3-ylamino)butyl)benzamido)propanoic acid, Isomer 1 and Example 167

3-(4-(1-(6-(4-ethyl-3-methyl-1H-pyrazol-1-yl)pyridin-3-ylamino)butyl)benzamido)propanoic acid, Isomer 2

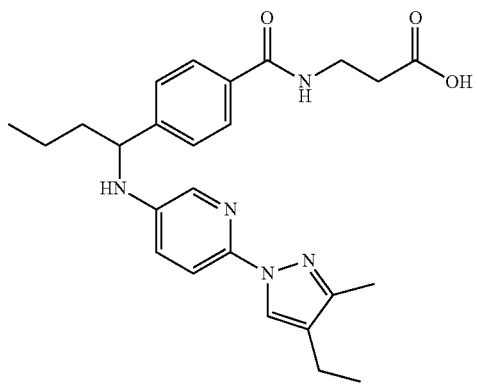 [SMILES: CCCC(Nc1ccc(-n2cc(CC)c(C)n2)nc1)c1ccc(C(=O)NCCC(=O)O)cc1]

Racemic 3-(4-(1-(6-(4-ethyl-3-methyl-1H-pyrazol-1-yl)pyridin-3-ylamino)butyl)benzamido)propanoic acid was prepared by a method analogous to that described for Example 62, using Intermediate (110). $^1$H NMR (400 MHz, CD$_3$OD, δ): 7.95 (s, 1H), 7.72-7.76 (m, 2H), 7.61 (d, J=2.5 Hz, 1H), 7.40-7.47 (m, 3H), 7.08 (dd, J=8.9, 2.8 Hz, 1H), 4.41 (t, J=6.9 Hz, 1H), 3.58 (t, J=6.9 Hz, 2H), 2.60 (t, J=6.9 Hz, 2H), 2.44 (q, J=7.5 Hz, 2H), 2.20 (s, 3H), 1.67-1.92 (m, 2H), 1.31-1.56 (m, 2H), 1.18 (t, J=7.5 Hz, 3H), 0.95 (t, J=7.4 Hz, 3H). MS (M+1) 450.4.

Racemic 3-(4-(1-(6-(4-ethyl-3-methyl-1H-pyrazol-1-yl)pyridin-3-ylamino)butyl)benzamido)propanoic acid was resolved by chiral SFC to afford the two single enantiomers. Chiral SFC: Chiralcel OJ-H, 10×250 mm; Mobile Phase 65:35 CO$_2$/methanol, 10 mL/min, Retention time: 3.03 minutes (Isomer 1), 5.47 minutes (Isomer 2).

Example 168

(R)-3-(6-((1-(3,5-dimethyl-4-(4-(trifluoromethyl)-1H-pyrazol-1-yl)phenyl)-3-methybutyl)amino)nicotinamido)propanoic acid

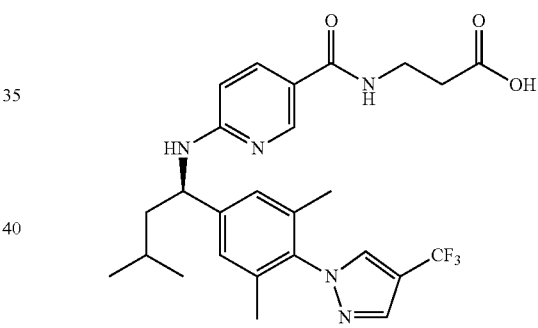

To a solution of Intermediate (118) (218 mg, 0.400 mmol) in tetrahydrofuran (2.00 mL) and methanol (2.00 mL) was added 1 N aq sodium hydroxide (2.00 mL, 2.00 mmol). After 10 minutes, the solution was concentrated under reduced pressure to remove tetrahydrofuran and methanol. 1 N aq hydrochloric acid was added until the mixture was at pH 4. The mixture was diluted with sat. aq sodium chloride (20 mL) and extracted with ethyl acetate (3×25 mL). The combined organics were dried (Na$_2$SO$_4$) and filtered, and the filtrate was concentrated under reduced pressure to provide (R)-3-(6-((1-(3,5-dimethyl-4-(4-(trifluoromethyl)-1H-pyrazol-1-yl)phenyl)-3-methylbutyl)amino)nicotinamido)propanoic acid. $^1$H NMR (400 MHz, CDCl$_3$, δ): 9.25-9.15 (m, 1H), 8.25 (s, 1H), 8.18 (d, J=9.2 Hz, 1H), 7.93 (s, 1H), 7.78-7.68 (m, 2H), 7.11 (s, 2H), 6.46 (d, J=9.2 Hz, 1H), 4.48-4.39 (m, 1H), 3.85-3.65 (m, 2H), 2.64 (t, J=5.6 Hz, 2H), 2.10 (s, 1H), 2.00 (s, 6H), 1.96-1.86 (m, 1H), 1.81-1.70 (m, 1H), 1.70-1.59 (m, 1H), 1.02 (d, J=6.4 Hz, 3H), 0.96 (d, J=6.4 Hz, 3H). MS (M+1): 518.7.

Example 169

(S)-3-(6-((1-(3,5-dimethyl-4-(4-(trifluoromethyl)-1H-pyrazol-1-yl)phenyl)-3-methylbutyl)amino)nicotinamido)propanoic acid

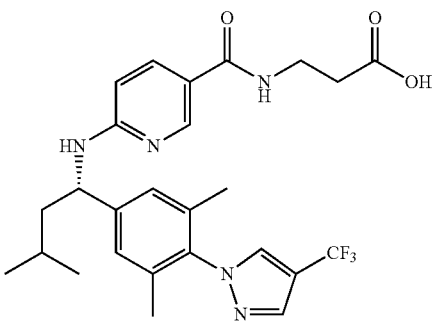 [SMILES: Cc1cc([C@H](CC(C)C)Nc2ccc(C(=O)NCCC(=O)O)cn2)cc(C)c1-n1cc(C(F)(F)F)cn1]

The title compound was prepared by a method analogous to that described for Example 168 using Intermediate (119). $^1$H NMR (400 MHz, CDCl$_3$, δ): 9.25-9.15 (m, 1H), 8.25 (s, 1H), 8.18 (d, J=9.2 Hz, 1H), 7.93 (s, 1H), 7.78-7.68 (m, 2H), 7.11 (s, 2H), 6.46 (d, J=9.2 Hz, 1H), 4.48-4.39 (m, 1H), 3.85-3.65 (m, 2H), 2.64 (t, J=5.6 Hz, 2H), 2.10 (s, 1H), 2.00 (s, 6H), 1.96-1.86 (m, 1H), 1.81-1.70 (m, 1H), 1.70-1.59 (m, 1H), 1.02 (d, J=6.4 Hz, 3H), 0.96 (d, J=6.4 Hz, 3H). MS (M+1): 518.7.

Example 170

(3-(6-((cyclopentyl(3,5-dimethyl-4-(4-(trifluoromethyl)-1H-pyrazol-1-yl)phenyl)methyl)amino)nicotinamido)propanoic acid, Isomer 1

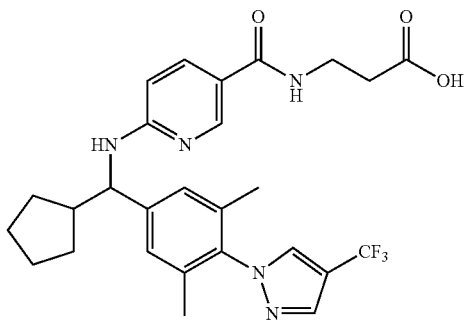 [SMILES: Cc1cc(C(Nc2ccc(C(=O)NCCC(=O)O)cn2)C2CCCC2)cc(C)c1-n1cc(C(F)(F)F)cn1]

Step A: (+/−)-N-(cyclopentyl(3,5-dimethyl-4-(4-trifluoromethyl)-1H-pyrazol-1-yl)phenyl)methyl)-2-methylpropane-2-sulfinamide

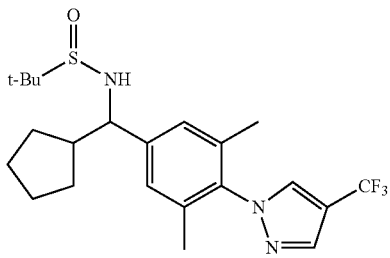 [SMILES: Cc1cc(C(NS(=O)C(C)(C)C)C2CCCC2)cc(C)c1-n1cc(C(F)(F)F)cn1]

Cyclopentylmagnesium bromide (2 M in diethyl ether, 3.46 mL, 6.92 mmol) and dimethylzinc (2 M in toluene, 3.89 mL, 7.78 mmol) were allowed to stir for 15 minutes. This solution was then added dropwise to a solution of Intermediate (1003) (1.28 g, 3.46 mmol) in tetrahydrofuran (34.6 mL) at −78° C. After 5 hours, an additional portion of cyclopentylmagnesium bromide (2 M in diethyl ether, 0.86 mL, 1.72 mmol) and dimethylzinc (2 M in toluene, 0.95 mL, 1.90 mmol) that had been allowed to mix for 15 minutes was added dropwise to the reaction mixture at −78° C. After 1 hour, the solution was quenched at −78° C. by addition of sat. aq ammonium chloride (10 mL). The resulting slurry was allowed to warm to room temperature. The mixture was diluted with 120 mL sat. aq ammonium chloride and enough water to dissolve precipitated solids. This solution was then extracted with ethyl acetate (3×120 mL). The combined organics were dried (Na$_2$SO$_4$) and filtered, and the filtrate was concentrated under reduced pressure. Purification by column chromatography (ethyl acetate/heptane) gave (+/−)-N-(cyclopentyl(3,5-dimethyl-4-(4-(trifluoromethyl)-1H-pyrazol-1-yl)phenyl)methyl)-2-methylpropane-2-sulfinamide. $^1$H NMR (400 MHz, CDCl$_3$, δ): 7.94 (s, 1H), 7.75 (s, 1H), 7.09 (s, 2H), 4.03 (d, J=9.2 Hz, 1H), 2.41-2.27 (m, 1H), 2.02 (s, 6H), 1.99-1.87 (m, 1H), 1.72-1.35 (m, 7H), 1.23 (s, 9H), 1.16-1.04 (m, 1H). MS (M+1): 442.5.

Step B: (+/−)-cyclopentyl(3,5-dimethyl-4-(4-(trifluoromethyl)-1H-pyrazol-1-yl)phenyl)methanamine hydrochloride

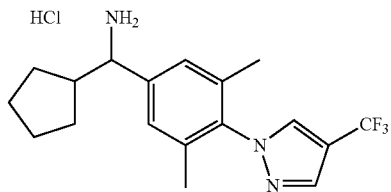 [SMILES: Cc1cc(C(N)C2CCCC2)cc(C)c1-n1cc(C(F)(F)F)cn1 ; Cl]

To a solution of (+/−)-N-(cyclopentyl(3,5-dimethyl-4-(4-(trifluoromethyl)-1H-pyrazol-1-yl)phenyl)methyl)-2-methylpropane-2-sulfinamide (1.184 g, 2.680 mmol) in methanol (13.4 mL) was added hydrogen chloride (4 M in dioxane, 3.35 mL, 13.4 mmol) dropwise. The reaction was concentrated under reduced pressure to provide (+/−)-cyclopentyl(3,5-dimethyl-4-(4-(trifluoromethyl)-1H-pyrazol-1-yl)phenyl)methanamine hydrochloride. $^1$H NMR (400 MHz, CD$_3$OD, δ): 8.33 (s, 1H), 8.07 (s, 1H), 7.31 (s, 2H), 4.05 (d, J=10.6 Hz, 1H), 2.35-2.51 (m, 1H), 2.10-1.98 (m, 7H), 1.89-1.39 (m, 6H), 1.20-1.14 (m, 1H).

Step C: methyl (+/−)-6-((cyclopentyl(3,5-dimethyl-4-(4-(trifluoromethyl)-1H-pyrazol-1-yl)phenyl)methyl)amino)nicotinate

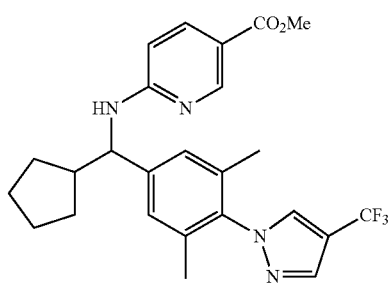 [SMILES: COC(=O)c1ccc(NC(c2cc(C)c(-n3cc(C(F)(F)F)cn3)c(C)c2)C2CCCC2)nc1]

To a mixture of (+/−)-cyclopentyl(3,5-dimethyl-4-(trifluoromethyl)-1H-pyrazol-1-yl)phenyl)methanamine hydrochloride (1.002 g, 2.680 mmol) and potassium carbonate (1.51 g, 10.7 mmol) in N,N-dimethylformamide (5.36 mL) was added methyl 6-fluoronicotinate (472 mg, 2.95 mmol). The reaction was heated to 85° C. After 15 h, the reaction was cooled to room temperature, diluted with water (50 mL), and extracted with ethyl acetate (3×50 mL). The combined organics were dried (Na$_2$SO$_4$) and filtered, and the filtrate was concentrated under reduced pressure. Purification by column chromatography (ethyl acetate/heptane) gave methyl (+/−)-6-((cyclopentyl(3,5-dimethyl-4-(4-(trifluoromethyl)-1H-pyrazol-1-yl)phenyl)methyl)amino)nicotinate. $^1$H NMR (400 MHz, CDCl$_3$, δ): 8.67 (d, J=1.6 Hz, 1H), 7.99 (dd, J=9.0, 2.0 Hz, 1H), 7.93 (s, 1H), 7.75 (s, 1H), 7.12 (s, 2H), 6.28 (d, J=9.0 Hz, 1H), 4.43-4.33 (m, 1H), 3.87 (s, 3H), 2.36-2.23 (m, 1H), 2.04-1.97 (m, 7H), 1.77-1.41 (m, 6H), 1.37-1.28 (m, 1H). MS (M+1): 4732.

Step D: (+/−)-6-((cyclopentyl(3,5-dimethyl-4-(4-(trifluoromethyl)-1H-pyrazol-1-yl)phenyl)methyl)amino)nicotinic acid

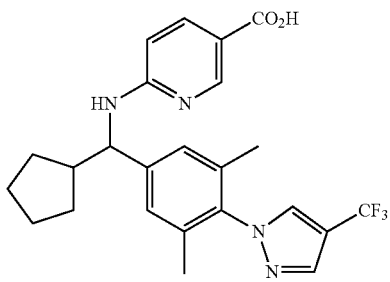 [SMILES: Cc1cc(C(Nc2ccc(C(=O)O)cn2)C2CCCC2)cc(C)c1-n1cc(C(F)(F)F)cn1]

To a solution of methyl (+/−)-(cyclopentyl(3,5-dimethyl-4-(4-(trifluoromethyl)-1H-pyrazol-1-yl)phenyl)methyl)amino)nicotinate (753 mg, 1.59 mmol) in tetrahydrofuran (7.97 mL) and methanol (7.97 mL) was added 1 N aq sodium hydroxide (7.97 mL, 7.97 mmol). After 16 h, the solution was concentrated under reduced pressure to remove tetrahydrofuran and methanol. 1 N aq hydrochloric acid was added until the mixture was at pH 4. The mixture was diluted with sat. aq sodium chloride (30 mL) and extracted with ethyl acetate (3×50 mL). The combined organics were dried (Na$_2$SO$_4$) and filtered, and the filtrate was concentrated under reduced pressure to provide (+/−)-6-((cyclopentyl(3,5-dimethyl-4-(4-(trifluoromethyl)-1H-pyrazol-1-yl)phenyl)methyl)amino)nicotinic acid. $^1$H NMR (400 MHz, CDCl$_3$, δ): 8.68 (s, 1H), 8.14 (d, J=9.2 Hz, 1H), 7.94 (s, 1H), 7.75 (s, 1H), 7.15 (s, 2H), 6.39 (d, J=9.2 Hz, 1H), 4.28-4.18 (m, 1H), 2.44-2.31 (m, 1H), 2.12-2.05 (m, 1H), 2.01 (s, 6H), 1.78-1.40 (m, 6H), 1.36-1.28 (m, 1H). MS (M+1): 459.5.

Step E: ethyl 3-(6-((cyclopentyl(3,5-dimethyl-4-(4-(trifluoromethyl)-1H-pyrazol-1-yl)phenyl)methyl)amino)nicotinamido)propanoate, Isomer 1 and ethyl 3-(6-((cyclopentyl(3,5-dimethyl-4-(4-(trifluoromethyl)-1H-pyrazol-1-yl)phenyl)methyl)amino)nicotinamido)propanoate, Isomer 2

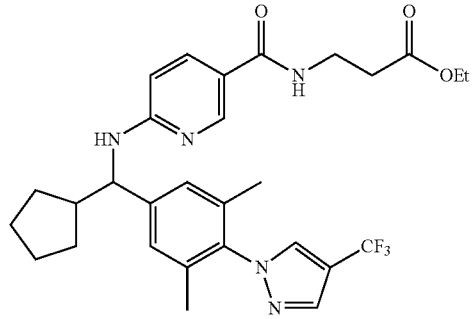 [SMILES: CCOC(=O)CCNC(=O)c1ccc(NC(c2cc(C)c(-n3cc(C(F)(F)F)cn3)c(C)c2)C2CCCC2)nc1]

To a mixture of (+/−)-((cyclopentyl(3,5-dimethyl-4-(4-(trifluoroethyl)-1H-pyrazol-1-yl)phenyl)methyl)amino) nicotinic acid (731 mg, 1.59 mmol), β-alanine ethyl ester hydrochloride (516 mg, 3.19 mmol), and 1-hydroxy-7-azabenzotriazole (336 mg, 2.39 mmol) in dichloromethane (15.9 mL) was added triethylamine (0.782 mL, 5.58 mmol) followed by N-(3-dimethylaminopropyl)-N'-ethylcarbodiimide hydrochloride (465 mg, 2.39 mmol). After 70 hours, the mixture was diluted with dichloromethane (50 mL) and washed with water (3×50 mL) and sat aq sodium chloride (50 mL). The organic layer was dried (Na$_2$SO$_4$) and filtered, and the filtrate was concentrated under reduced pressure. Purification by column chromatography (ethyl acetate/heptane) followed by chiral SFC (Cellulose-2 column, 21 mm×250 mm, 35% methanol/carbon dioxide eluent) gave ethyl 3-(6-((cyclopentyl(3,5-dimethyl-4-(4-(trifluoromethyl)-1H-pyrazol-1-yl)phenyl)methyl)amino)nicotinamido)propanoate, Isomer 1 (SFC retention time 2.71 min) and ethyl 3-(6-((cyclopentyl (3,5-dimethyl-4-(4-(trifluoromethyl)-1H-pyrazol-1-yl)phenyl)methyl)amino)nicotinamido)propanoate, Isomer 2 (SFC retention time 3.43 min). $^1$H NMR (400 MHz, CDCl$_3$, δ): 8.45 (d, J=2.0 Hz, 1H), 7.91 (s, 1H), 7.81-7.72 (m, 2H), 7.09 (s, 2H), 6.84 (t, J=5.7 Hz, 1H), 6.41-6.27 (m, 1H), 6.26 (d, J=9.0 Hz, 1H), 4.33 (t, J=7.6 Hz, 1H), 4.14 (q, J=7.1 Hz, 2H), 3.65 (q, J=6.0 Hz, 2H), 2.59 (t, J=6.0 Hz, 2H), 2.33-2.19 (m, 1H), 1.98 (s, 6H), 1.96-1.85 (m, 1H), 1.74-1.37 (m, 6H), 1.34-1.21 (m, 4H). MS (M+1): 558.5.

Step F: 3-(6-((cyclopentyl(3,5-dimethyl-4-(4-(trifluoromethyl)-1H-pyrazol-1-yl)phenyl)methyl)amino)nicotinamido)propanoic acid, Isomer 1 (Example 170)

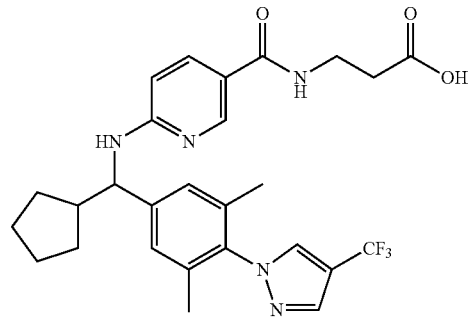 [SMILES: Cc1cc(C(Nc2ccc(C(=O)NCCC(=O)O)cn2)C2CCCC2)cc(C)c1-n1cc(C(F)(F)F)cn1]

To a solution of ethyl 3-(6-((cyclopentyl(3,5-dimethyl-4-(4-difluoromethyl)-1H-pyrazol-1-yl)phenyl)methyl)amino)nicotinamido)propenoate, Isomer 1 (255 mg, 0.457 mmol) in tetrahydrofuran (2.29 mL) and methanol (2.28 mL) was added 1 N aq sodium hydroxide (2.28 mL, 2.28 mmol). After 10 minutes, the solution was concentrated under reduced pressure to remove tetrahydrofuran and methanol. 1 N aq hydrochloric acid was added until the mixture was at pH 3. The mixture was diluted with sat. aq sodium chloride (15 mL) and extracted with ethyl acetate (3×25 mL). The combined organics were dried ($Na_2SO_4$) and filtered, and the filtrate was concentrated under reduced pressure to provide 3-(6-((cyclopentyl(3,5-dimethyl-4-(4-(trifluoromethyl)-1H-pyrazol-1-yl)phenyl)methyl)amino)nicotinamido)propanoic acid, Isomer 1. $^1$H NMR (400 MHz, $CDCl_3$, δ): 9.54-9.42 (m, 1H), 8.58-8.48 (m, 1H), 8.22 (d, J=9.2 Hz, 1H), 7.93 (s, 1H), 7.82-7.72 (m, 2H), 7.12 (s, 2H), 6.54 (d, J=9.4 Hz, 1H), 4.20-4.08 (m, 1H), 3.81-3.64 (m, 2H), 2.67 (t, J=5.5 Hz, 2H), 2.44-2.33 (m, 1H), 2.18-2.06 (m, 1H), 2.01 (s, 6H), 1.75-1.36 (m, 6H), 1.33-1.19 (m, 1H). MS (M+1): 530.4.

Example 171

3-(6-((cyclopentyl(3,5-dimethyl-4-(4-(trifluoromethyl)-1H-pyrazol-1-yl)phenyl)methyl)amino)nicotinamido)propanoic acid, Isomer 2

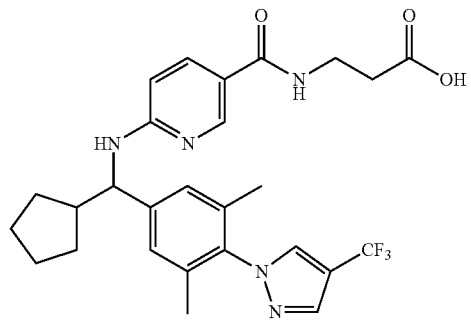 [SMILES: Cc1cc(C(Nc2ccc(C(=O)NCCC(=O)O)cn2)C2CCCC2)cc(C)c1-n1cc(C(F)(F)F)cn1]

The title compound was prepared by a method analogous to that described for Example 170, Step F, using ethyl 3-(6-((cyclopentyl(3,5-dimethyl-4-(4-(trifluoromethyl)-1H-pyrazol-1-yl)phenyl)methyl)amino)nicotinamido)propanoate, Isomer 2. $^1$H NMR (400 MHz, $CDCl_3$, δ): 9.54-9.42 (m, 1H), 8.58-8.48 (m, 1H), 8.22 (d, J=9.2 Hz, 1H), 7.93 (s, 1H), 7.82-7.72 (m, 2H), 7.12 (s, 2H), 6.54 (d, J=9.4 Hz, 1H), 4.20-4.08 (m, 1H), 3.81-3.64 (m, 2H), 2.67 (t, J=5.5 Hz, 2H), 2.44-2.33 (m, 1H), 2.18-2.06 (m, 1H), 2.01 (s, 6H), 1.75-1.36 (m, 6H), 1.33-1.19 (m, 1H). MS (M+1): 530.4.

Example 172

N-{4-[4,4,4-trifluoro-1-({6-[4-(trifluoromethyl)-1H-pyrazol-1-yl]pyridin-3-yl}amino)butyl]benzoyl}-beta-alanine, Isomer 1 and Example 173

N-{4-[4,4,4-trifluoro-1-({6-[4-(trifluoromethyl)-1H-pyrazol-1-yl]pyridin-3-yl}amino)butyl]benzoyl}-beta-alanine, Isomer 2

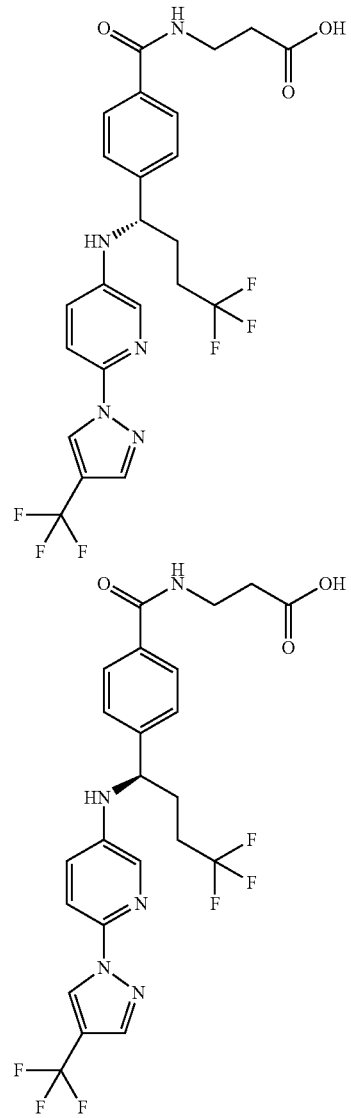

Step A: (+/−)-ethyl 4-(4,4,4-trifluoro-1-hydroxybutyl)benzoate

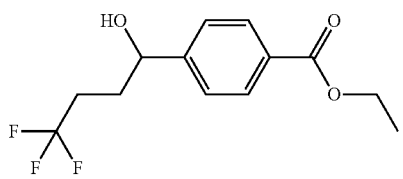 [SMILES: CCOC(=O)c1ccc(C(O)CCC(F)(F)F)cc1]

To a solution of the ethyl 4-iodobenzoate (1.21 ml, 7.24 mmol) in tetrahydrofuran (12 ml) at −40° C. was added isopropylmagnesium chloride lithium chloride complex (6.13 ml, 7.97 mmol, 1.3M in tetrahydrofuran) dropwise. The mixture was stirred for approximately 1 hour whereupon the 4,4,4-trifluorobutanal (0.761 ml, 0.724 mmol) was added dropwise. The mixture was stirred at −40° C. for 15 minutes and slowly warmed to ambient temperature over 12 hours. The reaction was quenched with aqueous 1.0M hydrochloric acid and the aqueous layer was extracted with ethyl acetate (3×). The combined organic layers were dried over magnesium sulfate, filtered, and concentrated in vacuo. The alcohol was used without further purification.

Step B: ethyl 4-(4,4,4-trifluorobutanoyl)benzoate

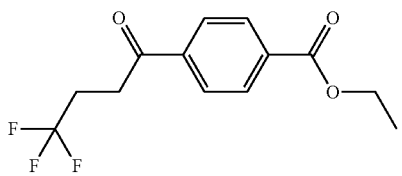 [SMILES: CCOC(=O)c1ccc(C(=O)CCC(F)(F)F)cc1]

A mixture of (+/−)-ethyl 4-(4,4,4-trifluoro-1-hydroxybutyl)benzoate (2.10 g, 7.60 mmol) in dichloromethane (28 ml), dimethyl sulfoxide (22 ml), and triethylamine (5.29 ml, 38.0 mmol) was cooled to 0° C. Sulfur trioxide pyridine complex (3.63 g, 22.8 mmol) was added in portions and the mixture stirred at 0° C. for 1 hour, then slowly raised to ambient temperature over 12 h. The reaction was quenched with water and diluted with diethylether. The aqueous layer was extracted with diethylether and the combined organic layers were washed with brine. The combined organic extracts were dried over magnesium sulfate, filtered, and concentrated in vacuo to affording the crude product as a solid that was used without further purification.

Step C: (+/−)-ethyl 4-[4,4,4-trifluoro-1-({6-[4-(trifluoromethyl)-1H-pyrazol-1-yl]pyridin-3-yl}amino)butyl]benzoate

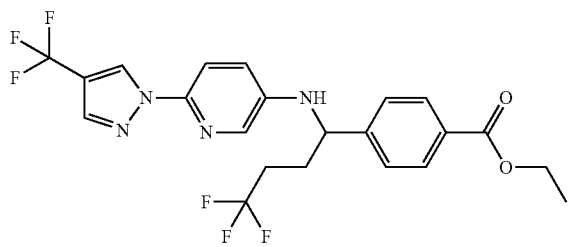 [SMILES: CCOC(=O)c1ccc(C(CCC(F)(F)F)Nc2ccc(-n3cc(C(F)(F)F)cn3)nc2)cc1]

To a solution of crude ethyl 4-(4,4,4-trifluorobutanoyl)benzoate (0.060 g, 0.22 mmol) and 6-[4-(trifluoromethyl)-1H-pyrazol-1-yl]pyridin-3-amine (0.050 g, 0.22 mmol) in methanol (2.2 ml) was added decaborane (8.0 mg, 0.066 mmol). The reaction was stirred for 12 hours at ambient temperature. The reaction mixture was quenched with aqueous 1.0M hydrochloric acid and concentrated in vacuo. The crude material was purified via ISCO MPLC (SiO$_2$, 0-100% ethyl acetate in heptane) to yield the product (47 g, 42%) as an oil. $^1$H NMR (400 MHz, CDCl$_3$): δ 8.63 (s, 1H), 8.06 (d, J=8.4 Hz, 2H), 7.80 (s, 1H), 7.75 (d, J=2.5 Hz, 1H), 7.70 (d, J=8.8 Hz, 1H), 7.38-7.45 (m, 2H), 6.96 (dd, J=8.8, 2.7 Hz, 1H), 4.50 (t, J=6.2 Hz, 1H), 4.37 (q, J=7.0 Hz, 2H), 2.07-2.32 (m, 4H), 1.39 (t, J=7.2 Hz, 3H). MS (M+1): 487.3.

Step D: (+/−)-4-[4,4,4-trifluoro-1-({6-[4-(trifluoromethyl)-1H-pyrazol-1-yl]pyridin-3-yl}amino)butyl]benzoic acid

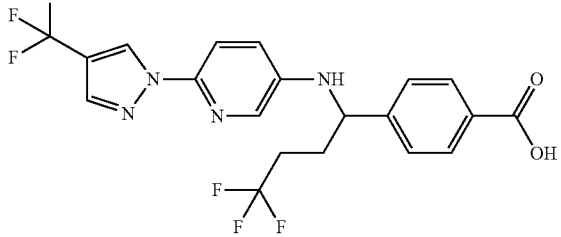

A mixture of (+/−)-ethyl 4-[4,4,4-trifluoro-1-({6-[4-(trifluoromethyl)-1H-pyrazol-1-yl]pyridin-3-yl}amino)butyl]benzoate (46 mg, 0.095 mmol) in methanol (0.19 ml) and tetrahydrofuran (0.095 ml) was treated with aqueous lithium hydroxide (0.095 ml, 0.19 mmol, 2.0M). The mixture was stirred at ambient temperature for 12 hours. The reaction was concentrated in vacuo, then diluted with water and acidified with aqueous 1.0M hydrochloric acid. The mixture was then concentrated in vacuo a second time, and the crude residue was used directly for further transformations.

Step E: (+/−)-ethyl N-{4-[4,4,4-trifluoro-1-({6-[4-(trifluoromethyl)-1H-pyrazol-1-yl]pyridin-3-yl}amino)butyl]benzoyl}-beta-alaninate

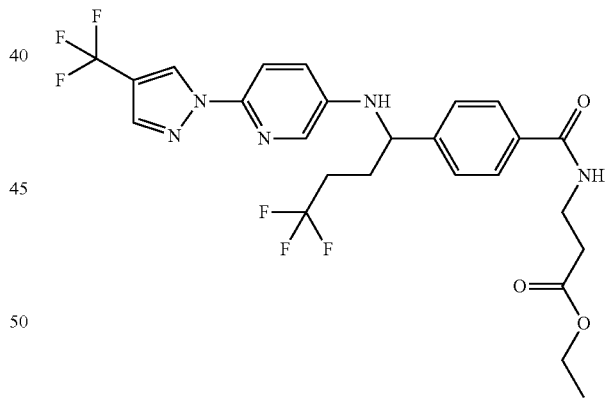

To a mixture of ethyl 3-aminopropionate hydrochloride (23 mg, 0.19 mmol), (+/−)-4-[4,4,4-trifluoro-1-({6-[4-(trifluoromethyl)-1H-pyrazol-1-yl]pyridin-3-yl}amino)butyl]benzoic acid (44 mg, 0.096 mmol), hydroxybenzotriazole hydrate (15 mg, 0.096 mmol), and triethylamine (55 ul, 0.39 mmol) in dichloromethane (0.96 ml) was added 1-ethyl-3-(3-dimethylaminopropyl)carbodiimide hydrochloride (21 mg, 0.11 mmol). The mixture was stirred for 2 hours at ambient temperature. The reaction was diluted with water and the organic layer was separated. The aq. layer was extracted with dichloromethane (2×) and the combined organic layers were dried over sodium sulfate, filtered, and concentrated in vacuo. The crude material was used without further purification.

Step F: (+) & (−)-N-{4-[4,4,4-trifluoro-1-({6-[4-(trifluoromethyl)-1H-pyrazol-1-yl]pyridin-3-yl}amino)butyl]benzoyl}-beta-alanine A mixture of crude (+/−)-ethyl N-{4-[4,4,4-trifluoro-1-({6-[4-(trifluoromethyl)-1H-pyrazol-1-yl]pyridin-3-yl}amino)butyl]benzoyl}-beta-alaninate (52 mg, 0.093 mmol) was dissolved in methanol (0.20 ml) and tetrahydrofuran (0.10 ml) and treated with aqueous lithium hydroxide (0.093 ml, 0.19 mmol, 2.0M). The mixture was stirred at ambient temperature for 1 hour. The crude reaction mixture was concentrated in vacuo and the residual solid was dissolved in water (0.50 ml) and treated with aqueous 1.0M hydrochloric acid until approximately pH 6 was reached, resulting in the precipitation of racemic N-{4-[4,4,4-trifluoro-1-({6-[4-(trifluoromethyl)-1H-pyrazol-1-yl]pyridin-3-yl}amino)butyl]benzoyl}-beta-alanine as a white gummy solid. The two enantiomeric products were separated by chiral SFC Column: Chiralpak AD-H. Dimensions: 21×250 mm. Mobile Phase: 70/30 CO2/methanol, (peak 1, 0.30 g, 22% and peak 2, 0.30 g, 22%). Flow Rate: 65 mL/min. Modifier: none. Analytical SFC: Chiralpak AD-H, 4.6 mm×25 cm: SFC Mobile Phase 70:30 CO2/Methanol, 2.5 mL/min, analytical retention time: 2.97 min (Isomer 1) and 5.15 (Isomer 2). $^1$H NMR (400 MHz, CDCl$_3$): δ 8.64 (s, 1H), 7.73-7.84 (m, 4H), 7.70 (d, J=8.8 Hz, 1H), 7.37-7.43 (m, 2H), 6.98 (br. dd, J=8.6, 2.0 Hz, 1H), 6.73-6.86 (m, 1H), 4.48 (br. t, J=6.3 Hz, 1H), 3.73 (br. q, J=5.9 Hz, 2H), 2.72 (br. t, J=5.8 Hz, 2H), 2.06-2.34 (m, 4H). MS (M+1): 530.3.

Example 174

N-{4-[{[6-(4-cyclopropyl-1H-pyrazol-1-yl)pyridin-3-yl]amino}(3,3-dimethylcyclobutyl)methyl]benzoyl}-beta-alanine, Isomer 1 and Example 175

N-{4-[{[6-(4-cyclopropyl-1H-pyrazol-1-yl)pyridin-3-yl]amino}(3,3-dimethylcyclobutyl)methyl]benzoyl}-beta-alanine, Isomer 2

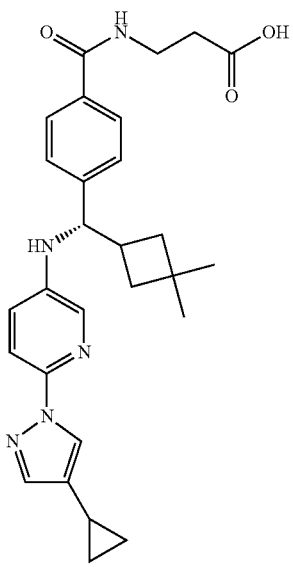

-continued

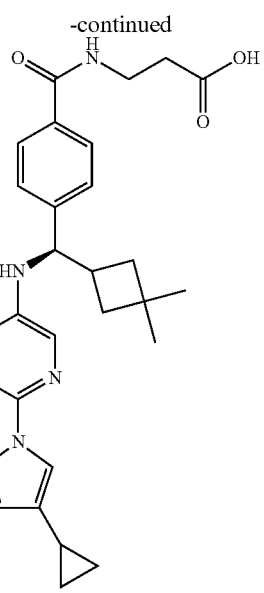

Step A: 2-(4-iodo-1H-pyrazol-1-yl)-5-nitropyridine

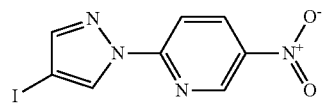

A mixture of the 4-iodo-1H-pyrazole (4.59 g, 23.7 mmol) and 2-chloro-5-nitropyridine (3.75 g, 23.7 mmol) in N,N-dimethylformamide (11.8 ml) was treated with potassium carbonate (3.76 g, 27.2 mmol). The mixture was heated to 80° C. for 12 hours. The reaction mixture was diluted with excess water resulting in the precipitation of a solid that was collected by filtration. Further drying in vacuo afforded the product (7.5 g, 100%) as a yellow solid. $^1$H NMR (400 MHz, CDCl$_3$): δ 9.27 (d, J=2.3 Hz, 1H), 8.70 (s, 1H), 8.62 (dd, J=9.0, 2.5 Hz, 1H), 8.12 (d, J=9.0 Hz, 1H), 7.80 (s, 1H).

Step B: 2-(4-cyclopropyl-1H-pyrazol-1-yl)-5-nitropyridine

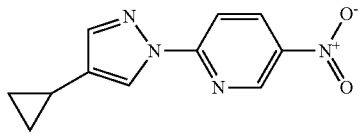 [SMILES: O=[N+]([O-])c1ccc(-n2cc(C3CC3)cn2)nc1]

A flask was charged with a mixture of the 2-(4-iodo-1H-pyrazol-1-yl)-5-nitropyridine (0.600 g, 1.90 mmol), cyclopropylboronic acid (652 mg, 7.59 mmol), palladium acetate (43 mg, 0.19 mmol), tricyclohexylphosphine (112 mg, 0.380 mmol), and tripotassium phosphate (1.41 g, 6.64 mmol) and then equipped with a micro reflux condenser and purged with dry nitrogen. Freshly degassed toluene (10 ml) was added followed by degassed water (0.4 ml) and the mixture was heated to reflux for 12 hours. The reaction mixture was cooled to ambient temperature, then diluted with ethyl acetate and water. The aqueous layer was extracted with ethyl acetate (3×) and the combined organic extracts were dried over sodium sulfate, filtered, and concentrated in vacuo. The crude material was purified via ISCO MPLC (SiO$_2$, 0-25% ethyl acetate in heptane) to yield the product (0.12 g, 28%) as a solid. $^1$H NMR (400 MHz, CDCl$_3$): δ 9.24 (d, J=2.7 Hz, 1H), 8.56 (dd, J=9.1, 2.6 Hz, 1H), 8.32 (s, 1H), 8.08 (d, J=9.0 Hz, 1H), 7.62 (s, 1H), 1.79 (tt, J=8.6, 5.1 Hz, 1H), 0.97 (ddd, J=8.2, 6.1, 4.3 Hz, 2H), 0.64 (dt, J=6.3, 4.7 Hz, 2H).

Step C:
6-(4-cyclopropyl-1H-pyrazol-1-yl)pyridin-3-amine

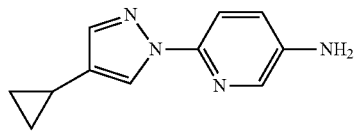 [SMILES: Nc1ccc(-n2cc(C3CC3)cn2)nc1]

A solution of 2-(4-cyclopropyl-1H-pyrazol-1-yl)-5-nitropyridine (2.91 g, 12.7 mmol) in ethyl acetate (250 ml) was passed through an H-Cube reactor equipped with a 10% Pd(OH)$_2$/C cartridge at 50° C., 50 bar, at 1 ml/min. The solution was concentrated in vacuo. The crude material was purified via ISCO MPLC (SiO$_2$, 0-100% ethyl acetate in heptane) to yield the product (964 mg, 38%) as a solid. $^1$H NMR (400 MHz, CDCl$_3$): δ 8.12 (s, 1H), 7.85 (d, J=2.7 Hz, 1H), 7.71 (d, J=8.8 Hz, 1H), 7.48 (s, 1H), 7.12 (dd, J=8.7, 2.8 Hz, 1H), 3.70 (br. s., 2H), 1.75 (tt, J=8.6, 5.3 Hz, 1H), 0.88 (ddd, J=8.4, 6.3, 4.5 Hz, 1H), 0.59 (dt, J=5.7, 4.5 Hz, 2H).

Step D: (+/−)-ethyl N-{4-[{[6-(4-cyclopropyl-1H-pyrazol-1-yl)pyridin-3-yl]amino}(3,3-dimethylcyclobutyl)methyl]benzoyl}-beta-alaninate

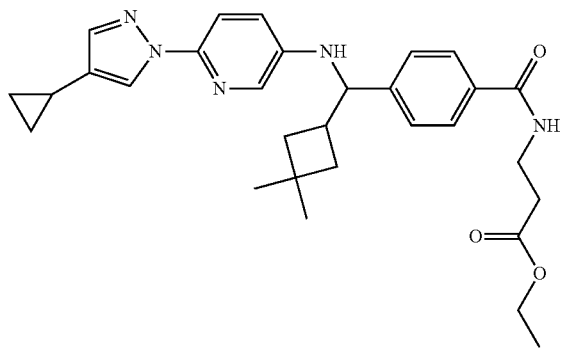 [SMILES: CCOC(=O)CCNC(=O)c1ccc(C(Nc2ccc(-n3cc(C4CC4)cn3)nc2)C2CC(C)(C)C2)cc1]

To a solution of Intermediate (101) (964 mg, 4.81 mmol) and 6-(4-cyclopropyl-1H-pyrazol-1-yl)pyridin-3-amine (1.60 g, 4.81 mmol) in methanol (10.9 ml) was added decaborane (235 mg, 1.93 mmol) in a single portion. The mixture was stirred for 12 hours. An additional aliquot of decaborane (235 mg, 1.93 mmol) was added and the mixture stirred a further 4 hours. The reaction mixture was concentrated in vacuo then treated with aqueous 1.0M hydrochloric acid for 12 hours at ambient temperature. The crude product was concentrated in vacuo and used directly for further transformations.

Step E: (+) & (−)-N-{4-[{[6-(4-cyclopropyl-1H-pyrazol-1-yl)pyridin-3-yl]amino}(3,3-dimethylcyclobutyl)methyl]benzoyl}-beta-alanine A mixture of crude (+/−)-ethyl N-{4-[{[6-(4-cyclopropyl-1H-pyrazol-1-yl)pyridin-3-yl]amino}(3,3-dimethylcyclobutyl)methyl]benzoyl}-beta-alaninate (2.48 g, 4.91 mmol) was dissolved in methanol (4.8 ml) and tetrahydrofuran (2.4 ml) and treated with aqueous 2.0M lithium hydroxide (4.8 ml, 9.6 mmol). The mixture was stirred at ambient temperature for 12 hours. The reaction was concentrated in vacuo, then diluted with water and acidified with aqueous 1.0M hydrochloric acid. A yellow precipitate formed and was collected by filtration. The two enantiomeric products were separated by chiral SFC Column: Chiralpak AD-H. Dimensions: 21×250 mm. Mobile Phase: 50/50 CO2/methanol, (peak 1, 638 mg, 27% and peak 2, 682 g, 29%). Flow Rate: 65 mL/min. Modifier: none. Analytical SFC: Chiralpak AD-H, 4.6 mm×25 cm; SFC Mobile Phase 50:50 CO2/Methanol, 2.5 mL/min, analytical retention time: 3.90 min (Isomer 2) and 9.30 (Isomer 1). $^1$H NMR (400 MHz, CDCl$_3$): δ 8.01 (s, 1H), 7.70 (d, J=8.0 Hz, 2H), 7.60 (d, J=2.5 Hz, 1H), 7.55 (d, J=8.8 Hz, 1H), 7.42 (s, 1H), 7.32 (d, J=8.0 Hz, 2H), 6.84 (dd, J=8.8, 2.7 Hz, 1H), 4.14 (d, J=9.4 Hz, 1H), 3.56-3.67 (m, 2H), 2.40-2.47 (m, 2H), 1.96 (ddd, J=11.2, 8.0, 3.9 Hz, 1H), 1.60-1.74 (m, 3H), 1.54 (ddd, J=11.9, 8.4, 3.7 Hz, 1H), 1.28-1.34 (m, 1H), 1.09 (s, 3H), 1.07 (s, 3H), 0.81-0.86 (m, 2H), 0.50-0.56 (m, 2H) MS (M+1): 488.4.

Example 176

(+/−)-N-[4-(1-{[6-(4-cyclopropyl-1H-pyrazol-1-yl)pyridin-3-yl]amino}butyl)benzoyl]-beta-alanine

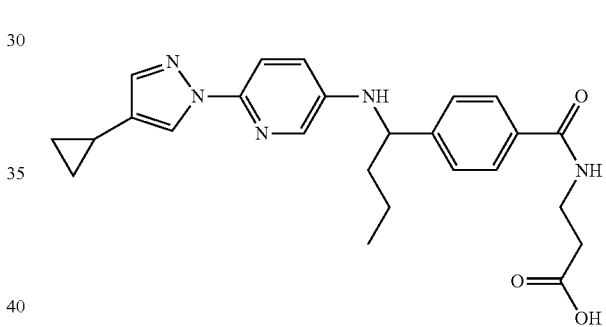

Step A: (+/−)-ethyl 4-{[6-(4-cyclopropyl-1H-pyrazol-1-yl)pyridin-3-yl]amino}butyl)benzoate

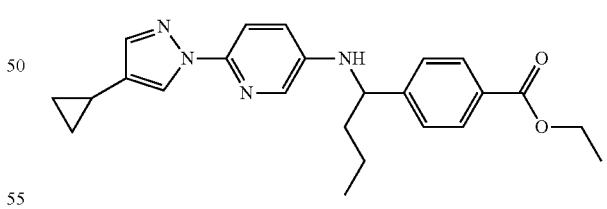

To a solution of ethyl 4-butyrylbenzoate (121 mg, 0.549 mmol) and 6-(4-cyclopropyl-1H-pyrazol-1-yl)pyridin-3-amine (0.110 g, 0.549 mmol) in methanol (1.3 ml) was added decaborane (27 mg, 0.22 mmol). The reaction was stirred for 12 hours at ambient temperature. The reaction mixture was quenched with aqueous 1.0M hydrochloric acid and concentrated in vacuo. The crude material was purified via ISCO MPLC (SiO$_2$, 0-100% ethyl acetate in heptane) to yield the product (26 mg, 12%) as an oil. $^1$H NMR (400 MHz, CDCl$_3$): δ 8.05 (s, 1H), 8.01 (d, J=8.2 Hz, 2H), 7.67 (br. s., 1H), 7.62 (d, J=9.0 Hz, 1H), 7.44 (s, 1H), 7.40 (d, J=8.2 Hz, 2H), 6.90

(d, J=6.8 Hz, 1H), 4.37 (q, J=7.2 Hz, 3H), 1.76-1.90 (m, 2H), 1.72 (tt, J=108.4, 5.1 Hz, 1H), 1.41-1.52 (m, 2H), 1.38 (t, J=7.1 Hz, 3H), 0.96 (t, J=7.3 Hz, 3H), 0.86 (ddd, J=8.2, 5.9, 3.9 Hz, 2H), 0.56 (dt, J=5.9, 4.1 Hz, 2H).

Step B: (+/−)-4-(1-{[6-(4-cyclopropyl-1H-pyrazol-1-yl)pyridin-3-yl]amino}butyl)benzoic acid

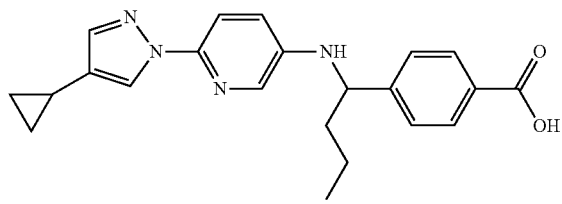 [SMILES: CCCC(Nc1ccc(-n2cc(C3CC3)cn2)nc1)c1ccc(C(=O)O)cc1]

A mixture of (+/−)-ethyl 4-(1-{[6-(4-cyclopropyl-1H-pyrazol-1-yl)pyridin-3-yl]amino}butyl)benzoate (26 mg, 0.064 mmol) was dissolved in methanol (0.13 ml) and tetrahydrofuran (0.070 ml) and treated with aqueous 2.0M lithium hydroxide (64 ul, 0.13 mmol). The mixture was stirred at ambient temperature for 12 hours. The reaction was concentrated in vacuo and the residue was acidified with aqueous 1.0M hydrochloric acid. The crude product was concentrated in vacuo a second time and was used without further purification.

Step C: (+/−)-ethyl N-[4-(1-{[6-(4-cyclopropyl-1H-pyrazol-1-yl)pyridin-3-yl]amino}butyl)benzoyl]-beta-alaninate

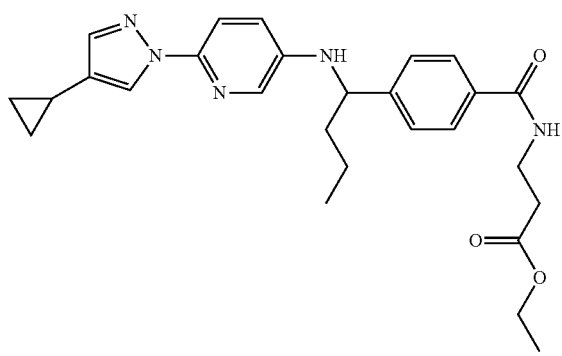 [SMILES: CCCC(Nc1ccc(-n2cc(C3CC3)cn2)nc1)c1ccc(C(=O)NCCC(=O)OCC)cc1]

To a mixture of ethyl 3-aminopropionate hydrochloride (31 mg, 0.27 mmol), (+/−)-4-(1-{[6-(4-cyclopropyl-1H-pyrazol-1-yl)pyridin-3-yl]amino}butyl)benzoic acid (0.050 g, 0.13 mmol), hydroxybenzotriazole hydrate (0.020 g, 0.13 mmol), and triethylamine (76 ul, 0.55 mmol) in dichloromethane (1.3 ml) was added 1-ethyl-3-(3-dimethylaminopropyl)carbodiimide hydrochloride (38.9 g, 201 mmol) (28 mg, 0.15 mmol) at rt. The mixture was stirred for 2 hours at ambient temperature. The reaction was diluted with water and the organic layer was separated. The aqueous layer was extracted with dichloromethane (2×) and the combined organic layers were dried over sodium sulfate, filtered, and concentrated in vacuo. The crude material was used without further purification.

Step D: (+/−)-N-[4-(1-{[6-(4-cyclopropyl-1H-pyrazol-1-yl)pyridin-3-yl]amino}butyl)benzoyl]-beta-alanine A mixture of crude (+/−)-ethyl N-[4-(1-{[6-(4-cyclopropyl-1H-pyrazol-1-yl)pyridin-3-yl]amino}butyl)benzoyl]-beta-alaninate (63 mg, 0.13 mmol) was dissolved in methanol (0.26 ml) and tetrahydrofuran (0.13 ml) and treated with aqueous 2.0M lithium hydroxide (0.13 ml, 0.26 mmol). The mixture was stirred at ambient temperature for 12 hours. The reaction was concentrated in vacuo. The residue was acidified with aqueous 1.0M hydrochloric acid and concentrated in vacuo a second time. Purification by reversed-phase HPLC on a Waters Sunfire C18 19×100 mm, 0.005 mm column eluting with a gradient of water in acetonitrile (0.05% trifluoroacetic acid modifier) gave the product Analytical LCMS: retention time 2.94 minutes (Atlantis C18 4.6×50 mm, 5 µM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute); MS (M+1): 448.2.

Example 177

(±)-3-(4-((tetrahydro-2H-pyran-4-yl)((6-(4-(trifluoromethyl)-1H-pyrazol-1-yl)pyridin-3-yl)amino)methyl)benzamido)propanoic acid

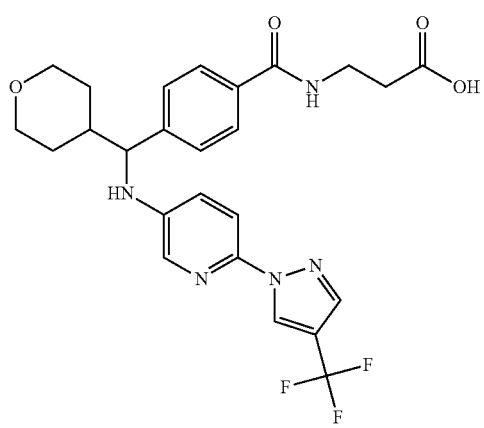 [SMILES: O=C(O)CCNC(=O)c1ccc(C(Nc2ccc(-n3cc(C(F)(F)F)cn3)nc2)C2CCOCC2)cc1]

The title compound is obtained by a method analogous to the one described for Example 2 (step B, C and D) using Intermediate (121) as starting material. Filtration of the solid formed after acidification to ca. pH 3 with citric acid (10%, aq.), provide (±)-3-(4-((tetrahydro-2H-pyran-4-yl)((6-(4-(trifluoromethyl)-1H-pyrazol-1-yl)pyridin-3-yl)amino)methyl)benzamido)propanoic acid (98.8 mg, 77.9%) as a white solid. $^1$H NMR (400 MHz, DMSO-d$_6$) δ 1.13 (br. s., 1H) 1.22-1.47 (m, 2H) 1.84-1.94 (m, 2H) 2.43-2.48 (m, 2H) 3.14-3.23 (m, 1H) 3.23-3.30 (m, 1H) 3.38-3.47 (m, 2H) 3.75-3.84 (m, 1H) 3.87-3.95 (m, 1H) 4.32 (t, J=7.83 Hz, 1H) 6.80 (d, J=8.02 Hz, 1H) 7.12 (dd, J=8.80, 2.74 Hz, 1H) 7.45 (d, J=8.22 Hz, 2H) 7.57 (d, J=8.80 Hz, 1H) 7.73-7.80 (m, 3H) 8.09 (s, 1H) 8.42 (t, J=5.28 Hz, 1H) 8.84 (s, 1H) 12.18 (s, 1H); MS (M+1): 518.4.

Example 178

(±)-3-(4-(2,2-dimethyl-1-((6-(4-(trifluoromethyl)-1H-pyrazol-1-yl)pyridin-3-yl)amino)prop)benzamido)propanoic acid

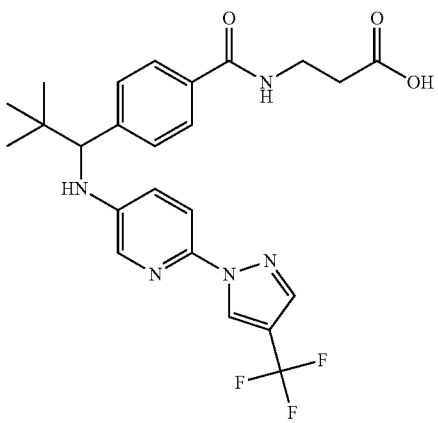 [SMILES: CC(C)(C)C(Nc1ccc(-n2cc(C(F)(F)F)cn2)nc1)c1ccc(C(=O)NCCC(=O)O)cc1]

A 20 drams vial was charged with methyl (±)-3-(4-(2,2-dimethyl-1-((6-(4-(trifluoromethyl)-1H-pyrazol-1-yl)pyridin-3-yl)amino)propyl)benzamido)propanoate (92 mg, 0.18 mmol), THF (1.8 mL) and MeOH (1.8 mL). NaOH 1M aq. (0.9 mL) was then added in one portion and the resulting mixture stirred for 30 minutes at room temperature. Organic solvents removed under reduced pressure and 5 mL of water added to the vial. Under magnetic stirring, citric acid solution (10%, aq.) added dropwise to reach ca. pH 3. The solid formed was recovered with a büchner funnel, washed with water and dried under high vacuum to provide (±)-3-(4-(2,2-dimethyl-1-((6-(4-(trifluoromethyl)-1H-pyrazol-1-yl)pyridin-3-yl)amino)propyl)benzamido) propanoic acid as a white solid (76.9 mg, 86.0%). $^1$H NMR (400 MHz, DMSO-d$_6$) δ 0.98 (s, 9H) 2.44-2.48 (m, 2H) 3.38-3.47 (m, 2H) 4.33 (d, J=8.22 Hz, 1H) 6.54 (d, J=8.41 Hz, 1H) 7.17 (dd, J=8.90, 2.84 Hz, 1H) 7.44 (d, J=8.22 Hz, 2H) 7.55 (d, J=9.00 Hz, 1H) 7.74 (d, J=8.41 Hz, 2H) 7.84 (d, J=2.54 Hz, 1H) 8.08 (s, 1H) 8.44 (t, J=5.28 Hz, 1H) 8.84 (s, 1H) 12.18 (br. s., 1H); MS (M+1): 490.4.

Example 179

3-(4-(2,2-dimethyl-1-((6-(4-(trifluoromethyl)-1H-pyrazol-1-yl)pyridin-3-yl)amino)propyl)benzamido) propanoic acid, Isomer 1 and Example 180

3-(4-(2,2-dimethyl-1-((6-(4-(trifluoromethyl)-1H-pyrazol-1-yl)pyridin-3-yl)amino)propyl)benzamido) propanoic acid, Isomer 2

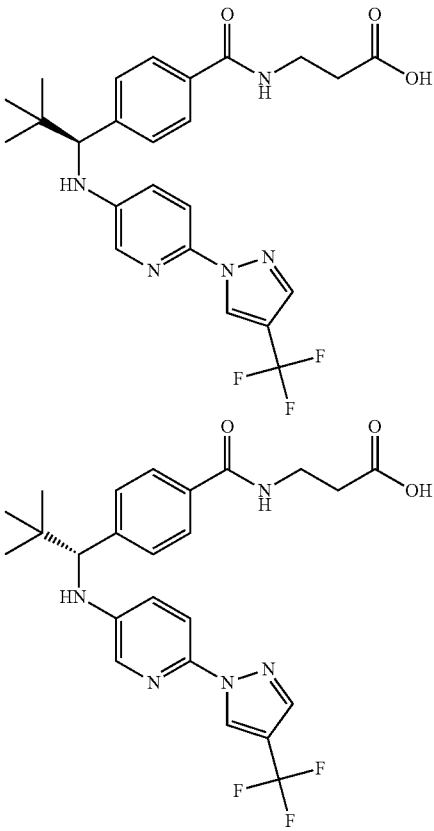

Intermediate (123) was resolved using preparative SFC (Column: Chiralpak AD-H. Dimensions: 21 mm×250 cm. Mobile Phase: 65/35 CO$_2$/2-propanol. Flow Rate: 65 mL/min. Modifier: none) to give ethyl 3-(4-(2,2-dimethyl-1-((6-(4-(trifluoromethyl)-1H-pyrazol-1-yl)pyridin-3-yl) amino)propyl)benzamido)propanoate, isomer 1 (Retention time: 2.87 min) and ethyl 3-(4-(2,2-dimethyl-1-((6-(4-(trifluoromethyl)-1H-pyrazol-1-yl)pyridin-3-yl)amino)propyl) benzamido)propanoate, Isomer 2 (retention time 5.10 min). Subsequent saponification of ethyl 3-(4-(2,2-dimethyl-1-((6-(4-(trifluoromethyl)-1H-pyrazol-1-yl)pyridin-3-yl)amino) propyl)benzamido)propanoate, Isomers 1 and 2 separately by a method analogous to the one described for Example 178 provided 3-(4-(2,2-dimethyl-1-((6-(4-(trifluoromethyl)-1H-pyrazol-1-yl)pyridin-3-yl)amino)propyl)benzamido)propanoic acid, Isomer 1 and 3-(4-(2,2-dimethyl-1-((6-(4-(trifluoromethyl)-1H-pyrazol-1-yl)pyridin-3-yl)amino)propyl) benzamido)propanoic acid, Isomer 2, respectively, as light yellow solids. $^1$H NMR (400 MHz, DMSO-d6) δ 0.98 (s, 9H) 2.44-2.48 (m, 2H) 3.38-3.46 (m, 2H) 4.33 (d, J=8.19 Hz, 1H) 6.54 (d, J=8.19 Hz, 1H) 7.17 (dd, J=8.97, 2.73 Hz, 1H) 7.44 (d, J=8.39 Hz, 2H) 7.55 (d, J=8.78 Hz, 1H) 7.74 (d, J=8.39 Hz, 2H) 7.84 (d, J=2.73 Hz, 1H) 8.08-8.09 (m, 1H) 8.44 (t, J=5.46 Hz, 1H) 8.82-8.85 (m, 1H) 12.20 (br. s., 1H); MS (M+1): 490.4.

Example 181

(±)-3-(4-(2,2-dimethyl-1-((6-(4-(trifluoromethyl)-1H-imidazol-1-yl)pyridin-3-yl)amino)propyl)benzamido)propanoic acid

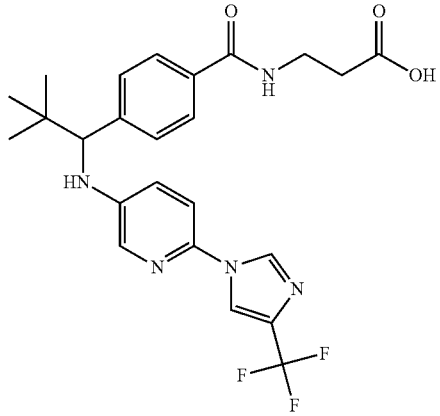

A round bottom flask was charged with Intermediate (124) (33 mg, 64 µmol), Ethanol (1 mL), THF (1 mL). NaOH 1M aq. (0.2 mL) was then added and the reaction mixture was stirred at room temperature for 30 minutes. Organic solvent removed under reduced pressure and water added to obtain a nice solution. Acidification of the aqueous solution with HCl (1N aq.) to reach ca. pH 4.5 led to a precipitate. The solid formed was recovered over a büchner funnel and washed with plenty of water. The solid was dried under high vacuum overnight to provide (±)-3-(4-(2,2-dimethyl-1-((6-(4-(trifluoromethyl)-1H-imidazol-1-yl)pyridin-3-yl)amino)propyl)benzamido)propanoic acid as a white solid (25.7 mg, 82%). $^1$H NMR (400 MHz, DMSO-d6) δ 0.98 (s, 9H) 2.44-2.48 (m, 2H) 3.38-3.46 (m, 2H) 4.33 (d, J=8.19 Hz, 1H) 6.55 (d, J=8.39 Hz, 1H) 7.11 (dd, J=8.88, 2.83 Hz, 1H) 7.40-7.47 (m, 3H) 7.74 (d, J=8.39 Hz, 2H) 7.89 (d, J=2.73 Hz, 1H) 8.24-8.29 (m, 1H) 8.37 (s, 1H) 8.44 (t, J=5.46 Hz, 1H) 12.19 (br. s., 1H); MS (M+1): 490.4.

Example 182

3-(4-(2,2-dimethyl-1-((6-(4-(trifluoromethyl)-1H-imidazol-1-yl)pyridin-3-yl)amino)propyl)benzamido)propanoic acid, Isomer 1 and

Example 183

3-(4-(2,2-dimethyl-1-((6-(4-(trifluoromethyl)-1H-imidazol-1-yl)pyridin-3-yl)amino)propyl)benzamido)propanoic acid, Isomer 2

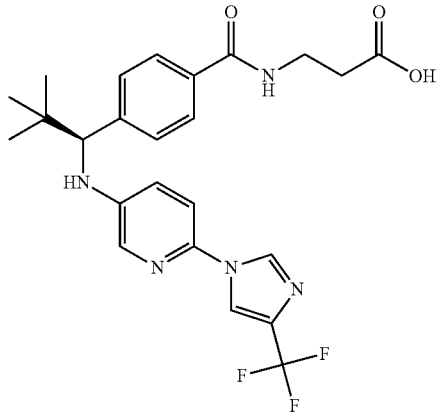

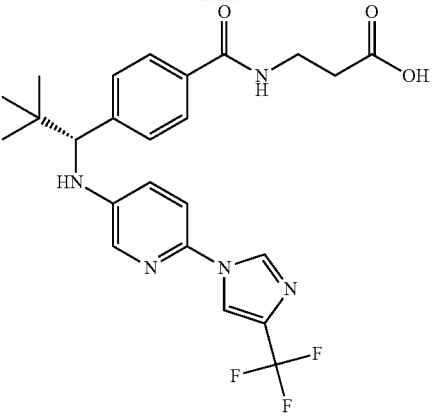 [SMILES: CC(C)(C)C(Nc1ccc(-n2cnc(C(F)(F)F)c2)nc1)c1ccc(C(=O)NCCC(=O)O)cc1]

Intermediate (124) was resolved using preparative SFC (Column: Chiralpak AD-H. Dimensions: 21 mm×250 cm. Mobile Phase: 55/45 CO$_2$/ethanol. Flow Rate: 65 mL/min. Modifier: 0.2% isopropylamine) to provide ethyl 3-(4-(2,2-dimethyl-1-((6-(4-(trifluoromethyl)-1H-imidazol-1-yl)pyridin-3-yl)amino)propyl)benzamido)propanoate, Isomer 1 (retention time: 4.77 min) and ethyl 3-(4-(2,2-dimethyl-1-((6-(4-(trifluoromethyl)-1H-imidazol-1-yl)pyridin-3-yl)amino)propyl)benzamido)propanoate, Isomer 2 (retention time: 6.45 min). Subsequent saponification of ethyl 3-(4-(2,2-dimethyl-1-((6-(4-(trifluoromethyl)-1H-imidazol-1-yl)pyridin-3-yl)amino)propyl)benzamido)propanoate, Isomer 1 and ethyl 3-(4-(2,2-dimethyl-1-((6-(4-(trifluoromethyl)-1H-imidazol-1-yl)pyridin-3-yl)amino)propyl)benzamido)propanoate, Isomer 2 separately by a method analogous to the one described for Example 181 provided 3-(4-(2,2-dimethyl-1-((6-(4-(trifluoromethyl)-1H-imidazol-1-yl)pyridin-3-yl)amino)propyl)benzamido)propanoic acid, Isomer 1 and 3-(4-(2,2-dimethyl-1-((6-(4-(trifluoromethyl)-1H-imidazol-1-yl)pyridin-3-yl)amino)propyl)benzamido)propanoic acid, Isomer 2, respectively, as white solids. $^1$H NMR (400 MHz, DMSO-d6) δ 0.98 (s, 9H) 2.44-2.48 (m, 2H) 3.38-3.46 (m, 2H) 4.33 (d, J=8.19 Hz, 1H) 6.55 (d, J=8.39 Hz, 1H) 7.11 (dd, J=8.88, 2.83 Hz, 1H) 7.40-7.47 (m, 3H) 7.74 (d, J=8.39 Hz, 2H) 7.89 (d, J=2.73 Hz, 1H) 8.24-8.29 (m, 1H) 8.37 (s, 1H) 8.44 (t, J=5.46 Hz, 1H) 12.19 (br. s., 1H); MS (M+1): 490.4.

Example 184

(+/−)-3-(4-{1-[3,5-difluoro-4-(4-trifluoromethyl-pyrazol-1-yl)-phenoxy]-butyl}-benzoylamino)-propionic acid

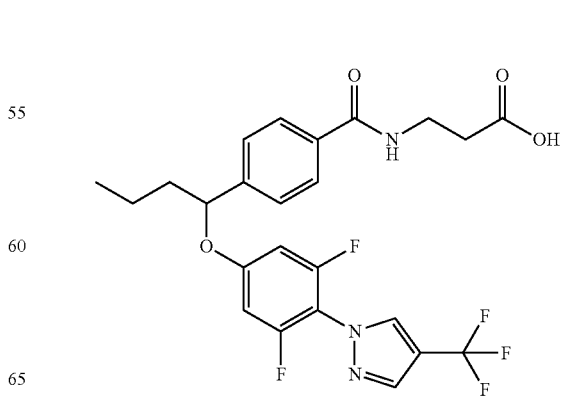

Step A: di-tert-butyl 1-(2,6-difluoro-4-methoxyphenyl)hydrazine-1,2-dicarboxylate

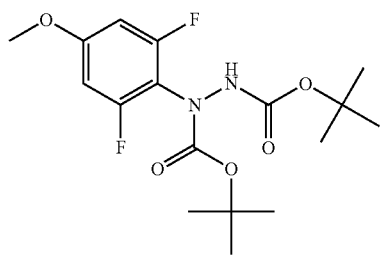 [SMILES: COc1cc(F)c(N(NC(=O)OC(C)(C)C)C(=O)OC(C)(C)C)c(F)c1]

In an oven-dried, N₂-purged round bottom, 4-bromo-3,5-difluoroanisole (500 mg, 2.24 mmol) was dissolved in anhydrous THF (11 mL) and brought to −78° C. nBuLi (0.96 mL, 2.44 M in THF, 2.35 mmol) was added over 2 min. This was stirred for 5 min and then a solution di-tert-butyl azodicarboxylate (542 mg, 2.35 mmol) in anhydrous THF (3 mL) in an oven-dried, N₂-purged pear flask was added in one portion via syringe. The reaction was removed from the ice bath and allowed to warm to room temperature over 30 min. The reaction, a clear solution, was quenched by the addition of aq. sat. NH₄Cl. The material was extracted with two portions of ethyl acetate and the combined organics were dried over MgSO₄ and concentrated in vacuo. Purification by silica gel flash chromatography (ethyl acetate in heptane) gave di-tert-butyl 1-(2,6-difluoro-4-methoxyphenyl)hydrazine-1,2-dicarboxylate (0.868 g, impure with ethyl acetate) as a clear oil. $^1$H NMR (400 MHz, CDCl₃, δ): 6.48 (d, J=10.1 Hz, 2H) 3.73-3.85 (m, 3H) 1.36-1.60 (m, 18H).

Step B: (2,6-difluoro-4-methoxy-phenyl)-hydrazine hydrochloride

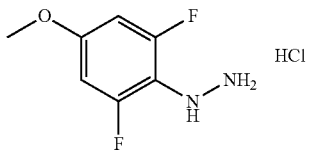

Di-tert-butyl 1-(2,6-difluoro-4-methoxyphenyl)hydrazine-1,2-dicarboxylate (616 mg, 1.64 mmol) was heated in 4 M HCl in dioxane (5 mL, 20 mmol) at reflux. The solution over time became a suspension. At 30 min, the reaction was cooled, diethylether was added, and the solid was collected with a medium frit, washing with diethylether. This gave (2,6-difluo-4-methoxy-phenyl)-hydrazine hydrochloride (0.246 g, 86%) as a tan solid. $^1$H NMR (400 MHz, DMSO-d₆, δ): 9.75 (br. s., 3H) 7.46 (s, 1H) 6.79-6.90 (m, 2H) 3.78 (s, 3H).

Step C: 1-(2,6-difluoro-4-methoxy-phenyl)-4-trifluoromethyl-1H-pyrazole

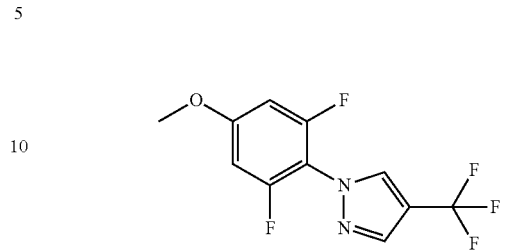

(2,6-Difluoro-4-methoxy-phenyl)-hydrazine hydrochloride (244 mg, 1.40 mmol) was combined with Intermediate (7A) (477 mg, 1.40 mmol) and anhydrous tetrahydrofuran (5 mL). This suspension was brought to 0° C. and solid NaOMe (87.6 mg, 1.54 mmol) was added. The reaction was stirred overnight allowing the bath to melt. At 21 h, the reaction was a brown solution with some solid present. Trifluoroacetic acid (0.48 mL, 6.19 mmol) was added and the reaction refluxed. At 5 h, the reaction was cooled and partitioned between ethyl acetate and sat. NaHCO₃. The aqueous was extracted with ethyl acetate and the combined organics dried over MgSO₄. Purification by silica gel flash chromatography (ethyl acetate in heptane) gave 1-(2,6-difluoro-4-methoxy-phenyl)-4-trifluoromethyl-1H-pyrazole (0.230 g, 59%) as a yellow oil. $^1$H NMR (400 MHz, CDCl₃, δ): 7.97 (s, 1H) 7.89 (s, 1H) 6.64 (d, J=9.4 Hz, 2H) 3.87 (s, 3H); MS (M+1): 279.2.

Step D: 3,5-difluoro-4-(4-trifluoromethyl-pyrazol-1-yl-phenol

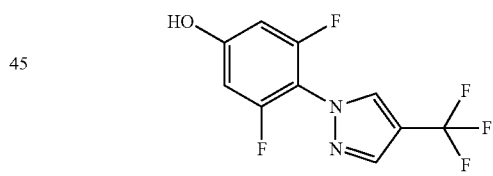

1-(2,6-Difluoro-4-methoxy-phenyl)-4-trifluoromethyl-1H-pyrazole (278 mg, 0.999 mmol) was dissolved in dichloromethane (3 mL). Boron tribromide (20.0 mL, 1.0 M in DCM, 20.0 mmol) was added and the reaction was refluxed. At 42 h, the reaction was cooled in an ice bath and slowly quenched with methanol. The combined materials were then concentrated and partitioned between ethyl acetate and sat. NaHCO₃. The aqueous layer was extracted with ethyl acetate and the combined organics dried over MgSO₄. Purification by silica gel flash chromatography (ethyl acetate in heptane) gave 3,5-difluoro-4-(4-trifluoromethyl-pyrazol-1-yl)-phenol (0.231 g, 88%) as a tan oil that solidified upon standing. $^1$H NMR (400 MHz, CDCl₃, δ): 7.99 (s, 1H) 7.90 (s, 1H) 6.50-6.60 (m, 2H); MS (M+1): 265.2.

Step E: (+/−)-4-{1-[3,5-difluoro-4-(4-trifluoromethyl-pyrazol-1-yl)-phenoxy]-butyl}-benzoic acid ethyl ester

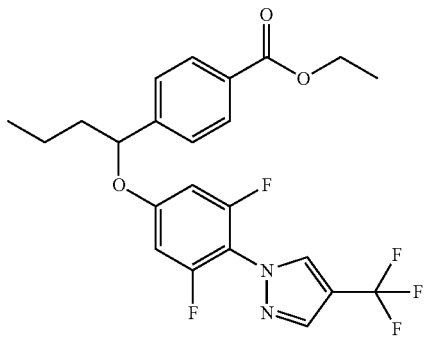 [SMILES: CCCC(Oc1cc(F)c(-n2cc(C(F)(F)F)cn2)c(F)c1)c1ccc(C(=O)OCC)cc1]

3,5-Difluoro-4-(4-trifluoromethyl-pyrazol-1-yl)-phenol (230 mg, 0.871 mmol) was combined with ethyl 4-(1-hydroxybutyl)benzoate (see Intermediate 5) (194 mg, 0.871 mmol) and dissolved in anhydrous tetrahydrofuran (4 mL). Triphenylphosphine (457 mg, 1.74 mmol) was added followed by diazopropyl azodicarboxylate (0.451 mL, 2.18 mmol). This was stirred at room temperature as a yellow solution. At 17 h. the reaction was concentrated. Purification by silica gel flash chromatography (ethyl acetate in heptane) gave impure (+/−)-4-{1-[3,5-difluoro-4-(4-trifluoromethyl-pyrazol-1-yl)-phenoxy]-butyl}-benzoic acid ethyl ester (0.411 g) as a clear oil. $^1$H NMR (400 MHz, CDCl$_3$, δ): 8.06 (d, J=8.2 Hz, 2H) 7.93 (s, 1H) 7.82 (s, 1H) 7.39 (d, J=8.4 Hz, 2H) 6.54 (d, J=9.4 Hz, 2H) 5.15 (dd, J=7.6, 5.3 Hz, 1H) 4.39 (q, J=7.2 Hz, 2H) 1.96-2.10 (m, 1H) 1.77-1.91 (m, 1H) 1.19-1.61 (m, 5H) 0.98 (t, J=7.3 Hz, 3H); MS (M+1): 469.3.

Step F: (+/−)-3-(4-{1-[3,5-difluoro-4-(4-trifluoromethyl-pyrazol-1-yl)-phenoxy]-butyl}-benzoylamino)-propionic acid The title compound was prepared by a method analogous to that described for Example 20 using (+/−)-4-{1-[3,5-difluoro-4-(4-trifluoromethyl-pyrazol-1-yl)-phenoxy]-butyl}benzoic acid ethyl ester. Column: Waters Atlantis d C18 4.6×50 mm, 5 μm; Modifier: TFA 0.05%; Gradient: 95% H$_2$O/5% acetonitrile linear to 5% H$_2$O/95% acetonitrile over 4.0 min, hold at 5% H$_2$O/95% acetonitrile to 5.0 min. Flow: 2.0 mL/min.; Retention time: 3.31 minutes. MS (M+1): 512.1.

Example 185

(+/−)-3-(4-{1-[4-(5-fluoro-indazol-2-yl)-phenoxy]-butyl}-benzoylamino)-propionic acid

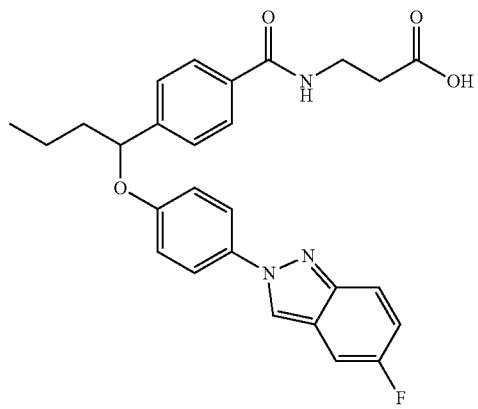

The title compound was prepared by a method analogous to that described for Example 184 using Intermediate (125). Column: Waters Atlantis d C18 4.6×50 mm, 5 μm; Modifier TFA 0.05%; Gradient: 95% H$_2$O/5% acetonitrile linear to 5% H$_2$O/95% acetonitrile over 4.0 min, hold at 5% H$_2$O/95% acetonitrile to 5.0 min. Flow: 2.0 mL/min.; Retention time: 3.35 minutes. MS (M+1): 476.0.

Example 186

(+/−)-3-(4-{1-[4-(6-fluoro-indazol-2-yl)-phenoxy]-butyl}-benzoylamino)propionic acid

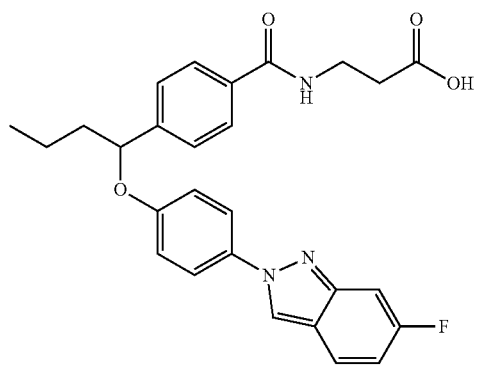

The title compound was prepared by a method analogous to that described for Example 184 using Intermediate (126). Column: Waters Atlantis d C18 4.6×50 mm, 5 μm; Modifier: TFA 0.05%; Gradient: 95% H$_2$O/15% acetonitrile linear to 5% H$_2$O/95% acetonitrile over 4.0 min, hold at 5% H$_2$O/95% acetonitrile to 5.0 min. Flow: 2.0 mL/min.; Retention time: 3.33 minutes. MS (M+1): 476.0.

Example 187

(S)-3-(4-(1-(4-(2H-indazol-2-yl)-3,5-dimethylphenoxy)butyl)benzamido)propanoic acid

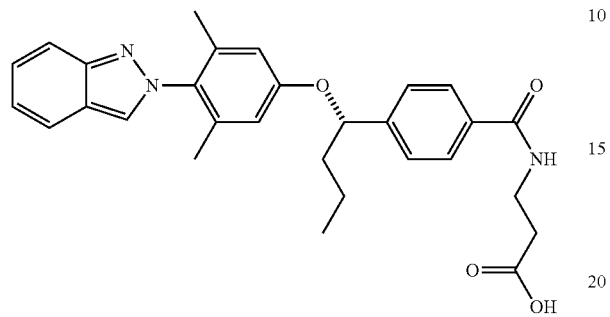

The title compound was prepared using a method analogous to that described in Example 83, starting from Intermediate (127). $^1$H NMR (400 MHz, CDCl$_3$) δ ppm 0.95 (t, J=7.32 Hz, 3H) 1.35-1.59 (m, 2H) 1.74-1.86 (m, 1H) 1.82 (s, 3H) 1.90-2.03 (m, 1H) 2.55 (t, J=5.85 Hz, 2H) 3.55-3.67 (m, 2H) 5.10-5.25 (m, 1H) 6.57 (br. s., 2H) 7.08-7.17 (m, 2H) 7.31 (ddd, J=8.73, 6.68, 0.98 Hz, 1H) 7.37 (d, J=8.19 Hz, 2H) 7.67-7.78 (m, 4H) 7.88 (d. J=0.78 Hz, 1H). LCMS: m/z=486.2 [M+H].

Example 188

(+\−)-3-(4-((3,3-dimethylcyclobutyl)(6-(4-(trifluoromethyl)-1H-imidazol-1-yl)pyridin-3-ylamino)methyl)benzamido)propanoic acid

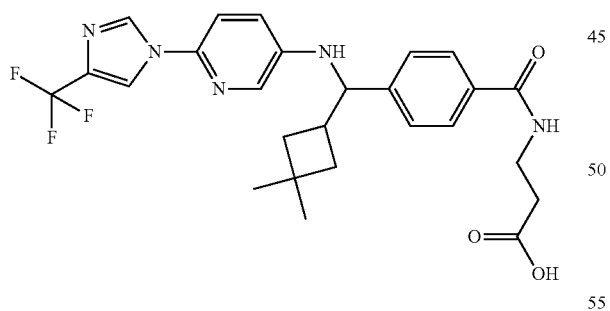

The title compound was prepared using a method analogous to that described in Example 62, starting from Intermediate (101) and Intermediate 6. $^1$H NMR (400 MHz, CDCl$_3$) δ ppm 1.05 (s, 3H) 1.08 (s, 3H) 1.49-1.72 (m, 3H) 1.90-2.01 (m, 1H) 2.45 (d, J=8.80 Hz, 1H) 2.62 (m, 2H) 3.54-3.71 (m, 2H) 4.16 (d, J=9.19 Hz, 1H) 6.80 (dd, J=8.80, 2.74 Hz, 1H) 7.07 (d, J=8.80 Hz, 1H) 7.12-7.19 (m, 1H) 7.32 (d, J=8.22 Hz, 2H) 7.67 (d, J=8.02 Hz, 2H) 7.72 (d, J=2.74 Hz, 1H) 7.82 (s, 1H) 8.36 (s, 1H). LCMS: m/z=516.2 [M+H].

Example 189

(+\−)-3-(4-(1-(4-(2H-indazol-2-yl)-3,5-dimethylphenoxy)butyl)benzamido)propanoic acid

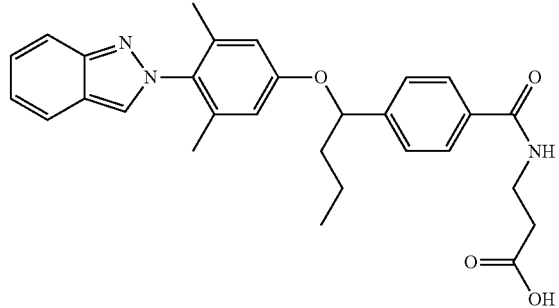 [SMILES: CCCC(Oc1cc(C)c(-n2cc3ccccc3n2)c(C)c1)c1ccc(C(=O)NCCC(=O)O)cc1]

The title compound was prepared using a method analogous to that described in Example 83, starting from Intermediate (127). $^1$H NMR (400 MHz, CDCl$_3$) δ ppm 0.95 (t, J=7.32 Hz, 3H) 1.35-1.59 (m, 2H) 1.74-1.86 (m, 1H) 1.82 (s, 3H) 1.90-2.03 (m, 1H) 2.55 (t, J=5.85 Hz, 2H) 3.55-3.67 (m, 2H) 5.10-5.25 (m, 1H) 6.57 (br. s., 2H) 7.08-7.17 (m, 2H) 7.31 (ddd, J=8.73, 6.68, 0.98 Hz, 1H) 7.37 (d, J=8.19 Hz, 2H) 7.67-7.78 (m, 4H) 7.88 (d, J=0.78 Hz, 1H). LCMS: m/z=486.2 [M+H].

Example 190

(+\−)-3-(6-(1-(6-(4-(trifluoromethyl)-1H-pyrazol-1-yl)pyridin-3-yl)butylamino)nicotinamido)propanoic acid

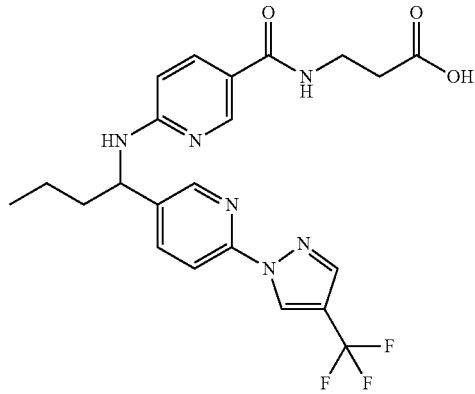 [SMILES: CCCC(Nc1ccc(C(=O)NCCC(=O)O)cn1)c1ccc(-n2cc(C(F)(F)F)cn2)nc1]

The title compound was prepared using a method analogous to that described for Example 142, starting from Intermediate (90) and Intermediate (128). $^1$H NMR (400 MHz, CDCl$_3$) δ 8.85-9.00 (br s, 1H), 8.80 (s, 1H), 8.40 (d, J=1.95 Hz, 1H), 8.25 (s, 1H), 8.13 (dd, J=9.7, 2.1 Hz, 1H), 7.96 (d, J=8.4 Hz, 1H), 7.81-7.87 (m, 2H), 7.50-7.57 (m, 1H), 6.42 (d, J=9.2 Hz, 1H), 4.47-4.56 (m, 1H), 3.65-3.76 (m, 2H), 2.58-

2.64 (m, 2H), 1.77-2.06 (m, 2H), 1.30-1.53 (m, 2H), 0.95 (t, J=7.4 Hz, 3H). MS (M+H)=477.4.

Example 191

3-(4-((6-(4-chloro-3-methyl-1H-pyrazol-1-yl)pyridin-3-ylamino)(cyclopentyl)methyl benzamido)propanoic acid, Isomer 1 and Example 192

3-(4-((6-(4-chloro-3-methy-1H-pyrazol-1-yl)pyridin-3-ylamino)(cyclopentyl)methyl)benzamido)propanoic acid, Isomer 2

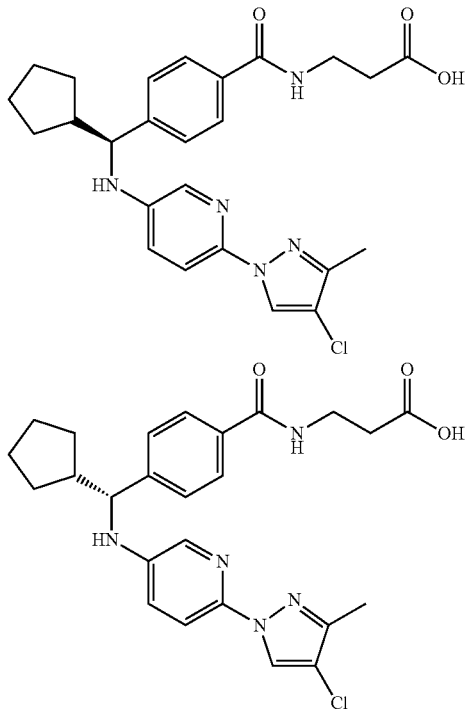

Racemic ethyl 3-(4-((6-(4-chloro-3-methyl-1H-pyrazol-1-yl)pyridin-3-ylamino)(cyclopentyl)methyl)benzamido)propanoate was prepared using a method analogous to that described in Example 163, Steps A-C, using ethyl 3-aminopropanoate hydrochloride in Step 3. This material was resolved by SFC (column: Chiralcel OD-H 10×250 mm: mobile phase: 60/40 CO$_2$/methanol; no modifier; flow rate: 10 mL/min) to give ethyl 3-(4-((6-(4-chloro-3-methyl-1H-pyrazol-1-yl)pyridin-3-ylamino)(cyclopentyl)methyl)benzamido)propanoate, Isomer 1 (retention time 3.23 min) and ethyl 3-(4-((6-(4-chloro-3-methyl-1H-pyrazol-1-yl)pyridin-3-ylamino)(cyclopentyl)methyl)benzamido)propenoate, Isomer 2 (retention time 4.54 min). ethyl 3-(4-((6-(4-chloro-3-methyl-1H-pyrazol-1-yl)pyridin-3-ylamino)(cyclopentyl)methyl)benzamido)propanoate, Isomer 1 and ethyl 3-(4-((6-(4-chloro-3-methyl-1H-pyrazol-1-yl)pyridin-3-ylamino)(cyclopentyl)methyl)benzamido)propanoate, Isomer 2 were saponified separately using a method analogous to that described in Example X158, Step D, to give 3-(4-((6-(4-chloro-3-methyl-1H-pyrazol-1-yl)pyridin-3-ylamino)(cyclopentyl)methyl)benzamido)propanoic acid, Isomer 1 and 3-(4-((6-(4-chloro-3-methyl-1H-pyrazol-1-yl)pyridin-3-ylamino)(cyclopentyl)methyl)benzamido)propanoic acid, Isomer 2, respectively. Spectral data for Isomer 1: $^1$H NMR (400 MHz, CDCl$_3$) δ 8.17 (s, 1H), 7.68 (d, J=8.0 Hz, 2H), 7.59-7.64 (m, 1H), 7.50 (d, J=9.2 Hz, 1H), 7.35 (d, J=8.2 Hz, 2H), 6.81-6.88 (m, 1H), 6.74-6.81 (m, 1H), 4.10 (d, J=8.4 Hz, 1H), 3.64-3.73 (m, 2H), 2.62-2.72 (m, 2H), 2.25 (s, 3H), 2.10-2.21 (m, 1H), 1.83-1.95 (m, 2H), 1.33-1.72 (m, 4H), 1.15-1.30 (m, 2H). MS (M+H)=482.3.

Example 193

3-(4-(cyclopentyl(2-(4-(trifluoromethyl)-1H-imidazol-1-yl)pyrimidin-5-ylamino)methyl)benzamido) propanoic acid

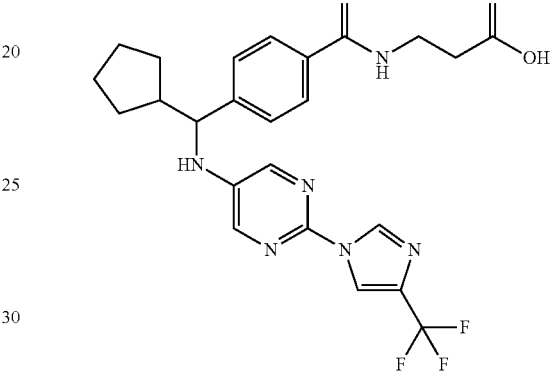

The title compound was prepared using a method analogous to that described in Example 163, starting from Intermediate (31) and Intermediate (129). Analytical HPLC: retention time 2.99 min (Column: Waters Atlantis dC18 4.6× 50 mm, 5 um. Modifier: TFA 0.05%. Gradient 95% H20/5% MeCN linear to 5% H20/95% MeCN over 4.0 min. HOLD at 5% H20/95% MeCN to 5.0 min. Flow: 2.0 mL/min). LCMS: m/z=503.2 [M+H].

Biological Data

Glucagon cAMP Assay

The Cisbio cAMP detection assay is used to determine the ability of punitive glucagon antagonist to block glucagon induced cAMP production. Potential glucagon antagonists are re-suspended and diluted in 100% DMSO. Prior to use in the Glucagon cAMP assay 100×DMSO compound stocks are diluted 20× with DMEM-F12 media (Invitrogen) containing either 0.1% or 4% BSA. 2 μls of 5× compound stocks are spotted into the appropriate wells of low binding white solid bottom 384 well plates (Corning). 2 μls of 5% DMSO or known glucagon antagonist are added to each plate to define the assay window. CHOK1 cells stably transfected with the human glucagon receptor are removed from culture flasks with cell dissociation buffer. Cell pellets are re-suspended, at a concentration of 8.3 e$^5$ cells/ml in DMEM-F12 with or without 4% BSA and 200 uM IBMX. 6 μls of cell suspensions are added to the assay plates. Plates are incubated for 20 min at room temperature prior to the addition of a 100 pM challenge dose of glucagon. On a separate plate glucagon dose response curves are run to determine the EC$_{50}$ of glucagon. After a 30 min room temperature incubation the reaction is terminated by the addition of lysis buffer containing the cAMP detection reagents. Plates are incubated for an additional 60 min at room temperature prior to being read on the Perkin Elmer fluorescent plate reader. Raw is converted to nM of CAMP produced based on a cAMP standard curve. Converted data is then analyzed using the Pfizer data analysis program. $IC_{50}$ values are determined from the generated sigmoidal dose response curves. Kb values are calculated using a modified Cheng-Prusoff equation. N is the number of times the compound was assayed.

Table of cAMP data

| Example | N | cAMP (Kb nM) |
|---|---|---|
| Example 1 | 4 | 1500 |
| Example 2 | 6 | 5280 |
| Example 3 | 6 | 1820 |
| Example 4 | 10 | 1270 |
| Example 5 | 12 | 242 |
| Example 6 | 30 | 77.3 |
| Example 7 | 6 | 760 |
| Example 8 | 12 | 155 |
| Example 9 | 21 | 572 |
| Example 10 | 8 | 15500 |
| Example 11 | 8 | 612 |
| Example 12 | 9 | 491 |
| Example 13 | 16 | 297 |
| Example 14 | 10 | 293 |
| Example 15 | 4 | 1170 |
| Example 16 | 8 | 717 |
| Example 17 | 6 | 419 |
| Example 18 | 7 | 3860 |
| Example 19 | 12 | 2860 |
| Example 20 | 6 | 800 |
| Example 21 | 6 | 824 |
| Example 22 | 4 | 835 |
| Example 23 | 6 | 948 |
| Example 24 | 4 | 1030 |
| Example 25 | 4 | 1120 |
| Example 26 | 6 | 1050 |
| Example 27 | 4 | 1080 |
| Example 28 | 6 | 1300 |
| Example 29 | 4 | 1360 |
| Example 30 | 6 | 1410 |
| Example 31 | 2 | 1450 |
| Example 32 | 2 | 1590 |
| Example 33 | 4 | 1560 |
| Example 34 | 2 | 1710 |
| Example 35 | 2 | 1790 |
| Example 36 | 2 | 1820 |
| Example 37 | 2 | 1760 |
| Example 38 | 2 | 2130 |
| Example 39 | 4 | 2460 |
| Example 40 | 2 | 2540 |
| Example 41 | 2 | 2840 |
| Example 42 | 2 | 2810 |
| Example 43 | 2 | 2910 |
| Example 44 | 2 | 3110 |
| Example 45 | 2 | 3350 |
| Example 46 | 2 | 6890 |
| Example 47 | 2 | 7810 |
| Example 48 | 2 | 8150 |
| Example 49 | 2 | 10300 |
| Example 50 | 4 | 1560 |
| Example 51 | 8 | 1810 |
| Example 52 | 2 | 2410 |
| Example 53 | 4 | 2610 |
| Example 54 | 2 | 3530 |
| Example 55 | 2 | 3720 |
| Example 56 | 2 | 4370 |
| Example 57 | 4 | 6100 |
| Example 58 | 2 | 7300 |
| Example 59 | 14 | 1390 |
| Example 60 | 13 | 1270 |
| Example 61 | 14 | 3250 |
| Example 62 | 12 | 32.2 |
| Example 63 | 12 | 613 |
| Example 64 | 14 | 494 |
| Example 65 | 6 | 2880 |
| Example 66 | 2 | 1450 |
| Example 67 | 14 | 526 |
| Example 68 | 6 | 1710 |
| Example 69 | 4 | 1510 |
| Example 70 | 6 | 1910 |
| Example 71 | 2 | 2120 |
| Example 72 | 6 | 2300 |
| Example 73 | 6 | 2640 |
| Example 74 | 5 | 4680 |
| Example 75 | 6 | 7710 |
| Example 76 | 2 | 6130 |
| Example 77 | 6 | 2390 |
| Example 78 | 6 | 4330 |
| Example 79 | | 4140 |
| Example 80 | 2 | 1290 |
| Example 81 | 10 | 1830 |
| Example 82 | 10 | 388 |
| Example 83 | 22 | 164 |
| Example 84 | 12 | 3900 |
| Example 85 | 6 | 4140 |
| Example 86 | 4 | 615 |
| Example 87 | 2 | 9390 |
| Example 88 | 2 | 4740 |
| Example 89 | 6 | 1420 |
| Example 90 | 4 | >2500 |
| Example 91 | 11 | 213 |
| Example 92 | 2 | 5600 |
| Example 93 | 4 | 3840 |
| Example 94 | 10 | 57.5 |
| Example 95 | 10 | 32.8 |
| Example 96 | 4 | 871 |
| Example 97 | 10 | 90.8 |
| Example 98 | 4 | 1060 |
| Example 99 | 6 | 376 |
| Example 100 | 6 | 226 |
| Example 101 | 6 | 79.3 |
| Example 102 | 4 | 3540 |
| Example 103 | 8 | 1080 |
| Example 104 | 8 | 169 |
| Example 105 | 6 | 455 |
| Example 106 | 4 | 187 |
| Example 107 | 2 | 252 |
| Example 108 | 7 | 224 |
| Example 109 | 2 | 1710 |
| Example 110 | 4 | 97 |
| Example 111 | 2 | 2350 |
| Example 112 | 4 | 126 |
| Example 113 | 10 | 103 |
| Example 114 | 8 | 17 |
| Example 115 | 6 | 231 |
| Example 116 | 4 | 450 |
| Example 117 | 4 | 227 |
| Example 118 | 2 | 1020 |
| Example 119 | 6 | 67 |
| Example 120 | 10 | 65 |
| Example 121 | 2 | 764 |
| Example 122 | 6 | 43 |
| Example 123 | 4 | 106 |
| Example 124 | 12 | 82 |
| Example 125 | 4 | 144 |
| Example 126 | 4 | 212 |
| Example 127 | 3 | 202 |
| Example 128 | 3 | 268 |
| Example 129 | 5 | 13 |
| Example 130 | 2 | 195 |
| Example 131 | 10 | 247 |
| Example 132 | 4 | 153 |
| Example 133 | 8 | 75 |
| Example 134 | 2 | 876 |
| Example 135 | 6 | 28 |
| Example 136 | 4 | 222 |
| Example 137 | 7 | 27 |
| Example 138 | 4 | 40 |
| Example 139 | 4 | 147 |
| Example 140 | 4 | 154 |
| Example 141 | 8 | 586 |

Table of cAMP data

| Example | N | cAMP (Kb nM) |
|---|---|---|
| Example 142 | 2 | 883 |
| Example 143 | 8 | 179 |
| Example 144 | 6 | 174 |
| Example 145 | 10 | 156 |
| Example 146 | 8 | 21 |
| Example 147 | 6 | 343 |
| Example 148 | 14 | 423 |
| Example 149 | 4 | 2250 |
| Example 150 | 4 | 1640 |
| Example 151 | 6 | 227 |
| Example 152 | 6 | 301 |
| Example 153 | 6 | 225 |
| Example 154 | 6 | 629 |
| Example 155 | 8 | 313 |
| Example 156 | 6 | 246 |
| Example 157 | 10 | 18.6 |
| Example 158 | 10 | 155 |
| Example 159 | 8 | 730 |
| Example 160 | 6 | 111 |
| Example 161 | 8 | 9.49 |
| Example 162 | 8 | 55.8 |
| Example 163 | 8 | 42.7 |
| Example 164 | 8 | 52.4 |
| Example 165 | 6 | 305 |
| Example 166 | 5 | 94.8 |
| Example 167 | 3 | 1140 |
| Example 168 | 8 | 185 |
| Example 169 | 4 | 1150 |
| Example 170 | 6 | 1300 |
| Example 171 | 8 | 150 |
| Example 172 | 8 | 59.9 |
| Example 173 | 4 | 641 |
| Example 174 | 4 | 252 |
| Example 175 | 6 | 10.5 |
| Example 176 | 8 | 79.1 |
| Example 177 | 4 | 2340 |
| Example 178 | 8 | 215 |
| Example 179 | 4 | 134 |
| Example 180 | 6 | 45 |
| Example 181 | 2 | 195 |
| Example 182 | 8 | 424 |
| Example 183 | 8 | 154 |
| Example 184 | 4 | 321 |
| Example 185 | 6 | 175 |
| Example 186 | 6 | 192 |
| Example 187 | 8 | 167 |
| Example 188 | 8 | 106 |
| Example 189 | 2 | 370 |
| Example 190 | 8 | 978 |
| Example 191 | 4 | 11.7 |
| Example 192 | 4 | 88.5 |
| Example 193 | 6 | 84.1 |

Human Glucagon SPA Assay

The Glucagon SPA assay is used to determine the ability of test compounds to block the binding of glucagon-cex to the glucagon receptor. Test compounds are re-suspended and serially diluted in 100% DMSO. 1 µl of test compound at the desired concentrations is spotted into the appropriate wells of 96 well low binding white clear bottom plate (Corning). 1 µl of DMSO is spotted into total binding wells. 1 µl of a known glucagon antagonist at a concentration of 20 µM is added to non specific binding wells, 0.3-0.75 µg of membrane from chem-1 cells stably transfected with the human glucagon receptor (Millipore), 125 pM of [$^{125}$I]Glucagon-Cex (Perkin Elmer) and 175 µg of WGA PVT SPA beads (Perkin Elmer) are added to all wells of the assay plate. All assay ingredients with the exception of test compounds are re-suspended in the following buffer; 50 mM Hepes pH 7.4; 5 mM MgCl$_2$; 1 mM CaCl; 5% glycerol and 0.2% BSA. Following a 6-10 hr incubation at room temperature the amount of hot ligand bound to the cell membranes is determined by reading the plates on a Wallac Trilux radioactive emission detector. Data is analyzed using Pfizer's Data analysis program. IC$_{50}$ values are then determined from the generated sigmoidal dose response curves. Ki values are calculated using Cheng-Prusoff equation. N is the number of times the compound was assayed.

Table for SPA Binding data

| Example number | N | Binding Ki (nM) |
|---|---|---|
| Example 97 | 2 | 93 |
| Example 98 | 4 | 1.100 |
| Example 86 | 2 | 233 |
| Example 101 | 2 | 17 |
| Example 31 | 1 | 1331 |
| Example 22 | 2 | 665 |
| Example 28 | 2 | 1659 |
| Example 53 | 2 | 556 |
| Example 105 | 4 | 69.8 |
| Example 106 | 3 | 91.9 |
| Example 107 | 2 | 71.6 |
| Example 108 | 4 | 203 |
| Example 109 | 2 | 153 |
| Example 110 | 3 | 57.2 |
| Example 111 | 2 | 202 |
| Example 112 | 3 | 143 |
| Example 113 | 4 | 38.2 |
| Example 114 | 5 | 7.6 |
| Example 115 | 4 | 15.8 |
| Example 116 | 2 | 464 |
| Example 117 | 2 | 183 |
| Example 118 | 1 | 297 |
| Example 119 | 4 | 103 |
| Example 120 | 5 | 225 |
| Example 121 | 1 | 298 |
| Example 122 | 4 | 45.7 |
| Example 123 | 3 | 88.4 |
| Example 124 | 6 | 109 |
| Example 125 | 3 | 98.2 |
| Example 126 | 3 | 161 |
| Example 127 | 3 | 316 |
| Example 128 | 3 | 208 |
| Example 129 | 4 | 29.3 |
| Example 130 | 2 | 116 |
| Example 131 | 6 | 51 |
| Example 132 | 3 | 132 |
| Example 133 | 5 | 58 |
| Example 134 | 1 | 110 |
| Example 135 | 3 | 35 |
| Example 136 | 2 | 30.2 |
| Example 137 | 4 | 20.2 |
| Example 138 | 2 | 5.75 |
| Example 139 | 3 | 354 |
| Example 140 | 3 | 62.8 |
| Example 141 | 5 | 89.5 |
| Example 142 | 2 | 636 |
| Example 143 | 5 | 57.4 |
| Example 144 | 4 | 62.6 |
| Example 145 | 6 | 93.2 |
| Example 146 | 4 | 9.05 |
| Example 147 | 3 | 26.7 |
| Example 148 | 7 | 125 |
| Example 149 | 2 | 1050 |
| Example 150 | 2 | 446 |
| Example 151 | 3 | 20.2 |
| Example 152 | 3 | 35.2 |
| Example 153 | 3 | 32.3 |
| Example 154 | 3 | 235 |
| Example 155 | 4 | 94.9 |
| Example 156 | 3 | 251 |
| Example 157 | 5 | 5.55 |
| Example 158 | 5 | 41 |
| Example 159 | 4 | 315 |
| Example 160 | 4 | 29 |
| Example 161 | 5 | 25.7 |
| Example 162 | 5 | 47.3 |
| Example 163 | 5 | 65.9 |

-continued

Table for SPA Binding data

| Example number | N | Binding Ki (nM) |
|---|---|---|
| Example 164 | 5 | 192 |
| Example 165 | 4 | 142 |
| Example 166 | 4 | 91.5 |
| Example 167 | 3 | 414 |
| Example 168 | 4 | 27.4 |
| Example 169 | 2 | 193 |
| Example 170 | 2 | 224 |
| Example 171 | 4 | 28 |
| Example 172 | 4 | 8.18 |
| Example 173 | 2 | 26.6 |
| Example 174 | 2 | 57 |
| Example 175 | 3 | 28.7 |
| Example 176 | 4 | 101 |
| Example 177 | 2 | 432 |
| Example 178 | 4 | 37.4 |
| Example 179 | 4 | 22.1 |
| Example 180 | 5 | 10.3 |
| Example 181 | 1 | 87.2 |
| Example 182 | 4 | 156 |
| Example 183 | 4 | 53.5 |
| Example 184 | 2 | 240 |
| Example 185 | 3 | 137 |
| Example 186 | 3 | 175 |
| Example 187 | 5 | 47.8 |
| Example 188 | 4 | 42.2 |
| Example 189 | 2 | 109 |
| Example 190 | 4 | 399 |
| Example 191 | 2 | 29.3 |
| Example 192 | 2 | 50.3 |
| Example 193 | 4 | 44.7 |

We claim:

1. A compound of Formula I

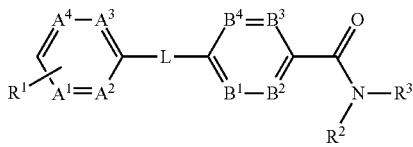

or a pharmaceutically acceptable salt thereof, wherein
$R^1$ is a 5 membered heteroaryl group attached through either a carbon or nitrogen atom and which is optionally fused to a $(C_4-C_7)$cycloalkyl, phenyl or 6 membered heteroaryl; wherein the optionally fused 5 membered heteroaryl is optionally substituted with one to four substituents each independently selected from halo, $—S(O)_2—(C_1-C_3)$alkyl, $—S—(C_1-C_3)$alkyl, hydroxy, $—C(O)NR^aR^b$, $(C_3-C_5)$cycloalkyl, cyano, phenyl which is optionally substituted with one to three halo, cyano, $(C_1-C_3)$alkyl or $(C_1-C_3)$alkoxy, 6 membered heteroaryl which is optionally substituted with one to three halo, cyano, $(C_1-C_3)$alkyl or $(C_1-C_3)$alkoxy, $(C_1-C_6)$alkyl optionally substituted with one to three fluoro, or $(C_1-C_6)$alkoxy optionally substituted with one to three fluoro;
$R^a$ and $R^b$ are each independently H or $(C_1-C_3)$alkyl;
$R^2$ is H or methyl;
$R^3$ is tetrazolyl, $—CH_2$-tetrazolyl, $—(CH_2)_2SO_3H$ or $—(CH_2)_2CO_2H$, $—CH_2CHFCO_2H$ or $—CH_2CHOHCO_2H$;
$A^1, A^2, A^3$ and $A^4$ are each independently $CR^4$ or N, with the proviso that no more than two of $A^1, A^2, A^3$ and $A^4$ are N;

$R^4$ at each occurrence is independently H, halo, cyano, $(C_1-C_3)$alkyl optionally substituted with one to three fluoro, or $(C_1-C_3)$alkoxy optionally substituted with one to three fluoro;
L is $—X—CH(R^5)—$ or $—CH(R^5)—X—$;
X is $CH_2$, O or NH;
$R^5$ is $(C_1-C_6)$alkyl which is optionally substituted with one to three fluoro, hydroxy or methoxy; $(C_3-C_7)$cycloalkyl which is optionally substituted with one to two $(C_1-C_3)$alkyl which are optionally substituted with one to three fluoro and wherein one to two carbons of the $(C_3-C_7)$cycloalkyl can be replaced with a NH, $N(C_1-C_3)$alkyl, O or S; or $(C_3-C_7)$cycloalkyl-$(C_1-C_6)$alkyl wherein the $(C_3-C_7)$cycloalkyl group of said $(C_3-C_7)$cycloalkyl-$(C_1-C_6)$alkyl is optionally substituted with one to two $(C_1-C_3)$alkyl which are optionally substituted with one to three fluoro;
$B^1, B^2, B^3$ and $B^4$ are each independently $CR^6$ or N, with the proviso that no more than two of $B^1, B^2, B^3$ and $B^4$ are N; and
$R^6$ at each occurrence is independently H, halo, $(C_1-C_3)$ alkyl optionally substituted with one to three fluoro, or $(C_1-C_3)$alkoxy optionally substituted with one to three fluoro.

2. The compound of claim 1 or a pharmaceutically acceptable salt thereof, wherein L is $—X—CH(R^5)—$; $R^1$ is a 5 membered heteroaryl attached through a nitrogen atom to the carbon between $A^1$ and $A^4$ of the ring containing $A^1, A^2, A^3$ and $A^4$;
$R^2$ is hydrogen; and $R^3$ is $—(CH_2)_2CO_2H$.

3. The compound of claim 2 or a pharmaceutically acceptable salt thereof, wherein X is O.

4. The compound of claim 2 or a pharmaceutically acceptable salt thereof, wherein X is NH.

5. The compound of claim 3 or a pharmaceutically acceptable salt thereof wherein $A^1$ and $A^4$ are each N and $A^2$ and $A^3$ are each $CR^4$; $R^4$ at each $B^2$, occurrence is independently H or methyl; $B^1, B^2, B^3$ and $B^4$ are each $CR^6$; and $R^6$ at each occurrence is H.

6. The compound of claim 4 or a pharmaceutically acceptable salt thereof wherein $A^4$ is N and $A^1, A^2$ and $A^3$ are each $CR^4$; $R^4$ at each occurrence is independently H or methyl; $B^1, B^2, B^3$ and $B^4$ are each $CR^6$; and $R^6$ at each occurrence is independently H or methyl.

7. The compound of claim 5 or a pharmaceutically acceptable salt thereof wherein $R^5$ is ethyl, propyl, isopropyl, isobutyl, neopentyl, cyclopropyl, cyclobutyl, dimethylcycobutyl, cyclopentyl or cyclopropylmethyl.

8. The compound of claim 6 or a pharmaceutically acceptable salt thereof wherein $R^5$ is ethyl, propyl, isopropyl, isobutyl, neopentyl, cyclopropyl, cyclobutyl, dimethylcycobutyl, cyclopentyl or cyclopropylmethyl.

9. The compound of claim 7 or a pharmaceutically acceptable salt thereof wherein $R^1$ is imidazolyl, pyrazolyl, triazolyl or indazolyl optionally substituted with one to two substituents each independently selected from methyl, trifluoromethyl, ethyl, propyl, isopropyl, butyl, t-butyl, methoxy, ethoxy, cyano, chloro or fluoro.

10. The compound of claim 8 or a pharmaceutically acceptable salt thereof wherein $R^1$ is imidazolyl, pyrazolyl, triazolyl or indazolyl optionally substituted with one to two substituents each independently selected from methyl, trifluoromethyl, ethyl, propyl, isopropyl, butyl, t-butyl, methoxy, ethoxy, cyano, chloro or fluoro.

11. The compound of claim 7 or a pharmaceutically acceptable salt thereof wherein $R^1$ is 4-trifluoromethylpyrazol-1-yl.

12. The compound of claim 8 or a pharmaceutically acceptable salt thereof wherein $R^1$ is 4-trifluoromethylpyrazol-1-yl or 4-tert-butylpyrazol-1-yl.

13. 3-(4-((3,3-dimethylcyclobutyl)(2-(4-(trifluoromethyl)-1H-pyrazol-1-yl)pyrimidin-5-yloxy)methyl)benzamido)propanoic acid, Isomer 1, or a pharmaceutically acceptable salt thereof.

14. 3-(4-(1-(6-(4-tert-butyl-1H-pyrazol-1-yl)pyridin-3-ylamino)butyl)benzamido)propanoic acid, Isomer 2, or a pharmaceutically acceptable salt thereof.

15. 3-(4-(cyclopentyl(6-(4-(trifluoromethyl)-1H-pyrazol-1-yl)pyridine-3-ylamino)methyl)benzamido)propanoic acid, Isomer 1, or a pharmaceutically acceptable salt thereof.

16. A pharmaceutical composition comprising (i) a therapeutically effective amount of a compound of claim 1 or a pharmaceutically acceptable salt thereof and (ii) a pharmaceutically acceptable excipient, diluent, or carrier.

17. A method for treating or delaying the progression or onset of Type 2 diabetes in a human comprising the step of administering to the human in need of such treatment a therapeutically effective amount of a compound of claim 1 or a pharmaceutically acceptable salt thereof.

18. A method for treating or delaying the progression or onset of Type 2 diabetes in a human comprising the step of administering to the human in need of such treatment the pharmaceutical composition of claim 16.

* * * * *